(12) United States Patent
von Maltzahn et al.

(10) Patent No.: US 11,576,872 B2
(45) Date of Patent: Feb. 14, 2023

(54) COMPOSITIONS FOR FACILITATING MEMBRANE FUSION AND USES THEREOF

(71) Applicant: FLAGSHIP PIONEERING INNOVATIONS V, INC., Cambridge, MA (US)

(72) Inventors: Geoffrey A. von Maltzahn, Somerville, MA (US); John Miles Milwid, Denver, CO (US); Michael Travis Mee, Montreal (CA); Jacob Rosenblum Rubens, Cambridge, MA (US); Nathan Wilson Stebbins, Cambridge, MA (US); Molly Krisann Gibson, Medford, MA (US); Neal Francis Gordon, Brookline, MA (US); Bo Zhang, Lynnfield, MA (US); Kyle Marvin Trudeau, Boston, MA (US); Brigham Jay Hartley, Long Island City, NY (US); Tamar Rose Putiri, Milton, MA (US); Kiana Mahdaviani, Chestnut Hill, MA (US); Matthew Milnes Dobbin, Medford, MA (US)

(73) Assignee: FLAGSHIP PIONEERING INNOVATIONS V, INC., Cambridge, MA (US)

( * ) Notice: Subject to any disclaimer, the term of this patent is extended or adjusted under 35 U.S.C. 154(b) by 421 days.

(21) Appl. No.: 16/611,768

(22) PCT Filed: May 8, 2018

(86) PCT No.: PCT/US2018/031515
§ 371 (c)(1),
(2) Date: Nov. 7, 2019

(87) PCT Pub. No.: WO2018/208728
PCT Pub. Date: Nov. 15, 2018

(65) Prior Publication Data
US 2020/0060980 A1 Feb. 27, 2020

Related U.S. Application Data

(60) Provisional application No. 62/595,862, filed on Dec. 7, 2017, provisional application No. 62/575,147, filed
(Continued)

(51) Int. Cl.
*A61K 9/50* (2006.01)
*A61K 9/127* (2006.01)
(Continued)

(52) U.S. Cl.
CPC .......... *A61K 9/5068* (2013.01); *A61K 9/1271* (2013.01); *A61K 9/1277* (2013.01);
(Continued)

(58) Field of Classification Search
CPC .. A61K 9/5068; A61K 9/1271; A61K 9/1277; A61K 38/177; A61K 38/45;
(Continued)

(56) References Cited

U.S. PATENT DOCUMENTS

| | | |
|---|---|---|
| 6,099,857 A | 8/2000 | Gross |
| 6,120,797 A | 9/2000 | Meers et al. |

(Continued)

FOREIGN PATENT DOCUMENTS

| | | |
|---|---|---|
| EP | 1 115 879 A1 | 7/2001 |
| EP | 1519714 A1 | 4/2005 |

(Continued)

OTHER PUBLICATIONS

"Cre Recombinase Gesicles Protocol-At-A-Glance" Clontech Laboratories, Inc. (2015) pp. 1-2.
(Continued)

*Primary Examiner* — Gollamudi S Kishore
(74) *Attorney, Agent, or Firm* — K&L Gates LLP

(57) ABSTRACT

In some aspects, fusosome compositions and methods are described herein that comprise membrane enclosed preparations, comprising a fusogen. In some embodiments, the
(Continued)

fusosome can the target cell, thereby delivering complex biologic agents to the target cell cytoplasm.

40 Claims, 63 Drawing Sheets

Specification includes a Sequence Listing.

Related U.S. Application Data on Oct. 20, 2017, provisional application No. 62/502,998, filed on May 8, 2017.

(51) Int. Cl.

| | | |
|---|---|---|
| A61K 38/17 | (2006.01) | |
| A61K 38/45 | (2006.01) | |
| A61K 48/00 | (2006.01) | |
| C12N 9/22 | (2006.01) | |
| C12N 15/11 | (2006.01) | |
| C12N 15/113 | (2010.01) | |
| C12N 15/88 | (2006.01) | |

(52) U.S. Cl.
CPC ............ *A61K 38/177* (2013.01); *A61K 38/45* (2013.01); *A61K 48/0008* (2013.01); *C12N 9/22* (2013.01); *C12N 15/11* (2013.01); *C12N 15/113* (2013.01); *C12N 15/88* (2013.01); *C12Y 207/07* (2013.01); C12N 2310/14 (2013.01); C12N 2310/141 (2013.01); C12N 2310/20 (2017.05); C12N 2320/32 (2013.01); C12N 2800/80 (2013.01)

(58) Field of Classification Search
CPC .... A61K 48/0008; A61K 35/12; A61K 35/28; A61K 9/127; A61K 38/00; C12N 9/22; C12N 15/11; C12N 15/113; C12N 15/88; C12N 2310/14; C12N 2310/141; C12N 2310/20; C12N 2320/32; C12N 2800/80; C12N 2760/20222; C12N 5/0012; C12Y 207/07

See application file for complete search history.

(56) References Cited

U.S. PATENT DOCUMENTS

| | | |
|---|---|---|
| 6,416,997 B1 | 7/2002 | Mir-Shekari et al. |
| 6,562,320 B1 | 5/2003 | Swaerd-Nordmo et al. |
| 6,693,086 B1 | 2/2004 | Dow et al. |
| 7,329,807 B2 | 2/2008 | Vadrucci et al. |
| 7,635,752 B2 | 12/2009 | Cattaneo et al. |
| 7,745,651 B2 | 6/2010 | Heyes et al. |
| 7,799,565 B2 | 9/2010 | MacLachlan et al. |
| 7,803,397 B2 | 9/2010 | Heyes et al. |
| 7,820,185 B2 | 10/2010 | Gorringe et al. |
| 7,838,658 B2 | 11/2010 | MacLachlan et al. |
| 7,842,673 B2 | 11/2010 | Brink et al. |
| 7,901,708 B2 | 3/2011 | MacLachlan et al. |
| 7,915,399 B2 | 3/2011 | MacLachlan et al. |
| 7,982,027 B2 | 7/2011 | MacLachlan et al. |
| 8,058,069 B2 | 11/2011 | Yaworski et al. |
| 8,101,741 B2 | 1/2012 | MacLachlan et al. |
| 8,188,263 B2 | 5/2012 | MacLachlan et al. |
| 8,236,943 B2 | 8/2012 | Lee et al. |
| 8,252,901 B2 | 8/2012 | Duncan |
| 8,283,333 B2 | 10/2012 | Yaworski et al. |
| 8,518,437 B2 | 8/2013 | Tardi et al. |
| 8,758,991 B2 | 6/2014 | Klein et al. |
| 9,050,251 B2 | 6/2015 | Boyden et al. |
| 9,060,926 B2 | 6/2015 | Boyden et al. |
| 9,066,866 B2 | 6/2015 | Ehringer et al. |
| 9,687,511 B2 | 6/2017 | Weston et al. |
| 9,695,446 B2 | 7/2017 | Mangeot et al. |
| 9,737,480 B2 | 8/2017 | Lu et al. |
| 9,816,080 B2 | 11/2017 | Lu et al. |
| 2001/0021526 A1 | 9/2001 | Davis et al. |
| 2003/0207445 A1 | 11/2003 | Schauber et al. |
| 2004/0009604 A1 | 1/2004 | Zhang et al. |
| 2004/0028687 A1 | 2/2004 | Waelti |
| 2005/0019836 A1 | 1/2005 | Vogel et al. |
| 2005/0064024 A1 | 3/2005 | Vadrucci et al. |
| 2006/0045910 A1 | 3/2006 | Ehringer |
| 2007/0224176 A1 | 9/2007 | Brink et al. |
| 2007/0298118 A1 | 12/2007 | Lotvall et al. |
| 2008/0014144 A1 | 1/2008 | Saltzman et al. |
| 2009/0202622 A1 | 8/2009 | Fleury et al. |
| 2010/0189662 A1 | 7/2010 | Neubourg |
| 2011/0003008 A1 | 1/2011 | Lim |
| 2012/0020878 A1 | 1/2012 | Qi |
| 2012/0177574 A1 | 7/2012 | Gho et al. |
| 2012/0322147 A1 | 12/2012 | Mangeot et al. |
| 2013/0273549 A1* | 10/2013 | Sullivan ................ C12Q 1/701 435/6.12 |
| 2014/0044647 A1 | 2/2014 | Gho et al. |
| 2014/0314831 A1 | 10/2014 | Duncan et al. |
| 2014/0348904 A1 | 11/2014 | Wood et al. |
| 2015/0125864 A1 | 5/2015 | Kang et al. |
| 2015/0157666 A1 | 6/2015 | Katakowski et al. |
| 2015/0290343 A1 | 10/2015 | Lotvall et al. |
| 2016/0136240 A1 | 5/2016 | Olson et al. |
| 2016/0137716 A1 | 5/2016 | El Andaloussi et al. |
| 2016/0168572 A1 | 6/2016 | Lotvall et al. |
| 2016/0256490 A1 | 9/2016 | Weston et al. |
| 2016/0354313 A1 | 12/2016 | De Beer |
| 2017/0020927 A1 | 1/2017 | Ganey et al. |
| 2017/0087087 A1 | 3/2017 | Leonard et al. |
| 2017/0112773 A1 | 4/2017 | Stachowiak et al. |
| 2017/0130197 A1 | 5/2017 | Haugwitz et al. |
| 2017/0165348 A1 | 6/2017 | Cantore et al. |
| 2017/0175086 A1 | 6/2017 | Schmitt et al. |
| 2018/0028600 A1 | 2/2018 | Hong et al. |

FOREIGN PATENT DOCUMENTS

| | | |
|---|---|---|
| EP | 1664316 A1 | 6/2006 |
| EP | 1766035 A1 | 3/2007 |
| EP | 1781593 A2 | 5/2007 |
| EP | 3 204 022 A1 | 8/2017 |
| WO | 1994/006920 A1 | 3/1994 |
| WO | 1997/012622 A1 | 4/1997 |
| WO | 1999/013905 A1 | 3/1999 |
| WO | 2001074861 A2 | 10/2001 |
| WO | 2002/044206 A2 | 6/2002 |
| WO | 2004002453 A1 | 1/2004 |
| WO | 2004087748 A1 | 10/2004 |
| WO | 2005026372 A1 | 3/2005 |
| WO | 2005020152 A2 | 12/2005 |
| WO | 2005121348 A1 | 12/2005 |
| WO | 2006/028786 A2 | 3/2006 |
| WO | 2006027202 A1 | 3/2006 |
| WO | 2006/059141 A2 | 6/2006 |
| WO | 2007/000668 A2 | 1/2007 |
| WO | 2008071959 A1 | 6/2008 |
| WO | 2008115199 A2 | 9/2008 |
| WO | 2009/010719 A1 | 1/2009 |
| WO | 2009130208 A1 | 10/2009 |
| WO | 2010/055413 A1 | 5/2010 |
| WO | 2011/011584 A1 | 1/2011 |
| WO | 2011/024172 A2 | 3/2011 |
| WO | 2011/058052 A1 | 5/2011 |
| WO | 2012/149376 A2 | 11/2012 |
| WO | 2013084000 A2 | 6/2013 |
| WO | 2014/063757 A1 | 5/2014 |
| WO | 2014/076137 A1 | 5/2014 |
| WO | 2014/210448 A1 | 12/2014 |
| WO | 2015011478 A1 | 1/2015 |
| WO | 2015/110957 A2 | 7/2015 |
| WO | 2016/009326 A1 | 1/2016 |
| WO | 2016057755 A1 | 4/2016 |
| WO | 2016/077639 A2 | 5/2016 |
| WO | 2016/138525 A1 | 9/2016 |

(56) References Cited

FOREIGN PATENT DOCUMENTS

| WO | 2016183482 A1 | 11/2016 |
|---|---|---|
| WO | 2017/095940 A1 | 6/2017 |
| WO | 2017/095944 A1 | 6/2017 |
| WO | 2017095946 A1 | 6/2017 |
| WO | 2017/117585 A1 | 7/2017 |
| WO | 2017/122095 A1 | 7/2017 |
| WO | 2017/161010 A1 | 9/2017 |
| WO | 2017151717 A1 | 9/2017 |
| WO | 2017/182585 A1 | 10/2017 |
| WO | 2017/211945 A1 | 12/2017 |
| WO | 2018009923 A1 | 1/2018 |
| WO | 2018022749 A1 | 2/2018 |
| WO | 2018208728 A1 | 11/2018 |
| WO | 2019/152692 A1 | 8/2019 |
| WO | 2019/222403 A2 | 11/2019 |

OTHER PUBLICATIONS

Abel et al., "Specific gene delivery to liver sinusoidal and artery endothelial cells," Blood (2013) 122(12):2030-38.

Alvarez-Erviti et al., "Delivery of siRNA to the mouse brain by systemic injection of targeted exosomes." Nature Biotechnology (2011) 29(4): 341-345.

Ammayappan et al., "Characteristics of Oncolytic Vesicular Stomatitis Virus Displaying Tumor-Targeting Ligands," J. Virol. (2013) 87 (24) 13543-13555.

Brown et al., "Endogenous microRNA regulation suppresses transgene expression in hematopoietic lineages and enables stable gene transfer," Nat. Med. (2006) 12(5):585-91.

Burns et al., "Vesicular stomatitis virus G glycoprotein pseudotyped retroviral vectors: concentration to very high titer and efficient gene transfer into mammalian and nonmammalian cells," Proc. Natl. Acad. Sci. USA (1993) 90 (17):8033-37.

Chiriaco et al., "Dual-regulated lentiviral vector for gene therapy of X linked chronic granulomatosis." Molecular Therapy (2014) 22(8): 1472-1483.

Dull et al., "A third-generation lentivirus vector with a conditional packaging system," J. Virol. (1998) 72(11):8463-71.

Enkirch et al., "Targeted lentiviral vectors pseudotyped with the Tupaia paramyxovirus glycoproteins," Gene Ther. (2013) 20:16-23.

Field et al., "Comparison of Lentiviral and Sleeping Beauty Mediated T Cell Receptor Gene Transfer", PLOS ONE (2013) 8(6):e68201.

Friedrich et al., "DARPin-targeting of Measles Virus: Unique Bispecificity, Effective Oncolysis, and Enhanced Safety," Mol. Ther. (2013) 21(4): 849-85.

Funke et al., "Targeted cell entry of lentiviral vectors," Mol. Ther. (2008) 16(8):1427-3.

Gollan et al., "Redirecting Retroviral Tropism by Insertion of Short, Nondisruptive Peptide Ligands into Envelope," J. Virol. (2002) 76(7): 3558-3563.

Haga et al., "Permanent, lowered HLA class I expression using lentivirus vectors with shRNA constructs: averting cytotoxicity by alloreactive T lymphocytes." Transplantation Proceedings (2006) 38(10):3184-3188.

Hiratsuka et al. ""Retargeting of microcell fusion towards recipient cell-oriented transfer of human artificial chromosome" BMC Biotechnology (2015) vol. 15, No. 58, pp. 1-8".

International Search Report and Written Opinion for International Application No. PCT/US2018/031515 dated Aug. 30, 2018.

Khetawat et a., "A Functional Henipavirus Envelope Glycoprotein Pseudotyped Lentivirus Assay System," Virol. J. (2010) 7:312.

Kuo et al., "Retargeting of Coronavirus by Substitution of the Spike Glycoprotein Ectodomain: Crossing the Host Cell Species Barrier," J. Virol (2000) 74(3):1393-1406.

Lin et al. "Incorporation of VSV-G produces fusogenic plasma membrane vesicles capable of efficient transfer of bioactive macromolecules and mitochondria" Biomed Microdevices (2016) vol. 18, No. 41, pp. 1-11.

Long et al. "Targeted Cell Fusion Facilitates Stable Heterokaryon Generation In Vitro and In Vivo" Plos ONE (2011) vol. 6, No. 10, e26381, pp. 1-9.

Menotti et al., "Construction of a fully retargeted herpes simplex virus 1 recombinant capable of entering cells solely via human epidermal growth factor receptor 2," J. Virol. (2008) 82(2): 10153-61.

Milani et al., "Phagocytosis-shielded lentiviral vectors improve liver gene therapy in nonhuman primates" Science Translational Medicine (2019) vol. 11, No. 7325, pp. 1-13.

Milani et al., "Genome editing for scalable production of alloantigen free lentiviral vectors for in vivo gene therapy." EMBO Molecular Medicine (2017) 9(11): 1558-1573.

Nakamura et al., "Antibody-targeted cell fusion," Nat. Biotechnol. (2004) 22(3):331-6.

Naldini et al., "In vivo gene delivery and stable transduction of nondividing cells by a lentiviral vector," Science (1996) 272(5259):263-7.

Nordlund et al., "SNARE-fusion mediated insertion of membrane proteins into native and artificial membranes," Nature Comm. (2014) 5(1):4303.

Pichard et al., Specific Micro-RNA regulated TetR-KRAB Transcriptional control of transgene expression in viral vector transduced cells.: PLOS ONE (2012) 7(12):e51952.

Schauber-Plewa et al., "Complement regulatory proteins are incorporated into lentiviral vectors and protect particles against complement inactivation." Gene Therapy. (2004) 12(3): 238-245.

Sosale et al., :Marker of self: CD47 on lentiviral vectors decreases macrophage-mediated clearance and increases delivery to SIRPA-expressing lung carcinoma tumors. Molecular Therapy (2016) 3(7): 16080.

Sugimoto et al. ""A novel human endogenous retroviral protein inhibits cell-cell fusion"" Nature Scientific Reports (2013) vol. 3, No. 1462, pp. 1-8.

Tang et al, "Therapeutic potential of CAR-T cell-derived exosomes: a cell-free modality for targeted cancer therapy", Oncotarget (2015) 6(42):44179-90.

Tomas et al., "Improved GaLV-TR glycoproteins to pseudotype lentiviral vectors: impact of viral protease activity in the production of LV pseudotypes" Molecular Therapy (2019) 15: 1-8.

Witting et al., "Characterization of a third generation lentiviral vector pseudotyped with Nipah virus envelope proteins for endothelial cell transduction" Gene therapy (2013) 20(10): 997-1005.

Yang et al., "Virus Mimetic Fusogenic Exosomes for Direct Delivery of Integral Membrane Proteins to Target Cell Membranes," Advanced Materials (2017) 29(13): 1605604.

Zakaria et al., "Combination of hepatocyte specific delivery and transformation dependent expression of shRNA inducing transcriptional gene silencing of c-Myc promoter in hepatocellular carcinoma cells", BMC Cancer, Biomed Central, London (2014) 14(1): 582.

Zufferey et al., "Multiply attenuated lentiviral vector achieves efficient gene delivery in vivo," Nat. Biotech. (1997) 15(9):871-5.

Ahmad et al. "Miro1 regulates intercellular mitochondrial transport & enhances mesenchymal stem cell rescue efficacy" EMBO Journal (2014) vol. 33 No. 9, pp. 994-1010.

Alfonzo et al. "Mitochondrial tRNA import-the challenge to understand has just begun" Biological Chemistry (2009) vol. 390, pp. 717-722.

Augustin et al. "Characterization of peptides released from mitochondria: evidence for constant proteolysis and peptide efflux" J Biol Chem (2005) vol. 280, No. 4, pp. 2691-2699.

Bayona-Bafaluy et al., "A chemical enucleation method for the transfer of mitochondrial DNA to ρ° cells" Nucleic Acids Res. (2003) vol. 31, No. 16, e98, pp. 1-4.

Bershteyn et al., "Polymer-supported lipid shells, onions, and flowers" Soft Matter (2008) vol. 4 pp. 1787-1787.

Bouma et al. "Determination of cytotoxic T-lymphocyte precursor frequencies using europium labeling as a nonradioactive alternative to labeling with chromium-51" Hum. Immunol. (1992) vol. 35 No. 2, pp. 85-92.

(56) References Cited

OTHER PUBLICATIONS

Bratosin et al., "Novel fluorescence assay using calcein-AM for the determination of human erythrocyte viability and aging" Cytometry (2005) vol. 66, No. 1, pp. 78-84.
Calvo et al. "MitoCarta2.0: an updated inventory of mammalian mitochondrial proteins" Nucleic Acid Res. (2016) vol. 44, Database Issue, pp. D1251-D1257.
Cameron et al. "Development of Therapeutics That Induce Mitochondrial Biogenesis for the Treatment of Acute and Chronic Degenerative Diseases" J Med Chem (2016) vol. 59, No. 23, pp. 10411-10434.
Chen et al. "Real-time quantification of microRNAs by stem-loop RT-PCR" Nucleic Acid Res. (2005) vol. 33, No. 20, e179, pp. 1-9.
Chen et al. "Sustained high level transgene expression in mammalian cells mediated by the optimized piggyBac transposon system" Genes Dis. (2015) vol. 2, No. 1, pp. 96-105.
Conner "Mouse Embryo Fibroblast (MEF) Feeder Cell Preparation" Current Protocols in Molecular Biology (2001) VOL/Pages Needed.
Crop et al. ""Human Mesenchymal Stem Cells Are Susceptibleto Lysis by CD8+ T Cells and NK Cells" Cell Transplantation (2011) vol. 20, pp. 1547-1559".
Deleavey et al., "Designing Chemically Modified Oligonucleotides for Targeted Gene Silencing" Chemistry & Biology (2012) vol. 19, No. 8, pp. 937-954.
Didiot et al., "Exosome-mediated Delivery of Hydrophobically Modified siRNA for Huntingtin mRNA Silencing" Molecular Therapy (2016) vol. 24, No. 10, pp. 1836-1847.
"Ejsing et al. ""Global analysis of the yeast lipidome by quantitativeshotgun mass spectrometry"" PNAS (2009) vol. 106, No. 7, pp. 2136-2141".
El-Amouri et al., "Secreted Luciferase for In Vivo Evaluation of Systemic Protein Delivery in Mice" Molecular Biotechnology (2013) vol. 53, No. 1, pp. 63-73.
Ellman et al., "A new and rapid colorimetric determination of acetylcholinesterase activity" Biochem. Pharmacol. (1961) vol. 7, pp. 88-90.
Galic et al. "Coordinated regulation of insulin signaling by the protein tyrosine phosphatases PTP1B and TCPTP" Molecular Cell Biology (2005) vol. 25, No. 2, pp. 819-829.
Gendelman et al. "Monocyte Chemotactic Protein-1 Regulates Voltage-Gated K+ Channels and Macrophage Transmigration" Journal of Neuroimmune Pharmacology (2009) vol. 4, No. 1, pp. 47-59.
Geng et al. "Microfluidic Electroporation for Cellular Analysis and Delivery" Lab Chip (2013) vol. 13, No. 19, pp. 3803-3821.
Green et al. "Metabolic, enzymatic, and transporter responses in human muscle during three consecutive days of exercise and recovery" Am J Physiol Regul Integr Comp Physiol (2008) vol. 295, No. 4, pp. R1238-R1250.
Herzog et al. "A novel informatics concept for high-throughput shotgun lipidomics based on the molecular fragmentation query language" Genome Biol. (2011) vol. 12, No. 1, R8, pp. 1-25.
Herzog et al. "LipidXplorer: A Software for Consensual Cross-Platform Lipidomics" PLOS One (2012) vol. 7, No. 1, e29851, pp. 1-7.
Hock et al. "Transcriptional Control of Mitochondrial Biogenesis and Function" Annu. Rev. Physiol. (2009) vol. 71, pp. 177-203.
Jacob et al. "Membrane cell permeabilisation with saponin and multiparametric analysis by flow cytometry" Cytometry (1991) vol. 12, No. 6, pp. 550-558.
Jeon et al. "In Vitro Model of Tumor Cell Extravasation" PLOS ONE (2013) vol. 8, No. 2, e56910, pp. 1-9.
"Kainu et al. ""Introduction of phospholipids to cultured cellswith cyclodextrin"" Journal of Lipid Research (2010) vol. 51, pp. 3533-3541".
Kamerkar et al. "Exosomes Facilitate Therapeutic Targeting of Oncogenic Kras in Pancreatic Cancer" Nature (2017) vol. 546, No. 7659, pp. 498-503.
Kanabus et al. "The pleiotropic effects of decanoic acid treatment on mitochondrial function in fibroblasts from patients with complex I deficient Leigh syndrome" J Inherit Metab Dis (2016) vol. 39, No. 3, pp. 415-426.
Kanada et al. "Differential fates of biomolecules delivered to target cells via extracellular vesicles" PNAS (2015) vol. 112, No. 12, pp. E1433-E1442.
Kaneda "New Vector Innovation for Drug Delivery: Development of Fusigenic Non-Viral Particles" Current Drug Targets (2003) vol. 4, No. 8, pp. 599-602.
Katoh et al. "Research article Exploitation of the interaction of measles virus fusogenic envelope proteins with the surface receptor CD46 on human cells for microcell-mediated chromosome transfer" BMC Biotechnology (2010) vol. 10, No. 37, pp. 1-11.
Kozlov et al. "Membrane tension and membrane fusion" Curr Opin Struct Biol (2015) vol. 33, pp. 61-67.
Lamichhane et al. "Oncogene Knockdown via Active Loading of Small RNAs into Extracellular Vesicles by Sonication" Cell Mol Bioeng (2016) vol. 9, No. 3, pp. 315-324.
Tsai et al, "Encapsulation of active cytoskeletal protein networks in cell-sized liposomes" Langmuir (2011) vol. 27, No. 16, pp. 10061-10071.
Lee et al. "A comparative study on the efficiency of two enucleation methods in pig somatic cell nuclear transfer: effects of the squeezing and the aspiration methods." Anim Biotechnol. (2008) vol. 19, No. 2, pp. 71-79.
Liang et al. "Rapid and highly efficient mammalian cell engineering viaCas9 protein transfection" Journal of Biotechnology (2015) vol. 208, pp. 44-53.
Mangeot et al. "Protein Transfer Into Human Cells by VSV-G-induced Nanovesicles" Mol Ther (2011) vol. 19, No. 9, pp. 1656-1666.
Soubannier et al. "A Vesicular Transport Pathway Shuttles Cargo from mitochondria to lysosomes" Current Biology (2012) vol. 22, pp. 135-141.
Millay et al. "Myomaker: A membrane activator of myoblast fusion and muscle formation" Nature (2013) vol. 499, No. 7458, pp. 301-305.
Novobrantseva et al. "Systemic RNAi-mediated Gene Silencing in Nonhuman Primate and Rodent Myeloid Cells" Mol Ther Nucleic Acids (2012) vol. 1, No. 1, e 4, pp. 1013.
Orive et al. "Cell encapsulation: technical and clinical advances" Trends in Pharmacology Sciences (2015) vol. 36, No. 8, pp. 537-546.
Plant et al. "Notexin causes greater myotoxic damage and slower functional repair in mouse skeletal muscles than bupivacaine" Muscle Nerve (2006) vol. 54, No. 5, pp. 577-585.
Quinn et al. "Myomerger induces fusion of non-fusogenic cells and is required for skeletal muscle development" Nature Communications (2017) vol. 8, No. 15665, pp. 1-9.
Quiros et al. "New roles for mitochondrial proteases in health, ageing and disease" Nature Reviews Molecular Cell Biology (2015) vol. 16, pp. 345-359.
Riedel et al. "Cell surface expression of fusogenic vesicular stomatitis virus G protein from cloned cDNA" The EMBO Journal (1984) vol. 3, No. 7, pp. 1477-1483.
Rosner et al. "Merging high-quality biochemical fractionation with a refined flow cytometry approach to monitor nucleocytoplasmic protein expression throughout the unperturbed mammalian cell cycle" Nature Protocols (2013) vol. 8, pp. 602-626.
Salic et al. "A chemical method for fast and sensitive detection of DNA synthesis in vivo" PNAS (2008) vol. 105, No. 7, pp. 2415-2420.
Sampaio et al. "Membrane lipidome of an epithelial cell line" PNAS (2011) vol. 108, No. 5, pp. 1903-1907.
Sanges et al. "Reprogramming Müller glia via in vivo cell fusion regenerates murine photoreceptors" Journal of Clinical Investigation (2016) vol. 126, No. 8, pp. 3104-3116.
Santra et al. "Ketogenic Treatment Reduces Deleted Mitochondrial DNAs in Cultured Human Cells" Ann Neurol. (2004) vol. 56, No. 5, pp. 662-669.

(56) References Cited

OTHER PUBLICATIONS

Scarpulla et al. "Transcriptional integration of mitochondrial biogenesis" Trends in Endocrinology & Metabolism (2012) vol. 23, Np 9, pp. 459-466.
Scourfield et al. "Growing functions of the ESCRT machinery in cell biology and viral replication" Biochemical Society Transactions (2017) vol. 45, No. 3, pp. 613-634.
Sezgin et al. "Elucidating membrane structure and protein behavior using giant membrane plasma vesicles" Nature Protocols (2012) vol. 7, No. 6, pp. 1042-1051.
Sharei et al. "A vector-free microfluidic platform for intracellular delivery" PNAS (2013) vol. 110, No. 6, pp. 2082-2087.

* cited by examiner

| Nanosight NS300 Conditions | | Nanosight NS300 Settings | |
|---|---|---|---|
| Temperature/C | 24.089 | Detection Threshold | 17 |
| Viscosity/cP | 0.907452 | Max Jump Mode | Auto |
| Camera Type | sCMOS | Max Jump Distance | 24.9209 |
| Laser Type | Green | Blur | Auto |
| Camera Level | 15 | Min Track Length | Auto |
| Slider shutter | 1206 | First frame | 0 |
| Slider Gain | 366 | Total frames analysed | 1498 |
| Shutter/ms | 30.15 | | |
| Camera Histogram Upper Limit | 3294 | | |
| Camera Histogram Lower Limit | 0 | | |
| Frame rate/fps | 24.9825 | | |
| Syringe Pump Speed/AU | 50 | | |

Fig. 17A

| Confocal Microscope Settings | |
|---|---|
| Objective | 63X |
| Excitation (nm) | 488 |
| Emission (nm) | 556 |

Fig. 17B

|                        | Fusosomes | Parental Cells |
|------------------------|-----------|----------------|
| Average diameter (nm)  | 128.7     | 175.4          |
| Average volume ($\mu m^3$) | 0.067 | 7.421          |

Fig.17D

|  | Fusosomes | Parental Cells |
|---|---|---|
| Average diameter (nm) | 128.7 | 175.4 |
| Min Diameter (nm) | 14 | 29 |
| Max Diameter (nm) | 18720 | 19802 |
| Median Diameter (nm) | 134 | 99 |
| 10% Quantile (nm) | 53 | 52 |
| 25% Quantile (nm) | 88 | 66 |
| 75% Quantile (nm) | 226 | 241 |
| 90% Quantile (nm) | 4450 | 10649 |
| Average volume ($\mu m^3$) | 0.067 | 7.421 |

Fig. 18

|  | Fusosomes | Parental Cells |
|---|---|---|
| Average diameter (nm) | 128.7 | 175.4 |
| Average volume ($\mu m^3$) | 0.067 | 7.421 |

Fig. 19

| Group | % RFP conversion (± SD) |
|---|---|
| Recipient + no fusosome | 0.4 ± 0.2% |
| Recipient + NivG+F fusosome | 88.9 ± 3.4% |
| Recipient + NivG+F fusosome + Baf | 68.1 ± 2.7% |

Fig. 29

| Group | % RFP conversion (± SD) |
|---|---|
| Recipient + no fusosome | 0.6 ± 0.2% |
| Recipient + VSV-G fusosome | 53.2 ± 0.7% |
| Recipient + VSV-G fusosome + Baf | 2.3 ± 1.2% | ns

SEQUENCE LISTING

```
<160> NUMBER OF SEQ ID NOS: 13

<210> SEQ ID NO 1
<211> LENGTH: 5
<212> TYPE: PRT
<213> ORGANISM: Unknown
<220> FEATURE:
<221> NAME/KEY: source
<223> OTHER INFORMATION: /note="Description of Unknown:
      Caspase 2 sequence"

<400> SEQUENCE: 1

Val Asp Val Ala Asp
1               5

<210> SEQ ID NO 2
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Pro Ser Ala Pro
1

<210> SEQ ID NO 3
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Pro Thr Ala Pro
1

<210> SEQ ID NO 4
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 4
ggagtccact ggcgtcttca c                                              21
```

-continued

```
<210> SEQ ID NO 5
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 5
gaggcattgc tgatgatctt gagg                                          24

<210> SEQ ID NO 6
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 6
atgagtaaag gagaagaact tttcac                                        26

<210> SEQ ID NO 7
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 7
gtccttttac cagacaacca ttac                                          24

<210> SEQ ID NO 8
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 8
gacguaaacg gccacaaguu c                                             21

<210> SEQ ID NO 9
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 9
cuuacgcuga guacuucgat t                                             21

<210> SEQ ID NO 10
<211> LENGTH: 20
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 10
gaagttcgag ggcgacaccc                                              20

<210> SEQ ID NO 11
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 11
gcactaccag agctaactca                                              20

<210> SEQ ID NO 12
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 12
acuuguggcc guuuacgucg c                                            21

<210> SEQ ID NO 13
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 13
ucgaaguacu cagcguaagt t                                            21
```

COMPOSITIONS FOR FACILITATING MEMBRANE FUSION AND USES THEREOF

RELATED APPLICATIONS

This application is a U.S. National Stage Application under 35 U.S.C. § 371 of International Application No. PCT/US2018/031515, filed May 8, 2018, which claims priority to U.S. Ser. No. 62/502,998 filed May 8, 2017, U.S. Ser. No. 62/575,147 filed Oct. 20, 2017, and U.S. Ser. No. 62/595,862 filed Dec. 7, 2017, each of which is incorporated herein by reference in its entirety.

BACKGROUND

Complex biologics are promising therapeutic candidiates for a variety of diseases. However, it is difficult to deliver large biologic agents into a cell because the plasma membrane acts as a barrier between the cell and the extracellular space. There is a need in the art for new methods of delivering complex biologics into cells in a subject.

SUMMARY OF THE INVENTION

Membrane fusion is required in biological processes as diverse as fertilization, development, immune response and tumorigenesis. The present disclosure provides fusion-based methods of delivering complex biologic cargo to cells.

Thus, the present disclosure provides, in some aspects, a fusosome comprising a lipid bilayer, a lumen surrounded by the lipid bilayer, and a fusogen. The fusosome can be used, e.g., for delivery of a cargo in the lumen or lipid bilayer to a target cell. Cargo includes, e.g., therapeutic proteins, nucleic acids, and small molecules.

The present disclosure provides, in some aspects, a fusosome comprising:
 (a) a lipid bilayer,
 (b) a lumen (e.g., comprising cytosol) surrounded by the lipid bilayer;
 (c) an exogenous or overexpressed fusogen, e.g., wherein the fusogen is disposed in the lipid bilayer,
 wherein the fusosome is derived from a source cell; and
 wherein the fusosome has partial or complete nuclear inactivation (e.g., nuclear removal).

In some embodiments, one or more of the following is present:
 i) the fusosome comprises or is comprised by a cytobiologic;
 ii) the fusosome comprises an enucleated cell;
 iii) the fusosome comprises an inactivated nucleus;
 iv) the fusosome fuses at a higher rate with a target cell than with a non-target cell, e.g., by at least at least 1%, 2%, 3%, 4%, 5%, 10%, 20%, 30%, 40%, 50%, 60%, 70%, 80%, 90%, 2-fold, 3-fold, 4-fold, 5-fold, 10-fold, 20-fold, 50-fold, or 100-fold, e.g., in an assay of Example 54;
 v) the fusosome fuses at a higher rate with a target cell than with other fusosomes, e.g., by at least 10%, 20%, 30%, 40%, 50%, 60%, 70%, 80%, or 90%, 2-fold, 3-fold, 4-fold, 5-fold, 10-fold, 20-fold, 50-fold, or 100-fold, e.g., in an assay of Example 54;
 vi) the fusosome fuses with target cells at a rate such that an agent in the fusosome is delivered to at least 10%, 20%, 30%, 40%, 50%, 60%, 70%, 80%, or 90% of target cells after 24, 48, or 72 hours, e.g., in an assay of Example 54;
 vii) the fusogen is present at a copy number of at least, or no more than, 10, 50, 100, 500, 1,000, 2,000, 5,000, 10,000, 20,000, 50,000, 100,000, 200,000, 500,000, 1,000,000, 5,000,000, 10,000,000, 50,000,000, 100,000,000, 500,000,000, or 1,000,000,000 copies, e.g., as measured by an assay of Example 29;
 viii) the fusosome comprises a therapeutic agent at a copy number of at least, or no more than, 10, 50, 100, 500, 1,000, 2,000, 5,000, 10,000, 20,000, 50,000, 100,000, 200,000, 500,000, 1,000,000, 5,000,000, 10,000,000, 50,000,000, 100,000,000, 500,000,000, or 1,000,000,000 copies, e.g., as measured by an assay of Example 43 or 156;
 ix) the ratio of the copy number of the fusogen to the copy number of the therapeutic agent is between 1,000,000:1 and 100,000:1, 100,000:1 and 10,000:1, 10,000:1 and 1,000:1, 1,000:1 and 100:1, 100:1 and 50:1, 50:1 and 20:1, 20:1 and 10:1, 10:1 and 5:1, 5:1 and 2:1, 2:1 and 1:1, 1:1 and 1:2, 1:2 and 1:5, 1:5 and 1:10, 1:10 and 1:20, 1:20 and 1:50, 1:50 and 1:100, 1:100 and 1:1,000, 1:1,000 and 1:10,000, 1:10,000 and 1:100,000, or 1:100,000 and 1:1,000,000;
 x) the fusosome comprises a lipid composition substantially similar to that of the source cell or wherein one or more of CL, Cer, DAG, HexCer, LPA, LPC, LPE, LPG, LPI, LPS, PA, PC, PE, PG, PI, PS, CE, SM and TAG is within 10%, 15%, 20%, 25%, 30%, 35%, 40%, 45%, 50%, 55%, 60%, 65%, 70%, or 75% of the corresponding lipid level in the source cell;
 xi) the fusosome comprises a proteomic composition similar to that of the source cell, e.g., using an assay of Example 42 or 155;
 xii) the fusosome comprises a ratio of lipids to proteins that is within 10%, 20%, 30%, 40%, or 50% of the corresponding ratio in the source cell, e.g., as measured using an assay of Example 49;
 xiii) the fusosome comprises a ratio of proteins to nucleic acids (e.g., DNA) that is within 10%, 20%, 30%, 40%, or 50% of the corresponding ratio in the source cell, e.g., as measured using an assay of Example 50;
 xiv) the fusosome comprises a ratio of lipids to nucleic acids (e.g., DNA) that is within 10%, 20%, 30%, 40%, or 50% of the corresponding ratio in the source cell, e.g., as measured using an assay of Example 51 or 159;
 xv) the fusosome has a half-life in a subject, e.g., in a mouse, that is within 1%, 2%, 3%, 4%, 5%, 10%, 20%, 30%, 40%, 50%, 60%, 70%, 80%, 90%, 100% of the half life of a reference cell, e.g., the source cell, e.g., by an assay of Example 75;
 xvi) the fusosome transports glucose (e.g., labeled glucose, e.g., 2-NBDG) across a membrane, e.g., by at least 1%, 2%, 3%, 4%, 5%, 10%, 20%, 30%, 40%, 50%, 60%, 70%, 80%, 90%, 100% more (e.g., about 11.6% more) than a negative control, e.g., an otherwise similar fusosome in the absence of glucose, e.g., as measured using an assay of Example 64;
 xvii) the fusosome comprises esterase activity in the lumen that is within 1%, 2%, 3%, 4%, 5%, 10%, 20%, 30%, 40%, 50%, 60%, 70%, 80%, 90%, or 100% of that of the esterase activity in a reference cell, e.g., the source cell or a mouse embryonic fibroblast, e.g., using an assay of Example 66;
 xviii) the fusosome comprises a metabolic activity level that is within 1%, 2%, 3%, 4%, 5%, 10%, 20%, 30%, 40%, 50%, 60%, 70%, 80%, 90%, or 100% of the citrate synthase activity in a reference cell, e.g., the source cell, e.g., as described in Example 68;

xix) the fusosome comprises a respiration level (e.g., oxygen consumption rate) that is within 1%, 2%, 3%, 4%, 5%, 10%, 20%, 30%, 40%, 50%, 60%, 70%, 80%, 90%, or 100% of the respiration level in a reference cell, e.g., the source cell, e.g., as described in Example 69;

xx) the fusosome comprises an Annexin-V staining level of at most 18,000, 17,000, 16,000, 15,000, 14,000, 13,000, 12,000, 11,000, or 10,000 MFI, e.g., using an assay of Example 70, or wherein the fusosome comprises an Annexin-V staining level at least 5%, 10%, 20%, 30%, 40%, or 50% lower than the Annexin-V staining level of an otherwise similar fusosome treated with menadione in the assay of Example 70, or wherein the fusosome comprises an Annexin-V staining level at least 5%, 10%, 20%, 30%, 40%, or 50% lower than the Annexin-V staining level of a macrophage treated with menadione in the assay of Example 70, xxi) the fusosome has a miRNA content level of at least at least 1%, 2%, 3%, 4%, 5%, 10%, 20%, 30%, 40%, 50%, 60%, 70%, 80%, 90%, or greater than that of the source cell, e.g., by an assay of Example 39;

xxii) the fusosome has a soluble: non-soluble protein ratio is within 1%, 2%, 3%, 4%, 5%, 10%, 20%, 30%, 40%, 50%, 60%, 70%, 80%, 90%, or greater than that of the source cell, e.g., within 1%-2%, 2%-3%, 3%-4%, 4%-5%, 5%-10%, 10%-20%, 20%-30%, 30%-40%, 40%-50%, 50%-60%, 60%-70%, 70%-80%, or 80%-90% of that of the source cell, e.g., by an assay of Example 47;

xxiii) the fusosome has an LPS level less than 5%, 1%, 0.5%, 0.01%, 0.005%, 0.0001%, 0.00001% or less of the LPS content of the source cell, e.g., as measured by mass spectrometry, e.g., in an assay of Example 48;

xxiv) the fusosome is capable of signal transduction, e.g., transmitting an extracellular signal, e.g., AKT phosphorylation in response to insulin, or glucose (e.g., labeled glucose, e.g., 2-NBDG) uptake in response to insulin, e.g., by at least 1%, 2%, 3%, 4%, 5%, 10%, 20%, 30%, 40%, 50%, 60%, 70%, 80%, 90%, 100% more than a negative control, e.g., an otherwise similar fusosome in the absence of insulin, e.g., using an assay of Example 63;

xxv) the fusosome targets a tissue, e.g., liver, lungs, heart, spleen, pancreas, gastrointestinal tract, kidney, testes, ovaries, brain, reproductive organs, central nervous system, peripheral nervous system, skeletal muscle, endothelium, inner ear, or eye, when administered to a subject, e.g., a mouse, e.g., wherein at least 0.1%, 0.5%, 1%, 1.5%, 2%, 2.5%, 3%, 4%, 5%, 10%, 20%, 30%, 40%, 50%, 60%, 70%, 80%, or 90% of the fusosomes in a population of administered fusosomes are present in the target tissue after 24, 48, or 72 hours, e.g., by an assay of Example 87 or 100;

xxvi) the fusosome has juxtacrine-signaling level of at least 1%, 2%, 3%, 4%, 5%, 10%, 20%, 30%, 40%, 50%, 60%, 70%, 80%, 90%, or 100% greater than the level of juxtacrine signaling induced by a reference cell, e.g., the source cell or a bone marrow stromal cell (BMSC), e.g., by an assay of Example 71;

xxvii) the fusosome has paracrine-signaling level of at least 1%, 2%, 3%, 4%, 5%, 10%, 20%, 30%, 40%, 50%, 60%, 70%, 80%, 90%, 100% greater than the level of paracrine signaling induced by a reference cell, e.g., the source cell or a macrophage, e.g., by an assay of Example 72;

xxviii) the fusosome polymerizes actin at a level within 1%, 2%, 3%, 4%, 5%, 10%, 20%, 30%, 40%, 50%, 60%, 70%, 80%, 90%, or 100% compared to the level of polymerized actin in a reference cell, e.g., the source cell or a C2Cl2 cell, e.g., by the assay of Example 73;

xxix) the fusosome has a membrane potential within about 1%, 2%, 3%, 4%, 5%, 10%, 20%, 30%, 40%, 50%, 60%, 70%, 80%, 90%, 100% of the membrane potential of a reference cell, e.g., the source cell or a C2Cl2 cell, e.g., by an assay of Example 74, or wherein the fusosome has a membrane potential of about −20 to −150 mV, −20 to −50 mV, −50 to −100 mV, or −100 to −150 mV;

xxx) the fusosome is capable of extravasation from blood vessels, e.g., at a rate at least 1%, 2%, 5%, 10%, 20%, 30%, 40%, 50%, 60%, 70%, 80%, or 90% the rate of extravasation of the source cell or of a cell of the same type as the source cell, e.g., using an assay of Example 57, e.g., wherein the source cell is a neutrophil, lymphocyte, B cell, macrophage, or NK cell;

xxxi) the fusosome is capable of crossing a cell membrane, e.g., an endothelial cell membrane or the blood brain barrier;

xxxii) the fusosome is capable of secreting a protein, e.g., at a rate at least 1%, 2%, 3%, 4%, 5%, 10%, 20%, 30%, 40%, 50%, 60%, 70%, 80%, 90%, or 100% greater than a reference cell, e.g., a mouse embryonic fibroblast, e.g., using an assay of Example 62;

xxxiii) the fusosome meets a pharmaceutical or good manufacturing practices (GMP) standard;

xxxiv) the fusosome was made according to good manufacturing practices (GMP);

xxxv) the fusosome has a pathogen level below a predetermined reference value, e.g., is substantially free of pathogens;

xxxvi) the fusosome has a contaminant level below a predetermined reference value, e.g., is substantially free of contaminants;

xxxvii) the fusosome has low immunogenicity, e.g., as described herein;

xxxviii) the source cell is selected from a neutrophil, a granulocyte, a mesenchymal stem cell, a bone marrow stem cell, an induced pluripotent stem cell, an embryonic stem cell, a myeloblast, a myoblast, a hepatocyte, or a neuron e.g., retinal neuronal cell; or xxxix) the source cell is other than a 293 cell, HEK cell, human endothelial cell, or a human epithelial cell, monocyte, macrophage, dendritic cell, or stem cell.

The present disclosure also provides, in some aspects, a fusosome comprising:

a) a lipid bilayer and a lumen that is miscible with an aqueous solution, e.g., water, wherein the fusosome is derived from a source cell, b) an exogenous or overexpressed fusogen disposed in the lipid bilayer, and c) an organelle, e.g., a therapeutically effective number of organelles, disposed in the lumen.

In some embodiments, one or more of the following is present:

i) the source cell is selected from an endothelial cell, a macrophage, a neutrophil, a granulocyte, a leukocyte, a stem cell (e.g., a mesenchymal stem cell, a bone marrow stem cell, an induced pluripotent stem cell, an embryonic stem cell), a myeloblast, a myoblast, a hepatocyte, or a neuron e.g., retinal neuronal cell;

ii) the organelle is selected from a Golgi apparatus, lysosome, endoplasmic reticulum, mitochondria, vacuole, endosome, acrosome, autophagosome, centriole, glycosome, glyoxysome, hydrogenosome, melanosome, mitosome, cnidocyst, peroxisome, proteasome, vesicle, and stress granule;
iii) the fusosome has a size of greater than 5 um, 10 um, 20 um, 50 um, or 100 um;
i) the fusosome, or a composition or preparation comprising a plurality of the fusosomes, has a density of other than between 1.08 g/ml and 1.12 g/ml, e.g., the fusosome has a density of 1.25 g/ml+/−0.05, e.g., as measured by an assay of Example 33;
iv) the fusosome is not captured by the scavenger system in circulation or by Kupffer cells in the sinus of the liver;
v) the source cell is other than a 293 cell;
vi) the source cell is not transformed or immortalized;
vii) the source cell is transformed, or immortalized using a method other than adenovirus-mediated immortalization, e.g., immortalized by spontaneous mutation, or telomerase expression;
viii) the fusogen is other than VSVG, a SNARE protein, or a secretory granule protein;
ix) the fusosome does not comprise Cre or GFP, e.g., EGFP;
x) the fusosome further comprises an exogenous protein other than Cre or GFP, e.g., EGFP
xi) the fusosome further comprises an exogenous nucleic acid (e.g., RNA, e.g., mRNA, miRNA, or siRNA) or an exogenous protein (e.g., an antibody, e.g., an antibody), e.g., in the lumen; or
xii) the fusosome does not comprise mitochondria.

The present disclosure also provides, in some aspects, a fusosome comprising:
(a) a lipid bilayer,
(b) a lumen (e.g., comprising cytosol) surrounded by the lipid bilayer,
(c) an exogenous or overexpressed fusogen, e.g., wherein the fusogen is disposed in the lipid bilayer, and
(d) a functional nucleus,
wherein the fusosome is derived from a source cell.
In some embodiments, one or more of the following is present:
i) the source cell is other than a dendritic cell or tumor cell, e.g., the source cell is selected from an endothelial cell, a macrophage, a neutrophil, a granulocyte, a leukocyte, a stem cell (e.g., a mesenchymal stem cell, a bone marrow stem cell, an induced pluripotent stem cell, an embryonic stem cell), a myeloblast, a myoblast, a hepatocyte, or a neuron e.g., retinal neuronal cell;
ii) the fusogen is other than a fusogenic glycoprotein;
iii) the fusogen is a mammalian protein other than fertilin-beta,
iv) the fusosome has low immunogenicity, e.g., as described herein;
v) the fusosome meets a pharmaceutical or good manufacturing practices (GMP) standard;
vi) the fusosome was made according to good manufacturing practices (GMP);
vii) the fusosome has a pathogen level below a predetermined reference value, e.g., is substantially free of pathogens; or
viii) the fusosome has a contaminant level below a predetermined reference value, e.g., is substantially free of contaminants.

The present disclosure also provides, in some aspects, a purified fusosome composition comprising a plurality of fusosomes, wherein at least one fusosome comprises:
a) a lipid bilayer and an aqueous lumen, wherein the fusosome is derived from a source cell, and
b) an exogenous or overexpressed fusogen disposed in the lipid bilayer, wherein the fusosome is at a temperature of less than 4, 0, −4, −10, −12, −16, −20, −80, or −160 C.

The present disclosure also provides, in some aspects, a purified fusosome composition comprising a plurality of fusosomes, wherein at least one fusosome comprises:
a) a lipid bilayer and an aqueous lumen, and
b) an exogenous or overexpressed protein fusogen disposed in the lipid bilayer,
wherein the fusosome is at a temperature of less than 4, 0, −4, −10, −12, −16, −20, −80, or −160 C.

The present disclosure also provides, in some aspects, a fusosome composition, comprising a plurality of fusosomes described herein.

The present disclosure also provides, in some aspects, a fusosome composition comprising a plurality of fusosomes derived from a source cell, wherein the fusosomes of the plurality comprise:
(a) a lipid bilayer,
(b) a lumen comprising cytosol, wherein the lumen is surrounded by the lipid bilayer;
(c) an exogenous or overexpressed fusogen disposed in the lipid bilayer,
(d) a cargo; and
wherein the fusosome does not comprise a nucleus;
wherein the amount of viral capsid protein in the fusosome composition is less than 1% of total protein;
wherein the plurality of fusosomes, when contacted with a target cell population in the presence of an inhibitor of endocytosis, and when contacted with a reference target cell population not treated with the inhibitor of endocytosis, delivers the cargo to at least 30% of the number of cells in the target cell population compared to the reference target cell population.

The present disclosure also provides, in some aspects, a fusosome composition comprising a plurality of fusosomes derived from a source cell, and wherein the fusosomes of the plurality comprise:
(a) a lipid bilayer,
(b) a lumen comprising cytosol, wherein the lumen is surrounded by the lipid bilayer;
(c) an exogenous or overexpressed re-targeted fusogen disposed in the lipid bilayer;
(d) a cargo; and
wherein the fusosome does not comprise a nucleus;
wherein the amount of viral capsid protein in the fusosome composition is less than 1% of total protein;
wherein:
(i) when the plurality of fusosomes are contacted with a cell population comprising target cells and non-target cells, the cargo is present in at least 2-fold, 5-fold, 10-fold, 20-fold, 50-fold, or 100-fold more target cells than non-target cells, or
(ii) the fusosomes of the plurality fuse at a higher rate with a target cell than with a non-target cell by at least at least 50%.

The present disclosure also provides, in some aspects, a fusosome composition comprising a plurality of fusosomes derived from a source cell, and wherein the fusosomes of the plurality comprise:
(a) a lipid bilayer,
(b) a lumen surrounded by the lipid bilayer;
(c) an exogenous or overexpressed fusogen, wherein the fusogen is disposed in the lipid bilayer; and
(d) a cargo;

wherein the fusosome does not comprise a nucleus; and wherein one or more of (e.g., at least 2, 3, 4, or 5 of):
  i) the fusogen is present at a copy number of at least 1,000 copies;
  ii) the fusosome comprises a therapeutic agent at a copy number of at least 1,000 copies;
  iii) the fusosome comprises a lipid wherein one or more of CL, Cer, DAG, HexCer, LPA, LPC, LPE, LPG, LPI, LPS, PA, PC, PE, PG, PI, PS, CE, SM and TAG is within 75% of the corresponding lipid level in the source cell;
  iv) the fusosome comprises a proteomic composition similar to that of the source cell;
  v) the fusosome is capable of signal transduction, e.g., transmitting an extracellular signal, e.g., AKT phosphorylation in response to insulin, or glucose (e.g., labeled glucose, e.g., 2-NBDG) uptake in response to insulin, e.g., by at least 10% more than a negative control, e.g., an otherwise similar fusosome in the absence of insulin;
  vi) the fusosome targets a tissue, e.g., liver, lungs, heart, spleen, pancreas, gastrointestinal tract, kidney, testes, ovaries, brain, reproductive organs, central nervous system, peripheral nervous system, skeletal muscle, endothelium, inner ear, or eye, when administered to a subject, e.g., a mouse, e.g., wherein at least 0.1%, or 10%, of the fusosomes in a population of administered fusosomes are present in the target tissue after 24 hours; or
  the source cell is selected from a neutrophil, a granulocyte, a mesenchymal stem cell, a bone marrow stem cell, an induced pluripotent stem cell, an embryonic stem cell, a myeloblast, a myoblast, a hepatocyte, or a neuron e.g., retinal neuronal cell.

The present disclosure also provides, in some aspects, a pharmaceutical composition comprising the fusosome composition described herein and pharmaceutically acceptable carrier.

This disclosure also provides, in certain aspects, a method of administering a fusosome composition to a subject (e.g., a human subject), a target tissue, or a cell, comprising administering to the subject, or contacting the target tissue or the cell with a fusosome composition comprising a plurality of fusosomes described herein, a fusosome composition described herein, or a pharmaceutical composition described herein, thereby administering the fusosome composition to the subject.

This disclosure also provides, in certain aspects, a method of delivering a therapeutic agent (e.g., a polypeptide, a nucleic acid, a metabolite, an organelle, or a subcellular structure) to a subject, a target tissue, or a cell, comprising administering to the subject, or contacting the target tissue or the cell with, a plurality of fusosomes described herein, a fusosome composition comprising a plurality of fusosomes described herein, a fusosome composition described herein, or a pharmaceutical composition described herein, wherein the fusosome composition is administered in an amount and/or time such that the therapeutic agent is delivered.

This disclosure also provides, in certain aspects, a method of delivering a function to a subject, a target tissue, or a cell, comprising administering to the subject, or contacting the target tissue or the cell with, a plurality of fusosomes described herein, a fusosome composition comprising a plurality of fusosomes described herein, a fusosome composition described herein, or a pharmaceutical composition described herein, wherein the fusosome composition is administered in an amount and/or time such that the function is delivered.

This disclosure also provides, in certain aspects, a method of targeting a function to a subject, a target tissue, or a cell, comprising administering to the subject, or contacting the target tissue or the cell with, a plurality of fusosomes described herein, a fusosome composition comprising a plurality of fusosomes described herein, a fusosome composition described herein, or a pharmaceutical composition described herein, wherein the fusosome composition is administered in an amount and/or time such that the function is targeted.

This disclosure also provides, in certain aspects, a method of modulating, e.g., enhancing, a biological function in a subject, a target tissue, or a cell, comprising administering to the subject, or contacting the target tissue or the cell with, a fusosome composition comprising a plurality of fusosomes described herein, a fusosome composition described herein, or a pharmaceutical composition described herein, thereby modulating the biological function in the subject.

This disclosure also provides, in certain aspects, a method of delivering or targeting a function to a subject, comprising administering to the subject a fusosome composition comprising a plurality of fusosomes described herein which comprise the function, a fusosome composition described herein, or a pharmaceutical composition described herein, wherein the fusosome composition is administered in an amount and/or time such that the function in the subject is delivered or targeted. In embodiments, the subject has a cancer, an inflammatory disorder, autoimmune disease, a chronic disease, inflammation, damaged organ function, an infectious disease, a degenerative disorder, a genetic disease, or an injury.

The disclosure also provides, in some aspects, a method of manufacturing a fusosome composition, comprising:
  a) providing a source cell comprising, e.g., expressing, a fusogen;
  b) producing a fusosome from the source cell, wherein the fusosome comprises a lipid bilayer, a lumen, and a fusogen, thereby making a fusosome; and
  c) formulating the fusosome, e.g., as a pharmaceutical composition suitable for administration to a subject.

In embodiments, one or more of the following is present:
  i) the source cell is other than a 293 cell, HEK cell, human endothelial cell, or a human epithelial cell;
  ii) the fusogen is other than a viral protein;
  iii) the fusosome, or a composition or preparation comprising a plurality of the fusosomes, has a density of other than between 1.08 g/ml and 1.12 g/ml, e.g.,
  iv) the fusosome has a density of 1.25 g/ml+/−0.05, e.g., as measured by an assay of Example 33;
  v) the fusosome is not captured by the scavenger system in circulation or by Kupffer cells in the sinus of the liver;
  vi) the fusosome is not captured by the reticulo-endothelial system (RES) in a subject, e.g., by an assay of Example 76;
  vii) when a plurality of fusosomes are administered to a subject, less than 1%, 2%, 3%, 4%, 5%, 10%, 20%, 30%, 40%, 50%, 60%, 70%, 80%, or 90% of the plurality are or are not captured by the RES after 24, 48, or 72 hours, e.g., by an assay of Example 76;
  viii) the fusosome has a diameter of greater than 5 um, 6 um, 7 um, 8 um, 10 um, 20 um, 50 um, 100 um, 150 um, or 200 um;
  ix) the fusosome comprises a cytobiologic;

x) the fusosome comprises an enucleated cell; or xi) the fusosome comprises an inactivated nucleus.

In some aspects, the present disclosure provides a method of manufacturing a fusosome composition, comprising:

a) providing a plurality of fusosomes described herein, a fusosome composition described herein, or a pharmaceutical composition described herein; and b) formulating the fusosomes, e.g., as a pharmaceutical composition suitable for administration to a subject.

In some aspects, the present disclosure provides a method of manufacturing a fusosome composition, comprising:

a) providing, e.g., producing, a plurality of fusosomes described herein or a fusosome composition described herein; and b) assaying one or more fusosomes from the plurality to determine whether one or more (e.g., 2, 3, or more) standards are met. In embodiments, the standard(s) are chosen from:

i) the fusosome fuses at a higher rate with a target cell than with a non-target cell, e.g., by at least at least 1%, 2%, 3%, 4%, 5%, 10%, 20%, 30%, 40%, 50%, 60%, 70%, 80%, 90%, 2-fold, 3-fold, 4-fold, 5-fold, 10-fold, 20-fold, 50-fold, or 100-fold, e.g., in an assay of Example 54;

ii) the fusosome fuses at a higher rate with a target cell than with other fusosomes, e.g., by at least 10%, 20%, 30%, 40%, 50%, 60%, 70%, 80%, or 90%, e.g., in an assay of Example 54;

iii) the fusosome fuses with target cells at a rate such that an agent in the fusosome is delivered to at least 10%, 20%, 30%, 40%, 50%, 60%, 70%, 80%, or 90%, of target cells after 24, 48, or 72 hours, e.g., in an assay of Example 54;

iv) the fusogen is present at a copy number of at least, or no more than, 10, 50, 100, 500, 1,000, 2,000, 5,000, 10,000, 20,000, 50,000, 100,000, 200,000, 500,000, 1,000,000, 5,000,000, 10,000,000, 50,000,000, 100,000,000, 500,000,000, or 1,000,000,000 copies, e.g., as measured by an assay of Example 29;

v) the fusosome comprises a therapeutic agent at a copy number of at least, or no more than, 10, 50, 100, 500, 1,000, 2,000, 5,000, 10,000, 20,000, 50,000, 100,000, 200,000, 500,000 1,000,000, 5,000,000, 10,000,000, 50,000,000, 100,000,000, 500,000,000, or 1,000,000, 000 copies, e.g., as measured by an assay of Example 43 or 156;

vi) the ratio of the copy number of the fusogen to the copy number of the therapeutic agent is between 1,000,000: 1, 100,000:1, 10,000:1, 1,000:1, 100:1 and 50:1, 1,000, 000:1 and 100,000:1, 100,000:1 and 10,000:1, 10,000:1 and 1,000:1, 1,000:1 and 100:1, 100:1 and 50:1, 50:1 and 20:1, 20:1 and 10:1, 10:1 and 5:1, 5:1 and 2:1, 1:1 and 2:1, 2:1 and 1:1, 1:1 and 1:2, 1:2 and 1:5, 1:5 and 1:10, 1:10 and 1:20, 1:20 and 1:50, 1:50 and 1:100, 1:100 and 1:1,000, 1:1,000 and 1:10,000, 1:10,000 and 1:100,000, or 1:100,000 and 1:1,000,000, or 1:20 and 1:50, 1:100, 1,000:1, 10,000:1, 100,000:1, and 1,000, 000:1;

vii) the fusosome comprises a lipid composition substantially similar to that of the source cell or wherein one or more of CL, Cer, DAG, HexCer, LPA, LPC, LPE, LPG, LPI, LPS, PA, PC, PE, PG, PI, PS, CE, SM and TAG is within 10%, 15%, 20%, 25%, 30%, 35%, 40%, 45%, 50%, or 75% of the corresponding lipid level in the source cell;

viii) the fusosome comprises a proteomic composition similar to that of the source cell, e.g., using an assay of Example 42 or 155;

ix) the fusosome comprises a ratio of lipids to proteins that is within 10%, 20%, 30%, 40%, or 50% of the corresponding ratio in the source cell, e.g., as measured using an assay of Example 49;

x) the fusosome comprises a ratio of proteins to nucleic acids (e.g., DNA) that is within 10%, 20%, 30%, 40%, or 50% of the corresponding ratio in the source cell, e.g., as measured using an assay of Example 50;

xi) the fusosome comprises a ratio of lipids to nucleic acids (e.g., DNA) that is within 10%, 20%, 30%, 40%, or 50% of the corresponding ratio in the source cell, e.g., as measured using an assay of Example 51 or 159;

xii) the fusosome has a half-life in a subject, e.g., in a mouse, that is within 1%, 2%, 3%, 4%, 5%, 10%, 20%, 30%, 40%, 50%, 60%, 70%, 80%, 90%, 100% of the half life of a reference cell, e.g., the source cell, e.g., by an assay of Example 75;

xiii) the fusosome transports glucose (e.g., labeled glucose, e.g., 2-NBDG) across a membrane, e.g., by at least 1%, 2%, 3%, 4%, 5%, 10%, 20%, 30%, 40%, 50%, 60%, 70%, 80%, 90%, 100% more than a negative control, e.g., an otherwise similar fusosome in the absence of glucose, e.g., as measured using an assay of Example 64;

xiv) the fusosome comprises esterase activity in the lumen that is within 1%, 2%, 3%, 4%, 5%, 10%, 20%, 30%, 40%, 50%, 60%, 70%, 80%, 90%, or 100% of that of the esterase activity in a reference cell, e.g., the source cell or a mouse embryonic fibroblast, e.g., using an assay of Example 66;

xv) the fusosome comprises a metabolic activity level that is within 1%, 2%, 3%, 4%, 5%, 10%, 20%, 30%, 40%, 50%, 60%, 70%, 80%, 90%, or 100% of the metabolic activity (e.g., citrate synthase activity) in a reference cell, e.g., the source cell, e.g., as described in Example 68;

xvi) the fusosome comprises a respiration level (e.g., oxygen consumption rate) that is within 1%, 2%, 3%, 4%, 5%, 10%, 20%, 30%, 40%, 50%, 60%, 70%, 80%, 90%, or 100% of the respiration level in a reference cell, e.g., the source cell, e.g., as described in Example 69;

xvii) the fusosome comprises an Annexin-V staining level of at most 18,000, 17,000, 16,000, 15,000, 14,000, 13,000, 12,000, 11,000, or 10,000 MFI, e.g., using an assay of Example 70, or wherein the fusosome comprises an Annexin-V staining level at least 5%, 10%, 20%, 30%, 40%, or 50% lower than the Annexin-V staining level of an otherwise similar fusosome treated with menadione in the assay of Example 70, or wherein the fusosome comprises an Annexin-V staining level at least 5%, 10%, 20%, 30%, 40%, or 50% lower than the Annexin-V staining level of a macrophage treated with menadione in the assay of Example 70, xviii) the fusosome has a miRNA content level of at least at least 1%, 2%, 3%, 4%, 5%, 10%, 20%, 30%, 40%, 50%, 60%, 70%, 80%, 90%, or greater than that of the source cell, e.g., by an assay of Example 39;

xix) the fusosome has a soluble: non-soluble protein ratio is within 1%, 2%, 3%, 4%, 5%, 10%, 20%, 30%, 40%, 50%, 60%, 70%, 80%, 90%, or greater than that of the source cell, e.g., within 1%-2%, 2%-3%, 3%-4%, 4%-5%, 5%-10%, 10%-20%, 20%-30%, 30%-40%, 40%-50%, 50%-60%, 60%-70%, 70%-80%, or 80%-90% of that of the source cell, e.g., by an assay of Example 47;

xx) the fusosome has an LPS level less than 5%, 1%, 0.5%, 0.01%, 0.005%, 0.0001%, 0.00001% or less of the LPS content of the source cell or of the lipid content of fusosomes, e.g., as measured by mass spectrometry, e.g., in an assay of Example 48;

xxi) the fusosome is capable of signal transduction, e.g., transmitting an extracellular signal, e.g., AKT phosphorylation in response to insulin, or glucose (e.g., labeled glucose, e.g., 2-NBDG) uptake in response to insulin, e.g., by at least 1%, 2%, 3%, 4%, 5%, 10%, 20%, 30%, 40%, 50%, 60%, 70%, 80%, 90%, 100% more than a negative control, e.g., an otherwise similar fusosome in the absence of insulin, e.g., using an assay of Example 63;

xxii) the fusosome has juxtacrine-signaling level of at least 1%, 2%, 3%, 4%, 5%, 10%, 20%, 30%, 40%, 50%, 60%, 70%, 80%, 90%, or 100% greater than the level of juxtacrine signaling induced by a reference cell, e.g., the source cell or a bone marrow stromal cell (BMSC), e.g., by an assay of Example 71;

xxiii) the fusosome has paracrine-signaling level of at least 1%, 2%, 3%, 4%, 5%, 10%, 20%, 30%, 40%, 50%, 60%, 70%, 80%, 90%, 100% greater than the level of paracrine signaling induced by a reference cell, e.g., the source cell or a macrophage, e.g., by an assay of Example 72;

xxiv) the fusosome polymerizes actin at a level within 1%, 2%, 3%, 4%, 5%, 10%, 20%, 30%, 40%, 50%, 60%, 70%, 80%, 90%, or 100% compared to the level of polymerized actin in a reference cell, e.g., the source cell or a C2Cl2 cell, e.g., by the assay of Example 73;

xxv) the fusosome has a membrane potential within about 1%, 2%, 3%, 4%, 5%, 10%, 20%, 30%, 40%, 50%, 60%, 70%, 80%, 90%, 100% of the membrane potential of a reference cell, e.g., the source cell or a C2Cl2 cell, e.g., by an assay of Example 74, or wherein the fusosome has a membrane potential of about −20 to −150 mV, −20 to −50 mV, −50 to −100 mV, or −100 to −150 mV;

xxvi) the fusosome is capable of secreting a protein, e.g., at a rate at least 1%, 2%, 3%, 4%, 5%, 10%, 20%, 30%, 40%, 50%, 60%, 70%, 80%, 90%, or 100% greater than a reference cell, e.g., a mouse embryonic fibroblast, e.g., using an assay of Example 62; or xxvii) the fusosome has low immunogenicity, e.g., as described herein; and c) (optionally) approving the plurality of fusosomes or fusosome composition for release if one or more of the standards is met.

The present disclosure also provides, in some aspects, a method of manufacturing a fusosome composition, comprising:

a) providing, e.g., producing, a plurality of fusosomes described herein or a fusosome composition described herein; and b) assaying one or more fusosomes from the plurality to determine the presence or level of one or more of the following factors:

i) an immunogenic molecule, e.g., an immunogenic protein, e.g., as described herein;
ii) a pathogen, e.g., a bacterium or virus; or
iii) a contaminant; and c) (optionally) approving the plurality of fusosomes or fusosome composition for release if one or more of the factors is below a reference value.

The present disclosure also provides, in some aspects, a method of administering a fusosome composition to a human subject, comprising:

a) administering to the subject a first fusogen, under conditions that allow for disposition of the first fusogen in one or more target cell in the subject, wherein one or more of:
  i) administering the first fusogen comprises administering a nucleic acid encoding the first fusogen, under conditions that allow for expression of the first fusogen in the one or more target cell, or
  ii) the first fusogen does not comprise a coiled-coil motif, and b) administering to the human subject a fusosome composition comprising a plurality of fusosomes comprising a second fusogen, wherein the second fusogen is compatible with the first fusogen, thereby administering the fusosome composition to the subject.

The present disclosure also provides, in some aspects, a method of delivering a therapeutic agent to a subject, comprising:

a) administering to the subject a first fusogen, under conditions that allow for disposition of the first fusogen in one or more target cell in the subject, wherein one or more of:
  i) administering the first fusogen comprises administering a nucleic acid encoding the first fusogen, under conditions that allow for expression of the first fusogen in the one or more target cell, or
  ii) the first fusogen does not comprise a coiled-coil motif, and b) administering to the human subject a fusosome composition comprising a plurality of fusosomes comprising a second fusogen and a therapeutic agent, wherein the second fusogen is compatible with the first fusogen,
thereby delivering the therapeutic agent to the subject.

The present disclosure also provides, in some aspects, a method of modulating, e.g., enhancing, a biological function in a subject, comprising:

a) administering to the subject first fusogen, under conditions that allow for disposition of the first fusogen in one or more target cell in the subject, wherein one or more of:
  i) administering the first fusogen comprises administering a nucleic acid encoding the first fusogen, under conditions that allow for expression of the first fusogen in the one or more target cell, or
  ii) the first fusogen does not comprise a coiled-coil motif, and b) administering to the human subject a fusosome composition comprising a plurality of fusosomes comprising a second fusogen, wherein the second fusogen is compatible with the first fusogen, thereby modulating the biological function in the subject.

In one aspect, the invention includes a fusosome comprising a chondrisome and a fusogen.

In one aspect, the invention includes a composition comprising a plurality of fusosomes, wherein at least one fusosome comprises a chondrisome and a fusogen.

The present disclosure also provides, in some aspects, a method of assessing fusosome content of a target cell (e.g., fusosome fusion to a target cell) in a subject, comprising providing a biological sample from a subject that has received a fusosome composition (e.g., a fusosome composition described herein), and performing an assay to determine one or more properties of the biological sample resulting from fusion of a target cell in the biological sample with a fusosome as described herein. In some aspects, the disclosure provides a method of measuring fusion with a target cell, e.g., as described in Example 54 or 124. In some embodiments, determining one or more properties of the biological sample comprises determining: the presence of a fusogen, the level of a cargo or payload, or an activity relating to a cargo or payload.

In some aspects, the present disclosure provides a method of assessing fusosome content of a target cell (e.g., fusosome fusion to a target cell) in a subject, comprising providing a biological sample from a subject that has received a fusosome composition, e.g., as described herein, and testing the biological sample for the presence of a fusogen, e.g., a fusogen described herein. In some instances, the level of the fusogen detected is greater (e.g., at least about 5%, 10%, 20%, 30%, 40%, 50%, 60%, 70%, 80%, 90%, 100%, 200%, 300%, 400%, 500%, 600%, 700%, 800%, 900%, 1000%, 2000%, 3000%, 4000%, 5000%, 10,000%, 50,000%, or 100,000% greater) than that observed in a corresponding biological sample from a subject that has not received a fusosome composition. In some embodiments, the subject is the same subject prior to administration of the fusosome composition, and in some embodiments, the subject is a different subject.

In some aspects, the present disclosure provides a method of assessing fusosome content of a target cell (e.g., fusosome fusion to a target cell) in a subject, comprising providing a biological sample from a subject that has received a fusosome composition, e.g., as described herein, and testing the biological sample for the presence of a cargo or payload, e.g., delivered by a fusosome as described herein. In some instances, the level of the cargo or payload detected is greater (e.g., at least about 5%, 10%, 20%, 30%, 40%, 50%, 60%, 70%, 80%, 90%, 100%, 200%, 300%, 400%, 500%, 600%, 700%, 800%, 900%, 1000%, 2000%, 3000%, 4000%, 5000%, 10,000%, 50,000%, or 100,000% greater) than that observed in a corresponding biological sample from a subject that has not received a fusosome composition. In some embodiments, the subject is the same subject prior to administration of the fusosome composition, and in some embodiments, the subject is a different subject.

In some aspects, the present disclosure provides a method of assessing fusosome content of a target cell (e.g., fusosome fusion to a target cell in a subject), comprising providing a biological sample from a subject that has received a fusosome composition, e.g., as described herein, and testing the biological sample for alteration of an activity relating to the fusosome composition, e.g., an activity relating to a cargo or payload delivered by the fusosome composition. In some instances, the level of the activity detected is increased, e.g., by at least about 5%, 10%, 20%, 30%, 40%, 50%, 60%, 70%, 80%, 90%, 100%, 200%, 300%, 400%, 500%, 600%, 700%, 800%, 900%, 1000%, 2000%, 3000%, 4000%, 5000%, 10,000%, 50,000%, or 100,000%, relative to that of a corresponding biological sample from a subject that has not received a fusosome composition (e.g., the same subject prior to administration of the fusosome composition). In some instances, the level of the activity detected is decreased, e.g., by at least about 5%, 10%, 20%, 30%, 40%, 50%, 60%, 70%, 80%, 90%, 100%, 200%, 300%, 400%, 500%, 600%, 700%, 800%, 900%, 1000%, 2000%, 3000%, 4000%, 5000%, 10,000%, 50,000%, or 100,000%, relative to that of a corresponding biological sample from a subject that has not received a fusosome composition. In some embodiments, the subject is the same subject prior to administration of the fusosome composition, and in some embodiments, the subject is a different subject.

In one aspect, the present disclosure provides a method of assessing fusosome fusion to a target cell in a subject, comprising providing a biological sample from a subject that has received a fusosome composition, e.g., as described herein, and assessing a level of unfused fusosomes in the biological sample.

Any of the aspects herein, e.g., the fusosomes, fusosome compositions and methods above, can be combined with one or more of the embodiments herein, e.g., an embodiment below.

In some embodiments, the fusosome is capable of delivering (e.g., delivers) an agent, e.g., a protein, nucleic acid (e.g., mRNA), organelle, or metabolite to the cytosol of a target cell. Similarly, in some embodiments, a method herein comprises delivering an agent to the cytosol of a target cell. In some embodiments, the agent is a protein (or a nucleic acid encoding the protein, e.g., an mRNA encoding the protein) which is absent, mutant, or at a lower level than wild-type in the target cell. In some embodiments, the target cell is from a subject having a genetic disease, e.g., a monogenic disease, e.g., a monogenic intracellular protein disease. In some embodiments, the agent comprises a transcription factor, e.g., an exogenous transcription factor or an endogenous transcription factor. In some embodiments, the fusosome further comprises, or the method further comprises delivering, one or more (e.g., at least 2, 3, 4, 5, 10, 20, or 50) additional transcription factors, e.g., exogenous transcription factors, endogenous transcription factors, or a combination thereof.

In some embodiments, the fusosome comprises (e.g., is capable of delivering to the target cell) a plurality of agents (e.g., at least 2, 3, 4, 5, 10, 20, or 50 agents), wherein each agent of the plurality acts on a step of a pathway in the target cell, e.g., wherein the pathway is a biosynthetic pathway, a catabolic pathway, or a signal transduction cascade. In embodiments, each agent in the plurality upregulates the pathway or downregulates the pathway. In some embodiments, the fusosome further comprises, or the method further comprises delivering, one more additional agents (e.g., comprises a second plurality of agents) that do not act on a step of the pathway, e.g., that act on a step of a second pathway. In some embodiments, the fusosome comprises (e.g., is capable of delivering to the target cell), or the method further comprises delivering, a plurality of agents (e.g., at least 2, 3, 4, 5, 10, 20, or 50 agents), wherein each agent of the plurality is part of a single pathway, e.g., wherein the pathway is a biosynthetic pathway, a catabolic pathway, or a signal transduction cascade. In some embodiments, the fusosome further comprises, or the method further comprises delivering, one more additional agents (e.g., comprises a second plurality of agents) that are not part of the single pathway, e.g., are part of a second pathway.

In some embodiments, the target cell comprises an aggregated or misfolded protein. In some embodiments, the fusosome is capable of reducing levels (e.g., reduces levels) of the aggregated or misfolded protein in the target cell, or a method herein comprises reducing levels of the aggregated or misfolded protein in the target cell.

In some embodiments, the agent is selected from a transcription factor, enzyme (e.g., nuclear enzyme or cytosolic enzyme), reagent that mediates a sequence specific modification to DNA (e.g., Cas9, ZFN, or TALEN), mRNA (e.g., mRNA encoding an intracellular protein), organelle, or metabolite.

In some embodiments, the fusosome is capable of delivering (e.g., delivers) an agent, e.g., a protein, to the cell membrane of a target cell. Similarly, in some embodiments, a method herein comprises delivering an agent to the cell membrane of a target cell. In some embodiments, delivering the protein comprises delivering a nucleic acid (e.g., mRNA) encoding the protein to the target cell such that the target cell produces the protein and localizes it to the membrane. In some embodiments, the fusosome comprises, or the method further comprises delivering, the protein, and fusion of the fusosome with the target cell transfers the protein to the cell membrane of the target cell. In some embodiments, the agent comprises a cell surface ligand or an antibody that binds a cell surface receptor. In some embodiments, the fusosome further comprises, or the method further comprises delivering, a second agent that comprises or encodes a second cell surface ligand or antibody that binds a cell surface receptor, and optionally further comprising or encoding one or more additional cell surface ligands or antibodies that bind a cell surface receptor (e.g., 1, 2, 3, 4, 5, 10, 20, 50, or more). In some embodiments, the first agent and the second agent form a complex, wherein optionally the complex further comprises one or more additional cell surface ligands. In some embodiments, the agent comprises or encodes a cell surface receptor, e.g., an exogenous cell surface receptor. In some embodiments, the fusosome further comprises, or the method further comprises delivering, a second agent that comprises or encodes a second cell surface receptor, and optionally further comprises or encodes one or more additional cell surface receptors (e.g., 1, 2, 3, 4, 5, 10, 20, 50, or more cell surface receptors).

In some embodiments, the first agent and the second agent form a complex, wherein optionally the complex further comprises one or more additional cell surface receptors. In some embodiments, the agent comprises or encodes an antigen or an antigen presenting protein.

In some embodiments, the fusosome is capable of delivering (e.g., delivers) a secreted agent, e.g., a secreted protein to a target site (e.g., an extracellular region), e.g., by delivering a nucleic acid (e.g., mRNA) encoding the protein to the target cell under conditions that allow the target cell to produce and secrete the protein. Similarly, in some embodiments, a method herein comprises delivering a secreted agent as described herein. In embodiments, the secreted protein is endogenous or exogenous. In embodiments, the secreted protein comprises a protein therapeutic, e.g., an antibody molecule, a cytokine, or an enzyme. In embodiments, the secreted protein comprises an autocrine signalling molecule or a paracrine signalling molecule. In embodiments, the secreted agent comprises a secretory granule.

In some embodiments, the fusosome is capable of reprogramming (e.g., reprograms) a target cell (e.g., an immune cell), e.g., by delivering an agent selected from a transcription factor or mRNA, or a plurality of said agents. Similarly, in some embodiments, a method herein comprises reprogramming a target cell. In embodiments, reprogramming comprises inducing a pancreatic endocrine cell to take on one or more characteristics of a pancreatic beta cell, by inducing a non-dopaminergic neuron to take on one or more characteristics of a dopaminergic neuron, or by inducing an exhausted T cell to take on one or more characteristics of a non-exhausted T cell, e.g., a killer T cell. In some embodiments, the agent comprises an antigen. In some embodiments, the fusosome comprises a first agent comprising an antigen and a second agent comprising an antigen presenting protein.

In some embodiments, the fusosome is capable of donating (e.g., donates) one or more cell surface receptors to a target cell (e.g., an immune cell). Similarly, in some embodiments, a method herein comprises donating one or more cell surface receptors.

In some embodiments, a fusosome is capable of modifying, e.g., modifies, a target tumor cell. Similarly, in some embodiments, a method herein comprises modifying a target tumor cell. In embodiments, the fusosome comprises an mRNA encoding an immunostimulatory ligand, an antigen presenting protein, a tumor suppressor protein, or a pro-apoptotic protein. In some embodiments, the fusosome comprises an miRNA capable of reducing levels in a target cell of an immunosuppressive ligand, a mitogenic signal, or a growth factor.

In some embodiments, a fusosome comprises an agent that is immunomodulatory, e.g., immunostimulatory.

In some embodiments, a fusosome is capable of causing (e.g., causes) the target cell to present an antigen. Similarly, in some embodiments, a method herein comprises presenting an antigen on a target cell.

In some embodiments, the fusosome promotes regeneration in a target tissue. Similarly, in some embodiments, a method herein comprises promoting regeneration in a target tissue. In embodiments, the target cell is a cardiac cell, e.g., a cardiomyocyte (e.g., a quiescent cardiomyocyte), a hepatoblast (e.g., a bile duct hepatoblast), an epithelial cell, a naïve T cell, a macrophage (e.g., a tumor infiltrating macrophage), or a fibroblast (e.g., a cardiac fibroblast). In embodiments, the source cell is a T cell (e.g., a $T_{reg}$), a macrophage, or a cardiac myocyte.

In some embodiments, the fusosome is capable of delivering (e.g., delivers) a nucleic acid to a target cell, e.g., to stably modify the genome of the target cell, e.g., for gene therapy. Similarly, in some embodiments, a method herein comprises delivering a nucleic acid to a target cell. In some embodiments, the target cell has an enzyme deficiency, e.g., comprises a mutation in an enzyme leading to reduced activity (e.g., no activity) of the enzyme.

In some embodiments, the fusosome is capable of delivering (e.g., delivers) a reagent that mediates a sequence specific modification to DNA (e.g., Cas9, ZFN, or TALEN) in the target cell. Similarly, in some embodiments, a method herein comprises delivering the reagent to the target cell. In embodiments, the target cell is a muscle cell (e.g., skeletal muscle cell), kidney cell, or liver cell.

In some embodiments, the fusosome is capable of delivering (e.g., delivers) a nucleic acid to a target cell, e.g., to transiently modify gene expression in the target cell.

In some embodiments, the fusosome is capable of delivering (e.g., delivers) a protein to a target cell, e.g., to transiently rescue a protein deficiency. Similarly, in some embodiments, a method herein comprises delivering a protein to a target cell. In embodiments, the protein is a membrane protein (e.g., a membrane transporter protein), a cytoplasmic protein (e.g., an enzyme), or a secreted protein (e.g., an immunosuppressive protein).

In some embodiments, the fusosome is capable of delivering (e.g., delivers) an organelle to a target cell, e.g., wherein the target cell has a defective organelle network. Similarly, in some embodiments, a method herein comprises delivering an organelle to a target cell. In embodiments, the source cell is a hepatocyte, skeletal muscle cell, or neuron.

In some embodiments, the fusosome is capable of delivering (e.g., delivers) a nucleus to a target cell, e.g., wherein the target cell has a genetic mutation. Similarly, in some embodiments, a method herein comprises delivering a nucleus to a target cell. In some embodiments, the nucleus is autologous and comprises one or more genetic changes relative to the target cell, e.g., it comprises a sequence specific modification to DNA (e.g., Cas9, ZFN, or TALEN), or an artificial chromosome, an additional genetic sequence integrated into the genome, a deletion, or any combination thereof. In embodiments, the source of the autologous nucleus is a stem cell, e.g., a hematopoietic stem cell. In embodiments, the target cell is a muscle cell (e.g., a skeletal muscle cell or cardiomyocyte), a hepatocyte, or a neuron.

In some embodiments, the fusosome is capable of intracellular molecular delivery, e.g., delivers a protein agent to a target cell. Similarly, in some embodiments, a method herein comprises delivering a molecule to an intracellular region of a target cell. In embodiments, the protein agent is an inhibitor. In embodiments, the protein agent comprises a nanobody, scFv, camelid antibody, peptide, macrocycle, or small molecule.

In some embodiments, the fusosome is capable of causing (e.g., causes) a target cell to secrete a protein, e.g., a therapeutic protein. Similarly, in some embodiments, a method herein comprises causing a target cell to secrete a protein.

In some embodiments, the fusosome is capable of secreting (e.g., secretes) an agent, e.g., a protein. In some embodiments, the agent, e.g., secreted agent, is delivered to a target site in a subject. In some embodiments, the agent is a protein that can not be made recombinantly or is difficult to make recombinantly. In some embodiments, the fusosome that secretes a protein is from a source cell selected from an MSC or a chondrocyte.

In some embodiments, the fusosome comprises on its membrane one or more cell surface ligands (e.g., 1, 2, 3, 4, 5, 10, 20, 50, or more cell surface ligands). Similarly, in some embodiments, a method herein comprises presenting one or more cell surface ligands to a target cell. In some embodiments, the fusosome having a cell surface ligand is from a source cell chosen from a neutrophil (e.g., and the target cell is a tumor-infiltrating lymphocyte), dendritic cell (e.g., and the target cell is a naïve T cell), or neutrophil (e.g., and the target is a tumor cell or virus-infected cell). In some embodiments the fusosome comprises a membrane complex, e.g., a complex comprising at least 2, 3, 4, or 5 proteins, e.g., a homodimer, heterodimer, homotrimer, heterotrimer, homotetramer, or heterotetramer. In some embodiments, the fusosome comprises an antibody, e.g., a toxic antibody, e.g., the fusosome is capable of delivering the antibody to the target site, e.g., by homing to a target site. In some embodiments, the source cell is an NK cell or neutrophil.

In some embodiments, a method herein comprises causing secretion of a protein from a target cell or ligand presentation on the surface of a target cell. In some embodiments, the fusosome is capable of causing cell death of the target cell. In some embodiments, the fusosome is from a NK source cell.

In some embodiments, a fusosome or target cell is capable of phagocytosis (e.g., of a pathogen). Similarly, in some embodiments, a method herein comprises causing phagocytosis.

In some embodiments, a fusosome senses and responds to its local environment. In some embodiments, the fusosome is capable of sensing level of a metabolite, interleukin, or antigen.

In embodiments, a fusosome is capable of chemotaxis, extravasation, or one or more metabolic activities. In embodiments, the metabolic activity is selected from kyneurinine, gluconeogenesis, prostaglandin fatty acid oxidation, adenosine metabolism, urea cycle, and thermogenic respiration. In some embodiments, the source cell is a neutrophil and the fusosome is capable of homing to a site of injury. In some embodiments, the source cell is a macrophage and the fusosome is capable of phagocytosis. In some embodiments, the source cell is a brown adipose tissue cell and the fusosome is capable of lipolysis.

In some embodiments, the fusosome comprises (e.g., is capable of delivering to the target cell) a plurality of agents (e.g., at least 2, 3, 4, 5, 10, 20, or 50 agents). In embodiments, the fusosome comprises an inhibitory nucleic acid (e.g., siRNA or miRNA) and an mRNA.

In some embodiments, the fusosome comprises (e.g., is capable of delivering to the target cell) a membrane protein or a nucleic acid encoding the membrane protein. In embodiments, the fusosome is capable of reprogramming or transdifferentiating a target cell, e.g., the fusosome comprises one or more agents that induce reprogramming or transdifferentiation of a target cell.

In some embodiments, the subject is in need of regeneration. In some embodiments, the subject suffers from cancer, an autoimmune disease, an infectious disease, a metabolic disease, a neurodegenerative disease, or a genetic disease (e.g., enzyme deficiency).

In some embodiments (e.g., embodiments for assaying non-endocytic delivery of cargo) cargo delivery is assayed using one or more of (e.g., all of) the following steps: (a) placing 30,000 HEK-293T target cells into a first well of a 96-well plate comprising 100 nM bafilomycin A1, and placing a similar number of similar cells into a second well of a 96-well plate lacking bafilomycin A1, (b) culturing the target cells for four hours in DMEM media at 37° C. and 5% $CO_2$, (c) contacting the target cells with 10 ug of fusosomes that comprise cargo, (d) incubating the target cells and fusosomes for 24 hrs at 37° C. and 5% $CO_2$, and (e) determining the percentage of cells in the first well and in the second well that comprise the cargo. Step (e) may comprise detecting the cargo using microscopy, e.g., using immunofluorescence. Step (e) may comprise detecting the cargo indirectly, e.g., detecting a downstream effect of the cargo, e.g., presence of a reporter protein. In some embodiments, one or more of steps (a)-(e) above is performed as described in Example 135.

In some embodiments, an inhibitor of endocytosis (e.g., chloroquine or bafilomycin A1) inhibits inhibits endosomal acidification. In some embodiments, cargo delivery is independent of lysosomal acidification. In some embodiments, an inhibitor of endocytosis (e.g., Dynasore) inhibits dynamin. In some embodiments, cargo delivery is independent of dynamin activity.

In some embodiments (e.g., embodiments for specific delivery of cargo to a target cell versus a non-target cell), cargo delivery is assayed using one or more of (e.g., all of) the following steps: (a) placing 30,000 HEK-293T target cells that over-express CD8a and CD8b into a first well of a 96-well plate and placing 30,000 HEK-293T non-target cells that do not over-express CD8a and CD8b into a second well of a 96-well plate, (b) culturing the cells for four hours in DMEM media at 37° C. and 5% $CO_2$, (c) contacting the target cells with 10 ug of fusosomes that comprise cargo, (d) incubating the target cells and fusosomes for 24 hrs at 37° C. and 5% $CO_2$, and (e) determining the percentage of cells in the first well and in the second well that comprise the cargo. Step (e) may comprise detecting the cargo using microscopy, e.g., using immunofluorescence. Step (e) may comprise detecting the cargo indirectly, e.g., detecting a downstream effect of the cargo, e.g., presence of a reporter protein. In some embodiments, one or more of steps (a)-(e) above is performed as described in Example 124.

In some embodiments:
ii) the source cell is other than a 293 cell, HEK cell, human endothelial cell, or a human epithelial cell;
iii) the fusogen is other than a viral protein;
iv) the fusosome, or a composition or preparation comprising a plurality of the fusosomes, has a density of other than between 1.08 g/ml and 1.12 g/ml, e.g.,
v) the fusosome has a density of 1.25 g/ml+/−0.05, e.g., as measured by an assay of Example 33;
vi) the fusosome is not captured by the scavenger system in circulation or by Kupffer cells in the sinus of the liver;
vii) the fusosome is not captured by the reticulo-endothelial system (RES) in a subject, e.g., by an assay of Example 76;
viii) when a plurality of fusosomes are administered to a subject, less than 1%, 2%, 3%, 4%, 5%, 10%, 20%, 30%, 40%, 50%, 60%, 70%, 80%, or 90% of the plurality are captured by the RES after 24, 48, or 72 hours, e.g., by an assay of Example 76;
ix) the fusosome has a diameter of greater than 5 um, 6 um, 7 um, 8 um, 10 um, 20 um, 50 um, 100 um, 150 um, or 200 um.

In some embodiments, the fusosome comprises or is comprised by a cytobiologic. In some embodiments, the fusosome comprises an enucleated cell. In some embodiments, the fusosome comprises an inactivated nucleus. In some embodiments, the fusosome does not comprise a functional nucleus.

In some embodiments, the fusosome or fusosome composition has, or is identified as having, one or more of (e.g., at least 2, 3, 4, or 5 of) the properties herein, e.g., the properties below.

In some embodiments, the fusosome fuses at a higher rate with a target cell than with a non-target cell, e.g., by at least at least 1%, 2%, 3%, 4%, 5%, 10%, 20%, 30%, 40%, 50%, 60%, 70%, 80%, 90%, 2-fold, 3-fold, 4-fold, 5-fold, 10-fold, 20-fold, 50-fold, or 100-fold, e.g., in an assay of Example 54 In some embodiments, the fusosome fuses at a higher rate with a target cell than with other fusosomes, e.g., by at least 10%, 20%, 30%, 40%, 50%, 60%, 70%, 80%, or 90%, e.g., in an assay of Example 54. In some embodiments, the fusosome fuses with target cells at a rate such that an agent in the fusosome is delivered to at least 10%, 20%, 30%, 40%, 50%, 60%, 70%, 80%, or 90%, of target cells after 24, 48, or 72 hours, e.g., in an assay of Example 54. In embodiments, the amount of targeted fusion is about 30%-70%, 35%-65%, 40%-60%, 45%-55%, or 45%-50%, e.g., about 48.8% e.g., in an assay of Example 54. In embodiments, the amount of targeted fusion is about 20%-40%, 25%-35%, or 30%-35%, e.g., about 32.2% e.g., in an assay of Example 55.

In some embodiments, the fusogen is present at a copy number of at least, or no more than, 10, 50, 100, 500, 1,000, 2,000, 5,000, 10,000, 20,000, 50,000, 100,000, 200,000, 500,000, 1,000,000, 5,000,000, 10,000,000, 50,000,000, 100,000,000, 500,000,000, or 1,000,000,000 copies, e.g., as measured by an assay of Example 29. In some embodiments, at least 10%, 20%, 30%, 40%, 50%, 60%, 70%, 80%, 90%, 95%, 96%, 97%, 98%, or 99% of the fusogen comprised by the fusosome is disposed in the cell membrane. In embodiments, the fusosome also comprises fusogen internally, e.g., in the cytoplasm or an organelle. In some embodiments, the fusogen comprises (or is identified as comprising) about 0.1%, 0.2%, 0.3%, 0.4%, 0.5%, 0.6%, 0.7%, 0.8%, 0.9%, 1%, 5%, 10%, 11%, 12%, 13%, 14%, 15%, 20%, or more, or about 1-30%, 5-20%, 10-15%, 12-15%, 13-14%, or 13.6% of the total protein in a fusosome, e.g., as determined according to the method described in Example 162 and/or by a mass spectrometry assay. In embodiments, the fusogen comprises (or is identified as comprising) about 13.6% of the total protein in the fusosome. In some embodiments, the fusogen is (or is identified as being) more or less abundant than one or more additional proteins of interest, e.g., as determined according to the method described in Example 162. In an embodiment, the fusogen has (or is identified as having) a ratio to EGFP of about 140, 145, 150, 151, 152, 153, 154, 155, 156, 157 (e.g., 156.9), 158, 159, 160, 165, or 170. In another embodiment, the fusogen has (or is identified as having) a ratio to CD63 of about 2700, 2800, 2900, 2910 (e.g., 2912), 2920, 2930, 2940, 2950, 2960, 2970, 2980, 2990, or 3000, or about 1000-5000, 2000-4000, 2500-3500, 2900-2930, 2910-2915, or 2912.0, e.g., by a mass spectrometry assay. In an embodiment, the fusogen has (or is identified as having) a ratio to ARRDC1 of about 600, 610, 620, 630, 640, 650, 660 (e.g., 664.9), 670, 680, 690, or 700. In another embodiment, the fusogen has (or is identified as having) a ratio to GAPDH of about 50, 55, 60, 65, 70 (e.g., 69), 75, 80, or 85, or about 1-30%, 5-20%, 10-15%, 12-15%, 13-14%, or 13.6%. In another embodiment, the fusogen has (or is identified as having) a ratio to CNX of about 500, 510, 520, 530, 540, 550, 560 (e.g., 558.4), 570, 580, 590, or 600, or about 300-800, 400-700, 500-600, 520-590, 530-580, 540-570, 550-560, or 558.4, e.g., by a mass spectrometry assay.

In some embodiments, the fusosome comprises a therapeutic agent at a copy number of at least, or no more than, 10, 50, 100, 500, 1,000, 2,000, 5,000, 10,000, 20,000, 50,000, 100,000, 200,000, 500,000, 1,000,000, 5,000,000, 10,000,000, 50,000,000, 100,000,000, 500,000,000, or 1,000,000,000 copies, e.g., as measured by an assay of Example 43 or 156. In some embodiments, the fusosome comprises a protein therapeutic agent at a copy number of at least 10, 50, 100, 500, 1,000, 2,000, 5,000, 10,000, 20,000, 50,000, 100,000, 200,000, 500,000, 1,000,000, 5,000,000, 10,000,000, 50,000,000, 100,000,000, 500,000,000, or 1,000,000,000 copies, e.g., as measured by an assay of Example 43 or 156.

In some embodiments, the fusosome comprises a nucleic acid therapeutic agent at a copy number of at least 10, 50, 100, 500, 1,000, 2,000, 5,000, 10,000, 20,000, 50,000, 100,000, 200,000, 500,000, 1,000,000, 5,000,000, 10,000, 000, 50,000,000, 100,000,000, 500,000,000, or 1,000,000, 000 copies. In some embodiments, the fusosome comprises a DNA therapeutic agent at a copy number of at least 10, 50, 100, 500, 1,000, 2,000, 5,000, 10,000, 20,000, 50,000, 100,000, 200,000, 500,000, 1,000,000, 5,000,000, 10,000, 000, 50,000,000, 100,000,000, 500,000,000, or 1,000,000, 000 copies. In some embodiments, the fusosome comprises an RNA therapeutic agent at a copy number of at least 10, 50, 100, 500, 1,000, 2,000, 5,000, 10,000, 20,000, 50,000, 100,000, 200,000, 500,000, 1,000,000, 5,000,000, 10,000, 000, 50,000,000, 100,000,000, 500,000,000, or 1,000,000, 000 copies. In some embodiments, the fusosome comprises an exogenous therapeutic agent at a copy number of at least 10, 50, 100, 500, 1,000, 2,000, 5,000, 10,000, 20,000, 50,000, 100,000, 200,000, 500,000, 1,000,000, 5,000,000, 10,000,000, 50,000,000, 100,000,000, 500,000,000, or 1,000,000,000 copies. In some embodiments, the fusosome comprises an exogenous protein therapeutic agent at a copy number of at least 10, 50, 100, 500, 1,000, 2,000, 5,000, 10,000, 20,000, 50,000, 100,000, 200,000, 500,000, 1,000,000, 5,000,000, 10,000,000, 50,000,000, 100,000,000, 500,000,000, or 1,000,000,000 copies. In some embodiments, the fusosome comprises an exogenous nucleic acid (e.g., DNA or RNA) therapeutic agent at a copy number of at least 10, 50, 100, 500, 1,000, 2,000, 5,000, 10,000, 20,000, 50,000, 100,000, 200,000, 500,000, 1,000,000, 5,000,000, 10,000,000, 50,000,000, 100,000,000, 500,000,000, or 1,000,000,000 copies. In some embodiments, the ratio of the copy number of the fusogen to the copy number of the therapeutic agent is between 1,000,000:1 and 100,000:1, 100,000:1 and 10,000:1, 10,000:1 and 1,000:1, 1,000:1 and 100:1, 100:1 and 50:1, 50:1 and 20:1, 20:1 and 10:1, 10:1 and 5:1, 5:1 and 2:1, 2:1 and 1:1, 1:1 and 1:2, 1:2 and 1:5, 1:5 and 1:10, 1:10 and 1:20, 1:20 and 1:50, 1:50 and 1:100, 1:100 and 1:1,000, 1:1,000 and 1:10,000, 1:10,000 and 1:100,000, or 1:100,000 and 1:1,000,000.

In some embodiments, the fusosome delivers to a target cell at least 10, 50, 100, 500, 1,000, 2,000, 5,000, 10,000, 20,000, 50,000, 100,000, 200,000, 500,000, 1,000,000, 5,000,000, 10,000,000, 50,000,000, 100,000,000, 500,000,000, or 1,000,000,000 copies of a therapeutic agent. In some embodiments, the fusosome delivers to a target cell at least 10, 50, 100, 500, 1,000, 2,000, 5,000, 10,000, 20,000, 50,000, 100,000, 200,000, 500,000, 1,000,000, 5,000,000, 10,000,000, 50,000,000, 100,000,000, 500,000,000, or 1,000,000,000 copies of a protein therapeutic agent. In some embodiments, the fusosome delivers to a target cell at least 10, 50, 100, 500, 1,000, 2,000, 5,000, 10,000, 20,000, 50,000, 100,000, 200,000, 500,000, 1,000,000, 5,000,000, 10,000,000, 50,000,000, 100,000,000, 500,000,000, or 1,000,000,000 copies of a nucleic acid therapeutic agent. In some embodiments, the fusosome delivers to a target cell at least 10, 50, 100, 500, 1,000, 2,000, 5,000, 10,000, 20,000, 50,000, 100,000, 200,000, 500,000, 1,000,000, 5,000,000, 10,000,000, 50,000,000, 100,000,000, 500,000,000, or 1,000,000,000 copies of an RNA therapeutic agent. In some embodiments, the fusosome delivers to a target cell at least 10, 50, 100, 500, 1,000, 2,000, 5,000, 10,000, 20,000, 50,000, 100,000, 200,000, 500,000, 1,000,000, 5,000,000, 10,000,000, 50,000,000, 100,000,000, 500,000,000, or 1,000,000,000 copies of a DNA therapeutic agent.

In some embodiments, the fusosome delivers to a target cell at least 10%, 20%, 30%, 40%, 50%, 60%, 70%, 80%, 90%, 95%, 96%, 97%, 98%, or 99% of the cargo (e.g., a therapeutic agent, e.g., an endogenous therapeutic agent or an exogenous therapeutic agent) comprised by the fusosome. In some embodiments, the fusosomes that fuse with the target cell(s) deliver to the target cell an average of at least 10%, 20%, 30%, 40%, 50%, 60%, 70%, 80%, 90%, 95%, 96%, 97%, 98%, or 99% of the cargo (e.g., a therapeutic agent, e.g., an endogenous therapeutic agent or an exogenous therapeutic agent) comprised by the fusosomes that fuse with the target cell(s). In some embodiments, the fusosome composition delivers to a target tissue at least 10%, 20%, 30%, 40%, 50%, 60%, 70%, 80%, 90%, 95%, 96%, 97%, 98%, or 99% of the cargo (e.g., a therapeutic agent, e.g., an endogenous therapeutic agent or an exogenous therapeutic agent) comprised by the fusosome composition.

In some embodiments, the fusosome comprises 0.00000001 mg fusogen to 1 mg fusogen per mg of total protein in fusosome, e.g., 0.00000001-0.0000001, 0.0000001-0.000001, 0.000001-0.00001, 0.00001-0.0001, 0.0001-0.001, 0.001-0.01, 0.01-0.1, or 0.1-1 mg fusogen per mg of total protein in fusosome. In some embodiments, the fusosome comprises 0.00000001 mg fusogen to 5 mg fusogen per mg of lipid in fusosome, e.g., 0.00000001-0.0000001, 0.0000001-0.000001, 0.000001-0.00001, 0.00001-0.0001, 0.0001-0.001, 0.001-0.01, 0.01-0.1, 0.1-1, or 1-5 mg fusogen per mg of lipid in fusosome.

In some embodiments, the cargo is a protein cargo. In embodiments, the cargo is an endogenous or synthetic protein cargo. In some embodiments, the fusosomes have (or are identified as having) at least 1, 2, 3, 4, 5, 10, 20, 50, 100, or more protein cargo molecules per fusosome. In an embodiment, the fusosomes have (or are identified as having) about 100, 110, 120, 130, 140, 150, 160, 166, 170, 180, 190, or 200 protein agent molecules per fusosome, e.g., as quantified according to the method described in Example 156. In some embodiments, the endogenous or synthetic protein cargo comprises (or is identified as comprising) about 0.1%, 0.2%, 0.3%, 0.4%, 0.5%, 1%, 5%, 10%, 15%, 20%, 25% or more of the total protein in a fusosome. In an embodiment, the synthetic protein cargo comprises (or is identified as comprising) about 13.6% of the total protein in a fusosome. In some embodiments, the synthetic protein cargo has (or is identified as having) a ratio to VSV-G of about $4 \times 10^{-3}$, $5 \times 10^{-3}$, $6 \times 10^{-3}$ (e.g., $6.37 \times 10^{-3}$), $7 \times 10^{-3}$, or $8 \times 10^{-3}$. In embodiments, the synthetic protein cargo has (or is identified as having) a ratio to CD63 of about 10, 15, 16, 17, 18 (e.g., 18.6), 19, 20, 25, or 30, or about 10-30, 15-25, 16-19, 18-19, or 18.6. In embodiments, the synthetic protein cargo has (or is identified as having) a ratio to ARRDC1 of about 2, 3, 4 (e.g., 4.24), 5, 6, or 7. In embodiments, the synthetic protein cargo has (or is identified as having) a ratio to GAPDH of about 0.1, 0.2, 0.3, 0.4 (e.g., 0.44), 0.5, 0.6, or 0.7. In embodiments, the synthetic protein cargo has (or is identified as having) a ratio to CNX of about 1, 2, 3 (e.g., 3.56), 4, 5, or 6. In embodiments, the synthetic protein cargo has (or is identified as having) a ratio to TSG101 of about 10, 15, 16, 17, 18, 19 (e.g., 19.52), 20, 21, 22, 23, 24, 25, or 30.

In some embodiments, the fusogen comprises (or is identified as comprising) at least 0.5%, 1%, 5%, 10%, or more of the total protein in a fusosome, e.g., by a mass spectrometry assay. In an embodiment, the fusogen comprises (or is identified as comprising) about 1-30%, 5-20%, 10-15%, 12-15%, 13-14%, or 13.6% of the total protein in a fusosome, e.g., by a mass spectrometry assay. In some embodiments, the fusogen is more abundant than other proteins of interest. In embodiments, the fusogen has (or is identified as having) a ratio to a payload protein, e.g., EGFP, of about 145-170, 150-165, 155-160, 156.9, e.g., by a mass spectrometry assay. In embodiments, the fusogen has (or is identified as having) a ratio to CD63 of about 1000-5000, 2000-4000, 2500-3500, 2900-2930, 2910-2915, or 2912.0, e.g., by a mass spectrometry assay. In embodiments, the fusogen has a ratio to ARRDC1 of about 300-1000, 400-900, 500-800, 600-700, 640-690, 650-680, 660-670, or 664.9, e.g., by a mass spectrometry assay. In embodiments, the fusogen has (or is identified as having) a ratio to GAPDH of about 20-120, 40-100, 50-90, 60-80, 65-75, 68-70, or 69.0, e.g., by a mass spectrometry assay. In embodiments, the fusogen has a ratio to CNX of about 200-900, 300-800, 400-700, 500-600, 520-590, 530-580, 540-570, 550-560, or 558.4, e.g., by a mass spectrometry assay. In embodiments, the mass spectrometry assay is an assay of Example 162.

In some embodiments, the number of lipid species present in both of (e.g., shared between) the fusosomes and source cells is (or is identified as being) at least 300, 400, 500, 550, 560, or 569, or is between 500-700, 550-600, or 560-580, e.g., using a mass spectrometry assay. In embodiments, the number of lipid species present in fusosomes at a level at least 25% of the corresponding lipid level in the source cells (both normalized to total lipid levels within a sample) is (or is identified as being) at least 300, 400, 500, 530, 540, or 548, or is between 400-700, 500-600, 520-570, 530-560, or 540-550, e.g., using a mass spectrometry assay. In some embodiments, the fraction of lipid species present in both of (e.g., shared between) the fusosomes and source cells to total lipid species in the source cell is (or is identified as being) about 0.4-1.0, 0.5-0.9, 0.6-0.8, or 0.7, or at least 0.4, 0.5, 0.6, or 0.7, e.g., using a mass spectrometry assay. In some embodiments, the mass spectrometry assay is an assay of Example 154.

In some embodiments, the number of protein species present in both of (e.g., shared between) the fusosomes are source cells is (or is identified as being) at least 500, 1000, 1100, 1200, 1300, 1400, 1487, 1500, or 1600, or is (or is identified as being) between 1200-1700, 1300-1600, 1400-1500, 1450-1500, or 1480-1490, e.g., using a mass spectrometry assay. In embodiments, the number of protein species present in fusosomes at a level at least 25% of the corresponding protein level in the source cells (both normalized to total protein levels within a sample) is (or is identified as being) at least 500, 600, 700, 800, 900, 950, 957, 1000, or 1200, e.g., using a mass spectrometry assay. In some embodiments, the fraction of protein species present in both of (e.g., shared between) the fusosomes and source cells to total protein species in the source cell is (or is identified as being) about 0.1-0.6, 0.2-0.5, 0.3-0.4, or 0.333, or at least about 0.1, 0.2, 0.3, 0.333, or 0.4, e.g., using a mass spectrometry assay. In embodiments, the mass spectrometry assay is an assay of Example 155.

In some embodiments, CD63 is (or is identified as being) present at less than 0.048%, 0.05%, 0.1%, 0.5%, 1%, 2%, 3%, 4%, 5%, or 10% the amount of total protein in fusosomes, e.g., by a mass spectrometry assay, e.g., an assay of Example 157.

In some embodiments, the fusosomes are produced by extrusion through a filter, e.g., a filter of about 1-10, 2-8, 3-7, 4-6, or 5 um. In some embodiments, the fusosomes have (or is identified as having) an average diameter of about 1-5, 2-5, 3-5, 4-5, or 5 um. In some embodiments, the fusosomes have (or is identified as having) an average diameter of at least 1, 2, 3, 4, or 5 um.

In some embodiments, the fusosomes are enriched for (or are identified as being enriched for) one or more of (e.g., at least 2, 3, 4, 5, or all of) the following lipids compared to the source cells: cholesteryl ester, free cholesterol, ether-linked lyso-phosphatidylethanolamine, lyso-phosphatidylserine, phosphatidate, ether-linked phosphatidylethanolamine, phosphatidylserine, and sphingomyelin. In some embodiments, the fusosomes are depleted for (or are identified as being depleted for) one or more of (e.g., at least 2, 3, 4, 5, or all of) the following lipids compared to the source cells: ceramide, cardiolipin, lyso-phosphatidylcholine, lyso-phosphatidylethanolamine, lyso-phosphatidylglycerol, lyso-phosphatidylinositol, ether-linked phosphatidylcholine, phosphatidylethanolamine, phosphatidylglycerol, phosphatidylinositol, and triacylglycerol. In some embodiments, the fusosomes are enriched for (or are identified as being enriched for) one or more of the aforementioned enriched lipids and depleted for one or more of the aforementioned depleted lipids. In some embodiments, the fusosomes comprise (or are identified as comprising) the enriched lipid as a percentage of total lipid that is at least 10%, 20%, 30%, 40%, 50%, 60%, 70%, 80%, 90%, 2-fold, 5-fold, or 10-fold greater than the corresponding level in source cells. In some embodiments, the fusosome comprise (or are identified as comprising) the depleted lipid as a percentage of total lipid at a level that is less than 90%, 80%, 70%, 60%, 50%, 40%, 30%, 20%, or 10% of the corresponding level in the source cells. In embodiments, lipid enrichment is measured by a mass spectrometry assay, e.g., an assay of Example 164.

In some embodiments, CE lipid levels are (or are identified as being) about 2-fold greater in fusosomes than in exosomes and/or about 5, 6, 7, 8, 9, or 10-fold higher in fusosomes than in parental cells (relative to total lipid in a sample). In some embodiments, ceramide lipid levels are (or are identified as being) about 2, 3, 4, or 5-fold greater in parental cells than in fusosomes (relative to total lipid in a sample). In some embodiments, cholesterol levels are (or are identified as being) about 1.1, 1.2, 1.3, 1.4, 1.5, 1.6, 1.7, 1.8, 1.9, or 2-fold greater in exosomes than in fusosomes and/or about 2-fold higher in fusosomes than in parental cells (relative to total lipid in a sample). In some embodiments, CL lipid levels are (or are identified as being) at least about 5, 10, 20, 30, or 40-fold greater in parental cells than in fusosomes (relative to total lipid in a sample). In some embodiments, DAG lipid levels are (or are identified as being) about 2 or 3-fold greater in exosomes than in fusosomes and/or about 1.5 or 2-fold higher in parental cells than in fusosomes (relative to total lipid in a sample). In some embodiments, PC lipid levels are (or are identified as being) about equal between exosomes and fusosomes and/or about 1.3, 1.4, 1.5, 1.6, 1.7, or 1.8-fold higher in parental cells than in fusosomes (relative to total lipid in a sample). In some embodiments, PC O-lipid levels are (or are identified as being) about equal between exosomes and fusosomes and/or about 2-fold higher in parental cells than in fusosomes (relative to total lipid in a sample). In some embodiments, PE lipid levels are (or are identified as being) about 1.3, 1.4, 1.5, 1.6, 1.7, or 1.8-fold higher in fusosomes than in exosomes and/or about 1.3, 1.4, 1.5, 1.6, 1.7, or 1.8-fold higher in parental cells than in fusosomes (relative to total lipid in a sample). In some embodiments, PE O-lipid levels are (or are identified as being) about equal between exosomes and fusosomes and/or about 1.5, 1.6, 1.7, 1.8, 1.9, or 2-fold higher in parental cells than in fusosomes (relative to total lipid in a sample). In some embodiments, PG lipid levels are (or are identified as being) about equal between exosomes and fusosomes and/or about 2, 3, 4, 5, 6, 7, 8, 9, or 10-fold higher in parental cells than in fusosomes (relative to total lipid in a sample). In some embodiments, PI lipid levels are (or are identified as being) about equal between exosomes and fusosomes and/or about 3, 4, 5, 6, or 7-fold higher in parental cells than in fusosomes (relative to total lipid in a sample). In some embodiments, PS lipid levels are (or are identified as being) (or are identified as being) about equal between exosomes and fusosomes and/or about 2-fold higher in fusosomes than in parental cells (relative to total lipid in a sample). In some embodiments, SM lipid levels are (or are identified as being) about equal between exosomes and fusosomes and/or about 2, 2.5, or 3-fold higher in fusosomes than in parental cells (relative to total lipid in a sample). In some embodiments, TAG lipid levels are (or are identified as being) about equal between exosomes and fusosomes and/or about 10, 20, 30, 40, 50, 60, 70 80, 90, 100-fold, or more higher in parental cells than in fusosomes (relative to total lipid in a sample).

In some embodiments, the fusosomes are (or are identified as being) enriched for one or more of (e.g., at least 2, 3, 4, 5, or all of) the following lipids compared to exosomes: cholesteryl ester, ceramide, diacylglycerol, lyso-phosphatidate, and phosphatidylethanolamine, and triacylglycerol. In some embodiments, the fusosomes are (or are identified as being) depleted for one or more of (e.g., at least 2, 3, 4, 5, or all of) the following lipids compared to exosomes (relative to total lipid in a sample): free cholesterol, hexosyl ceramide, lyso-phosphatidylcholine, ether-linked lyso-phosphatidylcholine, lyso-phosphatidylethanolamine, ether-linked lyso-phosphatidylethanolamine, and lyso-phosphatidylserine. In some embodiments, the fusosomes are (or are identified as being) enriched for one or more of the aforementioned enriched lipids and depleted for one or more of the aforementioned depleted lipids. In some embodiments, the fusosomes comprise (or are identified as comprising) the enriched lipid as a percentage of total lipid that is at least 10%, 20%, 30%, 40%, 50%, 60%, 70%, 80%, 90%, 2-fold, 5-fold, or 10-fold greater than the corresponding level in exosomes. In some embodiments, the fusosome comprise (or are identified as comprising) the depleted lipid as a percentage of total lipid at a level that is less than 90%, 80%, 70%, 60%, 50%, 40%, 30%, 20%, or 10% of the corresponding level in exosomes. In embodiments, lipid enrichment is measured by a mass spectrometry assay, e.g., an assay of Example 164.

In some embodiments, ceramide lipid levels are (or are identified as being) about 2-fold higher in fusosomes than in exosomes and/or about 2-fold higher in parental cells than in fusosomes (relative to total lipid in a sample). In some embodiments, HexCer lipid levels are (or are identified as being) about 1.5, 1.6, 1.7, 1.8, 1.9, or 2-fold higher in exosomes than in fusosomes and/or about equal in parental cells and fusosomes (relative to total lipid in a sample). In some embodiments, LPA lipid levels are (or are identified as being) about 3 or 4-fold higher in fusosomes than in exosomes and/or about 1.3, 1.4, 1.5, 1.6, 1.7, or 1.8-fold higher in fusosomes than in parental cells (relative to total lipid in a sample). In some embodiments, LPC lipid levels are (or are identified as being) about 2-fold higher in exosomes than in fusosomes and/or about 1.5, 1.6, 1.7, 1.8, 1.9, or 2-fold higher in parental cells than in fusosomes (relative to total lipid in a sample). In some embodiments, LPC O-lipid levels are (or are identified as being) about 3 or 4-fold higher in exosomes than in fusosomes and/or about equal between parental cells and fusosomes (relative to total lipid in a sample). In some embodiments, LPE lipid levels are (or are identified as being) about 1.5, 1.6, 1.7, 1.8, 1.9, or 2-fold higher in exosomes than in fusosomes and/or about 1.5, 1.6, 1.7, 1.8, 1.9, or 2-fold higher in parental cells than in fusosomes (relative to total lipid in a sample). In some embodiments, LPE O-lipid levels are (or are identified as being) about 2 or 3-fold higher in exosomes than in fusosomes and/or about equal between parental cells and fusosomes (relative to total lipid in a sample). In some embodiments, LPS lipid levels are (or are identified as being) about 3-fold higher in exosomes than in fusosomes (relative to total lipid in a sample). In some embodiments, PA lipid levels are (or are identified as being) about 1.5, 1.6, 1.7, 1.8, 1.9, or 2-fold higher in fusosomes than in exosomes and/or about 2-fold higher in fusosomes than in parental cells (relative to total lipid in a sample). In some embodiments, PG lipid levels are (or are identified as being) about equal between fusosomes and exosomes and/or about 10, 11, 12, 13, 14, or 15-fold higher in parental cells than in fusosomes (relative to total lipid in a sample).

In some embodiments, the fusosome comprises a lipid composition substantially similar to that of the source cell or wherein one or more of CL, Cer, DAG, HexCer, LPA, LPC, LPE, LPG, LPI, LPS, PA, PC, PE, PG, PI, PS, CE, SM and TAG is within 10%, 15%, 20%, 25%, 30%, 35%, 40%, 45%, or 50% of the corresponding lipid level in the source cell. In embodiments, the lipid composition of fusosomes is similar to the cells from which they are derived. In embodiments, fusosomes and parental cells have (or are identified as having) a similar lipid composition if greater than or equal to about 50%, 55%, 60%, 65%, 70%, 75%, 80%, 85%, or 90% of the lipid species identified in any replicate sample of the parental cells are present (or are identified as being present) in any replicate sample of the fusosomes, e.g., as determined according to Example 154. In embodiments, of identified lipids, the average level in the fusosome is greater than about 10%, 15%, 20%, 25%, 30%, 35%, or 40% of the corresponding average lipid species level in the parental cell (relative to total lipid in a sample). In an embodiment, the lipid composition of the fusosome is enriched and/or depleted for specific lipids relative to the parental cell (relative to total lipid in a sample).

In some embodiments, the lipid composition of the fusosome is (or is identified as bring) enriched and/or depleted for specific lipids relative to the parental cell, e.g., as determined according to the method described in Example 164.

In some embodiments, the fusosome has (or is identified as having) a ratio of phosphatidylserine to total lipids that is greater than that of the parental cell. In embodiments, the fusosome has (or is identified as having) a ratio of phosphatidylserine to total lipids of about 110%, 115%, 120%, 121%, 122%, 123%, 124%, 125%, 130%, 135%, 140%, or more relative to that of the parental cell. In some embodiments, the fusosome is (or is identified as being) enriched for cholesteryl ester, free cholesterol, ether-linked lyso-phosphatidylethanolamine, lyso-phosphatidylserine, phosphatidate, ether-linked phosphatidylethanolamine, phosphatidylserine, and/or sphingomyelin relative to the parental cell. In some embodiments, the fusosomes is (or is identified as being) depleted for ceramide, cardiolipin, lyso-phosphatidylcholine, lyso-phosphatidylethanolamine, lyso-phosphatidylglycerol, lyso-phosphatidylinositol, ether-linked phosphatidylcholine, phosphatidylethanolamine, phosphatidylglycerol, phosphatidylinositol, and/or triacylglycerol relative to the parental cell. In some embodiments, the fusosome is (or is identified as being) enriched for cholesteryl ester, ceramide, diacylglycerol, lyso-phosphatidate, phosphatidylethanolamine, and/or triacylglycerol relative to an exosome. In some embodiments, the fusosome is (or is identified as being) depleted for free cholesterol, hexosyl ceramide, lyso-phosphatidylcholine, ether-linked lyso-phosphatidylcholine, lyso-phosphatidylethanolamine, ether-linked lyso-phosphatidylethanolamine, and/or lyso-phosphatidylserine relative to an exosome.

In some embodiments, the fusosome has a ratio of cardiolipin:ceramide that is within 10%, 20%, 30%, 40%, or 50% of the ratio of cardiolipin:ceramide in the source cell; or has a ratio of cardiolipin:diacylglycerol that is within 10%, 20%, 30%, 40%, or 50% of the ratio of cardiolipin:diacylglycerol in the source cell; or has a ratio of cardiolipin:hexosylceramide that is within 10%, 20%, 30%, 40%, or 50% of the ratio of cardiolipin:hexosylceramide in the source cell; or has a ratio of cardiolipin:lysophosphatidate that is within 10%, 20%, 30%, 40%, or 50% of the ratio of cardiolipin:lysophosphatidate in the source cell; or has a ratio of cardiolipin:lyso-phosphatidylcholine that is within 10%, 20%, 30%, 40%, or 50% of the ratio of cardiolipin:lyso-phosphatidylcholine in the source cell; or has a ratio of cardiolipin:lyso-phosphatidylethanolamine that is within 10%, 20%, 30%, 40%, or 50% of the ratio of cardiolipin:lyso-phosphatidylethanolamine in the source cell; or has a ratio of cardiolipin:lyso-phosphatidylglycerol that is within 10%, 20%, 30%, 40%, or 50% of the ratio of cardiolipin:

lyso-phosphatidylglycerol in the source cell; or has a ratio of cardiolipin:lyso-phosphatidylinositol that is within 10%, 20%, 30%, 40%, or 50% of the ratio of cardiolipin:lyso-phosphatidylinositol in the source cell; or has a ratio of cardiolipin:lyso-phosphatidylserine that is within 10%, 20%, 30%, 40%, or 50% of the ratio of cardiolipin:lyso-phosphatidylserine in the source cell; or has a ratio of cardiolipin:phosphatidate that is within 10%, 20%, 30%, 40%, or 50% of the ratio of cardiolipin:phosphatidate in the source cell; or has a ratio of cardiolipin:phosphatidylcholine that is within 10%, 20%, 30%, 40%, or 50% of the ratio of cardiolipin:phosphatidylcholine in the source cell; or has a ratio of cardiolipin:phosphatidylethanolamine that is within 10%, 20%, 30%, 40%, or 50% of the ratio of cardiolipin:phosphatidylethanolamine in the source cell; or has a ratio of cardiolipin:phosphatidylglycerol that is within 10%, 20%, 30%, 40%, or 50% of the ratio of cardiolipin:phosphatidylglycerol in the source cell; or has a ratio of cardiolipin:phosphatidylinositol that is within 10%, 20%, 30%, 40%, or 50% of the ratio of cardiolipin:phosphatidylinositol in the source cell; or has a ratio of cardiolipin:phosphatidylserine that is within 10%, 20%, 30%, 40%, or 50% of the ratio of cardiolipin:phosphatidylserine in the source cell; or has a ratio of cardiolipin:cholesterol ester that is within 10%, 20%, 30%, 40%, or 50% of the ratio of cardiolipin:cholesterol ester in the source cell; or has a ratio of cardiolipin:sphingomyelin that is within 10%, 20%, 30%, 40%, or 50% of the ratio of cardiolipin:sphingomyelin in the source cell; or has a ratio of cardiolipin:triacylglycerol that is within 10%, 20%, 30%, 40%, or 50% of the ratio of cardiolipin:triacylglycerol in the source cell; or has a ratio of phosphatidylcholine:ceramide that is within 10%, 20%, 30%, 40%, or 50% of the ratio of phosphatidylcholine:ceramide in the source cell; or has a ratio of phosphatidylcholine:diacylglycerol that is within 10%, 20%, 30%, 40%, or 50% of the ratio of phosphatidylcholine:diacylglycerol in the source cell; or has a ratio of phosphatidylcholine:hexosylceramide that is within 10%, 20%, 30%, 40%, or 50% of the ratio of phosphatidylcholine:hexosylceramide in the source cell; or has a ratio of phosphatidylcholine:lysophosphatidate that is within 10%, 20%, 30%, 40%, or 50% of the ratio of phosphatidylcholine:lysophosphatidate in the source cell; or has a ratio of phosphatidylcholine:lyso-phosphatidylcholine that is within 10%, 20%, 30%, 40%, or 50% of the ratio of phosphatidylcholine:lyso-phosphatidylcholine in the source cell; or has a ratio of phosphatidylcholine:lyso-phosphatidylethanolamine that is within 10%, 20%, 30%, 40%, or 50% of the ratio of phosphatidylcholine:lyso-phosphatidylethanolamine in the source cell; or has a ratio of phosphatidylcholine:lyso-phosphatidylglycerol that is within 10%, 20%, 30%, 40%, or 50% of the ratio of phosphatidylcholine:lyso-phosphatidylglycerol in the source cell; or has a ratio of phosphatidylcholine:lyso-phosphatidylinositol that is within 10%, 20%, 30%, 40%, or 50% of the ratio of phosphatidylcholine:lyso-phosphatidylinositol in the source cell; or has a ratio of phosphatidylcholine:lyso-phosphatidylserine that is within 10%, 20%, 30%, 40%, or 50% of the ratio of phosphatidylcholine:lyso-phosphatidylserine in the source cell; or has a ratio of phosphatidylcholine:phosphatidate that is within 10%, 20%, 30%, 40%, or 50% of the ratio of cardiolipin:phosphatidate in the source cell; or has a ratio of phosphatidylcholine:phosphatidylethanolamine that is within 10%, 20%, 30%, 40%, or 50% of the ratio of phosphatidylcholine:phosphatidylethanolamine in the source cell; or has a ratio of cardiolipin:phosphatidylglycerol that is within 10%, 20%, 30%, 40%, or 50% of the ratio of phosphatidylcholine:phosphatidylglycerol in the source cell; or has a ratio of phosphatidylcholine:phosphatidylinositol that is within 10%, 20%, 30%, 40%, or 50% of the ratio of phosphatidylcholine:phosphatidylinositol in the source cell; or has a ratio of phosphatidylcholine:phosphatidylserine that is within 10%, 20%, 30%, 40%, or 50% of the ratio of phosphatidylcholine:phosphatidylserine in the source cell; or has a ratio of phosphatidylcholine:cholesterol ester that is within 10%, 20%, 30%, 40%, or 50% of the ratio of phosphatidylcholine:cholesterol ester in the source cell; or has a ratio of phosphatidylcholine:sphingomyelin that is within 10%, 20%, 30%, 40%, or 50% of the ratio of phosphatidylcholine:sphingomyelin in the source cell; or has a ratio of phosphatidylcholine:triacylglycerol that is within 10%, 20%, 30%, 40%, or 50% of the ratio of phosphatidylcholine:triacylglycerol in the source cell; or has a ratio of phosphatidylethanolamine:ceramide that is within 10%, 20%, 30%, 40%, or 50% of the ratio of phosphatidylethanolamine:ceramide in the source cell; or has a ratio of phosphatidylethanolamine:diacylglycerol that is within 10%, 20%, 30%, 40%, or 50% of the ratio of phosphatidylethanolamine:diacylglycerol in the source cell; or has a ratio of phosphatidylethanolamine:hexosylceramide that is within 10%, 20%, 30%, 40%, or 50% of the ratio of phosphatidylethanolamine:hexosylceramide in the source cell; or has a ratio of phosphatidylethanolamine:lysophosphatidate that is within 10%, 20%, 30%, 40%, or 50% of the ratio of phosphatidylethanolamine:lysophosphatidate in the source cell; or has a ratio of phosphatidylethanolamine:lyso-phosphatidylcholine that is within 10%, 20%, 30%, 40%, or 50% of the ratio of phosphatidylethanolamine:lyso-phosphatidylcholine in the source cell; or has a ratio of phosphatidylethanolamine:lyso-phosphatidylethanolamine that is within 10%, 20%, 30%, 40%, or 50% of the ratio of phosphatidylethanolamine:lyso-phosphatidylethanolamine in the source cell; or has a ratio of phosphatidylethanolamine:lyso-phosphatidylglycerol that is within 10%, 20%, 30%, 40%, or 50% of the ratio of phosphatidylethanolamine:lyso-phosphatidylglycerol in the source cell; or has a ratio of phosphatidylethanolamine:lyso-phosphatidylinositol that is within 10%, 20%, 30%, 40%, or 50% of the ratio of phosphatidylethanolamine:lyso-phosphatidylinositol in the source cell; or has a ratio of phosphatidylethanolamine:lyso-phosphatidylserine that is within 10%, 20%, 30%, 40%, or 50% of the ratio of phosphatidylethanolamine:lyso-phosphatidylserine in the source cell; or has a ratio of phosphatidylethanolamine:phosphatidate that is within 10%, 20%, 30%, 40%, or 50% of the ratio of phosphatidylethanolamine:phosphatidate in the source cell; or has a ratio of phosphatidylethanolamine:phosphatidylglycerol that is within 10%, 20%, 30%, 40%, or 50% of the ratio of phosphatidylethanolamine:phosphatidylglycerol in the source cell; or has a ratio of phosphatidylethanolamine:phosphatidylinositol that is within 10%, 20%, 30%, 40%, or 50% of the ratio of phosphatidylethanolamine:phosphatidylinositol in the source cell; or has a ratio of phosphatidylethanolamine:phosphatidylserine that is within 10%, 20%, 30%, 40%, or 50% of the ratio of phosphatidylethanolamine:phosphatidylserine in the source cell; or has a ratio of phosphatidylethanolamine:cholesterol ester that is within 10%, 20%, 30%, 40%, or 50% of the ratio of phosphatidylethanolamine:cholesterol ester in the source cell; or has a ratio of phosphatidylethanolamine:sphingomyelin that is within 10%, 20%, 30%, 40%, or 50% of the ratio of phosphatidylethanolamine:sphingomyelin in the source cell; or has a ratio of phosphatidylethanolamine:triacylglycerol that is within 10%, 20%, 30%, 40%, or 50% of the ratio of phosphatidylethanolamine:triacylglycerol in the source cell;

or has a ratio of phosphatidylserine:ceramide that is within 10%, 20%, 30%, 40%, or 50% of the ratio of phosphatidylserine:ceramide in the source cell; or has a ratio of phosphatidylserine:diacylglycerol that is within 10%, 20%, 30%, 40%, or 50% of the ratio of phosphatidylserine:diacylglycerol in the source cell; or has a ratio of phosphatidylserine:hexosylceramide that is within 10%, 20%, 30%, 40%, or 50% of the ratio of phosphatidylserine:hexosylceramide in the source cell; or has a ratio of phosphatidylserine:lysophosphatidate that is within 10%, 20%, 30%, 40%, or 50% of the ratio of phosphatidylserine:lysophosphatidate in the source cell; or has a ratio of phosphatidylserine:lyso-phosphatidylcholine that is within 10%, 20%, 30%, 40%, or 50% of the ratio of phosphatidylserine:lyso-phosphatidylcholine in the source cell; or has a ratio of phosphatidylserine:lyso-phosphatidylethanolamine that is within 10%, 20%, 30%, 40%, or 50% of the ratio of phosphatidylserine:lyso-phosphatidylethanolamine in the source cell; or has a ratio of phosphatidylserine:lyso-phosphatidylglycerol that is within 10%, 20%, 30%, 40%, or 50% of the ratio of phosphatidylserine:lyso-phosphatidylglycerol in the source cell; or has a ratio of phosphatidylserine:lyso-phosphatidylinositol that is within 10%, 20%, 30%, 40%, or 50% of the ratio of phosphatidylserine:lyso-phosphatidylinositol in the source cell; or has a ratio of phosphatidylserine:lyso-phosphatidylserine that is within 10%, 20%, 30%, 40%, or 50% of the ratio of phosphatidylserine:lyso-phosphatidylserine in the source cell; or has a ratio of phosphatidylserine:phosphatidate that is within 10%, 20%, 30%, 40%, or 50% of the ratio of phosphatidylserine:phosphatidate in the source cell; or has a ratio of phosphatidylserine:phosphatidylglycerol that is within 10%, 20%, 30%, 40%, or 50% of the ratio of phosphatidylserine:phosphatidylglycerol in the source cell; or has a ratio of phosphatidylserine:phosphatidylinositol that is within 10%, 20%, 30%, 40%, or 50% of the ratio of phosphatidylserine:phosphatidylinositol in the source cell; or has a ratio of phosphatidylserine:cholesterol ester that is within 10%, 20%, 30%, 40%, or 50% of the ratio of phosphatidylserine:cholesterol ester in the source cell; or has a ratio of phosphatidylserine:sphingomyelin that is within 10%, 20%, 30%, 40%, or 50% of the ratio of phosphatidylserine:sphingomyelin in the source cell; or has a ratio of phosphatidylserine:triacylglycerol that is within 10%, 20%, 30%, 40%, or 50% of the ratio of phosphatidylserine:triacylglycerol in the source cell; or has a ratio of sphingomyelin:ceramide that is within 10%, 20%, 30%, 40%, or 50% of the ratio of sphingomyelin:ceramide in the source cell; or has a ratio of sphingomyelin:diacylglycerol that is within 10%, 20%, 30%, 40%, or 50% of the ratio of sphingomyelin:diacylglycerol in the source cell; or has a ratio of sphingomyelin:hexosylceramide that is within 10%, 20%, 30%, 40%, or 50% of the ratio of sphingomyelin:hexosylceramide in the source cell; or has a ratio of sphingomyelin:lysophosphatidate that is within 10%, 20%, 30%, 40%, or 50% of the ratio of sphingomyelin:lysophosphatidate in the source cell; or has a ratio of sphingomyelin:lyso-phosphatidylcholine that is within 10%, 20%, 30%, 40%, or 50% of the ratio of sphingomyelin:lyso-phosphatidylcholine in the source cell; or has a ratio of sphingomyelin:lyso-phosphatidylethanolamine that is within 10%, 20%, 30%, 40%, or 50% of the ratio of sphingomyelin:lyso-phosphatidylethanolamine in the source cell; or has a ratio of sphingomyelin:lyso-phosphatidylglycerol that is within 10%, 20%, 30%, 40%, or 50% of the ratio of sphingomyelin:lyso-phosphatidylglycerol in the source cell; or has a ratio of sphingomyelin:lyso-phosphatidylinositol that is within 10%, 20%, 30%, 40%, or 50% of the ratio of sphingomyelin:lyso-phosphatidylinositol in the source cell; or has a ratio of sphingomyelin:lyso-phosphatidylserine that is within 10%, 20%, 30%, 40%, or 50% of the ratio of sphingomyelin:lyso-phosphatidylserine in the source cell; or has a ratio of sphingomyelin:phosphatidate that is within 10%, 20%, 30%, 40%, or 50% of the ratio of sphingomyelin:phosphatidate in the source cell; or has a ratio of sphingomyelin:phosphatidylglycerol that is within 10%, 20%, 30%, 40%, or 50% of the ratio of sphingomyelin:phosphatidylglycerol in the source cell; or has a ratio of sphingomyelin:phosphatidylinositol that is within 10%, 20%, 30%, 40%, or 50% of the ratio of sphingomyelin:phosphatidylinositol in the source cell; or has a ratio of sphingomyelin:cholesterol ester that is within 10%, 20%, 30%, 40%, or 50% of the ratio of sphingomyelin:cholesterol ester in the source cell; or has a ratio of sphingomyelin:triacylglycerol that is within 10%, 20%, 30%, 40%, or 50% of the ratio of sphingomyelin:triacylglycerol in the source cell; or has a ratio of cholesterol ester:ceramide that is within 10%, 20%, 30%, 40%, or 50% of the ratio of cholesterol ester:ceramide in the source cell; or has a ratio of cholesterol ester:diacylglycerol that is within 10%, 20%, 30%, 40%, or 50% of the ratio of cholesterol ester:diacylglycerol in the source cell; or has a ratio of cholesterol ester:hexosylceramide that is within 10%, 20%, 30%, 40%, or 50% of the ratio of cholesterol ester:hexosylceramide in the source cell; or has a ratio of cholesterol ester:lysophosphatidate that is within 10%, 20%, 30%, 40%, or 50% of the ratio of cholesterol ester:lysophosphatidate in the source cell; or has a ratio of cholesterol ester:lyso-phosphatidylcholine that is within 10%, 20%, 30%, 40%, or 50% of the ratio of cholesterol ester:lyso-phosphatidylcholine in the source cell; or has a ratio of cholesterol ester:lyso-phosphatidylethanolamine that is within 10%, 20%, 30%, 40%, or 50% of the ratio of cholesterol ester:lyso-phosphatidylethanolamine in the source cell; or has a ratio of cholesterol ester:lyso-phosphatidylglycerol that is within 10%, 20%, 30%, 40%, or 50% of the ratio of cholesterol ester:lyso-phosphatidylglycerol in the source cell; or has a ratio of cholesterol ester:lyso-phosphatidylinositol that is within 10%, 20%, 30%, 40%, or 50% of the ratio of cholesterol ester:lyso-phosphatidylinositol in the source cell; or has a ratio of cholesterol ester:lyso-phosphatidylserine that is within 10%, 20%, 30%, 40%, or 50% of the ratio of cholesterol ester:lyso-phosphatidylserine in the source cell; or has a ratio of cholesterol ester:phosphatidate that is within 10%, 20%, 30%, 40%, or 50% of the ratio of cholesterol ester:phosphatidate in the source cell; or has a ratio of cholesterol ester:phosphatidylglycerol that is within 10%, 20%, 30%, 40%, or 50% of the ratio of cholesterol ester:phosphatidylglycerol in the source cell; or has a ratio of cholesterol ester:phosphatidylinositol that is within 10%, 20%, 30%, 40%, or 50% of the ratio of cholesterol ester:phosphatidylinositol in the source cell; or has a ratio of cholesterol ester:triacylglycerol that is within 10%, 20%, 30%, 40%, or 50% of the ratio of cholesterol ester:triacylglycerol in the source cell.

In some embodiments, the fusosome comprises a proteomic composition similar to that of the source cell, e.g., using an assay of Example 42 or 155. In some embodiments, the protein composition of fusosomes are similar to the parental cells from which they are derived. In some embodiments, the fractional content of each of a plurality of categories of proteins is determined as the sum of intensity signals from each category divided by the sum of the intensity signals of all identified proteins in the sample, e.g., as described in Example 155. In some embodiments, the fusosome comprises (or is identified as comprising) varying amounts of compartment-specific proteins relative to parental cells and/or exosomes, e.g., as determined according to the method described in Example 165. In some embodiments, fusosomes are (or are identified as being) depleted with endoplasmic reticulum protein compared to parental cells and exosomes. In some embodiments, fusosomes are (or are identified as being) depleted for exosomal protein compared to exosomes. In some embodiments, fusosomes have (or are identified as having) less than 15%, 20%, or 25% of the protein in the fusosome as being exosomal protein. In some embodiments, fusosomes are (or are identified as being) depleted for mitochondrial protein compared to parental cells. In some embodiments, fusosomes are (or are identified as being) enriched for nuclear protein compared to parental cells. In some embodiments, fusosomes are (or are identified as being) enriched for ribosomal proteins compared to parental cells and exosomes. In some embodiments, at least 0.025%, 0.03%, 0.04%, 0.05%, 0.06%, 0.07%, 0.08%, 0.09%, 0.1%, 1%, 2%, 3%, 4%, 5%, 6%, 7% 8%, 9% or 10% of the protein in the fusosome is ribosomal protein, or about 0.025-0.2%, 0.05-0.15%, 0.06-1.4%, 0.07%-1.3%, 0.08%-1.2%, 0.09%-1.1%, 1%-20%, 3%-15%, 5%-12.5%, 7.5%-11%, or 8.5%-10.5%, or 9%-10% of the protein in the fusosome is ribosomal protein.

In some embodiments, the fusosome comprises a ratio of lipids to proteins that is within 10%, 20%, 30%, 40%, or 50% of the corresponding ratio in the source cell, e.g., as measured using an assay of Example 49. In embodiments, the fusosome comprises (or is identified as comprising) a ratio of lipid mass to proteins approximately equal to the lipid mass to protein ratio for nucleated cells. In embodiments, the fusosome comprises (or is identified as comprising) a greater lipid:protein ratio than the parental cell. In embodiments, the fusosome comprises (or is identified as comprising) a lipid:protein ratio of about 110%, 115%, 120%, 125%, 130%, 131%, 132%, 132.5%, 133%, 134%, 135%, 140%, 145%, or 150% of the lipid:protein ratio of the parental cell. In some embodiments, the fusosome or fusosome composition has (or is identified as having) a phospholipid:protein ratio of about 100-180, 110-170, 120-160, 130-150, 135-145, 140-142, or 141 µmol/g, e.g., in an assay of Example 150. In some embodiments, the fusosome or fusosome composition has (or is identified as having) a phospholipid:protein ratio that is about 60-90%, 70-80%, or 75% of the corresponding ratio in the source cells, e.g., in an assay of Example 150.

In some embodiments, the fusosome comprises a ratio of proteins to nucleic acids (e.g., DNA or RNA) that is within 10%, 20%, 30%, 40%, or 50% of the corresponding ratio in the source cell, e.g., as measured using an assay of Example 50. In embodiments, the fusosome comprises (or is identified as comprising) a ratio of protein mass to DNA mass similar to that of a parental cell. In embodiments, the fusosome comprises (or is identified as comprising) a ratio of protein:DNA that is about 85%, 90%, 95%, 96%, 97%, 98%, 98.2%, 99%, 100%, 101%, 102%, 103%, 104%, 105%, or 110% of the parental cell. In some embodiments, the fusosome comprises a ratio of proteins to DNA that is greater than the corresponding ratio in the source cell, e.g., at least 10%, 20%, 30%, 40%, 50%, 60%, 70%, 80%, or 90% greater, e.g., as measured using an assay of Example 50. In some embodiments, the fusosome or fusosome composition comprises (or is identified as comprising) a ratio of protein:DNA that is about 20-35, 25-30, 26-29, 27-28, or 27.8 g/g, e.g., by an assay of Example 151. In some embodiments, the fusosome or fusosome composition comprises (or is identified as comprising) a ratio of protein:DNA that is within about 1%, 2%, 5%, 10%, or 20% of the corresponding ratio in the source cells, e.g., by an assay of Example 151.

In some embodiments, the fusosome comprises a ratio of lipids to nucleic acids (e.g., DNA) that is within 10%, 20%, 30%, 40%, or 50% of the corresponding ratio in the source cell, e.g., as measured using an assay of Example 51 or 159. In some embodiments, the fusosome or fusosome composition comprises (or is identified as comprising) a ratio of lipids:DNA that is about 2.0-6.0, 3.0-5.0, 3.5-4.5, 3.8-4.0, or 3.92 µmol/mg, e.g., by an assay of Example 152. In some embodiments, the fusosome comprises a ratio of lipids to nucleic acids (e.g., DNA) that is greater than the corresponding ratio in the source cell, e.g., at least 10%, 20%, 30%, 40%, 50%, 60%, 70%, 80%, or 90% greater, e.g., as measured using an assay of Example 51 or 159. In embodiments, the fusosome comprises (or is identified as comprising) a greater lipid:DNA ratio than the parental cell. In embodiments, the fusosome comprises about a 105%, 110%, 115%, 120%, 125%, 130%, 135%, 140%, 145%, 150%, or greater lipid:DNA ratio compared to the parental cell.

In some embodiments, the fusosome composition has a half-life in a subject, e.g., in a mouse, that is within 1%, 2%, 3%, 4%, 5%, 10%, 20%, 30%, 40%, 50%, 60%, 70%, 80%, 90%, 100% of the half life of a reference cell composition, e.g., the source cell, e.g., by an assay of Example 75. In some embodiments, the fusosome composition has a half-life in a subject, e.g., in a mouse, that is at least 1 hour, 2 hours, 3 hours, 4 hours, 5 hours, 6 hours, 12 hours, or 24 hours, e.g., in a human subject or in a mouse, e.g., by an assay of Example 75. In embodiments, the fusosome composition has a half-life of at least 1, 2, 4, 6, 12, or 24 hours in a subject, e.g., in an assay of Example 134. In some embodiments, the therapeutic agent has a half-life in a subject that is longer than the half-life of the fusosome composition, e.g., by at least 10%, 20%, 50%, 2-fold, 5-fold, or 10-fold. For instance, the fusosome may deliver the therapeutic agent to the target cell, and the therapeutic agent may be present after the fusosome is no longer present or detectable.

In some embodiments, the fusosome transports glucose (e.g., labeled glucose, e.g., 2-NBDG) across a membrane, e.g., by at least 1%, 2%, 3%, 4%, 5%, 10%, 20%, 30%, 40%, 50%, 60%, 70%, 80%, 90%, 100% more than a negative control, e.g., an otherwise similar fusosome in the absence of glucose, e.g., as measured using an assay of Example 64. In some embodiments, the fusosome transports (or is identified as transporting) glucose (e.g., labeled glucose, e.g., 2-NBDG) across a membrane at a greater level than otherwise similar fusosomes treated with phloretin, e.g., in an assay of Example 126. In embodiments, a fusosome not treated with phloretin transports (or is identified as not transporting) glucose at a level at least 1%, 2%, 3%, 5%, or 10% higher (and optionally up to 15% higher) than an otherwise similar fusosome treated with phloretin, e.g., in an assay of Example 126. In some embodiments, the fusosome comprises esterase activity in the lumen that is within 1%, 2%, 3%, 4%, 5%, 10%, 20%, 30%, 40%, 50%, 60%, 70%, 80%, 90%, or 100% of that of the esterase activity in a reference cell, e.g., the source cell or a mouse embryonic fibroblast, e.g., using an assay of Example 66. In some embodiments, the fusosome comprises (or is identified as comprising) esterase activity in the lumen that is at least 10-fold, 20-fold, 50-fold, 100-fold, 200-fold, 500-fold, 1000-fold, 2000-fold, or 5000-fold higher than an unstained control, e.g., by an assay of Example 127. In some embodiments, the fusosome comprises (or is identified as comprising) esterase activity in the lumen that is about 10-100-fold lower than that of the source cells, e.g., by an assay of Example 127. In some embodiments, the fusosome comprises (or is identified as comprising) an acetylcholinesterase activity of about 1E5-1E6, 6E5-8E5, 6.5E5-7E5, or 6.83E5 exosome equivalents, e.g., by an assay of Example 128. In some embodiments, the fusosome comprises a metabolic activity level (e.g., citrate synthase activity) that is within 1%, 2%, 3%, 4%, 5%, 10%, 20%, 30%, 40%, 50%, 60%, 70%, 80%, 90%, or 100% of the metabolic activity level in a reference cell, e.g., the source cell, e.g., as described in Example 68. In some embodiments, the fusosome comprises a metabolic activity level (e.g., citrate synthase activity) that is at least 1%, 2%, 3%, 4%, 5%, 10%, 20%, 30%, 40%, 50%, 60%, 70%, 80%, 90%, or 100% of the metabolic activity level in a reference cell, e.g., the source cell, e.g., as described in Example 68. In some embodiments, the fusosome comprises (or is identified as comprising) a citrate synthase activity that is about 1E-2-2 E-2, 1.3E-2-1.8E-2, 1.4E-2-1.7E-2, 1.5E-2-1.6E-2, or 1.57E-2 umol/ug fusosome/min, e.g., by an assay of Example 129. In some embodiments, the fusosome comprises a respiration level (e.g., oxygen consumption rate), e.g., basal, uncoupled, or maximal respiration level, that is within 1%, 2%, 3%, 4%, 5%, 10%, 20%, 30%, 40%, 50%, 60%, 70%, 80%, 90%, or 100% of the respiration level in a reference cell, e.g., the source cell, e.g., as described in Example 69. In some embodiments, the fusosome comprises a respiration level (e.g., oxygen consumption rate), e.g., basal, uncoupled, or maximal respiration level, that is at least 1%, 2%, 3%, 4%, 5%, 10%, 20%, 30%, 40%, 50%, 60%, 70%, 80%, 90%, or 100% of the respiration level in a reference cell, e.g., the source cell, e.g., as described in Example 69. In embodiments, the fusosome comprises (or is identified as comprising) a basal respiration rate of about 8-15, 9-14, 10-13, 11-12, or 11.3 pmol/min/20 µg fusosome, e.g., by an assay of Example 130. In embodiments, the fusosome comprises (or is identified as comprising) an uncoupled respiration rate of about 8-13, 9-12, 10-11, 10-10.2, or 10.1 pmol/min/20 µg fusosome, e.g., by an assay of Example 130. In embodiments, the fusosome comprises (or is identified as comprising) a maximal respiration rate of about 15-25, 16-24, 17-23, 18-22, 19-21, or 20 pmol/min/20 µg fusosome, e.g., by an assay of Example 130. In embodiments, the fusosome has (or is identified as having) a higher basal respiration rate than uncoupled respiration rate, e.g., by about 1%, 2%, 5%, or 10%, e.g., up to about 15%, e.g., by an assay of Example 130. In embodiments, the fusosome has (or is identified as having) a higher maximal respiration rate than basal respiration rate, e.g., by about 1%, 2%, 5%, 10%, 20%, 30%, 40%, 50%, 60%, 70%, 80%, or 90%, e.g., by an assay of Example 130. In some embodiments, the fusosome comprises an Annexin-V staining level of at most 18,000, 17,000, 16,000, 15,000, 14,000, 13,000, 12,000, 11,000, or 10,000 MFI, e.g., using an assay of Example 70, or wherein the fusosome comprises an Annexin-V staining level at least 5%, 10%, 20%, 30%, 40%, 50%, 60%, 70%, 80%, or 90% lower than the Annexin-V staining level of an otherwise similar fusosome treated with menadione in the assay of Example 70, or wherein the fusosome comprises an Annexin-V staining level at least 5%, 10%, 20%, 30%, 40%, 50%, 60%, 70%, 80%, or 90% lower than the Annexin-V staining level of a macrophage treated with menadione in the assay of Example 70. In embodiments, the fusosome comprises (or is identified as comprising) an Annexin V-staining level that is at least about 1%, 2%, 5%, or 10% lower than the Annexin V-staining level of an otherwise similar fusosome treated with antimycin A, e.g., in an assay of Example 131. In embodiments, the fusosome comprises (or is identified as comprising) an Annexin V-staining level that is within about 1%, 2%, 5%, or 10% of the Annexin V-staining level of an otherwise similar fusosome treated with antimycin A, e.g., in an assay of Example 131.

In some embodiments, the fusosome has a miRNA content level of at least at least 1%, 2%, 3%, 4%, 5%, 10%, 20%, 30%, 40%, 50%, 60%, 70%, 80%, 90%, or greater than that of the source cell, e.g., by an assay of Example 39. In some embodiments, the fusosome has a miRNA content level of at least 1%, 2%, 3%, 4%, 5%, 10%, 20%, 30%, 40%, 50%, 60%, 70%, 80%, 90%, or greater of the miRNA content level of the source cell (e.g., up to 100% of the miRNA content level of the source cell), e.g., by an assay of Example 39. In some embodiments, the fusosome has a total RNA content level of at least 1%, 2%, 3%, 4%, 5%, 10%, 20%, 30%, 40%, 50%, 60%, 70%, 80%, 90%, or greater of the total RNA content level of the source cell (e.g., up to 100% of the total RNA content level of the source cell), e.g., as measured by an assay of Example 108.

In some embodiments, the fusosome has a soluble: non-soluble protein ratio is within 1%, 2%, 3%, 4%, 5%, 10%, 20%, 30%, 40%, 50%, 60%, 70%, 80%, 90%, or greater than that of the source cell, e.g., within 1%-2%, 2%-3%, 3%-4%, 4%-5%, 5%-10%, 10%-20%, 20%-30%, 30%-40%, 40%-50%, 50%-60%, 60%-70%, 70%-80%, or 80%-90% of that of the source cell, e.g., by an assay of Example 47. In embodiments, the fusosome has a soluble: non-soluble protein ratio of about 0.3-0.8, 0.4-0.7, or 0.5-0.6, e.g., about 0.563, e.g., by an assay of Example 47. In some embodiments, the population of fusosomes has (or is identified as having) a soluble:insoluble protein mass ratio of about 0.3-0.8, 0.4-0.7, 0.5-0.6, or 0.563, or greater than about 0.1, 0.2, 0.3, 0.4, or 0.5. In some embodiments, the population of fusosomes has (or is identified as having) a soluble:insoluble protein mass ratio that is greater than that of the source cells, e.g., at least 2-fold, 3-fold, 4-fold, 5-fold, 10-fold, or 20-fold higher. In embodiments, the soluble:insoluble protein mass ratio is determined by an assay of Example 123. In embodiments, the soluble: insoluble protein mass ratio is (or is identified as being) lower in the fusosome population than in the parental cells. In embodiments, when the ratio of fusosomes to parental cells is (or is identified as being) about 3%, 4%, 5%, 6%, 7%, or 8%, the soluble: insoluble ratio of the population of fusosomes is (or is identified as being) about equal to the soluble: insoluble ratio of the parental cells.

In some embodiments, the fusosome has an LPS level less than 5%, 1%, 0.5%, 0.01%, 0.005%, 0.0001%, 0.00001% or less of the LPS content of the source cell, e.g., as measured by mass spectrometry, e.g., in an assay of Example 48. In some embodiments, the fusosome is capable of signal transduction, e.g., transmitting an extracellular signal, e.g., AKT phosphorylation in response to insulin, or glucose (e.g., labeled glucose, e.g., 2-NBDG) uptake in response to insulin, e.g., by at least 1%, 2%, 3%, 4%, 5%, 10%, 20%, 30%, 40%, 50%, 60%, 70%, 80%, 90%, 100% more than a negative control, e.g., an otherwise similar fusosome in the absence of insulin, e.g., using an assay of Example 63. In some embodiments, the fusosome targets a tissue, e.g., liver, lungs, heart, spleen, pancreas, gastrointestinal tract, kidney, testes, ovaries, brain, reproductive organs, central nervous system, peripheral nervous system, skeletal muscle, endothelium, inner ear, or eye, when administered to a subject, e.g., a mouse, e.g., wherein at least 0.1%, 0.5%, 1%, 1.5%, 2%, 2.5%, 3%, 4%, 5%, 10%, 15%, 20%, 25%, 30%, 35%, 40%, 50%, 60%, 70%, 80%, or 90% of the fusosomes in a population of administered fusosomes are present in the target tissue after 24, 48, or 72 hours, e.g., by an assay of Example 87 or 100. In some embodiments, the fusosome has a juxtacrine-signaling level of at least 1%, 2%, 3%, 4%, 5%, 10%, 20%, 30%, 40%, 50%, 60%, 70%, 80%, 90%, or 100% greater than the level of juxtacrine signaling induced by a reference cell, e.g., the source cell or a bone marrow stromal cell (BMSC), e.g., by an assay of Example 71. In some embodiments, the fusosome has a juxtacrine-signaling level of at least 1%, 2%, 3%, 4%, 5%, 10%, 20%, 30%, 40%, 50%, 60%, 70%, 80%, or 90% (e.g., up to 100%) of the level of juxtacrine signaling induced by a reference cell, e.g., the source cell or a bone marrow stromal cell (BMSC), e.g., by an assay of Example 71. In some embodiments, the fusosome has a paracrine-signaling level of at least 1%, 2%, 3%, 4%, 5%, 10%, 20%, 30%, 40%, 50%, 60%, 70%, 80%, 90%, 100% greater than the level of paracrine signaling induced by a reference cell, e.g., the source cell or a macrophage, e.g., by an assay of Example 72. In some embodiments, the fusosome has a paracrine-signaling level of at least 1%, 2%, 3%, 4%, 5%, 10%, 20%, 30%, 40%, 50%, 60%, 70%, 80%, or 90% (e.g., up to 100%) of the level of paracrine signaling induced by a reference cell, e.g., the source cell or a macrophage, e.g., by an assay of Example 72. In some embodiments, the fusosome polymerizes actin at a level within 1%, 2%, 3%, 4%, 5%, 10%, 20%, 30%, 40%, 50%, 60%, 70%, 80%, 90%, or 100% compared to the level of polymerized actin in a reference cell, e.g., the source cell or a C2Cl2 cell, e.g., by the assay of Example 73. In some embodiments, the fusosome polymerizes actin (or is identified as polymerizing actin) at a level that is constant over time, e.g, over at least 3, 5, or 24 hours, e.g., by an assay of Example 147. In embodiments, the level of actin polymerization changes by less than 1%, 2%, 5%, 10%, or 20% over a 5-hour period, e.g. by the assay of Example 147. In some embodiments, the fusosome has a membrane potential within about 1%, 2%, 3%, 4%, 5%, 10%, 20%, 30%, 40%, 50%, 60%, 70%, 80%, 90%, 100% of the membrane potential of a reference cell, e.g., the source cell or a C2Cl2 cell, e.g., by an assay of Example 74, or wherein the fusosome has a membrane potential of about −20 to −150 mV, −20 to −50 mV, −50 to −100 mV, or −100 to −150 mV, or wherein the fusosome has a membrane potential of less than −1 mv, −5 mv, −10 mv, −20 mv, −30 mv, −40 mv, −50 mv, −60 mv, −70 mv, −80 mv, −90 mv, −100 mv. In some embodiments, the fusosome has (or is identified as having) a membrane potential of about −25 to −35, −27 to −32, −28 to −31, −29 to −30, or −29.6 millivolts, e.g., in an assay of Example 132. In some embodiments, the fusosome is capable of extravasation from blood vessels, e.g., at a rate at least 1%, 2%, 5%, 10%, 20%, 30%, 40%, 50%, 60%, 70%, 80%, or 90% the rate of extravasation of the source cell, e.g., using an assay of Example 57, e.g., wherein the source cell is a neutrophil, lymphocyte, B cell, macrophage, or NK cell. In some embodiments, the fusosome is capable of chemotaxis, e.g., of at least 1%, 2%, 3%, 4%, 5%, 10%, 20%, 30%, 40%, 50%, 60%, 70%, 80%, or 90% (e.g., up to 100%) compared to a reference cell, e.g., a macrophage, e.g., using an assay of Example 58. In some embodiments, the fusosome is capable of phagocytosis, e.g., at least 1%, 2%, 3%, 4%, 5%, 10%, 20%, 30%, 40%, 50%, 60%, 70%, 80%, or 90% (e.g., up to 100%) compared to a reference cell, e.g., a macrophage, e.g., using an assay of Example 60. In some embodiments, the fusosome is capable of crossing a cell membrane, e.g., an endothelial cell membrane or the blood brain barrier. In some embodiments, the fusosome is capable of secreting a protein, e.g., at a rate at least 1%, 2%, 3%, 4%, 5%, 10%, 20%, 30%, 40%, 50%, 60%, 70%, 80%, 90%, or 100% greater than a reference cell, e.g., a mouse embryonic fibroblast, e.g., using an assay of Example 62. In some embodiments, the fusosome is capable of secreting a protein, e.g., at a rate at least 1%, 2%, 3%, 4%, 5%, 10%, 20%, 30%, 40%, 50%, 60%, 70%, 80%, or 90% (e.g., up to 100%) compared to a reference cell, e.g., a mouse embryonic fibroblast, e.g., using an assay of Example 62.

In some embodiments, the fusosome is not capable of transcription or has transcriptional activity of less than 1%, 2.5% 5%, 10%, 20%, 30%, 40%, 50%, 60%, 70%, 80%, or 90% of that of the transcriptional activity of a reference cell, e.g., the source cell, e.g., using an assay of Example 19. In some embodiments, the fusosome is not capable of nuclear DNA replication or has nuclear DNA replication of less than 1%, 2.5% 5%, 10%, 20%, 30%, 40%, 50%, 60%, 70%, 80%, or 90% of the nuclear DNA replication of a reference cell, e.g., the source cell, e.g., using an assay of Example 20. In some embodiments, the fusosome lacks chromatin or has a chromatin content of less than 1%, 2.5% 5%, 10%, 20%, 30%, 40%, 50%, 60%, 70%, 80%, or 90% of the of the chromatin content of a reference cell, e.g., the source cell, e.g., using an assay of Example 37.

In some embodiments, a characteristic of a fusosome is described by comparison to a reference cell. In embodiments, the reference cell is the source cell. In embodiments, the reference cell is a HeLa, HEK293, HFF-1, MRC-5, WI-38, IMR 90, IMR 91, PER.C6, HT-1080, or BJ cell. In some embodiments, a characteristic of a population of fusosomes is described by comparison to a population of reference cells, e.g., a population of source cells, or a population of HeLa, HEK293, HFF-1, MRC-5, WI-38, IMR 90, IMR 91, PER.C6, HT-1080, or BJ cells.

In some embodiments, the fusosome meets a pharmaceutical or good manufacturing practices (GMP) standard. In some embodiments, the fusosome was made according to good manufacturing practices (GMP). In some embodiments, the fusosome has a pathogen level below a predetermined reference value, e.g., is substantially free of pathogens. In some embodiments, the fusosome has a contaminant level below a predetermined reference value, e.g., is substantially free of contaminants. In some embodiments, the fusosome has low immunogenicity, e.g., as described herein.

In some embodiments, immunogenicity of a fusosome composition is assayed by a serum inactivation assay (e.g., an assay that detects antibody-mediated neutralization or complement mediated degradation). In some embodiments, fusosomes are not inactivated by serum, or are inactivated at a level below a predetermined value. In some embodiments, serum of a fusosome-naïve subject (e.g., human or mouse) is contacted with a test fusosome composition. In some embodiments, the serum of a subject that has received one or more administrations of fusosomes, e.g., has received at least two administrations of fusosomes, is contacted with the test fusosome composition. In embodiments, serum-exposed fusosomes are then tested for ability to deliver a cargo to target cells. In some embodiments, the percent of cells that detectably comprise the cargo after treatment with serum-incubated fusosomes is at least 50%, 60%, 70%, 80%, 90%, or 95% the percent of cells that detectably comprise the cargo after treatment with positive control fusosomes not contacted with serum. In some embodiments, serum inactivation is measured using an assay of Example 168.

In some embodiments, immunogenicity of a fusosome composition is assayed by detecting complement activation in response to the fusosomes. In some embodiments, the fusosomes do not activate complement, or activate complement at a level below a predetermined value. In some embodiments, serum of a fusosome-naïve subject (e.g., human or mouse) is contacted with a test fusosome composition. In some embodiments, the serum of a subject that has received one or more administrations of fusosomes, e.g., has received at least two administrations of fusosomes, is contacted with the test fusosome composition. In embodiments, the composition comprising serum and fusosomes is then tested for an activated complement factor (e.g., C3a), e.g., by ELISA. In some embodiments, a fusosome comprising a modification described herein (e.g., elevated levels of a complement regulatory protein compared to a reference cell) undergoes reduced complement activation compared to an otherwise similar fusosome that lacks the modification, e.g., reduced by at least 5%, 10%, 20%, 30%, 40%, 50%, 60%, 70%, 80%, 90%, 95%, 98%, or 99%. In some embodiments, complement activation is measured using an assay of Example 169.

In some embodiments, a fusosome or population of fusosomes will not be substantially inactivated by serum. In some embodiments, a fusosome or population of fusosomes is resistant to serum inactivation, e.g., as quantified according to the method described in Example 167 or 168. In embodiments, the fusosome or population of fusosomes is not substantially inactivated by serum or is resistant to serum inactivation following multiple administrations of the fusosome or population of fusosomes to a subject, e.g., according to the methods described herein. In some embodiments, a fusosome is modified to have a reduced serum inactivation, e.g., compared to a corresponding unmodified fusosome, e.g., following multiple administrations of the modified fusosome, e.g., as quantified according to the method described in Example 167 or 168.

In some embodiments, a fusosome does not substantially induce complement activity, e.g., as measured according to the method described in Example 169. In some embodiments, a fusosome is modified to induce reduced complement activity compared to a corresponding unmodified fusosome. In embodiments, complement activity is measured by determining expression or activity of a complement protein (e.g., DAF, proteins that bind decay-accelerating factor (DAF, CD55), e.g., factor H (FH)-like protein-1 (FHL-1), C4b-binding protein (C4BP), complement receptor 1 (CD35), Membrane cofactor protein (MCP, CD46), Profectin (CD59), proteins that inhibit the classical and alternative complement pathway CD/C5 convertase enzymes, or proteins that regulate MAC assembly) in a cell In some embodiments, the source cell is an endothelial cell, a fibroblast, a blood cell (e.g., a macrophage, a neutrophil, a granulocyte, a leukocyte), a stem cell (e.g., a mesenchymal stem cell, an umbilical cord stem cell, bone marrow stem cell, a hematopoietic stem cell, an induced pluripotent stem cell e.g., an induced pluripotent stem cell derived from a subject's cells), an embryonic stem cell (e.g., a stem cell from embryonic yolk sac, placenta, umbilical cord, fetal skin, adolescent skin, blood, bone marrow, adipose tissue, erythropoietic tissue, hematopoietic tissue), a myoblast, a parenchymal cell (e.g., hepatocyte), an alveolar cell, a neuron (e.g., a retinal neuronal cell) a precursor cell (e.g., a retinal precursor cell, a myeloblast, myeloid precursor cells, a thymocyte, a meiocyte, a megakaryoblast, a promegakaryoblast, a melanoblast, a lymphoblast, a bone marrow precursor cell, a normoblast, or an angioblast), a progenitor cell (e.g., a cardiac progenitor cell, a satellite cell, a radial gial cell, a bone marrow stromal cell, a pancreatic progenitor cell, an endothelial progenitor cell, a blast cell), or an immortalized cell (e.g., HeLa, HEK293, HFF-1, MRC-5, WI-38, IMR 90, IMR 91, PER.C6, HT-1080, or BJ cell). In some embodiments, the source cell is other than a 293 cell, HEK cell, human endothelial cell, or a human epithelial cell, monocyte, macrophage, dendritic cell, or stem cell.

In some embodiments, the source cell expresses (e.g., overexpresses) ARRDC1 or an active fragment or variant thereof. In some embodiments, the fusosome or fusosome composition has a ratio of fusogen to ARRDC1 of about 1-3, 1-10, 1-100, 3-10, 4-9, 5-8, 6-7, 15-100, 60-200, 80-180, 100-160, 120-140, 3-100, 4-100, 5-100, 6-100, 15-100, 80-100, 3-200, 4-200, 5-200, 6-200, 15-200, 80-200, 100-200, 120-200, 300-1000, 400-900, 500-800, 600-700, 640-690, 650-680, 660-670, 100-10,000, or about 664.9, e.g., by a mass spectrometry assay. In some embodiments, the level of ARRDC1 as a percentage of total protein content is at least about 0.01%, 0.02%, 0.03%, 0.04%, 0.05%; 0.1%, 0.15%, 0.2%, 0.25%; 0.5%, 1%, 2%, 3%, 4%, 5%; or the level of ARRDC1 as a percentage of total protein content is about 0.05-1.5%, 0.1%-0.3%, 0.05-0.2%, 0.1-0.2%, 0.25-7.5%, 0.5%-1.5%, 0.25-1%, 0.5-1%, 0.05-1.5%, 10%-30%, 5-20%, or 10-20%, e.g., by mass spectrometry, e.g., as measured according to the method described in Example 166. In some embodiments, the fusosome or fusosome composition has a ratio of fusogen to TSG101 of about 100-1,000, 100-400, 100-500, 200-400, 200-500, 200-1,000, 300-400, 1,000-10,000, 2,000-5,000, 3,000-4,000, 3,050-3,100, 3,060-3,070, or about 3,064, 10,000-100,000, 10,000-200,000, 10,000-500,000, 20,000-500,000, 30,000-400,000, e.g., using a mass spectrometry assay, e.g., an assay of Example 162. In some embodiments, the fusosome or fusosome composition has a ratio of cargo to tsg101 of about 1-3, 1-30, 1-20, 1-25, 1.5-30, 10-30, 15-25, 18-21, 19-20, 10-300, 10-200, 15-300, 15-200, 100-300, 100-200, 150-300, or about 19.5, e.g., using a mass spectrometry assay, e.g., an assay of Example 163. In some embodiments, the level of TSG101 as a percentage of total protein content is at least about 0.0001%, 0.0002%, 0.0003%, 0.0004%, 0.0005%, 0.0006%, 0.0007%, 0.001%, 0.002%, 0.003%, 0.004%, 0.005%, 0.006%, 0.007%; 0.01%, 0.02%, 0.03%, 0.04%, 0.05%, 0.06%, 0.07%; or the level of TSG101 as a percentage of total protein content is about 0.0001-0.001, 0.0001-0.002, 0.0001-0.01, 0.0001-0.1, 0.001-0.01, 0.002-0.006, 0.003-0.005, 0.001-0.1, 0.01-0.1, 0.02-0.06, 0.03-0.05, or 0.004, e.g., by mass spectrometry, e.g., as measured according to the method described in Example 166.

In some embodiments, the fusosome comprises a cargo, e.g., a therapeutic agent, e.g., an endogenous therapeutic agent or an exogenous therapeutic agent. In some embodiments, the therapeutic agent is chosen from one or more of a protein, e.g., an enzyme, a transmembrane protein, a receptor, an antibody; a nucleic acid, e.g., DNA, a chromosome (e.g. a human artificial chromosome), RNA, mRNA, siRNA, miRNA, or a small molecule. In some embodiments, the therapeutic agent is an organelle other than a mitochondrion, e.g., an organelle selected from: nucleus, Golgi apparatus, lysosome, endoplasmic reticulum, vacuole, endosome, acrosome, autophagosome, centriole, glycosome, glyoxysome, hydrogenosome, melanosome, mitosome, cnidocyst, peroxisome, proteasome, vesicle, and stress granule. In some embodiments, the organelle is a mitochondrion.

In some embodiments, the fusosome enters the target cell by endocytosis, e.g., wherein the level of therapeutic agent delivered via an endocytic pathway is 0.01-0.6, 0.01-0.1, 0.1-0.3, or 0.3-0.6, or at least 1%, 2%, 3%, 4%, 5%, 10%, 20%, 30%, 40%, 50%, 60%, 70%, 80%, 90% or greater than a chloroquine treated reference cell contacted with similar fusosomes, e.g., using an assay of Example 91. In some embodiments, at least 1%, 2%, 3%, 4%, 5%, 10%, 20%, 30%, 40%, 50%, 60%, 70%, 80%, 90% of fusosomes in a fusosome composition that enter a target cell enter via a non-endocytic pathway, e.g., the fusosomes enter the target cell via fusion with the cell surface. In some embodiments, the level of a therapeutic agent delivered via a non-endocytic pathway for a given fusosome is 0.1-0.95, 0.1-0.2, 0.2-0.3, 0.3-0.4, 0.4-0.5, 0.5-0.6, 0.6-0.7, 0.7-0.8, 0.8-0.9, 0.9-0.95, or at least at least 1%, 2%, 3%, 4%, 5%, 10%, 20%, 30%, 40%, 50%, 60%, 70%, 80%, 90% or greater than a chloroquine treated reference cell, e.g., using an assay of Example 90. In some embodiments, at least 1%, 2%, 3%, 4%, 5%, 10%, 20%, 30%, 40%, 50%, 60%, 70%, 80%, 90% of fusosomes in a fusosome composition that enter a target cell enter the cytoplasm (e.g., do not enter an endosome or lysosome). In some embodiments, less than 90%, 80%, 70%, 60%, 50%, 40%, 30%, 20%, 10%, 5%, 4%, 3%, 2%, or 1% of fusosomes in a fusosome composition that enter a target cell enter an endosome or lysosome. In some embodiments, the fusosome enters the target cell by a non-endocytic pathway, e.g., wherein the level of therapeutic agent delivered is at least 90%, 95%, 98%, or 99% that of a chloroquine treated reference cell, e.g., using an assay of Example 91. In an embodiment, a fusosome delivers an agent to a target cell via a dynamin mediated pathway. In an embodiment, the level of agent delivered via a dynamin mediated pathway is in the range of 0.01-0.6, or at least 1%, 2%, 3%, 4%, 5%, 10%, 20%, 30%, 40%, 50%, 60%, 70%, 80%, 90% or greater than Dynasore treated target cells contacted with similar fusosomes, e.g., as measured in an assay of Example 92. In an embodiment, a fusosome delivers an agent to a target cell via macropinocytosis. In an embodiment, the level of agent delivered via macropinocytosis is in the range of 0.01-0.6, or at least 1%, 2%, 3%, 4%, 5%, 10%, 20%, 30%, 40%, 50%, 60%, 70%, 80%, 90% or greater than EIPA treated target cells contacted with similar fusosomes, e.g., as measured in an assay of Example 92. In an embodiment, a fusosome delivers an agent to a target cell via an actin-mediated pathway. In an embodiment, the level of agent delivered via an actin-mediated pathway will be in the range of 0.01-0.6, or at least 1%, 2%, 3%, 4%, 5%, 10%, 20%, 30%, 40%, 50%, 60%, 70%, 80%, 90% or greater than Latrunculin B treated target cells contacted with similar fusosomes, e.g., as measured in an assay of Example 92.

In some embodiments, the fusosome has a density of <1, 1-1.1, 1.05-1.15, 1.1-1.2, 1.15-1.25, 1.2-1.3, 1.25-1.35, or >1.35 g/ml, e.g., by an assay of Example 33.

In some embodiments, the fusosome composition comprises less than 0.01%, 0.05%, 0.1%, 0.5%, 1%, 1.5%, 2%, 2.5%, 3%, 4%, 5%, or 10% source cells by protein mass or less than 0.01%, 0.05%, 0.1%, 0.5%, 1%, 1.5%, 2%, 2.5%, 3%, 4%, 5%, or 10% of cells have a functional nucleus. In some embodiments, at least 10%, 20%, 30%, 40%, 50%, 60%, 70%, 80%, 90%, 95%, or 99% of fusosomes in the fusosome composition comprise an organelle, e.g., a mitochondrion.

In some embodiments, the fusosome further comprises an exogenous therapeutic agent. In some embodiments, the exogenous therapeutic agent is chosen from one or more of a protein, e.g., an enzyme, a transmembrane protein, a receptor, an antibody; a nucleic acid, e.g., DNA, a chromosome (e.g. a human artificial chromosome), RNA, mRNA, siRNA, miRNA, or a small molecule.

In some embodiments, the fusosome enters the cell by endocytosis or a non-endocytic pathway.

In some embodiments, the fusosome or fusosome composition is refrigerated or frozen. In embodiments, the fusosome does not comprise a functional nucleus, or the fusosome composition comprises a fusosome without a functional nucleus. In embodiments, the fusosome composition comprises less than 0.01%, 0.05%, 0.1%, 0.5%, 1%, 1.5%, 2%, 2.5%, 3%, 4%, 5%, or 10% source cells by protein mass or less than 0.01%, 0.05%, 0.1%, 0.5%, 1%, 1.5%, 2%, 2.5%, 3%, 4%, 5%, or 10% of cells have a functional nucleus. In embodiments, the fusosome composition has been maintained at said temperature for at least 1, 2, 3, 6, or 12 hours; 1, 2, 3, 4, 5, or 6 days; 1, 2, 3, or 4 weeks; 1, 2, 3, or 6 months; or 1, 2, 3, 4, or 5 years. In embodiments, the fusosome composition has an activity of at least 50%, 60%, 70%, 80%, 90%, 95%, or 99% of the activity of the population before maintenance at said temperature, e.g., by one or more of:
  i) the fusosome fuses at a higher rate with a target cell than with a non-target cell, e.g., by at least at least 1%, 2%, 3%, 4%, 5%, 10%, 20%, 30%, 40%, 50%, 60%, 70%, 80%, 90%, 2-fold, 3-fold, 4-fold, 5-fold, 10-fold, 20-fold, 50-fold, or 100-fold, e.g., in an assay of Example 54;
  ii) the fusosome fuses at a higher rate with a target cell than with other fusosomes, e.g., by at least 10%, 20%, 30%, 40%, 50%, 60%, 70%, 80%, or 90%, e.g., in an assay of Example 54;
  iii) the fusosome fuses with target cells at a rate such that an agent in the fusosome is delivered to at least 10%, 20%, 30%, 40%, 50%, 60%, 70%, 80%, or 90%, of target cells after 24, 48, or 72 hours, e.g., in an assay of Example 54; or
  iv) the fusogen is present at a copy number of at least, or no more than, 10, 50, 100, 500, 1,000, 2,000, 5,000, 10,000, 20,000, 50,000, 100,000, 200,000, 500,000 or 1,000,000 copies, e.g., as measured by an assay of Example 29.

In embodiments, the fusosome composition is stable at a temperature of less than 4 C for at least 1, 2, 3, 6, or 12 hours; 1, 2, 3, 4, 5, or 6 days; 1, 2, 3, or 4 weeks; 1, 2, 3, or 6 months; or 1, 2, 3, 4, or 5 years. In embodiments, the fusosome composition is stable at a temperature of less than −20 C for at least 1, 2, 3, 6, or 12 hours; 1, 2, 3, 4, 5, or 6 days; 1, 2, 3, or 4 weeks; 1, 2, 3, or 6 months; or 1, 2, 3, 4, or 5 years. In embodiments, the fusosome composition is stable at a temperature of less than −80 C for at least 1, 2, 3, 6, or 12 hours; 1, 2, 3, 4, 5, or 6 days; 1, 2, 3, or 4 weeks; 1, 2, 3, or 6 months; or 1, 2, 3, 4, or 5 years.

In embodiments, one or more of:
  i) the source cell is other than a 293 cell;
  ii) the source cell is not transformed or immortalized;
  iii) the source cell is transformed or immortalized using a method other than adenovirus-mediated immortalization, e.g., immortalized by spontaneous mutation or telomerase expression;
  iv) the fusogen is other than VSVG, a SNARE protein, or a secretory granule protein;
  v) the therapeutic agent is other than Cre or EGFP;
  vi) the therapeutic agent is a nucleic acid (e.g., RNA, e.g., mRNA, miRNA, or siRNA) or an exogenous protein (e.g., an antibody, e.g., an antibody), e.g., in the lumen; or
  vii) the fusosome does not comprise mitochondria.

In embodiments, one or more of:
  i) the source cell is other than a 293 or HEK cell;
  ii) the source cell is not transformed or immortalized;

iii) the source cell is transformed or immortalized using a method other than adenovirus-mediated immortalization, e.g., immortalized by spontaneous mutation or telomerase expression;
iv) the fusogen is not a viral fusogen; or
v) the fusosome has a size of other than between 40 and 150 nm, e.g., greater than 150 nm, 200 nm, 300 nm, 400 nm, or 500 nm.

In embodiments, one or more of:
i) the therapeutic agent is a soluble protein expressed by the source cell;
ii) the fusogen is other than TAT, TAT-HA2, HA-2, gp41, Alzheimer's beta-amyloid peptide, a Sendai virus protein, or amphipathic net-negative peptide (WAE 11);
iii) the fusogen is a mammalian fusogen;
iv) the fusosome comprises in its lumen a polypeptide selected from an enzyme, antibody, or anti-viral polypeptide;
v) the fusosome does not comprise an exogenous therapeutic transmembrane protein; or
vi) the fusosome does not comprise CD63 or GLUT4, or the fusosome comprises less than or equal to 0.05%, 0.1%, 0.5%, 1%, 2%, 3%, 4%, 5%, or 10% CD63 (e.g., about 0.048% or less), e.g., as determined according to the method described in Example 157.

In embodiments, the fusosome:
i) does not comprise a virus, is not infectious, or does not propagate in a host cell;
ii) is not a viral vector
iii) is not a VLP (virus like particle);
iv) does not comprise a viral structural protein, e.g., a protein derived from gag, e.g. a viral capsid protein, e.g. a viral capsule protein, e.g., a viral nucleocapsid protein, or wherein the amount of viral capsid protein is less than 10%, 5%, 4%, 3%, 2%, 1%, 0.5%, 0.2%, or 0.1% of total protein, e.g., by mass spectrometry, e.g. using an assay of Example 53 or 161;
v) does not comprise a viral matrix protein;
vi) does not comprise a viral non-structural protein; e.g. pol or a fragment or variant thereof, a viral reverse transcriptase protein, a viral integrase protein, or a viral protease protein.
vii) does not comprise viral nucleic acid; e.g. viral RNA or viral DNA;
viii) comprises less than 10, 50, 100, 500, 1,000, 2,000, 5,000, 10,000, 20,000, 50,000, 100,000, 200,000, 500,000, 1,000,000, 5,000,000, 10,000,000, 50,000,000, 100,000,000, 500,000,000, or 1,000,000,000 copies per vesicle of a viral structural protein; or
ix) the fusosome is not a virosome.

In some embodiments, the fusosome comprises (or is identified as comprising) less than about 0.01%, 0.05%, 0.1%, 0.5%, 1%, 5%, 10%, 15%, 20%, 25%, 30%, 35%, 40%, 45%, 50%, 60%, 70%, 80%, 90%, 95%, 96%, 97%, 98%, or 99% viral capsid protein (e.g., about 0.05% viral capsid protein). In embodiments, the viral capsid protein is Complex of Rabbit Endogenous Lentivirus (RELIK) Capsid with Cyclophilin A. In embodiments, the viral capsid protein: total protein ratio is (or is identified as being) about 0.01, 0.02, 0.03, 0.04, 0.05, 0.06, 0.07, 0.08, 0.09, or 0.1.

In some embodiments, the fusosome does not comprise (or is identified as not comprising) a gag protein or a fragment or variant thereof, or the amount of gag protein or fragment or variant thereof is less than 10%, 5%, 4%, 3%, 2%, 1%, 0.5%, 0.2%, or 0.1% of total protein, e.g., by an assay of Example 53 or 161.

In embodiments, the ratio of the copy number of the fusogen to the copy number of viral structural protein on the fusosome is at least 1,000,000:1, 100,000:1, 10,000:1, 1,000:1, 100:1, 50:1, 20:1, 10:1, 5:1, or 1:1; or is between 100:1 and 50:1, 50:1 and 20:1, 20:1 and 10:1, 10:1 and 5:1 or 1:1. In embodiments, the ratio of the copy number of the fusogen to the copy number of viral matrix protein on the fusosome is at least 1,000,000:1, 100.000:1, 10,000:1, 1,000:1, 100:1, 50:1, 20:1, 10:1, 5:1, or 1:1.

In embodiments, one or more of:
i) the fusosome does not comprise a water-immiscible droplet;
ii) the fusosome comprises an aqueous lumen and a hydrophilic exterior;
iii) the fusogen is a protein fusogen; or
iv) the organelle is selected from a mitochondrion, Golgi apparatus, lysosome, endoplasmic reticulum, vacuole, endosome, acrosome, autophagosome, centriole, glycosome, glyoxysome, hydrogenosome, melanosome, mitosome, cnidocyst, peroxisome, proteasome, vesicle, and stress granule.

In embodiments, one or more of:
i) the fusogen is a mammalian fusogen or a viral fusogen;
ii) the fusosome was not made by loading the fusosome with a therapeutic or diagnostic substance;
iii) the source cell was not loaded with a therapeutic or diagnostic substance;
iv) the fusosome does not comprise doxorubicin, dexamethasone, cyclodextrin; polyethylene glycol, a micro RNA e.g., miR125, VEGF receptor, ICAM-1, E-selectin, iron oxide, a fluorescent protein e.g., GFP or RFP, a nanoparticle, or an RNase, or does not comprise an exogenous form of any of the foregoing; or
v) the fusosome further comprises an exogenous therapeutic agent having one or more post-translational modifications, e.g., glycosylation.

In embodiments, the fusosome is unilamellar or multilamellar.

In embodiments, the fusosome has a size, or the population of fusosomes has an average size, within about 0.01%, 0.05%, 0.1%, 0.5%, 1%, 2%, 3%, 4%, 5%, 10%, 20%, 30%, 40%, 50%, 60%, 70%, 80%, 90%, of that of the source cell, e.g., as measured by an assay of Example 30. In embodiments, the fusosome has a size, or the population of fusosomes has an average size, that is less than about 0.01%, 0.05%, 0.1%, 0.5%, 1%, 2%, 3%, 4%, 5%, 10%, 20%, 30%, 40%, 50%, 60%, 70%, 80%, 90%, of that of the source cell, e.g., as measured by an assay of Example 30. In embodiments, the fusosomes have (or are identified as having) a size less than parental cells. In embodiments, the fusosomes have (or are identified as having) a size within about 50%, 60%, 65%, 70%, 71%, 72%, 73%, 74%, 75%, 80%, or 90% of parental cells. In embodiments, the fusosomes have (or are identified as having) less than about 70%, 60%, 50%, 40%, 30%, 20%, 10%, 5%, 1%, or less of the parental cell's variability in size distribution, e.g., within about 90% of the sample. In embodiments, the fusosomes have (or are identified as having) about 40%, 45%, 50%, 55%, 56%, 57%, 58%, 59%, 60%, 65%, or 70% less of the parental cell's variability in size distribution, e.g., within about 90% of the sample. In some embodiments, fusosomes have (or are identified as having) an average size of greater than 30, 35, 40, 45, 50, 55, 60, 65, or 70 nm in diameter. In embodiments, fusosomes have an average size of about 100, 110, 120, 125, 126, 127, 128, 129, 130, 131, 132, 133, 134, 135, 140, or 150 nm in diameter. In embodiments, the fusosome has a size, or the population of fusosomes has an average size, within about 0.01%-0.05%, 0.05%-0.1%, 0.1%-0.5%, 0.5%-1%, 1%-2%, 2%-3%, 3%-4%, 4%-5%, 5%-10%, 10%-20%, 20%-30%, 30%-40%, 40%-50%, 50%-60%, 60%-70%, 70%-80%, or 80%-90% the size of the source cell, e.g., as measured by an assay of Example 30. In embodiments, the fusosome has a size, or the population of fusosomes has an average size, that is less than about 0.01%-0.05%, 0.05%-0.1%, 0.1%-0.5%, 0.5%-1%, 1%-2%, 2%-3%, 3%-4%, 4%-5%, 5%-10%, 10%-20%, 20%-30%, 30%-40%, 40%-50%, 50%-60%, 60%-70%, 70%-80%, or 80%-90% of the size of the source cell, e.g., as measured by an assay of Example 30. In embodiments, the fusosome has a diameter, or the population of fusosomes has an average diameter, of less than about 500 nm (e.g., less than about 10, 50, 100, 150, 200, 250, 300, 350, 400, or 450 nm), e.g., as measured by an assay of Example 119, 120, or 121. In embodiments, the fusosome has a diameter, or the population of fusosomes has an average diameter, of about 80-180, 90-170, 100-160, 110-150, 120-140, or 130 nm, e.g., as measured by an assay of Example 119, 120, or 121. In embodiments, the fusosome has a diameter, or the population of fusosomes has an average diameter, of between about 11,000 nm and 21,000 nm, e.g., as measured by an assay of Example 119, 120, or 121. In embodiments, the fusosome has a diameter, or the population of fusosomes has an average diameter, between about 10-22,000, 12-20,000, 14-18,720 nm, 20-16,000 nm, e.g., as measured by an assay of Example 119, 120, or 121. In embodiments, the fusosome has a volume, or the population of fusosomes has an average volume, of about 0.01-0.1 $\mu m^3$, 0.02-1 $\mu m^3$, 0.03-1 $\mu m^3$, 0.04-1 $\mu m^3$, 0.05-0.09 $\mu m^3$, 0.06-0.08 $\mu m^3$, 0.07 $\mu m^3$, e.g., as measured by an assay of Example 119, 120, or 121. In embodiments, the fusosome has a diameter, or the population of fusosomes has an average diameter, of at least about 10 nm, 20 nm, 30 nm, 40 nm, 50 nm, 60 nm, 70 nm, 80 nm, 90 nm, 100 nm, 150 nm, 200 nm, or 250 nm e.g., as measured by an assay of Example 32. In embodiments, the fusosome has a diameter, or the population of fusosomes has an average diameter, of about 10 nm, 20 nm, 30 nm, 40 nm, 50 nm, 60 nm, 70 nm, 80 nm, 90 nm, 100 nm, 150 nm, 200 nm, or 250 nm (e.g., ±20%) e.g., as measured by an assay of Example 32. In embodiments, the fusosome has a diameter, or the population of fusosomes has an average diameter, of at least about 500 nm, 750 nm, 1,000 nm, 1,500 nm, 2,000 nm, 2,500 nm, 3,000 nm, 5,000 nm, 10,000 nm, or 20,000 nm, e.g., as measured by an assay of Example 32. In embodiments, the fusosome has a diameter, or the population of fusosomes has an average diameter, of about 500 nm, 750 nm, 1,000 nm, 1,500 nm, 2,000 nm, 2,500 nm, 3,000 nm, 5,000 nm, 10,000 nm, or 20,000 nm (e.g., +20%), e.g., as measured by an assay of Example 32. In embodiments, the population of fusosomes has (or is identified as having) one or more of: a 10% quantile diameter of about 40-90 nm, 45-60 nm, 50-55 nm or 53 nm; a 25% quantile diameter of about 70-100 nm, 80-95 nm, 85-90 nm, or 88 nm; a 75% quantile diameter of about 200-250 nm, 210-240 nm, 220-230 nm, or 226 nm; or a 90% quantile of about 4000-5000 nm, 4300-4600 nm, 4400-4500 nm, 4450 nm, e.g., by an assay of Example 120.

In embodiments, the fusosome composition comprises (or is identified as comprising) a GAPDH concentration of about 35-40, 36-39, 37-38, or 37.2 ng/mL, e.g., in an assay of Example 149. In embodiments, the GAPDH concentration of the fusosome composition is (or is identified as being) within about 1%, 2%, 5%, 10%, or 20% of the GAPDH concentration of the source cells, e.g., in an assay of Example 149. In embodiments, the GAPDH concentration of the fusosome composition is (or is identified as being) at least 1%, 2%, 5%, 10%, or 20% lower than the GAPDH concentration of the source cells, e.g., in an assay of Example 149. In embodiments, the fusosome composition comprises (or is identified as comprising) less than about 30, 35, 40, 45, 46, 47, 48, 49, 50, 55, 60, 65, or 70 µg GAPDH per gram total protein. In embodiments, the fusosome composition comprises (or is identified as comprising) less than about 500, 250, 100, or 50 µg GAPDH per gram total protein. In embodiments, the parental cell comprises (or is identified as comprising) at least 1%, 2.5%, 5%, 10%, 15%, 20%, 30%, 30%, 50%, or more GAPDH per total protein than the fusosome composition.

In embodiments, one or more of:
i) the fusosome is not an exosome;
ii) the fusosome is a microvesicle;
iii) the fusosome comprises a non-mammalian fusogen;
iv) the fusosome has been engineered to incorporate a fusogen;
v) the fusosome comprises an exogenous fusogen;
vi) the fusosome has a size of at least 80 nm, 100 nm, 200 nm, 500 nm, 1000 nm, 1200 nm, 1400 nm, or 1500 nm, or a population of fusosomes has an average size of at least 80 nm, 100 nm, 200 nm, 500 nm, 1000 nm, 1200 nm, 1400 nm, or 1500 nm;
vii) the fusosome comprises one or more organelles, e.g., a mitochondrion, Golgi apparatus, lysosome, endoplasmic reticulum, vacuole, endosome, acrosome, autophagosome, centriole, glycosome, glyoxysome, hydrogenosome, melanosome, mitosome, cnidocyst, peroxisome, proteasome, vesicle, and stress granule;
viii) the fusosome comprises a cytoskeleton or a component thereof, e.g., actin, Arp2/3, formin, coronin, dystrophin, keratin, myosin, or tubulin;
ix) the fusosome, or a composition or preparation comprising a plurality of the fusosomes, does not have a flotation density of 1.08-1.22 g/ml, or has a density of at least 1.18-1.25 g/ml, or 1.05-1.12 g/ml, e.g., in a sucrose gradient centrifugation assay, e.g., as described in Théry et al., "Isolation and characterization of exosomes from cell culture supernatants and biological fluids." Curr Protoc Cell Biol. 2006 April; Chapter 3:Unit 3.22;
x) the lipid bilayer is enriched for ceramides or sphingomyelins or a combination thereof compared to the source cell, or the lipid bilayer is not enriched (e.g., is depleted) for glycolipids, free fatty acids, or phosphatidylserine, or a combination thereof, compared to the source cell;
xi) the fusosome comprises Phosphatidyl serine (PS) or CD40 ligand or both of PS and CD40 ligand, e.g., when measured in an assay of Example 52 or 160;
xii) the fusosome is enriched for PS compared to the source cell, e.g., in a population of fusosomes at least 5%, 10%, 20%, 30%, 40%, 50%, 60%, 70%, 80%, or 90% are positive for PS, e.g., by an assay of Kanada M, et al. (2015) Differential fates of biomolecules delivered to target cells via extracellular vesicles. Proc Natl Acad Sci USA 112:E1433-E1442;
xiii) the fusosome is substantially free of acetylcholinesterase (AChE), or contains less than 0.001, 0.002, 0.005, 0.01, 0.02, 0.05, 0.1, 0.2, 0.5, 1, 2, 5, 10, 20, 50, 100, 200, 500, or 1000 AChE activity units/ug of protein, e.g., by an assay of Example 67;
xiv) the fusosome is substantially free of a Tetraspanin family protein (e.g., CD63, CD9, or CD81), an ESCRT-related protein (e.g., TSG101, CHMP4A-B, or VPS4B), Alix, TSG101, MHCI, MHCII, GP96, actinin-4, mitofilin, syntenin-1, TSG101, ADAM10, EHD4, syntenin-1, TSG101, EHD1, flotillin-1, heat-shock 70-kDa proteins (HSC70/HSP73, HSP70/HSP72), or any combination thereof, or contains less than 0.05%, 0.1%, 0.5%, 1%, 2%, 3%, 4%, 5%, 5%, or 10% of any individual exosomal marker protein and/or less than 0.05%, 0.1%, 0.5%, 1%, 2%, 3%, 4%, 5%, 10%, 15%, 20%, or 25% of total exosomal marker proteins of any of said proteins, or is de-enriched for any one or more of these proteins compared to the source cell, or is not enriched for any one or more of these proteins, e.g., by an assay of Example 44 or 157;

xv) the fusosome comprises a level of Glyceraldehyde 3-phosphate dehydrogenase (GAPDH) that is below 500, 250, 100, 50, 20, 10, 5, or 1 ng GAPDH/ug total protein or below the level of GAPDH in the source cell, e.g., less than 1%, 2.5%, 5%, 10%, 15%, 20%, 30%, 40%, 50%, 60%, 70%, 80%, or 90%, less than the level of GAPDH per total protein in ng/ug in the source cell, e.g., using an assay of Example 45;

xvi) the fusosome is enriched for one or more endoplasmic reticulum proteins (e.g., calnexin), one or more proteasome proteins, or one or more mitochondrial proteins, or any combination thereof, e.g., wherein the amount of calnexin is less than 500, 250, 100, 50, 20, 10, 5, or 1 ng Calnexin/ug total protein, or wherein the fusosome comprises less Calnexin per total protein in ng/ug compared to the source cell by 1%, 2.5%, 5%, 10%, 15%, 20%, 30%, 40%, 50%, 60%, 70%, 80%, or 90%, e.g., using an assay of Example 46 or 158, or wherein the average fractional content of Calnexin in the fusosome is less than about $1 \times 10^{-4}$, $1.5 \times 10^{-4}$, $2 \times 10^{-4}$, $2.1 \times 10^{-4}$, $2.2 \times 10^{-4}$, $2.3 \times 10^{-4}$, $2.4 \times 10^{-4}$, $2.43 \times 10^{-4}$, $2.5 \times 10^{-4}$, $2.6 \times 10^{-4}$, $2.7 \times 10^{-4}$, $2.8 \times 10^{-4}$, $2.9 \times 10^{-4}$, $3 \times 10^{-4}$, $3.5 \times 10^{-4}$, or $4 \times 10^{-4}$, or wherein the fusosome comprises an amount of Calnexin per total protein that is lower than that of the parental cell by about 70%, 75%, 80%, 85%, 88%, 90%, 95%, 99%, or more;

xvii) the fusosome comprises an exogenous agent (e.g., an exogenous protein, mRNA, or siRNA) e.g., as measured using an assay of Example 39 or 40; or xviii) the fusosome can be immobilized on a mica surface by atomic force microscopy for at least 30 min, e.g., by an assay of Kanada M, et al. (2015) Differential fates of biomolecules delivered to target cells via extracellular vesicles. Proc Natl Acad Sci USA 112:E1433-E1442.

In embodiments, one or more of:

i) the fusosome is an exosome;

ii) the fusosome is not a microvesicle;

iii) the fusosome has a size of less than 80 nm, 100 nm, 200 nm, 500 nm, 1000 nm, 1200 nm, 1400 nm, or 1500 nm, or a population of fusosomes has an average size of less than 80 nm, 100 nm, 200 nm, 500 nm, 1000 nm, 1200 nm, 1400 nm, or 1500 nm;

iv) the fusosome does not comprise an organelle;

v) the fusosome does not comprise a cytoskeleton or a component thereof, e.g., actin, Arp2/3, formin, coronin, dystrophin, keratin, myosin, or tubulin;

vi) the fusosome, or a composition or preparation comprising a plurality of the fusosomes, has flotation density of 1.08-1.22 g/ml, e.g., in a sucrose gradient centrifugation assay, e.g., as described in Théry et al., "Isolation and characterization of exosomes from cell culture supernatants and biological fluids." Curr Protoc Cell Biol. 2006 April; Chapter 3:Unit 3.22;

vii) the lipid bilayer is not enriched (e.g., is depleted) for ceramides or sphingomyelins or a combination thereof compared to the source cell, or the lipid bilayer is enriched for glycolipids, free fatty acids, or phosphatidylserine, or a combination thereof, compared to the source cell;

viii) the fusosome does not comprise, or is depleted for relative to the source cell, Phosphatidyl serine (PS) or CD40 ligand or both of PS and CD40 ligand, e.g., when measured in an assay of Example 52 or 160;

ix) the fusosome is not enriched (e.g., is depleted) for PS compared to the source cell, e.g., in a population of fusosomes less than 20%, 30%, 40%, 50%, 60%, 70%, 80%, or 90% are positive for PS, e.g., by an assay of Kanada M, et al. (2015) Differential fates of biomolecules delivered to target cells via extracellular vesicles. Proc Natl Acad Sci USA 112:E1433-E1442;

x) the fusosome comprises acetylcholinesterase (AChE), e.g. at least 0.001, 0.002, 0.005, 0.01, 0.02, 0.05, 0.1, 0.2, 0.5, 1, 2, 5, 10, 20, 50, 100, 200, 500, or 1000 AChE activity units/ug of protein, e.g., by an assay of Example 67;

xi) the fusosome comprises a Tetraspanin family protein (e.g., CD63, CD9, or CD81), an ESCRT-related protein (e.g., TSG101, CHMP4A-B, or VPS4B), Alix, TSG101, MHCI, MHCII, GP96, actinin-4, mitofilin, syntenin-1, TSG101, ADAM10, EHD4, syntenin-1, TSG101, EHD1, flotillin-1, heat-shock 70-kDa proteins (HSC70/HSP73, HSP70/HSP72), or any combination thereof, e.g., contains more than 0.05%, 0.1%, 0.5%, 1%, 2%, 3%, 4%, 5%, 5%, or 10% of any individual exosomal marker protein and/or less than 0.05%, 0.1%, 0.5%, 1%, 2%, 3%, 4%, 5%, 10%, 15%, 20%, or 25% of total exosomal marker proteins of any of said proteins, or is enriched for any one or more of these proteins compared to the source cell, e.g., by an assay of Example 44 or 157;

xii) the fusosome comprises a level of Glyceraldehyde 3-phosphate dehydrogenase (GAPDH) that is above 500, 250, 100, 50, 20, 10, 5, or 1 ng GAPDH/ug total protein or below the level of GAPDH in the source cell, e.g., at least 1%, 2.5%, 5%, 10%, 15%, 20%, 30%, 40%, 50%, 60%, 70%, 80%, or 90%, greater than the level of GAPDH per total protein in ng/ug in the source cell, e.g., using an assay of Example 45;

xiii) the fusosome is not enriched for (e.g., is depleted for) one or more endoplasmic reticulum proteins (e.g., calnexin), one or more proteasome proteins, or one or more mitochondrial proteins, or any combination thereof, e.g., wherein the amount of calnexin is less than 500, 250, 100, 50, 20, 10, 5, or 1 ng Calnexin/ug total protein, or wherein the fusosome comprises less Calnexin per total protein in ng/ug compared to the source cell by 1%, 2.5%, 5%, 10%, 15%, 20%, 30%, 40%, 50%, 60%, 70%, 80%, or 90%, e.g., using an assay of Example 46 or 158, or wherein the average fractional content of Calnexin in the fusosome is less than about $1 \times 10^{-4}$, $1.5 \times 10^{-4}$, $2 \times 10^{-4}$, $2.1 \times 10^{-4}$, $2.2 \times 10^{-4}$, $2.3 \times 10^{-4}$, $2.4 \times 10^{-4}$, $2.43 \times 10^{-4}$, $2.5 \times 10^{-4}$, $2.6 \times 10^{-4}$, $2.7 \times 10^{-4}$, $2.8 \times 10^{-4}$, $2.9 \times 10^{-4}$, $3 \times 10^{-4}$, $3.5 \times 10^{-4}$, or $4 \times 10^{-4}$, or wherein the fusosome comprises an amount of Calnexin per total protein that is lower than that of the parental cell by about 70%, 75%, 80%, 85%, 88%, 90%, 95%, 99%, or more; or xiv) the fusosome can not be immobilized on a mica surface by atomic force microscopy for at least 30 min, e.g., by an assay of Kanada M, et al. (2015) Differential fates of biomolecules delivered to target cells via extracellular vesicles. Proc Natl Acad Sci USA 112: E1433-E1442.

In embodiments, the average fractional content of calnexin in the fusosome is (or is identified as being) less than about $1\times10^{-4}$, $1.5\times10^{-4}$, $2\times10^{-4}$, $2.1\times10^{-4}$, $2.2\times10^{-4}$, $2.3\times10^{-4}$, $2.4\times10^{-4}$, $2.43\times10^{-4}$, $2.5\times10^{-4}$, $2.6\times10^{-4}$, $2.7\times10^{-4}$, $2.8\times10^{-4}$, $2.9\times10^{-4}$, $3\times10^{-4}$, $3.5\times10^{-4}$, or $4\times10^{-4}$. In embodiments, the fusosome comprises an amount of calnexin per total protein that is lower than that of the parental cell by about 70%, 75%, 80%, 85%, 88%, 90%, 95%, 99%, or more.

In embodiments, one or more of:
i) the fusosome does not comprise a VLP;
ii) the fusosome does not comprise a virus;
iii) the fusosome does not comprise a replication-competent virus;
iv) the fusosome does not comprise a viral protein, e.g., a viral structural protein, e.g., a capsid protein or a viral matrix protein;
v) the fusosome does not comprise a capsid protein from an enveloped virus;
vi) the fusosome does not comprise a nucleocapsid protein; or
vii) the fusogen is not a viral fusogen.

In embodiments, the fusosome comprises cytosol.

In embodiments, one or more of:
i) the fusosome or the source cell does not form a teratoma when implanted into subject, e.g., by an assay of Example 102;
ii) the fusosome is capable of chemotaxis, e.g., of within 1%, 2%, 3%, 4%, 5%, 10%, 20%, 30%, 40%, 50%, 60%, 70%, 80%, 90%, 100% or greater than a reference cell, e.g., a macrophage, e.g., using an assay of Example 58;
iii) the fusosome is capable of homing, e.g., at the site of an injury, wherein the fusosome or cytobiologic is from a human cell, e.g., using an assay of Example 59, e.g., wherein the source cell is a neutrophil; or
iv) the fusosome is capable of phagocytosis, e.g., wherein phagocytosis by the fusosome is detectable within 0.5, 1, 2, 3, 4, 5, or 6 hours in using an assay of Example 60, e.g., wherein the source cell is a macrophage.

In embodiments, the fusosome or fusosome composition retains one, two, three, four, five, six or more of any of the characteristics for 5 days or less, e.g., 4 days or less, 3 days or less, 2 days or less, 1 day or less, e.g., about 12-72 hours, after administration into a subject, e.g., a human subject.

In embodiments, the fusosome has one or more of the following characteristics:
a) comprises one or more endogenous proteins from a source cell, e.g., membrane proteins or cytosolic proteins;
b) comprises at least 10, 20, 50, 100, 200, 500, 1000, 2000, or 5000 different proteins;
c) comprises at least 1, 2, 5, 10, 20, 50, or 100 different glycoproteins;
d) at least 10%, 20%, 30%, 40%, 50%, 60%, 70%, 80%, or 90% by mass of the proteins in the fusosome are naturally-occurring proteins;
e) comprises at least 10, 20, 50, 100, 200, 500, 1000, 2000, or 5000 different RNAs; or
f) comprises at least 2, 3, 4, 5, 10, or 20 different lipids, e.g., selected from CL, Cer, DAG, HexCer, LPA, LPC, LPE, LPG, LPI, LPS, PA, PC, PE, PG, PI, PS, CE, SM and TAG.

In embodiments, the fusosome has been manipulated to have, or the fusosome is not a naturally occurring cell and has, or wherein the nucleus does not naturally have one, two, three, four, five or more of the following properties:
a) the partial nuclear inactivation results in a reduction of at least 50%, 60%, 70%, 80%, 90% or more in nuclear function, e.g., a reduction in transcription or DNA replication, or both, e.g., wherein transcription is measured by an assay of Example 19 and DNA replication is measured by an assay of Example 20;
b) the fusosome is not capable of transcription or has transcriptional activity of less than 1%, 2.5% 5%, 10%, 20%, 30%, 40%, 50%, 60%, 70%, 80%, or 90% of that of the transcriptional activity of a reference cell, e.g., the source cell, e.g., using an assay of Example 19;
c) the fusosome is not capable of nuclear DNA replication or has nuclear DNA replication of less than 1%, 2.5% 5%, 10%, 20%, 30%, 40%, 50%, 60%, 70%, 80%, or 90% of the nuclear DNA replication of a reference cell, e.g., the source cell, e.g., using an assay of Example 20;
d) the fusosome lacks chromatin or has a chromatin content of less than 1%, 2.5% 5%, 10%, 20%, 30%, 40%, 50%, 60%, 70%, 80%, or 90% of the of the chromatin content of a reference cell, e.g., the source cell, e.g., using an assay of Example 37;
e) the fusosome lacks a nuclear membrane or has less than 50%, 40%, 30%, 20%, 10%, 5%, 4%, 3%, 2%, or 1% the amount of nuclear membrane of a reference cell, e.g., the source cell or a Jurkat cell, e.g., by an assay of Example 36;
f) the fusosome lacks functional nuclear pore complexes or has reduced nuclear import or export activity, e.g., by at least 50%, 40%, 30%, 20%, 10%, 5%, 4%, 3%, 2%, or 1% by an assay of Example 36, or the fusosome lacks on or more of a nuclear pore protein, e.g., NUP98 or Importin 7;
g) the fusosome does not comprise histones or has histone levels less than 1%, 2%, 3%, 4%, 5%, 10%, 20%, 30%, 40%, 50%, 60%, 70%, 80%, or 90% of the histone level of the source cell (e.g., of H1, H2a, H2b, H3, or H4), e.g., by an assay of Example 37;
h) the fusosome comprises less than 20, 10, 5, 4, 3, 2, or 1 chromosome;
i) nuclear function is eliminated;
j) the fusosome is an enucleated mammalian cell;
k) the nucleus is removed or inactivated, e.g., extruded by mechanical force, by radiation or by chemical ablation; or
l) the fusosome is from a mammalian cell having DNA that is completely or partially removed, e.g., during interphase or mitosis.

In embodiments, the fusosome comprises mtDNA or vector DNA. In embodiments, the fusosome does not comprise DNA.

In embodiments, the source cell is a primary cell, immortalized cell or a cell line (e.g., myelobast cell line, e.g., C2Cl2). In embodiments, the fusosome is from a source cell having a modified genome, e.g., having reduced immunogenicity (e.g., by genome editing, e.g., to remove an MHC protein or MHC complexes). In embodiments, the source cell is from a cell culture treated with an anti-inflammatory signal. In embodiments, the source cell is from a cell culture treated with an immunosuppressive agent. In embodiments, the source cell is substantially non-immunogenic, e.g., using an assay described herein. In embodiments, the source cell comprises an exogenous agent, e.g., a therapeutic agent. In embodiments, the source cell is a recombinant cell.

In embodiments, the fusosome further comprises an exogenous agent, e.g., a therapeutic agent, e.g., a protein or a nucleic acid (e.g., a DNA, a chromosome (e.g. a human artificial chromosome), an RNA, e.g., an mRNA or miRNA). In embodiments, the exogenous agent is present at at least, or no more than, 10, 20, 50, 100, 200, 500, 1,000, 2,000, 5,000, 10,000, 20,000, 50,000, 100,000, 200,000, 500,000, 1,000,000, 5,000,000, 10,000,000, 50,000,000, 100,000,000, 500,000,000, or 1,000,000,000 copies, e.g., comprised by the fusosome, or is present at an average level of at least, or no more than, 10, 20, 50, 100, 200, 500, 1,000, 2,000, 5,000, 10,000, 20,000, 50,000, 100,000, 200,000, 500,000 or 1,000,000 copies per fusosome. In embodiments, the fusosome has an altered, e.g., increased or decreased level of one or more endogenous molecules, e.g., protein or nucleic acid, e.g., due to treatment of the mammalian cell with a siRNA or gene editing enzyme. In embodiments, the endogenous molecule is present at, e.g. an average level, of at least, or no more than, 10, 20, 50, 100, 200, 500, 1,000, 2,000, 5,000, 10,000, 20,000, 50,000, 100,000, 200,000, 500,000, 1,000,000, 5,000,000, 10,000,000, 50,000,000, 100,000,000, 500,000,000, or 1,000,000,000 copies (e.g., copies comprised by the fusosome), or is present at an average level of at least, or no more than, 10, 20, 50, 100, 200, 500, 1,000, 2,000, 5,000, 10,000, 20,000, 50,000, 100,000, 200,000, 500,000 or 1,000,000 copies per fusosome. In embodiments, the endogenous molecule (e.g., an RNA or protein) is present at a concentration of at least 1, 2, 3, 4, 5, 10, 20, 50, 100, 500, $10^3$, $5.0 \times 10^3$, $10^4$, $5.0 \times 10^4$, $10^5$, $5.0 \times 10^5$, $10^6$, $5.0 \times 10^6$, $1.0 \times 10^7$, $5.0 \times 10^7$, or $1.0 \times 10^8$, greater than its concentration in the source cell.

In embodiments, the active agent is selected from a protein, protein complex (e.g., comprising at least 2, 3, 4, 5, 10, 20, or 50 proteins, e.g., at least at least 2, 3, 4, 5, 10, 20, or 50 different proteins) polypeptide, nucleic acid (e.g., DNA, chromosome, or RNA, e.g., mRNA, siRNA, or miRNA) or small molecule. In embodiments, the exogenous agent comprises a site-specific nuclease, e.g., Cas9 molecule, TALEN, or ZFN.

In embodiments, the fusogen is a viral fusogen, e.g., HA, HIV-1 ENV, HHV-4, gp120, or VSV-G. In embodiments, the fusogen is a mammalian fusogen, e.g., a SNARE, a Syncytin, myomaker, myomixer, myomerger, or FGFRL1. In embodiments, the fusogen is active at a pH of 4-5, 5-6, 6-7, 7-8, 8-9, or 9-10. In embodiments, the fusogen is not active at a pH of 4-5, 5-6, 6-7, 7-8, 8-9, or 9-10. In embodiments, the fusosome fuses to a target cell at the surface of the target cell. In embodiments, the fusogen promotes fusion in a lysosome-independent manner. In embodiments, the fusogen is a protein fusogen. In embodiments, the fusogen is a lipid fusogen, e.g., oleic acid, glycerol mono-oleate, a glyceride, diacylglycerol, or a modified unsaturated fatty acid. In embodiments, the fusogen is a chemical fusogen, e.g., PEG. In embodiments, the fusogen is a small molecule fusogen, e.g., halothane, an NSAID such as meloxicam, piroxicam, tenoxicam, and chlorpromazine. In embodiments, the fusogen is recombinant. In embodiments, the fusogen is biochemically incorporated, e.g., the fusogen is provided as a purified protein and contacted with a lipid bilayer under conditions that allow for associate of the fusogen with the lipid bilayer. In embodiments, the fusogen is biosynthetically incorporated, e.g. expressed in a source cell under conditions that allow the fusogen to associate with the lipid bilayer.

In embodiments, the fusosome binds a target cell. In embodiments, the target cell is other than a HeLa cell, or the target cell is not transformed or immortalized.

In some embodiments involving fusosome compositions, the plurality of fusosomes are the same. In some embodiments, the plurality of fusosomes are different. In some embodiments the plurality of fusosomes are from one or more source cells. In some embodiments at least 50%, 60%, 70%, 80%, 90%, 95%, or 99% of fusosomes in the plurality have a diameter within 10%, 20%, 30%, 40%, or 50% of the mean diameter of the fusosomes in the fusosome composition. In some embodiments at least 50%, 60%, 70%, 80%, 90%, 95%, or 99% of fusosomes in the plurality have a volume within 10%, 20%, 30%, 40%, or 50% of the mean volume of the fusosomes in the fusosome composition. In some embodiments, the fusosome composition has less than about 90%, 80%, 70%, 60%, 50%, 40%, 30%, 20%, 10%, 5%, variability in size distribution within 10%, 50%, or 90% of the source cell population variability in size distribution, e.g., based on Example 31. In some embodiments, at least 50%, 60%, 70%, 80%, 90%, 95%, or 99% of fusosomes in the plurality have a copy number of the fusogen within 10%, 20%, 30%, 40%, 50%, 60%, 70%, 80%, or 90% of the mean fusogen copy number in the fusosomes in the fusosome composition. In some embodiments, at least 50%, 60%, 70%, 80%, 90%, 95%, or 99% of fusosomes in the plurality have a copy number of the therapeutic agent within 10%, 20%, 30%, 40%, 50%, 60%, 70%, 80%, or 90% of the mean therapeutic agent copy number in the fusosomes in the fusosome composition. In some embodiments, the fusosome composition comprises at least $10^5$, $10^6$, $10^7$, $10^8$, $10^9$, $10^{10}$, $10^{11}$, $10^{12}$, $10^{13}$, $10^{14}$, or $10^{15}$ or more fusosomes. In some embodiments, the fusosome composition is in a volume of at least 1 ul, 2 ul, 5 ul, 10 ul, 20 ul, 50 ul, 100 ul, 200 ul, 500 ul, 1 ml, 2 ml, 5 ml, or 10 ml.

In some embodiments, the fusosome composition delivers the cargo to at least 40%, 45%, 50%, 55%, 60%, 65%, 70%, 75%, 80%, 85%, 90%, 95%, 96%, 97%, 98%, or 99% of the number of cells in the target cell population compared to the reference target cell population.

In some embodiments, the fusosome composition delivers at least 40%, 45%, 50%, 55%, 60%, 65%, 70%, 75%, 80%, 85%, 90%, 95%, 96%, 97%, 98%, or 99% of the cargo to the target cell population compared to the reference target cell population or to a non-target cell population. In some embodiments, the fusosome composition delivers at least 40%, 45%, 50%, 55%, 60%, 65%, 70%, 75%, 80%, 85%, 90%, 95%, 96%, 97%, 98%, or 99% more of the cargo to the target cell population compared to the reference target cell population or to a non-target cell population.

In some embodiments, less than 10% of cargo enters the cell by endocytosis.

In some embodiments, the inhibitor of endocytosis is an inhibitor of lysosomal acidification, e.g., bafilomycin A1. In some embodiments, the inhibitor of endocytosis is a dynamin inhibitor, e.g., Dynasore.

In some embodiments, the target cell population is at a physiological pH (e.g., between 7.3-7.5, e.g., between 7.38-7.42).

In some embodiments, the cargo delivered is determined using an endocytosis inhibition assay, e.g., an assay of Example 90, 92, or 135.

In some embodiments, cargo enters the cell through a dynamin-independent pathway or a lysosomal acidification-independent pathway, a macropinocytosis-independent pathway (e.g., wherein the inhibitor of endocytosis is an inhibitor of macropinocytosis, e.g., 5-(N-ethyl-N-isopropyl) amiloride (EIPA), e.g., at a concentration of 25 μM), or an actin-independent pathway (e.g., wherein the inhibitor of endocytosis is an inhibitor of actin polymerization is, e.g., Latrunculin B, e.g., at a concentration of 6 μM).

In some embodiments, the fusosomes of the plurality further comprise a targeting moiety. In embodiments, the targeting moiety is comprised by the fusogen or is comprised by a separate molecule.

In some embodiments, when the plurality of fusosomes are contacted with a cell population comprising target cells and non-target cells, the cargo is present in at least 10-fold more target cells than non-target cells.

In some embodiments, when the plurality of fusosomes are contacted with a cell population comprising target cells and non-target cells, the cargo is present at least 2-fold, 5-fold, 10-fold, 20-fold, or 50-fold higher in target cells than non-target cells and/or the cargo is present at least 2-fold, 5-fold, 10-fold, 20-fold, or 50-fold higher in target cells than reference cells.

In some embodiments, the fusosomes of the plurality fuse at a higher rate with a target cell than with a non-target cell by at least 50%.

In some embodiments, presence of cargo is measured by microscopy, e.g., using an assay of Example 124. In some embodiments, fusion is measured by microscopy, e.g., using an assay of Example 54.

In some embodiments, the targeting moiety is specific for a cell surface marker on the target cell. In embodiments, the cell surface marker is a cell surface marker of a skin cell, cardiomyocyte, hepatocyte, intestinal cell (e.g., cell of the small intestine), pancreatic cell, brain cell, prostate cell, lung cell, colon cell, or bone marrow cell.

In some embodiments, the fusogen (e.g., re-targeted fusogen) comprises a rhabdoviridae fusogen (e.g., VSV-G), a filoviridae fusogen, an arenaviridae fusogen, a togaviridae fusogen, a flaviviridae fusogen, a bunyaviridae fusogen, or a hapadnaviridae fusogen (e.g., Hep B), or a derivative thereof.

In some embodiments, the plurality of fusosomes, when contacted with a target cell population in the presence of an inhibitor of endocytosis, and when contacted with a reference target cell population not treated with the inhibitor of endocytosis, delivers the cargo to at least 30% of the number of cells in the target cell population compared to the reference target cell population.

In some embodiments, the plurality of fusosomes, when contacted with a target cell population in the presence of an inhibitor of endocytosis, and when contacted with a reference target cell population not treated with the inhibitor of endocytosis, delivers least 30% of the cargo in the target cell population compared to the reference target cell population.

In some embodiments, the fusosome, when contacted with a target cell population, delivers cargo to a target cell location other than an endosome or lysosome, e.g., to the cytosol. In embodiments, less 50%, 40%, 30%, 20%, or 10% of the cargo is delivered to an endosome or lysosome.

In some embodiments, the amount of viral capsid protein in the fusosome composition is determined using mass spectrometry, e.g., using an assay of Example 53 or 161.

In some embodiments, the fusosomes of the plurality comprise exosomes, microvesicles, or a combination thereof.

In some embodiments, the plurality of fusosomes has an average size of at least 50 nm, 100 nm, 200 nm, 500 nm, 1000 nm, 1200 nm, 1400 nm, or 1500 nm. In other embodiments, the plurality of fusosomes has an average size of less than 100 nm, 80 nm, 60 nm, 40 nm, or 30 nm.

In some embodiments, the source cell is selected from a neutrophil, a HEK293 cell, a granulocyte, a mesenchymal stem cell, a bone marrow stem cell, an induced pluripotent stem cell, an embryonic stem cell, a myeloblast, a myoblast, a hepatocyte, or a neuron e.g., retinal neuronal cell.

In some embodiments, the fusosomes in the plurality comprise cytobiologics. In some embodiments, the fusosomes in the plurality comprise enucleated cells.

In some embodiments, the fusogen (e.g., re-targeted fusogen) comprises a mammalian fusogen. In some embodiments, the fusogen (e.g., re-targeted fusogen) comprises a viral fusogen. In some embodiments, the fusogen (e.g., re-targeted fusogen) is a protein fusogen. In some embodiments, the fusogen (e.g., re-targeted fusogen) comprises a sequence chosen from a Nipah virus protein F, a measles virus F protein, a tupaia paramyxovirus F protein, a paramyxovirus F protein, a Hendra virus F protein, a Henipavirus F protein, a Morbilivirus F protein, a respirovirus F protein, a Sendai virus F protein, a rubulavirus F protein, or an avulavirus F protein, or a derivative thereof.

In some embodiments, the fusogen (e.g., re-targeted fusogen) is active at a pH of 4-5, 5-6, 6-7, 7-8, 8-9, or 9-10. In some embodiments, the fusogen (e.g., re-targeted fusogen) is not active at a pH of 4-5, 5-6, 6-7, 7-8, 8-9, or 9-10.

In some embodiments, the fusogen is present at a copy number of at least 1, 2, 5, or 10 copies per fusosome.

In some embodiments, the fusogen (e.g., re-targeted fusogen) comprises a Nipah virus protein G, a measles protein H, a tupaia paramyxovirus H protein, a paramyxovirus G protein, a paramyxovirus H protein, a paramyxovirus HN protein, a Morbilivirus H protein, a respirovirus HN protein, a sendai HN protein, a rubulavirus HN protein, an avulavirus HN protein, or a derivative thereof. In some embodiments, the fusogen (e.g., re-targeted fusogen) comprises a sequence chosen from Nipah virus F and G proteins, measles virus F and H proteins, tupaia paramyxovirus F and H proteins, paramyxovirus F and G proteins or F and H proteins or F and HN proteins, Hendra virus F and G proteins, Henipavirus F and G proteins, Morbilivirus F and H proteins, respirovirus F and HN protein, a Sendai virus F and HN protein, rubulavirus F and HN proteins, or avulavirus F and HN proteins, or a derivative thereof, or any combination thereof.

In some embodiments, the cargo comprises an exogenous protein or an exogenous nucleic acid. In some embodiments, the cargo comprises or encodes a cytosolic protein. In some embodiments the cargo comprises or encodes a membrane protein. In some embodiments, the cargo comprises a therapeutic agent. In some embodiments, the cargo is present at a copy number of at least 1, 2, 5, 10, 20, 50, 100, or 200 copies per fusosome (e.g., up to about 1,000 copies per fusosome). In some embodiments, the ratio of the copy number of the fusogen (e.g., re-targeted fusogen) to the copy number of the cargo is between 1000:1 and 1:1, or between 500:1 and 1:1 or between 250:1 and 1:1, or between 150:1 and 1:1, or between 100:1 and 1:1, or between 75:1 and 1:1 or between 50:1 and 1:1 or between 25:1 and 1:1 or between 20:1 and 1:1 or between 15:1 and 1:1 or between 10:1 and 1:1 or between 5:1 and 1:1 or between 2:1 and 1:1 or between 1:1 and 1:2.

In some embodiments, the fusosome composition:
  a) meets a pharmaceutical or good manufacturing practices (GMP) standard;
  b) was made according to good manufacturing practices (GMP);
  c) has a pathogen level below a predetermined reference value, e.g., is substantially free of pathogens; or
  d) has a contaminant level below a predetermined reference value, e.g., is substantially free of contaminants.

In some embodiments, the fusosome composition is at a temperature of less than 4, 0, −4, −10, −12, −16, −20, −80, or −160° C.

In some embodiments, the fusosome composition comprises a viral capsid protein or a DNA integration polypeptide. In some embodiments, the cargo comprises a viral genome.

In some embodiments, the fusosome composition is capable of delivering a nucleic acid to a target cell, e.g., to stably modify the genome of the target cell, e.g., for gene therapy.

In some embodiments, the fusosome composition does not comprise a viral nucleocapsid protein, or the amount of viral nucleocapside protein is less than 10%, 5%, 4%, 3%, 2%, 1%, 0.5%, 0.2%, or 0.1% of total protein, e.g., by mass spectrometry, e.g. using an assay of Example 53 or 161

In embodiments, a pharmaceutical composition described herein has one or more of the following characteristics:
 a) the pharmaceutical composition meets a pharmaceutical or good manufacturing practices (GMP) standard;
 b) the pharmaceutical composition was made according to good manufacturing practices (GMP);
 c) the pharmaceutical composition has a pathogen level below a predetermined reference value, e.g., is substantially free of pathogens;
 d) the pharmaceutical composition has a contaminant level below a predetermined reference value, e.g., is substantially free of contaminants; or
 e) the pharmaceutical composition has low immunogenicity, e.g., as described herein.

In embodiments, the cargo of the pharmaceutical composition comprises a therapeutic agent.

In embodiments, the biological function is selected from:
 a) modulating, e.g., inhibiting or stimulating, an enzyme;
 b) modulating, e.g., increasing or decreasing levels of, a molecule (e.g., a protein, nucleic acid, or metabolite, drug, or toxin) in the subject, e.g., by inhibiting or stimulating synthesis or by inhibiting or stimulating degradation of the factor;
 c) modulating, e.g., increasing or decreasing, viability of a target cell or tissue; or
 d) modulating a protein state, e.g., increasing or decreasing phosphorylation of the protein, or modulating the protein conformation;
 e) promoting healing of an injury;
 f) modulating, e.g., increasing or decreasing, an interaction between two cells;
 g) modulating, e.g., promoting or inhibiting, cell differentiation;
 h) altering distribution of a factor (e.g., a protein, nucleic acid, metabolite, drug, or toxin) in the subject;
 i) modulating, e.g. increasing or decreasing, an immune response; or
 j) modulating, e.g. increasing or decreasing, recruitment of cells to a target tissue.

In some embodiments of the therapeutic methods herein, the plurality of fusosomes has a local effect. In some embodiments, the plurality of fusosomes has a distal effect.

In some embodiments, the subject has a cancer, an inflammatory disorder, autoimmune disease, a chronic disease, inflammation, damaged organ function, an infectious disease, metabolic disease, degenerative disorder, genetic disease (e.g., a genetic deficiency, a recessive genetic disorder, or a dominant genetic disorder), or an injury. In some embodiments, the subject has an infectious disease and the fusosome comprises an antigen for the infectious disease. In some embodiments, the subject has a genetic deficiency and the fusosome comprises a protein for which the subject is deficient, or a nucleic acid (e.g., mRNA) encoding the protein, or a DNA encoding the protein, or a chromosome encoding the protein, or a nucleus comprising a nucleic acid encoding the protein. In some embodiments, the subject has a dominant genetic disorder, and the fusosome comprises a nucleic acid inhibitor (e.g., siRNA or miRNA) of the dominant mutant allele. In some embodiments, the subject has a dominant genetic disorder, and/or the fusosome comprises a nucleic acid inhibitor (e.g., siRNA or miRNA) of the dominant mutant allele, and/or the fusosome also comprises an mRNA encoding a non-mutated allele of the mutated gene that is not targeted by the nucleic acid inhibitor. In some embodiments, the subject is in need of vaccination. In some embodiments, the subject is in need of regeneration, e.g., of an injured site.

In some embodiments, the fusosome composition is administered to the subject at least 1, 2, 3, 4, or 5 times.

In some embodiments, the fusosome composition is administered to the subject systemically (e.g., orally, parenterally, subcutaneously, intravenously, intramuscularly, intraperitoneally) or locally. In some embodiments, the fusosome composition is administered to the subject such that the fusosome composition reaches a target tissue selected from liver, lungs, heart, spleen, pancreas, gastrointestinal tract, kidney, testes, ovaries, brain, reproductive organs, central nervous system, peripheral nervous system, skeletal muscle, endothelium, inner ear, or eye. In some embodiments (e.g., wherein the subject has an autoimmune disease), the fusosome composition is co-administered with an immunosuppressive agent, e.g., a glucocorticoid, cytostatic, antibody, or immunophilin modulator. In some embodiments (e.g., wherein the subject has a cancer or an infectious disease), the fusosome composition is co-administered with an immunostimulatory agent, e.g., an adjuvant, interleukin, cytokine, or chemokine. In some embodiments, administration of the fusosome composition results in upregulation or downregulation of a gene in a target cell in the subject, e.g., wherein the fusosome comprises a transcriptional activator or repressor, a translational activator or repressor, or an epigenetic activator or repressor.

In some embodiments of the methods of making herein, providing a source cell expressing a fusogen comprises expressing an exogenous fusogen in the source cell or upregulating expression of an endogenous fusogen in the source cell. In some embodiments, the method comprises inactivating the nucleus of the source cell.

In embodiments, the fusosome composition comprises at least $10^5$, $10^6$, $10^7$, $10^8$, $10^9$, $10^{10}$, $10^{11}$, $10^{12}$, $10^{13}$, $10^{14}$, or $10^{15}$ fusosomes. In embodiments, the fusosome composition comprises at least 10 ml, 20 ml, 50 ml, 100 ml, 200 ml, 500 ml, 1 L, 2 L, 5 L, 10 L, 20 L, or 50 L. In embodiments, the method comprises enucleating the mammalian cell, e.g., by chemical enucleation, use of mechanical force e.g., use of a filter or centrifuge, at least partial disruption of the cytoskeleton, or a combination thereof. In embodiments, the method comprises expressing a fusogen or other membrane protein in the source cell. In embodiments, the method comprises one or more of: vesiculation, hypotonic treatment, extrusion, or centrifugation. In embodiments, the method comprises genetically expressing an exogenous agent in the cell or loading the exogenous agent into the cell or fusosome. In embodiments, the method comprises contacting the cell (e.g., the source cell) with DNA encoding a polypeptide agent, e.g., before inactivating the nucleus, e.g., enucleating the cell (e.g., the source cell). In embodiments, the method comprises contacting the cell with RNA encoding a polypeptide agent, e.g., before or after inactivating the nucleus, e.g., enucleating the cell. In embodiments, the method comprises introducing a therapeutic agent (e.g., a nucleic acid or protein) into a fusosome, e.g., by electroporation.

In embodiments, the fusosome is from a mammalian cell having a modified genome, e.g., to reduce immunogenicity (e.g., by genome editing, e.g., to remove an MHC protein or MHC complexes). In embodiments, the source cell is from a cell culture treated with an anti-inflammatory signal. In embodiments, the method further comprises contacting the source cell of step a) with an immunosuppressive agent or anti-inflammatory signal, e.g., before or after inactivating the nucleus, e.g., enucleating the cell.

In some embodiments, if a detectable level, e.g., a value above a reference value, is determined, a sample containing the plurality of fusosomes or fusosome composition is discarded.

In some embodiments, the first fusogen is not a lipopeptide.

In some embodiments of the methods of assessing fusosome content of a target cell (e.g., fusosome fusion to a target cell), resulting in formation of a recipient cell, in the subject, the method further comprises collecting the biological sample from the subject. In embodiments, the biological sample includes one or more recipient cells.

In some embodiments of the methods of assessing fusosome content of a target cell (e.g., fusosome fusion to a target cell) in the subject, the method further comprises separating recipient cells in the biological sample from unfused fusosomes in the biological sample, e.g., by centrifugation. In some embodiments, the method further comprises enriching recipient cells relative to unfused fusosomes in the biological sample, e.g., by centrifugation. In some embodiments, the method further comprises enriching target cells relative to non-target cells in the biological sample, e.g., by FACS.

In some embodiments of the methods of assessing fusosome content of a target cell (e.g., fusosome fusion to a target cell) in a subject, the activity relating to the fusosome composition is chosen from the presence or level of a metabolite, the presence or level of a biomarker (e.g., a protein level or post-translational modification, e.g., phosphorylation or cleavage).

In some embodiments of the methods of assessing fusosome content of a target cell (e.g., fusosome fusion to a target cell) in a subject, the activity relating to the fusosome composition is immunogenicity. In embodiments, the target cell is a CD3+ cell and the biological sample is a blood sample collected from the subject. In embodiments, blood cells are enriched from the blood sample, e.g., using a buffered ammonium chloride solution. In embodiments, enriched blood cells are incubated with an anti-CD3 antibody (e.g., a murine anti-CD3-FITC antibody) and CD3+ cells are selected, e.g., by fluorescence activated cell sorting. In embodiments, cells, e.g., sorted cells, e.g., CD3+ cells are analyzed for the presence of antibodies on the cell surface, e.g., by staining with an anti-IgM antibody. In some embodiments, if antibodies are present at a level above a reference level, the subject is identified as having an immune response against recipient cells.

In embodiments, immunogenicity is assayed by a cell lysis assay. In embodiments, recipient cells from the biological sample are co-incubated with immune effector cells capable of lysing other cells. In embodiments, the immune effector cells are from the subject or from a subject not administered the fusosome composition. For instance, in embodiments, immunogenicity is assessed by a PBMC cell lysis assay. In embodiments, recipient cells from the biological sample are co-incubated with peripheral blood mononuclear cells (PBMCs) from the subject or control PBMCs from a subject not administered the fusosome composition and then assessed for lysis of the recipient cells by PBMCs. In embodiments, immunogenicity is assessed by a natural killer (NK) cell lysis assay. In embodiments, recipient cells are co-incubated with NK cells from the subject or control NK cells from a subject not administered the fusosome composition and then assessed for lysis of the recipient cells by the NK cells. In embodiments, immunogenicity is assessed by a CD8+ T-cell lysis assay. In embodiments, recipient cells are co-incubated with CD8+ T-cells from the subject or control CD8+ T-cells from a subject not administered the fusosome composition and then assessed for lysis of the target cells by the CD8+ T-cells. In some embodiments, if cell lysis occurs at a level above a reference level, the subject is identified as having an immune response against recipient cells.

In some embodiments, immunogenicity is assayed by phagocytosis of recipient cells, e.g., by macrophages. In embodiments, recipient cells are not targeted by macrophages for phagocytosis. In embodiments, the biological sample is a blood sample collected from the subject. In embodiments, blood cells are enriched from the blood sample, e.g., using a buffered ammonium chloride solution. In embodiments, enriched blood cells are incubated with an anti-CD3 antibody (e.g., a murine anti-CD3-FITC antibody) and CD3+ cells are selected, e.g., by fluorescence activated cell sorting. In embodiments, fluorescently-labeled CD3+ cells are incubated with macrophages and then tested for intracellular fluorescence within the macrophages, e.g., by flow cytometry. In some embodiments, if macrophage phagocytosis occurs at a level above a reference level, the subject is identified as having an immune response against recipient cells.

In some embodiments, the methods described herein comprise measuring or determining fusosome content of a target cell, e.g., fusion of a fusosome with a target cell (e.g., determining whether fusion has occurred), e.g., as described in Example 54 or 124. In embodiments, a detectable marker may be present in the fusosome (e.g., conjugated to a cargo or payload molecule in the fusosome). In embodiments in which the cargo or payload comprises a protein, the cargo or payload may be detected directly, e.g., using a binding moiety (e.g., an antibody, or antigen-binding fragment thereof). In certain embodiments, a protein payload is associated with (e.g., conjugated to) a detectable moiety, e.g., a moiety that can be specifically bound by an antibody molecule. In embodiments in which the cargo or payload comprises a nucleic acid (e.g., DNA or mRNA), the cargo or payload may be detected using a nucleic acid probe capable of hybridizing to the nucleic acid, or using a binding moiety (e.g., an antibody, or antigen-binding fragment thereof) capable of specifically binding to a polypeptide encoded by the nucleic acid. In embodiments, the fusion of the fusosome to the target cell is determined by detecting the detectable marker. In embodiments, the fusion of the fusosome to the target cell is determined by measuring expression of the cargo or payload (e.g., a polypeptide or noncoding RNA encoded by a nucleic acid cargo or payload). In embodiments, the fusion of the fusosome to the target cell is determined by measuring a downstream marker of cargo or payload activity. In some embodiments, the target cells or recipient cells are isolated from a subject prior to measuring or determining fusogen content of a target cell or recipient cell, e.g., fusion of a fusosome with a target cell. In embodiments, the target cell or recipient cells are also stained with an endosomal or lysosomal dye or antibody to determine whether payload is present in an endosome or lysosome. In some embodiments, the payload does not colocalize with the endosome or lysosome, or less than 50%, 40%, 30%, 20%, 10%, 5%, 2%, or 1% of payload colocalizes with the endosome or lysosome. In embodiments, the recipient cells are also stained with a cytoplasmic, nuclear, mitochondrial, or plasma membrane dye or antibody to determine whether payload colocalizes with a target compartment, such as the cytoplasm, nucleus, mitochondria, or plasma membrane; in such embodiments, the payload would localize with the nucleus, mitochondria, or plasma membrane.

In embodiments, a method of manufacturing fusosomes herein comprises expressing (e.g., overexpressing) ARRDC1 or an active fragment or variant thereof in a source cell. In embodiments, the method further comprises separating fusosomes from the ARRDC1-expressing source cells. In embodiments, the method yields at least $1.2 \times 10^{11}$, $1.4 \times 10^{11}$, $1.6 \times 10^{11}$, $1.8 \times 10^{11}$, $2.0 \times 10^{11}$, $2.2 \times 10^{11}$, $2.4 \times 10^{11}$, $2.6 \times 10^{11}$, or $2.8 \times 10^{11}$ particles per mL, e.g., up to about $3 \times 10^{11}$ particles per mL. In some embodiments, the method yields about 1.2, 1.4, 1.6, 1.8, 2, 3, 4, 5, 6, 7, 8, 9, or 10 times as many particles per mL than the same method performed with otherwise similar source cells that do not express or do not overexpress ARRDC1 or an active fragment or variant thereof. In some embodiments, fusosomes produced from the source cells comprises expressing (e.g., overexpressing) ARRDC1 or an active fragment or variant thereof, when contacted with target cells, produce detectable cargo delivery in at least 2, 3, 4, 5, 6, 7, 8, 9, 10, 15, or 20 times as many cells as fusosomes produced from wise similar source cells that do not express or do not overexpress ARRDC1 or an active fragment or variant thereof, e.g., using a microscopy assay, e.g., an assay of Example 170.

Enumerated Embodiments

1. A fusosome composition comprising a plurality of fusosomes derived from a source cell, wherein the fusosomes of the plurality comprise:
    (a) a lipid bilayer,
    (b) a lumen comprising cytosol, wherein the lumen is surrounded by the lipid bilayer;
    (c) an exogenous or overexpressed fusogen disposed in the lipid bilayer;
    (d) a cargo; and
    wherein the fusosome does not comprise a nucleus;
    wherein the amount of viral capsid protein in the fusosome composition is less than 1% of total protein;
    wherein the plurality of fusosomes, when contacted with a target cell population in the presence of an inhibitor of endocytosis, and when contacted with a reference target cell population not treated with the inhibitor of endocytosis, delivers the cargo to at least 30% of the number of cells in the target cell population compared to the reference target cell population.
2. The fusosome composition of embodiment 1, which delivers the cargo to at least 40%, 50%, 60%, 70%, or 80% of the number of cells in the target cell population compared to the reference target cell population or to a non-target cell population; or which delivers the cargo to at least 40%, 50%, 60%, 70%, or 80% of the cargo to the target cell population compared to the reference target cell population or to a non-target cell population.
3. The fusosome composition of embodiment 1 or 2, wherein less than 10% of cargo enters the cell by endocytosis.
4. The fusosome composition of any of the preceding embodiments, wherein the inhibitor of endocytosis is an inhibitor of lysosomal acidification, e.g., bafilomycin A1.
5. The fusosome composition of any of the preceding embodiments, wherein cargo delivered is determined using an endocytosis inhibition assay, e.g., an assay of Example 90 or 135.
6. The fusosome composition of any of the preceding embodiments, wherein cargo enters the cell through a dynamin-independent pathway or a lysosomal acidification-independent pathway, a macropinocytosis-independent pathway (e.g., wherein the inhibitor of endocytosis is an inhibitor of macropinocytosis, e.g., 5-(N-ethyl-N-isopropyl) amiloride (EIPA), e.g., at a concentration of 25 μM), or an actin-independent pathway (e.g., wherein the inhibitor of endocytosis is an inhibitor of actin polymerization is, e.g., Latrunculin B, e.g., at a concentration of 6 μM).
7. The fusosome composition of any of the preceding embodiments, wherein the fusosomes of the plurality further comprise a targeting moiety.
8. The fusosome composition of embodiment 7, wherein the targeting moiety is comprised by the fusogen or is comprised by a separate molecule.
9. The fusosome composition of any of the preceding embodiments, wherein, when the plurality of fusosomes are contacted with a cell population comprising target cells and non-target cells:
    (i) the cargo is present in at least 10-fold more target cells than non-target cells, or
    (ii) the cargo is present at least 2-fold, 5-fold, 10-fold, 20-fold, or 50-fold higher in target cells than non-target cells and/or reference cells.
10. The fusosome composition of any of the preceding embodiments wherein, the fusosomes of the plurality fuse at a higher rate with a target cell than with a non-target cell by at least 50%.
11. A fusosome composition comprising a plurality of fusosomes derived from a source cell, and wherein the fusosomes of the plurality comprise:
    (a) a lipid bilayer,
    (b) a lumen comprising cytosol, wherein the lumen is surrounded by the lipid bilayer;
    (c) an exogenous or overexpressed re-targeted fusogen disposed in the lipid bilayer;
    (d) a cargo; and
    wherein the fusosome does not comprise a nucleus;
    wherein the amount of viral capsid protein in the fusosome composition is less than 1% of total protein;
    wherein:
    (i) when the plurality of fusosomes are contacted with a cell population comprising target cells and non-target cells, the cargo is present in at least 10-fold more target cells than non-target cells, or at least 10-fold more cargo is delivered to the cell population compared to a reference cell population, or
    (ii) the fusosomes of the plurality fuse at a higher rate with a target cell than with a non-target cell by at least at least 50%, or at least 50% more cargo is delivered to the cell population compared to a reference cell population.
12. The fusosome composition of embodiment 11, wherein presence of cargo is measured by microscopy, e.g., using an assay of Example 124.
13. The fusosome composition of embodiment 11, wherein fusion is measured by microscopy, e.g., using an assay of Example 54.

14. The fusosome composition of any of embodiments 7-13, wherein the targeting moiety is specific for a cell surface marker on the target cell.

15. The fusosome composition of embodiment 14, wherein the cell surface marker is a cell surface marker of a skin cell, cardiomyocyte, hepatocyte, intestinal cell (e.g., cell of the small intestine), pancreatic cell, brain cell, prostate cell, lung cell, colon cell, or bone marrow cell.

16. The fusosome composition of any of embodiments 11-15, wherein the fusogen (e.g., re-targeted fusogen) comprises a rhabdoviridae fusogen (e.g., VSV-G), a filoviridae fusogen, an arenaviridae fusogen, a togaviridae fusogen, a flaviviridae fusogen, a bunyaviridae fusogen, or a hapadnaviridae fusogen (e.g., Hep B), or a derivative thereof.

17. The fusosome composition of any of embodiments 7-16, wherein the plurality of fusosomes, when contacted with a target cell population in the presence of an inhibitor of endocytosis, and when contacted with a reference target cell population not treated with the inhibitor of endocytosis:
   (i) delivers the cargo to at least 30% of the number of cells in the target cell population compared to the reference target cell population,
   (ii) delivers at least 30% of the cargo to the target cell population compared to the reference target cell population; or
   (iii) delivers at least 30% more of the cargo to the target cell population compared to the reference target cell population.

18. The fusosome composition of any of the preceding embodiments, which, when contacted with a target cell population, delivers cargo to a target cell location other than an endosome or lysosome, e.g., to the cytosol.

19. The fusosome composition of embodiment 18, wherein less 50%, 40%, 30%, 20%, or 10% of the cargo is delivered to an endosome or lysosome.

20. The fusosome composition of any of the preceding embodiments, wherein the amount of viral capsid protein in the fusosome composition is determined using mass spectrometry, e.g., using an assay of Example 53 or 161; and/or
   wherein the fusosome composition does not comprise a viral nucleocapsid protein, or the amount of viral nucleocapsid protein is less than 10%, 5%, 4%, 3%, 2%, 1%, 0.5%, 0.2%, or 0.1% of total protein, e.g., by mass spectrometry, e.g. using an assay of Example 53 or 161.

21. The fusosome composition of any of the preceding embodiments, wherein the fusosomes of the plurality comprise exosomes, microvesicles, or a combination thereof.

22. The fusosome composition of any of the preceding embodiments, wherein the plurality of fusosomes has an average size of at least 50 nm, 100 nm, 200 nm, 500 nm, 1000 nm, 1200 nm, 1400 nm, or 1500 nm.

23. The fusosome composition of any of embodiments 1-21, wherein the plurality of fusosomes has an average size of less than 100 nm, 80 nm, 60 nm, 40 nm, or 30 nm.

24. The fusosome composition of any of the preceding embodiments, wherein the source cell is selected from a neutrophil, a HEK293 cell, a granulocyte, a mesenchymal stem cell, a bone marrow stem cell, an induced pluripotent stem cell, an embryonic stem cell, a myeloblast, a myoblast, a hepatocyte, or a neuron e.g., retinal neuronal cell.

25. The fusosome composition of any of the preceding embodiments, wherein the fusosomes in the plurality comprise cytobiologics.

26. The fusosome composition of any of the preceding embodiments, wherein the fusosomes in the plurality comprise enucleated cells.

27. The fusosome composition of any of the preceding embodiments, wherein the fusogen (e.g., re-targeted fusogen) comprises a mammalian fusogen.

28. The fusosome composition of any of the preceding embodiments, wherein the fusogen (e.g., re-targeted fusogen) comprises a viral fusogen.

29. The fusosome composition of any of the preceding embodiments, wherein the fusogen (e.g., re-targeted fusogen) is active at a pH of 4-5, 5-6, 6-7, 7-8, 8-9, or 9-10.

30. The fusosome composition of any of the preceding embodiments, wherein the fusogen (e.g., re-targeted fusogen) is not active at a pH of 4-5, 5-6, 6-7, 7-8, 8-9, or 9-10.

31. The fusosome composition of any of the preceding embodiments, wherein the fusogen (e.g., re-targeted fusogen) is a protein fusogen.

32. The fusosome composition of any of the preceding embodiments, wherein the fusogen (e.g., re-targeted fusogen) comprises a sequence chosen from a Nipah virus protein F, a measles virus F protein, a tupaia paramyxovirus F protein, a paramyxovirus F protein, a Hendra virus F protein, a Henipavirus F protein, a Morbilivirus F protein, a respirovirus F protein, a Sendai virus F protein, a rubulavirus F protein, or an avulavirus F protein, or a derivative thereof.

33. The fusosome composition of any of the preceding embodiments, wherein the fusogen is present at a copy number of at least, 2, 5, or 10 copies per fusosome.

34. The fusosome composition of any of the preceding embodiments, wherein the fusogen (e.g., re-targeted fusogen) comprises a Nipah virus protein G, a measles protein H, a tupaia paramyxovirus H protein, a paramyxovirus G protein, a paramyxovirus H protein, a paramyxovirus HN protein, a Morbilivirus H protein, a respirovirus HN protein, a sendai HN protein, a rubulavirus HN protein, an avulavirus HN protein, or a derivative thereof.

35. The fusosome composition of any of the preceding embodiments, wherein the fusogen (e.g., re-targeted fusogen) comprises a sequence chosen from Nipah virus F and G proteins, measles virus F and H proteins, tupaia paramyxovirus F and H proteins, paramyxovirus F and G proteins or F and H proteins or F and HN proteins, Hendra virus F and G proteins, Henipavirus F and G proteins, Morbilivirus F and H proteins, respirovirus F and HN protein, a Sendai virus F and HN protein, rubulavirus F and HN proteins, or avulavirus F and HN proteins, or a derivative thereof, or any combination thereof.

36. The fusosome composition of any of the preceding embodiments, wherein the cargo comprises an exogenous protein or an exogenous nucleic acid.

37. The fusosome composition of any of the preceding embodiments, wherein the cargo comprises or encodes a cytosolic protein or a membrane protein.

38. The fusosome composition of any of the preceding embodiments, wherein the cargo comprises a therapeutic agent.

39. The fusosome composition of any of the preceding embodiments, wherein the cargo is present at a copy number of at least 1, 2, 5, 10, 20, 50, 100, or 200 copies per fusosome (e.g., up to about 1,000 copies per fusosome).

40. The fusosome composition of any of the preceding embodiments, wherein the ratio of the copy number of the fusogen (e.g., re-targeted fusogen) to the copy number of the cargo is between 1000:1 and 1:1, between 500:1 and 1:1, between 250:1 and 1:1, between 150:1 and 1:1, between 100:1 and 1:1, between 75:1 and 1:1, between 50:1 and 1:1, between 25:1 and 1:1, between 20:1 and 1:1, between 15:1 and 1:1, between 10:1 and 1:1, between 5:1 and 1:1, between 2:1 and 1:1, or between 1:1 and 1:2.

41. The fusosome composition of any of the preceding embodiments, wherein one or more of:
   a) the fusosome composition has a ratio of fusogen to CD63 of about 100-10,000, 500-5,000, 1000-5000, 2000-4000, 2500-3500, 2900-2930, 2910-2915, or 2912.0, e.g., by a mass spectrometry assay; or
   b) the fusosome composition has a ratio of protein cargo to CD63 of about 5-35, 10-30, 15-25, 16-19, 18-19, or 18.6; or
   c) less than 15%, 20%, or 25% of the protein in the fusosome is exosomal protein.

42. The fusosome composition of any of the preceding embodiments, wherein one or more of:
   a) the fusogen comprises about 1-30%, 5-20%, 10-15%, 12-15%, 13-14%, or 13.6% of the total protein in a fusosome, e.g., by a mass spectrometry assay;
   b) fusogen has a ratio to GAPDH of about 20-120, 40-100, 50-90, 60-80, 65-75, 68-70, or 69, e.g., by a mass spectrometry assay;
   c) fusogen has a ratio to CNX of about 200-900, 300-800, 400-700, 500-600, 520-590, 530-580, 540-570, 550-560, or 558.4, e.g., by a mass spectrometry assay;
   d) at least 1%, 2%, 3%, 4%, 5%, 6%, 7% 8%, 9% or 10% of the protein in the fusosome is ribosomal protein, or about 1%-20%, 3%-15%, 5%-12.5%, 7.5%-11%, or 8.5%-10.5%, or 9%-10% of the protein in the fusosome is ribosomal protein.

43. The fusosome composition of any of the preceding embodiments, wherein the source cell expresses (e.g., overexpresses) ARRDC1 or an active fragment or variant thereof.

44. The fusosome composition of any of the preceding embodiments, which has a ratio of fusogen to ARRDC1 of about 1-3, 1-10, 1-100, 3-10, 4-9, 5-8, 6-7, 15-100, 60-200, 80-180, 100-160, 120-140, 3-100, 4-100, 5-100, 6-100, 15-100, 80-100, 3-200, 4-200, 5-200, 6-200, 15-200, 80-200, 100-200, 120-200, 300-1000, 400-900, 500-800, 600-700, 640-690, 650-680, 660-670, 100-10,000, or 664.9, e.g., by a mass spectrometry assay.

45. The fusosome composition of any of the preceding embodiments, wherein the level of ARRDC1 as a percentage of total protein content is at least about 0.01%, 0.02%, 0.03%, 0.04%, 0.05%, 0.1%, 0.5%, 1%, 5%, 10%, 15%, 20%, or 25%; or the level of ARRDC1 as a percentage of total protein content is about 0.01-25%, 0.0.5%-20%, 2%-15%, or 5%-10%.

46. The fusosome composition of any of the preceding embodiments, which has a ratio of fusogen to tsg101 of about 1,000-10,000, 2,000-5,000, 3,000-4,000, 3,050-3,100, 3,060-3,070, or 3,064, e.g., using a mass spectrometry assay, e.g., an assay of Example 162.

47. The fusosome composition of any of the preceding embodiments, which has a ratio of cargo to tsg101 of about 10-30, 15-25, 18-21, 19-20, or 19.5, e.g., using a mass spectrometry assay, e.g., an assay of Example 163.

48. The fusosome composition of any of the preceding embodiments, wherein the level of TSG101 as a percentage of total protein content is at least about 0.001%, 0.002%, 0.003%, 0.004%, 0.005%, 0.006%, or 0.007%; or the level of TSG101 as a percentage of total protein content is about 0.001-0.01, 0.002-0.006, 0.003-0.005, or 0.004.

49. The fusosome composition of any of the preceding embodiments, which:
   e) meets a pharmaceutical or good manufacturing practices (GMP) standard;
   f) was made according to good manufacturing practices (GMP);
   g) has a pathogen level below a predetermined reference value, e.g., is substantially free of pathogens; or
   h) has a contaminant level below a predetermined reference value, e.g., is substantially free of contaminants.

50. The fusosome composition of any of the preceding embodiments, which is at a temperature of less than 4, 0, −4, −10, −12, −16, −20, −80, or −160° C.

51. A pharmaceutical composition comprising the fusosome composition of any of the preceding embodiments and pharmaceutically acceptable carrier.

52. The pharmaceutical composition of embodiment 51, wherein the cargo comprises a therapeutic agent.

53. A method of delivering a therapeutic agent to a subject, comprising administering to the subject a pharmaceutical composition of embodiment 52, wherein the fusosome composition is administered in an amount and/or time such that the therapeutic agent is delivered.

54. A method of manufacturing a fusosome composition, comprising:
   a) providing a fusosome composition of any of embodiments 1-50; and
   b) formulating the fusosomes as a pharmaceutical composition suitable for administration to a subject.

55. A method of manufacturing a fusosome composition, comprising:
   a) providing a fusosome composition of any of embodiments 1-50; and
   b) assaying one or more fusosomes from the plurality to determine the presence or level of one or more of the following factors: (i) an immunogenic molecule; (ii) a pathogen; or (iii) a contaminant; and
   c) approving the plurality of fusosomes or fusosome composition for release if one or more of the factors is below a reference value.

56. A fusosome composition comprising a plurality of fusosomes derived from a source cell, and wherein the fusosomes of the plurality comprise:
   (a) a lipid bilayer,
   (b) a lumen surrounded by the lipid bilayer;
   (c) an exogenous or overexpressed fusogen, wherein the fusogen is disposed in the lipid bilayer; and
   (d) a cargo;
wherein the fusosome does not comprise a nucleus; and wherein one or more of (e.g., at least 2, 3, 4, or 5 of):
   i) the fusogen is present at a copy number of at least 1,000 copies;
   ii) the fusosome comprises a therapeutic agent at a copy number of at least 1,000 copies;
   iii) the fusosome comprises a lipid wherein one or more of CL, Cer, DAG, HexCer, LPA, LPC, LPE, LPG, LPI, LPS, PA, PC, PE, PG, PI, PS, CE, SM and TAG is within 75% of the corresponding lipid level in the source cell;
   iv) the fusosome comprises a proteomic composition similar to that of the source cell;
   v) the fusosome is capable of signal transduction, e.g., transmitting an extracellular signal, e.g., AKT phosphorylation in response to insulin, or glucose (e.g., labeled glucose, e.g., 2-NBDG) uptake in response to insulin, e.g., by at least 10% more than a negative control, e.g., an otherwise similar fusosome in the absence of insulin;
   vi) the fusosome targets a tissue, e.g., liver, lungs, heart, spleen, pancreas, gastrointestinal tract, kidney, testes, ovaries, brain, reproductive organs, central nervous system, peripheral nervous system, skeletal muscle, endothelium, inner ear, or eye, when administered to a subject, e.g., a mouse, e.g., wherein at least 0.1%, or 10%, of the fusosomes in a population of administered fusosomes are present in the target tissue after 24 hours; or vii) the source cell is selected from a neutrophil, a granulocyte, a mesenchymal stem cell, a bone marrow stem cell, an induced pluripotent stem cell, an embryonic stem cell, a myeloblast, a myoblast, a hepatocyte, or a neuron e.g., retinal neuronal cell.

57. The fusosome composition of embodiment 56, which comprises a viral capsid protein, or a DNA integration polypeptide.

58. The fusosome composition of embodiment 56, wherein the cargo comprises a viral genome.

59. The fusosome composition of embodiment 56, which is capable of delivering a nucleic acid to a target cell, e.g., to stably modify the genome of the target cell, e.g., for gene therapy.

Other features, objects, and advantages of the invention will be apparent from the description and drawings, and from the claims.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. For example, all GenBank, Unigene, and Entrez sequences referred to herein, e.g., in any Table herein, are incorporated by reference. Unless otherwise specified, the sequence accession numbers specified herein, including in any Table herein, refer to the database entries current as of May 8, 2017. When one gene or protein references a plurality of sequence accession numbers, all of the sequence variants are encompassed. In addition, the materials, methods, and examples are illustrative only and not intended to be limiting.

BRIEF DESCRIPTION OF THE DRAWINGS

The following detailed description of the invention will be better understood when read in conjunction with the appended drawings. For the purpose of illustrating the invention, there are shown in the drawings described herein certain embodiments, which are presently exemplified. It should be understood, however, that the invention is not limited to the precise arrangement and instrumentalities of the embodiments shown in the drawings.

FIG. 17A is a table showing sub-micron fusosome measurement parameters and settings.

FIG. 17B is a table showing supra-micron fusosome measurement parameters and settings.

FIG. 17D is a table showing the average diameter of fusosomes and parental cells as measured by NTA and microscopy.

FIG. 18 is a table showing size distribution statistics of fusosomes and parental cells as measured by NTA and microscopy.

FIG. 19 is a table showing the average size and volume of fusosomes and parental cells.

FIG. 29 is a table showing delivery of Cre cargo by NivG+F fusosomes via a non-endocytic pathway.

DETAILED DESCRIPTION

Figure 1:
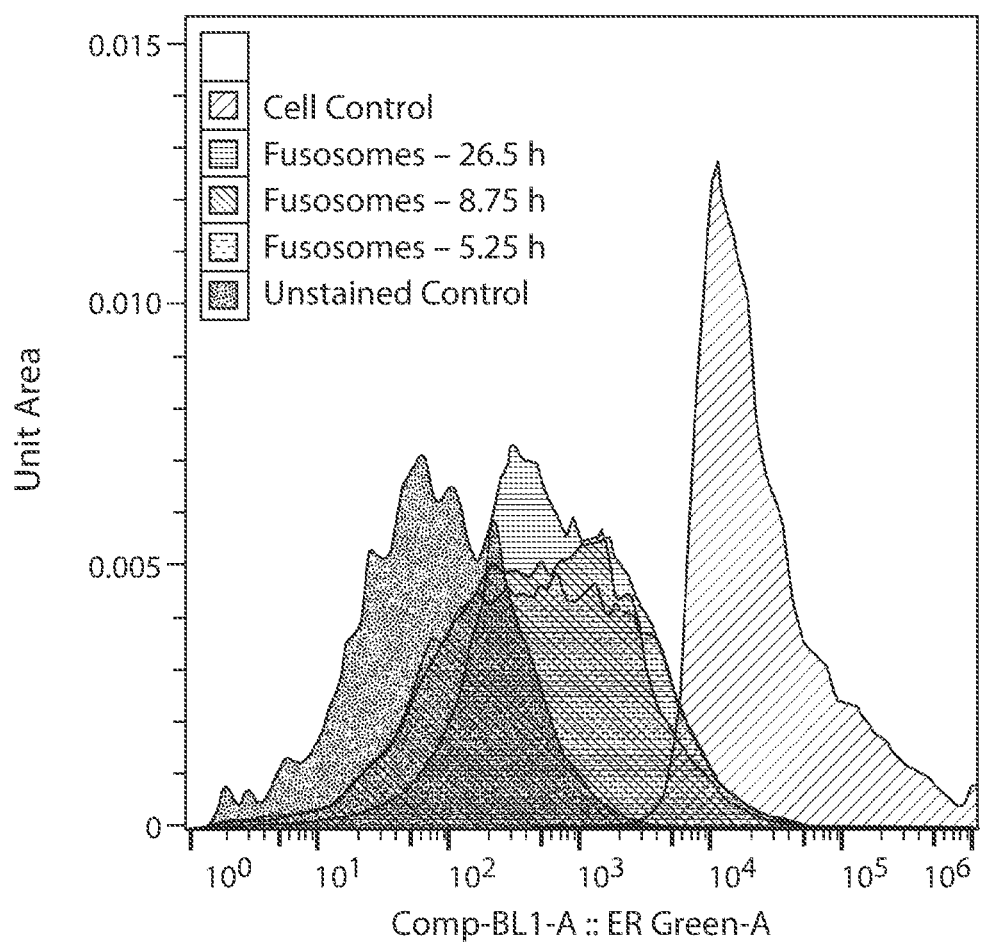
FIG. 1 quantifies staining of fusosomes with a dye for endoplasmic reticulum.

The invention describes naturally derived or engineered bilipid membranes that comprise a fusogen.

Definitions

As used herein, a "cell membrane" refers to a membrane derived from a cell, e.g., a source cell or a target cell.

As used herein, a "chondrisome" is a subcellular apparatus derived and isolated or purified from the mitochondrial network of a natural cell or tissue source. A "chondrisome preparation" has bioactivity (can interact with, or have an effect on, a cell or tissue) and/or pharmaceutical activity.

As used herein, "cytobiologic" refers to a portion of a cell that comprises a lumen and a cell membrane, or a cell having partial or complete nuclear inactivation. In some embodiments, the cytobiologic comprises one or more of a cytoskeleton component, an organelle, and a ribosome. In embodiments, the cytobiologic is an enucleated cell, a microvesicle, or a cell ghost.

As used herein, "cytosol" refers to the aqueous component of the cytoplasm of a cell. The cytosol may comprise proteins, RNA, metabolites, and ions.

An "exogenous agent" as used herein, refers to an agent that: i) does not naturally exist, such as a protein that has a sequence that is altered (e.g., by insertion, deletion, or substitution) relative to an endogenous protein, or ii) does not naturally occur in the naturally occurring source cell of the fusosome in which the exogenous agent is disposed.

As used herein, "fuse" denotes creating an interaction between two membrane enclosed lumens, e.g., facilitating fusion of two membranes or creating a connection, e.g., a pore, between two lumens.

As used herein, "fusogen" refers to an agent or molecule that creates an interaction between two membrane enclosed lumens. In embodiments, the fusogen facilitates fusion of the membranes. In other embodiments, the fusogen creates a connection, e.g., a pore, between two lumens (e.g., the lumen of the fusosome and a cytoplasm of a target cell). In some embodiments, the fusogen comprises a complex of two or more proteins, e.g., wherein neither protein has fusogenic activity alone. In some embodiments, the fusogen comprises a targeting domain.

As used herein, "fusogen binding partner" refers to an agent or molecule that interacts with a fusogen to facilitate fusion between two membranes. In some embodiments, a fusogen binding partner may be or comprise a surface feature of a cell.

As used herein, "fusosome" refers to a membrane enclosed preparation and a fusogen that interacts with the amphipathic lipid bilayer.

As used herein, "fusosome composition" refers to a composition comprising one or more fusosomes.

As used herein, "membrane enclosed preparation" refers to a bilayer of amphipathic lipids enclosing a cargo in a lumen or cavity. In some embodiments, the cargo is exogenous to the lumen or cavity. In other embodiments, the cargo is endogenous to the lumen or cavity, e.g., endogenous to a source cell.

As used herein, "mitochondrial biogenesis" denotes the process of increasing biomass of mitochondria. Mitochondrial biogenesis includes increasing the number and/or size of mitochondria in a cell.

As used herein, the term "purified" means altered or removed from the natural state. For example, a cell or cell fragment naturally present in a living animal is not "purified," but the same cell or cell fragment partially or completely separated from the coexisting materials of its natural state is "purified." A purified fusosome composition can exist in substantially pure form, or can exist in a non-native environment such as, for example, a culture medium such as a culture medium comprising cells.

As used herein, a "re-targeted fusogen" refers to a fusogen that comprises a targeting moiety having a sequence that is not part of the naturally-occurring form of the fusogen. In embodiments, the fusogen comprises a different targeting moiety relative to the targeting moiety in the naturally-occurring form of the fusogen. In embodiments, the naturally-occurring form of the fusogen lacks a targeting domain, and the re-targeted fusogen comprises a targeting moiety that is absent from the naturally-occurring form of the fusogen. In embodiments, the fusogen is modified to comprise a targeting moiety. In embodiments, the fusogen comprises one or more sequence alterations outside of the targeting moiety relative to the naturally-occurring form of the fusogen, e.g., in a transmembrane domain, fusogenically active domain, or cytoplasmic domain.

As used herein, a "source cell" (used interchangeably with "parental cell") refers to a cell from which a fusosome is derived.

Fusosomes

In some aspects, the fusosome compositions and methods described herein comprise membrane enclosed preparations, e.g., naturally derived or engineered lipid membranes, comprising a fusogen. In some aspects, the disclosure provides a portion of a non-plant cell, e.g., a mammalian cell, or derivative thereof (e.g., a mitochondrion, a chondrisome, an organelle, a vesicle, or an enucleated cell), which comprises a fusogen, e.g., protein, lipid and chemical fusogens.

Encapsulation

In some embodiments of the compositions and methods described herein include fusosomes, e.g., naturally derived or engineered bilayer of amphipathic lipids with a fusogen. Such compositions can surprisingly be used in the methods of the invention. In some instances, membranes may take the form of an autologous, allogeneic, xenogeneic or engineered cell such as is described in Ahmad et al. 2014 Mirol regulates intercellular mitochondrial transport & enhances mesenchymal stem cell rescue efficacy. EMBO Journal. 33(9):994-1010. In some embodiments, the compositions include engineered membranes such as described in, e.g. in Orive. et al. 2015. Cell encapsulation: technical and clinical advances. Trends in Pharmacology Sciences; 36 (8):537-46; and in Mishra. 2016. Handbook of Encapsulation and Controlled Release. CRC Press. In some embodiments, the compositions include naturally occurring membranes (McBride et al. 2012. A Vesicular Transport Pathway Shuttles Cargo from mitochondria to lysosomes. Current Biology 22:135-141).

In some embodiments, a composition described herein includes a naturally derived membrane, e.g., membrane vesicles prepared from cells or tissues. In one embodiment, the fusosome is a vesicle from MSCs or astrocytes.

In one embodiment, the fusosome is an exosome.

Exemplary exosomes and other membrane-enclosed bodies are described, e.g., in US2016137716, which is herein incorporated by reference in its entirety. In some embodiments, the fusosome comprises a vesicle that is, for instance, obtainable from a cell, for instance a microvesicle, an exosome, an apoptotic body (from apoptotic cells), a microparticle (which may be derived from e.g. platelets), an ectosome (derivable from, e.g., neutrophiles and monocytes in serum), a prostatosome (obtainable from prostate cancer cells), a cardiosome (derivable from cardiac cells), and the like.

Exemplary exosomes and other membrane-enclosed bodies are also described in WO/2017/161010, WO/2016/077639, US20160168572, US20150290343, and US20070298118, each of which is incorporated by reference herein in its entirety. In some embodiments, the fusosome comprises an extracellular vesicle, nanovesicle, or exosome. In embodiment the fusosome comprises an extracellular vesicle, e.g., a cell-derived vesicle comprising a membrane that encloses an internal space and has a smaller diameter than the cell from which it is derived. In embodiments the extracellular vesicle has a diameter from 20 nm to 1000 nm. In embodiments the fusosome comprises an apoptotic body, a fragment of a cell, a vesicle derived from a cell by direct or indirect manipulation, a vesiculated organelle, and a vesicle produced by a living cell (e.g., by direct plasma membrane budding or fusion of the late endosome with the plasma membrane). In embodiments the extracellular vesicle is derived from a living or dead organism, explanted tissues or organs, or cultured cells. In embodiments, the fusosome comprises a nanovesicle, e.g., a cell-derived small (e.g., between 20-250 nm in diameter, or 30-150 nm in diameter) vesicle comprising a membrane that encloses an internal space, and which is generated from said cell by direct or indirect manipulation. The production of nanovesicles can, in some instances, result in the destruction of the source cell. The nanovesicle may comprise a lipid or fatty acid and polypeptide. In embodiments, the fusosome comprises an exosome. In embodiments, the exosome is a cell-derived small (e.g., between 20-300 nm in diameter, or 40-200 nm in diameter) vesicle comprising a membrane that encloses an internal space, and which is generated from said cell by direct plasma membrane budding or by fusion of the late endosome with the plasma membrane. In embodiments, production of exosomes does not result in the destruction of the source cell. In embodiments, the exosome comprises lipid or fatty acid and polypeptide.

Exemplary exosomes and other membrane-enclosed bodies are also described in US 20160354313, which is herein incorporated by reference in its entirety. In embodiments, the fusosome comprises a Biocompatible Delivery Module, an exosome (e.g., about 30 nm to about 200 nm in diameter), a microvesicle (e.g., about 100 nm to about 2000 nm in diameter) an apoptotic body (e.g., about 300 nm to about 2000 nm in diameter), a membrane particle, a membrane vesicle, an exosome-like vesicle, an ectosome-like vesicle, an ectosome, or an exovesicle.

In one embodiment, the fusosome is microvesicle. In some embodiments, the microvesicle is a subcellular or extracellular vesicle between about 10-10,000 nm in diameter. In some embodiments, a microvesicle is released naturally from a cell, and in some embodiments, the cell is treated to enhance formation of vesicles. In one embodiment, the fusosome is an exosome. In some instances, an exosome is between about 30-100 nm in diameter. In some embodiments, an exosome is generated from multivesicular bodies. In some embodiments, a cell is treated to enhance formation of exosomes. In one embodiment, the fusosome is a cell ghost. In one embodiment, the vesicle is a plasma membrane vesicle, e.g. a giant plasma membrane vesicle.

Fusosomes can be made from several different types of lipids, e.g., amphipathic lipids, such as phospholipids. The fusosome may comprise a lipid bilayer as the outermost surface. This bilayer may be comprised of one or more lipids of the same or different type. Examples include without limitation phospholipids such as phosphocholines and phosphoinositols. Specific examples include without limitation DMPC, DOPC, and DSPC.

A fusosome may be mainly comprised of natural phospholipids and lipids such as 1,2-distearoryl-sn-glycero-3-phosphatidyl choline (DSPC), sphingomyelin, egg phosphatidylcholines and monosialoganglioside. In embodiments, a fusosome comprises only phospholipids and is less stable in plasma. However, manipulation of the lipid membrane with cholesterol can, in embodiments, increase stability and reduce rapid release of the encapsulated bioactive compound into the plasma. In some embodiments, the fusosome comprises 1,2-dioleoyl-sn-glycero-3-phosphoethanolamine (DOPE), e.g., to increase stability (see, e.g., Spuch and Navarro, Journal of Drug Delivery, vol. 2011, Article ID 469679, 12 pages, 2011. doi:10.1155/2011/469679 for review).

In some embodiments, fusosomes comprise or are enriched for lipids that affect membrane curvature (see, e.g., Thiam et al., Nature Reviews Molecular Cell Biology, 14(12): 775-785, 2013). Some lipids have a small hydrophilic head group and large hydrophobic tails, which facilitate the formation of a fusion pore by concentrating in a local region. In some embodiments, fusosomes comprise or are enriched for negative-curvature lipids, such as cholesterol, phosphatidylethanolamine (PE), diglyceride (DAG), phosphatidic acid (PA), fatty acid (FA). In some embodiments, fusosomes do not comprise, are depleted of, or have few positive-curvature lipids, such as lysophosphatidylcholine (LPC), phosphatidylinositol (PtdIns), lysophosphatidic acid (LPA), lysophosphatidylethanolamine (LPE), monoacylglycerol (MAG).

In some embodiments, the lipids are added to a fusosome. In some embodiments, the lipids are added to source cells in culture which incorporate the lipids into their membranes prior to or during the formation of a fusosome. In some embodiments, the lipids are added to the cells or fusosomes in the form of a liposome. In some embodiments methyl-betacyclodextrane (mβ-CD) is used to enrich or deplete lipids (see, e.g., Kainu et al, Journal of Lipid Research, 51(12): 3533-3541, 2010).

Fusosomes may comprise without limitation DOPE (dioleoylphosphatidylethanolamine), DOTMA, DOTAP, DOTIM, DDAB, alone or together with cholesterol to yield DOPE and cholesterol, DOTMA and cholesterol, DOTAP and cholesterol, DOTIM and cholesterol, and DDAB and cholesterol. Methods for preparation of multilamellar vesicle lipids are known in the art (see for example U.S. Pat. No. 6,693,086, the teachings of which relating to multilamellar vesicle lipid preparation are incorporated herein by reference). Although formation of fusosomes can be spontaneous when a lipid film is mixed with an aqueous solution, it can also be expedited by applying force in the form of shaking by using a homogenizer, sonicator, or an extrusion apparatus (see, e.g., Spuch and Navarro, Journal of Drug Delivery, vol. 2011, Article ID 469679, 12 pages, 2011. doi:10.1155/2011/469679 for review). Extruded lipids can be prepared by extruding through filters of decreasing size, as described in Templeton et al., Nature Biotech, 15:647-652, 1997, the teachings of which relating to extruded lipid preparation are incorporated herein by reference.

In another embodiment, lipids may be used to form fusosomes. Lipids including, but are not limited to, DLin-KC2-DMA4, C12-200 and colipids disteroylphosphatidyl choline, cholesterol, and PEG-DMG may be formulated (see, e.g., Novobrantseva, Molecular Therapy-Nucleic Acids (2012) 1, e4; doi:10.1038/mtna.2011.3) using a spontaneous vesicle formation procedure. Tekmira publications describe various aspects of lipid vesicles and lipid vesicle formulations (see, e.g., U.S. Pat. Nos. 7,982,027; 7,799,565; 8,058, 069; 8,283,333; 7,901,708; 7,745,651; 7,803,397; 8,101, 741; 8,188,263; 7,915,399; 8,236,943 and 7,838,658 and European Pat. Nos. 1766035; 1519714; 1781593 and 1664316), all of which are herein incorporated by reference and may be used and/or adapted to the present invention.

In some embodiments, a fusosome described herein may include one or more polymers. The polymers may be biodegradable. Biodegradable polymer vesicles may be synthesized using methods known in the art. Exemplary methods for synthesizing polymer vesicles are described by Bershteyn et al., Soft Matter 4:1787-1787, 2008 and in US 2008/0014144 A1, the specific teachings of which relating to microparticle synthesis are incorporated herein by reference.

Exemplary synthetic polymers which can be used include without limitation aliphatic polyesters, polyethylene glycol (PEG), poly (lactic acid) (PLA), poly (glycolic acid) (PGA), co-polymers of lactic acid and glycolic acid (PLGA), polycarprolactone (PCL), polyanhydrides, poly(ortho)esters, polyurethanes, poly(butyric acid), poly(valeric acid), and poly(lactide-co-caprolactone), and natural polymers such as albumin, alginate and other polysaccharides including dextran and cellulose, collagen, chemical derivatives thereof, including substitutions, additions of chemical groups such as for example alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Fusogens

In some embodiments, the fusosome described herein (e.g., comprising a vesicle or a portion of a cell) includes one or more fusogens, e.g., to facilitate the fusion of the fusosome to a membrane, e.g., a cell membrane. Also these compositions may include surface modifications made during or after synthesis to include one or more fusogens, e.g., fusogens may be complementary to a target cell. The surface modification may comprise a modification to the membrane, e.g., insertion of a lipid or protein into the membrane.

In some embodiments, the fusosomes comprise one or more fusogens on their exterior surface (e.g., integrated into the cell membrane) to target a specific cell or tissue type (e.g., cardiomyocytes). Fusogens include without limitation protein based, lipid based, and chemical based fusogens. The fusogen may bind a partner on a target cells' surface. In some embodiments, the fusosome comprising the fusogen will integrate the membrane into a lipid bilayer of a target cell.

In some embodiments, one or more of the fusogens described herein may be included in the fusosome.

Protein Fusogens

In some embodiments, the fusogen is a protein fusogen, e.g., a mammalian protein or a homologue of a mammalian protein (e.g., having 50%, 60%, 70%, 80%, 85%, 90%, 95%, 96%, 97%, 98%, 99%, or greater identity), a non-mammalian protein such as a viral protein or a homologue of a viral protein (e.g., having 50%, 60%, 70%, 80%, 85%, 90%, 95%, 96%, 97%, 98%, 99%, or greater identity), a native protein or a derivative of a native protein, a synthetic protein, a fragment thereof, a variant thereof, a protein fusion comprising one or more of the fusogens or fragments, and any combination thereof.

In some embodiments, the fusogen results in mixing between lipids in the fusosome and lipids in the target cell. In some embodiments, the fusogen results in formation of one or more pores between the lumen of the fusosome and the cytosol of the target cell, e.g., the fusosome is, or comprises, a connexin as described herein.

Mammalian Proteins

In some embodiments, the fusogen may include a mammalian protein, see Table 1. Examples of mammalian fusogens may include, but are not limited to, a SNARE family protein such as vSNAREs and tSNAREs, a syncytin protein such as Syncytin-1 (DOI: 10.1128/JVI.76.13.6442-6452.2002), and Syncytin-2, myomaker (biorxiv.org/content/early/2017/04/02/123158, doi.org/10.1101/123158, doi: 10.1096/fj.201600945R, doi:10.1038/nature12343), myomixer (www.nature.com/nature/journal/v499/n7458/full/nature12343.html, doi: 10.1038/nature12343), myomerger (science.sciencemag.org/content/early/2017/04/05/science.aam9361, DOI: 10.1126/science.aam9361), FGFRL1 (fibroblast growth factor receptor-like 1), Minion (doi.org/10.1101/122697), an isoform of glyceraldehyde-3-phosphate dehydrogenase (GAPDH) (e.g., as disclosed in U.S. Pat. No. 6,099,857A), a gap junction protein such as connexin 43, connexin 40, connexin 45, connexin 32 or connexin 37 (e.g., as disclosed in US 2007/0224176, Hap2, any protein capable of inducing syncytium formation between heterologous cells (see Table 2), any protein with fusogen properties (see Table 3), a homologue thereof, a fragment thereof, a variant thereof, and a protein fusion comprising one or more proteins or fragments thereof. In some embodiments, the fusogen is encoded by a human endogenous retroviral element (hERV) found in the human genome. Additional exemplary fusogens are disclosed in U.S. Pat. No. 6,099,857A and US 2007/0224176, the entire contents of which are hereby incorporated by reference.

TABLE 1

Non-limiting examples of human and non-human fusogens.
Human and Non-Human Fusogen Classes

| Fusogen Class | Uniprot Protein Family ID | # of sequences |
|---|---|---|
| EFF-AFF | PF14884 | 191 |
| SNARE | PF05739 | 5977 |
| DC-STAMP | PF07782 | 633 |
| ENV | PF00429 | 312 |

TABLE 2

Genes that encode proteins with fusogen properties.
Human genes with the gene ontology annotation of:
Syncytium formation by plasma membrane fusion proteins

| ID | Symbol |
|---|---|
| A0A024R0I0 | DYRK1B |
| A0A024R1N1 | MYH9 |
| A0A024R2D8 | CAV3 |
| A0A096LNV2 | FER1L5 |
| A0A096LPA8 | FER1L5 |
| A0A096LPB1 | FER1L5 |
| A0AVI2 | FER1L5 |
| A6NI61 | TMEM8C (myomaker) |
| B3KSL7 | — |
| B7ZLI3 | FER1L5 |
| H0YD14 | MYOF |
| O43184 | ADAM12 |
| O60242 | ADGRB3 |
| O60500 | NPHS1 |
| O95180 | CACNA1H |
| O95259 | KCNH1 |
| P04628 | WNT1 |
| P15172 | MYOD1 |
| P17655 | CAPN2 |
| P29475 | NOS1 |
| P35579 | MYH9 |
| P56539 | CAV3 |
| Q2NNQ7 | FER1L5 |
| Q4KMG0 | CDON |
| Q53GL0 | PLEKHO1 |
| Q5TCZ1 | SH3PXD2A |
| Q6YHK3 | CD109 |
| Q86V25 | VASH2 |

TABLE 2-continued

Genes that encode proteins with fusogen properties.
Human genes with the gene ontology annotation of:
Syncytium formation by plasma membrane fusion proteins

| ID | Symbol |
|---|---|
| Q99697 | PITX2 |
| Q9C0D5 | TANC1 |
| Q9H295 | DCSTAMP |
| Q9NZM1 | MYOF |
| Q9Y463 | DYRK1B |

TABLE 3

Human Fusogen Candidates

| Fusogen Class | Gene ID |
|---|---|
| SNARE | O15400 |
| | Q16623 |
| | K7EQB1 |
| | Q86Y82 |
| | E9PN33 |
| | Q96NA8 |
| | H3BT82 |
| | Q9UNK0 |
| | P32856 |
| | Q13190 |
| | O14662 |
| | P61266 |
| | O43752 |
| | O60499 |
| | Q13277 |
| | B7ZBM8 |
| | A0AVG3 |
| | Q12846 |
| DC-STAMP | Q9H295 |
| | Q5T1A1 |
| | Q5T197 |
| | E9PJX3 |
| | Q9BR26 |
| ENV | Q9UQF0 |
| | Q9N2K0 |
| | P60507 |
| | P60608 |
| | B6SEH9 |
| | P60508 |
| | B6SEH8 |
| | P61550 |
| | P60509 |
| | Q9N2J8 |
| Muscle Fusion (Myomaker) | H0Y5B2 |
| | H7C1S0 |
| | Q9HCN3 |
| | A6NDV4 |
| | K4DI83 |
| Muscle Fusion (Myomixer) | NP_001302423.1 |
| | ACT64390.1 |
| | XP_018884517.1 |
| | XP_017826615.1 |
| | XP_020012665.1 |
| | XP_017402927.1 |
| | XP_019498363.1 |
| | ELW65617.1 |
| | ERE90100.1 |
| | XP_017813001.1 |
| | XP_017733785.1 |
| | XP_017531750.1 |
| | XP_020142594.1 |
| | XP_019649987.1 |
| | XP_019805280.1 |
| | NP_001170939.1 |
| | NP_001170941.1 |
| | XP_019590171.1 |
| | XP_019062106.1 |
| | EPQ04443.1 |
| | EPY76709.1 |
| | XP_017652630.1 |
| | XP_017459263.1 |
| | OBS58441.1 |
| | XP_017459262.1 |
| | XP_017894180.1 |
| | XP_020746447.1 |
| | ELK00259.1 |
| | XP_019312826.1 |
| | XP_017200354.1 |
| | BAH40091.1 |
| HA | P03452 |
| | Q9Q0U6 |
| | P03460 |
| GAP JUNCTION | P36382 |
| | P17302 |
| | P36383 |
| | P08034 |
| | P35212 |
| Other | FGFRL1 |
| | GAPDH |

In some embodiments, the fusosome comprises a curvature-generating protein, e.g., Epsin1, dynamin, or a protein comprising a BAR domain. See, e.g., Kozlov et al, CurrOp StrucBio 2015, Zimmerberg et al. Nat Rev 2006, Richard et al, Biochem J 2011.

Non-Mammalian Proteins

Viral Proteins

In some embodiments, the fusogen may include a non-mammalian protein, e.g., a viral protein. In some embodiments, a viral fusogen is a Class I viral membrane fusion protein, a Class II viral membrane protein, a Class III viral membrane fusion protein, a viral membrane glycoprotein, or other viral fusion proteins, or a homologue thereof, a fragment thereof, a variant thereof, or a protein fusion comprising one or more proteins or fragments thereof.

In some embodiments, Class I viral membrane fusion proteins include, but are not limited to, Baculovirus F protein, e.g., F proteins of the nucleopolyhedrovirus (NPV) genera, e.g., *Spodoptera exigua* MNPV (SeMNPV) F protein and *Lymantria dispar* MNPV (LdMNPV), and paramyxovirus F proteins.

In some embodiments, Class II viral membrane proteins include, but are not limited to, tick bone encephalitis E (TBEV E), Semliki Forest Virus E1/E2.

In some embodiments, Class III viral membrane fusion proteins include, but are not limited to, rhabdovirus G (e.g., fusogenic protein G of the Vesicular Stomatatis Virus (VSV-G)), herpesvirus glycoprotein B (e.g., Herpes Simplex virus 1 (HSV-1) gB)), Epstein Barr Virus glycoprotein B (EBV gB), thogotovirus G, baculovirus gp64 (e.g., *Autographa california* multiple NPV (AcMNPV) gp64), and Borna disease virus (BDV) glycoprotein (BDV G).

Examples of other viral fusogens, e.g., membrane glycoproteins and viral fusion proteins, include, but are not limited to: viral syncytia proteins such as influenza hemagglutinin (HA) or mutants, or fusion proteins thereof; human immunodeficiency virus type 1 envelope protein (HIV-1 ENV), gp120 from HIV binding LFA-1 to form lymphocyte syncytium, HIV gp41, HIV gp160, or HIV Trans-Activator of Transcription (TAT); viral glycoprotein VSV-G, viral glycoprotein from vesicular stomatitis virus of the Rhabdoviridae family; glycoproteins gB and gH-gL of the varicella-zoster virus (VZV); murine leukaemia virus (MLV)-10A1; Gibbon Ape Leukemia Virus glycoprotein (GaLV);

type G glycoproteins in Rabies, Mokola, vesicular stomatitis virus and Togaviruses; murine hepatitis virus JHM surface projection protein; porcine respiratory coronavirus spike- and membrane glycoproteins; avian infectious bronchitis spike glycoprotein and its precursor; bovine enteric coronavirus spike protein; the F and H, HN or G genes of Measles virus; canine distemper virus, Newcastle disease virus, human parainfluenza virus 3, simian virus 41, Sendai virus and human respiratory syncytial virus; gH of human herpesvirus 1 and simian varicella virus, with the chaperone protein gL; human, bovine and cercopithicine herpesvirus gB; envelope glycoproteins of Friend murine leukaemia virus and Mason Pfizer monkey virus; mumps virus hemagglutinin neuraminidase, and glyoproteins F1 and F2; membrane glycoproteins from Venezuelan equine encephalomyelitis; paramyxovirus F protein; SIV gp160 protein; Ebola virus G protein; or Sendai virus fusion protein, or a homologue thereof, a fragment thereof, a variant thereof, and a protein fusion comprising one or more proteins or fragments thereof.

Non-mammalian fusogens include viral fusogens, homologues thereof, fragments thereof, and fusion proteins comprising one or more proteins or fragments thereof. Viral fusogens include class I fusogens, class II fusogens, class III fusogens, and class IV fusogens. In embodiments, class I fusogens such as human immunodeficiency virus (HIV) gp41, have a characteristic postfusion conformation with a signature trimer of α-helical hairpins with a central coiled-coil structure. Class I viral fusion proteins include proteins having a central postfusion six-helix bundle. Class I viral fusion proteins include influenza HA, parainfluenza F, HIV Env, Ebola GP, hemagglutinins from orthomyxoviruses, F proteins from paramyxoviruses (e.g. Measles, (Katoh et al. BMC Biotechnology 2010, 10:37)), ENV proteins from retroviruses, and fusogens of filoviruses and coronaviruses. In embodiments, class II viral fusogens such as dengue E glycoprotein, have a structural signature of β-sheets forming an elongated ectodomain that refolds to result in a trimer of hairpins. In embodiments, the class II viral fusogen lacks the central coiled coil. Class II viral fusogen can be found in alphaviruses (e.g., E1 protein) and flaviviruses (e.g., E glycoproteins). Class II viral fusogens include fusogens from Semliki Forest virus, Sinbis, rubella virus, and dengue virus. In embodiments, class III viral fusogens such as the vesicular stomatitis virus G glycoprotein, combine structural signatures found in classes I and II. In embodiments, a class III viral fusogen comprises a helices (e.g., forming a six-helix bundle to fold back the protein as with class I viral fusogens), and 3 sheets with an amphiphilic fusion peptide at its end, reminiscent of class II viral fusogens. Class III viral fusogens can be found in rhabdoviruses and herpesviruses. In embodiments, class IV viral fusogens are fusion-associated small transmembrane (FAST) proteins (doi: 10.1038/sj.emboj.7600767, Nesbitt, Rae L., "Targeted Intracellular Therapeutic Delivery Using Liposomes Formulated with Multifunctional FAST proteins" (2012). Electronic Thesis and Dissertation Repository. Paper 388), which are encoded by nonenveloped reoviruses. In embodiments, the class IV viral fusogens are sufficiently small that they do not form hairpins (doi: 10.1146/annurev-cellbio-101512-122422, doi:10.1016/j.devcel.2007.12.008).

In some embodiments the fusogen is a paramyxovirus fusogen. In some embodiments the fusogen is a Nipah virus protein F, a measles virus F protein, a tupaia paramyxovirus F protein, a paramyxovirus F protein, a Hendra virus F protein, a Henipavirus F protein, a Morbilivirus F protein, a respirovirus F protein, a Sendai virus F protein, a rubulavirus F protein, or an avulavirus F protein.

In some embodiments, the fusogen is a poxviridae fusogen.

Additional exemplary fusogens are disclosed in U.S. Pat. No. 9,695,446, US 2004/0028687, U.S. Pat. Nos. 6,416,997, 7,329,807, US 2017/0112773, US 2009/0202622, WO 2006/027202, and US 2004/0009604, the entire contents of all of which are hereby incorporated by reference.

Other Proteins

In some embodiments, the fusogen may include a pH dependent (e.g., as in cases of ischemic injury) protein, a homologue thereof, a fragment thereof, and a protein fusion comprising one or more proteins or fragments thereof. Fusogens may mediate membrane fusion at the cell surface or in an endosome or in another cell-membrane bound space.

In some embodiments, the fusogen includes a EFF-1, AFF-1, gap junction protein, e.g., a connexin (such as Cn43, GAP43, CX43) (DOI: 10.1021/jacs.6b05191), other tumor connection proteins, a homologue thereof, a fragment thereof, a variant thereof, and a protein fusion comprising one or more proteins or fragments thereof.

Modifications to Protein Fusogens

Protein fusogens may be re-targeted by mutating amino acid residues in a fusion protein or a targeting protein (e.g. the hemagglutinin protein). In some embodiments the fusogen is randomly mutated. In some embodiments the fusogen is rationally mutated. In some embodiments the fusogen is subjected to directed evolution. In some embodiments the fusogen is truncated and only a subset of the peptide is used in the fusosome. For example, amino acid residues in the measles hemagglutinin protein may be mutated to alter the binding properties of the protein, redirecting fusion (doi: 10.1038/nbt942, Molecular Therapy vol. 16 no. 8, 1427-1436 August 2008, doi:10.1038/nbt1060, DOI: 10.1128/JVI.76.7.3558-3563.2002, DOI: 10.1128/JVI.75.17.8016-8020.2001, doi: 10.1073pnas.0604993103).

Protein fusogens may be re-targeted by covalently conjugating a targeting-moiety to the fusion protein or targeting protein (e.g. the hemagglutinin protein). In some embodiments, the fusogen and targeting moiety are covalently conjugated by expression of a chimeric protein comprising the fusogen linked to the targeting moiety. A target includes any peptide (e.g. a receptor) that is displayed on a target cell. In some examples the target is expressed at higher levels on a target cell than non-target cells. For example, single-chain variable fragment (scFv) can be conjugated to fusogens to redirect fusion activity towards cells that display the scFv binding target (doi: 10.1038/nbt1060, DOI 10.1182/blood-2012-11-468579, doi: 10.1038/nmeth. 1514, doi: 10.1006/mthe.2002.0550, HUMAN GENE THERAPY 11:817-826, doi:10.1038/nbt942, doi:10.1371/journal.pone.0026381, DOI 10.1186/s12896-015-0142-z). For example, designed ankyrin repeat proteins (DARPin) can be conjugated to fusogens to redirect fusion activity towards cells that display the DARPin binding target (doi:10.1038/mt.2013.16, doi: 10.1038/mt.2010.298, doi: 10.4049/jimmunol.1500956), as well as combinations of different DARPins (doi:10.1038/mto.2016.3). For example, receptor ligands and antigens can be conjugated to fusogens to redirect fusion activity towards cells that display the target receptor (DOI: 10.1089/hgtb.2012.054, DOI: 10.1128/JVI.76.7.3558-3563.2002). A targeting protein can also include, e.g., an antibody or an antigen-binding fragment thereof (e.g., Fab, Fab', F(ab')2, Fv fragments, scFv antibody fragments, disulfide-linked Fvs (sdFv), a Fd fragment consisting of the VH and CH1 domains, linear antibodies, single domain antibodies such as sdAb (either VL or VH), nanobodies, or camelid VHH domains), an antigen-binding fibronectin type III (Fn3) scaffold such as a fibronectin polypeptide minibody, a ligand, a cytokine, a chemokine, or a T cell receptor (TCRs). Protein fusogens may be re-targeted by non-covalently conjugating a targeting moiety to the fusion protein or targeting protein (e.g. the hemagglutinin protein). For example, the fusion protein can be engineered to bind the Fc region of an antibody that targets an antigen on a target cell, redirecting the fusion activity towards cells that display the antibody's target (DOI: 10.1128/JVI.75.17.8016-8020.2001, doi:10.1038/nm1192). Altered and non-altered fusogens may be displayed on the same fusosome (doi: 10.1016/j.biomaterials.2014.01.051).

A targeting moiety may comprise, e.g., a humanized antibody molecule, intact IgA, IgG, IgE or IgM antibody; bi- or multi-specific antibody (e.g., Zybodies®, etc); antibody fragments such as Fab fragments, Fab' fragments, F(ab')2 fragments, Fd' fragments, Fd fragments, and isolated CDRs or sets thereof; single chain Fvs; polypeptide-Fc fusions; single domain antibodies (e.g., shark single domain antibodies such as IgNAR or fragments thereof); cameloid antibodies; masked antibodies (e.g., Probodies®); Small Modular ImmunoPharmaceuticals ("SMIPs™"); single chain or Tandem diabodies (TandAb®); VHHs; Anticalins®; Nanobodies®; minibodies; BiTE®s; ankyrin repeat proteins or DARPINs®; Avimers®; DARTs; TCR-like antibodies; Adnectins®; Affilins®; Trans-bodies@; Affibodies®; TrimerX®; MicroProteins; Fynomers®, Centyrins®; and KALBITOR®s.

In embodiments, the re-targeted fusogen binds a cell surface marker on the target cell, e.g., a protein, glycoprotein, receptor, cell surface ligand, agonist, lipid, sugar, class I transmembrane protein, class II transmembrane protein, or class III transmembrane protein.

Fusosomes may display targeting moieties that are not conjugated to protein fusogens in order to redirect the fusion activity towards a cell that is bound by the targeting moiety, or to affect fusosome homing.

The targeting moiety added to the fusosome may be modulated to have different binding strengths. For example, scFvs and antibodies with various binding strengths may be used to alter the fusion activity of the fusosome towards cells that display high or low amounts of the target antigen (doi: 10.1128/JVI.01415-07, doi: 10.1038/cgt.2014.25, DOI: 10.1002/jgm.1151). For example DARPins with different affinities may be used to alter the fusion activity of the fusosome towards cells that display high or low amounts of the target antigen (doi: 10.1038/mt.2010.298). Targeting moieties may also be modulated to target different regions on the target ligand, which will affect the fusion rate with cells displaying the target (doi: 10.1093/protein/gzv005).

In some embodiments protein fusogens can be altered to reduce immunoreactivity. For instance, protein fusogens may be decorated with molecules that reduce immune interactions, such as PEG (DOI: 10.1128/JVI.78.2.912-921.2004). Thus, in some embodiments, the fusogen comprises PEG, e.g., is a PEGylated polypeptide. Amino acid residues in the fusogen that are targeted by the immune system may be altered to be unrecognized by the immune system (doi: 10.1016/j.virol.2014.01.027, doi:10.1371/journal.pone.0046667). In some embodiments the protein sequence of the fusogen is altered to resemble amino acid sequences found in humans (humanized). In some embodiments the protein sequence of the fusogen is changed to a protein sequence that binds MHC complexes less strongly. In some embodiments, the protein fusogens are derived from viruses or organisms that do not infect humans (and which humans have not been vaccinated against), increasing the likelihood that a patient's immune system is naïve to the protein fusogens (e.g., there is a negligible humoral or cell-mediated adaptive immune response towards the fusogen) (doi: 10.1006/mthe.2002.0550, doi:10.1371/journal.ppat.1005641, doi:10.1038/gt.2011.209, DOI 10.1182/blood-2014-02-558163). In some embodiments, glycosylation of the fusogen may be changed to alter immune interactions or reduce immunoreactivity. Without wishing to be bound by theory, in some embodiments, a protein fusogen derived from a virus or organism that do not infect humans does not have a natural fusion targets in patients, and thus has high specificity.

Lipid Fusogens

In some embodiments, the fusosome may be treated with fusogenic lipids, such as saturated fatty acids. In some embodiments, the saturated fatty acids have between 10-14 carbons. In some embodiments, the saturated fatty acids have longer-chain carboxylic acids. In some embodiments, the saturated fatty acids are mono-esters.

In some embodiments, the fusosome may be treated with unsaturated fatty acids. In some embodiments, the unsaturated fatty acids have between C16 and C18 unsaturated fatty acids. In some embodiments, the unsaturated fatty acids include oleic acid, glycerol mono-oleate, glycerides, diacylglycerol, modified unsaturated fatty acids, and any combination thereof.

Without wishing to be bound by theory, in some embodiments negative curvature lipids promote membrane fusion. In some embodiments, the fusosome comprises one or more negative curvature lipids, e.g., exogenous negative curvature lipids, in the membrane. In embodiments, the negative curvature lipid or a precursor thereof is added to media comprising source cells or fusosomes. In embodiments, the source cell is engineered to express or overexpress one or more lipid synthesis genes. The negative curvature lipid can be, e.g., diacylglycerol (DAG), cholesterol, phosphatidic acid (PA), phosphatidylethanolamine (PE), or fatty acid (FA).

Without wishing to be bound by theory, in some embodiments positive curvature lipids inhibit membrane fusion. In some embodiments, the fusosome comprises reduced levels of one or more positive curvature lipids, e.g., exogenous positive curvature lipids, in the membrane. In embodiments, the levels are reduced by inhibiting synthesis of the lipid, e.g., by knockout or knockdown of a lipid synthesis gene, in the source cell. The positive curvature lipid can be, e.g., lysophosphatidylcholine (LPC), phosphatidylinositol (PtdIns), lysophosphatidic acid (LPA), lysophosphatidylethanolamine (LPE), or monoacylglycerol (MAG).

Chemical Fusogens

In some embodiments, the fusosome may be treated with fusogenic chemicals. In some embodiments, the fusogenic chemical is polyethylene glycol (PEG) or derivatives thereof.

In some embodiments, the chemical fusogen induces a local dehydration between the two membranes that leads to unfavorable molecular packing of the bilayer. In some embodiments, the chemical fusogen induces dehydration of an area near the lipid bilayer, causing displacement of aqueous molecules between cells and allowing interaction between the two membranes together.

In some embodiments, the chemical fusogen is a positive cation. Some nonlimiting examples of positive cations include $Ca^{2+}$, $Mg^{2+}$, $Mn^{2+}$, $Zn^{2+}$, $La^{3+}$, $Sr^{3+}$, and $H^+$.

In some embodiments, the chemical fusogen binds to the target membrane by modifying surface polarity, which alters the hydration-dependent intermembrane repulsion.

In some embodiments, the chemical fusogen is a soluble lipid soluble. Some nonlimiting examples include oleoylglycerol, dioleoylglycerol, trioleoylglycerol, and variants and derivatives thereof.

In some embodiments, the chemical fusogen is a water-soluble chemical. Some nonlimiting examples include polyethylene glycol, dimethyl sulphoxide, and variants and derivatives thereof.

In some embodiments, the chemical fusogen is a small organic molecule. A nonlimiting example includes n-hexyl bromide.

In some embodiments, the chemical fusogen does not alter the constitution, cell viability, or the ion transport properties of the fusogen or target membrane.

In some embodiments, the chemical fusogen is a hormone or a vitamin. Some nonlimiting examples include abscisic acid, retinol (vitamin A1), a tocopherol (vitamin E), and variants and derivatives thereof.

In some embodiments, the fusosome comprises actin and an agent that stabilizes polymerized actin. Without wishing to be bound by theory, stabilized actin in a fusosome can promote fusion with a target cell. In embodiments, the agent that stabilizes polymerized actin is chosen from actin, myosin, biotin-streptavidin, ATP, neuronal Wiskott-Aldrich syndrome protein (N-WASP), or formin. See, e.g., Langmuir. 2011 Aug. 16; 27(16):10061-71 and Wen et al., Nat Commun. 2016 Aug. 31; 7. In embodiments, the fusosome comprises exogenous actin, e.g., wild-type actin or actin comprising a mutation that promotes polymerization. In embodiments, the fusosome comprises ATP or phosphocreatine, e.g., exogenous ATP or phosphocreatine.

Small Molecule Fusogens

In some embodiments, the fusosome may be treated with fusogenic small molecules. Some nonlimiting examples include halothane, nonsteroidal anti-inflammatory drugs (NSAIDs) such as meloxicam, piroxicam, tenoxicam, and chlorpromazine.

In some embodiments, the small molecule fusogen may be present in micelle-like aggregates or free of aggregates.

Fusogen Modifications

In some embodiments, the fusogen is linked to a cleavable protein. In some cases, a cleavable protein may be cleaved by exposure to a protease. An engineered fusion protein may bind any domain of a transmembrane protein. The engineered fusion protein may be linked by a cleavage peptide to a protein domain located within the intermembrane space. The cleavage peptide may be cleaved by one or a combination of intermembrane proteases (e.g. HTRA2/OMI which requires a non-polar aliphatic amino acid-valine, isoleucine or methionine are preferred—at position P1, and hydrophilic residues-arginine is preferred—at the P2 and P3 positions).

In some embodiments the fusogen is linked to an affinity tag. In some embodiments the affinity tag aids in fusosome separation and isolation. In some embodiments the affinity tag is cleavable. In some embodiments the affinity tag is non-covalently linked to the fusogen. In some embodiments the affinity tag is present on the fusosome and separate from the fusogen.

In some embodiments, fusogen proteins are engineered by any methods known in the art or any method described herein to comprise a proteolytic degradation sequence, e.g., a mitochondrial or cytosolic degradation sequence. Fusogen proteins may be engineered to include, but is not limited to a proteolytic degradation sequence, e.g., a Caspase 2 protein sequence (e.g., Val-Asp-Val-Ala-Asp-I-) or other proteolytic sequences (see, for example, Gasteiger et al., The Proteomics Protocols Handbook; 2005: 571-607), a modified proteolytic degradation sequence that has at least 75%, 80%, 85%, 90%, 95% or greater identity to the wildtype proteolytic degradation sequence, a cytosolic proteolytic degradation sequence, e.g., ubiquitin, or a modified cytosolic proteolytic degradation sequence that has at least 75%, 80%, 85%, 90%, 95% or greater identity to the wildtype proteolytic degradation sequence. In one embodiment, the invention includes a composition of mitochondria in a source or chondrisomes comprising a protein modified with a proteolytic degradation sequence, e.g., at least 75%, 80%, 85%, 90%, 95% or greater identity to the wildtype proteolytic degradation sequence, a cytosolic proteolytic degradation sequence, e.g., ubiquitin, or a modified cytosolic proteolytic degradation sequence that has at least 75%, 80%, 85%, 90%, 95% or greater identity to the wildtype proteolytic degradation sequence.

In some embodiments, the fusogen may be modified with a protease domain that recognizes specific proteins, e.g., over-expression of a protease, e.g., an engineered fusion protein with protease activity. For example, a protease or protease domain from a protease, such as MMP, mitochondrial processing peptidase, mitochondrial intermediate peptidase, inner membrane peptidase.

See, Alfonzo, J. D. & Soll, D. Mitochondrial tRNA import—the challenge to understand has just begun. Biological Chemistry 390: 717-722. 2009; Langer, T. et al. Characterization of Peptides Released from Mitochondria. THE JOURNAL OF BIOLOGICAL CHEMISTRY. Vol. 280, No. 4. 2691-2699, 2005; Vliegh, P. et al. Synthetic therapeutic peptides: science and market. Drug Discovery Today. 15(1/2). 2010; Quiros P. M. m et al., New roles for mitochondrial proteases in health, ageing and disease. Nature Reviews Molecular Cell Biology. V16, 2015; Weber-Lotfi, F. et al. DNA import competence and mitochondrial genetics. Biopolymers and Cell. Vol. 30. N 1. 71-73, 2014.

Fusosome Generation

Fusosomes Generated from Cells

Compositions of fusosomes may be generated from cells in culture, for example cultured mammalian cells, e.g., cultured human cells. The cells may be progenitor cells or non-progenitor (e.g., differentiated) cells. The cells may be primary cells or cell lines (e.g., a mammalian, e.g., human, cell line described herein). In embodiments, the cultured cells are progenitor cells, e.g., bone marrow stromal cells, marrow derived adult progenitor cells (MAPCs), endothelial progenitor cells (EPC), blast cells, intermediate progenitor cells formed in the subventricular zone, neural stem cells, muscle stem cells, satellite cells, liver stem cells, hematopoietic stem cells, bone marrow stromal cells, epidermal stem cells, embryonic stem cells, mesenchymal stem cells, umbilical cord stem cells, precursor cells, muscle precursor cells, myoblast, cardiomyoblast, neural precursor cells, glial precursor cells, neuronal precursor cells, hepatoblasts.

In some embodiments, the source cell is an endothelial cell, a fibroblast, a blood cell (e.g., a macrophage, a neutrophil, a granulocyte, a leukocyte), a stem cell (e.g., a mesenchymal stem cell, an umbilical cord stem cell, bone marrow stem cell, a hematopoietic stem cell, an induced pluripotent stem cell e.g., an induced pluripotent stem cell derived from a subject's cells), an embryonic stem cell (e.g., a stem cell from embryonic yolk sac, placenta, umbilical cord, fetal skin, adolescent skin, blood, bone marrow, adipose tissue, erythropoietic tissue, hematopoietic tissue), a myoblast, a parenchymal cell (e.g., hepatocyte), an alveolar cell, a neuron (e.g., a retinal neuronal cell) a precursor cell (e.g., a retinal precursor cell, a myeloblast, myeloid precursor cells, a thymocyte, a meiocyte, a megakaryoblast, a promegakaryoblast, a melanoblast, a lymphoblast, a bone marrow precursor cell, a normoblast, or an angioblast), a progenitor cell (e.g., a cardiac progenitor cell, a satellite cell, a radial glial cell, a bone marrow stromal cell, a pancreatic progenitor cell, an endothelial progenitor cell, a blast cell), or an immortalized cell (e.g., HeLa, HEK293, HFF-1, MRC-5, WI-38, IMR 90, IMR 91, PER.C6, HT-1080, or BJ cell).

The cultured cells may be from epithelial, connective, muscular, or nervous tissue or cells, and combinations thereof. Fusosome can be generated from cultured cells from any eukaryotic (e.g., mammalian) organ system, for example, from the cardiovascular system (heart, vasculature); digestive system (esophagus, stomach, liver, gallbladder, pancreas, intestines, colon, rectum and anus); endocrine system (hypothalamus, pituitary gland, pineal body or pineal gland, thyroid, parathyroids, adrenal glands); excretory system (kidneys, ureters, bladder); lymphatic system (lymph, lymph nodes, lymph vessels, tonsils, adenoids, thymus, spleen); integumentary system (skin, hair, nails); muscular system (e.g., skeletal muscle); nervous system (brain, spinal cord, nerves); reproductive system (ovaries, uterus, mammary glands, testes, vas deferens, seminal vesicles, prostate); respiratory system (pharynx, larynx, trachea, bronchi, lungs, diaphragm); skeletal system (bone, cartilage), and combinations thereof. In embodiments, the cells are from a highly mitotic tissue (e.g., a highly mitotic healthy tissue, such as epithelium, embryonic tissue, bone marrow, intestinal crypts). In embodiments, the tissue sample is a highly metabolic tissue (e.g., skeletal tissue, neural tissue, cardiomyocytes).

In some embodiments, the cells are from a young donor, e.g., a donor 25 years, 20 years, 18 years, 16 years, 12 years, 10 years, 8 years of age, 5 years of age, 1 year of age, or less. In some embodiments, the cells are from fetal tissue.

In some embodiments, the cells are derived from a subject and administered to the same subject or a subject with a similar genetic signature (e.g., MHC-matched).

In certain embodiments, the cells have telomeres of average size greater than 3000, 4000, 5000, 6000, 7000, 8000, 9000, or 10000 nucleotides in length (e.g., between 4,000-10,000 nucleotides in length, between 6,000-10,000 nucleotides in length).

Fusosomes may be generated from cells generally cultured according to methods known in the art. In some embodiments, the cells may be cultured in 2 or more "phases", e.g., a growth phase, wherein the cells are cultured under conditions to multiply and increase biomass of the culture, and a "production" phase, wherein the cells are cultured under conditions to alter cell phenotype (e.g., to maximize mitochondrial phenotype, to increase number or size of mitochondria, to increase oxidative phosphorylation status). There may also be an "expression" phase, wherein the cells are cultured under conditions to maximize expression of protein fusogens or exogenous agents on the cell membrane and to restrict unwanted fusion in other phases.

In some embodiments, fusosomes are generated from cells synchronized, e.g., during a growth phase or the production phase. For example, cells may be synchronized at G1 phase by elimination of serum from the culture medium (e.g., for about 12-24 hours) or by the use in the culture media of DNA synthesis inhibitors such as thymidine, aminopterin, hydroxyurea and cytosine arabinoside. Additional methods for mammalian cell cycle synchronization are known and disclosed, e.g., in Rosner et al. 2013. Nature Protocols 8:602-626 (specifically Table 1 in Rosner).

In some embodiments, the cells can be evaluated and optionally enriched for a desirable phenotype or genotype for use as a source for fusosome composition as described herein. For example, cells can be evaluated and optionally enriched, e.g., before culturing, during culturing (e.g., during a growth phase or a production phase) or after culturing but before fusosome production, for example, for one or more of: membrane potential (e.g., a membrane potential of −5 to −200 mV; cardiolipin content (e.g., between 1-20% of total lipid); cholesterol, phosphatidylethanolamine (PE), diglyceride (DAG), phosphatidic acid (PA), or fatty acid (FA) content; genetic quality >80%, >85%, >90%; fusogen expression or content; cargo expression or content.

In some embodiments, fusosomes are generated from a cell clone identified, chosen, or selected based on a desirable phenotype or genotype for use as a source for fusosome composition described herein. For example, a cell clone is identified, chosen, or selected based on low mitochondrial mutation load, long telomere length, differentiation state, or a particular genetic signature (e.g., a genetic signature to match a recipient).

A fusosome composition described herein may be comprised of fusosomes from one cellular or tissue source, or from a combination of sources. For example, a fusosome composition may comprise fusosomes from xenogeneic sources (e.g., animals, tissue culture of the aforementioned species' cells), allogeneic, autologous, from specific tissues resulting in different protein concentrations and distributions (liver, skeletal, neural, adipose, etc.), from cells of different metabolic states (e.g., glycolytic, respiring). A composition may also comprise fusosomes in different metabolic states, e.g. coupled or uncoupled, as described elsewhere herein.

In some embodiments, fusosomes are generated from source cells expressing a fusogen, e.g., a fusogen described herein. In some embodiments, the fusogen is disposed in a membrane of the source cell, e.g., a lipid bilayer membrane, e.g., a cell surface membrane, or a subcellular membrane (e.g., lysosomal membrane). In some embodiments, fusosomes are generated from source cells with a fusogen disposed in a cell surface membrane.

In some embodiments, fusosomes are generated by inducing budding of an exosome, microvesicle, membrane vesicle, extracellular membrane vesicle, plasma membrane vesicle, giant plasma membrane vesicle, apoptotic body, mitoparticle, pyrenocyte, lysosome, or other membrane enclosed vesicle.

In some embodiments, producing fusosomes comprises upregulating the expression of a protein that is heterologous or endogenous to the source cell. In some embodiments the protein upregulates fusosome release from the plasma membrane. In some embodiments the protein is a viral structural protein, e.g. viral Gag protein, matrix protein, capsid protein, or nucleocapsid protein. In some embodiments the protein is a viral late protein. In some embodiments the protein is a protein encoded by the human genome. In some embodiments the protein engages the ESCRT pathway. In some embodiments the protein engages ESCRT-1. In some embodiments the protein engages Tsg101. In some embodiments the protein is incorporated into fusosomes. In some embodiments the protein is not incorporated into fusosomes. In some embodiments the protein is an arrestin. In some embodiments the protein is ARRDC1. In some embodiments, TSG101 is present at greater levels in fusosomes than parental cells or exosomes. In some embodiments, the level of TSG101 as a percentage of total protein content is at least about 0.001%, 0.002%, 0.003%, 0.004%, 0.005%, 0.006%, or 0.007% in fusosomes. In some embodiments, ARRDC1 is present at greater levels in fusosomes than parental cells or exosomes. In some embodiments, the level of ARRDC1 as a percentage of total protein content will be at least about 0.01%, 0.02%, 0.03%, 0.04%, or 0.05% in fusosomes. In some embodiments the protein contains a PSAP, PTAP, PPxY, or YPxL motif that recruits ESCRT-1, Nedd4 family ubiquitin ligases such as WWP2, or Alix. For example, such proteins are described in U.S. Pat. No. 9,737,480B2, Scourfield and Martin-Serrano, *Biochemical Society Transactions* 2017, Zhadina and Bieniasz, *PLoS Pathogens* 2010, all of which are incorporated by reference.

In some embodiments, fusosomes are generated by inducing cell enucleation. Enucleation may be performed using assays such as genetic, chemical (e.g., using Actinomycin D, see Bayona-Bafaluyet al., "A chemical enucleation method for the transfer of mitochondrial DNA to ρ° cells" Nucleic Acids Res. 2003 Aug. 15; 31(16): e98), mechanical methods (e.g., squeezing or aspiration, see Lee et al., "A comparative study on the efficiency of two enucleation methods in pig somatic cell nuclear transfer: effects of the squeezing and the aspiration methods." Anim Biotechnol. 2008; 19(2):71-9), or combinations thereof. Enucleation refers not only to a complete removal of the nucleus but also the displacement of the nucleus from its typical location such that the cell contains the nucleus but it is non-functional.

In embodiments, making a fusosome comprises producing cell ghosts, giant plasma membrane vesicle, or apoptotic bodies. In embodiments, a fusosome composition comprises one or more of cell ghosts, giant plasma membrane vesicle, and apoptotic bodies.

In some embodiments, fusosomes are generated by inducing cell fragmentation. In some embodiments, cell fragmentation can be performed using the following methods, including, but not limited to: chemical methods, mechanical methods (e.g., centrifugation (e.g., ultracentrifugation, or density centrifugation), freeze-thaw, or sonication), or combinations thereof.

In an embodiment, a fusosome can be generated from a source cell expressing a fusogen, e.g., as described herein, by any one, all of, or a combination of the following methods:
i) inducing budding of a mitoparticle, exosome, or other membrane enclosed vesicle;
ii) inducing nuclear inactivation, e.g., enucleation, by any of the following methods or a combination thereof:
  a) a genetic method;
  b) a chemical method, e.g., using Actinomycin D; or
  c) a mechanical method, e.g., squeezing or aspiration; or
iii) inducing cell fragmentation, e.g., by any of the following methods or a combination thereof:
  a) a chemical method;
  b) a mechanical method, e.g., centrifugation (e.g., ultracentrifugation or density centrifugation); freeze thaw; or sonication.

For avoidance of doubt, it is understood that in many cases the source cell actually used to make the fusosome will not be available for testing after the fusosome is made. Thus, a comparison between a source cell and a fusosome does not need to assay the source cell that was actually modified (e.g., enucleated) to make the fusosome. Rather, cells otherwise similar to the source cell, e.g., from the same culture, the same genotype same tissue type, or any combination thereof, can be assayed instead.

Modifications to Cells Prior to Fusosome Generation

In one aspect, a modification is made to a cell, such as modification of a subject, tissue or cell, prior to fusosome generation. Such modifications can be effective to, e.g., improve fusion, fusogen expression or activity, structure or function of the cargo, or structure or function of the target cell.

Physical Modifications

In some embodiments, a cell is physically modified prior to generating the fusosome. For example, as described elsewhere herein, a fusogen may be linked to the surface of the cell.

In some embodiments, a cell is treated with a chemical agent prior to generating the fusosome. For example, the cell may be treated with a chemical or lipid fusogen, such that the chemical or lipid fusogen non-covalently or covalently interacts with the surface of the cell or embeds within the surface of the cell. In some embodiments, the cell is treated with an agent to enhance fusogenic properties of the lipids in the cell membrane.

In some embodiments, the cell is physically modified prior to generating the fusosome with one or more covalent or non-covalent attachment sites for synthetic or endogenous small molecules or lipids on the cell surface that enhance targeting of the fusosome to an organ, tissues, or cell-type.

In embodiments, a fusosome comprises increased or decreased levels of an endogenous molecule. For instance, the fusosome may comprise an endogenous molecule that also naturally occurs in the naturally occurring source cell but at a higher or lower level than in the fusosome. In some embodiments, the polypeptide is expressed from an exogenous nucleic acid in the source cell or fusosome. In some embodiments, the polypeptide is isolated from a source and loaded into or conjugated to a source cell or fusosome.

In some embodiments, a cell is treated with a chemical agent prior to generating the fusosome to increase the expression or activity of an endogenous fusogen in the cell. In one embodiment, the small molecule may increase expression or activity of a transcriptional activator of the endogenous fusogen. In another embodiment, the small molecule may decrease expression or activity of a transcriptional repressor of the endogenous fusogen. In yet another embodiment, the small molecule is an epigenetic modifier that increases expression of the endogenous fusogen.

In some embodiments, the fusosomes are generated from cells treated with fusion arresting compounds, e.g., lysophosphatidylcholine. In some embodiments, the fusosomes are generated from cells treated with dissociation reagents that do not cleave fusogens, e.g., Accutase.

In some embodiments, the cell is physically modified with, e.g., CRISPR activators, to prior to generating the fusosome to add or increase the concentration of fusogens.

In some embodiments, the cell is physically modified to increase or decrease the quantity, or enhance the structure or function of organelles, e.g., mitochondria, Golgi apparatus, endoplasmic reticulum, intracellular vesicles (such as lysosomes, autophagosomes).

Genetic Modifications

In some embodiments, a cell is genetically modified prior to generating the fusosome to increase the expression of an endogenous fusogen in the cell. In one embodiment, the genetic modification may increase expression or activity of a transcriptional activator of the endogenous fusogen. In another embodiment, the genetic modification may decrease expression or activity of a transcriptional repressor of the endogenous fusogen. In some embodiments the activator or repressor is a nuclease-inactive cas9 (dCas9) linked to a transcriptional activator or repressor that is targeted to the endogenous fusogen by a guide RNA. In yet another embodiment, the genetic modification epigenetically modifies an endogenous fusogen gene to increase its expression. In some embodiments the epigenetic activator a nuclease-inactive cas9 (dCas9) linked to an epigenetic modifier that is targeted to the endogenous fusogen by a guide RNA.

In some embodiments, a cell is genetically modified prior to generating the fusosome to increase the expression of an exogenous fusogen in the cell, e.g., delivery of a transgene. In some embodiments, a nucleic acid, e.g., DNA, mRNA or siRNA, is transferred to the cell prior to generating the fusosome, e.g., to increase or decrease the expression of a cell surface molecule (protein, glycan, lipid or low molecular weight molecule) used for organ, tissue, or cell targeting. In some embodiments, the nucleic acid targets a repressor of a fusogen, e.g., an shRNA, siRNA construct. In some embodiments, the nucleic acid encodes an inhibitor of a fusogen repressor.

In some embodiments, the method comprises introducing an exogenous nucleic acid encoding a fusogen into the source cell. The exogenous nucleic acid may be, e.g., DNA or RNA. In some embodiments, the exogenous DNA may be linear DNA, circular DNA, or an artificial chromosome. In some embodiments the DNA is maintained episomally. In some embodiments the DNA is integrated into the genome. The exogenous RNA may be chemically modified RNA, e.g., may comprise one or more backbone modification, sugar modifications, noncanonical bases, or caps. Backbone modifications include, e.g., phosphorothioate, N3' phosphoramidite, boranophosphate, phosphonoacetate, thio-PACE, morpholino phosphoramidites, or PNA. Sugar modifications include, e.g., 2'-O-Me, 2'F, 2'F-ANA, LNA, UNA, and 2'-O-MOE. Noncanonical bases include, e.g., 5-bromo-U, and 5-iodo-U, 2,6-diaminopurine, C-5 propynyl pyrimidine, difluorotoluene, difluorobenzene, dichlorobenzene, 2-thiouridine, pseudouridine, and dihydrouridine. Caps include, e.g., ARCA. Additional modifications are discussed, e.g., in Deleavey et al., "Designing Chemically Modified Oligonucleotides for Targeted Gene Silencing" Chemistry & Biology Volume 19, Issue 8, 24 Aug. 2012, Pages 937-954, which is herein incorporated by reference in its entirety.

In some embodiments, a cell is treated with a chemical agent prior to generating the fusosome to increase the expression or activity of an exogenous fusogen in the cell. In one embodiment, the small molecule may increase expression or activity of a transcriptional activator of the exogenous fusogen. In another embodiment, the small molecule may decrease expression or activity of a transcriptional repressor of the exogenous fusogen. In yet another embodiment, the small molecule is an epigenetic modifier that increases expression of the exogenous fusogen.

In some embodiments, the nucleic acid encodes a modified fusogen. For example, a fusogen that has regulatable fusogenic activity, e.g., specific cell-type, tissue-type or local microenvironment activity. Such regulatable fusogenic activity may include, activation and/or initiation of fusogenic activity by low pH, high pH, heat, infrared light, extracellular enzyme activity (eukaryotic or prokaryotic), or exposure of a small molecule, a protein, or a lipid. In some embodiments, the small molecule, protein, or lipid is displayed on a target cell.

In some embodiments, a cell is genetically modified prior to generating the fusosome to alter (i.e., upregulate or downregulate) the expression of signaling pathways (e.g., the Wnt/Beta-catenin pathway). In some embodiments, a cell is genetically modified prior to generating the fusosome to alter (e.g., upregulate or downregulate) the expression of a gene or genes of interest. In some embodiments, a cell is genetically modified prior to generating the fusosome to alter (e.g., upregulate or downregulate) the expression of a nucleic acid (e.g. a miRNA or mRNA) or nucleic acids of interest. In some embodiments, nucleic acids, e.g., DNA, mRNA or siRNA, are transferred to the cell prior to generating the fusosome, e.g., to increase or decrease the expression of signaling pathways, genes, or nucleic acids. In some embodiments, the nucleic acid targets a repressor of a signaling pathway, gene, or nucleic acid, or represses a signaling pathway, gene, or nucleic acid. In some embodiments, the nucleic acid encodes a transcription factor that upregulates or downregulates a signaling pathway, gene, or nucleic acid. In some embodiments the activator or repressor is a nuclease-inactive cas9 (dCas9) linked to a transcriptional activator or repressor that is targeted to the signaling pathway, gene, or nucleic acid by a guide RNA. In yet another embodiment, the genetic modification epigenetically modifies an endogenous signaling pathway, gene, or nucleic acid to its expression. In some embodiments the epigenetic activator a nuclease-inactive cas9 (dCas9) linked to a epigenetic modifier that is targeted to the signaling pathway, gene, or nucleic acid by a guide RNA. In some embodiments, a cell's DNA is edited prior to generating the fusosome to alter (e.g. upregulate or downregulate) the expression of signaling pathways (e.g. the Wnt/Beta-catenin pathway), gene, or nucleic acid. In some embodiments, the DNA is edited using a guide RNA and CRISPR-Cas9/Cpf1 or other gene editing technology.

A cell may be genetically modified using recombinant methods. A nucleic acid sequence coding for a desired gene can be obtained using recombinant methods, such as, for example by screening libraries from cells expressing the gene, by deriving the gene from a vector known to include the same, or by isolating directly from cells and tissues containing the same, using standard techniques. Alternatively, a gene of interest can be produced synthetically, rather than cloned.

Expression of natural or synthetic nucleic acids is typically achieved by operably linking a nucleic acid encoding the gene of interest to a promoter, and incorporating the construct into an expression vector. The vectors can be suitable for replication and integration in eukaryotes. Typical cloning vectors contain transcription and translation terminators, initiation sequences, and promoters useful for expression of the desired nucleic acid sequence.

In some embodiments, a cell may be genetically modified with one or more expression regions, e.g., a gene. In some embodiments, the cell may be genetically modified with an exogenous gene (e.g., capable of expressing an exogenous gene product such as an RNA or a polypeptide product) and/or an exogenous regulatory nucleic acid. In some embodiments, the cell may be genetically modified with an exogenous sequence encoding a gene product that is endogenous to a target cell and/or an exogenous regulatory nucleic acid capable of modulating expression of an endogenous gene. In some embodiments, the cell may be genetically modified with an exogenous gene and/or a regulatory nucleic acid that modulates expression of an exogenous gene. In some embodiments, the cell may be genetically modified with an exogenous gene and/or a regulatory nucleic acid that modulates expression of an endogenous gene. It will be understood by one of skill in the art that the cell described herein may be genetically modified to express a variety of exogenous genes that encode proteins or regulatory molecules, which may, e.g., act on a gene product of the endogenous or exogenous genome of a target cell. In some embodiments, such genes confer characteristics to the fusosome, e.g., modulate fusion with a target cell. In some embodiments, the cell may be genetically modified to express an endogenous gene and/or regulatory nucleic acid. In some embodiments, the endogenous gene or regulatory nucleic acid modulates the expression of other endogenous genes. In some embodiments, the cell may be genetically modified to express an endogenous gene and/or regulatory nucleic acid which is expressed differently (e.g., inducibly, tissue-specifically, constitutively, or at a higher or lower level) than a version of the endogenous gene and/or regulatory nucleic acid on other chromosomes.

The promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter.

Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a tissue-specific promoter, metallothionine promoter, a glucocorticoid promoter, a progesterone promoter, and a tetracycline promoter. In some embodiments, expression of a fusogen is upregulated before fusosomes are generated, e.g., 3, 6, 9, 12, 24, 26, 48, 60, or 72 hours before fusosomes are generated.

The expression vector to be introduced into the source can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes may be used for identifying potentially transfected cells and for evaluating the functionality of regulatory sequences. In general, a reporter gene is a gene that is not present in or expressed by the recipient source and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

In some embodiments, a cell may be genetically modified to alter expression of one or more proteins. Expression of the one or more proteins may be modified for a specific time, e.g., development or differentiation state of the source. In one embodiment, the invention includes fusosomes generated from a source of cells genetically modified to alter expression of one or more proteins, e.g., fusogen proteins or non-fusogen proteins that affect fusion activity, structure or function. Expression of the one or more proteins may be restricted to a specific location(s) or widespread throughout the source.

In some embodiments, the expression of a fusogen protein is modified. In one embodiment, the invention includes fusosomes generated from cells with modified expression of a fusogen protein, e.g., an increase or a decrease in expression of a fusogen by at least 10%, 15%, 20%, 30%, 40%, 50%, 60%, 75%, 80%, 90% or more.

In some embodiments, cells may be engineered to express a cytosolic enzyme (e.g., proteases, phosphatases, kinases, demethylases, methyltransferases, acetylases) that targets a fusogen protein. In some embodiments, the cytosolic enzyme affects one or more fusogens by altering post-translational modifications. Post-translational protein modifications of proteins may affect responsiveness to nutrient availability and redox conditions, and protein-protein interactions. In one embodiment, the invention includes a fusosome comprising fusogens with altered post-translational modifications, e.g., an increase or a decrease in post-translational modifications by at least 10%, 15%, 20%, 30%, 40%, 50%, 60%, 75%, 80%, 90% or more.

Methods of introducing a modification into a cell include physical, biological and chemical methods. See, for example, Geng. & Lu, Microfluidic electroporation for cellular analysis and delivery. Lab on a Chip. 13(19):3803-21. 2013; Sharei, A. et al. A vector-free microfluidic platform for intracellular delivery. PNAS vol. 110 no. 6. 2013; Yin, H. et al., Non-viral vectors for gene-based therapy. Nature Reviews Genetics. 15: 541-555. 2014. Suitable methods for modifying a cell for use in generating the fusosomes described herein include, for example, diffusion, osmosis, osmotic pulsing, osmotic shock, hypotonic lysis, hypotonic dialysis, ionophoresis, electroporation, sonication, microinjection, calcium precipitation, membrane intercalation, lipid mediated transfection, detergent treatment, viral infection, receptor mediated endocytosis, use of protein transduction domains, particle firing, membrane fusion, freeze-thawing, mechanical disruption, and filtration.

Confirming the presence of a genetic modification includes a variety of assays. Such assays include, for example, molecular biological assays, such as Southern and Northern blotting, RT-PCR and PCR; biochemical assays, such as detecting the presence or absence of a particular peptide, e.g., by immunological means (ELISAs and Western blots) or by assays described herein.

Modifications to Mitochondrial Biogenesis

In some embodiments, a method described herein comprises:

(a) providing a plurality of source cells that has been contacted with a modulator of mitochondrial biogenesis, e.g., contacting a plurality of source cells with a modulator of mitochondrial biogenesis (e.g., (i) an agent that modulates mtDNA amplification, (ii) an agent that modulates mitochondrial lipid synthesis, or (iii) an agent that modulates production of nuclear-encoded mitochondrial proteins or a combination thereof), and (b) separating fusosomes from the plurality of cells.

In embodiments, the modulator of mitochondrial biogenesis upregulates or stimulates mitochondrial biogenesis. In other embodiments, the modulator of mitochondrial biogenesis downregulates or inhibits mitochondrial biogenesis.

In embodiments, the agent that modulates mtDNA amplification is an agent that promotes or inhibits mtDNA amplification. In embodiments, the agent that modulates mitochondrial lipid synthesis is an agent that promotes or inhibits mitochondrial lipid synthesis. In embodiments, the agent that modulates production of nuclear-encoded mitochondrial proteins is an agent that promotes or inhibits production of nuclear-encoded mitochondrial proteins.

In embodiments, the agent that promotes mtDNA amplification comprises: a protein that participates in mtDNA amplification, a protein that upregulates a protein that participates in mtDNA replication, or a deoxyribonucleotide or precursor thereof. In embodiments, the agent that promotes mitochondrial lipid synthesis is a lipid synthesis gene. In embodiments, the agent that promotes production of nuclear-encoded mitochondrial proteins is a transcription factor.

In embodiments, the agent that inhibits mtDNA amplification comprises: an inhibitor of a protein that participates in mtDNA amplification (e.g., a topoisomerase inhibitor, an intercalating agent, a siRNA that downregulates a protein that participates in mtDNA amplification, a targeted nuclease that downregulates a protein that participates in mtDNA amplification, a CRISPR/Cas9 molecule that that interferes with a gene for protein that participates in mtDNA amplification), a protein that downregulates a protein that participates in mtDNA replication, or a deoxyribonucleotide analog or precursor thereof. In embodiments, the agent that inhibits mitochondrial lipid synthesis is an inhibitor of a lipid synthesis gene. In embodiments, the agent that inhibits production of nuclear-encoded mitochondrial proteins is a transcriptional repressor.

In embodiments, modulating mitochondrial biogenesis comprises modulating a protein of Table 4. In embodiments, modulating mitochondrial biogenesis comprises modulating upregulating, downregulating, stimulating, or inhibiting a direct control gene (e.g., a master regulator or DNA binding factor). In embodiments, modulating mitochondrial biogenesis comprises upregulating, downregulating, stimulating, or inhibiting a direct control gene of Table 4 (e.g., a master regulator of Table 4 or a DNA binding factor of Table 4). In embodiments, modulating mitochondrial biogenesis comprises upregulating, downregulating, stimulating, or inhibiting an indirect control gene (e.g., an activator or inhibitor). In embodiments, modulating mitochondrial biogenesis comprises upregulating, downregulating, stimulating, or inhibiting an indirect control gene of Table 4 (e.g., an activator of Table 4 or an inhibitor of Table 4). In embodiments, modulating mitochondrial biogenesis comprises upregulating or downregulating a metabolite, e.g., a metabolite of Table 4.

In embodiments, an agent that promotes or inhibits synthesis of a mitochondrial lipid is capable of causing, or results in, an altered proportion of lipids in the mitochondrial membrane. In embodiments, the agent that modulates synthesis of a mitochondrial lipid results in an increase or decrease in the proportion of one of the following mitochondrial lipids: cardiolipin, phosphatidylglycerol, phosphatidylethanolamine, phosphatidic acid, CDP-diacylglycerol, phosphatidylcholine, phosphatidylserine, phosphatidylinositol, cholesterol, or ceramide e.g., by at least 10%, 20%, 30%, 40%, 50%, 60%, 70%, 80%, or 90%.

In some embodiments, the method comprises providing one, two, or all three of (i), (ii), and (iii). In some embodiments, the method comprises providing two of (i), (ii), and (iii), e.g., (i) and (ii), (i) and (iii), or (ii) and (iii). In some embodiments, the method comprises providing one of one, two, or all three of (i), (ii), and (iii) at a level sufficient to stimulate mitochondrial biogenesis.

In embodiments, the method comprises modulating (e.g., stimulating) mtDNA amplification (e.g., by at least 10%, 20%, 30%, 40%, 50%, 60%, 70%, 80%, or 90%). In embodiments, modulating mtDNA amplification occurs without detectable modulation (e.g. stimulation) of one or both of lipid synthesis and production of nuclear encoded mitochondrial proteins. In embodiments, the method comprises modulating (e.g., stimulating) lipid synthesis (e.g., by at least 10%, 20%, 30%, 40%, 50%, 60%, 70%, 80%, or 90%). In embodiments, modulating occurs without detectable modulation (e.g. stimulation) of one or both of mtDNA amplification and production of nuclear encoded mitochondrial proteins. In embodiments, the method comprises modulating (e.g., stimulating) production of nuclear encoded mitochondrial proteins (e.g., by at least 10%, 20%, 30%, 40%, 50%, 60%, 70%, 80%, or 90%). In embodiments, modulating production of nuclear encoded mitochondrial proteins occurs without detectable modulation (e.g. stimulation) of one or both of lipid synthesis and mtDNA amplification.

In embodiments, the method comprises modulating (e.g., stimulating) mtDNA amplification and lipid synthesis (e.g., each independently by at least 10%, 20%, 30%, 40%, 50%, 60%, 70%, 80%, or 90%). In embodiments, modulating mtDNA amplification and lipid synthesis occurs without detectable modulation (e.g. stimulation) of production of nuclear encoded mitochondrial proteins. In embodiments, the method comprises modulating (e.g., stimulating) mtDNA amplification and production of nuclear encoded mitochondrial proteins (e.g., each independently by at least 10%, 20%, 30%, 40%, 50%, 60%, 70%, 80%, or 90%). In embodiments, modulating mtDNA amplification and production of nuclear encoded mitochondrial proteins occurs without detectable modulation (e.g. stimulation) of lipid synthesis. In embodiments, the method comprises modulating (e.g., stimulating) lipid synthesis and production of nuclear encoded mitochondrial proteins (e.g., each independently by at least 10%, 20%, 30%, 40%, 50%, 60%, 70%, 80%, or 90%). In embodiments, modulating lipid synthesis and production of nuclear encoded mitochondrial proteins occurs without detectable modulation (e.g. stimulation) of mtDNA amplification.

In embodiments, the method comprises modulating (e.g., stimulating) mtDNA amplification, lipid synthesis, and production of nuclear encoded mitochondrial proteins (e.g., each independently by at least 10%, 20%, 30%, 40%, 50%, 60%, 70%, 80%, or 90%).

In embodiments, the modulator of mitochondrial biogenesis is a stimulator of mitochondrial biogenesis. In embodiments, the modulator of mitochondrial biogenesis is a stimulator of browning. In embodiments, the stimulator of browning is PGC1a. In embodiments, the stimulator of browning is quinone, FGF21, irisin, apelin, or isoproterenol. In embodiments, the plurality of source cells or a fusosome composition derived from the plurality of source cells is assayed for browning, e.g., by ELISA for UCP1 expression, e.g., as described in Spaethling et al "Single-cell transcriptomics and functional target validation of brown adipocytes show their complex roles in metabolic homeostasis." in: FASEB Journal, Vol. 30, Issue 1, pp. 81-92, 2016.

In embodiments, the plurality of source cells or a fusosome composition derived from the plurality is assayed for the presence or level of mtDNA amplification, mitochondrial lipid synthesis, or production of nuclear-encoded mitochondrial proteins, or any combination thereof.

The source cell may be contacted with a modulator of mitochondrial biogenesis in an amount and for a time sufficient to increase mitochondrial biogenesis in the source cell (e.g., by at least 10%, 15%, 20%, 30%, 40%, 50%, 60%, 75%, 80%, 90% or more). Such modulator of mitochondrial biogenesis are described, e.g., in Cameron et al. 2016. *Development of Therapeutics That Induce Mitochondrial Biogenesis for the Treatment of Acute and Chronic Degenerative Diseases.* DOI:10.1021/acs.jmedchem.6b00669. In embodiments, the modulator of mitochondrial biogenesis is added to the source cell culture during the growth phase and/or during the production phase. In embodiments, the modulator of mitochondrial biogenesis is added when the source cell culture has a predetermined target density.

In one embodiment, the modulator of mitochondrial biogenesis is an agent extracted from a natural product or its synthetic equivalent, sufficient to increase mitochondrial biogenesis in the source cell. Examples of such agents include resveratrol, epicatechin, curcumin, a phytoestrogen (e.g., genistein, daidzein, pyrroloquinoline, quinone, coumestrol and equol).

In another embodiment, the modulator of mitochondrial biogenesis is a metabolite sufficient to increase mitochondrial biogenesis in the source cell, mitochondria in the source cell, e.g., a primary or secondary metabolite. Such metabolites, e.g., primary metabolites include alcohols such as ethanol, lactic acid, and certain amino acids and secondary metabolites include organic compounds produced through the modification of a primary metabolite, are described in "Primary and Secondary Metabolites." Boundless Microbiology. Boundless, 26 May 2016.

In one embodiment, the modulator of mitochondrial biogenesis is an energy source sufficient to increase mitochondrial biogenesis in the source cell, or mitochondria in the source cell, e.g., sugars, ATP, redox cofactors as NADH and FADH2. Such energy sources, e.g., pyruvate or palmitate, are described in Mehlman, M. *Energy Metabolism and the Regulation of Metabolic Processes in Mitochondria*; Academic Press, 1972.

In one embodiment, the modulator of mitochondrial biogenesis is a transcription factor modulator sufficient to increase mitochondrial biogenesis in the source cell. Examples of such transcription factor modulators include: thiazolidinediones (e.g., rosiglitazone, pioglitazone, troglitazone and ciglitazone), estrogens (e.g., 17β-Estradiol, progesterone) and estrogen receptor agonists; SIRT1 Activators (e.g., SRT1720, SRT1460, SRT2183, SRT2104).

In one embodiment, the modulator of mitochondrial biogenesis is a kinase modulator sufficient to increase mitochondrial biogenesis in the source cell. Examples include: AMPK and AMPK activators such as AICAR, metformin, phenformin, A769662; and ERK1/2 inhibitors, such as U0126, trametinib.

In one embodiment, the modulator of mitochondrial biogenesis is a cyclic nucleotide modulator sufficient to increase mitochondrial biogenesis in the source cell. Examples include modulators of the NO-cGMP-PKG pathway (for example nitric oxide (NO) donors, such as sodium nitroprusside, (±)S-nitroso-N-acetylpenicillamine (SNAP), diethylamine NONOate (DEA-NONOate), diethylenetriamine-NONOate (DETA-NONOate); sGC stimulators and activators, such as cinaciguat, riociguat, and BAY 41-2272; and phosphodiesterase (PDE) inhibitors, such as zaprinast, sildenafil, udenafil, tadalafil, and vardenafil) and modulators of the cAMP-PKA-CREB Axis, such as phosphodiesterase (PDE) inhibitors such as rolipram.

In one embodiment, the modulator of mitochondrial biogenesis is a modulator of a G protein coupled receptor (GPCR) such as a GPCR ligand sufficient to increase mitochondrial biogenesis in the source cell.

In one embodiment, the modulator of mitochondrial biogenesis is a modulator of a cannabinoid-1 receptor sufficient to increase mitochondrial biogenesis in the source cell. Examples include taranabant and rimonobant.

In one embodiment, the modulator of mitochondrial biogenesis is a modulator of a 5-Hydroxytryptamine receptor sufficient to increase mitochondrial biogenesis in the source cell. Examples include alpha-methyl-5-hydroxytryptamine, DOI, CP809101, SB242084, serotonin reuptake inhibitors such as fluoxetine, alpha-methyl 5HT, 1-(2,5-dimethoxy-4-iodophenyl)-2-aminopropane, LY334370, and LY344864.

In one embodiment, the modulator of mitochondrial biogenesis is a modulator of a beta adrenergic receptor sufficient to increase mitochondrial biogenesis in the source cell. Examples include epinephrine, norepinephrine, isoproterenol, metoprolol, formoterol, fenoterol and procaterol.

In one embodiment, the source cells are modified, e.g., genetically modified, to express a transcriptional activator of mitochondrial biogenesis, e.g., a transcription factor or transcriptional coactivator such as PGC1α. In some embodiments, the cells express PGC1α (e.g., over express an endogenous, or express an exogenous, PGC1α).

TABLE 4

Transcriptional Control of Mitochondrial Biogenesis. See, e.g., Scarpulla et al., "Transcriptional integration of mitochondrial biogenesis" Trends in Endocrinology & Metabolism, Volume 23, Issue 9, p459-466, September 2012; Hock et al. "Transcriptional control of mitochondrial biogenesis and function." Annu Rev Physiol. 2009; 71: 177-203. Santra et al., "Ketogenic Treatment Reduces Deleted Mitochondrial DNAs in Cultured Human Cells" Ann Neurol. 2004 Nov; 56(5): 662-9. Kanabus et al., "The pleiotropic effects of decanoic acid treatment on mitochondrial function in fibroblasts from patients with complex I deficient Leigh syndrome" J Inherit Metab Dis. 2016 May; 39(3): 415-26, each of which is herein incorporated by reference in its entirety.

| Direct control genes | |
|---|---|
| Gene | Target or function controlled |

TABLE 4-continued

Transcriptional Control of Mitochondrial Biogenesis. See, e.g., Scarpulla
et al., "Transcriptional integration of mitochondrial biogenesis" Trends
in Endocrinology & Metabolism, Volume 23, Issue 9, p459-466,
September 2012; Hock et al. "Transcriptional control of mitochondrial
biogenesis and function." Annu Rev Physiol. 2009; 71: 177-203. Santra
et al., "Ketogenic Treatment Reduces Deleted Mitochondrial DNAs in
Cultured Human Cells" Ann Neurol. 2004 Nov; 56(5): 662-9. Kanabus
et al., "The pleiotropic effects of decanoic acid treatment on
mitochondrial function in fibroblasts from patients with complex I
deficient Leigh syndrome" J Inherit Metab Dis. 2016 May; 39(3): 415-
26, each of which is herein incorporated by reference in its entirety.

| Master regulators | |
|---|---|
| PGC-1a | Master regulator, co-activator for PPAR-delta, a, gamma; ERRa, b, gamma; GABP; NRF-1; YY1; CREB; c-MYC |
| PGC-1b | Master regulator, co-activator for PPAR-delta, a, gamma; ERRa, b, gamma; GABP; NRF-1; YY1; CREB; c-MYC |
| RIP140 | Co-repressor with PPAR-delta, a, gamma and ERRa, beta, gamma |
| PRC | Master regulator, co-activator for PPAR-delta, a, gamma; ERRa, b, gamma; GABP; NRF-1; YY1; CREB; c-MYC |

| DNA binding factors | |
|---|---|
| RXR (Retinoid X receptor) | Fatty Acid Beta Oxidation & Uncoupling protein |
| PPARa | Fatty Acid Beta Oxidation & Uncoupling protein |
| PPAR-delta | Fatty Acid Beta Oxidation & Uncoupling protein |
| PPAR-gamma | Uncoupling protein |
| NRF-1 | Maintenance of mtDNA and expression of ETC; mtDNA transcription; mitochondrial import |
| NRF-2 | Maintenance of mtDNA and expression of multiple ETC components |
| ERR (a, B and gamma) | Through interactions with PGC1a, regulated expression of fatty acid B-ox, Mitochondrial dynamics (fission/fusion); ETC; mtDNA replication and transcription; mitochondrial import |
| GABP | Maintenance of mtDNA and expression of ETC; mtDNA transcription; mitochondrial import |
| YY1 | Maintenance of mtDNA and expression of ETC; mtDNA transcription; mitochondrial import |
| c-MYC | Maintenance of mtDNA and expression of ETC; mtDNA transcription; mitochondrial import |
| CREB | Maintenance of mtDNA and expression of ETC; mtDNA transcription; mitochondrial import |

| Indirect control genes | |
|---|---|
| Gene | Target or function controlled |

| Inhibitors | |
|---|---|
| SRC-3 | Acetylates and inhibits PGC-1a |
| GCN5 | Acetylates and inhibits PGC-1a |
| AKT | |
| SCF-cdc4 | |
| MYBBP1a | |

| Activators | |
|---|---|
| SIRT1 | Deacetylates and activates PCG-1a |
| AMPK | Phosphorylates and activates PGC-1a |
| Cdk/cyclin | |
| H/MAT1 | |
| PRMT1 | |
| GSK-3B | |

| Indirect control genes for other processes | |
|---|---|
| Gene | Target or function controlled |
| SIRT3 | Controls mtSOD2 and GSH/GPX to inhibit ROS levels |

| Metabolites stimulating biogenesis | |
|---|---|
| Name | Class |
| β-hydroxybutyrate (BHB) | Ketone body |
| Acetoacetate (ACA) | Ketone Body |
| decanoic acid (C10) | Medium chain triglyceride |
| octanoic acid | Medium chain triglyceride |

Fusosome Modifications

In one aspect, a modification is made to the fusosome. Such modifications can be effective to, e.g., improve targeting, function, or structure.

In some embodiments, the fusosome is treated with a fusogen, e.g., a chemical fusogen described herein, that may non-covalently or covalently link to the surface of the membrane. In some embodiments, the fusosome is treated with a fusogen, e.g., a protein or a lipid fusogen, that may non-covalently or covalently link or embed itself in the membrane.

In some embodiments, a ligand is conjugated to the surface of the fusosome via a functional chemical group (carboxylic acids, aldehydes, amines, sulfhydryls and hydroxyls) that is present on the surface of the fusosome.

Such reactive groups include without limitation maleimide groups. As an example, fusosomes may be synthesized to include maleimide conjugated phospholipids such as without limitation DSPE-MaL-PEG2000.

In some embodiments, a small molecule or lipid, synthetic or native, may be covalently or non-covalent linked to the surface of the fusosome. In some embodiments, a membrane lipid in the fusosome may be modified to promote, induce, or enhance fusogenic properties.

In some embodiments, the fusosome is modified by loading with modified proteins (e.g., enable novel functionality, alter post-translational modifications, bind to the mitochondrial membrane and/or mitochondrial membrane proteins, form a cleavable protein with a heterologous function, form a protein destined for proteolytic degradation, assay the agent's location and levels, or deliver the agent as a carrier). In one embodiment, the invention includes a fusosome loaded with modified proteins.

In some embodiments, an exogenous protein is non-covalently bound to the fusosome. The protein may include a cleavable domain for release. In one embodiment, the invention includes a fusosome comprising an exogenous protein with a cleavable domain.

In some embodiments, the fusosome is modified with a protein destined for proteolytic degradation. A variety of proteases recognize specific protein amino acid sequences and target the proteins for degradation. These protein degrading enzymes can be used to specifically degrade proteins having a proteolytic degradation sequence. In one embodiment, the invention includes a fusosome comprising modulated levels of one or more protein degrading enzymes, e.g., an increase or a decrease in protein degrading enzymes by at least 10%, 15%, 20%, 30%, 40%, 50%, 60%, 75%, 80%, 90% or more.

As described herein, non-fusogen additives may be added to the fusosome to modify their structure and/or properties. For example, either cholesterol or sphingomyelin may be added to the membrane to help stabilize the structure and to prevent the leakage of the inner cargo. Further, membranes can be prepared from hydrogenated egg phosphatidylcholine or egg phosphatidylcholine, cholesterol, and dicetyl phosphate. (see, e.g., Spuch and Navarro, Journal of Drug Delivery, vol. 2011, Article ID 469679, 12 pages, 2011. doi:10.1155/2011/469679 for review).

In some embodiments, the fusosome comprises one or more targeting groups (e.g., a targeting protein) on the exterior surface to target a specific cell or tissue type (e.g., cardiomyocytes). These targeting groups include without limitation receptors, ligands, antibodies, and the like. These targeting groups bind their partner on the target cells' surface. In embodiments, the targeting protein is specific for a cell surface marker on a target cell described herein, e.g., a skin cell, cardiomyocyte, hepatocyte, intestinal cell (e.g., cell of the small intestine), pancreatic cell, brain cell, prostate cell, lung cell, colon cell, or bone marrow cell.

In some embodiments, the targeting protein binds a cell surface marker on a target cell. In embodiments, the cell surface marker comprises a protein, glycoprotein, receptor, cell surface ligand, class I transmembrane protein, class II transmembrane protein, or class III transmembrane protein.

In some embodiments, the targeting moiety is comprised by a polypeptide that is a separate polypeptide from the fusogen. In some embodiments, the polypeptide comprising a targeting moiety comprises a transmembrane domain and an extracellular targeting domain. In embodiments, the extracellular targeting domain comprises an scFv, DARPin, nanobody, receptor ligand, or antigen. In some embodiments, the extracellular targeting domain comprises an antibody or an antigen-binding fragment thereof (e.g., Fab, Fab', F(ab')2, Fv fragments, scFv antibody fragments, disulfide-linked Fvs (sdFv), a Fd fragment consisting of the VH and CH1 domains, linear antibodies, single domain antibodies such as sdAb (either VL or VH), or camelid VHH domains), an antigen-binding fibronectin type III (Fn3) scaffold such as a fibronectin polypeptide minibody, a ligand, a cytokine, a chemokine, or a T cell receptor (TCRs).

In some embodiments, the fusosome described herein is functionalized with a diagnostic agent. Examples of diagnostic agents include, but are not limited to, commercially available imaging agents used in positron emissions tomography (PET), computer assisted tomography (CAT), single photon emission computerized tomography, x-ray, fluoroscopy, and magnetic resonance imaging (MRI); and contrast agents. Examples of suitable materials for use as contrast agents in MRI include gadolinium chelates, as well as iron, magnesium, manganese, copper, and chromium.

Another example of introducing functional groups to the fusosome is during post-preparation, by direct crosslinking fusosome and ligands with homo- or heterobifunctional crosslinkers. This procedure may use a suitable chemistry and a class of crosslinkers (CDI, EDAC, glutaraldehydes, etc. as discussed herein) or any other crosslinker that couples a ligand to the fusosome surface via chemical modification of the fusosome surface after preparation. This also includes a process whereby amphiphilic molecules such as fatty acids, lipids or functional stabilizers may be passively adsorbed and adhered to the fusosome surface, thereby introducing functional end groups for tethering to ligands.

Cargo

In some embodiments, a fusosome described herein includes a cargo, e.g., subcellular cargo.

In some embodiments, a fusosome described herein includes a cargo, e.g., a therapeutic agent, e.g., an endogenous therapeutic agent or an exogenous therapeutic agent.

In some embodiments, the cargo is not expressed naturally in the cell from which the fusosome is derived. In some embodiments, the cargo is expressed naturally in the cell from which the fusosome is derived. In some embodiments, the cargo is a mutant of a wild type nucleic acid or protein expressed naturally in the cell from which the fusosome is derived or is a wild type of a mutant expressed naturally in the cell from which the fusosome is derived.

In some embodiments, the cargo is loaded into the fusosome via expression in the cell from which the fusosome is derived (e.g. expression from DNA or mRNA introduced via transfection, transduction, or electroporation). In some embodiments, the cargo is expressed from DNA integrated into the genome or maintained episosomally. In some embodiments, expression of the cargo is constitutive. In some embodiments, expression of the cargo is induced. In some embodiments, expression of the cargo is induced immediately prior to generating the fusosome. In some embodiments, expression of the cargo is induced at the same time as expression of the fusogen.

In some embodiments, the cargo is loaded into the fusosome via electroporation into the fusosome itself or into the cell from which the fusosome is derived. In some embodiments, the cargo is loaded into the fusosome via transfection (e.g., of a DNA or mRNA encoding the cargo) into the fusosome itself or into the cell from which the fusosome is derived.

In some aspects, the disclosure provides a fusosome composition (e.g., a pharmaceutical composition) comprising:

(i) one or more of a chondrisome (e.g., as described in international application, PCT/US16/64251), a mitochondrion, an organelle (e.g., Mitochondria, Lysosomes, nucleus, cell membrane, cytoplasm, endoplasmic reticulum, ribosomes, vacuoles, endosomes, spliceosomes, polymerases, capsids, acrosome, autophagosome, centriole, glycosome, glyoxysome, hydrogenosome, melanosome, mitosome, myofibril, cnidocyst, peroxisome, proteasome, vesicle, stress granule, and networks of organelles), or an enucleated cell, e.g., an enucleated cell comprising any of the foregoing, and (ii) a fusogen, e.g., a myomaker protein.

In embodiments, the fusogen is present in a lipid bilayer external to the mitochondrion or chondrisome. In embodiments, the chondrisome has one or more of the properties as described, for example, in international application, PCT/US16/64251, which is herein incorporated by reference in its entirety, including the Examples and the Summary of the Invention.

In some embodiments, the cargo may include one or more nucleic acid sequences, one or more polypeptides, a combination of nucleic acid sequences and/or polypeptides, one or more organelles, and any combination thereof. In some embodiments, the cargo may include one or more cellular components. In some embodiments, the cargo includes one or more cytosolic and/or nuclear components.

In some embodiments, the cargo includes a nucleic acid, e.g., DNA, nDNA (nuclear DNA), mtDNA (mitochondrial DNA), protein coding DNA, gene, operon, chromosome, genome, transposon, retrotransposon, viral genome, intron, exon, modified DNA, mRNA (messenger RNA), tRNA (transfer RNA), modified RNA, microRNA, siRNA (small interfering RNA), tmRNA (transfer messenger RNA), rRNA (ribosomal RNA), mtRNA (mitochondrial RNA), snRNA (small nuclear RNA), small nucleolar RNA (snoRNA), SmY RNA (mRNA trans-splicing RNA), gRNA (guide RNA), TERC (telomerase RNA component), aRNA (antisense RNA), cis-NAT (Cis-natural antisense transcript), CRISPR RNA (crRNA), lncRNA (long noncoding RNA), piRNA (piwi-interacting RNA), shRNA (short hairpin RNA), tasiRNA (trans-acting siRNA), eRNA (enhancer RNA), satellite RNA, pcRNA (protein coding RNA), dsRNA (double stranded RNA), RNAi (interfering RNA), circRNA (circular RNA), reprogramming RNAs, aptamers, and any combination thereof. In some embodiments, the nucleic acid is a wild-type nucleic acid. In some embodiments, the protein is a mutant nucleic acid. In some embodiments the nucleic acid is a fusion or chimera of multiple nucleic acid sequences.

In some embodiments, DNA in the fusosome or DNA in the cell that the fusosome is derived from is edited to correct a genetic mutation using a gene editing technology, e.g., a guide RNA and CRISPR-Cas9/Cpf1, or using a different targeted endonuclease (e.g., Zinc-finger nucleases, transcription-activator-like nucleases (TALENs)). In some embodiments, the genetic mutation is linked to a disease in a subject. Examples of edits to DNA include small insertions/deletions, large deletions, gene corrections with template DNA, or large insertions of DNA. In some embodiments, gene editing is accomplished with non-homologous end joining (NHEJ) or homology directed repair (HDR). In some embodiments, the edit is a knockout. In some embodiments, the edit is a knock-in. In some embodiments, both alleles of DNA are edited. In some embodiments, a single allele is edited. In some embodiments, multiple edits are made. In some embodiments, the fusosome or cell is derived from a subject, or is genetically matched to the subject, or is immunologically compatible with the subject (e.g. having similar MHC).

In some embodiments, the cargo may include a nucleic acid. For example, the cargo may comprise RNA to enhance expression of an endogenous protein, or a siRNA or miRNA that inhibits protein expression of an endogenous protein. For example, the endogenous protein may modulate structure or function in the target cells. In some embodiments, the cargo may include a nucleic acid encoding an engineered protein that modulates structure or function in the target cells. In some embodiments, the cargo is a nucleic acid that targets a transcriptional activator that modulate structure or function in the target cells.

In some embodiments, the cargo includes a polypeptide, e.g., enzymes, structural polypeptides, signaling polypeptides, regulatory polypeptides, transport polypeptides, sensory polypeptides, motor polypeptides, defense polypeptides, storage polypeptides, transcription factors, antibodies, cytokines, hormones, catabolic polypeptides, anabolic polypeptides, proteolytic polypeptides, metabolic polypeptides, kinases, transferases, hydrolases, lyases, isomerases, ligases, enzyme modulator polypeptides, protein binding polypeptides, lipid binding polypeptides, membrane fusion polypeptides, cell differentiation polypeptides, epigenetic polypeptides, cell death polypeptides, nuclear transport polypeptides, nucleic acid binding polypeptides, reprogramming polypeptides, DNA editing polypeptides, DNA repair polypeptides, DNA recombination polypeptides, transposase polypeptides, DNA integration polypeptides, targeted endonucleases (e.g. Zinc-finger nucleases, transcription-activator-like nucleases (TALENs), cas9 and homologs thereof), recombinases, and any combination thereof. In some embodiments the protein targets a protein in the cell for degradation. In some embodiments the protein targets a protein in the cell for degradation by localizing the protein to the proteasome. In some embodiments, the protein is a wild-type protein. In some embodiments, the protein is a mutant protein. In some embodiments the protein is a fusion or chimeric protein.

In some embodiments, the cargo includes a small molecule, e.g., ions (e.g. $Ca^{2+}$, $Cl^-$, $Fe^{2+}$), carbohydrates, lipids, reactive oxygen species, reactive nitrogen species, isoprenoids, signaling molecules, heme, polypeptide cofactors, electron accepting compounds, electron donating compounds, metabolites, ligands, and any combination thereof. In some embodiments the small molecule is a pharmaceutical that interacts with a target in the cell. In some embodiments the small molecule targets a protein in the cell for degradation. In some embodiments the small molecule targets a protein in the cell for degradation by localizing the protein to the proteasome. In some embodiments that small molecule is a proteolysis targeting chimera molecule (PROTAC).

In some embodiments, the cargo includes a mixture of proteins, nucleic acids, or metabolites, e.g., multiple polypeptides, multiple nucleic acids, multiple small molecules; combinations of nucleic acids, polypeptides, and small molecules; ribonucleoprotein complexes (e.g. Cas9-gRNA complex); multiple transcription factors, multiple epigenetic factors, reprogramming factors (e.g. Oct4, Sox2, cMyc, and Klf4); multiple regulatory RNAs; and any combination thereof.

In some embodiments, the cargo includes one or more organelles, e.g., chondrisomes, mitochondria, lysosomes, nucleus, cell membrane, cytoplasm, endoplasmic reticulum, ribosomes, vacuoles, endosomes, spliceosomes, polymerases, capsids, acrosome, autophagosome, centriole, glycosome, glyoxysome, hydrogenosome, melanosome, mitosome, myofibril, cnidocyst, peroxisome, proteasome, vesicle, stress granule, networks of organelles, and any combination thereof.

In some embodiments, the cargo is enriched at the fusosome or cell membrane. In some embodiments, the cargo is enriched by targeting to the membrane via a peptide signal sequence. In some embodiments, the cargo is enriched by binding with a membrane associated protein, lipid, or small molecule. In some embodiments the cargo binds covalently to a membrane associated protein, lipid, or small molecule. In some embodiments the covalent bond is cleavable by a protease. In some embodiments the cargo associates via a non-covalent interaction with a membrane associated protein, lipid, or small molecule. In some embodiments the membrane protein is a fusogen. In some embodiments the cargo is enriched via a secondary mediator. For example, in some embodiments the cargo is a nucleic acid that is bound by an intermediary protein, and the intermediary protein binds to a membrane associated protein, lipid, or small molecule, thereby localizing the nucleic acid cargo to the membrane. In some embodiments the interaction between the nucleic acid and intermediary protein is covalent or non-covalent. In some embodiments the interaction between the intermediary protein and membrane associated protein, lipid, or small molecule is covalent, or covalent and cleavable by a protease, or non-covalent. For example, US20170175086A1 and U.S. Pat. No. 9,816,080B2 describe the enrichment of a cargo protein through the non-covalent association between a fragment of the cargo protein and a membrane associated protein. In some embodiments, the cargo is enriched by dimerizing with a membrane associated protein, lipid, or small molecule. In some embodiments the cargo is chimeric (e.g. a chimeric protein, or nucleic acid) and comprises a domain that mediates binding or dimerization with a membrane associated protein, lipid, or small molecule. Membrane-associated proteins of interest include, but are not limited to, any protein having a domain that stably associates, e.g., binds to, integrates into, etc., a cell membrane (i.e., a membrane-association domain), where such domains may include myristoylated domains, farnesylated domains, transmembrane domains, and the like. Specific membrane-associated proteins of interest include, but are not limited to: myristoylated proteins, e.g., p 60 v-src and the like; farnesylated proteins, e.g., Ras, Rheb and CENP-E,F, proteins binding specific lipid bilayer components e.g. AnnexinV, by binding to phosphatidyl-serine, a lipid component of the cell membrane bilayer and the like; membrane anchor proteins; transmembrane proteins, e.g., transferrin receptors and portions thereof; and membrane fusion proteins. In some embodiment, the membrane associated protein contains a first dimerization domain. The first dimerization domain may be, e.g., a domain that directly binds to a second dimerization domain of a cargo or binds to a second dimerization domain via a dimerization mediator. In some embodiments the cargo contains a second dimerization domain. The second dimerization domain may be, e.g., a domain that dimerizes (e.g., stably associates with, such as by non-covalent bonding interaction, either directly or through a mediator) with the first dimerization domain of the membrane associated protein either directly or through a dimerization mediator. With respect to the dimerization domains, these domains are domains that participate in a binding event, either directly or via a dimerization mediator, where the binding event results in production of the desired multimeric, e.g., dimeric, complex of the membrane associated and target proteins. The first and second dimerization domains may be homodimeric, such that they are made up of the same sequence of amino acids, or heterodimeric, such that they are made up of differing sequences of amino acids. Dimerization domains may vary, where domains of interest include, but are not limited to: ligands of target biomolecules, such as ligands that specifically bind to particular proteins of interest (e.g., protein:protein interaction domains), such as SH2 domains, Paz domains, RING domains, transcriptional activator domains, DNA binding domains, enzyme catalytic domains, enzyme regulatory domains, enzyme subunits, domains for localization to a defined cellular location, recognition domains for the localization domain, the domains listed at URL: pawsonlab.mshri.on.ca/index.php?option=com_content&task=view&id=30&Itemid=63/, etc. In some embodiments the first dimerization domain binds nucleic acid (e.g. mRNA, miRNA, siRNA, DNA) and the second dimerization domain is a nucleic acid sequence present on the cargo (e.g. the first dimerization domain is MS2 and the second dimerization domain is the high affinity binding loop of MS2 RNA). Any convenient compound that functions as a dimerization mediator may be employed. A wide variety of compounds, including both naturally occurring and synthetic substances, can be used as dimerization mediators. Applicable and readily observable or measurable criteria for selecting a dimerization mediator include: (A) the ligand is physiologically acceptable (i.e., lacks undue toxicity towards the cell or animal for which it is to be used); (B) it has a reasonable therapeutic dosage range; (C) it can cross the cellular and other membranes, as necessary (where in some instances it may be able to mediate dimerization from outside of the cell), and (D) binds to the target domains of the chimeric proteins for which it is designed with reasonable affinity for the desired application. A first desirable criterion is that the compound is relatively physiologically inert, but for its dimerization mediator activity. In some instances, the ligands will be non-peptide and non-nucleic acid. Additional dimerization domains are described, e.g., in US20170087087 and US20170130197, each of which is herein incorporated by reference in its entirety.

Characteristics of Chondrisomes

In one aspect, the fusosome, e.g., a pharmaceutical composition of fusosomes, or a composition of fusosomes, comprises isolated chondrisomes (e.g., a chondrisome preparation), derived from a cellular source of mitochondria.

In another aspect, the fusosome, e.g., a pharmaceutical composition of fusosomes, or a composition of fusosomes, comprises isolated, modified chondrisomes (e.g., modified chondrisome preparation) derived from a cellular source of mitochondria.

In another aspect, the fusosome, e.g., a pharmaceutical composition of fusosomes, or a composition of fusosomes, comprises chondrisomes (e.g., chondrisome preparation) expressing an exogenous protein.

Additional features and embodiments including chondrisomes (e.g., chondrisome preparations), methods, and uses disclosed herein include one or more of the following.

In some embodiments, the chondrisome (or the chondrisomes in the composition) has one or more (2, 3, 4, 5, 6, 7, 8, 9 or more, e.g., all) of the following characteristics:

outer chondrisome membrane integrity wherein the composition exhibits <20% (e.g., <15%, <10%, <5%, <4%, <3%, <2%, <1%) increase in oxygen consumption rate over state 4 rate following addition of reduced cytochrome c;

genetic quality >80%, e.g., >85%, >90%, >95%, >97%, >98%, >99%, wherein "genetic quality" of a chondrisome preparation means, for all the loci described in Table 5, the percent of sequencing reads mapping to the wild type allele;

glutamate/malate RCR 3/2 of 1-15, e.g., 2-15, 5-15, 2-10, 2-5, 10-15;

glutamate/malate RCR 3/4o of 1-30, 1-20, 2-20, 5-20, 3-15, 10-30;

succinate/rotenone RCR 3/2 of 1-15, 2-15, 5-15, 1-10, 10-15;

succinate/rotenone RCR 3/4o of 1-30, 1-20, 2-20, 5-20, 3-15, 10-30;

palmitoyl carnitine and malate RCR3/2 state 3/state 2 respiratory control ratio (RCR 3/2) of 1-10 (e.g., 1-5);

cardiolipin content 0.05-25 (0.1-20, 0.5-20, 1-20, 5-20, 5-25, 1-25, 10-25, 15-25) 100*pmol/pmol total lipid;

genomic concentration 0.001-2 (e.g., 0.001-1, 0.01-1, 0.01-.1, 0.01-.05, 0.1-.2) mtDNA ug/mg protein; or relative ratio of mtDNA/nuclear DNA of >1000 (e.g., >1,500, >2000, >2,500, >3,000, >4,000, >5000, >10,000, >25,000, >50,000, >100,000, >200,000, >500,000).

In some embodiments, the chondrisome (or the chondrisomes in the composition) has one or more (2, 3, 4, 5, 6 or more) of the following characteristics:

the chondrisomes in the composition have a mean average size between 150-1500 nm, e.g., between 200-1200 nm, e.g., between 500-1200 nm, e.g., 175-950 nm;

the chondrisomes in the composition have a polydispersity (D90/D10) between 1.1 to 6, e.g., between 1.5-5. In embodiments, chondrisomes in the composition from a cultured cell source (e.g., cultured fibroblasts) have a polydispersity (D90/D10) between 2-5, e.g., between 2.5-5;

outer chondrisome membrane integrity wherein the composition exhibits <20% (e.g., <15%, <10%, <5%, <4^, <3%, <2%, <1%) increase in oxygen consumption rate over state 4 rate following addition of reduced cytochrome c;

complex I level of 1-8 mOD/ug total protein, e.g., 3-7 mOD/ug total protein, 1-5 mOD/ug total protein. In embodiments, chondrisomes of a preparation from a cultured cell source (e.g., cultured fibroblasts) have a complex I level of 1-5 mOD/ug total protein;

complex II level of 0.05-5 mOD/ug total protein, e.g., 0.1-4 mOD/ug total protein, e.g., 0.5-3 mOD/ug total protein. In embodiments, chondrisomes of a preparation from a cultured cell source (e.g., cultured fibroblasts) have a complex II level of 0.05-1 mOD/ug total protein;

complex III level of 1-30 mOD/ug total protein, e.g., 2-30, 5-10, 10-30 mOD/ug total protein.

In embodiments, chondrisomes from a cultured cell source (e.g., cultured fibroblasts) have a complex III level of 1-5 mOD/ug total protein;

complex IV level of 4-50 mOD/ug total protein, e.g., 5-50, e.g., 10-50, 20-50 mOD/ug total protein. In embodiments, chondrisomes from a cultured cell source (e.g., cultured fibroblasts) have a complex IV level of 3-10 mOD/ug total protein;

genomic concentration 0.001-2 (e.g., 0.001-1, 0.01-1, 0.01-.1, 0.01-.05, 0.1-.2) mtDNA ug/mg protein;

membrane potential of the preparation is between −5 to −200 mV, e.g., between −100 to −200 mV, −50 to −200 mV, −50 to −75 mV, −50 to −100 mV. In some embodiments, membrane potential of the preparation is less than −150 mV, less than −100 mV, less than −75 mV, less than −50 mV, e.g., −5 to −20 mV;

a protein carbonyl level of less than 100 nmol carbonyl/mg chondrisome protein (e.g., less than 90 nmol carbonyl/mg chondrisome protein, less than 80 nmol carbonyl/mg chondrisome protein, less than 70 nmol carbonyl/mg chondrisome protein, less than 60 nmol carbonyl/mg chondrisome protein, less than 50 nmol carbonyl/mg chondrisome protein, less than 40 nmol carbonyl/mg chondrisome protein, less than 30 nmol carbonyl/mg chondrisome protein, less than 25 nmol carbonyl/mg chondrisome protein, less than 20 nmol carbonyl/mg chondrisome protein, less than 15 nmol carbonyl/mg chondrisome protein, less than 10 nmol carbonyl/mg chondrisome protein, less than 5 nmol carbonyl/mg chondrisome protein, less than 4 nmol carbonyl/mg chondrisome protein, less than 3 nmol carbonyl/mg chondrisome protein;

<20% mol/mol ER proteins (e.g., >15%, >10%, >5%, >3%, >2%, >1%) mol/mol ER proteins;

>5% mol/mol mitochondrial proteins (proteins identified as mitochondrial in the MitoCarta database (Calvo et al., NAR 20151 doi:10.1093/nar/gkv1003)), e.g., >10%, >15%, >20%, >25%, >30%, >35%, >40%; >50%, >55%, >60%, >65%, >70%, >75%, >80%; >90% mol/mol mitochondrial proteins);

>0.05% mol/mol of MT-$CO_2$, MT-ATP6, MT-ND5 and MT-ND6 protein (combined) (e.g., >0.1%; >05%, >1%, >2%, >3%, >4%, >5%, >7, >8%, >9%, >10, >15% mol/mol of MT-$CO_2$, MT-ATP6, MT-ND5 and MT-ND6 protein);

genetic quality >80%, e.g., >85%, >90%, >95%, >97%, >98%, >99%;

relative ratio mtDNA/nuclear DNA is >1000 (e.g., >1,500, >2000, >2,500, >3,000, >4,000, >5000, >10,000, >25,000, >50,000, >100,000, >200,000, >500,000);

endotoxin level <0.2 EU/ug protein (e.g., <0.1, 0.05, 0.02, 0.01 EU/ug protein);

substantially absent exogenous non-human serum;

glutamate/malate RCR 3/2 of 1-15, e.g., 2-15, 5-15, 2-10, 2-5, 10-15;

glutamate/malate RCR 3/4o of 1-30, 1-20, 2-20, 5-20, 3-15, 10-30;

succinate/rotenone RCR 3/2 of 1-15, 2-15, 5-15, 1-10, 10-15;

succinate/rotenone RCR 3/4o of 1-30, 1-20, 2-20, 5-20, 3-15, 10-30;

complex I activity of 0.05-100 nmol/min/mg total protein (e.g., 0.05-50, 0.05-20, 0.5-10, 0.1-50, 1-50, 2-50, 5-100, 1-20 nmol/min/mg total protein);

complex II activity of 0.05-50 nmol/min/mg total protein (e.g., 0.05-50, 0.05-20, 0.5-10, 0.1-50, 1-50, 2-50, 5-50, 1-20 nmol/min/mg total protein);

complex III activity of 0.05-20 nmol/min/mg total protein (e.g., 0.05-50, 0.05-20, 0.5-10, 0.1-50, 1-50, 2-50, 5-100, 1-20 nmol/min/mg total protein);

complex IV activity of 0.1-50 nmol/min/mg total protein (e.g., 0.05-50, 0.05-20, 0.5-10, 0.1-50, 1-50, 2-50, 5-50, 1-20 nmol/min/mg total protein);

complex V activity of 1-500 nmol/min/mg total protein (e.g., 10-500, 10-250, 10-200, 100-500 nmol/min/mg total protein);

reactive oxygen species (ROS) production level of 0.01-50 pmol $H_2O_2$/ug protein/hr (e.g., 0.05-40, 0.05-25, 1-20, 2-20, 0.05-20, 1-20 pmol $H_2O_2$/ug protein/hr);

citrate synthase activity of 0.05-5 (e.g., 0.5-5, 0.5-2, 1-5, 1-4) mOD/min/ug total protein;

alpha ketoglutarate dehydrogenase activity of 0.05-10 (e.g., 0.1-10, 0.1-8, 0.5-8, 0.1-5, 0.5-5, 0.5-3, 1-3) mOD/min/ug total protein;

creatine kinase activity of 0.1-100 (e.g., 0.5-50, 1-100, 1-50, 1-25, 1-15, 5-15) mOD/min/ug total protein;

pyruvate dehydrogenase activity of 0.1-10 (e.g., 0.5-10, 0.5-8, 1-10, 1-8, 1-5, 2-3) mOD/min/ug total protein;

aconitase activity of 0.1-50 (e.g., 5-50, 0.1-2, 0.1-20, 0.5-30) mOD/min/ug total protein. In embodiments, aconitase activity in a chondrisome preparation from platelets is between 0.5-5 mOD/min/ug total protein. In embodiments, aconitase activity in a chondrisome preparation from cultured cells, e.g., fibroblasts, is between 5-50 mOD/min/ug total protein;

maximal fatty acid oxidation level of 0.05-50 (e.g., 0.05-40, 0.05-30, 0.05-10, 0.5-50, 0.5-25, 0.5-10, 1-5) pmol $O_2$/min/ug chondrisome protein;

palmitoyl carnitine & malate RCR3/2 state 3/state 2 respiratory control ratio (RCR 3/2) of 1-10 (e.g., 1-5);

electron transport chain efficiency of 1-1000 (e.g., 10-1000, 10-800, 10-700, 50-1000, 100-1000, 500-1000, 10-400, 100-800) nmol Om/min/mg protein/ΔGATP (in kcal/mol);

total lipid content of 50,000-2,000,000 pmol/mg (e.g., 50,000-1,000,000; 50,000-500,000 pmol/mg);

double bonds/total lipid ratio of 0.8-8 (e.g., 1-5, 2-5, 1-7, 1-6) pmol/pmol;

phospholipid/total lipid ratio of 50-100 (e.g., 60-80, 70-100, 50-80) 100*pmol/pmol;

phosphosphingolipid/total lipid ratio of 0.2-20 (e.g., 0.5-15, 0.5-10, 1-10, 0.5-10, 1-5, 5-20) 100*pmol/pmol;

ceramide content 0.05-5 (e.g., 0.1-5, 0.1-4, 1-5, 0.05-3) 100*pmol/pmol total lipid;

cardiolipin content 0.05-25 (0.1-20, 0.5-20, 1-20, 5-20, 5-25, 1-25, 10-25, 15-25) 100*pmol/pmol total lipid;

lyso-phosphatidylcholine (LPC) content of 0.05-5 (e.g., 0.1-5, 1-5, 0.1-3, 1-3, 0.05-2) 100*pmol/pmol total lipid;

lyso-phosphatidylethanolamine (LPE) content of 0.005-2 (e.g., 0.005-1, 0.05-2, 0.05-1) 100*pmol/pmol total lipid;

phosphatidylcholine (PC) content of 10-80 (e.g., 20-60, 30-70, 20-80, 10-60m 30-50) 100*pmol/pmol total lipid;

phosphatidylcholine-ether (PC O-) content 0.1-10 (e.g., 0.5-10, 1-10, 2-8, 1-8) 100*pmol/pmol total lipid;

phosphatidylethanolamine (PE) content 1-30 (e.g., 2-20, 1-20, 5-20) 100*pmol/pmol total lipid; phosphatidylethanolamine-ether (PE O-) content 0.05-30 (e.g., 0.1-30, 0.1-20, 1-20, 0.1-5, 1-10, 5-20) 100*pmol/pmol total lipid;

phosphatidylinositol (PI) content 0.05-15 (e.g., 0.1-15, 0.1-10, 1-10, 0.1-5, 1-10, 5-15) 100*pmol/pmol total lipid;

phosphatidylserine (PS) content 0.05-20 (e.g., 0.1-15, 0.1-20, 1-20, 1-10, 0.1-5, 1-10, 5-15) 100*pmol/pmol total lipid;

sphingomyelin (SM) content 0.01-20 (e.g., 0.01-15, 0.01-10, 0.5-20, 0.5-15, 1-20, 1-15, 5-20) 100*pmol/pmol total lipid;

triacylglycerol (TAG) content 0.005-50 (e.g., 0.01-50, 0.1-50, 1-50, 5-50, 10-50, 0.005-30, 0.01-25, 0.1-30) 100*pmol/pmol total lipid;

PE:LPE ratio 30-350 (e.g., 50-250, 100-200, 150-300);

PC:LPC ratio 30-700 (e.g., 50-300, 50-250, 100-300, 400-700, 300-500, 50-600, 50-500, 100-500, 100-400);

PE 18:n (n>0) content 0.5-20% (e.g., 1-20%, 1-10%, 5-20%, 5-10%, 3-9%) pmol AA/pmol lipid class;

PE 20:4 content 0.05-20% (e.g., 1-20%, 1-10%, 5-20%, 5-10%) pmol AA/pmol lipid class;

PC 18:n (n>0) content 5-50% (e.g., 5-40%, 5-30%, 20-40%, 20-50%) pmol AA/pmol lipid class;

PC 20:4 content 1-20% (e.g., 2-20%, 2-15%, 5-20%, 5-15%) pmol AA/pmol lipid class.

In certain embodiments, the chondrisome (or the chondrisomes in the composition) has one or more of the following characteristics upon administration to a recipient cell, tissue or subject (a control may be a negative control (e.g., a control tissue or subject that has not been administered a composition), or a baseline prior to administration, e.g., a cell, tissue or subject prior to administration of the composition):

Increases basal respiration of recipient cells at least 10% (e.g., >15%, >20%, >30%, >40%, >50%, >60%, >70%, >80%, >90%) relative to a control;

chondrisomes in the composition are taken up by at least 1% (e.g., at least 2%, 5%, 10%, 20%, 30%, 40%, 50%, 60%, 70%) of recipient cells;

chondrisomes in the composition are taken up and maintain membrane potential in recipient cells;

chondrisomes in the composition persist in recipient cells at least 6 hours, e.g., at least 12 hours, 18 hours, 24 hours, 2 days, 3 days, 4 days, a week, 2 weeks, a month, 2 months, 3 months, 6 months;

increase ATP levels in a recipient cell, tissue or subject (e.g., by at least 5%, 10%, 15%, 20%, 25%, 30%, 35%, 40%, 45%, 50%, 60%, 70%, 80%, 90%, or more, e.g., compared to a reference value, e.g., a control value, e.g., an untreated control);

decrease apotosis in a recipient cell, tissue or subject (e.g., by at least 5%, 10%, 15%, 20%, 25%, 30%, 35%, 40%, 45%, 50%, 60%, 70%, 80%, 90%, or more, e.g., compared to a reference value, e.g., a control value, e.g., an untreated control);

decrease cellular lipid levels in a recipient cell, tissue or subject (e.g., by at least 5%, 10%, 15%, 20%, 25%, 30%, 35%, 40%, 45%, 50%, 60%, 70%, 80%, 90%, or more, e.g., compared to a reference value, e.g., a control value, e.g., an untreated control);

increase membrane potential in a recipient cell, tissue or subject (e.g., by at least 5%, 10%, 15%, 20%, 25%, 30%, 35%, 40%, 45%, 50%, 60%, 70%, 80%, 90%, or more, e.g., compared to a reference value, e.g., a control value, e.g., an untreated control);

increase uncoupled respiration in a recipient cell, tissue or subject (e.g., by at least 5%, 10%, 15%, 20%, 25%, 30%, 35%, 40%, 45%, 50%, 509%, 60%, 70%, 80%, 90%, or more, e.g., compared to a reference value, e.g., a control value, e.g., an untreated control);

increase PI3K activity in a recipient cell, tissue or subject (e.g., by at least 5%, 10%, 15%, 20%, 25%, 30%, 35%, 40%, 45%, 509%, 60%, 70%, 80%, 90%, or more, e.g., compared to a reference value, e.g., a control value, e.g., an untreated control);

reduce reductive stress in a recipient cell, tissue or subject (e.g., by at least 5%, 10%, 15%, 20%, 25%, 30%, 35%, 40%, 45%, 509%, 60%, 70%, 80%, 90%, or more, e.g., compared to a reference value, e.g., a control value, e.g., an untreated control);

decrease reactive oxygen species (e.g. $H_2O_2$) in the cell, tissue of subject (e.g., in serum of a target subject) (e.g., by at least 5%, 10%, 15%, 20%, 25%, 30%, 35%, 40%, 45%, 509%, 60%, 70%, 80%, 90%, or more, e.g., compared to a reference value, e.g., a control value, e.g., an untreated control);

decrease cellular lipid levels of recipient cells at least 5% (e.g., >10%, >15%, >20%, >30%, >40%, >50%, >60%, >70%, >80%, >90%) relative to a control;

increases uncoupled respiration of recipient cells at least 5% (e.g., >10%, >15%, >20%, >30%, >40%, >50%, >60%, >70%, >80%, >90%) relative to a control;

decrease mitochondrial permeability transition pore (MPTP) formation in recipient cells at least 5% and does not increase more than 10% relative to a control;

increase Akt levels in recipient cells at least 10% (e.g., >10%, >15%, >20%, >30%, >40%, >50%, >60%, >70%, >80%, >90%) relative to a control;

decrease total NAD/NADH ratio in recipient cells at least 5% (e.g., >10%, >15%, >20%, >30%, >40%, >50%, >60%, >70%, >80%, >90%) relative to a control;

reduce ROS levels in recipient cells at least 5% (e.g., >10%, >15%, >20%, >30%, >40%, >50%, >60%, >70%, >80%, >90%) relative to a control;

increase fractional shortening in subject with cardiac ischemia at least 5% (e.g., >10%, >15%, >20%, >30%, >40%, >50%, >60%, >70%, >80%, >90%) relative to a control;

increase end diastolic volume in subject with cardiac ischemia at least 5% (e.g., >10%, >15%, >20%, >30%, >40%, >50%, >60%, >70%, >80%, >90%) relative to a control;

decrease end systolic volume in subject with cardiac ischemia at least 5% (e.g., >10%, >15%, >20%, >30%, >40%, >50%, >60%, >70%, >80%, >90%) relative to a control;

decrease infarct area of ischemic heart at least 5% (e.g., >10%, >15%, >20%, >30%, >40%, >50%, >60%, >70%, >80%, >90%) relative to a control;

increase stroke volume in subject with cardiac ischemia at least 5% (e.g., >10%, >15%, >20%, >30%, >40%, >50%, >60%, >70%, >80%, >90%) relative to a control;

increase ejection fraction in subject with cardiac ischemia at least 5% (e.g., >10%, >15%, >20%, >30%, >40%, >50%, >60%, >70%, >80%, >90%) relative to a control;

increase cardia output in subject with cardiac ischemia at least 5% (e.g., >10%, >15%, >20%, >30%, >40%, >50%, >60%, >70%, >80%, >90%) relative to a control;

increase cardiac index in subject with cardiac ischemia at least 5% (e.g., >10%, >15%, >20%, >30%, >40%, >50%, >60%, >70%, >80%, >90%) relative to a control;

decrease serum CKNB levels in subject with cardiac ischemia at least 5% (e.g., >10%, >15%, >20%, >30%, >40%, >50%, >60%, >70%, >80%, >90%) relative to a control;

decrease serum cTnI levels in subject with cardiac ischemia at least 5% (e.g., >10%, >15%, >20%, >30%, >40%, >50%, >60%, >70%, >80%, >90%) relative to a control;

decrease serum hydrogen peroxide in subject with cardiac ischemia at least 5% (e.g., >10%, >15%, >20%, >30%, >40%, >50%, >60%, >70%, >80%, >90%) relative to a control;

decrease serum cholesterol levels and/or triglycerides in a subject at least 5% (e.g., >10%, >15%, >20%, >30%, >40%, >50%, >60%, >70%, >80%, >90%) relative to a control.

In some embodiments, the fusosome comprises a chondrisome, e.g., isolated chondrisomes from a mitochondrial source, having one or more of the following characteristics:
the chondrisomes in the composition have a mean average size between 150-1500 nm;
the chondrisomes in the composition have a polydispersity (D90/D10) between 1.1 to 6;
outer chondrisome membrane integrity of the chondrisomes in the composition exhibits <20% increase in oxygen consumption rate over state 4 rate following addition of reduced cytochrome c;
complex I level of 1-8 mOD/ug total protein;
complex II level of 0.05-5 mOD/ug total protein;
complex III level of 1-30 mOD/ug total protein;
complex IV level of 4-50 mOD/ug total protein;
genomic concentration 0.001-2 mtDNA ug/mg protein; and/or
membrane potential of the chondrisomes in the composition is between −5 to −200 mV.

In some embodiments, the fusosome comprises a chondrisome, e.g., isolated chondrisomes from a mitochondrial source, having one or more of the following characteristics:
a protein carbonyl level of less than 100 nmol carbonyl/mg chondrisome protein.
<20% mol/mol ER proteins
>5% mol/mol mitochondrial proteins (MitoCarta);
>0.05% mol/mol of MT-$CO_2$, MT-ATP6, MT-ND5 and MT-ND6 protein;
genetic quality >80%;
relative ratio mtDNA/nuclear DNA >1000;
endotoxin level <0.2 EU/ug protein; and/or
substantially absent exogenous non-human serum.

In some embodiments, the fusosome comprises a chondrisome, e.g., isolated chondrisomes from a mitochondrial source, having one or more of the following characteristics:
glutamate/malate RCR 3/2 of 1-15;
glutamate/malate RCR 3/4o of 1-30;
succinate/rotenone RCR 3/2 of 1-15;
succinate/rotenone RCR 3/4o of 1-30;
complex I activity of 0.05-100 nmol/min/mg total protein;
complex II activity of 0.05-50 nmol/min/mg total protein;
complex III activity of 0.05-20 nmol/min/mg total protein;
complex IV activity of 0.1-50 nmol/min/mg total protein;
complex V activity of 1-500 nmol/min/mg total protein;
reactive oxygen species (ROS) production level of 0.01-50 pmol $H_2O_2$/ug protein/hr;
citrate synthase activity of 0.05-5 mOD/min/ug total protein;
alpha ketoglutarate dehydrogenase activity of 0.05-10 mOD/min/ug total protein;
creatine kinase activity of 0.1-100 mOD/min/ug total protein;
pyruvate dehydrogenase activity of 0.1-10 mOD/min/ug total protein;
aconitase activity of 0.1-50 mOD/min/ug total protein;
maximal fatty acid oxidation level of 0.05-50 pmol $O_2$/min/ug chondrisome protein;
palmitoyl carnitine & malate RCR3/2 state 3/state 2 respiratory control ratio (RCR 3/2) of 1-10; and/or
electron transport chain efficiency of 1-1000 nmol $O_2$/min/mg protein/ΔGATP (in kcal/mol).

In some embodiments, the fusosome comprises chondrisomes, e.g., isolated chondrisomes from a mitochondrial source, having one or more of the following characteristics:
total lipid content of 50,000-2,000,000 pmol/mg;
double bonds/total lipid ratio of 0.8-8 pmol/pmol;
phospholipid/total lipid ratio of 50-100 100*pmol/pmol;
phosphosphingolipid/total lipid ratio of 0.2-20 100*pmol/pmol;
ceramide content 0.05-5 100*pmol/pmol total lipid;
cardiolipin content 0.05-25 100*pmol/pmol total lipid;
lyso-phosphatidylcholine (LPC) content of 0.05-5 100*pmol/pmol total lipid;
lyso-phosphatidylethanolamine (LPE) content of 0.005-2 100*pmol/pmol total lipid;
phosphatidylcholine (PC) content of 10-80 100*pmol/pmol total lipid;
phosphatidylcholine-ether (PC O-) content 0.1-10 100*pmol/pmol total lipid;
phosphatidylethanolamine (PE) content 1-30 100*pmol/pmol total lipid;
phosphatidylethanolamine-ether (PE O-) content 0.05-30 100*pmol/pmol total lipid;
phosphatidylinositol (PI) content 0.05-15 100*pmol/pmol total lipid;
phosphatidylserine (PS) content 0.05-20 100*pmol/pmol total lipid;
sphingomyelin (SM) content 0.01-20 100*pmol/pmol total lipid;
triacylglycerol (TAG) content 0.005-50 100*pmol/pmol total lipid;
PE:LPE ratio 30-350;
PC:LPC ratio 30-700;
PE 18:n (n>0) content 0.5-20% pmol AA/pmol lipid class;
PE 20:4 content 0.05-20% pmol AA/pmol lipid class;
PC 18:n (n>0) content 5-50% pmol AA/pmol lipid class; and/or
PC 20:4 content 1-20%.

In some embodiments, the fusosome comprises a chondrisome, e.g., isolated chondrisomes from a mitochondrial source, having one or more of the following characteristics:
increases basal respiration of recipient cells at least 10%;
chondrisomes in the composition are taken up by at least 1% of recipient cells;
chondrisomes in the composition are taken up and maintain membrane potential in recipient cells;
chondrisomes in the composition persist in recipient cells at least 6 hours;
decrease cellular lipid levels of recipient cells at least 5%;
increases uncoupled respiration of recipient cells at least 5%;
decreases mitochondrial permeability transition pore (MPTP) formation in recipient cells at least 5% and does not increase more than 10%;
increases Akt levels in recipient cells at least 10%;

decreases total NAD/NADH ratio in recipient cells at least 5%; and/or reduces ROS levels in recipient cells at least 5%.

In some embodiments, a fusosome comprising a chondrisome further has one or more of the following characteristics:

increases fractional shortening in subject with cardiac ischemia at least 5%;

increases end diastolic volume in subject with cardiac ischemia at least 5%;

decreases end systolic volume in subject with cardiac ischemia at least 5%;

decreases infarct area of ischemic heart at least 5%;

increases stroke volume in subject with cardiac ischemia at least 5%;

increases ejection fraction in subject with cardiac ischemia at least 5%;

increases cardia output in subject with cardiac ischemia at least 5%;

increases cardiac index in subject with cardiac ischemia at least 5%;

decreases serum CKNB levels in subject with cardiac ischemia at least 5%;

decreases serum cTnI levels in subject with cardiac ischemia at least 5%; and/or decreases serum hydrogen peroxide in subject with cardiac ischemia at least 5%.

In embodiments, the fusosome comprising a chondrisome is stable for at least 6 hours, 12 hours, 24 hours, 48 hours, 72 hours, 96 hours, 5 days, 7 days, 10 days, 14 days, 21 days, 30 days, 45 days, 60 days, 90 days, 120 days, 180 days, or longer (for example, at 4° C., 0° C., −4° C., or −20° C., −80° C.).

In embodiments, the fusosome comprising an agent (e.g., a chondrisome) may comprise, e.g., a natural, synthetic or engineered encapsulation material such as a lipid based material, vesicle, exosome, lipid raft, clathrin coated vesicle, or platelet (mitoparticle), MSC or astrocyte microvesicle membrane.

In embodiments, the fusosome comprising a chondrisome is in a composition at between 150-20,000 ug protein/ml; between 150-15,000 ug/ml; 200-15,000 ug/ml; 300-15,000 ug/ml; 500-15,000 ug/ml; 200-10,000 ug/ml; 200-5,000 ug/ml; 300-10,000 ug/ml; >200 ug/ml; >250 ug/ml; >300 ug/ml; >350 ug/ml; >400 ug/ml; >450 ug/ml; >500 ug/ml; >600 ug/ml; >700 ug/ml; >800 ug/ml; >900 ug/ml; >1 mg/ml; >2 mg/ml; >3 mg/ml; >4 mg/ml; >5 mg/ml; >6 mg/ml; >7 mg/ml; >8 mg/ml; >9 mg/ml; >10 mg/ml; >11 mg/ml; >12 mg/ml; >14 mg/ml; >15 mg/ml (and, e.g., <20 mg/ml).

In embodiments, the fusosome comprising a chondrisome does not produce an undesirable immune response in a recipient animal, e.g., a recipient mammal such as a human (e.g., does not significantly increase levels of IL-1-beta, IL-6, GM-CSF, TNF-alpha, or lymph node size, in the recipient).

Modifications to the cargo include, for example, modifications to chondrisomes or the source of chondrisomes as described in international application, PCT/US 16/64251. In some embodiments, the fusosome comprises a chondrisome made using a method of making a pharmaceutical composition described herein.

In some embodiments, a fusosome composition described herein, e.g., a fusosome composition comprising mitochondria or chondrisomes, is capable of one or more of (e.g., 2, 3, or 4 of):

a) increasing maximal respiration in a target cell, e.g., wherein the increase in maximal respiration is at least 10%, 20%, 30%, 40%, 50%, 60%, 70%, 75% 80%, 90%, 2-fold, 3-fold, 4-fold, or 5-fold, or from 10%-20%, 20%-30%, 30%-40%, 40%-50%, 50%-60%, 60%-70%, 70%-80%, 80%-90%, 90%-100%, 1-fold-2-fold, 2-fold-3-fold, 3-fold-4-fold, or 4-fold-5-fold;

b) increasing spare respiratory capacity in a target cell, e.g., wherein the increase in spare respiratory capacity is at least 10%, 20%, 30%, 40%, 50%, 60%, 70%, 80%, 90%, 2-fold, 3-fold, 4-fold, or 5-fold, or from 10%-20%, 20%-30%, 30%-40%, 40%-50%, 50%-60%, 60%-70%, 70%-80%, 80%-90%, 90%-100%, 1-fold-2-fold, 2-fold-3-fold, 3-fold-4-fold, or 4-fold-5-fold;

c) stimulating mitochondrial biogenesis in a target cell, e.g., wherein stimulating mitochondrial biogenesis comprises increasing mitochondrial biomass by at least 10%, 20%, 30%, 40%, 50%, 60%, 70%, 80%, 90%, 2-fold, 3-fold, 4-fold, or 5-fold, or from 10%-20%, 20%-30%, 30%-40%, 40%-50%, 50%-60%, 60%-70%, 70%-80%, 80%-90%, 90%-100%, 1-fold-2-fold, 2-fold-3-fold, 3-fold-4-fold, or 4-fold-5-fold; or d) modulating (e.g., stimulating or inhibiting) transcription of a nuclear gene in a target cell, e.g., wherein the change in transcript levels of the nuclear gene is at least 10%, 20%, 30%, 40%, 50%, 60%, 70%, 80%, 90%, 2-fold, 3-fold, 4-fold, or 5-fold, or from 10%-20%, 20%-30%, 30%-40%, 40%-50%, 50%-60%, 60%-70%, 70%-80%, 80%-90%, 90%-100%, 1-fold-2-fold, 2-fold-3-fold, 3-fold-4-fold, or 4-fold-5-fold.

Immunogenicity

In some embodiments of any of the aspects described herein, the fusosome composition is substantially non-immunogenic. Immunogenicity can be quantified, e.g., as described herein.

In some embodiments, a fusosome fuses with a target cell to produce a recipient cell. In some embodiments, a recipient cell that has fused to one or more fusosomes is assessed for immunogenicity. In embodiments, a recipient cell is analyzed for the presence of antibodies on the cell surface, e.g., by staining with an anti-IgM antibody. In other embodiments, immunogenicity is assessed by a PBMC cell lysis assay. In embodiments, a recipient cell is incubated with peripheral blood mononuclear cells (PBMCs) and then assessed for lysis of the cells by the PBMCs. In other embodiments, immunogenicity is assessed by a natural killer (NK) cell lysis assay. In embodiments, a recipient cell is incubated with NK cells and then assessed for lysis of the cells by the NK cells. In other embodiments, immunogenicity is assessed by a CD8+ T-cell lysis assay. In embodiments, a recipient cell is incubated with CD8+ T-cells and then assessed for lysis of the cells by the CD8+ T-cells.

In some embodiments, the fusosome composition has membrane symmetry of a cell which is, or is known to be, substantially non-immunogenic, e.g., a stem cell, mesenchymal stem cell, induced pluripotent stem cell, embryonic stem cell, sertoli cell, or retinal pigment epithelial cell. In some embodiments, the fusosome has an immunogenicity no more than 5%, 10%, 20%, 30%, 40%, or 50% greater than the immunogenicity of a stem cell, mesenchymal stem cell, induced pluripotent stem cell, embryonic stem cell, sertoli cell, or retinal pigment epithelial cell as measured by an assay described herein.

In some embodiments, the fusosome composition comprises elevated levels of an immunosuppressive agent as compared to a reference cell, e.g., an unmodified cell otherwise similar to the source cell, or a Jurkat cell. In some embodiments, the elevated level is at least 5%, 10%, 20%, 30%, 40%, 50%, 60%, 70%, 80%, 90%, 2-fold, 3-fold, 5-fold, 10-fold, 20-fold, 50-fold, or 100-fold. In some embodiments, the fusosome composition comprises an immunosuppressive agent that is absent from the reference cell. In some embodiments, the fusosome composition comprises reduced levels of an immune activating agent as compared to a reference cell, e.g., an unmodified cell otherwise similar to the source cell, or a Jurkat cell. In some embodiments, the reduced level is at least 5%, 10%, 20%, 30%, 40%, 50%, 60%, 70%, 80%, 90%, 95%, 98%, or 99% compared to the reference cell. In some embodiments, the immune activating agent is substantially absent from the fusosome.

In some embodiments, the fusosome composition comprises a membrane with composition substantially similar, e.g., as measured by proteomics, to that of a source cell, e.g., a substantially non-immunogenic source cell. In some embodiments, the fusosome composition comprises a membrane comprising at least 1%, 2%, 3%, 4%, 5%, 10%, 20%, 30%, 40%, 50%, 60%, 70%, 80%, 90%, 95%, 99%, or 100% of the membrane proteins of the source cell. In some embodiments, the fusosome composition comprises a membrane comprising membrane proteins expressed at, at least 1%, 2%, 3%, 4%, 5%, 10%, 20%, 30%, 40%, 50%, 60%, 70%, 80%, 90%, 95%, 99%, or 100% of the level of expression of the membrane proteins on a membrane of the source cell.

In some embodiments, the fusosome composition, or the source cell from which the fusosome composition is derived from, has one, two, three, four, five, six, seven, eight, nine, ten, eleven, twelve, or more of the following characteristics:

a. less than 50%, 40%, 30%, 20%, 15%, 10%, or 5% or lesser expression of MHC class I or MHC class II, compared to a reference cell, e.g., an unmodified cell otherwise similar to the source cell, or a HeLa cell;

b. less than 50%, 40%, 30%, 20%, 15%, 10%, or 5% or lesser expression of one or more co-stimulatory proteins including but not limited to: LAG3, ICOS-L, ICOS, Ox40L, OX40, CD28, B7, CD30, CD30L 4-1BB, 4-1BBL, SLAM, CD27, CD70, HVEM, LIGHT, B7-H3, or B7-H4, compared to a reference cell, e.g., an unmodified cell otherwise similar to the source cell, or a reference cell described herein;

c. expression of surface proteins which suppress macrophage engulfment e.g., CD47, e.g., detectable expression by a method described herein, e.g., more than 1.5-fold, 2-fold, 3-fold, 4-fold, 5-fold, 10-fold, or more expression of the surface protein which suppresses macrophage engulfment, e.g., CD47, compared to a reference cell, e.g., an unmodified cell otherwise similar to the source cell, or a Jurkat cell;

d. expression of soluble immunosuppressive cytokines, e.g., IL-10, e.g., detectable expression by a method described herein, e.g., more than 1.5-fold, 2-fold, 3-fold, 4-fold, 5-fold, 10-fold, or more expression of soluble immunosuppressive cytokines, e.g., IL-10, compared to a reference cell, e.g., an unmodified cell otherwise similar to the source cell, or a Jurkat cell;

e. expression of soluble immunosuppressive proteins, e.g., PD-L1, e.g., detectable expression by a method described herein, e.g., more than 1.5-fold, 2-fold, 3-fold, 4-fold, 5-fold, 10-fold, or more expression of soluble immunosuppressive proteins, e.g., PD-L1, compared to a reference cell e.g., an unmodified cell otherwise similar to the source cell, or a Jurkat cell;

f. less than 50%, 40%, 30%, 20%, 15%, 10%, or 5% or lesser expression of soluble immune stimulating cytokines, e.g., IFN-gamma or TNF-a, compared to a reference cell, e.g., an unmodified cell otherwise similar to the source cell, or a U-266 cell;

g. less than 50%, 40%, 30%, 20%, 15%, 10%, or 5% or lesser expression of endogenous immune-stimulatory antigen, e.g., Zg16 or Hormad1, compared to a reference cell, e.g., an unmodified cell otherwise similar to the source cell, or an A549 cell or a SK-BR-3 cell;

h. expression of, e.g., detectable expression by a method described herein, HLA-E or HLA-G, compared to a reference cell, e.g., an unmodified cell otherwise similar to the source cell, or a Jurkat cell;

i. surface glycosylation profile, e.g., containing sialic acid, which acts to, e.g., suppress NK cell activation;

j. less than 50%, 40%, 30%, 20%, 15%, 10%, or 5% or lesser expression of TCRα/β, compared to a reference cell, e.g., an unmodified cell otherwise similar to the source cell, or a Jurkat cell;

k. less than 50%, 40%, 30%, 20%, 15%, 10%, or 5% or lesser expression of ABO blood groups, compared to a reference cell, e.g., an unmodified cell otherwise similar to the source cell, or a HeLa cell;

l. less than 50%, 40%, 30%, 20%, 15%, 10%, or 5% or lesser expression of Minor Histocompatibility Antigen (MHA), compared to a reference cell, e.g., an unmodified cell otherwise similar to the source cell, or a Jurkat cell; or m. has less than 10%, 9%, 8%, 7%, 6%, 5%, 4%, 3%, 2%, 1%, or less, of mitochondrial MHAs, compared to a reference cell e.g., an unmodified cell otherwise similar to the source cell, or a Jurkat cell, or has no detectable mitochondrial MHAs.

In embodiments, the co-stimulatory protein is 4-1BB, B7, SLAM, LAG3, HVEM, or LIGHT, and the ref cell is HDLM-2. In some embodiments, the co-stimulatory protein is BY-H3 and the reference cell is HeLa. In some embodiments, the co-stimulatory protein is ICOSL or B7-H4, and the reference cell is SK-BR-3. In some embodiments, the co-stimulatory protein is ICOS or OX40, and the reference cell is MOLT-4. In some embodiments, the co-stimulatory protein is CD28, and the reference cell is U-266. In some embodiments, the co-stimulatory protein is CD30L or CD27, and the reference cell is Daudi. In some embodiments, the fusosome composition does not substantially elicit an immunogenic response by the immune system, e.g., innate immune system. In embodiments, an immunogenic response can be quantified, e.g., as described herein. In some embodiments, the an immunogenic response by the innate immune system comprises a response by innate immune cells including, but not limited to NK cells, macrophages, neutrophils, basophils, eosinophils, dendritic cells, mast cells, or gamma/delta T cells. In some embodiments, an immunogenic response by the innate immune system comprises a response by the complement system which includes soluble blood components and membrane bound components.

In some embodiments, the fusosome composition does not substantially elicit an immunogenic response by the immune system, e.g., adaptive immune system. In embodiments, an immunogenic response can be quantified, e.g., as described herein. In some embodiments, an immunogenic response by the adaptive immune system comprises an immunogenic response by an adaptive immune cell including, but not limited to a change, e.g., increase, in number or activity of T lymphocytes (e.g., CD4 T cells, CD8 T cells, and or gamma-delta T cells), or B lymphocytes. In some embodiments, an immunogenic response by the adaptive immune system includes increased levels of soluble blood components including, but not limited to a change, e.g., increase, in number or activity of cytokines or antibodies (e.g., IgG, IgM, IgE, IgA, or IgD).

In some embodiments, the fusosome composition is modified to have reduced immunogenicity. Immunogenicity can be quantified, e.g., as described herein. In some embodiments, the fusosome composition has an immunogenicity less than 5%, 10%, 20%, 30%, 40%, or 50% lesser than the immunogenicity of a reference cell, e.g., an unmodified cell otherwise similar to the source cell, or a Jurkat cell.

In some embodiments of any of the aspects described herein, the fusosome composition is derived from a source cell, e.g., a mammalian cell, having a modified genome, e.g., modified using a method described herein, to reduce, e.g., lessen, immunogenicity. Immunogenicity can be quantified, e.g., as described herein.

In some embodiments, the fusosome composition is derived from a mammalian cell depleted of, e.g., with a knock out of, one, two, three, four, five, six, seven or more of the following:
  a. MHC class I, MHC class II or MHA;
  b. one or more co-stimulatory proteins including but not limited to: LAG3, ICOS-L, ICOS, Ox40L, OX40, CD28, B7, CD30, CD30L 4-1BB, 4-1BBL, SLAM, CD27, CD70, HVEM, LIGHT, B7-H3, or B7-H4;
  c. soluble immune-stimulating cytokines e.g., IFN-gamma or TNF-a;
  d. endogenous immune-stimulatory antigen, e.g., Zg16 or Hormad1;
  e. T-cell receptors (TCR);
  f. The genes encoding ABO blood groups, e.g., ABO gene;
  g. transcription factors which drive immune activation, e.g., NFkB;
  h. transcription factors that control MHC expression e.g., class II trans-activator (CIITA), regulatory factor of the Xbox 5 (RFX5), RFX-associated protein (RFXAP), or RFX ankyrin repeats (RFXANK; also known as RFXB); or
  i. TAP proteins, e.g., TAP2, TAP1, or TAPBP, which reduce MHC class I expression.

In some embodiments, the fusosome is derived from a source cell with a genetic modification which results in increased expression of an immunosuppressive agent, e.g., one, two, three or more of the following (e.g., wherein before the genetic modification the cell did not express the factor):
  a. surface proteins which suppress macrophage engulfment, e.g., CD47; e.g., increased expression of CD47 compared to a reference cell, e.g., an unmodified cell otherwise similar to the source cell, or a Jurkat cell;
  b. soluble immunosuppressive cytokines, e.g., IL-10, e.g., increased expression of IL-10 compared to a reference cell, e.g., an unmodified cell otherwise similar to the source cell, or a Jurkat cell;
  c. soluble immunosuppressive proteins, e.g., PD-1, PD-L1, CTLA4, or BTLA; e.g., increased expression of immunosuppressive proteins compared to a reference cell, e.g., an unmodified cell otherwise similar to the cell source, or a Jurkat cell;
  d. a tolerogenic protein, e.g., an ILT-2 or ILT-4 agonist, e.g., HLA-E or HLA-G or any other endogenous ILT-2 or ILT-4 agonist, e.g., increased expression of HLA-E, HLA-G, ILT-2 or ILT-4 compared to a reference cell, e.g., an unmodified cell otherwise similar to the source cell, or a Jurkat cell; or
  e. surface proteins which suppress complement activity, e.g., complement regulatory proteins, e.g. proteins that bind decay-accelerating factor (DAF, CD55), e.g. factor H (FH)-like protein-1 (FHL-1), e.g. C4b-binding protein (C4BP), e.g. complement receptor 1 (CD35), e.g. Membrane cofactor protein (MCP, CD46), eg. Profectin (CD59), e.g. proteins that inhibit the classical and alternative complement pathway CD/C5 convertase enzymes, e.g. proteins that regulate MAC assembly; e.g. increased expression of a complement regulatory protein compared to a reference cell, e.g. an umodified cell otherwise similar to the source cell, or a Jurkat cell.

In some embodiments, the increased expression level is at least 5%, 10%, 20%, 30%, 40%, 50%, 60%, 70%, 80%, 90%, 2-fold, 3-fold, 5-fold, 10-fold, 20-fold, 50-fold, or 100-fold higher as compared to a reference cell.

In some embodiments, the fusosome is derived from a source cell modified to have decreased expression of an immune activating agent, e.g., one, two, three, four, five, six, seven, eight or more of the following:
  a. less than 50%, 40%, 30%, 20%, 15%, 10%, or 5% or lesser expression of MHC class I or MHC class II, compared to a reference cell, e.g., an unmodified cell otherwise similar to the source cell, or a HeLa cell;
  b. less than 50%, 40%, 30%, 20%, 15%, 10%, or 5% or lesser expression of one or more co-stimulatory proteins including but not limited to: LAG3, ICOS-L, ICOS, Ox40L, OX40, CD28, B7, CD30, CD30L 4-1BB, 4-1BBL, SLAM, CD27, CD70, HVEM, LIGHT, B7-H3, or B7-H4, compared to a reference cell, e.g., an unmodified cell otherwise similar to the source cell, or a reference cell described herein;
  c. less than 50%, 40%, 30%, 20%, 15%, 10%, or 5% or lesser expression of soluble immune stimulating cytokines, e.g., IFN-gamma or TNF-a, compared to a reference cell, e.g., an unmodified cell otherwise similar to the source cell, or a U-266 cell;
  d. less than 50%, 40%, 30%, 20%, 15%, 10%, or 5% or lesser expression of endogenous immune-stimulatory antigen, e.g., Zg16 or Hormad1, compared to a reference cell, e.g., an unmodified cell otherwise similar to the source cell, or an A549 cell or a SK-BR-3 cell;
  e. less than 50%, 40%, 30%, 20%, 15%, 10%, or 5% or lesser expression of T-cell receptors (TCR) compared to a reference cell, e.g., an unmodified cell otherwise similar to the source cell, or a Jurkat cell;
  f. less than 50%, 40%, 30%, 20%, 15%, 10%, or 5% or lesser expression of ABO blood groups, compared to a reference cell, e.g., an unmodified cell otherwise similar to the source cell, or a HeLa cell;
  g. less than 50%, 40%, 30%, 20%, 15%, 10%, or 5% or lesser expression of transcription factors which drive immune activation, e.g., NFkB; compared to a reference cell, e.g., an unmodified cell otherwise similar to the source cell, or a Jurkat cell
  h. less than 50%, 40%, 30%, 20%, 15%, 10%, or 5% or lesser expression of transcription factors that control MHC expression, e.g., class II trans-activator (CIITA), regulatory factor of the Xbox 5 (RFX5), RFX-associated protein (RFXAP), or RFX ankyrin repeats (RFXANK; also known as RFXB) compared to a reference cell, e.g., an unmodified cell otherwise similar to the source cell, or a Jurkat cell; or
  i. less than 50%, 40%, 30%, 20%, 15%, 10%, or 5% or lesser expression of TAP proteins, e.g., TAP2, TAP1, or TAPBP, which reduce MHC class I expression compared to a reference cell, e.g., an unmodified cell otherwise similar to the source cell, or a HeLa cell.

In some embodiments, a fusosome composition derived from a mammalian cell, e.g., a mesenchymal stem cell, modified using shRNA expressing lentivirus to decrease MHC Class I expression, has lesser expression of MHC Class I compared to an unmodified cell, e.g., a mesenchymal stem cell that has not been modified. In some embodiments, a fusosome composition derived from a mammalian cell, e.g., a mesenchymal stem cell, modified using lentivirus expressing HLA-G to increase expression of HLA-G, has increased expression of HLA-G compared to an unmodified cell, e.g., a mesenchymal stem cell that has not been modified.

In some embodiments, the fusosome composition is derived from a source cell, e.g., a mammalian cell, which is not substantially immunogenic, wherein the source cells stimulate, e.g., induce, T-cell IFN-gamma secretion, at a level of 0 pg/mL to >0 pg/mL, e.g., as assayed in vitro, by IFN-gamma ELISPOT assay.

In some embodiments, the fusosome composition is derived from a source cell, e.g., a mammalian cell, wherein the mammalian cell is from a cell culture treated with an immunosuppressive agent, e.g., a glucocorticoid (e.g., dexamethasone), cytostatic (e.g., methotrexate), antibody (e.g., Muromonab-CD3), or immunophilin modulator (e.g., Ciclosporin or rapamycin).

In some embodiments, the fusosome composition is derived from a source cell, e.g., a mammalian cell, wherein the mammalian cell comprises an exogenous agent, e.g., a therapeutic agent.

In some embodiments, the fusosome composition is derived from a source cell, e.g., a mammalian cell, wherein the mammalian cell is a recombinant cell.

In some embodiments, the fusosome is derived from a mammalian cell genetically modified to express viral immunoevasins, e.g., hCMV US2, or US11.

In some embodiments, the surface of the fusosome, or the surface of the mammalian cell the fusosome is derived from, is covalently or non-covalently modified with a polymer, e.g., a biocompatible polymer that reduces immunogenicity and immune-mediated clearance, e.g., PEG.

In some embodiments, the surface of the fusosome, or the surface of the mammalian cell the fusosome is derived from is covalently or non-covalently modified with a sialic acid, e.g., a sialic acid comprising glycopolymers, which contain NK-suppressive glycan epitopes.

In some embodiments, the surface of the fusosome, or the surface of the mammalian cell the fusosome is derived from is enzymatically treated, e.g., with glycosidase enzymes, e.g., α-N-acetylgalactosaminidases, to remove ABO blood groups In some embodiments, the surface of the fusosome, or the surface of the mammalian cell the fusosome is derived from is enzymatically treated, to give rise to, e.g., induce expression of, ABO blood groups which match the recipient's blood type.

Parameters for Assessing Immunogenicity

In some embodiments, the fusosome composition is derived from a source cell, e.g., a mammalian cell which is not substantially immunogenic, or modified, e.g., modified using a method described herein, to have a reduction in immunogenicity. Immunogenicity of the source cell and the fusosome composition can be determined by any of the assays described herein.

In some embodiments, the fusosome composition has an increase, e.g., an increase of 1%, 5%, 10%, 20%, 30%, 40%, 50%, 60%, 70%, 80%, 90%, or more, in in vivo graft survival compared to a reference cell, e.g., an unmodified cell otherwise similar to the source cell. In some embodiments, graft survival is determined by an assay measuring in vivo graft survival as described herein, in an appropriate animal model, e.g., an animal model described herein.

In some embodiments, the fusosome composition has an increase, e.g., an increase of 1%, 5%, 10%, 20%, 30%, 40%, 50%, 60%, 70%, 80%, 90%, or more in teratoma formation compared to a reference cell, e.g., an unmodified cell otherwise similar to the source cell. In some embodiments, teratroma formation is determined by an assay measuring teratoma formation as described herein, in an appropriate animal model, e.g., in an animal model described herein.

In some embodiments, the fusosome composition has an increase, e.g., an increase of 1%, 5%, 10%, 20%, 30%, 40%, 50%, 60%, 70%, 80%, 90%, or more in teratoma survival compared to a reference cell, e.g., an unmodified cell otherwise similar to the source cell. In some embodiments, the fusosome composition survives for one or more days in an assay of teratoma survival. In some embodiments, teratroma survival is determined by an assay measuring teratoma survival as described herein, in an appropriate animal model, e.g., in an animal model described herein. In an embodiment, teratoma formation is measured by imaging analysis, e.g., IHC staining, fluorescent staining or H&E, of fixed tissue, e.g., frozen or formalin fixed, as described in the Examples. In some embodiments, fixed tissue can be stained with any one or all of the following antibodies: anti-human CD3, anti-human CD4, or anti-human CD8.

In some embodiments, the fusosome composition has a reduction, e.g., a reduction of 1%, 5%, 10%, 20%, 30%, 40%, 50%, 60%, 70%, 80%, 90%, or more in CD8+ T cell infiltration into a graft or teratoma compared to a reference cell, e.g., an unmodified cell otherwise similar to the source cell. In an embodiment, CD8 T cell infiltration is determined by an assay measuring CD8+ T cell infiltration as described herein, e.g., histological analysis, in an appropriate animal model, e.g., an animal model described herein. In some embodiments, teratomas derived from the fusosome composition have CD8+ T cell infiltration in 0%, 0.1%, 1% 5%, 10%, 20%, 30%, 40% 50%, 60%, 70%, 80%, 90%, or 100% of 50× image fields of a histology tissue section.

In some embodiments, the fusosome composition has a reduction, e.g., a reduction of 1%, 5%, 10%, 20%, 30%, 40%, 50%, 60%, 70%, 80%, 90%, or more in CD4+ T cell infiltration into a graft or teratoma compared to a reference cell, e.g., an unmodified cell otherwise similar to the source cell. In some embodiments, CD4 T cell infiltration is determined by an assay measuring CD4+ T cell infiltration as described herein, e.g., histological analysis, in an appropriate animal model, e.g., an animal model described herein. In some embodiments, teratomas derived from the fusosome composition have CD4+ T cell infiltration in 0%, 0.1%, 1% 5%, 10%, 20%, 30%, 40% 50%, 60%, 70%, 80%, 90%, or 100% of 50× image fields of a histology tissue section.

In some embodiments, the fusosome composition has a reduction, e.g., a reduction of 1%, 5%, 10%, 20%, 30%, 40%, 50%, 60%, 70%, 80%, 90%, or more in CD3+NK cell infiltration into a graft or teratoma compared to a reference cell, e.g., an unmodified cell otherwise similar to the source cell. In an embodiment, CD3+NK cell infiltration is determined by an assay measuring CD3+NK cell infiltration as described herein, e.g., histological analysis, in an appropriate animal model, e.g., an animal model described herein. In some embodiments, teratomas derived from the fusosome composition have CD3+NK T cell infiltration in 0%, 0.1%, 1% 5%, 10%, 20%, 30%, 40% 50%, 60%, 70%, 80%, 90%, or 100% of 50× image fields of a histology tissue section.

In some embodiments, the fusosome composition has a reduction in immunogenicity as measured by a reduction in humoral response following one or more implantation of the fusosome derived into an appropriate animal model, e.g., an animal model described herein, compared to a humoral response following one or more implantation of a reference cell, e.g., an unmodified cell otherwise similar to the source cell, into an appropriate animal model, e.g., an animal model described herein. In some embodiments, the reduction in humoral response is measured in a serum sample by an anti-cell antibody titre, e.g., anti-fusosome antibody titre, e.g., by ELISA. In some embodiments, the serum sample from animals administered the fusosome composition has a reduction of 1%, 5%, 10%, 20%, 30%, 40%, 50%, 60%, 70%, 80%, 90%, or more of an anti-cell antibody titer compared to the serum sample from animals administered an unmodified cell. In some embodiments, the serum sample from animals administered the fusosome composition has an increased anti-cell antibody titre, e.g., increased by 1%, 2%, 5%, 10%, 20%, 30%, or. 40% from baseline, e.g., wherein baseline refers to serum sample from the same animals before administration of the fusosome composition.

In some embodiments, the fusosome composition has a reduction in macrophage phagocytosis, e.g., a reduction of 1%, 5%, 10%, 20%, 30%, 40%, 50%, 60%, 70%, 80%, 90%, or more in macrophage phagocytosis compared to a reference cell, e.g., an unmodified cell otherwise similar to the source cell, wherein the reduction in macrophage phagocytosis is determined by assaying the phagocytosis index in vitro, e.g., as described in Example 82. In some embodiments, the fusosome composition has a phagocytosis index of 0, 1, 10, 100, or more, e.g., as measured by an assay of Example 82, when incubated with macrophages in an in vitro assay of macrophage phagocytosis.

In some embodiments, the source cell has a reduction in cytotoxicity mediated cell lysis by PBMCs, e.g., a reduction of 1%, 5%, 10%, 20%, 30%, 40%, 50%, 60%, 70%, 80%, 90%, or more in cell lysis compared to a reference cell, e.g., an unmodified cell otherwise similar to the source cell or a mesenchymal stem cells, e.g., using an assay of Example 83. In embodiments, the source cell expresses exogenous HLA-G.

In some embodiments, the fusosome composition has a reduction in NK-mediated cell lysis, e.g., a reduction of 1%, 5%, 10%, 20%, 30%, 40%, 50%, 60%, 70%, 80%, 90%, or more in NK-mediated cell lysis compared to a reference cell, e.g., an unmodified cell otherwise similar to the source cell, wherein NK-mediated cell lysis is assayed in vitro, by a chromium release assay or europium release assay.

In some embodiments, the fusosome composition has a reduction in CD8+ T-cell mediated cell lysis, e.g., a reduction of 1%, 5%, 10%, 20%, 30%, 40%, 50%, 60%, 70%, 80%, 90%, or more in CD8 T cell mediated cell lysis compared to a reference cell, e.g., an unmodified cell otherwise similar to the source cell, wherein CD8 T cell mediated cell lysis is assayed in vitro, by a chromium release assay or europium release assay. In embodiments, activation and/or proliferation is measured as described in Example 85.

In some embodiments, the fusosome composition has a reduction in CD4+ T-cell proliferation and/or activation, e.g., a reduction of 1%, 5%, 10%, 20%, 30%, 40%, 50%, 60%, 70%, 80%, 90%, or more compared to a reference cell, e.g., an unmodified cell otherwise similar to the source cell, wherein CD4 T cell proliferation is assayed in vitro (e.g. co-culture assay of modified or unmodified mammalian source cell, and CD4+ T-cells with CD3/CD28 Dynabeads), e.g., as described in Example 86.

In some embodiments, the fusosome composition has a reduction in T-cell IFN-gamma secretion, e.g., a reduction of 1%, 5%, 10%, 20%, 30%, 40%, 50%, 60%, 70%, 80%, 90%, or more in T-cell IFN-gamma secretion compared to a reference cell, e.g., an unmodified cell otherwise similar to the source cell, wherein T-cell IFN-gamma secretion is assayed in vitro, e.g., by IFN-gamma ELISPOT.

In some embodiments, the fusosome composition has a reduction in secretion of immunogenic cytokines, e.g., a reduction of 1%, 5%, 10%, 20%, 30%, 40%, 50%, 60%, 70%, 80%, 90%, or more in secretion of immunogenic cytokines compared to a reference cell, e.g., an unmodified cell otherwise similar to the source cell, wherein secretion of immunogenic cytokines is assayed in vitro using ELISA or ELISPOT.

In some embodiments, the fusosome composition results in increased secretion of an immunosuppressive cytokine, e.g., an increase of 1%, 5%, 10%, 20%, 30%, 40%, 50%, 60%, 70%, 80%, 90%, or more in secretion of an immunosuppressive cytokine compared to a reference cell, e.g., an unmodified cell otherwise similar to the source cell, wherein secretion of the immunosuppressive cytokine is assayed in vitro using ELISA or ELISPOT.

In some embodiments, the fusosome composition has an increase in expression of HLA-G or HLA-E, e.g., an increase in expression of 1%, 5%, 10%, 20%, 30%, 40%, 50%, 60%, 70%, 80%, 90%, or more of HLA-G or HLA-E, compared to a reference cell, e.g., an unmodified cell otherwise similar to the source cell, wherein expression of HLA-G or HLA-E is assayed in vitro using flow cytometry, e.g., FACS. In some embodiments, the fusosome composition is derived from a source cell which is modified to have an increased expression of HLA-G or HLA-E, e.g., compared to an unmodified cell, e.g., an increased expression of 1%, 5%, 10%, 20%, 30%, 40%, 50%, 60%, 70%, 80%, 90%, or more of HLA-G or HLA-E, wherein expression of HLA-G or HLA-E is assayed in vitro using flow cytometry, e.g., FACS. In some embodiments, the fusosome composition derived from a modified cell with increased HLA-G expression demonstrates reduced immunogenicity, e.g., as measured by reduced immune cell infiltration, in a teratoma formation assay, e.g., a teratoma formation assay as described herein.

In some embodiments, the fusosome composition has an increase in expression of T cell inhibitor ligands (e.g. CTLA4, PD1, PD-L1), e.g., an increase in expression of 1%, 5%, 10%, 20%, 30%, 40%, 50%, 60%, 70%, 80%, 90%, or more of T cell inhibitor ligands as compared to a reference cell, e.g., an unmodified cell otherwise similar to the source cell, wherein expression of T cell inhibitor ligands is assayed in vitro using flow cytometry, e.g., FACS.

In some embodiments, the fusosome composition has a decrease in expression of co-stimulatory ligands, e.g., a decrease of 1%, 5%, 10%, 20%, 30%, 40%, 50%, 60%, 70%, 80%, 90%, or more in expression of co-stimulatory ligands compared to a reference cell, e.g., an unmodified cell otherwise similar to the source cell, wherein expression of co-stimulatory ligands is assayed in vitro using flow cytometry, e.g., FACS.

In some embodiments, the fusosome composition has a decrease in expression of MHC class I or MHC class II, e.g., a decrease in expression of 1%, 5%, 10%, 20%, 30%, 40%, 50%, 60%, 70%, 80%, 90%, or more of MHC Class I or MHC Class II compared to a reference cell, e.g., an unmodified cell otherwise similar to the source cell or a HeLa cell, wherein expression of MHC Class I or II is assayed in vitro using flow cytometry, e.g., FACS.

In some embodiments, the fusosome composition is derived from a cell source, e.g., a mammalian cell source, which is substantially non-immunogenic. In some embodiments, immunogenicity can be quantified, e.g., as described herein. In some embodiments, the mammalian cell source comprises any one, all or a combination of the following features:
- a. wherein the source cell is obtained from an autologous cell source; e.g., a cell obtained from a recipient who will be receiving, e.g., administered, the fusosome composition;
- b. wherein the source cell is obtained from an allogeneic cell source which is of matched, e.g., similar, gender to a recipient, e.g., a recipient described herein who will be receiving, e.g., administered; the fusosome composition;
- c. wherein the source cell is obtained is from an allogeneic cell source is which is HLA matched with a recipient's HLA, e.g., at one or more alleles;
- d. wherein the source cell is obtained is from an allogeneic cell source which is an HLA homozygote;
- e. wherein the source cell is obtained is from an allogeneic cell source which lacks (or has reduced levels compared to a reference cell) MHC class I and II; or
- f. wherein the source cell is obtained is from a cell source which is known to be substantially non-immunogenic including but not limited to a stem cell, a mesenchymal stem cell, an induced pluripotent stem cell, an embryonic stem cell, a sertoli cell, or a retinal pigment epithelial cell.

In some embodiments, the subject to be administered the fusosome composition has, or is known to have, or is tested for, a pre-existing antibody (e.g., IgG or IgM) reactive with a fusosome. In some embodiments, the subject to be administered the fusosome composition does not have detectable levels of a pre-existing antibody reactive with the fusosome. Tests for the antibody are described, e.g., in Example 78.

In some embodiments, a subject that has received the fusosome composition has, or is known to have, or is tested for, an antibody (e.g., IgG or IgM) reactive with a fusosome. In some embodiments, the subject that received the fusosome composition (e.g., at least once, twice, three times, four times, five times, or more) does not have detectable levels of antibody reactive with the fusosome. In embodiments, levels of antibody do not rise more than 1%, 2%, 5%, 10%, 20%, or 50% between two timepoints, the first timepoint being before the first administration of the fusosome, and the second timepoint being after one or more administrations of the fusosome. Tests for the antibody are described, e.g., in Example 79.

Additional Therapeutic Agents

In some embodiments, the fusosome composition is co-administered with an additional agent, e.g., a therapeutic agent, to a subject, e.g., a recipient, e.g., a recipient described herein. In some embodiments, the co-administered therapeutic agent is an immunosuppressive agent, e.g., a glucocorticoid (e.g., dexamethasone), cytostatic (e.g., methotrexate), antibody (e.g., Muromonab-CD3), or immunophilin modulator (e.g., Ciclosporin or rapamycin). In embodiments, the immunosuppressive agent decreases immune mediated clearance of fusosomes. In some embodiments the fusosome composition is co-administered with an immunostimulatory agent, e.g., an adjuvant, an interleukin, a cytokine, or a chemokine.

In some embodiments, the fusosome composition and the immunosuppressive agent are administered at the same time, e.g., contemporaneously administered. In some embodiments, the fusosome composition is administered before administration of the immunosuppressive agent. In some embodiments, the fusosome composition is administered after administration of the immunosuppressive agent.

In some embodiments, the immunosuppressive agent is a small molecule such as ibuprofen, acetaminophen, cyclosporine, tacrolimus, rapamycin, mycophenolate, cyclophosphamide, glucocorticoids, sirolimus, azathriopine, or methotrexate.

In some embodiments, the immunosuppressive agent is an antibody molecule, including but not limited to: muronomab (anti-CD3), Dacliziumab (anti-IL12), Basiliximab, Infliximab (Anti-TNFa), or rituximab (Anti-CD20).

In some embodiments, co-administration of the fusosome composition with the immunosuppressive agent results in enhanced persistence of the fusosome composition in the subject compared to administration of the fusosome composition alone. In some embodiments, the enhanced persistence of the fusosome composition in the co-administration is at least 10%, 20%, 30%, 40%, 50%, 60%, 70%, 80%, 90% or longer, compared to persistence of the fusosome composition when administered alone. In some embodiments, the enhanced persistence of the fusosome composition in the co-administration is at least 1, 2, 3, 4, 5, 6, 7, 10, 15, 20, 25, or 30 days or longer, compared to survival of the fusosome composition when administered alone.

Delivery

In some embodiments, a fusogen (e.g., protein, lipid or chemical fusogen) or a fusogen binding partner is delivered to a target cell or tissue prior to, at the same time, or after the delivery of a fusosome.

In some embodiments, a fusogen (e.g., protein, lipid or chemical fusogen) or a fusogen binding partner is delivered to a non-target cell or tissue prior to, at the same time, or after the delivery of a fusosome.

In some embodiments, a nucleic acid that encodes a fusogen (e.g., protein or lipid fusogen) or a fusogen binding partner is delivered to a target cell or tissue prior to, at the same time, or after the delivery of a fusosome.

In some embodiments, a polypeptide, nucleic acid, ribonucleoprotein, or small-molecule that upregulates or downregulates expression of a fusogen (e.g., protein, lipid or chemical fusogen) or a fusogen binding partner is delivered to a target cell or tissue prior to, at the same time, or after the delivery of a fusosome.

In some embodiments, a polypeptide, nucleic acid, ribonucleoprotein, or small-molecule that upregulates or downregulates expression of a fusogen (e.g., protein, lipid or chemical fusogen) or a fusogen binding partner is delivered to a non-target cell or tissue prior to, at the same time, or after the delivery of a fusosome.

In some embodiments, the target cell or tissue is modified by (e.g., inducing stress or cell division) to increase the rate of fusion prior to, at the same time, or after the delivery of a fusosome. Some nonlimiting examples include, inducing ischemia, treatment with chemotherapy, antibiotic, irradiation, toxin, inflammation, inflammatory molecules, anti-inflammatory molecules, acid injury, basic injury, burn, polyethylene glycol, neurotransmitters, myelotoxic drugs, growth factors, or hormones, tissue resection, starvation, and/or exercise.

In some embodiments, the target cell or tissue is treated with a vasodilator (e.g. nitric oxide (NO), carbon monoxide, prostacyclin (PGI2), nitroglycerine, phentolamine) or vasoconstrictors (e.g. angiotensin (AGT), endothelin (EDN), norepinephrine)) to increase the rate of fusosome transport to the target tissue.

In some embodiments, the target cell or tissue is treated with a chemical agent, e.g., a chemotherapeutic. In such embodiments, the chemotherapeutic induces damage to the target cell or tissue that enhances fusogenic activity of target cells or tissue.

In some embodiments, the target cell or tissue is treated with a physical stress, e.g., electrofusion. In such embodiments, the physical stress destabilizes the membranes of the target cell or tissue to enhance fusogenic activity of target cells or tissue.

In some embodiments, the target cell or tissue may be treated with an agent to enhance fusion with a fusosome. For example, specific neuronal receptors may be stimulated with an anti-depressant to enhance fusogenic properties.

Compositions comprising the fusosomes described herein may be administered or targeted to the circulatory system, hepatic system, renal system, cardio-pulmonary system, central nervous system, peripheral nervous system, musculoskeletal system, lymphatic system, immune system, sensory nervous systems (sight, hearing, smell, touch, taste), digestive system, endocrine systems (including adipose tissue metabolic regulation), and reproductive system.

In embodiments, a fusosome composition described herein is delivered ex-vivo to a cell or tissue, e.g., a human cell or tissue. In some embodiments, the composition is delivered to an ex vivo tissue that is in an injured state (e.g., from trauma, disease, hypoxia, ischemia or other damage).

In some embodiments, the fusosome composition is delivered to an ex-vivo transplant (e.g., a tissue explant or tissue for transplantation, e.g., a human vein, a musculoskeletal graft such as bone or tendon, cornea, skin, heart valves, nerves; or an isolated or cultured organ, e.g., an organ to be transplanted into a human, e.g., a human heart, liver, lung, kidney, pancreas, intestine, thymus, eye). The composition improves viability, respiration, or other function of the transplant. The composition can be delivered to the tissue or organ before, during and/or after transplantation.

In some embodiments, a fusosome composition described herein is delivered ex-vivo to a cell or tissue derived from a subject. In some embodiments the cell or tissue is readministered to the subject (i.e., the cell or tissue is autologous).

The fusosomes may fuse with a cell from any mammalian (e.g., human) tissue, e.g., from epithelial, connective, muscular, or nervous tissue or cells, and combinations thereof. The fusosomes can be delivered to any eukaryotic (e.g., mammalian) organ system, for example, from the cardiovascular system (heart, vasculature); digestive system (esophagus, stomach, liver, gallbladder, pancreas, intestines, colon, rectum and anus); endocrine system (hypothalamus, pituitary gland, pineal body or pineal gland, thyroid, parathyroids, adrenal glands); excretory system (kidneys, ureters, bladder); lymphatic system (lymph, lymph nodes, lymph vessels, tonsils, adenoids, thymus, spleen); integumentary system (skin, hair, nails); muscular system (e.g., skeletal muscle); nervous system (brain, spinal cord, nerves)'; reproductive system (ovaries, uterus, mammary glands, testes, vas deferens, seminal vesicles, prostate); respiratory system (pharynx, larynx, trachea, bronchi, lungs, diaphragm); skeletal system (bone, cartilage), and combinations thereof.

In embodiments, the fusosome targets a tissue, e.g., liver, lungs, heart, spleen, pancreas, gastrointestinal tract, kidney, testes, ovaries, brain, reproductive organs, central nervous system, peripheral nervous system, skeletal muscle, endothelium, inner ear, adipose tissue (e.g., brown adipose tissue or white adipose tissue) or eye, when administered to a subject, e.g., wherein at least 0.1%, 0.5%, 1%, 1.5%, 2%, 2.5%, 3%, 4%, 5%, 10%, 20%, 30%, 40%, 50%, 60%, 70%, 80%, or 90% of the fusosomes in a population of administered fusosomes are present in the target tissue after 24, 48, or 72 hours, e.g., by an assay of Example 87 or 100.

In embodiments, the fusosomes may fuse with a cell from a source of stem cells or progenitor cells, e.g., bone marrow stromal cells, marrow-derived adult progenitor cells (MAPCs), endothelial progenitor cells (EPC), blast cells, intermediate progenitor cells formed in the subventricular zone, neural stem cells, muscle stem cells, satellite cells, liver stem cells, hematopoietic stem cells, bone marrow stromal cells, epidermal stem cells, embryonic stem cells, mesenchymal stem cells, umbilical cord stem cells, precursor cells, muscle precursor cells, myoblast, cardiomyoblast, neural precursor cells, glial precursor cells, neuronal precursor cells, hepatoblasts.

In embodiments, the target cell is not a cancer cell, e.g., is not a glioblastoma cell. In embodiments, the target cell is a stem cell or a fully differentiated cell.

Fusogen Binding Partners, e.g., for Landing Pad Embodiments

In certain aspects, the disclosure provides a method of delivering a membrane enclosed preparation to a target cell in a subject. In some embodiments, the method comprises administering to a subject a fusosome, e.g., a membrane enclosed preparation comprising a nucleic acid encoding a fusogen, e.g., a myomaker protein, wherein the nucleic acid is not present or is not expressed (e.g., is present but is not transcribed or not translated) within a cell, under conditions that allow the fusogen to be expressed on the surface of the fusosome in the subject. In some embodiments, the method further comprises administering to the subject a composition comprising an agent, e.g., a therapeutic agent, and a fusogen binding partner, optionally, comprising a carrier, e.g., a membrane, under conditions that allow fusion of the fusogen on the fusosome, and the fusogen binding partner. In some embodiments, the carrier comprises a membrane, e.g., a lipid bilayer, e.g., the agent is disposed within a lipid bilayer. In some embodiments, the lipid bilayer fuses with the target cell, thereby delivering the agent to the target cell in the subject.

In an embodiment, a fusogen binding partner is a moiety, e.g., a protein molecule, disposed in a membrane (e.g., a lipid bilayer), of a target cell, e.g., a target cell disclosed herein. In an embodiment, the membrane can be a cell surface membrane, or a subcellular membrane of an organelle, e.g., a mitochondrion, lysosome, or Golgi apparatus. In an embodiment, the fusogen binding partner can be endogenously expressed or exogenously expressed (e.g., by a method described herein). In an embodiment, the fusogen binding partner can cluster with other fusogen binding partners at the membrane.

In an embodiment, the presence of a fusogen binding partner, or a plurality of fusogen binding partners, in a membrane of a target cell, creates an interface that can facilitate the interaction, e.g., binding, between a fusogen binding partner on a target cell (e.g., a cell described herein), and a fusogen on a fusosome (e.g., a fusosome described herein). In some embodiments, the fusogen on a fusosome interacts with, e.g., binds to, a fusogen binding partner on target cell, e.g., on the membrane (e.g., lipid bilayer), of a target cell, to induce fusion of the fusosome with the target membrane. In some embodiments, the fusogen interacts with, e.g., binds to, a fusogen binding partner on a landing pad on a subcellular organelle, including a mitochondrion, to induce fusion of the fusosome with the subcellular organelle.

A fusogen binding partner can be introduced in a target cell, e.g., a target cell disclosed herein, by any of the methods discussed below.

In an embodiment, a method of introducing a fusogen binding partner to a target cell comprises removal, e.g., extraction, of a target cell (e.g., via apheresis or biopsy), from a subject (e.g., a subject described herein), and administration of, e.g., exposure to, a fusogen binding partner under conditions that allow the fusogen binding partner to be expressed on a membrane of the target cell. In an embodiment, the method further comprises contacting the target cell expressing a fusogen binding partner ex vivo with a fusosome comprising a fusogen to induce fusion of the fusosome with the target cell membrane. In an embodiment, the target cell fused to the fusosome is reintroduced into the subject, e.g., intravenously.

In an embodiment, the target cell expressing a fusogen binding partner is reintroduced into the subject, e.g., intravenously. In an embodiment, the method further comprises administering to the subject a fusosome comprising a fusogen to allow interaction, e.g., binding, of the fusogen on the fusosome with the fusogen binding partner on the target cell, and fusion of the fusosome with the target cell membrane.

In some embodiments, the target cells are treated with an epigenetic modifier, e.g., a small molecule epigenetic modifier, to increase or decrease expression of an endogenous cell surface molecule, e.g., a fusogen binding partner, e.g., an organ, tissue, or cell targeting molecule, where the cell surface molecule is a protein, glycan, lipid or low molecular weight molecule. In an embodiment, the target cell is genetically modified to increase the expression of an endogenous cell surface molecule, e.g., a fusogen binding partner, e.g., an organ, tissue, or cell targeting molecule, where the cell surface molecule is a protein, glycan, lipid or low molecular weight molecule. In an embodiment, the genetic modification may decrease expression of a transcriptional activator of the endogenous cell surface molecule, e.g., a fusogen binding partner.

In an embodiment, the target cell is genetically modified to express, e.g., overexpress, an exogenous cell surface molecule, e.g., a fusogen binding partner, where the cell surface molecule is a protein, glycan, lipid or low molecular weight molecule.

In some embodiments, the target cell is genetically modified to increase the expression of an exogenous fusogen in the cell, e.g., delivery of a transgene. In some embodiments, a nucleic acid, e.g., DNA, mRNA or siRNA, is transferred to the target cell, e.g., to increase or decrease the expression of a cell surface molecule (protein, glycan, lipid or low molecular weight molecule). In some embodiments, the nucleic acid targets a repressor of a fusogen binding partner, e.g., an shRNA, or siRNA construct. In some embodiments, the nucleic acid encodes an inhibitor of a fusogen binding partner repressor.

Methods of Use

The administration of a pharmaceutical composition described herein may be by way of oral, inhaled, transdermal or parenteral (including intravenous, intratumoral, intraperitoneal, intramuscular, intracavity, and subcutaneous) administration. The fusosomes may be administered alone or formulated as a pharmaceutical composition.

The fusosomes may be administered in the form of a unit-dose composition, such as a unit dose oral, parenteral, transdermal or inhaled composition. Such compositions are prepared by admixture and are suitably adapted for oral, inhaled, transdermal or parenteral administration, and as such may be in the form of tablets, capsules, oral liquid preparations, powders, granules, lozenges, reconstitutable powders, injectable and infusable solutions or suspensions or suppositories or aerosols.

In some embodiments, delivery of a fusosome composition described herein may induce or block cellular differentiation, de-differentiation, or trans-differentiation. The target mammalian cell may be a precursor cell. Alternatively, the target mammalian cell may be a differentiated cell, and the cell fate alteration includes driving de-differentiation into a pluripotent precursor cell, or blocking such de-differentiation. In situations where a change in cell fate is desired, effective amounts of a fusosome described herein encoding a cell fate inductive molecule or signal is introduced into a target cell under conditions such that an alteration in cell fate is induced. In some embodiments, a fusosome described herein is useful to reprogram a subpopulation of cells from a first phenotype to a second phenotype. Such a reprogramming may be temporary or permanent. Optionally, the reprogramming induces a target cell to adopt an intermediate phenotype.

Also provided are methods of reducing cellular differentiation in a target cell population. For example, a target cell population containing one or more precursor cell types is contacted with a fusosome composition described herein, under conditions such that the composition reduces the differentiation of the precursor cell. In certain embodiments, the target cell population contains injured tissue in a mammalian subject or tissue affected by a surgical procedure. The precursor cell is, e.g., a stromal precursor cell, a neural precursor cell, or a mesenchymal precursor cell.

A fusosome composition described herein, comprising a cargo, may be used to deliver such cargo to a cell tissue or subject. Delivery of a cargo by administration of a fusosome composition described herein may modify cellular protein expression levels. In certain embodiments, the administered composition directs upregulation of (via expression in the cell, delivery in the cell, or induction within the cell) of one or more cargo (e.g., a polypeptide or mRNA) that provide a functional activity which is substantially absent or reduced in the cell in which the polypeptide is delivered. For example, the missing functional activity may be enzymatic, structural, or regulatory in nature. In related embodiments, the administered composition directs up-regulation of one or more polypeptides that increases (e.g., synergistically) a functional activity which is present but substantially deficient in the cell in which the polypeptide is upregulated. In certain embodiments, the administered composition directs downregulation of (via expression in the cell, delivery in the cell, or induction within the cell) of one or more cargo (e.g., a polypeptide, siRNA, or miRNA) that repress a functional activity which is present or upregulated in the cell in which the polypeptide, siRNA, or miRNA is delivered. For example, the upregulated functional activity may be enzymatic, structural, or regulatory in nature. In related embodiments, the administered composition directs down-regulation of one or more polypeptides that decreases (e.g., synergistically) a functional activity which is present or upregulated in the cell in which the polypeptide is downregulated. In certain embodiments, the administered composition directs upregulation of certain functional activities and downregulation of other functional activities.

In embodiments, the fusosome composition (e.g., one comprising mitochondria or DNA) mediates an effect on a target cell, and the effect lasts for at least 1, 2, 3, 4, 5, 6, or 7 days, 2, 3, or 4 weeks, or 1, 2, 3, 6, or 12 months. In some embodiments (e.g., wherein the fusosome composition comprises an exogenous protein), the effect lasts for less than 1, 2, 3, 4, 5, 6, or 7 days, 2, 3, or 4 weeks, or 1, 2, 3, 6, or 12 months.

Ex-Vivo Applications

In embodiments, the fusosome composition described herein is delivered ex-vivo to a cell or tissue, e.g., a human cell or tissue. In embodiments, the composition improves function of a cell or tissue ex-vivo, e.g., improves cell viability, respiration, or other function (e.g., another function described herein).

In some embodiments, the composition is delivered to an ex vivo tissue that is in an injured state (e.g., from trauma, disease, hypoxia, ischemia or other damage).

In some embodiments, the composition is delivered to an ex-vivo transplant (e.g., a tissue explant or tissue for transplantation, e.g., a human vein, a musculoskeletal graft such as bone or tendon, cornea, skin, heart valves, nerves; or an isolated or cultured organ, e.g., an organ to be transplanted into a human, e.g., a human heart, liver, lung, kidney, pancreas, intestine, thymus, eye). The composition can be delivered to the tissue or organ before, during and/or after transplantation.

In some embodiments, the composition is delivered, administered or contacted with a cell, e.g., a cell preparation. The cell preparation may be a cell therapy preparation (a cell preparation intended for administration to a human subject). In embodiments, the cell preparation comprises cells expressing a chimeric antigen receptor (CAR), e.g., expressing a recombinant CAR. The cells expressing the CAR may be, e.g., T cells, Natural Killer (NK) cells, cytotoxic T lymphocytes (CTL), regulatory T cells. In embodiments, the cell preparation is a neural stem cell preparation. In embodiments, the cell preparation is a mesenchymal stem cell (MSC) preparation. In embodiments, the cell preparation is a hematopoietic stem cell (HSC) preparation. In embodiments, the cell preparation is an islet cell preparation.

In Vivo Uses

The fusosome compositions described herein can be administered to a subject, e.g., a mammal, e.g., a human. In such embodiments, the subject may be at risk of, may have a symptom of, or may be diagnosed with or identified as having, a particular disease or condition (e.g., a disease or condition described herein).

In some embodiments, the source of fusosomes are from the same subject that is administered a fusosome composition. In other embodiments, they are different. For example, the source of fusosomes and recipient tissue may be autologous (from the same subject) or heterologous (from different subjects). In either case, the donor tissue for fusosome compositions described herein may be a different tissue type than the recipient tissue. For example, the donor tissue may be muscular tissue and the recipient tissue may be connective tissue (e.g., adipose tissue). In other embodiments, the donor tissue and recipient tissue may be of the same or different type, but from different organ systems.

A fusosome composition described herein may be administered to a subject having a cancer, an autoimmune disease, an infectious disease, a metabolic disease, a neurodegenerative disease, or a genetic disease (e.g., enzyme deficiency). In some embodiments, the subject is in need of regeneration.

In some embodiments, the fusosome is co-administered with an inhibitor of a protein that inhibits membrane fusion. For example, Suppressyn is a human protein that inhibits cell-cell fusion (Sugimoto et al., "A novel human endogenous retroviral protein inhibits cell-cell fusion" Scientific Reports 3:1462 DOI: 10.1038/srep01462). Thus, in some embodiments, the fusosome is co-administered with an inhibitor of sypressyn, e.g., a siRNA or inhibitory antibody.

Non-Human Applications

Compositions described herein may also be used to similarly modulate the cell or tissue function or physiology of a variety of other organisms including but not limited to: farm or working animals (horses, cows, pigs, chickens etc.), pet or zoo animals (cats, dogs, lizards, birds, lions, tigers and bears etc.), aquaculture animals (fish, crabs, shrimp, oysters etc.), plants species (trees, crops, ornamentals flowers etc), fermentation species (saccharomyces etc.). Fusosome compositions described herein can be made from such non-human sources and administered to a non-human target cell or tissue or subject.

Fusosome compositions can be autologous, allogeneic or xenogeneic to the target.

All references and publications cited herein are hereby incorporated by reference.

The following examples are provided to further illustrate some embodiments of the present invention, but are not intended to limit the scope of the invention; it will be understood by their exemplary nature that other procedures, methodologies, or techniques known to those skilled in the art may alternatively be used.

EXAMPLES

Example 1. Generating Enucleated Fusogenic Cells Via Chemical Treatment (PEG)

Mito-DsRed (a mitochondrial specific targeted dye) expressing donor HeLa cells were trypsinized with 0.25% trypsin, collected, spun at 500×g for 5 min, washed once in PBS and counted. 10×10^6 cells were subsequently resuspended in 3 ml of 12.5% ficoll in complete MEM-alpha (+10% FBS, +1% penicillin/streptomycin, +glutamine) supplemented with 10 ug/ml cytochalasin-B for 15 min. To enucleate cells, they were transferred to a discontinuous ficoll gradient consisting of the following ficoll fractions (from top to bottom): 2 ml 12.5% ficoll, 0.5 ml 15% ficoll, 0.5 ml 16% ficoll, 2 ml 17% ficoll gradient, 2 ml 25% ficoll. All ficoll gradient fractions were made in complete DMEM supplemented with 10 ug/ml cytochalasin-B. Gradients were spun on a Beckman SW-40 ultracentrifuge, Ti-70 rotor at 107971×g for 1 h at 37 C. Following centrifugation, enucleated HeLa cells were collected from the 12.5%, 15%, 16%, and 1/2 of the 17% ficoll fractions and resuspended in complete DMEM (+10% FBS, +1% penicillin/streptomycin, +glutamine), and spun at 500×g for 5 min to pellet. Enucleated Mito-DsRed donor cells were washed 2× in DMEM. Simultaneously, Mito-GFP (a mitochondrial specific targeted dye) expressing recipient HeLa cells were trypsinized, counted, and prepared for fusion.

For fusion, enucleated Mito-DsRed donor HeLa cells were combined at a 1:1 ratio with Mito-GFP recipient HeLa cells (200,000 each) in a 50% polyethylene glycol solution (50% PEG by w/v prepared in DMEM complete w/10% DMSO) for 1 minute at 37 C. Cells were subsequently washed 3× in 10 ml complete DMEM and plated on 35 mm glass-bottom quadrant imaging dishes at density of 50 k cells/quadrant, with each quadrant having an area of 1.9 cm2.

Example 2. Generating Nucleated Fusogenic Cells Via Chemical Treatment (PEG)

Mito-DsRed (a mitochondrial specific targeted dye) expressing donor HeLa cells were trypsinized with 0.25% trypsin, collected, spun at 500×g for 5 min, washed once in PBS and counted. 2×10^6 cells were subsequently resuspended in complete DMEM (+10% FBS, +1% penicillin/streptomycin, +glutamine), counted, and prepared for fusion.

Mito-DsRed donor cells were washed 3× in DMEM. Simultaneously, Mito-GFP (a mitochondrial specific targeted dye) expressing recipient HeLa cells were trypsinized, counted, and prepared for fusion.

For fusion, Mito-DsRed donor HeLa cells were combined at a 1:1 ratio with Mito-GFP recipient HeLa cells (200,000 each) in a 50% polyethylene glycol solution (50% PEG by w/v prepared in DMEM complete w/10% DMSO) with for 1 minute at 37 C. Cells were subsequently washed 3× in 10 ml complete DMEM and plated on 35 mm glass-bottom quadrant imaging dishes at density of 50 k cells/quadrant, with each quadrant having an area of 1.9 cm2.

Example 3. Creation of HeLa Cells Expressing Exogenous Fusogens

This example describes the creation of tissue culture cells expressing an exogenous fusogen. The following example is equally applicable to any protein based fusogen and is equally applicable to production in primary cells (in suspension or adherent) and tissue. In certain cases, a fusogen pair can be used required to induce fusion (delineated as a fusogen and a fusogen binding partner).

The fusogen gene, fusion failure 1 (EFF-1), is cloned into pIRES2-AcGFP1 vector (Clontech), and this construct is then transfected into HeLa cells (CCL-2™, ATCC) using the Lipofectamine 2000 transfection reagent (Invitrogen). The fusogen binding partner gene, anchor-cell fusion failure 1 (AFF-1), is cloned into pIRES2 DsRed-Express 2 vector (Clontech), and this construct is then transfected into HeLa cells (CCL-2™, ATCC) using the Lipofectamine 2000 transfection reagent (Invitrogen). Transfected HeLa cells are kept at 37° C., 5% CO2 in Dulbecco's Modified Eagle Medium (DMEM) supplemented with GlutaMAX (GIBCO), 10% fetal calf serum (GIBCO) and 500 mg/mL zeocin. EFF-1 expressing cells are isolated by sorting fluorescent activated cell sorting (FACS) to get a pure population of GFP+ Hela cells expressing EFF-1 fusogen. AFF-1 expressing cells are isolated by sorting fluorescent activated cell sorting (FACS) to get a pure population of DSRED+ Hela cells expressing AFF-1 fusogen binding partner.

Example 4. Organelle Delivery Via Chemically Enhanced Fusogenic Enucleated Cells Fusogenic cells (Mito-DsRed donor enucleated cells and Mito-GFP recipient HeLa cells) produced and fused as described in Example 1 were imaged on a Zeiss LSM 780 inverted confocal microscope at 63× magnification 24 h following deposition in the imaging dish. Cells expressing only Mito-DsRed alone and Mito-GFP alone were imaged separately to configure acquisition settings in such a way as to ensure no signal overlap between the two channels in conditions where both Mito-DsRed and Mito-GFP were both present and acquired simultaneously. Ten regions of interest were chosen in a completely unbiased manner, with the only criteria being that a minimum of 10 cells be contained within each ROI, such that a minimum of 100 cells were available for downstream analysis. A given pixel in these images was determined to be positive for mitochondria if its intensity for either channel (mito-DsRed and mito-GFP) was greater than 10% of the maximum intensity value for each respective channel across all three ROIs.

Figure 7:
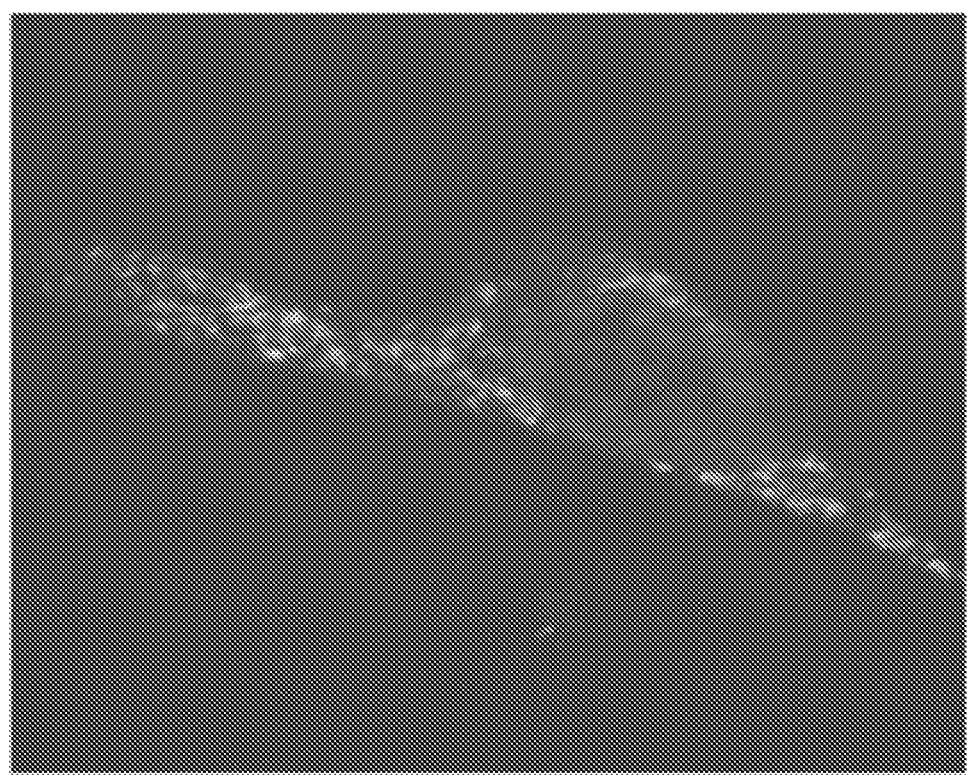
FIG. 7 is an image of a positive organelle delivery via fusion between donor and recipient HeLa cells. The intracellular areas indicated in white indicate overlap between donor and recipient mitochondria. The intracellular regions in grey indicate where donor and recipient organelles do not overlap.

Fusion events with organelle delivery were identified based on the criteria that >50% of the mitochondria (identified by all pixels that are either mito-GFP+ or mito-Ds-Red+) in a cell were positive for both mitoDs-Red and mito-GFP based on the above indicated threshold, indicating that organelles (in this case mitochondria) containing these proteins have been delivered, fused and their contents intermingled. At the 24-hour time point multiple cells exhibited positive organelle delivery via fusion as indicated in FIG. 7. This is the image of a positive organelle delivery via fusion between donor and recipient HeLa cells. The intracellular areas indicated in white indicate overlap between donor and recipient mitochondria. The intracellular regions in grey indicate where donor and recipient organelles do not overlap.

Example 5. Organelle Delivery Via Chemically Enhanced Fusogenic Nucleated Cells Fusogenic cells (Mito-DsRed donor cells and Mito-GFP recipient HeLa cells) produced and combined as described in example 2 were imaged on a Zeiss LSM 780 inverted confocal microscope at 63× magnification 24 h following deposition in the imaging dish. Cells expressing only Mito-DsRed alone and Mito-GFP alone were imaged separately to configure acquisition settings in such a way as to ensure no signal overlap between the two channels in conditions where both Mito-DsRed and Mito-GFP were both present and acquired simultaneously. Ten regions of interest were chosen in a completely unbiased manner, with the only criteria being that a minimum of 10 cells be contained within each ROI, such that a minimum of 100 cells were available for downstream analysis. A given pixel in these images was determined to be positive for mitochondria if it's intensity for either channel (mito-DsRed and mito-GFP) was greater than 20% of the maximum intensity value for each respective channel across all three ROIs.

Figure 8:
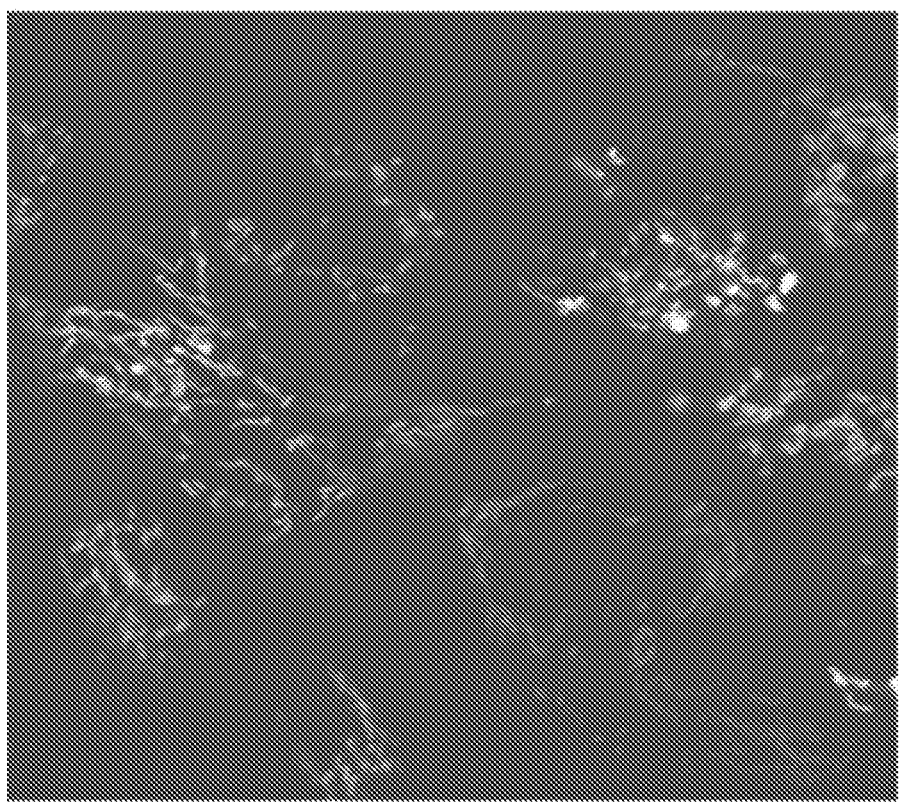
FIG. 8 is an image of a positive organelle delivery via fusion between donor and recipient HeLa cells. The intracellular areas indicated in white indicate overlap between donor and recipient mitochondria. The intracellular regions in grey indicate where donor and recipient organelles do not overlap.

Fusion events with organelle delivery were identified based on the criteria that >50% of the mitochondria (identified by all pixels that are either mito-GFP+ or mito-Ds-Red+) in a cell were positive for both mitoDs-Red and mito-GFP based on the above indicated threshold, indicating that organelles (in this case mitochondria) containing these proteins have been delivered, fused and their contents intermingled. At the 24-hour time point multiple cells exhibited positive organelle delivery via fusion as indicated in FIG. 8. This is the image of a positive organelle delivery via fusion between donor and recipient HeLa cells. The intracellular areas indicated in white indicate overlap between donor and recipient mitochondria. The intracellular regions in grey indicate where donor and recipient organelles do not overlap.

Example 6. Delivery of Mitochondria Via Protein Enhanced Fusogenic Enucleated Cells Fusogenic cells produced and combined as described in Example 3 are imaged on a Zeiss LSM 780 inverted confocal microscope at 63× magnification 24 h following deposition in the imaging dish. Cells expressing only Mito-DsRed alone and Mito-GFP alone are imaged separately to configure acquisition settings in such a way as to ensure no signal overlap between the two channels in conditions where both Mito-DsRed and Mito-GFP are both present and acquired simultaneously. Ten regions of interest are chosen in a completely unbiased manner, with the only criteria being that a minimum of 10 cells be contained within each ROI, such that a minimum number of cells are available for downstream analysis. A given pixel in these images is determined to be positive for mitochondria if it's intensity for either channel (mito-DsRed and mito-GFP) is greater than 10% of the maximum intensity value for each respective channel across all three ROIs.

Fusion events with organelle delivery will be identified based on the criteria that >50% of the mitochondria (identified by all pixels that are either mito-GFP+ or mito-Ds-Red+) in a cell are positive for both mitoDs-Red and mito-GFP based on the above indicated threshold, which will indicate that organelles (in this case mitochondria) containing these proteins are delivered, fused and their contents intermingled. At the 24-hour time point multiple cells are expected to exhibit positive organelle delivery via fusion.

Example 7: Generation of Fusosomes Through Nucleic Acid Electroporation

This example describes fusosome generation through electroporation of cells or vesicles with nucleic acids (e.g., mRNA or DNA) that encode a fusogen.

Transposase vectors (System Biosciences, Inc.) that include the open reading frame of the Puromycin resistance gene together with an open reading frame of a cloned fragment (e.g. Glycoprotein from Vesicular stomatitis virus [VSV-G], Oxford Genetics #OG592) are electroporated into 293 Ts using an electroporator (Amaxa) and a 293T cell line specific nuclear transfection kit (Lonza).

Following selection with 1 µg/gL puromycin for 3-5 days in DMEM containing 20% Fetal Bovine Serum and 1× Penicillin/Streptomycin, the cells are then washed with 1×PBS, ice-cold lysis buffer (150 mM NaCl, 0.1% Triton X-100, 0.5% sodium deoxycholate, 0.1% SDS, 50 mM Tris-HCl, pH 8.0 and protease inhibitor cocktail (Abcam, ab201117)), sonicated 3 times, 10-15 secs per time and centrifuged at 16,000×g for 20 min. A western blot is conducted on the recovered supernatant fraction with a probe specific to VSV-G to determine the non-membrane specific concentration of VSV-G from the fusosomes prepared from stably transfected cells or control cells and compared to the standard of VSV-G protein.

In embodiments, the fusosomes from stably transfected cells will have more VSV-G than fusosomes generated from cells that were not stably transfected.

Example 8: Generation of Fusosomes Through Protein Electroporation

This example describes electroporation of fusogens to generate fusosomes.

Approximately $5 \times 10^6$ cells or vesicles are used for electroporation using an electroporation transfection system (Thermo Fisher Scientific). To set up a master mix, 24 µg of purified protein fusogens is added to resuspension buffer (provided in the kit). The mixture is incubated at room temperature for 10 min. Meanwhile, the cells or vesicles are transferred to a sterile test tube and centrifuged at 500×g for 5 min. The supernatant is aspirated and the pellet is resuspended in 1 ml of PBS without $Ca^{2+}$ and $Mg^{2+}$. The buffer with the fusogens is then used to resuspend the pellet of cells or vesicles. A cell or vesicle suspension is also used for optimization conditions, which vary in pulse voltage, pulse width and the number of pulses. After electroporation, the electroporated cells or vesicles with fusogens are washed with PBS, resuspended in PBS, and kept on ice.

See, for example, Liang et al., Rapid and highly efficiency mammalian cell engineering via Cas9 protein transfection, *Journal of Biotechnology* 208: 44-53, 2015.

Example 9: Generating and Isolating Fusosomes Through Vesicle Formation and Centrifugation This example describes fusosome generation and isolation via vesiculation and centrifugation. This is one of the methods by which fusosomes may be isolated.

Fusosomes are prepared as follows. Approximately $4 \times 10^6$ HEK-293T cells are seeded in a 10 cm dish in complete media (DMEM+10% FBS+Pen/Strep). One day after seeding, 15 µg of fusogen expressing plasmid or virus is delivered to cells. After a sufficient period of time for fusogen expression, medium is carefully replaced by fresh medium supplemented with 100 µM ATP. Supernatants are harvested 48-72 hours after fusogen expression, clarified by filtration through a 0.45 gm filter, and ultracentrifuged at 150,000×g for 1 h. Pelleted material is resuspended overnight in ice cold PBS. Fusosomes are resuspended in desired buffer for experimentation.

See for example, Mangeot et al., Molecular Therapy, vol. 19 no. 9, 1656-1666, September 2011

Example 10: Generating and Isolating Giant Plasma Membrane Fusosomes

This example describes fusosome generation and isolation via vesiculation and centrifugation. This is one of the methods by which fusosomes may be isolated. Fusosomes are prepared as follows.

Briefly, HeLa cells that express a fusogen are washed twice in buffer (10 mM HEPES, 150 mM NaCl, 2 mM $CaCl_2$, pH 7.4), resuspended in a solution (1 mM DTT, 12.5 mM Paraformaldehyde, and 1 mM N-ethylmaleimide in GPMV buffer), and incubated at 37° C. for 1 h. Fusosomes are clarified from cells by first removing cells by centrifugation at 100×g for 10 minutes, and then harvesting fusosomes at 20,000×g for 1 h at 4° C. The fusosomes are resuspended in desired buffer for experimentation.

See for example, Sezgin E et al. Elucidating membrane structure and protein behavior using giant membrane plasma vesicles. *Nat. Protocols.* 7(6):1042-51 2012.

Example 11: Generating and Isolating Fusosome Ghosts

This example describes fusosome generation and isolation via hypotonic treatment and centrifugation. This is one of the methods by which fusosomes may be produced.

First, fusosomes are isolated from mesenchymal stem cells expressing fusogens ($10^9$ cells) primarily by using hypotonic treatment such that the cell ruptures and fusosomes are formed. According to a specific embodiment, cells are resuspended in hypotonic solution, Tris-magnesium buffer (TM, e.g., pH 7.4 or pH 8.6 at 4° C., pH adjustment made with HCl). Cell swelling is monitored by phase-contrast microscopy. Once the cells swell and fusosomes are formed, the suspension is placed in a homogenizer. Typically, about 95% cell rupture is sufficient as measured through cell counting and standard AOPI staining. The membranes/fusosomes are then placed in sucrose (0.25 M or higher) for preservation. Alternatively, fusosomes can be formed by other approaches known in the art to lyse cells, such as mild sonication (Arkhiv anatomii, gistologii i embriologii; 1979, August, 77(8) 5-13; PMID: 496657), freeze-thaw (Nature. 1999, Dec. 2; 402(6761):551-5; PMID: 10591218), French-press (Methods in Enzymology, Volume 541, 2014, Pages 169-176; PMID: 24423265), needle-passaging (www.sigmaaldrich.com/technical-documents/protocols/biology/nuclear-protein-extraction.html) or solublization in detergent-containing solutions (www.thermofisher.com/order/catalog/product/89900).

To avoid adherence, the fusosomes are placed in plastic tubes and centrifuged. A laminated pellet is produced in which the topmost lighter gray lamina includes mostly fusosomes. However, the entire pellet is processed, to increase yields. Centrifugation (e.g., 3,000 rpm for 15 min at 4° C.) and washing (e.g., 20 volumes of Tris magnesium/TM-sucrose pH 7.4) may be repeated.

In the next step, the fusosome fraction is separated by floatation in a discontinuous sucrose density gradient. A small excess of supernatant is left remaining with the washed pellet, which now includes fusosomes, nuclei, and incompletely ruptured whole cells. An additional 60% w/w sucrose in TM, pH 8.6, is added to the suspension to give a reading of 45% sucrose on a refractometer. After this step, all solutions are TM pH 8.6. 15 ml of suspension are placed in SW-25.2 cellulose nitrate tubes and a discontinuous gradient is formed over the suspension by adding 15 ml layers, respectively, of 40% and 35% w/w sucrose, and then adding 5 ml of TM-sucrose (0.25 M). The samples are then centrifuged at 20,000 rpm for 10 min, 4° C. The nuclei sediment form a pellet, the incompletely ruptured whole cells are collected at the 40%-45% interface, and the fusosomes are collected at the 35%-40% interface. The fusosomes from multiple tubes are collected and pooled.

See for example, International patent publication, WO2011024172A2.

Example 12: Generating Fusosomes Through Extrusion

This example describes fusosome manufacturing by extrusion through a membrane.

Briefly, hematopoietic stem cells that express fusogens are in a 37° C. suspension at a density of $1\times10^6$ cells/mL in serum-free media containing protease inhibitor cocktail (Set V, Calbiochem 539137-1 ML). The cells are aspirated with a luer lock syringe and passed once through a disposable 5 mm syringe filter into a clean tube. If the membrane fouls and becomes clogged, it is set aside and a new filter is attached. After the entire cell suspension has passed through the filter, 5 mL of serum-free media is passed through all filters used in the process to wash any remaining material through the filter(s). The solution is then combined with the extruded fusosomes in the filtrate.

Fusosomes may be further reduced in size by continued extrusion following the same method with increasingly smaller filter pore sizes, ranging from 5 mm to 0.2 mm. When the final extrusion is complete, suspensions are pelleted by centrifugation (time and speed required vary by size) and resuspended in media.

Additionally, this process can be supplemented with the use of an actin cytoskeleton inhibitor in order to decrease the influence of the existing cytoskeletal structure on extrusion. Briefly, a $1\times10^6$ cell/mL suspension is incubated in serum-free media with 500 nM Latrunculin B (ab144291, Abcam, Cambridge, Mass.) and incubated for 30 minutes at 37° C. in the presence of 5% $CO_2$. After incubation, protease inhibitor cocktail is added and cells are aspirated into a luer lock syringe, with the extrusion carried out as previously described.

Fusosomes are pelleted and washed once in PBS to remove the cytoskeleton inhibitor before being resuspended in media.

Example 13: Generation of Fusosomes Through Chemical Treatment with Protein

This example describes chemical-mediated delivery of fusogens to generate fusosomes. Approximately $5\times10^6$ cells or vesicles are used for chemical-mediated delivery of fusogens. The cells or vesicles are suspended in 50 µl of Opti-MEM medium. To set up a master mix, 24 µg of purified protein fusogens is mixed with 25 µl of Opti-MEM medium, followed by the addition of 25 µl of Opti-MEM containing 2 µl of lipid transfection reagent 3000. The cells or vesicles and fusogen solutions are mixed by gently swirling the plate and incubating at 37 C for 6 hours, such that the fusogen will be incorporated into the cell or vesicle membrane. Fusosomes are then washed with PBS, resuspended in PBS, and kept on ice.

See, also, Liang et al., Rapid and highly efficiency mammalian cell engineering via Cas9 protein transfection, *Journal of Biotechnology* 208: 44-53, 2015.

Example 14: Generation of Fusosomes Through Treatment with Fusogen-Containing Liposomes This example describes liposome-mediated delivery of fusogens to a source cell to generate fusosomes. Approximately $5\times10^6$ cells or vesicles are used for liposome-mediated delivery of fusogens. The cells or vesicles are suspended in 50 µl of Opti-MEM medium. The fusogen protein is purified from cells in the presence of n-octyl b-D-glucopyranoside. n-octyl b-D-glucopyranoside is a mild detergent used to solubilize integral membrane proteins. The fusogen protein is then reconstituted into large (400 nm diameter) unilamellar vesicles (LUVs) by mixing n-octyl b-D-glucopyranoside-suspended protein with LUVs pre-saturated with n-octyl b-D-glucopyranoside, followed by removal of n-octyl b-D-glucopyranoside, as described in Top et al., *EMBO* 24: 2980-2988, 2005. To set up a master mix, a mass of liposomes that contains 24 µg of total fusogen protein is mixed with 50 µl of Opti-MEM medium. The solutions of liposomes and source cells or vesicles are then combined, and the entire solution is mixed by gently swirling the plate and incubating at 37 C for 6 hours under conditions that allow fusion of the fusogen-containing liposomes and the source cells or vesicle, such that the fusogen protein will be incorporated into the source cell or vesicle membrane. Fusosomes are then washed with PBS, resuspended in PBS, and kept on ice.

See, also, Liang et al., Rapid and highly efficiency mammalian cell engineering via Cas9 protein transfection, *Journal of Biotechnology* 208: 44-53, 2015.

Example 15: Isolating Fusogenic Microvesicles Freely Released from Cells

This example describes isolation of fusosomes via centrifugation. This is one of the methods by which fusosomes may be isolated.

Fusosomes are isolated from cells expressing fusogens by differential centrifugation. Culture media (DMEM+10% fetal bovine serum) is first clarified of small particles by ultracentrifugation at >100,000×g for 1 h. Clarified culture media is then used to grow Mouse Embryonic Fibroblasts expressing fusogens. The cells are separated from culture media by centrifugation at 200×g for 10 minutes. Supernatants are collected and centrifuged sequentially twice at 500×g for 10 minutes, once at 2,000×g for 15 minutes, once at 10,000×g for 30 min, and once at 70,000×g for 60 minutes. Freely released fusosomes are pelleted during the final centrifugation step, resuspended in PBS and repelleted at 70,000×g. The final pellet is resuspended in PBS.

See also, Wubbolts R et al. Proteomic and Biochemical Analyses of Human B Cell-derived Exosomes: Potential Implications for their Function and Multivesicular Body Formation. *J. Biol. Chem.* 278:10963-10972 2003.

Example 16: Physical Enucleation of Fusosomes

This example describes enucleation of fusosomes via cytoskeletal inactivation and centrifugation. This is one of the methods by which fusosomes may be modified.

Fusosomes are isolated from mammalian primary or immortalized cell lines that express a fusogen. The cells are enucleated by treatment with an actin skeleton inhibitor and ultracentrifugation. Briefly, C2Cl2 cells are collected, pelleted, and resuspended in DMEM containing 12.5% Ficoll 400 (F2637, Sigma, St. Louis Mo.) and 500 nM Latrunculin B (ab144291, Abcam, Cambridge, Mass.) and incubated for 30 minutes at 37° C.+5% $CO_2$. Suspensions are carefully layered into ultracentrifuge tubes containing increasing concentrations of Ficoll 400 dissolved in DMEM (15%, 16%, 17%, 18%, 19%, 20%, 3 mL per layer) that have been equilibrated overnight at 37° C. in the presence of 5% $CO_2$. Ficoll gradients are spun in a Ti-70 rotor (Beckman-Coulter, Brea, Calif.) at 32,300 RPM for 60 minutes at 37 C. After ultracentrifugation, fusosomes found between 16-18% Ficoll are removed, washed with DMEM, and resuspended in DMEM.

Staining for nuclear content with Hoechst 33342 as described in Example 35 followed by the use of flow cytometry and/or imaging will be performed to confirm the ejection of the nucleus.

Example 17: Modifying Fusosomes Via Irradiation

The following example describes modifying fusosomes with gamma irradiation. Without being bound by theory, gamma irradiation may cause double stranded breaks in the DNA and drive cells to undergo apoptosis.

First, cells expressing fusogens are cultured in a monolayer on tissue culture flasks or plates below a confluent density (e.g. by culturing or plating cells). Then the medium is removed from confluent flasks, cells are rinsed with Ca2+ and Mg2+ free HBSS, and trypsinized to remove the cells from the culture matrix. The cell pellet is then resuspended in 10 ml of tissue-culture medium without penicillin/streptomycin and transferred to a 100-mm Petri dish. The number of cells in the pellet should be equivalent to what would be obtained from 10-15 confluent MEF cultures on 150 $cm^2$ flasks. The cells are then exposed to 4000 rads from a γ-radiation source to generate fusosomes. The fusosomes are then washed and resuspended in the final buffer or media to be used.

Example 18: Modifying Fusosomes Via Chemical Treatment

The following example describes modifying fusosomes with mitomycin C treatment. Without being bound by any particular theory, mitomycin C treatment modifies fusosomes by inactivating the cell cycle.

First, cells expressing fusogens are cultured from a monolayer in tissue culture flasks or plates at a confluent density (e.g. by culturing or plating cells). One mg/ml mitomycin C stock solution is added to the medium to a final concentration of 10 μg/ml. The plates are then returned to the incubator for 2 to 3 hours. Then the medium is removed from confluent flasks, cells are rinsed with Ca2+ and Mg2+ free HBSS, and trypsinized to remove the cells from the culture matrix. The cells are then washed and resuspended in the final buffer or media to be used.

See for example, Mouse Embryo Fibroblast (MEF) Feeder Cell Preparation, Current Protocols in Molecular Biology. David A. Conner 2001.

Example 19: Lack of Transcriptional Activity Infusosomes

This Example quantifies transcriptional activity in fusosomes compared to parent cells, e.g., source cells, used for fusosome generation. In an embodiment, transcriptional activity will be low or absent in fusosomes compared to the parent cells, e.g., source cells.

Fusosomes are a chassis for the delivery of therapeutic agent. Therapeutic agents, such as miRNA, mRNAs, proteins and/or organelles that can be delivered to cells or local tissue environments with high efficiency could be used to modulate pathways that are not normally active or active at pathological low or high levels in recipient tissue. In an embodiment, the observation that fusosomes are not capable of transcription, or that fusosomes have transcriptional activity of less than their parent cell, will demonstrate that removal of nuclear material has sufficiently occurred.

Fusosomes are prepared by any one of the methods described in previous Examples. A sufficient number of fusosomes and parent cells used to generate the fusosomes are then plated into a 6 well low-attachment multiwell plate in DMEM containing 20% Fetal Bovine Serum, 1× Penicillin/Streptomycin and the fluorescent-taggable alkyne-nucleoside EU for 1 hr at 37° C. and 5% CO2. For negative controls, a sufficient number of fusosomes and parent cells are also plated in multiwell plate in DMEM containing 20% Fetal Bovine Serum, 1× Penicillin/Streptomycin but with no alkyne-nucleoside EU.

After the 1 hour incubation the samples are processed following the manufacturer's instructions for an imaging kit (ThermoFisher Scientific). The cell and fusosome samples including the negative controls are washed thrice with 1×PBS buffer and resuspended in 1×PBS buffer and analyzed by flow cytometry (Becton Dickinson, San Jose, Calif., USA) using a 488 nm argon laser for excitation, and the 530+/−30 nm emission. BD FACSDiva software was used for acquisition and analysis. The light scatter channels are set on linear gains, and the fluorescence channels on a logarithmic scale, with a minimum of 10,000 cells analyzed in each condition.

In an embodiment, transcriptional activity as measured by 530+/−30 nm emission in the negative controls will be null due to the omission of the alkyne-nucleoside EU. In some embodiments, the fusosomes will have less than about 70%, 60%, 50%, 40%, 30%, 20%, 10%, 5%, 4%, 3%, 2%, 1% or less transcriptional activity than the parental cells.

See also, Proc Natl Acad Sci USA, 2008, Oct. 14; 105(41):15779-84. doi: 10.1073/pnas.0808480105. Epub 2008 Oct. 7.

Example 20: Lack of DNA Replication or Replication Activity

This Example quantifies DNA replication in fusosomes. In an embodiment, fusosomes will replicate DNA at a low rate compared to cells.

Fusosomes are prepared by any one of the methods described in previous Examples. Fusosome and parental cell DNA replication activity is assessed by incorporation of a fluorescent-taggable nucleotide (ThermoFisher Scientific #C10632). Fusosomes and an equivalent number of cells are incubated with EdU at a final concentration of 10 uM for 2 hr, after preparation of an EdU stock solution with in dimethylsulfoxide. The samples are then fixed for 15 min using 3.7% PFA, washed with 1×PBS buffer, pH 7.4 and permeabilized for 15 min in 0.5% detergent solution in 1×PBS buffer, pH 7.4.

After permeabilization, fusosomes and cells in suspension in PBS buffer containing 0.5% detergent are washed with 1×PBS buffer, pH 7.4 and incubated for 30 min at 21° C. in reaction cocktail, 1×PBS buffer, CuSO4 (Component F), azide-fluor 488, 1× reaction buffer additive.

A negative control for fusosome and cell DNA replication activity is made with samples treated the same as above but with no azide-fluor 488 in the 1× reaction cocktail.

The cell and fusosome samples are then washed and resuspended in 1×PBS buffer and analyzed by flow cytometry. Flow cytometry is done with a FACS cytometer (Becton Dickinson, San Jose, Calif., USA) with 488 nm argon laser excitation, and a 530+/−30 nm emission spectrum is collected. FACS analysis software is used for acquisition and analysis. The light scatter channels are set on linear gains, and the fluorescence channels on a logarithmic scale, with a minimum of 10,000 cells analyzed in each condition. The relative DNA replication activity is calculated based on the median intensity of azide-fluor 488 in each sample. All events are captured in the forward and side scatter channels (alternatively, a gate can be applied to select only the fusosome population). The normalized fluorescence intensity value for the fusosomes is determined by subtracting from the median fluorescence intensity value of the fusosome the median fluorescence intensity value of the respective negative control sample. Then the normalized relative DNA replication activity for the fusosomes samples is normalized to the respective nucleated cell samples in order to generate quantitative measurements for DNA replication activity.

In an embodiment, fusosomes have less DNA replication activity than parental cells. See, also, Salic, 2415-2420, doi: 10.1073/pnas.0712168105.

Example 21: Electroporation to Modify Fusosome with Nucleic Acid Cargo

This example describes electroporation of fusosomes with nucleic acid cargo.

Fusosomes are prepared by any one of the methods described in a previous Example. Approximately $10^9$ fusosomes and 1 µg of nucleic acids, e.g., RNA, are mixed in electroporation buffer (1.15 mM potassium phosphate pH 7.2, 25 mM potassium chloride, 60% iodixanol w/v in water). The fusosomes are electroporated using a single 4 mm cuvette using an electroporation system (BioRad, 165-2081). The fusosomes and nucleic acids are electroporated at 400 V, 125 gF and ∞ ohms, and the cuvette is immediately transferred to ice. After electroporation, fusosomes are washed with PBS, resuspended in PBS, and kept on ice.

See, for example, Kamerkar et al., Exosomes facilitate therapeutic targeting of oncogenic KRAS in pancreatic cancer, Nature, 2017

Example 22: Electroporation to Modify Fusosome with Protein Cargo

This example describes electroporation of fusosomes with protein cargo.

Fusosomes are prepared by any one of the methods described in a previous Example. Approximately $5\times10^6$ fusosomes are used for electroporation using an electroporation transfection system (Thermo Fisher Scientific). To set up a master mix, 24 µg of purified protein cargo is added to resuspension buffer (provided in the kit). The mixture is incubated at room temperature for 10 min. Meanwhile, fusosomes are transferred to a sterile test tube and centrifuged at 500×g for 5 min. The supernatant is aspirated and the pellet is resuspended in 1 ml of PBS without $Ca^{2+}$ and $Mg^{2+}$. The buffer with the protein cargo is then used to resuspend the pellet of fusosomes. A fusosome suspension is then used for optimization conditions, which vary in pulse voltage, pulse width and the number of pulses. After electroporation, fusosomes are washed with PBS, resuspended in PBS, and kept on ice.

See, for example, Liang et al., Rapid and highly efficiency mammalian cell engineering via Cas9 protein transfection, *Journal of Biotechnology* 208: 44-53, 2015.

Example 23: Chemical Treatment of Fusosomes to Modify with Nucleic Acid Cargo This example describes loading of nucleic acid cargo into a fusosome via chemical treatments.

Fusosomes are prepared by any one of the methods described in previous Examples. Approximately $10^6$ fusosomes are pelleted by centrifugation at 10,000 g for 5 min at 4 C. The pelleted fusosomes are then resuspended in TE buffer (10 mM Tris-HCl (pH 8.0), 0.1 mM EDTA) with 20 g DNA. The fusosome:DNA solution is treated with a mild detergent to increase DNA permeability across the fusosome membrane (Reagent B, Cosmo Bio Co., LTD, Cat #ISK-GN-001-EX). The solution is centrifuged again and the pellet is resuspended in buffer with a positively-charged peptide, such as protamine sulfate, to increase affinity between the DNA loaded fusosomes and the target recipient cells (Reagent C, Cosmo Bio Co., LTD, Cat #ISK-GN-001-EX). After DNA loading, the loaded fusosomes are kept on ice before use.

See, also, Kaneda, Y., et al., New vector innovation for drug delivery: development of fusigenic non-viral particles. *Curr. Drug Targets,* 2003

Example 24: Chemical Treatment of Fusosomes to Modify with Protein Cargo

This example describes loading of protein cargo into a fusosome via chemical treatments.

Fusosomes are prepared by any one of the methods described in previous Examples. Approximately $10^6$ fusosomes are pelleted by centrifugation at 10,000 g for 5 min at 4 C. The pelleted fusosomes are then resuspended in buffer with positively-charged peptides, such as protamine sulfate, to increase the affinity between the fusosomes and the cargo proteins (Reagent A, Cosmo Bio Co., LTD, Cat #ISK-GN-001-EX). Next 10 g of cargo protein is added to the fusosome solution followed by addition of a mild detergent to increase protein permeability across the fusosome membrane (Reagent B, Cosmo Bio Co., LTD, Cat #ISK-GN-001-EX). The solution is centrifuged again and the pellet is resuspended in buffer with the positively-charged peptide, such as protamine sulfate, to increase affinity between the protein loaded fusosomes and the target recipient cells (Reagent C, Cosmo Bio Co., LTD, Cat #ISK-GN-001-EX). After protein loading, the loaded fusosomes are kept on ice before use.

See, also, Yasouka, E., et al., Needleless intranasal administration of HVJ-E containing allergen attenuates experimental allergic rhinitis. *J. Mol. Med.,* 2007

Example 25: Transfection of Fusosomes to Modify with Nucleic Acid Cargo

This example describes transfection of nucleic acid cargo (e.g., a DNA or mRNA) into a fusosome. Fusosomes are prepared by any one of the methods described in previous Examples.

$5 \times 10^6$ fusosomes are maintained in Opti-Mem. 0.5 µg of nucleic acid is mixed with 25 µl of Opti-MEM medium, followed by the addition of 25 µl of Opti-MEM containing 2 µl of lipid transfection reagent 2000. The mixture of nucleic acids, Opti-MEM, and lipid transfection reagent is maintained at room temperature for 15 minutes, then is added to the fusosomes. The entire solution is mixed by gently swirling the plate and incubating at 37 C for 6 hours. Fusosomes are then washed with PBS, resuspended in PBS, and kept on ice.

See, also, Liang et al., Rapid and highly efficiency mammalian cell engineering via Cas9 protein transfection, *Journal of Biotechnology* 208: 44-53, 2015.

Example 26: Transfection of Fusosomes to Modify with Protein Cargo

This example describes transfection of protein cargo into a fusosome.

Fusosomes are prepared by any one of the methods described in previous Examples. $5 \times 10^6$ fusosomes are maintained in Opti-Mem. 0.5 µg of purified protein is mixed with 25 µl of Opti-MEM medium, followed by the addition of 25 µl of Opti-MEM containing 2 µl of lipid transfection reagent 3000. The mixture of protein, Opti-MEM, and lipid transfection reagent is maintained at room temperature for 15 minutes, then is added to the fusosomes. The entire solution is mixed by gently swirling the plate and incubating at 37 C for 6 hours. Fusosomes are then washed with PBS, resuspended in PBS, and kept on ice.

See, also, Liang et al., Rapid and highly efficiency mammalian cell engineering via Cas9 protein transfection, Journal of Biotechnology 208: 44-53, 2015.

Example 27: Fusosomes with Lipid Bilayer Structure

This example describes the composition of fusosomes. In an embodiment, a fusosome composition will comprise a lipid bilayer structure, with a lumen in the center.

Without wishing to be bound by theory, the lipid bilayer structure of a fusosome promotes fusion with a target cell, and allows fusosomes to load different therapeutics.

Fusosomes are freshly prepared using the methods described in the previous Examples. The positive control is the native cell line (HEK293), and the negative control is cold DPBS and membrane-disrupted HEK293 cell prep, which has been passed through 36 gauge needles for 50 times.

Samples are spin down in Eppendorf tube, and the supernatant is carefully removed. Then a pre-warmed fixative solution (2.5% glutaraldehyde in 0.05 M cacodylate buffer with 0.1M NaCl, pH 7.5; keep at 37° C. for 30 min before use) is added to the sample pellet and kept at room temperature for 20 minutes. The samples are washed twice with PBS after fixation. Osmium tetroxide solution is added to the sample pellet and incubated 30 minutes. After rinsing once with PBS, 30%, 50%, 70% and 90% hexylene glycol is added and washed with swirling, 15 minutes each. Then 100% hexylene glycol is added with swirling, 3 times, 10 minutes each.

Resin is combined with hexylene glycol at 1:2 ratio, and then added to the samples and incubated at room temperature for 2 hours. After incubation, the solution is replaced with 100% resin and incubated for 4-6 hours. This step is repeated one more time with fresh 100% resin. Then it is replaced with 100% fresh resin, the level is adjusted to ~1-2 mm in depth, and baked for 8-12 hours. The Eppendorf tube is cut and pieces of epoxy cast with the sample is baked for an additional 16-24 hours. The epoxy cast is then cut into small pieces making note of the side with the cells. Pieces are glued to blocks for sectioning, using commercial 5-minute epoxy glue. A transmission electron microscope (JOEL, USA) is used to image the samples at a voltage of 80 kV.

In an embodiment, the fusosomes will show a lipid bilayer structure similar to the positive control (HEK293 cells), and no obvious structure is observed in the DPBS control. In an embodiment no lumenal structures will be observed in the disrupted cell preparation.

Example 28: Detecting Fusogen Expression

This example quantifies fusogen expression in fusosomes.

Transposase vectors (System Biosciences, Inc.) that include the open reading frame of the Puromycin resistance gene together with an open reading frame of a cloned fragment (e.g. Glycoprotein from Vesicular stomatitis virus [VSV-G], Oxford Genetics #OG592) are electroporated into 293 Ts using an electroporator (Amaxa) and a 293T cell line specific nuclear transfection kit (Lonza).

Following selection with 1 µg/L puromycin for 3-5 days in DMEM containing 20% Fetal Bovine Serum and 1× Penicillin/Streptomycin, fusosomes are prepared from the stably expressing cell line or from control cells by any one of the methods described in previous Examples.

The fusosomes are then washed with 1×PBS, ice-cold lysis buffer (150 mM NaCl, 0.1% Triton X-100, 0.5% sodium deoxycholate, 0.1% SDS, 50 mM Tris-HCl, pH 8.0 and Protease Inhibitor Cocktail III (Abcam, ab201117)), sonicated 3 times, 10-15 seconds each time and centrifuged at 16,000×g for 20 min. A western blot is conducted on the recovered supernatant fraction with a probe specific to VSV-G to determine the non-membrane specific concentration of VSV-G from the fusosomes prepared from stably transfected cells or control cells and compared to the standard of VSV-G protein.

In an embodiment, the fusosomes from stably transfected cells will have more VSV-G than fusosomes generated from cells that were not stably transfected.

Example 29: Quantification of Fusogens

This example describes quantification of the absolute number of fusogens per fusosome.

A fusosome composition is produced by any one of the methods described in the previous Examples, except the fusosome is engineered as described in a previous Example to express a fusogen (VSV-G) tagged with GFP. In addition, a negative control fusosome is engineered with no fusogen (VSV-G) or GFP present.

The fusosomes with the GFP-tagged fusogen and the negative control(s) are then assayed for the absolute number of fusogens as follows. Commercially acquired recombinant GFP is serially diluted to generate a calibration curve of protein concentration. The GFP fluorescence of the calibration curve and a sample of fusosomes of known quantity is then measured in a fluorimeter using a GFP light cube (469/35 excitation filter and a 525/39 emission filter) to calculate the average molar concentration of GFP molecules in the fusosome preparation. The molar concentration is then converted to the number of GFP molecules and divided by the number of fusosomes per sample to achieve an average number of GFP-tagged fusogen molecules per fusosome and thus provides a relative estimate of the number of fusogens per fusosome.

In an embodiment, GFP fluorescence will be higher in the fusosomes with GFP tag as compared to the negative controls, where no fusogen or GFP is present. In an embodiment, GFP fluorescence is relative to the number of fusogen molecules present.

Alternatively, individual fusosomes are isolated using a single cell prep system (Fluidigm) per manufacturer's instructions, and qRT-PCR is performed using a commercially available probeset (Taqman) and master mix designed to quantify fusogen or GFP cDNA levels based upon the $C_t$ value. A RNA standard of the same sequence as the cloned fragment of the fusogen gene or the GFP gene is generated by synthesis (Amsbio) and then added to single cell prep system qRT-PCR experimental reaction in serial dilutions to establish a standard curve of $C_t$ vs concentration of fusogen or GFP RNA.

The $C_t$ value from fusosomes is compared to the standard curve to determine the amount of fusogen or GFP RNA per fusosome.

In an embodiment, fusogen and GFP RNA will be higher in the fusosomes with engineered to express the fusogens as compared to the negative controls, where no fusogen or GFP is present.

Fusogens may further be quantified in the lipid bilayer by analyzing the lipid bilayer structure as previously described and quantifying fusogens in the lipid bilayer by LC-MS as described in other Examples herein.

Example 30: Measuring the Average Size of Fusosomes

This Example describes measurement of the average size of fusosomes.

Fusosomes are prepared by any one of the methods described in previous Examples. The fusosomes measured to determine the average size using commercially available systems (iZON Science). The system is used with software according to manufacturer's instructions and a nanopore designed to analyze particles within the 40 nm to 10 m size range. Fusosomes and parental cells are resuspended in phosphate-buffered saline (PBS) to a final concentration range of 0.01-0.1 µg protein/mL. Other instrument settings are adjusted as indicated in the following table:

TABLE 6

| Fusosome measurement parameters and settings | |
|---|---|
| Measurement Parameter | Setting |
| Pressure | 6 |
| Nanopore type | NP300 |
| Calibration sample | CPC400_6P |
| Gold standard analysis | no |
| Capture assistant | none |

All fusosomes are analyzed within 2 hours of isolation. In an embodiment, the fusosomes will have a size within about 1%, 2%, 3%, 4%, 5%, 10%, 20%, 30%, 40%, 50%, 60%, 70%, 80%, 90%, or greater than the parental cells.

Example 31: Measuring the Average Size Distribution of Fusosomes

This Example describes measurement of the size distribution of fusosomes.

Fusosomes are generated by any one of the methods described in previous Examples, and are tested to determine the average size of particles using a commercially available system, such as described in a previous Example. In an embodiment, size thresholds for 10%, 50%, and 90% of the fusosomes centered around the median are compared to parental cells to assess fusosome size distribution.

In an embodiment, the fusosomes will have less than about 90%, 80%, 70%, 60%, 50%, 40%, 30%, 20%, 10%, 5%, or less of the parental cell's variability in size distribution within 10%, 50%, or 90% of the sample.

Example 32: Average Volume of Fusosomes

This example describes measurement of the average volume of fusosomes. Without wishing to be bound by theory, varying the size (e.g., volume) of fusosomes can make them versatile for distinct cargo loading, therapeutic design or application.

Fusosomes are prepared as described in previous Examples. The positive control is HEK293 cells or polystyrene beads with a known size. The negative control is HEK293 cells that are passed through a 36 gauge needle approximately 50 times.

Analysis with a transmission electron microscope, as described in a previous Example, is used to determine the size of the fusosomes. The diameter of the fusosome is measured and volume is then calculated.

In an embodiment, fusosomes will have an average size of approximately 50 nm or greater in diameter.

Example 33: Average Density of Fusosomes

Fusosome density is measured via a continuous sucrose gradient centrifugation assay as described in Théry et al., Curr Protoc Cell Biol. 2006 April; Chapter 3:Unit 3.22. Fusosomes are obtained as described in previous Examples.

First, a sucrose gradient is prepared. A 2 M and a 0.25 sucrose solution are generated by mixing 4 ml HEPES/ sucrose stock solution and 1 ml HEPES stock solution or 0.5 ml HEPES/sucrose stock solution and 4.5 ml HEPES stock solution, respectively. These two fractions are loaded into the gradient maker with all shutters closed, the 2 M sucrose solution in the proximal compartment with a magnetic stir bar, and the 0.25 M sucrose solution in the distal compartment. The gradient maker is placed on a magnetic stir plate, the shutter between proximal and distal compartments is opened and the magnetic stir plate is turned on. HEPES stock solution is made as follows: 2.4 g N-2-hydroxyethylpiperazine-N'-2-ethanesulfonic acid (HEPES; 20 mMfinal), 300 H2O, adjust pH to 7.4 with 10 N NaOH and finally adjust volume to 500 ml with H2O. HEPES/sucrose stock solution is made as follows: 2.4 g hydroxyethylpiperazine-N'-2-ethanesulfonic acid (HEPES; 20 mM final), 428 g protease-free sucrose (ICN; 2.5 M final), 150 ml H2O, adjust pH to 7.4 with 10 N NaOH and finally adjust volume to 500 ml with H2O.

The fusosomes are resuspended in 2 ml of HEPES/sucrose stock solution and are poured on the bottom of an SW 41 centrifuge tube. The outer tubing is placed in the SW 41 tube, just above the 2 ml of fusosomes. The outer shutter is opened, and a continuous 2 M (bottom) to 0.25 M (top) sucrose gradient is slowly poured on top of the fusosomes. The SW 41 tube is lowered as the gradient is poured, so that the tubing is always slightly above the top of the liquid.

All tubes with gradients are balanced with each other, or with other tubes having the same weight of sucrose solutions. The gradients are centrifuged overnight (>14 hr) at 210,000×g, 4° C., in the SW 41 swinging-bucket rotor with the brake set on low.

With a micropipettor, eleven 1-ml fractions, from top to bottom, are collected and placed in a 3-ml tube for the TLA-100.3 rotor. The samples are set aside and, in separate wells of a 96-well plate, 50 µl of each fraction is used to measure the refractive index. The plate is covered with adhesive foil to prevent evaporation and stored for no more than 1 hour at room temperature. A refractometer is used to measure the refractive index (hence the sucrose concentration, and the density) of 10 to 20 µl of each fraction from the material saved in the 96-well plate.

A table for converting the refractive index into g/ml is available in the ultracentrifugation catalog downloadable from the Beckman website.

Each fraction is then prepared for protein content analysis. Two milliliters of 20 mM HEPES, pH 7.4, is added to each 1-ml gradient fraction, and mixed by pipetting up and down two to three times. One side of each tube is marked with a permanent marker, and the tubes are placed marked side up in a TLA-100.3 rotor.

The 3 ml-tubes with diluted fractions are centrifuged for 1 hr at 110,000×g, 4° C. The TLA-100.3 rotor holds six tubes, so two centrifugations for each gradient is performed with the other tubes kept at 4° C. until they can be centrifuged.

The supernatant is aspirated from each of the 3-ml tubes, leaving a drop on top of the pellet. The pellet most probably is not visible, but its location can be inferred from the mark on the tube. The invisible pellet is resuspended and transferred to microcentrifuge tubes. Half of each resuspended fraction is used for protein contentment analysis by bicinchoninic acid assay, described in another Example. This provides a distribution across the various gradient fractions of the fusosome preparation. This distribution is used to determine the average density of the fusosomes. The second half volume fraction is stored at −80° C. and used for other purposes (e.g. functional analysis, or further purification by immunoisolation) once protein analysis has revealed the fusosome distribution across fractions.

In an embodiment, using this assay, the average density of the fusosomes will be 1.25 g/ml+/−0.05 standard deviation.

In an embodiment, the average density of the fusosomes will be in the range of 1-1.1, 1.05-1.15, 1.1-1.2, 1.15-1.25, 1.2-1.3, or 1.25-1.35. In an embodiment, the average density of the fusosomes will be less than 1 or more than 1.35.

Example 34: Measuring Organelle Content in Fusosomes

This Example describes detection of organelles in fusosomes.

Fusosomes were prepared as described herein. For detection of endoplasmic reticulum (ER) and mitochondria, fusosomes or C2Cl2 cells were stained with 1 µM ER stain (E34251, Thermo Fisher, Waltham, Mass.) and 1 µM mitochondria stain (M22426, Thermo Fisher Waltham, Mass.). For detection of lysosomes, fusosomes or cells were stained with 50 nM lysosome stain (L7526, Thermo Fisher, Waltham, Mass.).

Stained fusosomes were run on a flow cytometer (Thermo Fisher, Waltham, Mass.) and fluorescence intensity was measured for each dye according to the table below. Validation for the presence of organelles was made by comparing fluorescence intensity of stained fusosomes to unstained fusosomes (negative control) and stained cells (positive control).

Figure 2:
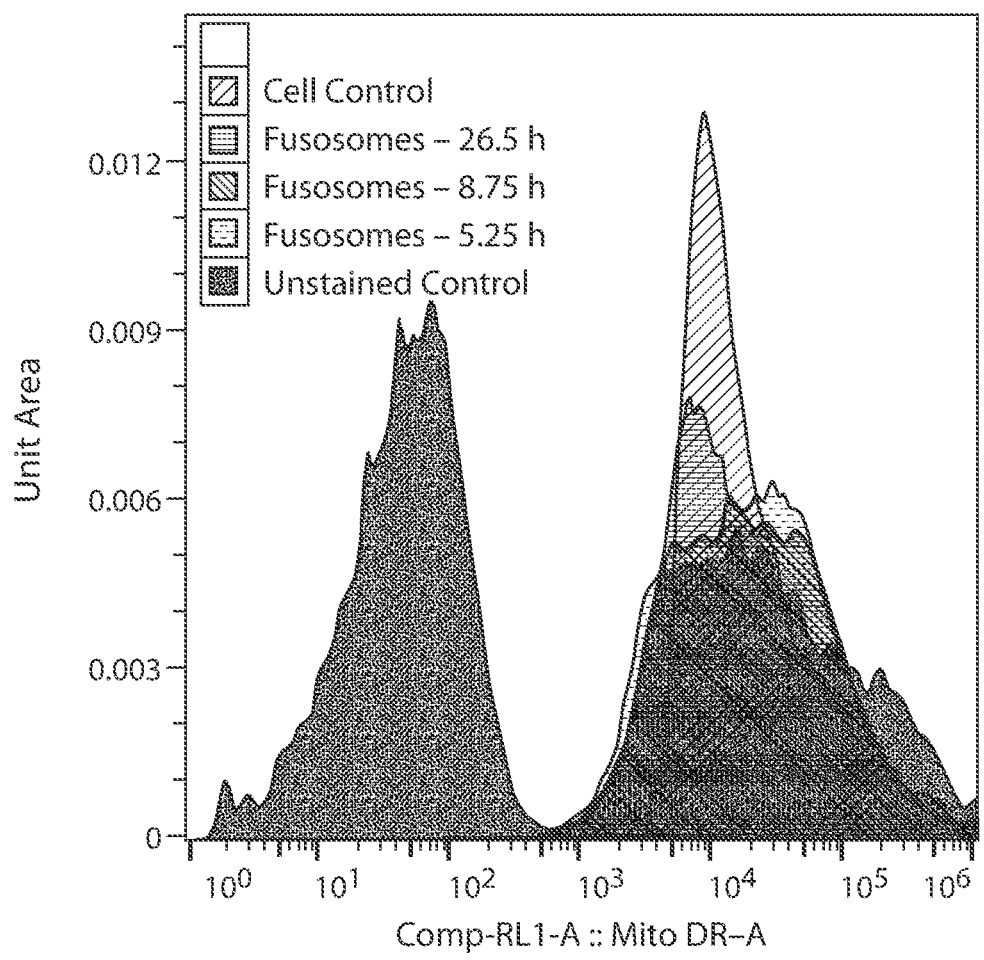
FIG. 2 quantifies staining of fusosomes with a dye for mitochondria.
Figure 3:
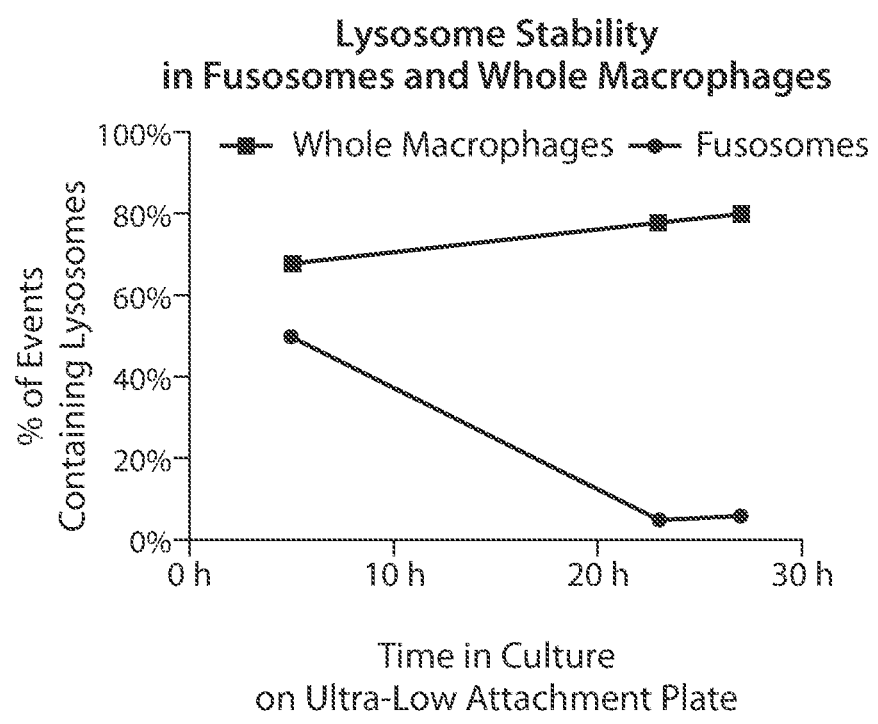
FIG. 3 quantifies staining of fusosomes with a dye for lysosomes.

Fusosomes stained positive for endoplasmic reticulum (FIG. 1), mitochondria (FIG. 2), and lysosomes (FIG. 3) 5 hours post-enucleation.

TABLE 7

| Fusosome stains | | | |
|---|---|---|---|
| Stain | Attune Laser/Filter | Laser Wavelength | Emission Filter (nm) |
| Hoechst 33342 | VL1 | 405 | 450/40 |
| ER-Tracker Green | BL1 | 488 | 530/30 |
| MitoTracker Deep Red FM | RL1 | 638 | 670/14 |
| LysoTracker Green | BL1 | 488 | 530/30 |

Example 35: Measuring Nuclear Content in Fusosomes

This Example describes one embodiment of measuring nuclear content in a fusosome. To validate that fusosomes do not contain nuclei, fusosomes are stained with 1 µg·mL$^{-1}$ Hoechst 33342 and 1 µM CalceinAM (C3100MP, Thermo Fisher, Waltham, Mass.) and the stained fusosomes are run on an Attune NXT Flow Cytometer (Thermo Fisher, Waltham, Mass.) to determine the fluorescence intensity of each dye according to the table below. In an embodiment, validation for the presence of cytosol (CalceinAM) and the absence of a nucleus (Hoechst 33342) will be made by comparing the mean fluorescence intensity of stained fusosomes to unstained fusosomes and stained cells.

TABLE 8

| Flow cytometer settings | | | |
|---|---|---|---|
| Stain | Attune Laser/Filter | Laser Wavelength | Emission Filter (nm) |
| Hoechst 33342 | VL1 | 405 | 450/40 |
| Calcein AM | BL1 | 488 | 530/30 |

Example 36: Measuring Nuclear Envelope Content

This Example describes a measurement of the nuclear envelope content in enucleated fusosomes. The nuclear envelope isolates DNA from the cytoplasm of the cell.

In an embodiment, a purified fusosome composition comprises a mammalian cell, such as HEK-293 Ts (293 [HEK-293] (ATCC® CRL-1573™), that has been enucleated as described herein. This Example describes the quantification of different nuclear membrane proteins as a proxy to measure the amount of intact nuclear membrane that remains after fusosome generation.

In this Example, $10 \times 10^6$ HEK-293 Ts and the equivalent amount of fusosomes prepared from $10 \times 10^6$ HEK-293 Ts are fixed for 15 min using 3.7% PFA, washed with 1×PBS buffer, pH 7.4 and permeabilized simultaneously, and then blocked for 15 min using 1×PBS buffer containing 1% Bovine Serum Albumin and 0.5% Triton® X-100, pH 7.4. After permeabilization, fusosomes and cells are incubated for 12 hours at 4° C. with different primary antibodies, e.g. (anti-RanGAP1 antibody [EPR3295](Abcam—ab92360), anti-NUP98 antibody [EPR6678]—nuclear pore marker (Abcam-ab124980), anti-nuclear pore complex proteins antibody [Mab414]—(Abcam-ab24609), anti-importin 7 antibody (Abcam—ab213670), at manufacturer suggested concentrations diluted in 1×PBS buffer containing 1% bovine serum albumin and 0.5% Triton® X-100, pH 7.4. Fusosomes and cells are then washed with 1×PBS buffer, pH 7.4, and incubated for 2 hr at 21° C. with an appropriate fluorescent secondary antibody that detects the previous specified primary antibody at manufacturer suggested concentrations diluted in 1×PBS buffer containing 1% bovine serum albumin and 0.5% detergent, pH 7.4. Fusosomes and cells are then washed with 1×PBS buffer, re-suspended in 300 gL of 1×PBS buffer, pH 7.4 containing 1 μg/ml Hoechst 33342, filtered through a 20 gm FACS tube and analyzed by flow cytometry.

Negative controls are generated using the same staining procedure but with no primary antibody added. Flow cytometry is performed on a FACS cytometer (Becton Dickinson, San Jose, Calif., USA) with 488 nm argon laser excitation, and a 530+/−30 nm emission spectrum is collected. FACS acquisition software is used for acquisition and analysis. The light scatter channels are set on linear gains, and the fluorescence channels on a logarithmic scale, with a minimum of 10,000 cells analyzed in each condition. The relative intact nuclear membrane content is calculated based on the median intensity of fluorescence in each sample. All events are captured in the forward and side scatter channels.

The normalized fluorescence intensity value for the fusosomes is determined by subtracting from the median fluorescence intensity value of the fusosome the median fluorescence intensity value of the respective negative control sample. Then the normalized fluorescence for the fusosomes samples is normalized to the respective nucleated cell samples in order to generate quantitative measurements of intact nuclear membrane content.

In an embodiment, enucleated fusosomes will comprise less than 1%, 2%, 3%, 4%, 5%, 10%, 20%, 30%, 40%, 50%, 60%, 70%, 80%, or 90% fluorescence intensity or nuclear envelope content compared to the nucleated parental cells.

Example 37: Measuring Chromatin Levels

This Example describes measurement of chromatin in enucleated fusosomes.

DNA can be condensed into chromatin to allow it to fit inside the nucleus. In an embodiment, a purified fusosome composition as produced by any one of the methods described herein will comprise low levels of chromatin.

Enucleated fusosomes prepared by any of the methods previously described and positive control cells (e.g., parental cells) are assayed for chromatin content using an ELISA with antibodies that are specific to histone protein H3 or histone protein H4. Histones are the chief protein component of chromatin, with H3 and H4 the predominant histone proteins.

Histones are extracted from the fusosome preparation and cell preparation using a commercial kit (e.g. Abcam Histone Extraction Kit (ab113476)) or other methods known in the art. These aliquots are stored at −80 C until use. A serial dilution of standard is prepared by diluting purified histone protein (either H3 or H4) from 1 to 50 ng/l in a solution of the assay buffer. The assay buffer may be derived from a kit supplied by a manufacturer (e.g. Abcam Histone H4 Total Quantification Kit (ab156909) or Abcam Histone H3 total Quantification Kit (ab115091)). The assay buffer is added to each well of a 48- or 96-well plate, which is coated with an anti-histone H3 or anti-H4 antibody and sample or standard control is added to the well to bring the total volume of each well to 50 μl. The plate is then covered and incubated at 37 degrees for 90 to 120 minutes.

After incubation, any histone bound to the anti-histone antibody attached to the plate is prepared for detection. The supernatant is aspirated and the plate is washed with 150 μl of wash buffer. The capture buffer, which includes an anti-histone H3 or anti-H4 capture antibody, is then added to the plate in a volume of 50 μl and at a concentration of 1 μg/mL. The plate is then incubated at room temperature on an orbital shaker for 60 minutes.

Next, the plate is aspirated and washed 6 times using wash buffer. Signal reporter molecule activatable by the capture antibody is then added to each well. The plate is covered and incubated at room temperature for 30 minutes. The plate is then aspirated and washed 4 times using wash buffer. The reaction is stopped by adding stop solution. The absorbance of each well in the plate is read at 450 nm, and the concentration of histones in each sample is calculated according to the standard curve of absorbance at 450 nm vs. concentration of histone in standard samples.

In an embodiment, fusosome samples will comprise less than 1%, 2%, 3%, 4%, 5%, 10%, 20%, 30%, 40%, 50%, 60%, 70%, 80%, or 90% the histone concentration of the nucleated parental cells.

Example 38: Measuring DNA Content in Fusosomes

This example describes quantification of the amount of DNA in a fusosome relative to nucleated counterparts. In an embodiment, fusosomes will have less DNA than nucleated counterparts. Nucleic acid levels are determined by measuring total DNA or the level of a specific house-keeping gene. In an embodiment, fusosomes having reduced DNA content or substantially lacking DNA will be unable to replicate, differentiate, or transcribe genes, ensuring that their dose and function is not altered when administered to a subject.

Fusosomes are prepared by any one of the methods described in previous Examples. Preparations of the same mass as measured by protein of fusosomes and source cells are used to isolate total DNA (e.g. using a kit such as Qiagen DNeasy catalog #69504), followed by determination of DNA concentration using standard spectroscopic methods to assess light absorbance by DNA (e.g. with Thermo Scientific NanoDrop).

In an embodiment, the concentration of DNA in enucleated fusosomes will be less than about 50%, 40%, 30%, 20%, 10%, 5%, 4%, 3%, 2%, 1% or less than in parental cells.

Alternatively, the concentration of a specific house-keeping gene, such as GAPDH, can be compared between nucleated cells and fusosomes with semi-quantitative real-time PCR (RT-PCR). Total DNA is isolated from parental cells and fusosome and DNA concentration is measured as described herein. RT-PCR is carried out with a PCR kit (Applied Biosystems, catalog #4309155) using the following reaction template:

SYBR Green Master Mix: 10 µL
0.45 µM Forward Primer: 1 µL
0.45 µM Reverse Primer: 1 µL
DNA Template: 10 ng
PCR-Grade Water: Variable Forward and reverse primers are acquired from Integrated DNA Technologies. The table below details the primer pairs and their associated sequences:

TABLE 9

Primer sequences

| Target | Forward Primer Sequence (5'→3') | Reverse Primer Sequence (5'→3') |
|---|---|---|
| Human (GAPDH) | nDNAGGAGTCCACTGGCGTCTTCAC | GAGGCATTGCTGATGATCTTGAGG |

A real-time PCR system (Applied Biosystems) is used to perform the amplification and detection with the following protocol:

| Denaturation, 94° C. | 2 min |
|---|---|

40 Cycles of the following sequence:

| Denaturation, 94° C. | 15 sec |
|---|---|
| Annealing, Extension, 60° C. | 1 min |

A standard curve of the $C_t$ vs. DNA concentration is prepared with serial dilutions of GAPDH DNA and used to normalize the Ct nuclear value from fusosome PCR results to a specific amount (ng) of DNA.

In an embodiment, the concentration of GAPDH DNA in enucleated fusosomes will be less than about 50%, 40%, 30%, 20%, 10%, 5%, 4%, 3%, 2%, 1% or less than in parental cells.

Example 39: Measuring miRNA Content in Fusosomes

This example describes quantification of microRNAs (miRNAs) in fusosomes. In an embodiment, a fusosome comprises miRNAs.

MiRNAs are regulatory elements that, among other activities, control the rate by which messenger RNAs (mRNAs) are translated into proteins. In an embodiment, fusosomes carrying miRNA may be used to deliver the miRNA to target sites.

Fusosomes are prepared by any one of the methods described in previous Examples. RNA from fusosomes or parental cells is prepared as described previously. At least one miRNA gene is selected from the Sanger Center miRNA Registry at www.sanger.ac.uk/Software/Rfam/mirna/index.shtml. miRNA is prepared as described in Chen et al, *Nucleic Acids Research*, 33(20), 2005. All TaqMan miRNA assays are available through Thermo Fisher (A25576, Waltham, Mass.).

qPCR is carried out according to manufacturer's specifications on miRNA cDNA, and $C_T$ values are generated and analyzed using a real-time PCR system as described herein.

In an embodiment, the miRNA content of fusosomes will be at least 1%, 2%, 3%, 4%, 5%, 10%, 20%, 30%, 40%, 50%, 60%, 70%, 80%, 90%, or greater than that of their parental cells.

Example 40: Quantifying Expression of an Endogenous RNA or Synthetic RNA in Fusosomes This example describes quantification of levels of endogenous RNA with altered expression, or a synthetic RNA that is expressed in a fusosome.

The fusosome or parental cell is engineered to alter the expression of an endogenous or synthetic RNA that mediates a cellular function to the fusosomes.

Transposase vectors (System Biosciences, Inc.) includes the open reading frame of the Puromycin resistance gene together with an open reading frame of a cloned fragment of a protein agent. The vectors are electroporated into 293 Ts using an electroporator (Amaxa) and a 293T cell line specific nuclear transfection kit (Lonza).

Following selection with puromycin for 3-5 days in DMEM containing 20% Fetal Bovine Serum and 1× Penicillin/Streptomycin, fusosomes are prepared from the stably expressing cell line by any one of the methods described in previous Examples.

Individual fusosomes are isolated and protein agent or RNA per fusosome is quantified as described in a previous Example.

In an embodiment, the fusosomes will have at least 1, 2, 3, 4, 5, 10, 20, 50, 100, 500, $10^3$, $5.0\times10^3$, $10^4$, $5.0\times10^4$, $10^5$, $5.0\times10^5$, $10^6$, $5.0\times10^6$, or more of the RNA per fusosome.

Example 41: Measuring Lipid Composition in Fusosomes

This Example describes quantification of the lipid composition of fusosomes. In an embodiment, the lipid composition of fusosomes is similar to the cells that they are derived from. Lipid composition affects important biophysical parameters of fusosomes and cells, such as size, electrostatic interactions, and colloidal behavior.

The lipid measurements are based on mass spectrometry. Fusosomes are prepared by any one of the methods described in previous Examples.

Mass spectrometry-based lipid analysis is performed at a lipid analysis service (Dresden, Germany) as described (Sampaio, et al., Proc Natl Acad Sci, 2011, Feb. 1; 108(5): 1903-7). Lipids are extracted using a two-step chloroform/methanol procedure (Ejsing, et al., Proc Natl Acad Sci, 2009, Mar. 17; 106(7):2136-41). Samples are spiked with an internal lipid standard mixture of: cardiolipin 16:1/15:0/15:0/15:0 (CL), ceramide 18:1; 2/17:0 (Cer), diacylglycerol 17:0/17:0 (DAG), hexosylceramide 18:1; 2/12:0 (HexCer), lysophosphatidate 17:0 (LPA), lyso-phosphatidylcholine 12:0 (LPC), lyso-phosphatidylethanolamine 17:1 (LPE), lyso-phosphatidylglycerol 17:1 (LPG), lyso-phosphatidylinositol 17:1 (LPI), lyso-phosphatidylserine 17:1 (LPS), phosphatidate 17:0/17:0 (PA), phosphatidylcholine 17:0/17:0 (PC), phosphatidylethanolamine 17:0/17:0 (PE), phosphatidylglycerol 17:0/17:0 (PG), phosphatidylinositol 16:0/16:0 (PI), phosphatidylserine 17:0/17:0 (PS), cholesterol ester 20:0 (CE), sphingomyelin 18:1; 2/12:0; 0 (SM) and triacylglycerol 17:0/17:0/17:0 (TAG).

After extraction, the organic phase is transferred to an infusion plate and dried in a speed vacuum concentrator. The first step dry extract is resuspended in 7.5 mM ammonium acetate in chloroform/methanol/propanol (1:2:4, V:V:V) and the second step dry extract is resuspended in 33% ethanol solution of methylamine in chloroform/methanol (0.003:5:1; V:V:V). All liquid handling steps are performed using a robotic platform for organic solvent with an anti-droplet control feature (Hamilton Robotics) for pipetting.

Samples are analyzed by direct infusion on a mass spectrometer (Thermo Scientific) equipped with an ion source (Advion Biosciences). Samples are analyzed in both positive and negative ion modes with a resolution of Rm/z=200=280000 for MS and Rm/z=200=17500 for tandem MS/MS experiments, in a single acquisition. MS/MS is triggered by an inclusion list encompassing corresponding MS mass ranges scanned in 1 Da increments (Surma, et al., Eur J lipid Sci Technol, 2015, October; 117(10):1540-9). Both MS and MS/MS data are combined to monitor CE, DAG and TAG ions as ammonium adducts; PC, PC O-, as acetate adducts; and CL, PA, PE, PE O-, PG, PI and PS as deprotonated anions. MS only is used to monitor LPA, LPE, LPE O-, LPI and LPS as deprotonated anions; Cer, HexCer, SM, LPC and LPC O- as acetate.

Data are analyzed with in-house developed lipid identification software as described in the following references (Herzog, et al., Genome Biol, 2011, Jan. 19; 12(1):R8; Herzog, et al., PLoS One, 2012, January; 7(1):e29851). Only lipid identifications with a signal-to-noise ratio >5, and a signal intensity 5-fold higher than in corresponding blank samples are considered for further data analysis.

Fusosome lipid composition is compared to parental cells' lipid composition. In an embodiment, fusosomes and parental cells will have a similar lipid composition if >50% of the identified lipids in the parental cells are present in the fusosomes, and of those identified lipids, the level in the fusosome will be >25% of the corresponding lipid level in the parental cell.

Example 42: Measuring Proteomic Composition in Fusosomes

This Example describes quantification of the protein composition of fusosomes. In an embodiment, the protein composition of fusosomes will be similar to the cells that they are derived from.

Fusosomes are prepared by any one of the methods described in previous Examples. Fusosomes are resuspended in lysis buffer (7M Urea, 2M Thiourea, 4% (w/v) Chaps in 50 mM Tris pH 8.0) and incubated for 15 minutes at room temperature with occasional vortexing. Mixtures are then lysed by sonication for 5 minutes in an ice bath and spun down for 5 minutes at 13,000 RPM. Protein content is determined by a colorimetric assay (Pierce) and protein of each sample is transferred to a new tube and the volume is equalized with 50 mM Tris pH 8.

Proteins are reduced for 15 minutes at 65 Celsius with 10 mM DTT and alkylated with 15 mM iodoacetamide for 30 minutes at room temperature in the dark. Proteins are precipitated with gradual addition of 6 volumes of cold (−20 Celsius) acetone and incubated overnight at −80 Celsius. Protein pellets are washed 3 times with cold (−20 Celsius) methanol. Proteins are resuspended in 50 mM Tris pH 8.3.

Next, trypsin/lysC is added to the proteins for the first 4 h of digestion at 37 Celsius with agitation. Samples are diluted with 50 mM Tris pH 8 and 0.1% sodium deoxycholate is added with more trypsin/lysC for digestion overnight at 37 Celsius with agitation. Digestion is stopped and sodium deoxycholate is removed by the addition of 2% v/v formic acid. Samples are vortexed and cleared by centrifugation for 1 minute at 13,000 RPM. Peptides are purified by reversed phase solid phase extraction (SPE) and dried down. Samples are reconstituted in 20 μl of 3% DMSO, 0.2% formic acid in water and analyzed by LC-MS.

To have quantitative measurements, a protein standard is also run on the instrument. Standard peptides (Pierce, equimolar, LC-MS grade, #88342) are diluted to 4, 8, 20, 40 and 100 fmol/ul and are analyzed by LC-MS/MS. The average AUC (area under the curve) of the 5 best peptides per protein (3 MS/MS transition/peptide) is calculated for each concentration to generate a standard curve.

Acquisition is performed with a high resolution mass spectrometer (ABSciex, Foster City, Calif., USA) equipped with an electrospray interface with a 25 μm iD capillary and coupled with micro-ultrahigh performance liquid chromatography (gUHPLC) (Eksigent, Redwood City, Calif., USA). Analysis software is used to control the instrument and for data processing and acquisition. The source voltage is set to 5.2 kV and maintained at 225° C., curtain gas is set at 27 psi, gas one at 12 psi and gas two at 10 psi. Acquisition is performed in Information Dependent Acquisition (IDA) mode for the protein database and in SWATH acquisition mode for the samples. Separation is performed on a reversed phase column 0.3 μm i.d., 2.7 μm particles, 150 mm long (Advance Materials Technology, Wilmington, Del.) which is maintained at 60° C. Samples are injected by loop overfilling into a 5 gL loop. For the 120 minute (samples) LC gradient, the mobile phase includes the following: solvent A (0.2% v/v formic acid and 3% DMSO v/v in water) and solvent B (0.2% v/v formic acid and 3% DMSO in EtOH) at a flow rate of 3 μL/min.

For the absolute quantification of the proteins, a standard curve (5 points, R2>0.99) is generated using the sum of the AUC of the 5 best peptides (3 MS/MS ion per peptide) per protein. To generate a database for the analysis of the samples, the DIAUmpire algorithm is run on each of the 12 samples and combined with the output MGF files into one database. This database is used with software (ABSciex) to quantify the proteins in each of the samples, using 5 transition/peptide and 5 peptide/protein maximum. A peptide is considered as adequately measured if the score computed is superior to 1.5 or had a FDR<1%. The sum of the AUC of each of the adequately measured peptides is mapped on the standard curve, and is reported as fmol.

The resulting protein quantification data is then analyzed to determine protein levels and proportions of known classes of proteins as follows: enzymes are identified as proteins that are annotated with an Enzyme Commission (EC) number; ER associated proteins are identified as proteins that had a Gene Ontology (GO; http://www.geneontology.org) cellular compartment classification of ER and not mitochondria; exosome associated proteins are identified as proteins that have a Gene Ontology cellular compartment classification of exosomes and not mitochondria; and mitochondrial proteins are identified as proteins that are identified as mitochondrial in the MitoCarta database (Calvo et al., NAR 20151 doi:

10.1093/nar/gkv1003). The molar ratios of each of these categories are determined as the sum of the molar quantities of all the proteins in each class divided by the sum of the molar quantities of all identified proteins in each sample.

Fusosome proteomic composition is compared to parental cell proteomic composition. In an embodiment, a similar proteomic compositions between fusosomes and parental cells will be observed when >50% of the identified proteins are present in the fusosome, and of those identified proteins the level is >25% of the corresponding protein level in the parental cell.

Example 43: Quantifying an Endogenous or Synthetic Protein Level Per Fusosome

This example describes quantification of an endogenous or synthetic protein cargo in fusosomes. In an embodiment, fusosomes comprise an endogenous or synthetic protein cargo.

The fusosome or parental cell is engineered to alter the expression of an endogenous protein or express a synthetic cargo that mediates a therapeutic or novel cellular function.

Transposase vectors (System Biosciences, Inc.) that include the open reading frame of the puromycin resistance gene together with an open reading frame of a cloned fragment of a protein agent, optionally translationally fused to the open reading frame of a green fluorescent protein (GFP). The vectors are electroporated into 293 Ts using an electroporator (Amaxa) and a 293T cell line specific nuclear transfection kit (Lonza).

Following selection with puromycin for 3-5 days in DMEM containing 20% fetal bovine serum and 1× penicillin/streptomycin, fusosomes are prepared from the stably expressing cell line by any one of the methods described in previous Examples.

Altered expression levels of an endogenous protein or expression levels of a synthetic protein that are not fused to GFP are quantified by mass spectrometry as described above. In an embodiment, the fusosomes will have at least 1, 2, 3, 4, 5, 10, 20, 50, 100, 500, $10^3$, $5.0×10^3$, $10^4$, $5.0×10^4$, $10^5$, $5.0×10^5$, $10^6$, $5.0×10^6$, or more protein agent molecules per fusosome.

Alternatively, purified GFP is serially diluted in DMEM containing 20% fetal bovine serum and 1× Penicillin/Streptomycin to generate a standard curve of protein concentration. GFP fluorescence of the standard curve and a sample of fusosomes is measured in a fluorimeter (BioTek) using a GFP light cube (469/35 excitation filter and a 525/39 emission filter) to calculate the average molar concentration of GFP molecules in the fusosomes. The molar concentration is then converted to number of GFP molecules and divided by the number of fusosomes per sample to achieve an average number of protein agent molecules per fusosome.

In an embodiment, the fusosomes will have at least 1, 2, 3, 4, 5, 10, 20, 50, 100, 500, $10^3$, $5.0×10^3$, $10^4$, $5.0×10^4$, $10^5$, $5.0×10^5$, $10^6$, $5.0×10^6$, or more protein agent molecules per fusosome.

Example 44: Measuring Markers of Exosomal Proteins in Fusosomes

This assay describes quantification of the proteomics makeup of the sample preparation, and quantifies the proportion of proteins that are known to be specific markers of exosomes.

Fusosomes are pelleted and shipped frozen to the proteomics analysis center per standard biological sample handling procedures.

The fusosomes are thawed for protein extraction and analysis. First, they are resuspended in lysis buffer (7M urea, 2M thiourea, 4% (w/v) chaps in 50 mM Tris pH 8.0) and incubated for 15 minutes at room temperature with occasional vortexing. The mixtures are then lysed by sonication for 5 minutes in an ice bath and spun down for 5 minutes at 13,000 RPM. Total protein content is determined by a colorimetric assay (Pierce) and 100 μg of protein from each sample is transferred to a new tube and the volume is adjusted with 50 mM Tris pH 8.

The proteins are reduced for 15 minutes at 650 Celsius with 10 mM DTT and alkylated with 15 mM iodoacetamide for 30 minutes at room temperature in the dark. The proteins are then precipitated with gradual addition of 6 volumes of cold (−20° Celsius) acetone and incubated over night at −80° Celsius.

The proteins are pelleted, washed 3 times with cold (−20° Celsius) methanol, and resuspended in 50 mM Tris pH 8. 3.33 g of trypsin/lysC is added to the proteins for a first 4 h of digestion at 37° Celsius with agitation. The samples are diluted with 50 mM Tris pH 8 and 0.1% sodium deoxycholate is added with another 3.3 μg of trypsin/lysC for digestion overnight at 370 Celsius with agitation. Digestion is stopped and sodium deoxycholate is removed by the addition of 2% v/v formic acid. Samples are vortexed and cleared by centrifugation for 1 minute at 13,000 RPM.

The proteins are purified by reversed phase solid phase extraction (SPE) and dried down. The samples are reconstituted in 3% DMSO, 0.2% formic acid in water and analyzed by LC-MS as described previously.

The resulting protein quantification data is analyzed to determine protein levels and proportions of know exosomal marker proteins. Specifically: tetraspanin family proteins (CD63, CD9, or CD81), ESCRT-related proteins (TSG101, CHMP4A-B, or VPS4B), Alix, TSG101, MHCI, MHCII, GP96, actinin-4, mitofilin, syntenin-1, TSG101, ADAM10, EHD4, syntenin-1, TSG101, EHD1, flotillin-1, heat-shock 70-kDa proteins (HSC70/HSP73, HSP70/HSP72). The molar ratio these exosomal marker proteins relative to all proteins measured is determined as the molar quantity of each specific exosome marker protein listed above divided by the sum of the molar quantities of all identified proteins in each sample and expressed as a percent.

Similarly, the molar ratio for all exosomal marker proteins relative to all proteins measured is determined as the sum of the molar quantity of all specific exosome marker protein listed above divided by the sum of the molar quantities of all identified proteins in each sample and expressed as a percent of the total.

In an embodiment, using this approach, a sample will comprise less than 5% of any individual exosomal marker protein and less than 15% of total exosomal marker proteins.

In an embodiment, any individual exosomal marker protein will be present at less than 0.05%, 0.1%, 0.5%, 1%, 2%, 3%, 4%, 5%, or 10%.

In an embodiment, the sum of all exosomal marker proteins will be less than 0.05%, 0.1%, 0.5%, 1%, 2%, 3%, 4%, 5%, 10%, 15%, 20%, or 25%.

Example 45: Measuring GAPDH in Fusosomes

This assay describes quantification of the level of glyceraldehyde 3-phosphate dehydrogenase (GAPDH) in the fusosomes, and the relative level of GAPDH in the fusosomes compared to the parental cells.

GAPDH is measured in the parental cells and the fusosomes using a standard commercially available ELISA for GAPDH (ab176642, Abcam) per the manufacturer's directions.

Total protein levels are similarly measured via bicinchoninic acid assay as previously described in the same volume of sample used to measure GAPDH. In embodiments, using this assay, the level of GAPDH per total protein in the fusosomes will be <100 ng GAPDH/g total protein. Similarly, in embodiments, the decrease in GAPDH levels relative to total protein from the parental cells to the fusosomes will be greater than a 10% decrease.

In an embodiment, GAPDH content in the preparation in ng GAPDH/g total protein will be less than 500, less than 250, less than 100, less than 50, less than 20, less than 10, less than 5, or less than 1.

In an embodiment, the decrease in GAPDH per total protein in ng/g from the parent cell to the preparation will be more than 1%, more than 2.5%, more than 5%, more than 10%, more than 15%, more than 20%, more than 30%, more than 40%, more than 50%, more than 60%, more than 70%, more than 80%, or more than 90%.

Example 46: Measuring Calnexin in Fusosomes

This assay describes quantification of the level of calnexin (CNX) in the fusosomes, and the relative level of CNX in the fusosomes compared to the parental cells.

Calnexin is measured in the starting cells and the preparation using a standard commercially available ELISA for calnexin (MBS721668, MyBioSource) per the manufacturer's directions.

Total protein levels are similarly measured via bicinchoninic acid assay as previously described in the same volume of sample used to measure calnexin. In embodiments, using this assay, the level of calnexin per total protein in the fusosomes will be <100 ng calnexin/µg total protein. Similarly, in embodiments, the increase in calnexin levels relative to total protein from the parental cell to the fusosomes will be greater than a 10% increase.

In an embodiment, calnexin content in the preparation in ng calnexin/µg total protein will be less than 500, 250, 100, 50, 20, 10, 5, or 1.

In an embodiment, the decrease in calnexin per total protein in ng/µg from the parent cell to the preparation will be more than 1%, 2.5%, 5%, 10%, 15%, 20%, 30%, 40%, 50%, 60%, 70%, 80%, or 90%.

Example 47: Comparison of Soluble to Insoluble Protein Mass

This Example describes quantification of the soluble: insoluble ratio of protein mass in fusosomes. In an embodiment, the soluble:insoluble ratio of protein mass in fusosomes will be similar to nucleated cells.

Fusosomes are prepared by any one of the methods described in previous Examples. The fusosome preparation is tested to determine the soluble: insoluble protein ratio using a standard bicinchoninic acid assay (BCA) (e.g. using the commercially available Pierce™ BCA Protein Assay Kit, Thermo Fischer product #23225). Soluble protein samples are prepared by suspending the prepared fusosomes or parental cells at a concentration of 1×10^7 cells or fusosomes/mL in PBS and centrifuging at 1600 g to pellet the fusosomes or cells. The supernatant is collected as the soluble protein fraction.

The fusosomes or cells in the pellet are lysed by vigorous pipetting and vortexing in PBS with 2% Triton-X-100. The lysed fraction represents the insoluble protein fraction.

A standard curve is generated using the supplied BSA, from 0 to 20 µg of BSA per well (in triplicate). The fusosome or cell preparation is diluted such that the quantity measured is within the range of the standards. The fusosome preparation is analyzed in triplicate and the mean value is used. The soluble protein concentration is divided by the insoluble protein concentration to yield the soluble:insoluble protein ratio.

In an embodiment, the fusosome soluble:insoluble protein ratio will be within 1%, 2%, 3%, 4%, 5%, 10%, 20%, 30%, 40%, 50%, 60%, 70%, 80%, 90%, or greater compared to the parental cells.

Example 48: Measuring LPS in Fusosomes

This example describes quantification of levels of lipopolysaccharides (LPS) in fusosomes as compared to parental cells. In an embodiment, fusosomes will have lower levels of LPS compared to parental cells.

LPS are a component of bacterial membranes and potent inducer of innate immune responses.

The LPS measurements are based on mass spectrometry as described in the previous Examples.

In an embodiment, less than 5%, 1%, 0.5%, 0.01%, 0.005%, 0.0001%, 0.00001% or less of the lipid content of fusosomes will be LPS.

Example 49: Ratio of Lipids to Proteins in Fusosomes

This Example describes quantification of the ratio of lipid mass to protein mass in fusosomes. In an embodiment, fusosomes will have a ratio of lipid mass to protein mass that is similar to nucleated cells.

Total lipid content is calculated as the sum of the molar content of all lipids identified in the lipidomics data set outlined in a previous Example. Total protein content of the fusosomes is measured via bicinchoninic acid assay as described herein.

Alternatively, the ratio of lipids to proteins can be described as a ratio of a particular lipid species to a specific protein. The particular lipid species is selected from the lipidomics data produced in a previous Example. The specific protein is selected from the proteomics data produced in a previous Example. Different combinations of selected lipid species and proteins are used to define specific lipid: protein ratios.

Example 50: Ratio of Proteins to DNA in Fusosomes

This Example describes quantification of the ratio of protein mass to DNA mass in fusosomes. In an embodiment, fusosomes will have a ratio of protein mass to DNA mass that is much greater than cells.

Total protein content of the fusosomes and cells is measured as described in in a previous Example. The DNA mass of fusosomes and cells is measured as described in a previous Example. The ratio of proteins to total nucleic acids is then determined by dividing the total protein content by the total DNA content to yield a ratio within a given range for a typical fusosome preparation.

Alternatively, the ratio of proteins to nucleic acids is determined by defining nucleic acid levels as the level of a specific house-keeping gene, such as GAPDH, using semi-quantitative real-time PCR (RT-PCR).

The ratio of proteins to GAPDH nucleic acids is then determined by dividing the total protein content by the total GAPDH DNA content to define a specific range of protein: nucleic acid ratio for a typical fusosome preparation.

Example 51: Ratio of Lipids to DNA in Fusosomes

This Example describes quantification of the ratio of lipids to DNA in fusosomes compared to parental cells. In an embodiment, fusosomes will have a greater ratio of lipids to DNA compared to parental cells.

This ratio is defined as total lipid content (outlined in an Example above) or a particular lipid species. In the case of a particular lipid species, the range depends upon the particular lipid species selected. The particular lipid species is selected from the lipidomics data produced in the previously described Example. Nucleic acid content is determined as described in the previously described Example.

Different combinations of selected lipid species normalized to nucleic acid content are used to define specific lipid:nucleic acid ratios that are characteristic of a particular fusosome preparation.

Example 52: Analyzing Surface Markers on Fusosomes

This assay describes identification of surface markers on the fusosomes.

Fusosomes are pelleted and shipped frozen to the proteomics analysis center per standard biological sample handling procedures.

To identify surface marker presence or absence on the fusosomes, they are stained with markers against phosphatidyl serine and CD40 ligand and analyzed by flow cytometry using a FACS system (Becton Dickinson). For detection of surface phosphatidylserine, the product is analyzed with an annexin V assay (556547, BD Biosciences) as described by the manufacturer.

Briefly, the fusosomes are washed twice with cold PBS and then resuspended in 1× binding buffer at a concentration of 1×10^6 fusosomes/ml. 10% of the resuspension is transferred to a 5 ml culture tube and 5 μl of FITC annexin V is added. The cells are gently vortexed and incubated for 15 min at room temperature (25° C.) in the dark.

In parallel, a separate 10% of the resuspension is transferred to a different tube to act as an unstained control. 1× binding buffer is added to each tube. The samples are analyzed by flow cytometry within 1 hr.

In some embodiments, using this assay, the mean of the population of the stained fusosomes will be determined to be above the mean of the unstained cells indicating that the fusosomes comprise phosphatidyl serine.

Similarly, for the CD40 ligand, the following monoclonal antibody is added to another 10% of the washed fusosomes: PE-CF594 mouse anti-human CD154 clone TRAP1 (563589, BD Pharmigen) as per the manufacturer's directions. Briefly, saturating amounts of the antibody are used. In parallel, a separate 10% of the fusosomes are transferred to a different tube to act as an unstained control. The tubes are centrifuged for 5 min at 400×g, at room temperature. The supernatant is decanted and the pellet is washed twice with flow cytometry wash solution. 0.5 ml of 1% paraformaldehyde fixative is added to each tube. Each is briefly vortexed and stored at 4° C. until analysis on the flow cytometer.

In an embodiment, using this assay, the mean of the population of the stained fusosomes will be above the mean of the unstained cells indicating that the fusosomes comprise CD40 ligand.

Example 53: Analysis of Viral Capsid Proteins in Fusosomes

This assay describes analysis of the makeup of the sample preparation and assesses the proportion of proteins that are derived from viral capsid sources.

Fusosomes are pelleted and shipped frozen to a proteomics analysis center per standard biological sample handling procedures.

The fusosomes are thawed for protein extraction and analysis. First, they are resuspended in lysis buffer (7M urea, 2M thiourea, 4% (w/v) chaps in 50 mM Tris pH 8.0) and incubated for 15 minutes at room temperature with occasional vortexing. The mixtures are then lysed by sonication for 5 minutes in an ice bath and spun down for 5 minutes at 13,000 RPM. Total protein content is determined by a colorimetric assay (Pierce) and 100 μg of protein from each sample is transferred to a new tube and the volume is adjusted with 50 mM Tris pH 8.

The proteins are reduced for 15 minutes at 650 Celsius with 10 mM DTT and alkylated with 15 mM iodoacetamide for 30 minutes at room temperature in the dark. The proteins are then precipitated with gradual addition of 6 volumes of cold (−20° Celsius) acetone and incubated over night at −80° Celsius.

The proteins are pelleted, washed 3 times with cold (−20° Celsius) methanol, and resuspended in 50 mM Tris pH 8. 3.33 g of trypsin/lysC is added to the proteins for a first 4 h of digestion at 37° Celsius with agitation. The samples are diluted with 50 mM Tris pH 8 and 0.1% sodium deoxycholate is added with another 3.3 μg of trypsin/lysC for digestion overnight at 370 Celsius with agitation. Digestion is stopped and sodium deoxycholate is removed by the addition of 2% v/v formic acid. Samples are vortexed and cleared by centrifugation for 1 minute at 13,000 RPM.

The proteins are purified by reversed phase solid phase extraction (SPE) and dried down. The samples are reconstituted in 3% DMSO, 0.2% formic acid in water and analyzed by LC-MS as described previously.

The molar ratio of the viral capsid proteins relative to all proteins measured is determined as the molar quantity of all viral capsid proteins divided by the sum of the molar quantities of all identified proteins in each sample and expressed as a percent.

In an embodiment, using this approach, the sample will comprise less than 10% viral capsid protein. In an embodiment, the sample will comprise less than 0.5%, 1%, 5%, 10%, 15%, 20%, 25%, 30%, 35%, 40%, 45%, 50%, 60%, 70%, 80%, or 90% viral capsid protein.

Example 54: Measuring Fusion with a Target Cell

This example describes quantification of fusosome fusion with a target cell compared to a non-target cell.

In an embodiment, fusosome fusion with a target cell allows the cell-specific delivery of a cargo, carried within the lumen of the fusosome, to the cytosol of the recipient cell. Fusosomes produced by the herein described methods are assayed for fusion rate with a target cell as follows.

In this example, the fusosome comprises a HEK293T cell expressing Myomaker on its plasma membrane. In addition, the fusosome expresses mTagBFP2 fluorescent protein and Cre recombinase. The target cell is a myoblast cell, which expresses both Myomaker and Myomixer, and the non-target cell is a fibroblast cell, which expresses neither Myomaker nor Myomixer. A Myomaker-expressing fusosome is predicted to fuse with the target cell that expresses both Myomaker and Myomixer but not the non-target cell (Quinn et al., 2017, Nature Communications, 8, 15665. doi.org/10.1038/ncomms15665) (Millay et al., 2013, Nature, 499(7458), 301-305. doi.org/10.1038/nature12343). Both the target and non-target cell types are isolated from mice and stably-express "LoxP-stop-Loxp-tdTomato" cassette under a CMV promoter, which upon recombination by Cre turns on tdTomato expression, indicating fusion.

The target or non-target recipient cells are plated into a black, clear-bottom 96-well plate. Both target and non-target cells are plated for the different fusion groups. Next, 24 hours after plating the recipient cells, the fusosomes expressing Cre recombinase protein and Myomaker are applied to the target or non-target recipient cells in DMEM media. The dose of fusosomes is correlated to the number of recipient cells plated in the well. After applying the fusosomes, the cell plate is centrifuged at 400 g for 5 minutes to help initiate contact between the fusosomes and the recipient cells.

Starting at four hours after fusosome application, the cell wells are imaged to positively identify RFP-positive cells versus GFP-positive cells in the field or well.

In this example, cell plates are imaged using an automated microscope (www.biotek. com/products/imaging-microscopy-automated-cell-imagers/lionheart-fx-automated-live-cell-imager/). The total cell population in a given well is determined by first staining the cells with Hoechst 33342 in DMEM media for 10 minutes. Hoechst 33342 stains cell nuclei by intercalating into DNA and therefore is used to identify individual cells. After staining, the Hoechst media is replaced with regular DMEM media.

The Hoechst is imaged using the 405 nm LED and DAPI filter cube. GFP is imaged using the 465 nm LED and GFP filter cube, while RFP is imaged using 523 nm LED and RFP filter cube. Images of target and non-target cell wells are acquired by first establishing the LED intensity and integration times on a positive-control well; i.e., recipient cells treated with adenovirus coding for Cre recombinase instead of fusosomes.

Acquisition settings are set so that RFP and GFP intensities are at the maximum pixel intensity values but not saturated. The wells of interest are then imaged using the established settings. Wells are imaged every 4 hours to acquire time-course data for rates of fusion activity.

Analysis of GFP and RFP-positive wells is performed with software provided with the fluorescent microscope or other software (Rasband, W. S., ImageJ, U. S. National Institutes of Health, Bethesda, Md., USA, rsb.info.nih.gov/ij/, 1997-2007).

The images are pre-processed using a rolling ball background subtraction algorithm with a 60 um width. The total cell mask is set on the Hoechst-positive cells. Cells with Hoechst intensity significantly above background intensities are thresholded and areas too small or large to be Hoechst-positive cells are excluded.

Within the total cell mask, GFP and RFP-positive cells are identified by again thresholding for cells significantly above background and extending the Hoechst (nuclei) masks for the entire cell area to include the entire GFP and RFP cellular fluorescence. The number of RFP-positive cells identified in control wells containing target or non-target recipient cells is used to subtract from the number of RFP-positive cells in the wells containing fusosome (to subtract for non-specific Loxp recombination). The number of RFP-positive cells (fused recipient cells) is then divided by the sum of the GFP-positive cells (recipient cells that have not fused) and RFP-positive cells at each time point to quantify the rate of fusosome fusion within the recipient cell population. The rate is normalized to the given dose of fusosome applied to the recipient cells. For rates of targeted fusion (fusosome fusion to targeted cells), the rate of fusion to the non-target cell is subtracted from the rate of fusion to the target cell in order to quantify rates of targeted fusion.

In an embodiment, the average rate of fusion for the fusosomes with the target cells will be in the range of 0.01-4.0 RFP/GFP cells per hour for target cell fusion or at least 1%, 2%, 3%, 4%, 5%, 10%, 20%, 30%, 40%, 50%, 60%, 70%, 80%, 90% or greater than non-target recipient cells with fusosomes. In an embodiment, groups with no fusosome applied will show a background rate of <0.01 RFP/GFP cells per hour.

Example 55: In Vitro Fusion to Deliver a Membrane Protein

This example describes fusosome fusion with a cell in vitro. In an embodiment, fusosome fusion with a cell in vitro results in delivery of an active membrane protein to the recipient cell.

In this example, the fusosomes are generated from a HEK293T cell expressing the Sendai virus HVJ-E protein (Tanaka et al., 2015, Gene Therapy, 22(October 2014), 1-8. doi.org/10.1038/gt.2014.12). In an embodiment, the fusosomes are generated to express the membrane protein, GLUT4, which is found primarily in muscle and fat tissues and is responsible for the insulin-regulated transport of glucose into cells. Fusosomes with and without GLUT4 are prepared from HEK293T cells as described by any of the methods described in a previous Example.

Muscles cells, such as, C2Cl2 cells, are then treated with fusosomes expressing GLUT4, fusosomes that do not express GLUT4, PBS (negative control), or insulin (positive control). The activity of GLUT4 on C2Cl2 cells is measured by the uptake of the fluorescent 2-deoxyglucose analog, 2-[N-(7-nitrobenz-2-oxa-1,3-diaxol-4-yl)amino]-2-deoxyglucose (2-NBDG). The fluorescence of C2Cl2 cells is assessed via microscopy using methods described in previous Examples.

In an embodiment, C2Cl2 cells that are treated with fusosomes that express GLUT4 and insulin are expected to demonstrate increased fluorescence compared to C2Cl2 cells treated with PBS or fusosomes not expressing GLUT4.

See, also, Yang et al., *Advanced Materials* 29, 1605604, 2017.

Example 56: In Vivo Delivery of Membrane Protein

This example describes fusosome fusion with a cell in vivo. In an embodiment, fusosome fusion with a cell in vivo results in delivery of an active membrane protein to the recipient cell.

In this example, the fusosomes are generated from a HEK293T cell expressing the Sendai virus HVJ-E protein as in the previous Example. In an embodiment, the fusosomes are generated to express the membrane protein, GLUT4. Fusosomes with and without GLUT4 are prepared from HEK293T cells as described by any of the methods described in a previous Example.

BALB/c-nu mice are administered fusosomes expressing GLUT4, fusosomes that do not express GLUT4, or PBS (negative control). Mice are injected intramuscularly in the tibialis anterior muscle with fusosomes or PBS. Immediately prior to fusosome administration, mice are fasted for 12 hours and injected with [$_{18}$F] 2-fluoro-2deoxy-$_d$-glucose ($_{18}$F-FDG), which is an analog of glucose that enables positron emission tomography (PET imaging). Mice are injected with $_{18}$F-FDG via the tail vein under anesthesia (2% isoflurane). PET imaging is performed using a nanoscale imaging system (1T, Mediso, Hungary). Imaging is conducted 4 hours after administration of fusosomes. Immediately after imaging, mice are sacrificed and the tibialis anterior muscle is weighed. PET images are reconstructed using a 3D imaging system in full detector mode, with all corrections on, high regularization, and eight iterations. Three-dimensional volume of interest (VOI) analysis of the reconstructed images is performed using the imaging software package (Mediso, Hungary) and applying standard uptake value (SUV) analysis. VOI fixed with a diameter of 2 mm sphere, is drawn for the tibialis anterior muscle site. The SUV of each VOI sites is calculated using the following formula: SUV=(radioactivity in volume of interest, measured as Bq/cc×body weight)/injected radioactivity.

In an embodiment, mice that are administered fusosomes expressing GLUT4 are expected to demonstrate an increased radioactive signal in VOI as compared to mice administered PBS or fusosomes that do not express GLUT4.

See, also, Yang et al., *Advanced Materials* 29, 1605604, 2017.

Example 57: Measuring Extravasation from Blood Vessels

This Example describes quantification of fusosome extravasation across an endothelial monolayer as tested with an in vitro microfluidic system (J. S Joen et al. 2013, journals.plos.org/plosone/article?id=10.1371/journal-.pone.0056910).

Cells extravasate from the vasculature into surrounding tissue. Without wishing to be bound by theory, extravasation is one way for fusosomes to reach extravascular tissues.

The system includes three independently addressable media channels, separated by chambers into which an ECM-mimicking gel can be injected. In brief, the microfluidics system has molded PDMS (poly-dimethyl siloxane; Silgard 184; Dow Chemical, MI) through which access ports are bored and bonded to a cover glass to form microfluidic channels. Channel cross-sectional dimensions are 1 mm (width) by 120 m (height). To enhance matrix adhesion, the PDMS channels are coated with a PDL (poly-D-lysine hydrobromide; 1 mg/ml; Sigma-Aldrich, St. Louis, Mo.) solution.

Next, collagen type I (BD Biosciences, San Jose, Calif., USA) solution (2.0 mg/ml) with phosphate-buffered saline (PBS; Gibco) and NaOH is injected into the gel regions of the device via four separate filling ports and incubated for 30 min to form a hydrogel. When the gel is polymerized, endothelial cell medium (acquired from suppliers such as Lonza or Sigma) is immediately pipetted into the channels to prevent dehydration of the gel. Upon aspirating the medium, diluted hydrogel (BD science) solution (3.0 mg/ml) is introduced into the cell channel and the excess hydrogel solution is washed away using cold medium.

Endothelial cells are introduced into the middle channel and allowed to settle to form an endothelium. Two days after endothelial cell seeding, fusosomes or macrophage cells (positive control) are introduced into the same channel where endothelial cells had formed a complete monolayer. The fusosomes are introduced so they adhere to and transmigrate across the monolayer into the gel region. Cultures are kept in a humidified incubator at 37° C. and 5% $CO_2$. A GFP-expressing version of the fusosome is used to enable live-cell imaging via fluorescent microscopy. On the following day, cells are fixed and stained for nuclei using DAPI staining in the chamber, and multiple regions of interest are imaged using confocal microscope to determine how many fusosomes passed through the endothelial monolayer.

In an embodiment, DAPI staining will indicate that fusosomes and positive control cells are able to pass through the endothelial barrier after seeding.

Example 58: Measuring Chemotactic Cell Mobility

This Example describes quantification of fusosome chemotaxis. Cells can move towards or away from a chemical gradient via chemotaxis. In an embodiment, chemotaxis will allow fusosomes to home to a site of injury, or track a pathogen. A purified fusosome composition as produced by any one of the methods described in previous Examples is assayed for its chemotactic abilities as follows.

A sufficient number of fusosomes or macrophage cells (positive control) are loaded in a micro-slide well according to the manufacturer's provided protocol in DMEM media (ibidi.com/img/cms/products/labware/channel_slides/ S_8032X_Chemotaxis/IN_8032X_Chemotaxis.pdf). Fusosomes are left at 37° C. and 5% CO2 for 1 h to attach. Following cell attachment, DMEM (negative control) or DMEM containing MCP1 chemoattractant is loaded into adjacent reservoirs of the central channel and the fusosomes are imaged continuously for 2 hours using a Zeiss inverted widefield microscope. Images are analyzed using ImageJ software (Rasband, W. S., ImageJ, U. S. National Institutes of Health, Bethesda, Md., USA, http://rsb.info.nih.gov/ij/, 1997-2007). Migration co-ordination data for each observed fusosome or cell is acquired with the manual tracking plugin (Fabrice Cordelibres, Institut Curie, Orsay, France). Chemotaxis plots and migration velocities is determined with the Chemotaxis and Migration Tool (ibidi).

In an embodiment, the average accumulated distance and migration velocity of fusosomes will be within 1%, 2%, 3%, 4%, 5%, 10%, 20%, 30%, 40%, 50%, 60%, 70%, 80%, 90%, 100% or greater than the response of the positive control cells to chemokine. The response of cells to a chemokine is described, e.g., in Howard E. Gendelman et al., *Journal of Neuroimmune Pharmacology*, 4(1): 47-59, 2009.

Example 59: Measuring Homing Potential

This Example describes homing of fusosomes to a site of injury. Cells can migrate from a distal site and/or accumulate at a specific site, e.g., home to a site. Typically, the site is a site of injury. In an embodiment, fusosomes will home to, e.g., migrate to or accumulate at, a site of injury.

Eight week old C57BL/6J mice (Jackson Laboratories) are dosed with notexin (NTX) (Accurate Chemical & Scientific Corp), a myotoxin, in sterile saline by intramuscular (IM) injection using a 30 G needle into the right tibialis anterior (TA) muscle at a concentration of 2 µg/mL. The skin over the tibialis anterior (TA) muscle is prepared by depilating the area using a chemical hair remover for 45 seconds, followed by 3 rinses with water. This concentration is chosen to ensure maximum degeneration of the myofibers, as well as minimal damage to their satellite cells, the motor axons and the blood vessels.

On day 1 after NTX injection, mice receive an IV injection of fusosomes or cells that express firefly luciferase. Fusosomes are produced from cells that stably express firefly luciferase by any one of the methods described in previous Examples. A bioluminescent imaging system (Perkin Elmer) is used to obtain whole animal images of bioluminescence at 0, 1, 3, 7, 21, and 28 post injection.

Five minutes before imaging, mice receive an intraperitoneal injection of bioluminescent substrate (Perkin Elmer) at a dose of 150 mg/kg in order to visualize luciferase. The imaging system is calibrated to compensate for all device settings. The bioluminescent signal is measured using Radiance Photons, with Total Flux used as a measured value. The region of interest (ROI) is generated by surrounding the signal of the ROI in order to give a value in photons/second. An ROI is assessed on both the TA muscle treated with NTX and on the contralateral TA muscle, and the ratio of photons/second between NTX-treated and NTX-untreated TA muscles is calculated as a measure of homing to the NTX-treated muscle.

In an embodiment, the ratio of photons/second between NTX-treated and NTX-untreated TA muscles in fusosomes and cells will be greater than 1 indicating site specific accumulation of luciferase-expressing fusosomes at the injury.

See, for example, Plant et al., Muscle Nerve 34(5)L 577-85, 2006.

Example 60: Measuring Phagocytic Activity

This Example demonstrates phagocytic activity of fusosomes. In an embodiment, fusosomes have phagocytic activity, e.g., are capable of phagocytosis. Cells engage in phagocytosis, engulfing particles, enabling the sequestration and destruction of foreign invaders, like bacteria or dead cells.

A purified fusosome composition as produced by any one of the methods described in previous Examples comprising a fusosome from a mammalian macrophage having partial or complete nuclear inactivation was capable of phagocytosis assayed via pathogen bioparticles. This estimation was made by using a fluorescent phagocytosis assay according to the following protocol.

Macrophages (positive control) and fusosomes were plated immediately after harvest in separate confocal glass bottom dishes. The macrophages and fusosomes were incubated in DMEM+10% FBS+1% P/S for 1 h to attach. Fluorescein-labeled *E. coli* K12 and non-fluorescein-labeled *Escherichia coli* K-12 (negative control) were added to the macrophages/fusosomes as indicated in the manufacturer's protocol, and were incubated for 2 h, tools.thermofisher.com/content/sfs/manuals/mp06694.pdf. After 2 h, free fluorescent particles were quenched by adding Trypan blue. Intracellular fluorescence emitted by engulfed particles was imaged by confocal microscopy at 488 excitation. The number of phagocytotic positive fusosome were quantified using image J software.

The average number of phagocytotic fusosomes was at least 30% 2 h after bioparticle introduction, and was greater than 30% in the positive control macrophages.

Example 61: Measuring Ability to Cross a Cell Membrane or the Blood Brain Barrier This Example describes quantification of fusosomes crossing the blood brain barrier. In an embodiment, fusosomes will cross, e.g., enter and exit, the blood brain barrier, e.g., for delivery to the central nervous system.

Eight week old C57BL/6J mice (Jackson Laboratories) are intravenously injected with fusosomes or leukocytes (positive control) that express firefly luciferase. Fusosomes are produced from cells that stably express firefly luciferase or cells that do not express luciferase (negative control) by any one of the methods described in previous Examples. A bioluminescent imaging system (Perkin Elmer) is used to obtain whole-animal images of bioluminescence at one, two, three, four, five, six, eight, twelve, and twenty-four hours after fusosome or cell injection.

Five minutes before imaging, mice receive an intraperitoneal injection of bioluminescent substrate (Perkin Elmer) at a dose of 150 mg/kg in order to visualize luciferase. The imaging system is calibrated to compensate for all device settings. The bioluminescent signal is measured, with total flux used as a measured value. The region of interest (ROI) is generated by surrounding the signal of the ROI in order to give a value in photons/second. The ROI selected is the head of the mouse around the area that includes the brain.

In an embodiment, the photons/second in the ROI will be greater in the animals injected with cells or fusosomes that express luciferase than the negative control fusosomes that do not express luciferase indicating accumulation of luciferase-expressing fusosomes in or around the brain.

Example 62: Measuring Potential for Protein Secretion

This Example describes quantification of secretion by fusosomes. In an embodiment, fusosomes will be capable of secretion, e.g., protein secretion. Cells can dispose or discharge of material via secretion. In an embodiment, fusosomes will chemically interact and communicate in their environment via secretion.

The capacity of fusosomes to secrete a protein at a given rate is determined using the *Gaussia* luciferase flash assay from ThermoFisher Scientific (catalog #16158). Mouse embryonic fibroblast cells (positive control) or fusosomes as produced by any one of the methods described in previous Examples are incubated in growth media and samples of the media are collected every 15 minutes by first pelleting the fusosomes at 1600 g for 5 min and then collecting the supernatant. The collected samples are pipetted into a clear-bottom 96-well plate. A working solution of assay buffer is then prepared according to the manufacturer's instructions.

Briefly, colenterazine, a luciferin or light-emitting molecule, is mixed with flash assay buffer and the mixture is pipetted into each well of the 96 well plate containing samples. Negative control wells that lack cells or fusosomes include growth media or assay buffer to determine background *Gaussia* luciferase signal. In addition, a standard curve of purified *Gaussia* luciferase (Athena Enzyme Systems, catalog #0308) is prepared in order to convert the luminescence signal to molecules of *Gaussia* luciferase secretion per hour.

The plate is assayed for luminescence, using 500 msec integration. Background *Gaussia* luciferase signal is subtracted from all samples and then a linear best-fit curve is calculated for the *Gaussia* luciferase standard curve. If sample readings do not fit within the standard curve, they are diluted appropriately and re-assayed. Using this assay, the capacity for fusosomes to secrete *Gaussia* luciferase at a rate (molecules/hour) within a given range is determined.

In an embodiment, fusosomes will be capable of secreting proteins at a rate that is 1%, 2%, 3%, 4%, 5%, 10%, 20%, 30%, 40%, 50%, 60%, 70%, 80%, 90%, 100% or greater than the positive control cells.

Example 63: Measuring Signal Transduction Potential

This Example describes quantification of signal transduction in fusosomes. In an embodiment, fusosomes are capable of signal transduction. Cells can send and receive molecular signals from the extracellular environment through signaling cascades, such as phosphorylation, in a process known as signal transduction. A purified fusosome composition as produced by any one of the methods described in previous Examples comprising a fusosome from a mammalian cell having partial or complete nuclear inactivation is capable of signal transduction induced by insulin. Signal transduction induced by insulin is assessed by measuring AKT phosphorylation levels, a key pathway in the insulin receptor signaling cascade, and glucose uptake in response to insulin.

To measure AKT phosphorylation, cells, e.g., Mouse Embryonic Fibroblasts (MEFs) (positive control), and fusosomes are plated in 48-well plates and left for 2 hours in a humidified incubator at 37° C. and 5% $CO_2$. Following cell adherence, insulin (e.g. at 10 nM), or a negative control solution without insulin, is add to the well containing cells or fusosomes for 30 min. After 30 minutes, protein lysate is made from the fusosomes or cells, and phospho-AKT levels are measured by western blotting in insulin stimulated and control unstimulated samples.

Glucose uptake in response to insulin or negative control solution is measured as it is explained in the glucose uptake section by using labeled glucose (2-NBDG). (S. Galic et al., *Molecular Cell Biology* 25(2): 819-829, 2005).

In an embodiment, fusosomes will enhance AKT phosphorylation and glucose uptake in response to insulin over the negative controls by at least 1%, 2%, 3%, 4%, 5%, 10%, 20%, 30%, 40%, 50%, 60%, 70%, 80%, 90%, 100% or greater.

Example 64: Measuring Ability to Transport Glucose Across Cell Membrane

This Example describes quantification of the levels of a 2-NBDG (2-(N-(7-Nitrobenz-2-oxa-1,3-diazol-4-yl) Amino)-2-Deoxyglucose) a fluorescent glucose analog that can be used to monitor glucose uptake in live cells, and thus measure active transport across the lipid bilayer. In an embodiment, this assay can be used to measure the level of glucose uptake and active transport across the lipid bilayer of the fusosome.

A fusosome composition is produced by any one of the methods described in previous Examples. A sufficient number of fusosomes are then incubated in DMEM with no glucose, 20% Fetal Bovine Serum and 1× Penicillin/Streptomycin for 2 hr at 37° C. and 5% $CO_2$. After a 2 hr glucose starvation period, the medium is changed such that it includes DMEM with no glucose, 20% Fetal Bovine Serum, 1× Penicillin/Streptomycin and 20 uM 2-NBDG (ThermoFisher) and incubated for an additional 2 hr at 37° C. and 5% $CO_2$.

Negative control fusosomes are treated the same, except an equal amount of DMSO is added in place of 2-NBDG.

The fusosomes are then washed thrice with 1×PBS and re-suspended in an appropriate buffer, and transferred to a 96 well imaging plate. 2-NBDG fluorescence is then measured in a fluorimeter using a GFP light cube (469/35 excitation filter and a 525/39 emission filter) to quantify the amount of 2-NBDG that has been transported across the fusosome membrane and accumulated in the fusosome in the 1 hr loading period.

In an embodiment, 2-NBDG fluorescence will be higher in the fusosome with 2-NBDG treatment as compared to the negative (DMSO) control. Fluorescence measure with a 525/39 emission filter will correlate with to the number of 2-NBDG molecules present.

Example 65: Lumen of Fusosomes are Miscible with Aqueous Solutions

This example assesses the miscibility of a fusosome lumen with aqueous solutions, such as water.

The fusosomes are prepared as described in previous Examples. The controls are dialysis membranes with either hypotonic solution, hyperosmotic solution or normal osmotic solutions.

Fusosomes, positive control (normal osmotic solution) and negative control (hypotonic solution) are incubated with hypotonic solution (150 mOsmol). The cell size is measured under a microscope after exposing each sample to the aqueous solution. In an embodiment, the fusosome and positive control sizes in the hypotonic solution increase in comparison to the negative control.

Fusosomes, positive control (normal osmotic solution) and negative control (hyperosmotic solution) are incubated with a hyperosmotic solution (400 mOsmol). The cell size is measured under a microscope after exposing each sample to the aqueous solution. In an embodiment, the fusosome and positive control sizes in the hyperosmotic solution will decrease in comparison to the negative control.

Fusosomes, positive control (hypotonic or hyperosmotic solution) and negative control (normal osmotic) are incubated with a normal osmotic solution (290 mOsmol). The cell size is measured under a microscope after exposing each sample to the aqueous solution. In an embodiment, the fusosome and positive control sizes in the normal osmotic solution will remain substantially the same in comparison to the negative control.

Example 66: Measuring Esterase Activity in the Cytosol

This Example describes quantification of esterase activity, as a surrogate for metabolic activity, in fusosomes. The cytosolic esterase activity in fusosomes is determined by quantitative assessment of calcein-AM staining (Bratosin et al., Cytometry 66(1): 78-84, 2005).

The membrane-permeable dye, calcein-AM (Molecular Probes, Eugene Oreg. USA), is prepared as a stock solution of 10 mM in dimethylsulfoxide and as a working solution of 100 mM in PBS buffer, pH 7.4. Fusosomes as produced by any one of the methods described in previous Examples or positive control parental Mouse Embryonic Fibroblast cells are suspended in PBS buffer and incubated for 30 minutes with calcein-AM working solution (final concentration in calcein-AM: 5 mM) at 37° C. in the dark and then diluted in PBS buffer for immediate flow cytometric analysis of calcein fluorescence retention.

Fusosomes and control parental Mouse Embryonic Fibroblast cells are experimental permeabilized as a negative control for zero esterase activity with saponin as described in (Jacob et al., *Cytometry* 12(6): 550-558, 1991). Fusosomes and cells are incubated for 15 min in 1% saponin solution in PBS buffer, pH 7.4, containing 0.05% sodium azide. Due to the reversible nature of plasma membrane permeabilization, saponin is included in all buffers used for further staining and washing steps. After saponin permeabilization, fusosomes and cells are suspended in PBS buffer containing 0.1% saponin and 0.05% sodium azide and incubated (37 C in the dark for 45 min) with calcein-AM to a final concentration of 5 mM, washed three times with the same PBS buffer containing 0.1% saponin and 0.05% sodium azide, and analyzed by flow cytometry. Flow cytometric analyses are performed on a FACS cytometer (Becton Dickinson, San Jose, Calif., USA) with 488 nm argon laser excitation and emission is collected at 530+/−30 nm. FACS software is used for acquisition and analysis. The light scatter channels are set on linear gains, and the fluorescence channels are set on a logarithmic scale, with a minimum of 10,000 cells analyzed in each condition. Relative esterase activities are calculated based on the intensity of calcein-AM in each sample. All events are captured in the forward and side scatter channels (alternatively, a gate can be applied to select only the fusosome population). The fluorescence intensity (FI) value for the fusosomes is determined by subtracting the FI value of the respective negative control saponin-treated sample. The normalized esterase activity for the fusosomes samples are normalized to the respective positive control cell samples in order to generate quantitative measurements for cytosolic esterase activities.

In an embodiment, a fusosome preparation will have within 1%, 2%, 3%, 4%, 5%, 10%, 20%, 30%, 40%, 50%, 60%, 70%, 80%, 90%, 100% or greater esterase activity compared to the positive control cell.

See also, Bratosin D, Mitrofan L, Palii C, Estaquier J, Montreuil J. Novel fluorescence assay using calcein-AM for the determination of human erythrocyte viability and aging. Cytometry A. 2005 July; 66(1):78-84; and Jacob B C, Favre M, Bensa J C. Membrane cell permeabilisation with saponin and multiparametric analysis by flow cytometry. Cytometry 1991; 12:550-558.

Example 67: Measuring Acetylcholinesterase Activity in Fusosomes

Acetylcholinesterase activity is measured using a kit (MAK119, SIGMA) that follows a procedure described previously (Ellman, et al., Biochem. Pharmacol. 7, 88, 1961) and following the manufacturer's recommendations.

Briefly, fusosomes are suspended in 1.25 mM acetylthiocholine in PBS, pH 8, mixed with 0.1 mM 5,5-dithio-bis(2-nitrobenzoic acid) in PBS, pH 7. The incubation is performed at room temperature but the fusosomes and the substrate solution are pre-warmed at 37° C. for 10 min before starting the optical density readings.

Changes in absorption are monitored at 450 nm for 10 min with a plate reader spectrophotometer (ELX808, BIO-TEK instruments, Winooski, Vt., USA). Separately, a sample is used for determining the protein content of the fusosomes via bicinchoninic acid assay for normalization. Using this assay, the fusosomes are determined to have <100 AChE activity units/g of protein.

In an embodiment, AChE activity units/pg of protein values will be less than 0.001, 0.01, 0.1, 1, 10, 100, or 1000.

Example 68: Measuring Metabolic Activity Level

This Example describes quantification of the measurement of citrate synthase activity in fusosomes.

Citrate synthase is an enzyme within the tricarboxylic acid (TCA) cycle that catalyzes the reaction between oxaloacetate (OAA) and acetyl-CoA to generate citrate. Upon hydrolysis of acetyl-CoA, there is a release of CoA with a thiol group (CoA-SH). The thiol group reacts with a chemical reagent, 5,5-Dithiobis-(2-nitrobenzoic acid) (DTNB), to form 5-thio-2-nitrobenzoic acid (TNB), which is a yellow product that can be measured spectrophotometrically at 412 nm (Green 2008). Commercially-available kits, such as the Abcam Human Citrate Synthase Activity Assay Kit (Product #ab119692) provide all the necessary reagents to perform this measurement.

The assay is performed as per the manufacturer's recommendations. Fusosome sample lysates are prepared by collecting the fusosomes as produced by any one of the methods described in previous Examples and solubilizing them in Extraction Buffer (Abcam) for 20 minutes on ice. Supernatants are collected after centrifugation and protein content is assessed by bicinchoninic acid assay (BCA, ThermoFisher Scientific) and the preparation remains on ice until the following quantification protocol is initiated.

Briefly, fusosome lysate samples are diluted in 1× Incubation buffer (Abcam) in the provided microplate wells, with one set of wells receiving only 1× Incubation buffer. The plate is sealed and incubated for 4 hours at room temperature with shaking at 300 rpm. The buffer is then aspirated from the wells and 1× Wash buffer is added. This washing step is repeated once more. Then, 1× Activity solution is added to each well, and the plate is analyzed on a microplate reader by measuring absorbance at 412 nm every 20 seconds for 30 minutes, with shaking between readings.

Background values (wells with only 1× Incubation buffer) are subtracted from all wells, and the citrate synthase activity is expressed as the change in absorbance per minute per ug of fusosome lysate sample loaded ($\Delta mOD@412$ nm/min/ug protein). Only the linear portion from 100-400 seconds of the kinetic measurement is used to calculate the activity.

In an embodiment, a fusosome preparation will have within 1%, 2%, 3%, 4%, 5%, 10%, 20%, 30%, 40%, 50%, 60%, 70%, 80%, 90%, 100% or greater synthase activity compared to the control cell.

See, for example, Green H J et al. Metabolic, enzymatic, and transporter response in human muscle during three consecutive days of exercise and recovery. Am J Physiol Regul Integr Comp Physiol 295: R1238-R1250, 2008.

Example 69: Measuring Respiration Levels

This Example describes quantification of the measurement of respiration level in fusosomes. Respiration level in cells can be a measure of oxygen consumption, which powers metabolism. Fusosome respiration is measured for oxygen consumption rates by a Seahorse extracellular flux analyzer (Agilent) (Zhang 2012).

Fusosomes as produced by any one of the methods described in previous Examples or cells are seeded in a 96-well Seahorse microplate (Agilent). The microplate is centrifuged briefly to pellet the fusosomes and cells at the bottom of the wells. Oxygen consumption assays are initiated by removing growth medium, replacing with a low-buffered DMEM minimal medium containing 25 mM glucose and 2 mM glutamine (Agilent) and incubating the microplate at 37° C. for 60 minutes to allow for temperature and pH equilibrium.

The microplate is then assayed in an extracellular flux analyzer (Agilent) that measures changes in extracellular oxygen and pH in the media immediately surrounding adherent fusosomes and cells. After obtaining steady state oxygen consumption (basal respiration rate) and extracellular acidification rates, oligomycin (5ΞM), which inhibits ATP synthase, and proton ionophore FCCP (carbonyl cyanide 4-(trifluoromethoxy) phenylhydrazone; 2 µM), which uncouples mitochondria, are added to each well in the microplate to obtain values for maximal oxygen consumption rates.

Finally, 5 µM antimycin A (inhibitor of mitochondria complex III) is added to confirm that respiration changes are due mainly to mitochondrial respiration. The minimum rate of oxygen consumption after antimycin A addition is subtracted from all oxygen consumption measurements to remove the non-mitochondrial respiration component. Cell samples that do not appropriately respond to oligomycin (at least a 25% decrease in oxygen consumption rate from basal) or FCCP (at least a 50% increase in oxygen consumption rate after oligomycin) are excluded from the analysis. Fusosomes respiration level is then measured as pmol $O_2$/min/1e4 fusosomes.

This respiration level is then normalized to the respective cell respiration level. In an embodiment, fusosomes will have at least 1%, 2%, 3%, 4%, 5%, 10%, 20%, 30%, 40%, 50%, 60%, 70%, 80%, 90%, 100% or greater respiration level compared to the respective cell samples.

See, for example, Zhang J, Nuebel E, Wisidagama D R R, et al. Measuring energy metabolism in cultured cells, including human pluripotent stem cells and differentiated cells. Nature protocols. 2012; 7(6):10.1038/nprot.2012.048. doi: 10.1038/nprot.2012.048.

Example 70: Measuring Phosphatidylserine Levels of Fusosomes

This Example describes quantification of the level of annexin-V binding to the surface of fusosomes.

Dying cells can display phosphatidylserine on the cell surface which is a marker of apoptosis in the programmed cell death pathway. Annexin-V binds to phosphatidylserine, and thus, annexin-V binding is a proxy for viability in cells.

Fusosomes were produced as described herein. For detection of apoptosis signals, fusosomes or positive control cells were stained with 5% annexin V fluor 594 (A13203, Thermo Fisher, Waltham, Mass.). Each group (detailed in the table below) included an experimental arm that was treated with an apoptosis-inducer, menadione. Menadione was added at 100 µM menadione for 4 h. All samples were run on a flow cytometer (Thermo Fisher, Waltham, Mass.) and fluorescence intensity was measured with the YL1 laser at a wavelength of 561 nm and an emission filter of 585/16 nm. The presence of extracellular phophatidyl serine was quantified by comparing fluorescence intensity of annexin V in all groups.

The negative control unstained fusosomes were not positive for annexin V staining.

In an embodiment, fusosomes were capable of upregulating phosphatidylserine display on the cell surface in response to menadione, indicating that non-menadione stimulated fusosomes are not undergoing apoptosis. In an embodiment, positive control cells that were stimulated with menadione demonstrated higher-levels of annexin V staining than fusosomes not stimulated with menadione.

TABLE 10

| Annexin V staining parameter | |
|---|---|
| Experimental Arm | Mean Fluorescence Intensity of Annexin V Signal (and standard deviation) |
| Unstained Fusosomes (negative control) | 941 (937) |
| Stained Fusosomes | 11257 (15826) |
| Stained Fusosomes + Menadione | 18733 (17146) |
| Stained Macrophages + Menadione (positive control) | 14301 (18142) |

Example 71: Measuring Juxtacrine-Signaling Levels

This Example describes quantification of juxtacrine-signaling in fusosomes.

Cells can form cell-contact dependent signaling via juxtacrine signaling. In an embodiment, presence of juxtacrine signaling in fusosomes will demonstrate that fusosomes can stimulate, repress, and generally communicate with cells in their immediate vicinity.

Fusosomes produced by any one of the methods described in previous Examples from mammalian bone marrow stromal cells (BMSCs) having partial or complete nuclear inactivation trigger IL-6 secretion via juxtacrine signaling in macrophages. Primary macrophages and BMSCs are co-cultured. Bone marrow-derived macrophages are seeded first into 6-well plates, and incubated for 24 h, then primary mouse BMSC-derived fusosomes or BMSC cells (positive control parental cells) are placed on the macrophages in a DMEM medium with 10% FBS. The supernatant is collected at different time points (2, 4, 6, 24 hours) and analyzed for IL-6 secretion by ELISA assay. (Chang J. et al., 2015).

In an embodiment, the level of juxtacrine signaling induced by BMSC fusosomes is measured by an increase in macrophage-secreted IL-6 levels in the media. In an embodiment, the level of juxtacrine signaling will be at least 1%, 2%, 3%, 4%, 5%, 10%, 20%, 30%, 40%, 50%, 60%, 70%, 80%, 90%, 100% or greater than the levels induced by the positive control bone marrow stromal cells (BMSCs).

Example 72: Measuring Paracrine-Signaling Levels

This Example describes quantification of paracrine signaling in fusosomes.

Cells can communicate with other cells in the local microenvironment via paracrine signaling. In an embodiment, fusosomes will be capable of paracrine signaling, e.g., to communicate with cells in their local environment. In an embodiment, the ability of fusosomes to trigger $Ca^{2+}$ signaling in endothelial cells via paracrine-derived secretion with the following protocol will measure $Ca^{2+}$ signaling via the calcium indicator, fluo-4 AM.

To prepare the experimental plate, murine pulmonary microvascular endothelial cells (MPMVECs) are plated on a 0.2% gelatin coated 25 mm glass bottom confocal dish (80% confluence). MPMVECs are incubated at room temperature for 30 min in ECM containing 2% BSA and 0.003% pluronic acid with 5 µM fluo-4 AM (Invitrogen) final concentration to allow loading of fluo-4 AM. After loading, MPMVECs are washed with experimental imaging solution (ECM containing 0.25% BSA) containing sulfinpyrazone to minimize dye loss. After loading fluo-4, 500 µl of pre-warmed experimental imaging solution is added to the plate, and the plate is imaged by a Zeiss confocal imaging system.

In a separate tube, freshly isolated murine macrophages are either treated with 1 µg/ml LPS in culture media (DMEM+10% FBS) or not treated with LPS (negative control). After stimulation, fusosomes are generated from macrophages by any one of the methods described in previous Examples.

Fusosomes or parental macrophages (positive control) are then labeled with cell tracker red, CMTPX (Invitrogen), in ECM containing 2% BSA and 0.003% pluronic acid. Fusosomes and macrophages are then washed and resuspended in experimental imaging solution. Labeled fusosomes and macrophages are added onto the fluo-4 AM loaded MPMVECs in the confocal plate.

Green and red fluorescence signal is recorded every 3 s for 10-20 min using Zeiss confocal imaging system with argon ion laser source with excitation at 488 and 561 nm for fluo-4 AM and cell tracker red fluorescence respectively. Fluo-4 fluorescence intensity changes are analyzed using imaging software (Mallilankaraman, K. et al., J Vis Exp. (58): 3511, 2011). The level of Fluo-4 intensity measured in negative control fusosome and cell groups is subtracted from LPS-stimulated fusosome and cell groups.

In an embodiment, fusosomes, e.g., activated fusosomes, will induce an increase in Fluo-4 fluorescence intensity that is at least 1%, 2%, 3%, 4%, 5%, 10%, 20%, 30%, 40%, 50%, 60%, 70%, 80%, 90%, 100% or greater than the positive control cell groups.

Example 73: Measuring Ability to Polymerize Actin for Mobility

This Example describes quantification of cytoskeletal components, such as actin, in fusosomes. In an embodiment, fusosomes comprise cytoskeletal components such as actin, and are capable of actin polymerization.

Cells use actin, which is a cytoskeletal component, for motility and other cytoplasmic processes. The cytoskeleton is essential to creating motility driven forces and coordinating the process of movement C2Cl2 cells were enucleated as described herein. Fusosomes obtained from the 12.5% and 15% Ficoll layers were pooled and labeled 'Light', while fusosomes from the 16-17% layers were pooled and labeled 'Medium'. Fusosomes or cells (parental C2Cl2 cells, positive control) were resuspended in DMEM+Glutamax+10% Fetal Bovine Serum (FBS), plated in 24-well ultra-low attachment plates (#3473, Corning Inc, Corning, N.Y.) and incubated at 37° C.+5% $CO_2$. Samples were taken periodically (5.25 hr, 8.75 hr, 26.5 hr) and stained with 165 µM rhodamine phalloidin (negative control was not stained) and measured on a flow cytometer (#A24858, Thermo Fisher, Waltham, Mass.) with a FC laser YL1 (561 nm with 585/16 filter) to measure F-actin cytoskeleton content. The fluorescence intensity of rhodamine phalloidin in fusosomes was measured along with unstained fusosomes and stained parental C2Cl2 cells.

Figure 4:
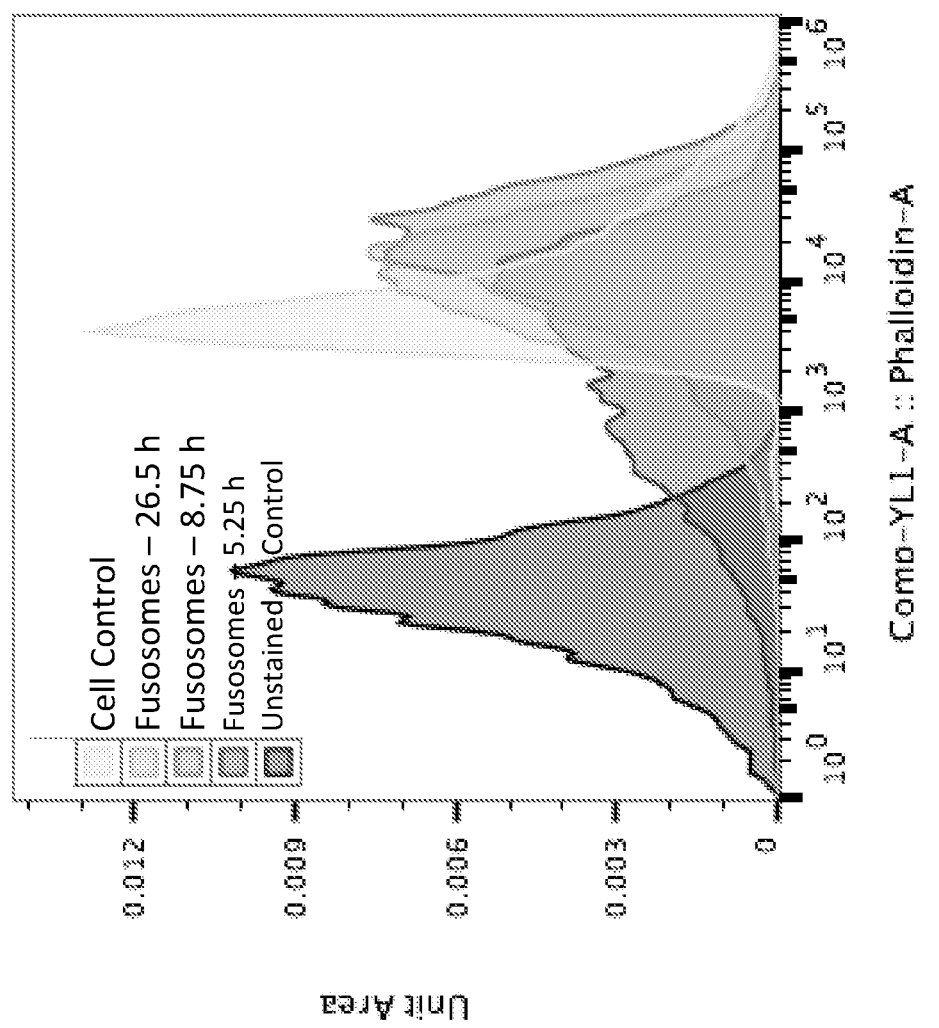
FIG. 4 quantifies staining of fusosomes with a dye for F-actin.

Fusosome fluorescence intensity was greater (FIG. 4) than the negative control at all timepoints, and fusosomes were capable of polymerizing actin at a similar rate to the parental C2Cl2 cells.

Additional cytoskeletal components, such as those listed in the table below, are measured via a commercially available ELISA systems (Cell Signaling Technology and MyBioSource), according to manufacturer's instructions.

TABLE 11

| Cytoskeletal components | | |
|---|---|---|
| Cytoskeletal protein measured | Commercial Kit Type | Kit ID |
| Actin | Path Scan Total B-Actin Sandwich ELISA Kit | Cell Signaling, 7880 |
| Arp2/3 | Human Actin Related protein 2/3 complex subunit(APRC2) ELISA KIT | MyBioSource, MBS7224740 |
| Formin | Formin Binding Protein 1 (FNBP1), ELISA Kit | MyBioSource, MBS9308864 |
| Coronin | Human Coronin 1A ELISA Kit | MyBioSource, MBS073640 |
| Dystrophin | Human dystrophin ELISA Kit | MyBioSource MBS722223 |
| Keratin | Human Keratin 5 ELISA Kit | MyBioSource, MBS081200 |
| Myosin | Human Myosin IG (MYO1G) ELISA Kit | MyBioSource, MBS9312965 |
| Tubulin | Human Tubulin Beta 3 ELISA Kit | MyBioSource, MBS097321 |

Then 100 uL of appropriately-diluted lysate is added to the appropriate well from the microwell strips. The microwells are sealed with tape and incubated for 2 hrs at 37 C. After incubation, the sealing tape is removed and the contents are discarded. Each microwell is washed four times with 200 uL of 1× Wash Buffer. After each individual wash, plates are struck onto an absorbent cloth so that the residual wash solution is removed from each well. However, wells are not completely dry at any time during the experiment.

Next, 100 ul of the reconstituted Detection Antibody (green) is added each individual well, except for negative control wells. Then wells are sealed and incubated for 1 hour at 37° C. The washing procedure is repeated after incubation is complete. 100 uL of reconstituted HRP-Linked secondary antibody (red) is added to each of the wells. The wells are sealed with tape and incubated for 30 minutes at 37° C. The sealing tape is then removed and the washing procedure is repeated. 100 uL of TMB Substrate is then added to each well. The wells are sealed with tape, then incubated for 10 minutes at 37° C. Once this final incubation is complete, 100 uL of STOP solution is added to each of the wells and the plate is shaken gently for several seconds.

Spectrophotometric analysis of the assay is conducted within 30 minutes of adding the STOP solution. The underside of the wells is wiped with lint-free tissue and then absorbance is read at 450 nm. In an embodiment, fusosome samples that have been stained with the detection antibody will absorb more light at 450 nm that negative control fusosome samples, and absorb less light than cell samples that have been stained with the detection antibody.

Example 74: Measuring Average Membrane Potential

This Example describes quantification of the mitochondrial membrane potential of fusosomes. In an embodiment, fusosomes comprising a mitochondrial membrane will maintain mitochondrial membrane potential.

Mitochondrial metabolic activity can be measured by mitochondrial membrane potential. The membrane potential of the fusosome preparation is quantified using a commercially available dye, TMRE, for assessing mitochondrial membrane potential (TMRE: tetramethyl rhodamine, ethyl ester, perchlorate, Abcam, Cat #T669).

Fusosomes are generated by any one of the methods described in previous Examples. Fusosomes or parental cells are diluted in growth medium (phenol-red free DMEM with 10% fetal bovine serum) in 6 aliquots (untreated and FCCP-treated triplicates). One aliquot of the samples is incubated with FCCP, an uncoupler that eliminates mitochondrial membrane potential and prevents TMRE staining. For FCCP-treated samples, 2 µM FCCP is added to the samples and incubated for 5 minutes prior to analysis. Fusosomes and parental cells are then stained with 30 nM TMRE. For each sample, an unstained (no TMRE) sample is also prepared in parallel. Samples are incubated at 37° C. for 30 minutes. The samples are then analyzed on a flow cytometer with 488 nm argon laser, and excitation and emission is collected at 530+/−30 nm.

Membrane potential values (in millivolts, mV) are calculated based on the intensity of TMRE. All events are captured in the forward and side scatter channels (alternatively, a gate can be applied to exclude small debris). The fluorescence intensity (FI) value for both the untreated and FCCP-treated samples are normalized by subtracting the geometric mean of the fluorescence intensity of the unstained sample from the geometric mean of the untreated and FCCP-treated sample. The membrane potential state for each preparation is calculated using the normalized fluorescent intensity values with a modified Nernst equation (see below) that can be used to determine mitochondrial membrane potential of the fusosomes or cells based on TMRE fluorescence (as TMRE accumulates in mitochondria in a Nernstian fashion).

Fusosome or cell membrane potential is calculated with the following formula: (mV)=−61.5*log(FIuntreated-normalized/FIFCCP-treated-normalized). In an embodiment, using this assay on fusosome preparations from C2Cl2 mouse myoblast cells, the membrane potential state of the fusosome preparation will be within about 1%, 2%, 3%, 4%, 5%, 10%, 20%, 30%, 40%, 50%, 60%, 70%, 80%, 90%, 100% or greater than the parental cells. In an embodiment, the range of membrane potential is about −20 to −150 mV.

Example 75: Measuring Persistence Half-Life in a Subject

This Example describes the measurement of fusosome half-life.

Fusosomes are derived from cells that express *Gaussia* luciferase produced by any one of the methods described in previous Examples, and pure, 1:2, 1:5, and 1:10 dilutions in buffered solution are made. A buffered solution lacking fusosomes is used as a negative control.

Each dose is administered to three eight week old male C57BL/6J mice (Jackson Laboratories) intravenously. Blood is collected from the retro-orbital vein at 1, 2, 3, 4, 5, 6, 12, 24, 48, and 72 hours after intravenous administration of the fusosomes. The animals are sacrificed at the end of the experiment by $CO_2$ inhalation.

Blood is centrifuged for 20 min at room temperature. The serum samples are immediately frozen at −80° C. until bioanalysis. Then, each blood sample is used to carry out a *Gaussia* luciferase activity assay after mixing the samples with *Gaussia* luciferase substrate (Nanolight, Pinetop, Ariz.). Briefly, colenterazine, a luciferin or light-emitting molecule, is mixed with flash assay buffer and the mixture is pipetted into wells containing blood samples in a 96 well plate. Negative control wells that lack blood contain assay buffer to determine background *Gaussia* luciferase signal.

In addition, a standard curve of positive-control purified *Gaussia* luciferase (Athena Enzyme Systems, catalog #0308) is prepared in order to convert the luminescence signal to molecules of *Gaussia* luciferase secretion per hour. The plate is assayed for luminescence, using 500 msec integration. Background *Gaussia* luciferase signal is subtracted from all samples and then a linear best-fit curve is calculated for the *Gaussia* luciferase standard curve. If sample readings do not fit within the standard curve, they are diluted appropriately and re-assayed. The luciferase signal from samples taken at 1, 2, 3, 4, 5, 6, 12, 24, 48, and 72 hours is interpolated to the standard curve. The elimination rate constant $k_e$ ($h^{-1}$) is calculated using the following equation of a one-compartment model: $C(t)=C_0 \times e^{-k_e xt}$, in which $C(t)$ (ng/mL) is the concentration of fusosomes at time t (h) and Co the concentration of fusosomes at time=0 (ng/mL). The elimination half-life $t_{1/2,e}$ (h) is calculated as $\ln(2)/k_e$.

In an embodiment, fusosomes will have a half-life of at least 1%, 2%, 3%, 4%, 5%, 10%, 20%, 30%, 40%, 50%, 60%, 70%, 80%, 90%, 100% or greater than the negative control cells.

Example 76: Measuring Retention of Fusosomes in Circulation

This example describes quantification of fusosome delivery into the circulation and retention at organs. In an embodiment, fusosomes are delivered into the circulation, and are not captured and retained in organ sites.

In an embodiment, fusosomes delivered into the peripheral circulation evade capture and retention by the reticuloendothelial system (RES) in order to reach target sites with high efficiency. The RES comprises a system of cells, primarily macrophages, which reside in solid organs such as the spleen, lymph nodes and the liver. These cells are usually tasked with the removal of "old" cells, such as red blood cells.

Fusosomes are derived from cells expressing CRE recombinase (agent), or cells not expressing CRE (negative control). These fusosomes are prepared for in vivo injection as in Example 62.

The recipient mice harbor a loxp-luciferase genomic DNA locus that is modified by CRE protein made from mRNA delivered by the fusosomes to unblock the expression of luciferase (JAX#005125). Luciferase can be detected by bioluminescent imaging in a living animal. The positive control for this example are offspring of recipient mice mated to a mouse strain that expresses the same protein exclusively in macrophage and monocyte cells from its own genome (Cx3cr1-CRE JAX#025524). Offspring from this mating harbor one of each allele (loxp-luciferase, Cx3cr1-CRE).

Fusosomes are injected into the peripheral circulation via tail vein injection (IV, Example #48) into mice that harbor a genetic locus that when acted on by the CRE protein results in the expression of luciferase. The non-specific capture mechanism of the RES is phagocytic in nature releasing a proportion of the CRE protein from the fusosome into the macrophage resulting in genomic recombination. IVIS measurements (as described in Example 62) identify where non-fusogen controls accumulate and fuse. Accumulation in the spleen, lymph nodes and liver will be indicative of non-specific RES-mediated capture of the fusosome. IVIS is carried out at 24, 48 and 96 hours post-fusosome injection.

Mice are euthanized and spleen, liver and major lymphatic chain in the gut are harvested.

Genomic DNA is isolated from these organs and subjected to quantitative polymerase chain reaction against the recombined genomic DNA remnant. An alternative genomic locus (not targeted by CRE) is also quantified to provide a measure of the number of cells in the sample.

In embodiments, low bioluminescent signals will be observed for both the agent and negative control throughout the animal and specifically at the liver and splenic sites. In embodiments, the positive control will show increased signal in the liver (over negative control and agent) and high signals in the spleen and a distribution consistent with lymph nodes.

In an embodiment, genomic PCR quantification of these tissues will indicate a high proportion of the recombination signals over the alternative locus in the positive control in all tissues examined, while for or agent and negative controls, the level of recombination will be negligible in all tissues.

In an embodiment, the result of this Example will indicate that the non-fusogen controls are not retained by the RES and will be able to achieve broad distribution and exhibit high bioavailability.

Example 77: Fusosome Longevity with Immunosuppression

This Example describes quantification of the immunogenicity of a fusosome composition when it is co-administered with an immunosuppressive drug.

Therapies that stimulate an immune response can sometimes reduce the therapeutic efficacy or cause toxicity to the recipient. In an embodiment, the fusosomes will be substantially non-immunogenic.

A purified composition of fusosomes as produced by any one of the methods described in previous Examples is co-administered with an immunosuppressive drug, and immunogenic properties are assayed by the longevity of the fusosome in vivo. A sufficient number of fusosomes, labeled with luciferase, are injected locally into the gastrocnemius muscle of a normal mouse with tacrolimus (TAC, 4 mg/kg/day; Sigma Aldrich), or vehicle (negative control), or without any additional agent (positive control). The mice are then subjected to in vivo imaging at 1, 2, 3, 4, 5, 6, 12, 24, 48, and 72 hours post injection.

Briefly, mice are anesthetized with isoflurane and D-luciferin is administered intraperitoneally at a dose of 375 mg per kilogram of body weight. At the time of imaging, animals are placed in a light-tight chamber, and photons emitted from luciferase expressing fusosomes transplanted into the animals are collected with integration times of 5 sec to 5 min, depending on the intensity of the bioluminescence emission. The same mouse is scanned repetitively at the various timepoints set forth above. BLI signal is quantified in units of photons per second (total flux) and presented as log [photons per second]. The data is analyzed by comparing the intensity and fusosome injection with and without TAC.

In embodiments, the assay will show an increase in fusosome longevity in the TAC co-administered group relative to the fusosome alone and vehicle groups at the final timepoint. In addition to the increase in fusosome longevity, in some embodiments, an increase in BLI signal from the fusosome plus TAC arm versus the fusosome plus vehicle or fusosomes alone at each of the time points will be observed.

Example 78: Measuring Pre-Existing IgG and IgM Antibodies Reactive Against Fusosomes This Example describes quantification of pre-existing anti-fusosome antibody titers measured using flow cytometry.

A measure of immunogenicity for fusosomes is antibody responses. Antibodies that recognize fusosomes can bind in manner that can limit fusosome activity or longevity. In an embodiment, some recipients of a fusosome described herein will have pre-existing antibodies which bind to and recognize fusosomes.

In this Example, anti-fusosome antibody titers are tested using fusosomes produced using a xenogeneic source cell by any one of the methods described in a previous Example. In this Example, a fusosome naïve mouse is assessed for the presence of anti-fusosome antibodies. Notably, the methods described herein may be equally applicable to humans, rats, monkeys with optimization to the protocol.

The negative control is mouse serum which has been depleted of IgM and IgG, and the positive control is serum derived from a mouse that has received multiple injections of fusosomes generated from a xenogeneic source cell.

To assess the presence of pre-existing antibodies which bind to fusosomes, sera from fusosome-naïve mice is first decomplemented by heating to 56° C. for 30 min and subsequently diluted by 33% in PBS containing 3% FCS and 0.1% NaN3. Equal amounts of sera and fusosomes ($1\times10^2$-$1\times10^8$ fusosomes per mL) suspensions are incubated for 30 min at 4° C. and washed with PBS through a calf-serum cushion.

IgM xenoreactive antibodies are stained by incubation of the cells with PE-conjugated goat antibodies specific for the Fc portion of mouse IgM (BD Bioscience) at 4° C. for 45 min. Notably, anti-mouse IgG1 or IgG2 secondary antibodies may also be used. Cells from all groups are washed twice with PBS containing 2% FCS and then analyzed on a FACS system (BD Biosciences). Fluorescence data are collected by use of logarithmic amplification and expressed as mean fluorescent intensity.

In an embodiment, the negative control serum will show negligible fluorescence comparable to the no serum or secondary alone controls. In an embodiment, the positive control will show more fluorescence than the negative control, and more than the no serum or secondary alone controls. In an embodiment, in cases where immunogenicity occurs, serum from fusosome-naïve mice will show more fluorescence than the negative control. In an embodiment, in cases where immunogenicity does not occur, serum from fusosome-naïve mice will show similar fluorescence compared to the negative control.

Example 79: Measuring IgG and IgM Antibody Responses after Multiple Administrations of Fusosomes This Example describes quantification of the humoral response of a modified fusosome following multiple administrations of the modified fusosome. In an embodiment, a modified fusosome, e.g., modified by a method described herein, will have a reduced (e.g., reduced compared to administration of an unmodified fusosome) humoral response following multiple (e.g., more than one, e.g., 2 or more), administrations of the modified fusosome.

A measure of immunogenicity for fusosomes is the antibody responses. In an embodiment, repeated injections of a fusosome can lead to the development of anti-fusosome antibodies, e.g., antibodies that recognize fusosomes. In an embodiment, antibodies that recognize fusosomes can bind in a manner that can limit fusosome activity or longevity.

In this Example, anti-fusosome antibody titers are examined after one or more administrations of fusosomes. Fusosomes are produced by any one of the previous Examples. Fusosomes are generated from: unmodified mesenchymal stem cells (hereafter MSCs), mesenchymal stem cells modified with a lentiviral-mediated expression of HLA-G (hereafter MSC-HLA-G), and mesenchymal stem cells modified with a lentiviral-mediated expression of an empty vector (hereafter MSC-empty vector). Serum is drawn from the different cohorts: mice injected systemically and/or locally with 1, 2, 3, 5, 10 injections of vehicle (Fusosome naïve group), MSC fusosomes, MSC-HLA-G fusosomes, or MSC-empty vectors fusosomes.

To assess the presence and abundance of anti-fusosomes antibodies, sera from the mice is first decomplemented by heating to 56° C. for 30 min and subsequently diluted by 33% in PBS with 3% FCS and 0.1% NaN3. Equal amounts of sera and fusosomes ($1\times10^2$-$1\times10^8$ fusosomes per mL) are incubated for 30 min at 4° C. and washed with PBS through a calf-serum cushion.

Fusosome reactive IgM antibodies are stained by incubation of the cells with PE-conjugated goat antibodies specific for the Fc portion of mouse IgM (BD Bioscience) at 4° C. for 45 min. Notably, anti-mouse IgG1 or IgG2 secondary antibodies may also be used. Cells from all groups are washed twice with PBS containing 2% FCS and then analyzed on a FACS system (BD Biosciences). Fluorescence data are collected by use of logarithmic amplification and expressed as mean fluorescent intensity.

In an embodiment, MSC-HLA-G fusosomes will have decreased anti-fusosome IgM (or IgG1/2) antibody titers (as measured by fluorescence intensity on FACS) after injections, as compared to MSC fusosomes or MSC-empty vector fusosomes.

Example 80: Modification of Fusosome Source Cells to Express Tolerogenic Protein to Reduce Immunogenicity This Example describes quantification of immunogenicity in fusosomes derived from a modified cell source. In an embodiment, fusosomes derived from a modified cell source have reduced immunogenicity in comparison to the fusosomes derived from an unmodified cell source.

Therapies that stimulate an immune response can sometimes reduce the therapeutic efficacy or cause toxicity to the recipient. In an embodiment, substantially non-immunogenic fusosomes are administered to a subject. In an embodiment, immunogenicity of the cell source can be assayed as a proxy for fusosome immunogenicity.

iPS cells modified using lentiviral mediated expression of HLA-G or expressing an empty vector (Negative control) are assayed for immunogenic properties as follows. A sufficient number of iPS cells, as a potential fusosome cell source, are injected into C57/B6 mice, subcutaneously in the hind flank and are given an appropriate amount of time to allow for teratomas to form.

Once teratomas are formed, tissues are harvested. Tissues prepared for fluorescent staining are frozen in OCT, and those prepared for immunohistochemistry and H&E staining are fixed in 10% buffered formalin and embedded in paraffin. The tissue sections are stained with antibodies, polyclonal rabbit anti-human CD3 anti-body (DAKO), mouse anti-human CD4 mAb (RPA-T4, BD PharMingen), mouse anti-human CD8 mAb (RPA-T8, BD PharMingen), in accordance with general immunohistochemistry protocols. These are detected by using an appropriate detection reagent, namely an anti-mouse secondary HRP (Thermofisher), or anti-rabbit secondary HRP (Thermofisher).

Detection is achieved using peroxidase-based visualization systems (Agilent). The data is analyzed by taking the average number of infiltrating CD4+ T-cells, CD8+ T-cells, CD3+NK-cells present in 25, 50 or 100 tissue sections examined in a 20× field using a light microscope. In an embodiment, iPSCs which are not modified or iPSCs expressing an empty vector will have a higher number of infiltrating CD4+ T-cells, CD8+ T-cells, CD3+NK-cells present in the fields examined as compared to iPSCs that express HLA-G.

In an embodiment, a fusosome's immunogenic properties will be substantially equivalent to that of the source cell. In an embodiment, fusosomes derived from iPS cells modified with HLA-G will have reduced immune cell infiltration versus their unmodified counterparts.

Example 81: Modification of Fusosome Source Cells to Knockdown Immunogenic Protein to Reduce Immunogenicity This Example describes quantification of the generation of a fusosome composition derived from a cell source, which has been modified to reduce expression of a molecule which is immunogenic. In an embodiment, a fusosome can be derived from a cell source, which has been modified to reduce expression of a molecule which is immunogenic.

Therapies that stimulate an immune response can reduce the therapeutic efficacy or cause toxicity to the recipient. Thus, immunogenicity is an important property for a safe and effective therapeutic fusosomes. Expression of certain immune activating agents can create an immune response. MHC class I represents one example of an immune activating agent.

In this Example, fusosomes are generated by any one of the methods described in previous Examples. Fusosomes are generated from: unmodified mesenchymal stem cells (hereafter MSCs, positive control), mesenchymal stem cells modified with a lentiviral-mediated expression of an shRNA targeting MHC class I (hereafter MSC-shMHC class I), and mesenchymal stem cells modified with a lentiviral-mediated expression of a non-targeted scrambled shRNA (hereafter MSC-scrambled, negative control).

Fusosomes are assayed for expression of MHC class I using flow cytometry. An appropriate number of fusosomes are washed and resuspended in PBS, held on ice for 30 minutes with 1: 10-1:4000 dilution of fluorescently conjugated monoclonal antibodies against MHC class I (Harlan Sera-Lab, Belton, UK). Fusosomes are washed three times in PBS and resuspended in PBS. Nonspecific fluorescence is determined, using equal aliquots of fusosomes preparation incubated with and appropriate fluorescently conjugated isotype control antibody at equivalent dilutions. Fusosomes are assayed in a flow cytometer (FACSort, Becton-Dickinson) and the data is analyzed with flow analysis software (Becton-Dickinson).

The mean fluorescence data of the fusosomes derived from MSCs, MSCs-shMHC class I, MSC-scrambled, is compared. In an embodiment, fusosomes derived from MSCs-shMHC class I will have lower expression of MHC class I compared to MSCs and MSC-scrambled.

Example 82: Modification of Fusosome Source Cells to Evade Macrophage Phagocytosis This Example describes quantification of the evasion of phagocytosis by modified fusosomes. In an embodiment, modified fusosomes will evade phagocytosis by macrophages.

Cells engage in phagocytosis, engulfing particles, enabling the sequestration and destruction of foreign invaders, like bacteria or dead cells. In some embodiments, phagocytosis of fusosomes by macrophages would reduce their activity.

Fusosomes are generated by any one of the methods described in previous Examples. Fusosomes are created from: CSFE-labelled mammalian cells which lack CD47 (hereafter NMC, positive control), CSFE-labelled cells that are engineered to express CD47 using lentiviral mediated expression of a CD47 cDNA (hereafter NMC-CD47), and CSFE-labelled cells engineered using lentiviral mediated expression of an empty vector control (hereafter NMC-empty vector, negative control).

Reduction of macrophage mediate immune clearance is determined with a phagocytosis assay according to the following protocol. Macrophages are plated immediately after harvest in confocal glass bottom dishes. Macrophages are incubated in DMEM+10% FBS+1% P/S for 1 h to attach. An appropriate number of fusosomes derived from NMC, NMC-CD47, NMC-empty vector are added to the macrophages as indicated in the protocol, and are incubated for 2 h, tools.thermofisher.com/content/sfs/manuals/mp06694.pdf.

After 2 h, the dish is gently washed and intracellular fluorescence is examined. Intracellular fluorescence emitted by engulfed particles is imaged by confocal microscopy at 488 excitation. The number of phagocytotic positive macrophage is quantified using imaging software. The data is expressed as the phagocytic index=(total number of engulfed cells/total number of counted macrophages)×(number of macrophages containing engulfed cells/total number of counted macrophages)×100.

In an embodiment, the phagocytic index will be reduced when macrophages are incubated with fusosomes derived from NMC-CD47, versus those derived from NMC, or NMC-empty vector.

Example 83: Modification of Fusosome Source Cells for Decreased Cytotoxicity Mediated by PBMC Cell Lysis This Example described the generation of fusosomes derived from cells modified to have decreased cytotoxicity due to cell lysis by PBMCs.

In an embodiment, cytotoxicity mediated cell lysis of source cells or fusosomes by PBMCs is a measure of immunogenicity for fusosomes, as lysis will reduce, e.g., inhibit or stop, the activity of a fusosome.

In this Example, fusosomes are generated by any one of the methods described in a previous Example. Fusosomes are created from: unmodified mesenchymal stem cells (hereafter MSCs, positive control), mesenchymal stem cells modified with a lentiviral-mediated expression of HLA-G (hereafter MSC-HLA-G), and mesenchymal stem cells modified with a lentiviral-mediated expression of an empty vector (hereafter MSC-empty vector, negative control).

PMBC mediated lysis of a fusosome is determined by europium release assays as described in Bouma, et al. Hum. Immunol. 35(2):85-92; 1992 & van Besouw et al. Transplantation 70(1):136-143; 2000. PBMCs (hereafter effector cells) are isolated from an appropriate donor, and stimulated with allogeneic gamma irradiated PMBCs and 200 IU/mL IL-2 (proleukin, Chiron BV Amsterdam, The Netherlands) in a round bottom 96 well plate for 7 days at 37 C. The fusosomes are labeled with europium-diethylenetriaminepentaacetate (DTPA) (sigma, St. Louis, Mo., USA).

At day 7 cytotoxicity-mediated lysis assays is performed by incubating $^{63}$Eu-labelled fusosomes with effector cells in a 96-well plate for 1, 2, 3, 4, 5, 6, 8, 10, 15, 20, 24, 48 hours after plating at effector/target ratios ranging from 1000:1-1:1 and 1:1.25-1:1000. After incubation, the plates are centrifuged and a sample of the supernatant is transferred to 96-well plates with low background fluorescence (fluoro-immunoplates, Nunc, Roskilde, Denmark).

Subsequently, enhancement solution (PerkinElmer, Groningen, The Netherlands) is added to each well. The released europium is measured in a time-resolved fluorometer (Victor 1420 multilabel counter, LKB-Wallac, Finland). Fluorescence is expressed in counts per second (CPS). Maximum percent release of europium by a target fusosome is determined by incubating an appropriate number ($1\times10^2$-$1\times10^8$) of fusosomes with 1% triton (sigma-aldrich) for an appropriate amount of time. Spontaneous release of europium by target fusosomes is measured by incubation of labeled target fusosomes without effector cells. Percentage leakage is then calculated as: (spontaneous release/maximum release)×100%. Finally, the percentage of cytotoxicity mediated lysis is calculated as % lysis=[(measured lysis−spontaneous lysis−spontaneous release)/(maximum release−spontaneous release)]×100%. The data is analyzed by looking at the percentage of lysis as a function of different effector target ratios.

In an embodiment, fusosomes generated from MSC-HLA-G cells will have a decreased percentage of lysis by target cells, at specific timepoints as compared to MSCs or MSC-scrambled generated fusosomes.

Example 84: Modification of Fusosome Source Cells for Decreased NK Lysis Activity This Example describes the generation of a fusosome composition derived from a cell source, which has been modified to decrease cytotoxicity mediated cell lysis by NK cells. In an embodiment cytotoxicity mediated cell lysis of source cells or fusosomes by NK cells is a measure of immunogenicity for fusosomes.

In this Example, fusosomes are generated by any one of the methods described in a previous Example. Fusosomes are created from: unmodified mesenchymal stem cells (hereafter MSCs, positive control), mesenchymal stem cells modified with a lentiviral-mediated expression of HLA-G (hereafter MSC-HLA-G), and mesenchymal stem cells modified with a lentiviral-mediated expression of an empty vector (hereafter MSC-empty vector, negative control).

NK cell mediated lysis of a fusosome is determined by europium release assays as described in Bouma, et al. Hum. Immunol. 35(2):85-92; 1992 & van Besouw et al. Transplantation 70(1):136-143; 2000. NK cells (hereafter effector cells) are isolated from an appropriate donor according to the methods in Crop et al. Cell transplantation (20):1547-1559; 2011, and stimulated with allogeneic gamma irradiated PMBCs and 200 IU/mL IL-2 (proleukin, Chiron BV Amsterdam, The Netherlands) in a round bottom 96 well plate for 7 days at 37 C. The fusosomes are labeled with europium-diethylenetriaminepentaacetate (DTPA) (sigma, St. Louis, Mo., USA).

At day 7 cytotoxicity-mediated lysis assays is performed by incubating $^{63}$Eu-labelled fusosomes with effector cells in a 96-well plate for 1, 2, 3, 4, 5, 6, 8, 10, 15, 20, 24, 48 hours after plating at effector/target ratios ranging from 1000:1-1:1 and 1:1.25-1:1000. After incubation, the plates are centrifuged and a sample of the supernatant is transferred to 96-well plates with low background fluorescence (fluoroimmunoplates, Nunc, Roskilde, Denmark).

Subsequently, enhancement solution (PerkinElmer, Groningen, The Netherlands) is added to each well. The released europium is measured in a time-resolved fluorometer (Victor 1420 multilabel counter, LKB-Wallac, Finland). Fluorescence is expressed in counts per second (CPS). Maximum percent release of europium by a target fusosome is determined by incubating an appropriate number ($1\times10^2$-$1\times10^8$) of fusosomes with 1% triton (Sigma-Aldrich) for an appropriate amount of time. Spontaneous release of europium by target fusosomes is measured by incubation of labeled target fusosomes without effector cells. Percentage leakage is then calculated as: (spontaneous release/maximum release)×100%. Finally, the percentage of cytotoxicity mediated lysis is calculated as % lysis=[(measured lysis−spontaneous lysis−spontaneous release)/(maximum release−spontaneous release)]×100%. The data is analyzed by looking at the percentage of lysis as a function of different effector target ratios.

In an embodiment, fusosomes generated from MSC-HLA-G cells will have a decreased percentage of lysis at appropriate timepoints as compared to MSCs or MSC-scrambled generated fusosomes.

Example 85: Modification of Fusosome Source Cells for Decreased CD8 Killer T Cell Lysis This Example describes the generation of a fusosome composition derived from a cell source, which has been modified to decrease cytotoxicity mediated cell lysis by CD8+ T-cells. In an embodiment, cytotoxicity mediated cell lysis of source cells or fusosomes by CD8+ T-cells is a measure of immunogenicity for fusosomes.

In this Example, fusosomes are generated by any one of the methods described in a previous Example. Fusosomes are created from: unmodified mesenchymal stem cells (hereafter MSCs, positive control), mesenchymal stem cells modified with a lentiviral-mediated expression of HLA-G (hereafter MSC-HLA-G), and mesenchymal stem cells modified with a lentiviral-mediated expression of an empty vector (hereafter MSC-empty vector, negative control).

CD8+ T cell mediated lysis of a fusosome is determined by europium release assays as described in Bouma, et al. Hum. Immunol. 35(2):85-92; 1992 & van Besouw et al. Transplantation 70(1):136-143; 2000. CD8+ T-cells (hereafter effector cells) are isolated from an appropriate donor according to the methods in Crop et al. Cell transplantation (20):1547-1559; 2011, and stimulated with allogeneic gamma irradiated PMBCs and 200 IU/mL IL-2 (proleukin, Chiron BV Amsterdam, The Netherlands) in a round bottom 96 well plate for 7 days at 37 C. The fusosomes are labeled with europium-diethylenetriaminepentaacetate (DTPA) (sigma, St. Louis, Mo., USA).

At day 7 cytotoxicity-mediated lysis assays is performed by incubating $^{63}$Eu-labelled fusosomes with effector cells in a 96-well plate for 1, 2, 3, 4, 5, 6, 8, 10, 15, 20, 24, 48 hours after plating at effector/target ratios ranging from 1000:1-1:1 and 1:1.25-1:1000. After incubation, the plates are centrifuged and 20 ul of the supernatant is transferred to 96-well plates with low background fluorescence (fluoroimmunoplates, Nunc, Roskilde, Denmark).

Subsequently, enhancement solution (PerkinElmer, Groningen, The Netherlands) is added to each well. The released europium is measured in a time-resolved fluorometer (Victor 1420 multilabel counter, LKB-Wallac, Finland). Fluorescence is expressed in counts per second (CPS). Maximum percent release of europium by a target fusosome is determined by incubating an appropriate number ($1\times10^2$-$1\times10^8$) of fusosomes with 1% triton (sigma-aldrich) for an appropriate amount of time. Spontaneous release of europium by target fusosomes is measured by incubation of labeled target fusosomes without effector cells. Percentage leakage is then calculated as: (spontaneous release/maximum release)×100%. Finally, the percentage of cytotoxicity mediated lysis is calculated as % lysis=[(measured lysis−spontaneous lysis−spontaneous release)/(maximum release−spontaneous release)]×100%. The data is analyzed by looking at the percentage of lysis as a function of different effector target ratios.

In an embodiment, fusosomes generated from MSC-HLA-G cells will have a decreased percentage of lysis at appropriate timepoints as compared to MSCs or MSC-scrambled generated fusosomes.

Example 86: Modification of Fusosome Source Cells for Decreased T-Cell Activation This Example describes the generation of modified fusosomes that will have reduced T cell activation and proliferation as assessed by a mixed lymphocyte reaction (MLR).

T-cell proliferation and activation are measures of immunogenicity for fusosomes. Stimulation of T cell proliferation in an MLR reaction by a fusosome composition, could suggest a stimulation of T cell proliferation in vivo.

In an embodiment, fusosomes generated from modified source cells have reduced T cell activation and proliferation as assessed by a mixed lymphocyte reaction (MLR). In an embodiment, fusosomes generated from modified source cells do not generate an immune response in vivo, thus maintaining the efficacy of the fusosome composition.

In this Example, fusosomes are generated by any one of the methods described in a previous Example. Fusosomes are generated from: unmodified mesenchymal stem cells (hereafter MSCs, positive control), mesenchymal stem cells modified with a lentiviral-mediated expression of IL-10 (hereafter MSC-IL-10), and mesenchymal stem cells modified with a lentiviral-mediated expression of an empty vector (hereafter MSC-empty vector, negative control).

BALB/c and C57BL/6 splenocytes are used as either stimulator or responder cells. Notably, the source of these cells can be exchanged with commonly used human-derived stimulator/responder cells. Additionally, any mammalian purified allogeneic CD4+ T cell population, CD8+ T-cell population, or CD4−/CD8− may be used as responder population.

Mouse Splenocytes are isolated by mechanical dissociation using fully frosted slides followed by red blood cell lysis with lysing buffer (Sigma-Aldrich, St-Louis, Mo.). Prior to the experiment, stimulator cells are irradiated with 20 Gy of γray to prevent them from reacting against responder cells. A co-culture is then made by adding equal numbers of stimulator and responder cells (or alternative concentrations while maintaining a 1:1 ratio) to a round bottom 96-well plate in complete DMEM-10 media. An appropriate number of fusosomes (at several concentrations from a range of 1×10'-1×10⁸) are added to the co-culture at different time intervals, t=0, 6, 12, 24, 36, 48 h.

Proliferation is assessed by adding 1 µCi of [$^3$H]-thymidine (Amersham, Buckinghamshire, UK) to allow for incorporation. [$^3$H]-thymidine is added to the MLR at t=2, 6, 12, 24, 36, 48, 72 h, and the cells are harvested onto glass fiber filters using a 96 well cell harvester (Inoteck, Bertold, Japan) after 2, 6, 12, 18, 24, 36 and 48 h of extended culture. All of the T-cell proliferation experiments are done in triplicate. [$^3$H]-thymidine incorporation is measured using a microbeta 1Luminescence counter (Perkin Elmer, Wellesley, Mass.). The results can be represented as counts per minute (cpm).

In an embodiment, MSC-IL10 fusosomes will show a decrease in T-cell proliferation as compared to the MSC-Empty vector or the MSC unmodified fusosome controls.

Example 87: Measuring Targeting Potential in a Subject

This Example assesses the ability of a fusosome to target a specific body site. In an embodiment, a fusosome can target a specific body site. Targeting is a way to restrict activity of a therapeutic to one or more relevant therapeutic sites.

Eight week old C57BL/6J mice (Jackson Laboratories) are intravenously injected with fusosomes or cells that express firefly luciferase. Fusosomes are produced from cells that stably express firefly luciferase or cells that do not express luciferase (negative control) by any one of the methods described in previous Examples. Groups of mice are euthanized at one, two, three, four, five, six, eight, twelve, and twenty-four hours after fusosome or cell injection.

Five minutes before euthanization, mice receive an IP injection of bioluminescent substrate (Perkin Elmer) at a dose of 150 mg/kg in order to visualize luciferase. The bioluminescent imaging system is calibrated to compensate for all device settings. Mice are then euthanized and liver, lungs, heart, spleen, pancreas, GI, and kidney are collected. The imaging system (Perkin Elmer) is used to obtain images of bioluminescence of these ex vivo organs. The bioluminescent signal is measured using Radiance Photons, with Total Flux used as a measured value. The region of interest (ROI) is generated by surrounding the ex vivo organ in order to give a value in photons/second. The ratio of photons/second between target organs (e.g. liver) and non-target organs (e.g. the sum of photons/second from lungs, heart, spleen, pancreas, GI, and kidney) is calculated as a measure of targeting to the liver.

In an embodiment, in both fusosomes and cells, the ratio of photons/second between liver and the other organs will be greater than 1, which would indicate that fusosomes target the liver. In an embodiment, negative control animals will display much lower photons/second in all organs.

Example 88: Measuring Delivery of an Exogenous Agent in a Subject

This Example describes quantification of delivery of fusosomes comprising an exogenous agent in a subject. Fusosomes are prepared from cells expressing *Gaussia* luciferase or from cells not expressing luciferase (negative control) by any one of the methods described in previous Examples.

Positive control cells or fusosomes are intravenously injected into mice. Fusosomes or cells are delivered within 5-8 seconds using a 26-gauge insulin syringe-needle. In vivo bioluminescent imaging is performed on mice 1, 2, or 3 days after injection using an in vivo imaging system (Xenogen Corporation, Alameda, Calif.).

Immediately before use, coelenterazine, a luciferin or light-emitting molecule, (5 mg/ml) is prepared in acidified methanol and injected immediately into the tail vein of the mice. Mice are under continuous anesthesia on a heated stage using the XGI-8 Gas Anesthesia System.

Bioluminescence imaging is obtained by acquiring photon counts over 5 min immediately after intravenous tail-vein injection of coelenterazine (4 µg/g body weight). Acquired data are analyzed using software (Xenogen) with the overlay on light-view image. Regions of interest (ROI) are created using an automatic signal intensity contour tool and normalized with background subtraction of the same animal. A sequential data acquisition using three filters at the wavelengths of 580, 600 and 620 nm with exposure time 3-10 min is conducted to localize bioluminescent light sources inside a mouse.

Furthermore, at each timepoint, urine samples are collected by abdominal palpation.

Blood samples (50 µl) are obtained from the tail vein of each mouse into heparinized or EDTA tubes. For plasma isolation, blood samples are centrifuged for 25 min at 1.3×g at 4° C.

Then, 5 µl of blood, plasma or urine sample are used to carry out a *Gaussia* luciferase activity assay after mixing the samples with 50 µM *Gaussia* luciferase substrate (Nanolight, Pinetop, Ariz.).

In an embodiment, the negative control samples will be negative for luciferase, and positive control samples will be from animals administered cells. In an embodiment, the samples from animals administered fusosomes expressing *Gaussia* luciferase will be positive for luciferase in each sample.

See, for example, El-Amouri S S et al., *Molecular biotechnology* 53(1): 63-73, 2013.

Example 89: Active Transport Across a Lipid Bilayer of a Fusosome

This example describes quantification of the level of 2-NBDG (2-(N-(7-Nitrobenz-2-oxa-1,3-diazol-4-yl) Amino)-2-Deoxyglucose), a fluorescent glucose analog that can be used to monitor glucose uptake in live cells and thus active transport across the lipid bilayer. In an embodiment, this assay can be used to measure the level of glucose uptake and active transport across the lipid bilayer of the fusosome.

A fusosome composition as produced by any one of the methods described in previous Examples. A sufficient number of fusosomes are then incubated in DMEM containing no glucose, 20% Fetal Bovine Serum and 1× Penicillin/Streptomycin for 2 hr at 37° C. and 5% $CO_2$. After the 2 hr glucose starvation period, the medium is changed such that it includes DMEM with no glucose, 20% Fetal Bovine Serum, 1×Penicillin/Streptomycin, and 20 uM 2-NBDG (ThermoFisher) and incubated for 2 hr at 37° C. and 5% $CO_2$. Negative control fusosomes are treated the same, except an equal amount of DMSO, the vehicle for 2-NBDG is added in place of 2-NBDG.

The fusosomes are then washed thrice with 1×PBS and re-suspended in an appropriate buffer, and transferred to a 96 well imaging plate. 2-NBDG fluorescence is then measured in a fluorimeter using a GFP light cube (469/35 excitation filter and a 525/39 emission filter) to quantify the amount of 2-NBDG that has transported across the fusosome membrane and accumulated in the fusosome in the 1 hr loading period.

In an embodiment, 2-NBDG fluorescence will be higher in the fusosomes with 2-NBDG treatment as compared to the negative (DMSO) control. Fluorescence measure with a 525/39 emission filter will be relatively to the number of 2-NBDG molecules present.

Example 90: Delivery of Fusosomes Via Non-Endocytic Pathway

This example describes quantification of fusosome delivery of Cre to a recipient cell via a non-endocytic pathway.

In an embodiment, fusosomes will deliver agents via a fusosome-mediated, non-endocytic pathway. Without wishing to be bound by theory, delivery of an agent, e.g., Cre, which is carried within the lumen of the fusosomes, directly to the cytosol of the recipient cells without any requirement for endocytosis-mediated uptake of the fusosomes, will occur through a fusosome-mediated, non-endocytic pathway delivery.

In this example, the fusosome comprises a HEK293T cell expressing the Sendai virus H and F protein on its plasma membrane (Tanaka et al., 2015, Gene Therapy, 22(October 2014), 1-8. https://doi.org/10.1038/gt.2014.123). In addition, the fusosome expresses mTagBFP2 fluorescent protein and Cre recombinase. The target cell is a RPMI8226 cell which stably-expresses "LoxP-GFP-stop-LoxP-RFP" cassette under a CMV promoter, which upon recombination by Cre switches from GFP to RFP expression, indicating fusion and Cre, as a marker, delivery.

Fusosomes produced by the herein described methods are assayed for delivery of Cre via a non-endocytic pathway as follows. The recipient cells are plated into a black, clear-bottom 96-well plate. Next, 24 hours after plating the recipient cells, the fusosomes expressing Cre recombinase protein and possessing the particular fusogen protein are applied to the recipient cells in DMEM media. To determine the level of Cre delivery via a non-endocytic pathway, a parallel group of recipient cells receiving fusosomes is treated with an inhibitor of endosomal acidification, chloroquine (30 µg/mL). The dose of fusosomes is correlated to the number of recipient cells plated in the well. After applying the fusosomes, the cell plate is centrifuged at 400 g for 5 minutes to help initiate contact between the fusosomes and the recipient cells. The cells are then incubated for 16 hours and agent delivery, Cre, is assessed via imaging.

The cells are imaged to positively identify RFP-positive cells versus GFP-positive cells in the field or well. In this example cell plates are imaged using an automated fluorescence microscope. The total cell population in a given well is determined by first staining the cells with Hoechst 33342 in DMEM media for 10 minutes. Hoechst 33342 stains cell nuclei by intercalating into DNA and therefore is used to identify individual cells. After staining, the Hoechst media is replaced with regular DMEM media.

The Hoechst is imaged using the 405 nm LED and DAPI filter cube. GFP is imaged using the 465 nm LED and GFP filter cube, while RFP is imaged using 523 nm LED and RFP filter cube. Images of the different cell groups are acquired by first establishing the LED intensity and integration times on a positive-control well; i.e., recipient cells treated with adenovirus coding for Cre recombinase instead of fusosomes.

Acquisition settings are set so that RFP and GFP intensities are at the maximum pixel intensity values but not saturated. The wells of interest are then imaged using the established settings.

Analysis of GFP and RFP-positive wells is performed with software provided with the fluorescence microscope or other software (Rasband, W. S., ImageJ, U. S. National Institutes of Health, Bethesda, Md., USA, 1997-2007). The images are pre-processed using a rolling ball background subtraction algorithm with a 60 µm width. The total cell mask is set on the Hoechst-positive cells. Cells with Hoechst intensity significantly above background intensities are used to set a threshold, and areas too small or large to be Hoechst-positive cells are excluded.

Within the total cell mask, GFP and RFP-positive cells are identified by again setting a threshold for cells significantly above background and extending the Hoechst (nuclei) masks for the entire cell area to include the entire GFP and RFP cellular fluorescence.

The number of RFP-positive cells identified in control wells containing recipient cells is used to subtract from the number of RFP-positive cells in the wells containing fusosomes (to subtract for non-specific Loxp recombination). The number of RFP-positive cells (recipient cells that received Cre) is then divided by the sum of GFP-positive cells (recipient cells that have not received Cre) and RFP-positive cells to quantify the fraction of fusosome Cre delivered to the recipient cell population. The level is normalized to the given dose of fusosomes applied to the recipient cells. To calculate the value of fusosome Cre delivered via a non-endocytic pathway, the level of fusosome Cre delivery in the presence of chloroquine (FusL+CQ) is determined as well as the level of fusosome Cre delivery in the absence of chloroquine (FusL−CQ). To determine the normalized value of fusosome Cre delivered via a non-endocytic pathway, the following equation is used: [(FusL−CQ)−(FusL+CQ)]/(FusL−CQ).

In an embodiment, the average level of fusosome Cre delivered via a non-endocytic pathway for a given fusosome will be in the range of 0.1-0.95, or at least 1%, 2%, 3%, 4%, 5%, 10%, 20%, 30%, 40%, 50%, 60%, 70%, 80%, 90% or greater than chloroquine treated recipient cells.

Example 91: Delivery of Fusosomes Via Endocytic Pathway

This example describes fusosome delivery of Cre to a recipient cell via an endocytic pathway.

In an embodiment, fusosomes will deliver agents via a fusosome-mediated, endocytic pathway. Without wishing to be bound by theory, delivery of an agent, e.g., a cargo, carried in the lumen of the fusosomes, to the recipient cells with the route of uptake being endocytosis-dependent will occur through a fusosome-mediated, endocytic pathway delivery.

In this example the fusosome comprises microvesicles that were produced by extruding a HEK293T cell expressing a fusogen protein on its plasma membrane through a 2 m filter (Lin et al., 2016, Biomedical Microdevices, 18(3). doi.org/10.1007/s10544-016-0066-y) (Riedel, Kondor-Koch, & Garoff, 1984, The EMBO Journal, 3(7), 1477-83. Retrieved from www.ncbi.nlm.nih.gov/pubmed/6086326). In addition, the fusosome expresses mTagBFP2 fluorescent protein and Cre recombinase. The target cell is a PC3 cell which stably-expresses "LoxP-GFP-stop-LoxP-RFP" cassette under a CMV promoter, which upon recombination by Cre switches from GFP to RFP expression, indicating fusion and Cre, as a marker, delivery.

Fusosomes produced by the herein described methods are assayed for delivery of Cre via an endocytic pathway as follows. The recipient cells are plated into a cell culture multi-well plate compatible with the imaging system to be used (in this example cells are plated in a black, clear-bottom 96-well plate). Next, 24 hours after plating the recipient cells, the fusosomes expressing Cre recombinase protein and possessing the particular fusogen protein are applied to the recipient cells in DMEM media. To determine the level of Cre delivery via an endocytic pathway, a parallel group of recipient cells receiving fusosomes is treated with an inhibitor of endosomal acidification, chloroquine (30 µg/mL). The dose of fusosomes is correlated to the number of recipient cells plated in the well. After applying the fusosomes, the cell plate is centrifuged at 400 g for 5 minutes to help initiate contact between the fusosomes and the recipient cells. The cells are then incubated for 16 hours and agent delivery, Cre, is assessed via imaging.

The cells are imaged to positively identify RFP-positive cells versus GFP-positive cells in the field or well. In this example cell plates are imaged using an automated fluorescent microscope. The total cell population in a given well is determined by first staining the cells with Hoechst 33342 in DMEM media for 10 minutes. Hoechst 33342 stains cell nuclei by intercalating into DNA and therefore is used to identify individual cells. After staining the Hoechst media is replaced with regular DMEM media.

The Hoechst is imaged using the 405 nm LED and DAPI filter cube. GFP is imaged using the 465 nm LED and GFP filter cube, while RFP is imaged using 523 nm LED and RFP filter cube. Images of the different cell groups are acquired by first establishing the LED intensity and integration times on a positive-control well; i.e., recipient cells treated with adenovirus coding for Cre recombinase instead of fusosomes.

Acquisition settings are set so that RFP and GFP intensities are at the maximum pixel intensity values but not saturated. The wells of interest are then imaged using the established settings.

Analysis of GFP and RFP-positive wells is performed with software provided with the fluorescent microscope or other software (Rasband, W. S., ImageJ, U. S. National Institutes of Health, Bethesda, Md., USA, 1997-2007). The images are pre-processed using a rolling ball background subtraction algorithm with a 60 um width. The total cell mask is set on the Hoechst-positive cells. Cells with Hoechst intensity significantly above background intensities are thresholded and areas too small or large to be Hoechst-positive cells are excluded.

Within the total cell mask, GFP and RFP-positive cells are identified by again thresholding for cells significantly above background and extending the Hoechst (nuclei) masks for the entire cell area to include the entire GFP and RFP cellular fluorescence.

The number of RFP-positive cells identified in control wells containing recipient cells is used to subtract from the number of RFP-positive cells in the wells containing fusosomes (to subtract for non-specific Loxp recombination). The number of RFP-positive cells (recipient cells that received Cre) is then divided by the sum of the GFP-positive cells (recipient cells that have not received Cre) and RFP-positive cells to quantify the fraction of fusosome Cre delivered to the recipient cell population. The level is normalized to the given dose of fusosomes applied to the recipient cells. To calculate the value of fusosome Cre delivered via an endocytic pathway, the level of fusosome Cre delivery in the presence of chloroquine (FusL+CQ) is determined as well as the level of fusosome Cre delivery in the absence of chloroquine (FusL−CQ). To determine the normalized value of fusosome Cre delivered via an endocytic pathway, the following equation is used: (FusL+CQ)/(FusL−CQ).

In an embodiment, the average level of fusosome Cre delivered via an endocytic pathway for a given fusosome will be in the range of 0.01-0.6, or at least 1%, 2%, 3%, 4%, 5%, 10%, 20%, 30%, 40%, 50%, 60%, 70%, 80%, 90% or greater than chloroquine treated recipient cells.

Example 92: Delivery of Fusosomes Via a Dynamin Mediated Pathway, a Macropinocytosis Pathway, or an Actin Mediated Pathway This example describes fusosome delivery of Cre to a recipient cell via a dynamin mediated pathway. A fusosome comprising a microvesicle may be produced as described in the preceding example. Fusosomes are assayed for delivery of Cre via a dynamin-mediated pathway according to the preceding example, except that a group of recipient cells receiving fusosomes is treated with an inhibitor of dynamin, Dynasore (120 µM). To calculate the value of fusosome Cre delivered via a dynamin-mediated pathway, the level of fusosome Cre delivery in the presence of Dynasore (FusL+DS) is determined as well as the level of fusosome Cre delivery in the absence of Dynasore (FusL−DS). The normalized value of fusosome Cre delivered may be calculated as described in the preceding example.

This example also describes delivery of Cre to a recipient cell via macropinocytosis. A fusosome comprising a microvesicle may be produced as described in the preceding example. Fusosomes are assayed for delivery of Cre via macropinocytosis according to the preceding example, except that a group of recipient cells receiving fusosomes is treated with an inhibitor of macropinocytosis, 5-(N-ethyl-N-isopropyl)amiloride (EIPA) (25 µM). To calculate the value of fusosome Cre delivered via macropinocytosis, the level of fusosome Cre delivery in the presence of EIPA (FusL+EPIA) is determined as well as the level of fusosome Cre delivery in the absence of EPIA (FusL−EIPA). The normalized value of fusosome Cre delivered may be calculated as described in the preceding example.

This example also describes fusosome delivery of Cre to a recipient cell via an actin mediated pathway. A fusosome comprising a microvesicle may be produced as described in the preceding example. Fusosomes are assayed for delivery of Cre via macropinocytosis according to the preceding example, except that a group of recipient cells receiving fusosomes is treated with an inhibitor of actin polymerization, Latrunculin B (6 µM). To calculate the value of fusosome Cre delivered via an actin-mediated pathway, the level of fusosome Cre delivery in the presence of Latrunculin B (FusL+LatB) is determined as well as the level of fusosome Cre delivery in the absence of Latrunculin B (FusL−LatB). The normalized value of fusosome Cre delivered may be calculated as described in the preceding example.

Example 93: Delivery of Organelles

This example describes fusosome fusion with a cell in vitro. In an embodiment, fusosome fusion with a cell in vitro can result in delivery of fusosomal mitochondrial cargo to the recipient cell.

A fusosome produced by the methods described by the herein described methods was assayed for its ability to deliver its mitochondria to the recipient cell as follows.

In this particular example, the fusosome was a HEK293T cell expressing a fusogen protein on its membrane, as well as mitochondrial-targeted DsRED (mito-DsRED) protein to label mitochondria. The recipient cells were plated into a cell culture multi-well plate compatible with the imaging system to be used (in this example cells were plated in a glass-bottom imaging dish). The recipient cells stably-expressed cytosolic GFP.

Next, 24 hours after plating the recipient cells, the fusosome expressing mito-DsRED and possessing the particular fusogen protein was applied to the recipient cells in DMEM media. The dose of fusosomes was correlated to the number of recipient cells plated in the well. After applying the fusosomes the cell plate was centrifuged at 400 g for 5 minutes to help initiate contact between the fusosomes and the recipient cells. The cells were then incubated for 4 hours and VSVG-mediated fusion was induced by one minute exposure to pH 6.0 phosphate-buffered saline (or control cells are exposed to pH 7.4 phosphate-buffered saline). Following induction of fusion, cells were incubated an additional 16 hours and mitochondria delivery was assessed via imaging.

In this example, cells were imaged on a Zeiss LSM 710 confocal microscope with a 63× oil immersion objective while maintained at 37 C and 5% CO2. GFP was subjected to 488 nm laser excitation and emission was recorded through a band pass 495-530 nm filter. DsRED was subjected to 543 nm laser excitation and emission was recorded through a band pass 560 to 610 nm filter. The cells were scanned to positively identify cells positive for cytosolic GFP fluorescence and mito-DsRED fluorescence.

The presence of both cytosolic GFP and mito-DsRED mitochondria were found in the same cell indicating the cell has undergone VSVG-mediated fusion, and thus mitochondria have been delivered from the fusosome to the recipient cell.

Example 94: In Vitro Delivery of DNA

This example describes the delivery of DNA using fusosomes to cells in vitro. This example quantifies the ability of fusosomes to deliver DNA using a plasmid encoding an exogenous gene, GFP, a surrogate therapeutic cargo.

A fusosome composition, resulting from cell-derived vesicles or cell-derived cytobiologics as produced by any one of the methods described in previous Examples, except the fusosome is engineered such that the fusogen is in-frame with the open reading frame of Cre. Following production of the fusosome, it is additionally nucleofected with a plasmid having a sequence that codes for GFP (System Biosciences, Inc.).

See, for example, Chen X, et al., Genes Dis. 2015 March; 2(1):96-105.DOI:10.1016/j.gendis.2014.12.001.

As a negative control, fusosomes are nucleofected with a plasmid having a sequence that codes for beta-actin.

A sufficient number of fusosomes are then incubated at 37° C. and 5% CO2 together with a recipient NIH/3T3 fibroblast cell line that has a loxP-STOP-loxP-tdTomato reporter for a period of 48 h in in DMEM containing 20% Fetal Bovine Serum and 1× Penicillin/Streptomycin. Following the 48 hr incubation, the tdTomato positive cells are then isolated via FACS, using a FACS cytometer (Becton Dickinson, San Jose, Calif., USA) with 561 nm laser excitation and emission is collected at 590+/−20 nm. Total DNA is then isolated using a DNA extraction solution (Epicentre) and PCR is performed using primers specific to GFP (see Table 12) that amplify a 600 bp fragment. A 600 bp fragment present on a gel following gel electrophoresis would then substantiate the present of DNA delivery to the recipient cell.

TABLE 12

| GFP Primers sequences that amplify a 500 bp fragment | |
|---|---|
| Primer | Sequence |
| GFP-F | ATGAGTAAAGGAGAAGAACTTTTCAC |
| GFP-R | GTCCTTTTACCAGACAACCATTAC |

In an embodiment, delivery of nucleic acid cargo with fusosomes in vitro is higher in fusosomes with GFP plasmid as compared to the negative control. Negligible GFP fluorescence is detected in the negative control.

Example 95: In Vivo Delivery of DNA

This example describes the delivery of DNA to cells in vivo via fusosomes. Delivery of DNA to cells in vivo results in the expression of proteins within the recipient cell.

Fusosome DNA delivery in vivo will demonstrates the delivery of DNA and protein expression in recipient cells within an organism (mouse).

Fusosomes that express a liver directed fusogen are prepared as described herein. Following production of the fusosome, it is additionally nucleofected with a plasmid having a sequence that codes for Cre recombinase.

Fusosomes are prepared for in vivo delivery. Fusosome suspensions are subjected to centrifugation. Pellets of the fusosomes are resuspended in sterile phosphate buffered saline for injection.

Fusosomes are verified to contain DNA using a nucleic acid detection method, e.g., PCR.

The recipient mice harbor a loxp-luciferase genomic DNA locus that is modified by CRE protein made from DNA delivered by the fusosomes to unblock the expression of luciferase (JAX#005125). The positive control for this example are offspring of recipient mice mated to a mouse strain that expresses the same protein exclusively in the liver from its own genome (albumin-CRE JAX#003574). Offspring from this mating harbor one of each allele (loxp-luciferase, albumin-CRE). Negative controls are carried out by injection of recipient mice with fusosomes not expressing fusogens or fusosomes with fusogens but not containing Cre DNA.

The fusosomes are delivered into mice by intravenous (IV) tail vein administration. Mice are placed in a commercially available mouse restrainer (Harvard Apparatus). Prior to restraint, animals are warmed by placing their cage on a circulating water bath. Once inside the restrainer, the animals are allowed to acclimate. An IV catheter consisting of a 30 G needle tip, a 3" length of PE-10 tubing, and a 28 G needle is prepared and flushed with heparinized saline. The tail is cleaned with a 70% alcohol prep pad. Then, the catheter needle is held with forceps and slowly introduced into the lateral tail vein until blood becomes visible in the tubing. The fusosome solution (~500K-5M fusosomes) is aspirated into a 1 cc tuberculin syringe and connected to an infusion pump. The fusosome solution is delivered at a rate of 20 uL per minute for 30 seconds to 5 minutes, depending on the dose. Upon completion of infusion, the catheter is removed, and pressure is applied to the injection site until cessation of any bleeding. Mice are returned to their cages and allowed to recover.

After fusion, the DNA will be transcribed and translated into CRE protein which will then translocates to the nucleus to carry out recombination resulting in the constitutive expression of luciferase. Intraperitoneal administration of D-luciferin (Perkin Elmer, 150 mg/kg) enables the detection of luciferase expression via the production of bioluminescence. The animal is placed into an in vivo bioluminescent imaging chamber (Perkin Elmer) which houses a cone anesthetizer (isoflurane) to prevent animal motion. Photon collection is carried out between 8-20 minutes post-injection to observe the maximum in bioluminescence due to D-luciferin pharmacokinetic clearance. A specific region of the liver is created in the software and collection exposure time set so that count rates are above 600 (in this region) to yield interpretable radiance (photons/sec/cm2/steradians) measurements. The maximum value of bioluminescent radiance is recorded as the image of bioluminescence distribution. The liver tissue is monitored specifically for radiance measurements above background (untreated animals) and those of negative controls. Measurements are carried out at 24 hours post-injection to observe luciferase activity. Mice are then euthanized and livers are harvested.

Freshly harvested tissue is subjected to fixation and embedding via immersion in 4% paraformaldehyde/0.1M sodium phosphate buffer pH7.4 at 4° C. for 1-3 hrs. Tissue is then immersed in sterile 15% sucrose/1×PBS (3 hrs. to overnight) at 4° C. Tissue is then embedded in O.C.T. (Baxter No. M7148-4). Tissue is oriented in the block appropriately for sectioning (cross-section). Tissue is then frozen in liquid nitrogen using the following method: place the bottom third of the block into the liquid nitrogen, allow to freeze until all but the center of the O.C.T. is frozen, and allow freezing to conclude on dry ice. Blocks are sectioned by cryostat into 5-7 micron sections placed on slides and refrozen for staining.

In situ hybridization is carried out (using standard methods) on tissue sections using digoxygenin labeled nucleic acid probes (for CRE DNA and luciferase mRNA detection), labeled by anti-digoxygenin fluorescent antibodies, and observed by confocal microscopy.

In embodiments, positive control animals (recombination via breeding without fusosome injection) will show bioluminescence intensity in liver as compared to untreated animals (no CRE and no fusosomes) and negative controls, while agent injected animals will show bioluminescence in liver as compared to negative controls (fusosomes without fusogen) and untreated animals.

In embodiments, detection of nucleic acid in tissue sections in agent injected animals will reveal detection of CRE recombinase and luciferase mRNA compared to negative controls and untreated animals in cells in the tissue, while positive controls will show levels of both luciferase mRNA and CRE recombinase DNA throughout the tissue.

Evidence of DNA delivery by fusosomes will be detected by in situ hybridization-based detection of the DNA and its colocalization in the recipient tissue of the animal. Activity of the protein expressed from the DNA will be detected by bioluminescent imaging. In embodiments, fusosomes will deliver DNA that will result in protein production and activity.

Example 96: In Vitro Delivery of mRNA

This example describes fusosome fusion with a cell in vitro. In an embodiment, fusosome fusion with a cell in vitro results in delivery of a specified mRNA to the recipient cell.

A fusosome produced by the herein described methods was assayed for its ability to deliver a specified mRNA to the recipient cell as follows. In this particular example, the fusosome was a cytobiologic (lacking a nucleus), which was generated from a 3T3 mouse fibroblast cell expressing Cre and GFP. The cytobiologic was then treated with HVJ-E fusogen protein to produce the fusosome.

The recipient mouse macrophage cells were plated into a cell culture multi-well plate compatible with the imaging system to be used (in this example cells are plated in a glass-bottom imaging dish). The recipient cells stably-expressed "LoxP-stop-LoxP-tdTomato" cassette under CMV promoter, which upon recombination by Cre induces tdTomato expression, indicating delivery of Cre protein to the recipient cell.

Next, 24 hours after plating the recipient cells, the fusosome expressing Cre recombinase protein and possessing the particular fusogen protein was applied to the recipient cells in DMEM media. The dose of fusosomes was correlated to the number of recipient cells plated in the well. After applying the fusosomes the cell plate was centrifuged at 400 g for 5 minutes to help initiate contact between the fusosomes and the recipient cells. The cells were then incubated for 16 hours and mRNA delivery was assessed via imaging.

The cells were stained with 1 µg/mL Hoechst 33342 in DMEM media for 10 minutes prior to imaging. In this example cells were imaged on a Zeiss LSM 710 confocal microscope with a 63× oil immersion objective while maintained at 37 C and 5% CO2. Hoechst was subjected to 405 nm laser excitation and emission was recorded through a band pass 430-460 nm filter. GFP was subjected to 488 nm laser excitation and emission was recorded through a band pass 495-530 nm filter. tdTomato was subjected to 543 nm laser excitation and emission was recorded through a band pass 560 to 610 nm filter.

First, the cells were scanned to positively identify single-nucleated, tdTomato-positive cells. The presence of a tdTomato-positive cell indicated a cell that has undergone fusion, and the single nucleus indicated the fusion was by a cytobiologic fusosome donor. These identified cells were first imaged and then subsequently photo-bleached using a 488 nm laser to partially quench GFP fluorescence. The cells were then imaged over-time to assess recovery of GFP fluorescence, which would demonstrate translation of new GFP protein and thus presence of GFP mRNA delivered by the donor fusosome.

Analysis of Hoechst, GFP, and tdTomato fluorescence in the cells of interest was performed using ImageJ software (Rasband, W. S., ImageJ, U. S. National Institutes of Health, Bethesda, Md., USA, rsb.info.nih.gov/ij/, 1997-2007). First the images were pre-processed using a rolling ball background subtraction algorithm with a 60 m width. Within a photo-bleached cell, the GFP fluorescence was thresholded to remove background. Then the GFP mean fluorescence intensity for the photo-bleached cell was analyzed at different times before and after photo-bleaching.

Figure 5:
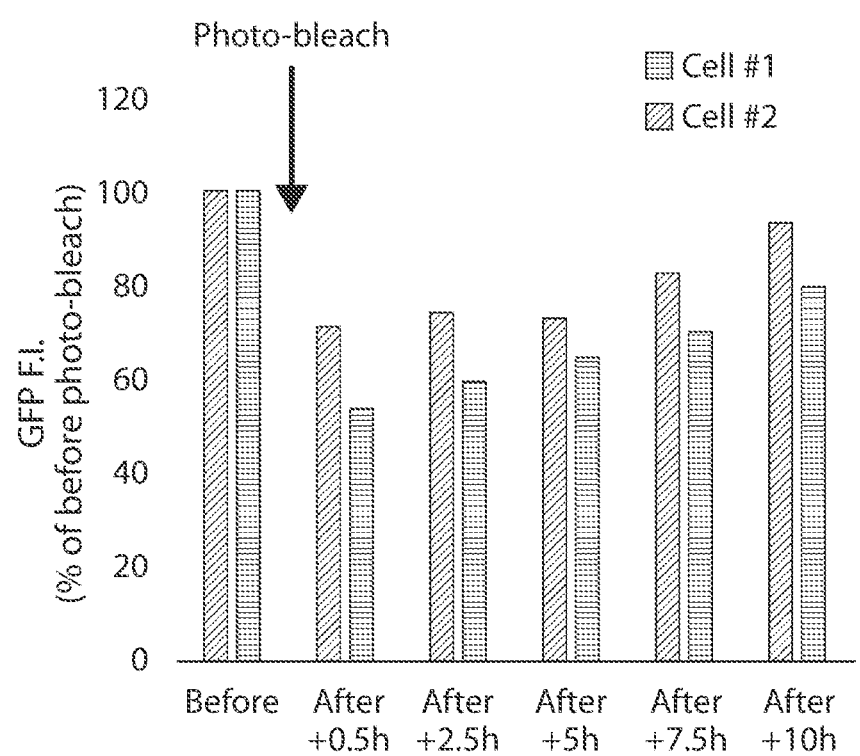
FIG. 5 is a graph showing recovery of GFP fluorescence after photobleaching of cells contacted with fusogens expressing Cre and GFP.

Within this particular Example, 3T3 mouse fibroblast cytobiologics expressing Cre and GFP and either possessing the applied fusogen HVJ-E (+fusogen) were applied to recipient mouse macrophage cells expressing "LoxP-stop-LoxP-tdTomato" cassette. Representative images and data are shown in FIG. 5. For this particular example the GFP fluorescence intensity recovered up to 25% of the original intensity 10 hours after photo-bleaching, indicating the delivery of actively-translated mRNA in the recipient cell.

Example 97: In Vitro Delivery of siRNA

This example describes delivery of short interfering RNA (siRNA) to cell in vitro via fusosomes. Delivery of siRNA to cells in vitro results in the suppression of the expression of proteins within the recipient cell. This can be used to inhibit the activity of a protein whose expression is injurious to the cell, thus permitting the cell to behave normally.

A fusosome produced by the herein described methods is assayed for its ability to deliver a specified siRNA to the recipient cell as follows. Fusosomes are prepared as described herein. Following production of the fusosome, it is additionally electroporated with an siRNA having a sequence that specifically inhibits GFP. The sequence of the double stranded siRNA targeted against GFP is 5' GACGUAAACGGCCACAAGUUC 3' and its complement 3' CGCUGCAUUUGCCGGUGUUCA 5' (note that there are overhangs 2 basepairs long at 3' ends of the siRNA sequence). As a negative control fusosomes are electroporated with an siRNA having a sequence that specifically inhibits luciferase. The sequence of the double stranded siRNA targeted against luciferase is 5' CUUACGCUGAGUACUUCGATT 3' and its complement 3' TTGAAUGCGACUCAUGAAGCU 5' (note that there are overhangs 2 basepairs long at 3' ends of the siRNA sequence).

The fusosomes are then applied to the recipient cells that constitutively express GFP. The recipient cells are plated into a black, clear-bottom 96-well plate. Next, 24 hours after plating the recipient cells, the fusosomes expressing are applied to the recipient cells in DMEM media. The dose of fusosomes is correlated to the number of recipient cells plated in the well. After applying the fusosomes, the cell plate is centrifuged at 400 g for 5 minutes to help initiate contact between the fusosomes and the recipient cells. The cells are then incubated for 16 hours and agent delivery, siRNA, is assessed via imaging.

The cells are imaged to positively identify GFP-positive cells in the field or well. In this example cell plates are imaged using an automated fluorescence microscope (www.biotek.com/products/imaging-microscopy-automated-cell-imagers/lionheart-fx-automated-live-cell-imager/). The total cell population in a given well is determined by first staining the cells with Hoechst 33342 in DMEM media for 10 minutes. Hoechst 33342 stains cell nuclei by intercalating into DNA and therefore is used to identify individual cells. After staining, the Hoechst media is replaced with regular DMEM media.

The Hoechst is imaged using the 405 nm LED and DAPI filter cube. GFP is imaged using the 465 nm LED and GFP filter cube. Images of the different cell groups are acquired by first establishing the LED intensity and integration times on an untreated well; i.e., recipient cells that were not treated with any fusosomes.

Acquisition settings are set so that GFP intensities are at the maximum pixel intensity values but not saturated. The wells of interest are then imaged using the established settings.

Analysis of GFP positive wells is performed with software provided with the fluorescence microscope or other software (Rasband, W. S., ImageJ, U. S. National Institutes of Health, Bethesda, Md., USA, http://rsb.info.nih.gov/ij/, 1997-2007). The images are pre-processed using a rolling ball background subtraction algorithm with a 60 um width. The total cell mask is set on the Hoechst-positive cells. Cells with Hoechst intensity significantly above background intensities are thresholded and areas too small or large to be Hoechst-positive cells are excluded.

Within the total cell mask, GFP—positive cells are identified by again thresholding for cells significantly above background and extending the Hoechst (nuclei) masks for the entire cell area to include the entire GFP cellular fluorescence. The percentage of GFP-positive cells out of total cells is calculated.

In embodiments, the percentage of GFP positive cells in wells treated with fusosomes containing an siRNA against GFP will be at least 1%, 2%, 3%, 4%, 5%, 10%, 20%, 30%, 40%, 50%, 60%, 70%, 80%, 90% less than the percentage of GFP positive cells in well treated with fusosomes containing an siRNA against luciferase.

Example 98: In Vivo Delivery of mRNA

This example describes the delivery of messenger RNA (mRNA) to cells in vivo via fusosomes. In an embodiment, delivery of mRNA to cells in vivo results in the expression of proteins within the recipient cell. In an embodiment, this method of delivery can be used to supplement a protein not present due to a genetic mutation, permitting the cell to behave normally, or re-direct the activity of a cell to carry out a function, e.g., a therapeutic function.

In an embodiment, fusosome mRNA delivery in vivo demonstrates the delivery of messenger RNA and protein expression in recipient cells within an organism (e.g., a mouse).

In an embodiment, fusosomes that express a liver directed fusogen, and produce mRNA expressing Cre are prepared for in vivo delivery.

Fusosomes are prepared as described herein. Fusosome suspensions are subjected to centrifugation. Pellets of the fusosomes are resuspended in sterile phosphate buffered saline for injection.

Fusosomes are verified to express mRNA using a nucleic acid detection method, e.g., PCR.

The recipient mice harbor a loxp-luciferase genomic DNA locus that is modified by CRE protein made from mRNA delivered by the fusosomes to unblock the expression of luciferase (JAX#005125). The positive controls for this example are offspring of recipient mice mated to a mouse strain that expresses the same protein exclusively in the liver from its own genome (albumin-CRE JAX#003574). Offspring from this mating harbor one of each allele (loxp-luciferase, albumin-CRE). Negative controls are carried out by injection of recipient mice with fusosomes not expressing fusogens or fusosomes with fusogens but not expressing Cre mRNA.

The fusosomes are delivered into mice by intravenous (IV) tail vein administration. Mice are placed in a commercially available mouse restrainer (Harvard Apparatus). Prior to restraint, animals are warmed by placing their cage on a circulating water bath. Once inside the restrainer, the animals are allowed to acclimate. An IV catheter consisting of a 30 G needle tip, a 3" length of PE-10 tubing, and a 28 G needle is prepared and flushed with heparinized saline. The tail is cleaned with a 70% alcohol prep pad. Then, the catheter needle is held with forceps and slowly introduced into the lateral tail vein until blood becomes visible in the tubing. The fusosome solution (~500K-5M fusosomes) is aspirated into a 1 cc tuberculin syringe and connected to an infusion pump. The fusosome solution is delivered at a rate of 20 uL per minute for 30 seconds to 5 minutes, depending on the dose. Upon completion of infusion, the catheter is removed, and pressure is applied to the injection site until cessation of any bleeding. Mice are returned to their cages and allowed to recover.

After fusion, the mRNA is translated in the recipient cytoplasm into CRE protein which then translocates to the nucleus to carry out recombination resulting in the constitutive expression of luciferase. Intraperitoneal administration of D-luciferin (Perkin Elmer, 150 mg/kg) enables the detection of luciferase expression via the production of bioluminescence. The animal is placed into an in vivo bioluminescent imaging chamber (Perkin Elmer) which houses a cone anesthetizer (isoflurane) to prevent animal motion. Photon collection is carried out between 8-20 minutes post-injection to observe the maximum in bioluminescence due to D-luciferin pharmacokinetic clearance. A specific region of the liver is created in the software and collection exposure time set so that count rates are above 600 (in this region) to yield interpretable radiance (photons/sec/cm2/steradians) measurements. The maximum value of bioluminescent radiance is recorded as the image of bioluminescence distribution. The liver tissue is monitored specifically for radiance measurements above background (untreated animals) and those of negative controls. Measurements are carried out at 24 hours post-injection to observe luciferase activity. Mice are then euthanized and livers are harvested.

Freshly harvested tissue is subjected to fixation and embedding via immersion in 4% paraformaldehyde/0.1M sodium phosphate buffer pH7.4 at 4° C. for 1-3 hrs. Tissue is then immersed in sterile 15% sucrose/1×PBS (3 hrs. to overnight) at 4° C. Tissue is then embedded in O.C.T. (Baxter No. M7148-4). Tissue is oriented in the block appropriately for sectioning (cross-section). Tissue is then frozen in liquid nitrogen using the following method: place the bottom third of the block into the liquid nitrogen, allow to freeze until all but the center of the O.C.T. is frozen, and allow freezing to conclude on dry ice. Blocks are sectioned by cryostat into 5-7 micron sections placed on slides and refrozen for staining.

In situ hybridization is carried out (using standard methods) on tissue sections using digoxygenin labeled RNA probes (for CRE mRNA and luciferase mRNA detection), labeled by anti-digoxygenin fluorescent antibodies, and observed by confocal microscopy.

In an embodiment, positive control animals (e.g., recombination via breeding without fusosome injection), will show bioluminescence intensity in liver as compared to untreated animals (e.g., no CRE or fusosomes), and negative controls. In an embodiment, fusosome injected animals will show bioluminescence in liver as compared to negative controls (e.g., fusosomes without fusogen), and untreated animals.

In an embodiment, detection of mRNA in tissue sections in animals administered fusosomes will reveal detection of CRE recombinase and luciferase mRNA compared to negative controls, and untreated animals in cells in the tissue. In an embodiment, positive controls will show levels of both luciferase mRNA and CRE recombinase mRNA throughout the tissue.

In an embodiment, evidence of mRNA delivery by fusosomes will be detected by in situ hybridization-based detection of the mRNA, and its colocalization in the recipient tissue of the animal. In an embodiment, activity of the protein expressed from the mRNA delivered by the fusosome is detected by bioluminescent imaging. In an embodiment, fusosomes deliver mRNA that will result in protein production and activity.

Example 99: In Vitro Delivery of Protein

This example demonstrates fusosome fusion with a cell in vitro. In this example, fusosome fusion with a cell in vitro results in delivery of Cre protein to the recipient cell.

In this example, the fusosomes were generated from a 3T3 mouse fibroblast cell possessing the Sendai virus HVJ-E protein (Tanaka et al., 2015, Gene Therapy, 22(October 2014), 1-8. doi.org/10.1038/gt.2014.12). In addition, the fusosomes expressed Cre recombinase. The target cell was a primary HEK293T cell which stably-expressed "LoxP-GFP-stop-LoxP-RFP" cassette under a CMV promoter, which upon recombination by Cre switches from GFP to RFP expression, indicating fusion and Cre, as a marker, delivery.

Fusosomes produced by the herein described methods were assayed for the ability to deliver Cre protein to recipient cells as follows. The recipient cells were plated into a cell culture multi-well plate compatible with the imaging system to be used (in this example cells were plated in a black, clear-bottom 96-well plate). Next, 24 hours after plating the recipient cells, the fusosome expressing Cre recombinase protein and possessing the particular fusogen protein were applied to the recipient cells in DMEM media. The dose of fusosomes was correlated to the number of recipient cells plated in the well. After applying the fusosomes the cell plate was centrifuged at 400 g for 5 minutes to help initiate contact between the fusosomes and the recipient cells. The cells were then incubated for 16 hours and protein delivery was assessed via imaging.

The cells were imaged to positively identify RFP-positive cells versus GFP-positive cells in the field or well. In this example cell plates were imaged using an automated microscope. The total cell population in a given well was determined by first staining the cells with 1 µg/mL Hoechst 33342 in DMEM media for 10 minutes. Hoechst 33342 stains cell nuclei by intercalating into DNA and therefore is used to identify individual cells. After staining the Hoechst media was replaced with regular DMEM media. The Hoechst was imaged using the 405 nm LED and DAPI filter cube. GFP was imaged using the 465 nm LED and GFP filter cube, while RFP was imaged using 523 nm LED and RFP filter cube. Images of the different cell groups were acquired by first establishing the LED intensity and integration times on a positive-control well; i.e., cells treated with adenovirus coding for Cre recombinase. Acquisition settings were set so that RFP and GFP intensities are at the maximum pixel intensity values but not saturated. The wells of interest were then imaged using the established settings.

Analysis of Hoechst, GFP, and RFP-positive wells was performed in the Gen5 software provided with the Lion-Heart FX or by ImageJ software (Rasband, W. S., ImageJ, U. S. National Institutes of Health, Bethesda, Md., USA, http://rsb.info.nih.gov/ij/, 1997-2007). First the images were preprocessed using a rolling ball background subtraction algorithm with a 60 um width. Next the total cell mask was set on the Hoechst-positive cells. Cells with Hoechst intensity significantly above background intensities were thresholded and areas too small or large to be Hoechst-positive cells were excluded. Within the total cell mask GFP and RFP-positive cells were identified by again thresholding for cells significantly above background and extending the Hoechst (nuclei) masks for the entire cell area to include the entire GFP and RFP cellular fluorescence.

The number of RFP-positive cells identified in control wells containing only recipient cells was used to subtract from the number of RFP-positive cells in the wells containing fusosome (to subtract for non-specific Loxp recombination). The number of RFP-positive cells (recipient cells that received the agent) was then divided by the sum of the GFP-positive cells (recipient cells that have not received the agent) and RFP-positive cells to quantify the fraction of fusosome agent delivery within the recipient cell population.

Figure 6:
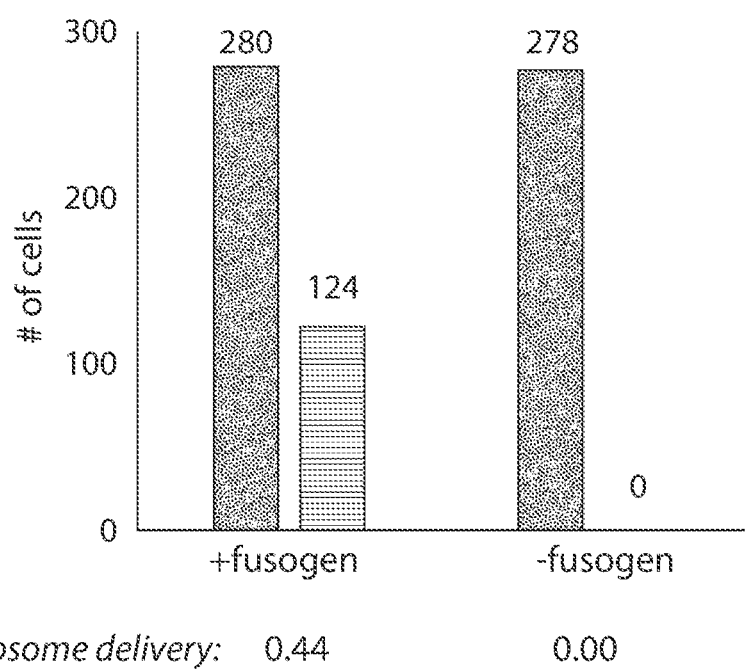
FIG. 6 is a graph showing the percentage of target cells expressing RFP after contacting with fusosomes or negative controls.

Within this particular example, 3T3 mouse fibroblast cells expressing Cre and either possessing the applied fusogen HVJ-E (+fusogen) or not (−fusogen) were applied to recipient 293T cells expressing "LoxP-GFP-stop-LoxP-RFP" cassette. Delivery of Cre protein is assessed by the induction of RFP expression in the recipient cells. The graph in FIG. 6 shows the quantification of the RFP-positive cells (rightmost bar of each pair) out of the total cells stained positive for Hoechst (leftmost bar of each pair). For this particular Example the fraction of fusosome delivery to recipient cells is 0.44 for 3T3 Cre cells possessing HVJ-E fusogen.

Example 100: In Vivo Delivery of Protein

This example describes the delivery of therapeutic agents to the eye by fusosomes.

Fusosomes are derived from hematopoietic stem and progenitor cells using any of the methods described in previous Examples and are loaded with a protein that is deficient in a mouse knock-out.

Fusosomes are injected subretinally into the right eye of a mouse that is deficient for the protein and vehicle control is injected into the left eye of the mice. A subset of the mice is euthanized when they reach 2 months of age.

Histology and H&E staining of the harvested retinal tissue is conducted to count the number of cells rescued in each retina of the mice (described in Sanges et al., The Journal of Clinical Investigation, 126(8): 3104-3116, 2016).

The level of the injected protein is measured in retinas harvested from mice euthanized at 2 months of age via a western blot with an antibody specific to the PDE6B protein.

In an embodiment, the left eyes of mice, which are administered fusosomes, will have an increased number of nuclei present in the outer nuclear level of the retina compared to the right eyes of mice, which are treated with vehicle. The increased protein is suggestive of complementation of the mutated PBE6B protein.

Example 101: Delivery to Edit Recipient DNA

This example describes fusosomes for delivery of genome CRISPR-Cas9 editing machinery to a cell in vitro. In an embodiment, delivery of genome CRISPR-Cas9 editing machinery to a cell in vitro via a fusosome results in a loss of function of a specific protein in a recipient cell. Genome editing machinery referred to, in this example, is the *S. pyogenes* Cas9 protein complexed with a guide RNA (gRNA) specific for GFP.

In an embodiment, fusosomes are a chassis for the delivery of therapeutic agents. In an embodiment, therapeutic agents, such as genome editing machinery that can be delivered to cells with high specificity and efficiency could be used to inactivate genes, and thus subsequent gene products (e.g. proteins) that when expressed at high levels or in the wrong cell type become pathological.

A fusosome composition as produced by any one of the methods described in previous Examples, except the fusosome is engineered such that the fusosome also includes the *S. pyogenes* Cas9 protein complexed with a guide RNA (gRNA) sequence that is specific for the sequence of A. Victoria EGFP. This is achieved by co-nucleofecting a PiggyBac vector that has the open reading frame of the Neomycin resistance gene that is an in-frame fusion with the open reading frame of *S. pyogenes* Cas9, separated by a P2A cleavage sequence. The additional co-nucleofected PiggyBac vector also includes the gRNA sequence (GAAGTTCGAGGGCGACACCC) driven by the U6 promoter. As a negative control a fusosome is engineered such that the fusosome includes the *S. pyogenes* Cas9 protein complexed with a scrambled gRNA (GCACTACCAGAGCTAACTCA) sequence that is not-specific for any target in the mouse genome.

A sufficient number of fusosomes are incubated at 37° C. and 5% $CO_2$ together with NIH/3T3 GFP+ cells for a period of 48 h in in DMEM containing 20% Fetal Bovine Serum and 1× Penicillin/Streptomycin. Following the 48 hr incubation, genomic DNA is prepared and used as a template with primers specific for region within 500 bp of the predicted gRNA cleavage site in the GFP gene (see Table 13).

TABLE 13

GFP Primers sequences that amplify a 500 bp fragment for TIDE analysis

| Primer | Sequence |
|---|---|
| GFP-F | ATGAGTAAAGGAGAAGAACTTTTCAC |
| GFP-R | GTCCTTTTACCAGACAACCATTAC |

The PCR amplicon is then purified, sequenced by capillary sequencing and then uploaded to Tide Calculator, a web tool that rapidly assesses genome editing by CRISPR-Cas9 of a target locus determined by a guide RNA. Based on the quantitative sequence trace data from two standard capillary sequencing reactions, the software quantifies the editing efficacy. An indel (insert or deletion) at the predicted gRNA cleavage site with the GFP locus results in the loss of GFP expression in the cells and is quantified via FACS using a FACS analysis (Becton Dickinson, San Jose, Calif., USA) with 488 nm argon laser excitation and emission is collected at 530+/−30 nm. FACS software is used for acquisition and analysis. The light scatter channels are set on linear gains, and the fluorescence channels on a logarithmic scale, with a minimum of 10,000 cells analyzed in each condition. The indel and subsequent loss of GFP function is calculated based on the intensity of GFP signal in each sample.

In an embodiment, an indel (insert or deletion) at the predicted gRNA cleavage site with the GFP locus and loss of GFP fluorescence in the cell, in comparison to the negative control, will indicate the ability of a fusosome to edit DNA and result in a loss of protein function in vitro. In an embodiment, fusosomes with the scrambled gRNA sequence will demonstrate no indels or subsequent loss of protein function.

Example 102: Assessment of Teratoma Formation after Administration of Fusosome

This Example describes the absence of teratoma formation with a fusosome. In an embodiment, a fusosome will not result in teratoma formation when administered to a subject.

The fusosomes are produced by any one of the methods described in a previous Example. Fusosomes, tumor cells (positive control) or vehicle (negative control) are subcutaneously injected in PBS into the left flank of mice (12-20 weeks old). Teratoma, e.g., tumor, growth is analyzed 2-3 times a week by determination of tumor volume by caliper measurements for eight weeks after fusosome, tumor cell, or vehicle injection.

In an embodiment, mice administered fusosomes or vehicle will not have a measurable tumor formation, e.g., teratoma, via caliper measurements. In an embodiment, positive control animals treated with tumor cells will demonstrate an appreciable tumor, e.g., teratoma, size as measured by calipers over the eight weeks of observation.

Example 103: Fusosomes Deliver Active Protein to Recipient Cells of a Subject In Vivo This Example demonstrates that fusosomes can deliver a protein to a subject in vivo. This is exemplified by delivery of the nuclear editing protein Cre. Once inside of a cell, Cre translocates to the nucleus, where it recombines and excises DNA between two LoxP sites. Cre-mediated recombination can be measured microscopically when the DNA between the two LoxP sites is a stop codon and is upstream of a distal fluorescent protein, such as the red fluorescent protein tdTomato.

Fusosomes that contain CRE and the fusogen VSV-G, purchased from Takara (Cre Recombinase Gesicles, Takara product 631449), were injected into B6.Cg-Gt(ROSA) 26Sor$^{tm9(CAG-tdTomato)Hze}$/J mice (Jackson Laboratories strain 007909). Animals were injected at the anatomical sites, injection volumes, and injection sites as described in Table 14. Mice that do not have tdTomato (FVB.129S6(B6)-GT(ROSA)26Sor$^{tm1(Luc)Kael}$/J, Jackson Laboratories strain 005125) and were injected with fusosomes and B6.Cg-Gt (ROSA)26Sor$^{tm14(CAG-tdTomato)Hze}$/J mice that were not injected with fusosomes were used as negative controls.

TABLE 14

Injection parameters

| | | |
|---|---|---|
| Brain | 10 ul | anterior posterior axis: −2 Lateral/medial axis: 1.8 ventral: 1.5 side: right |
| Eye | 1 ul | intravitreal |
| Liver | 25 ul | center of frontal lobe |
| Spleen | 10 ul | approximately in the center, both lengthwise and widthwise |
| Kidney | 20 ul | center of left kidney |
| Small intestine lining | 10 ul | loop of small intestine nearest the peritoneal wall was isolated outside peritoneum, and injected into lining |
| Heart | 5 ul | near apex |
| White Adipose (Epididymal fat pad) | 25 ul | left, top and central |
| Brown adipose (intrascapular) | 25 ul | left lobe, as central as possible |
| Lung | 10 ul | inferior lobe right lung |
| Testis | 10 ul | left testis, as central as possible |
| Ovary | 1 ul | left ovary, as central as possible |

Two days after injections, the animals were sacrificed and samples were collected. The samples were fixed for 8 hours in 2% PFA, fixed overnight in 30% sucrose, and shipped for immediate embedding in OCT and sectioning to slides. Slides were stained for nuclei with DAPI. DAPI and tdTomato fluorescence was imaged microscopically.

Figure 9:
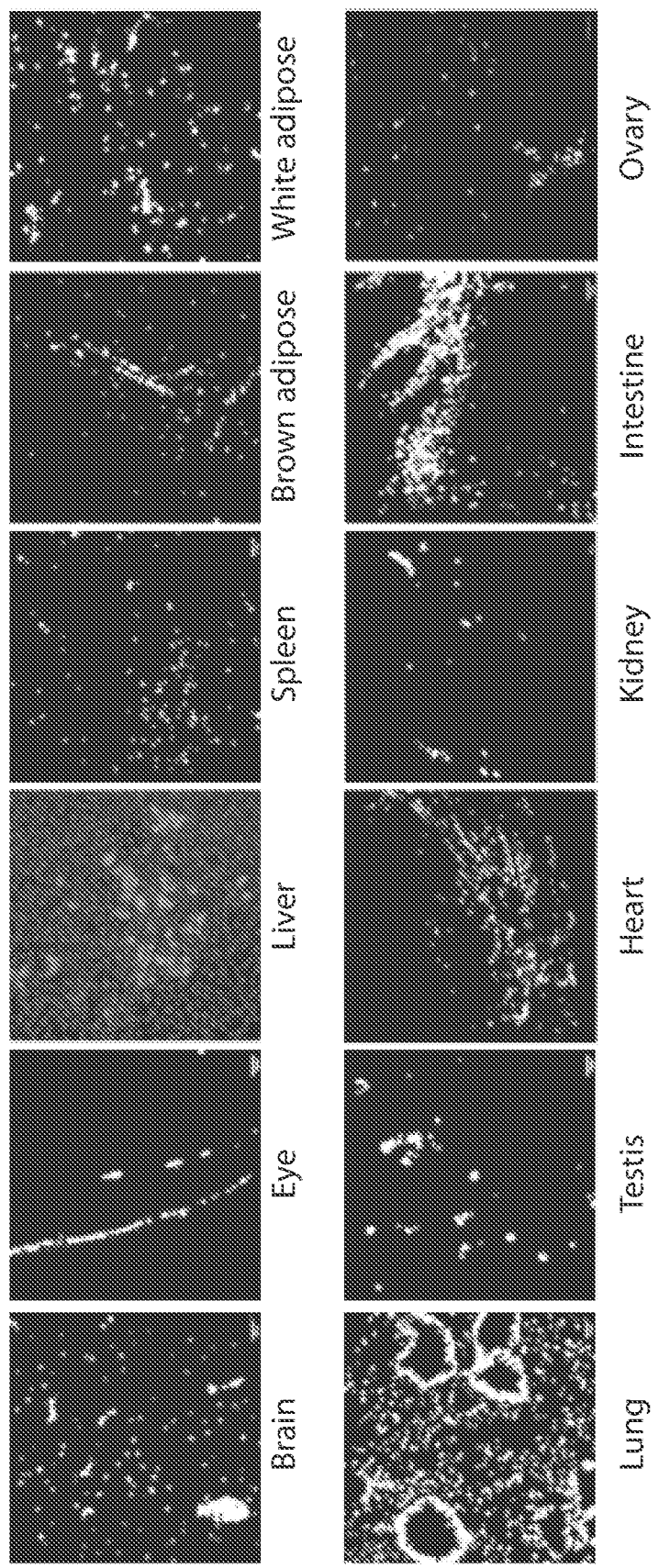
FIG. 9 shows microscopy images of the indicated tissues from mice injected with fusosomes. White indicates represent RFP-fluorescent cells, indicating delivery of a protein cargo to the cells in vivo.
Figure 11:
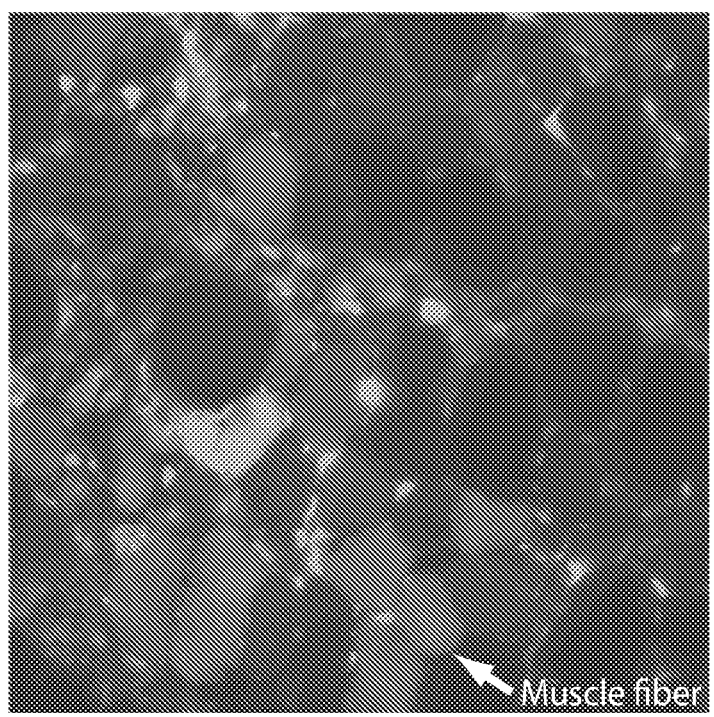
FIG. 11 shows microscopy images of tdTomato fluorescence in murine muscle tissue, indicating delivery of a protein cargo to muscle cells by cytobiologics.

All anatomical sites listed in Table 14 demonstrated tdTomato fluorescence (FIG. 9). In addition, delivery to muscle tissue was confirmed using fluorescence microscopy for tdTomato (FIG. 11). Negative control mice did not have any tissues with tdTomato fluorescence. This result demonstrates that fusosomes are capable of turning on tdTomato fluorescence in the cells of a mouse at various anatomical sites, and that this does not occur if the mice are not treated with fusosomes or if the mice do not have tdTomato in their genome. Hence, fusosomes deliver active Cre recombinase to the nucleus of mouse cells in vivo.

It was also shown that different routes of administration can deliver fusosomes to tissue in vivo. Fusosomes that contain CRE and the fusogen VSV-G, purchased from Takara (Cre Recombinase Gesicles, Takara product 631449), were injected into FVB. 129S6(B6)-GT(ROSA) 26Sor$^{tm1(Luc)Kael}$/J (Jackson Laboratories strain 005125) intramuscularly (in 50 ul to the right tibialis anterior muscle), intraperitoneally (in 50 ul to the peritoneal cavity), and subcutaneously (in 50 ul under the dorsal skin).

The legs, ventral side, and dorsal skin was prepared for intramuscular, intraperitoneal, and subcutaneous injection, respectively, by depilating the area using a chemical hair remover for 45 seconds, followed by 3 rinses with water.

On day 3 after injection, an in vivo imaging system (Perkin Elmer) was used to obtain whole animal images of bioluminescence. Five minutes before imaging, mice received an intraperitoneal injection of bioluminescent substrate (Perkin Elmer) at a dose of 150 mg/kg in order to visualize luciferase. The imaging system was calibrated to compensate for all device settings.

Figure 10:
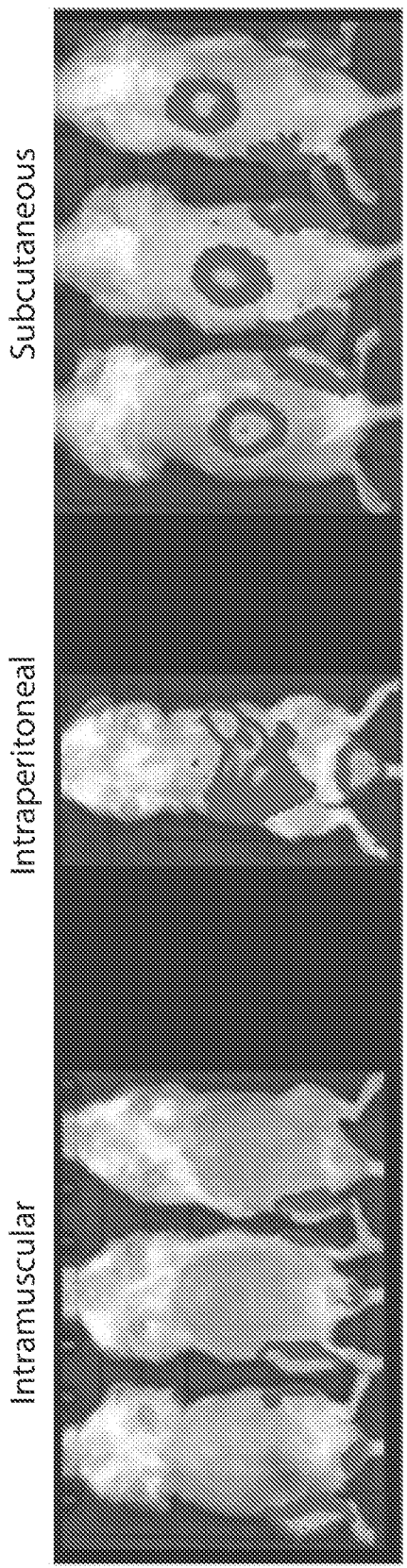
FIG. 10 is a series of images showing successful delivery of fusosomes to murine tissues in vivo by the indicated routes of administration, resulting in expression of luciferase by targeted cells.

Administration by all three routes resulted in luminescence (FIG. 10) indicating successful delivery of active Cre recombinase to mouse cells in vivo.

In conclusion, fusosomes are capable of delivering active protein to cells of a subject in vivo.

Example 104: Sonication-Mediated Loading of Nucleic Acid in Fusosomes

This example describes loading of nucleic acid payloads into a fusosome via sonication. Sonication methods are disclosed e.g., in Lamichhane, T N, et al., Oncogene Knockdown via Active Loading of Small RNAs into Extracellular Vesicles by Sonication. Cell Mol Bioeng, (2016), the entire contents of which are hereby incorporated by reference.

Fusosomes are prepared by any one of the methods described in a previous example. Approximately $10^6$ fusosomes are mixed with 5-20 g nucleic acid and incubated at room temperature for 30 minutes. The fusosome/nucleic acid mixture is then sonicated for 30 seconds at room temperature using a water bath sonicator (Brason model #1510R-DTH) operated at 40 kHz. The mixture is then placed on ice for one minute followed by a second round of sonication at 40 kHz for 30 seconds. The mixture is then centrifuged at 16,000 g for 5 minutes at 4° C. to pellet the fusosomes containing nucleic acid. The supernatant containing unincorporated nucleic acid is removed and the pellet is resuspended in phosphate-buffered saline. After DNA loading, the fusosomes are kept on ice before use.

Example 105: Sonication-Mediated Loading of Protein in Fusosomes

This example describes loading of protein payloads into a fusosome via sonication. Sonication methods are disclosed e.g., in Lamichhane, T N, et al., Oncogene Knockdown via Active Loading of Small RNAs into Extracellular Vesicles by Sonication. Cell Mol Bioeng, (2016), the entire contents of which are hereby incorporated by reference.

Fusosomes are prepared by any one of the methods described in a previous example. Approximately $10^6$ fusosomes are mixed with 5-20 g protein and incubated at room temperature for 30 minutes. The fusosome/protein mixture is then sonicated for 30 seconds at room temperature using a water bath sonicator (Brason model #1510R-DTH) operated at 40 kHz. The mixture is then placed on ice for one minute followed by a second round of sonication at 40 kHz for 30 seconds. The mixture is then centrifuged at 16,000 g for 5 minutes at 4 C to pellet the fusosomes containing protein. The supernatant containing unincorporated protein is removed and the pellet is resuspended in phosphate-buffered saline. After protein loading, the fusosomes are kept on ice before use.

Example 106: Hydrophobic Carrier-Mediated Loading of Nucleic Acid in Fusosomes

This example describes loading of nucleic acid payloads into a fusosome via hydrophobic carriers. Exemplary methods of hydrophobic loading are disclosed, e.g., in Didiot et al., Exosome-mediated Delivery of Hydrophobically Modified siRNA for Huntingtin mRNA Silencing, *Molecular Therapy* 24(10): 1836-1847, (2016), the entire contents of which are hereby incorporated by reference.

Fusosomes are prepared by any one of the methods described in a previous example. The 3' end of a RNA molecule is conjugated to a bioactive hydrophobic conjugate (triethylene glycol-Cholesterol). Approximately $10^6$ fusosomes are mixed in 1 ml with 10 µmol/l of siRNA conjugate in PBS by incubation at 370 C for 90 minutes with shaking at 500 rpm. The hydrophobic carrier mediates association of the RNA with the membrane of the fusosome. In some embodiments, some RNA molecules are incorporated into the lumen of the fusosome, and some are present on the surface of the fusosome. Unloaded fusosomes are separated from RNA-loaded fusosomes by ultracentrifugation for 1 hour at 100,000 g, 4° C. in a tabletop ultracentrifuge using a TLA-110 rotor. Unloaded fusosomes remain in the supernatant and RNA-loaded fusosomes form a pellet. The RNA-loaded fusosomes are resuspended in 1 ml PBS and kept on ice before use.

Example 107: Processing Fusosomes

This example described the processing of fusosomes. Fusosomes produced via any of the described methods in the previous Examples may be further processed.

In some embodiments, fusosomes are first homogenized, e.g., by sonication. For example, the sonication protocol includes a 5 second sonication using an MSE sonicator with microprobe at an amplitude setting of 8 (Instrumentation Associates, N.Y.). In some embodiments, this short period of sonication is enough to cause the plasma membrane of the fusosomes to break up into homogenously sized fusosomes. Under these conditions, organelle membranes are not disrupted and these are removed by centrifugation (3,000 rpm, 15 min 4° C.). Fusosomes are then purified by differential centrifugation as described in Example 16.

Extrusion of fusosomes through a commercially available polycarbonate membrane (e.g., from Sterlitech, Washington) or an asymmetric ceramic membrane (e.g., Membralox), commercially available from Pall Execia, France, is an effective method for reducing fusosome sizes to a relatively well defined size distribution. Typically, the suspension is cycled through the membrane one or more times until the desired fusosome size distribution is achieved. The fusosomes may be extruded through successively smaller pore membranes (e.g., 400 nm, 100 nm and/or 50 nm pore size) to achieve a gradual reduction in size and uniform distribution.

In some embodiments, at any step of fusosome production, though typically prior to the homogenization, sonication and/or extrusion steps, a pharmaceutical agent (such as a therapeutic), may be added to the reaction mixture such that the resultant fusosome encapsulates the pharmaceutical agent.

Example 108: Measuring Total RNA in a Fusosome and Source Cell

This Example describes a method to quantify the amount of RNA in a fusosome relative to a source cell. In an embodiment, a fusosome will have similar RNA levels to the source cell. In this assay, RNA levels are determined by measuring total RNA.

Fusosomes are prepared by any one of the methods described in previous Examples. Preparations of the same mass as measured by protein of fusosomes and source cells are used to isolate total RNA (e.g., using a kit such as Qiagen RNeasy catalog #74104), followed by determination of RNA concentration using standard spectroscopic methods to assess light absorbance by RNA (e.g. with Thermo Scientific NanoDrop).

In an embodiment, the concentration of RNA in fusosomes will be 5%, 10%, 20%, 30%, 40%, 50%, 60%, 70%, 80%, 90%, 95% of that of source cells per mass of protein.

Example 109. Creation of HEK-293T Cells Expressing Exogenous Fusogens

This example describes the creation of tissue culture cells expressing an exogenous fusogen. A fusogen gene, VSV-G (vesicular stomatitis virus G-protein), was cloned into pcDNA3.1 vector (ThermoFisher). VSV-G construct was then transfected into HEK-293T cells (ATCC, Cat #CRL-3216) using Xfect transfection reagent (Takara). Transfected HEK-293T cells were cultured at 37° C., 5% $CO_2$ in Dulbecco's Modified Eagle Medium (DMEM) supplemented with GlutaMAX (GIBCO), 10% fetal calf serum (GIBCO), and penicillin/streptomycin antibiotics (GIBCO) for the appropriate duration before utilizing for further experiments.

Example 110. Delivery of Mitochondria Via Protein Enhanced Fusogenic Enucleated Cells Fusogenic enucleated cells were generated comprising a HeLa cell expressing the envelope glycoprotein G from vesicular stomatitis virus (VSV-G) on the cell surface and protein-enhanced by expressing mitochondrial-targeted DsRED fluorescent protein (mtDsRED). HeLa cells expressing VSV-G were enucleated according to the standard procedure of ultracentrifugation through a Ficoll gradient to obtain enucleated cells (e.g., as described in Example 1). The recipient cell was a HeLa Rho0 cell, that had been produced to lack mitochondrial DNA (mtDNA) by long-term (>6 weeks) culture of HeLa cells in zalcitabine, a nucleoside analog reverse transcriptase inhibitor. The HeLa Rho0 cells are deficient in mtDNA (as assessed by qPCR) and show significantly deficient mitochondrial oxygen consumption (as measured by Seahorse extracellular flux assay). Recipient HeLa Rho0 cells were also engineered to expressing mitochondrial-targeted GFP (mtGFP) via adenoviral transduction for 2 days.

Recipient HeLa Rho0 cells were plated into 6-well dishes and one hour later enucleated VSV-G HeLa cells were applied to the recipient cells. The cells were then incubated for 24 hours at 37° C. and 5% $CO_2$. Cells were then sorted for double-positive (fused) cells via fluorescence-assisted cell sorting using a BD FACS Aria SORP cell sorter. The population of cells double-positive for mtGFP and mtDsRED was assessed in order to sort the recipient HeLa Rho0 cells that had received mitochondrial donation (mtDsRED) from the enucleated VSV-G HeLa cells. mtGFP was excited with a 488 nm laser and emission captured at 513±26 nm. mtDsRED was excited with a 543 nm laser and emission captured at 570±26 nm. Forward and side scatter gating was initially used to capture cell-sized events and discard small debris. Events double-positive for mtGFP and mtDsRED were determined by gating at the minimum level for which each appropriately negative control sample showed <1% of events positive for the specific fluorescent marker (i.e. unstained and single-mtGFP-positive samples show <1% events positive for mtDsRED). The double-positive events, as well as the single-positive mtGFP (recipient cells with no mitochondrial delivery) and single-positive mtDsRED (donor enucleated VSV-G HeLa cells that did not fuse to recipient cells) events were then sorted into DMEM media with 10% FBS and antibiotics. The sorted cells were counted and seeded at 25,000 cells per well (in 6 replicates for each group) in a 96-well Seahorse plate (Agilent). The plate was incubated at 37° C. and 5% $CO_2$ for 24 hours.

Oxygen consumption assays were initiated by removing growth medium, replacing with low-buffered DMEM minimal medium containing 25 mM glucose and 2 mM glutamine (Agilent) and incubating at 37° C. for 60 minutes to allow temperature and pH to reach equilibrium. The microplate was then assayed in the XF96 Extracellular Flux Analyzer (Agilent) to measure extracellular flux changes of oxygen and pH in the media immediately surrounding adherent cells. After obtaining steady state oxygen consumption and extracellular acidification rates, oligomycin (5 μM), which inhibits ATP synthase, and proton ionophore FCCP (carbonyl cyanide 4-(trifluoromethoxy) phenylhydrazone; 2 μM), which uncouples mitochondria, were injected sequentially through reagent delivery chambers for each cell well in the microplate to obtain values for maximal oxygen consumption rates. Finally, 5 M antimycin A (inhibitor of mitochondrial complex III) was injected in order to confirm that respiration changes were due mainly to mitochondrial respiration. The rates of antimycin A respiration were subtracted from the other three respiration rates in order to determine the basal, uncoupled (oligomycin-resistant), and maximal (FCCP-induced) mitochondrial respiration rates.

Figure 12:
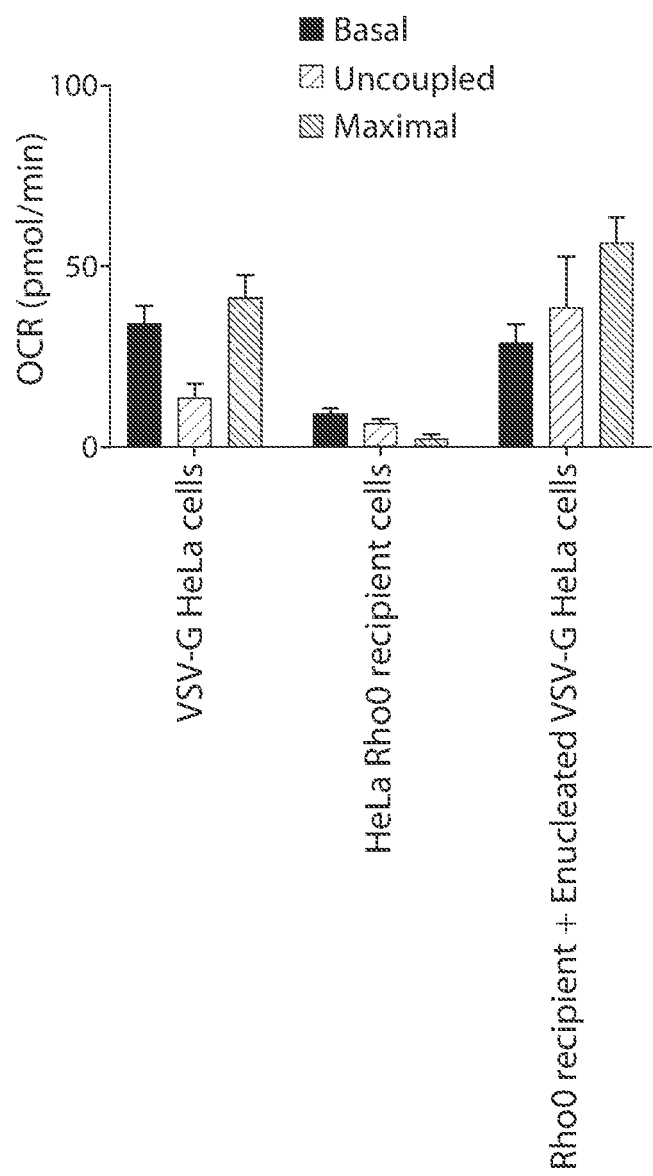
FIG. 12 is a graph showing delivery of mitochondria into recipient HeLa Rho0 cells using protein-enhanced, enucleated VSV-G HeLa cells.

Using this assay, it was determined that donor VSV-G HeLa cells showed active basal and maximal oxygen consumption rates, while target cells with no delivery showed low rates of all three states of mitochondrial oxygen consumption. Delivery of mitochondria with protein-enhanced, enucleated VSV-G HeLa cells to recipient HeLa Rho0 cells showed a return to mitochondrial oxygen consumption rates near donor VSV-G HeLa cell rates (FIG. 12).

Example 111: Generating and Isolating Fusosomes Through Vesicle Formation and Centrifugation This example describes fusosome generation and isolation via vesiculation and centrifugation. This is one of the methods by which fusosomes are isolated. Fusosomes were prepared as follows. $9.2 \times 10^6$ HEK-293T (ATCC, Cat #CRL-3216) were reverse transfected using Xfect transfection reagent (Takara, Cat #631317) with 10 μg of the pcDNA3.1 expression plasmid containing the open reading frame for VSVg and 15 ug of the pcDNA3.1 expression plasmid containing the open reading frame for bacteriophage P1 Cre recombinase with a SV40 Nuclear localization sequence in 7.5 mL of complete media (Dulbecco's Modified Eagle Medium (DMEM) supplemented with GlutaMAX (ThermoFisher), 10% fetal calf serum (ThermoFisher), and penicillin/streptomycin antibiotics (ThermoFisher)) in a 100 mm collagen coated dish (Corning). Twelve hours after seeding, medium was aspirated and carefully replaced with 15 mL of fresh complete medium supplemented with 100 μM ATP (Sigma). Supernatants were then collected 48 hours after transfection, clarified by centrifugation (2000×g, 10 mins), filtered through a 0.45 μm PES filter (CellTreat), and ultracentrifuged at 120,000×g for 1.5 hours. The pelleted material was then resuspended in an ice-cold mixture of 50% 1×PBS/50% complete media, vortexed at maximum speed for two minutes and frozen at −80° C. until utilizing for further experiments.

Example 112: Generating and Isolating Giant Plasma Membrane Fusosomes

This example describes fusosome generation, loading, and isolation via cellular vesiculation and centrifugation. This is one of the methods through which fusosomes can be generated, isolated and loaded with cargo.

Fusosomes were prepared as follows. $9.2 \times 10^6$ HEK-293T were reverse transfected using a polymeric transfection reagent with 10 μg of the pcDNA3.1 expression plasmid containing the open reading frame for VSVg and 15 ug of the pcDNA3.1 expression plasmid containing the open reading frame for bacteriophage P1 Cre Recombinase with a SV40 Nuclear localization sequence in 7.5 mL of complete media (DMEM+10% FBS+1× Pen/Strep) in a 100 mm collagen coated dish.

To produce cargo-loaded fusosomes, 24 hours after transfection the cells were washed twice in wash buffer (10 mM HEPES, pH 7.4, 150 mM NaCl, 2 mM CaCl2) and once in formation buffer (10 mM HEPES, pH 7.4, 2 mM CaCl2, 150 mM NaCl, 25 mM PFA, 2 mM DTT, 125 mM glycine). The cells were then incubated at 37° C. in formation buffer for a minimum of 6 hours. The supernatant containing the fusosomes was harvested, and fusosomes were then clarified from cells and cellular debris via a 5 minute centrifugation at 2,000×g. Finally, fusosomes were concentrated via a 20 minute centrifugation at 17,000×g and resuspended in the desired buffer for experimentation. To test whether fusosomes can fuse with recipient cells and deliver their cargo, resuspended fusosomes were added to recipient 293T LoxP Green/Red switch reporter cells at the desired dose. To verify vesicle fusion and cargo delivery, LoxP recombination of the recipient cells was imaged using an automated fluorescence microscope (www.biotek. com/products/imaging-microscopy-automated-cell-imagers/lionheart-fx-automated-live-cell-imager/). To positively identify RFP-positive cells in the field of view, the total cell population in each well was determined by first staining the cells with Hoechst 33342 in DMEM media for 10 minutes. Hoechst 33342 stains cell nuclei by intercalating into DNA and therefore may be used to identify individual cells. After staining, the Hoechst media was replaced with regular DMEM media and the RFP+ cells were identified.

The Hoechst staining was imaged using a 405 nm LED and DAPI filter cube. RFP was imaged using a 523 nm LED and RFP filter cube. Images of the different cell groups were acquired by first establishing the LED intensity and integration times on an untreated well; i.e., recipient cells that were not treated with any fusosomes. Acquisition settings were set so that RFP intensities were at the maximum pixel intensity values but not saturated. The wells of interest were then imaged using the established settings.

Analysis of RFP positive wells was performed with Gen 5 software (BioTek) provided with the fluorescence microscope. The images were pre-processed using a rolling ball background subtraction algorithm with a 10 m width (Hoechst 33342), 20 m width (RFP). The total cell mask was set on the Hoechst-positive cells. Cells with Hoechst intensity significantly above background intensities were thresholded and areas too small or large to be Hoechst-positive cells were excluded.

Figure 13:
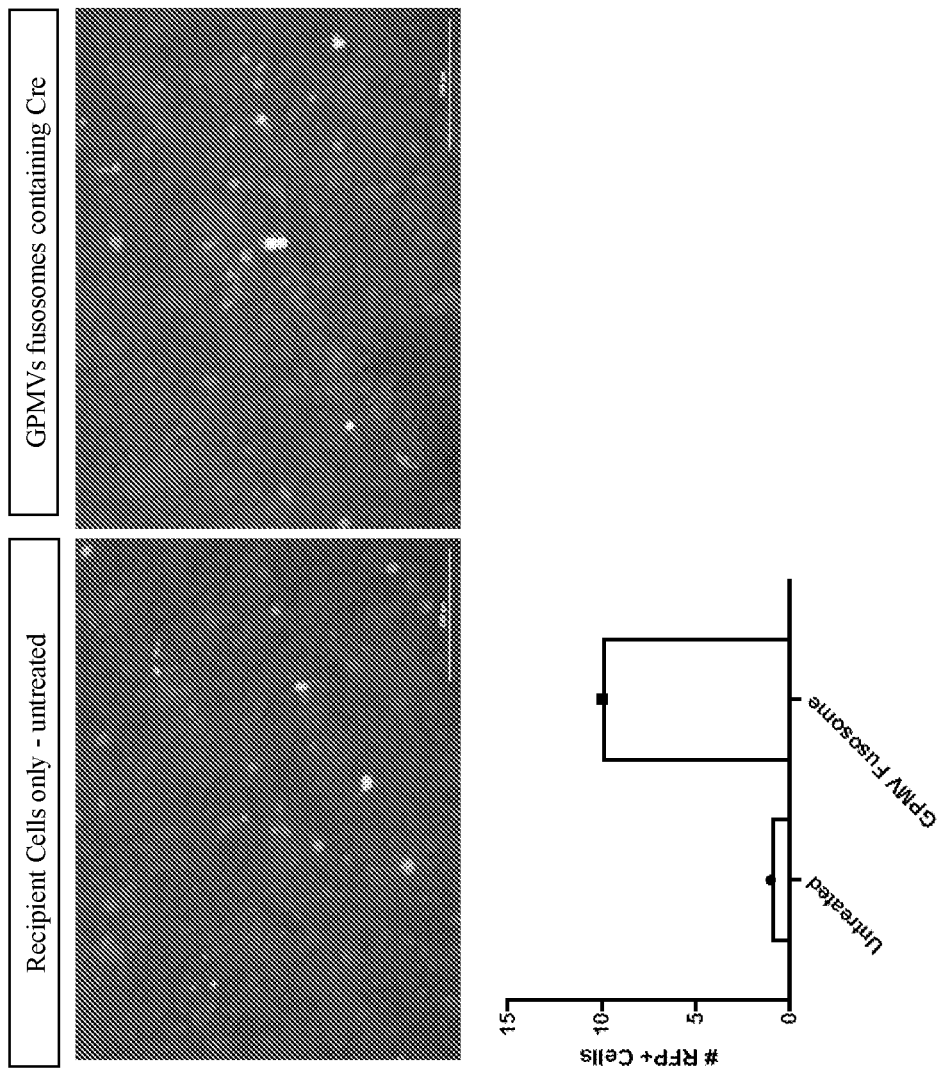
FIG. 13 is a series of images showing generation and isolation of giant plasma membrane fusosomes.

Within the total cell mask, RFP-positive cells were identified by again thresholding for cells significantly above background and extending the Hoechst (nuclei) masks for the entire cell area to include the entire RFP cellular fluorescence. The total number of RFP-positive cells out of total per field of view was calculated. In an embodiment, fusosome treated recipient cells had more RFP+ cells per field of view than non-treated cells (FIG. 13).

Example 113: Generating Fusosomes Through Extrusion

This example describes fusosome manufacturing by extrusion through a membrane.

HEK293T cells expressing VSV-G and Cre recombinase were trypsinized with TrypleE, collected, spun at 500×g for 5 min and counted. 30×10$^6$ cells were subsequently resuspended in 1 mL of 12.5% Ficoll in DMEM media supplemented with 500 nM Latrunculin B for 30 minutes at 37° C. To enucleate cells, they were transferred to a discontinuous Ficoll gradient consisting of the following Ficoll fractions (from top to bottom): 5 mL 12.5% Ficoll, 6 mL 16% Ficoll, 10 mL 18% Ficoll. All Ficoll gradient fractions were made in DMEM media supplemented with 500 nM Latrunculin B. Gradients were spun on a Beckman SW-40 ultracentrifuge with a Ti-70 rotor at 32,300 RPM for 1 h at 37° C. Following centrifugation, enucleated HEK293T cells were collected from the gradient between the 12.5% and 16% Ficoll layers and diluted with PBS, and spun at 3,000×g for 5 min. Enucleated cells were then resuspended in 1 mL of PBS.

Briefly, for extrusion, fusogenic enucleated HEK293T cells were resuspended to a density of 1-5 mg/mL protein as assayed by Bicinchoninic Acid Assay in PBS. The cells were aspirated with a 1 mL gas-tight syringe and passed through a 5 μm, 0.8 μm, or 0.4 μm membrane between 1 and 20 times. The filtrate was collected and added to a 96-well plate containing HEK293T cells stably expressing a loxP:GFP/RFP reporter construct. After 16-24 hours, the plate was imaged and analyzed for expression of RFP (FIG. 14).

Example 114: Isolating Fusogenic Microvesicles Freely Released from Cells

This example describes the isolation of fusogenic microvesicles freely released from cells. Fusogenic microvesicles were isolated as follows. 9.2×10$^6$ HEK-293T (ATCC, Cat #CRL-3216) were reverse transfected using Xfect transfection reagent (Takara, Cat #631317) with 10 μg of the pcDNA3.1 expression plasmid containing the open reading frame for VSVg and 15 ug of the pcDNA3.1 expression plasmid containing the open reading frame for bacteriophage P1 Cre Recombinase with a SV40 Nuclear localization sequence in 7.5 mL of complete media (Dulbecco's Modified Eagle Medium (DMEM) supplemented with GlutaMAX (ThermoFisher), 10% fetal calf serum (ThermoFisher), and penicillin/streptomycin antibiotics (ThermoFisher)) in a 100 mm collagen coated dish (Corning). Twelve hours after seeding, an additional 7.5 mL of complete medium was carefully added. The cells were separated from culture media by centrifugation at 200×g for 10 minutes. Supernatants were collected and centrifuged sequentially twice at 500×g for 10 minutes, once at 2,000×g for 15 minutes, once at 10,000×g for 30 min, and once at 70,000×g for 60 minutes. Freely released fusosomes were pelleted during the final centrifugation step, resuspended in PBS and repelleted at 70,000×g. The final pellet was resuspended in PBS.

See also, Wubbolts R et al. Proteomic and Biochemical Analyses of Human B Cell-derived Exosomes: Potential Implications for their Function and Multivesicular Body Formation. J. Biol. Chem. 278:10963-10972 2003.

Example 115: Lack of Transcriptional Activity in Fusosomes

This Example describes quantification of transcriptional activity in fusosomes compared to parent cells, e.g., source cells, used for fusosome generation. Transcriptional activity can be low or absent in fusosomes compared to the parent cells, e.g., source cells.

Fusosomes can be used as a chassis for the delivery of therapeutic agents. Therapeutic agents, such as miRNA, mRNAs, proteins and/or organelles that can be delivered to cells or local tissue environments with high efficiency could be used to modulate pathways that are not normally active or active at pathological low or high levels in recipient tissue. The observation that fusosomes can be incapable of transcription, or that fusosomes can have transcriptional activity of less than their parent cell, can demonstrate that removal of nuclear material has sufficiently occurred.

Fusosomes were prepared as described herein. Control particles (non-fusogenic fusosomes) were produced from HEK-293T cells reverse transiently transfected with pcDNA3.1 empty vector. Transcriptional activity of fusosomes was then compared to parent cells, e.g., source cells, used for fusosome generation by using the Click-iT EU Imaging kit (ThermoFisher).

Briefly, approximately 3×10$^6$ fusosomes corresponding to 60 μL of a standard VSV-G fusosome preparation and 1×10$^6$ parent cells used to generate the fusosomes were plated in, in triplicate, 1 mL of complete media in a 6 well low-attachment multi-well plate in complete containing 1 mM fluorescent-taggable alkyne-nucleoside EU for 4 hr at 37° C. and 5% CO2. For the negative control, 3×10$^6$ fusosomes were plated into a 6 well low-attachment multi-well plate in complete media but with no alkyne-nucleoside EU. After the 4-hour incubation, the samples were processed following the manufacturer's instructions (ThermoFisher Scientific). Briefly, the cell and fusosome samples including the negative controls are washed thrice with 1×PBS buffer and resuspended in 1×PBS buffer and analyzed by flow cytometry (Attune, ThermoFisher) using a 488 nm argon laser for excitation, and 530+/−30 nm filter emission, as shown in the table below:

Flow Cytometer Settings

| Dye | Attune Laser/Filter | Laser Wavelength | Emission Filter (nm) |
|---|---|---|---|
| AF488 | BL1 | 488 | 530/30 |

Figure 14A:
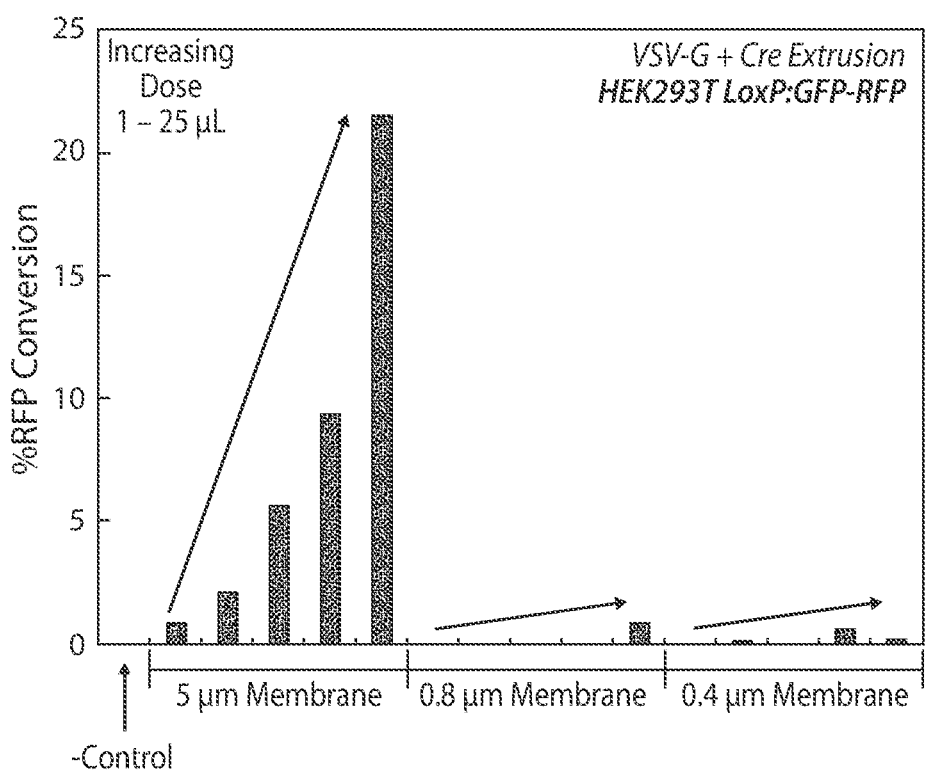
FIG. 14A is a graph showing expression of RFP in HEK293T cells incubated with fusosomes carrying Cre recombinase and generated by extrusion through membranes having pores of varying sizes, as indicated.
Figure 14B:
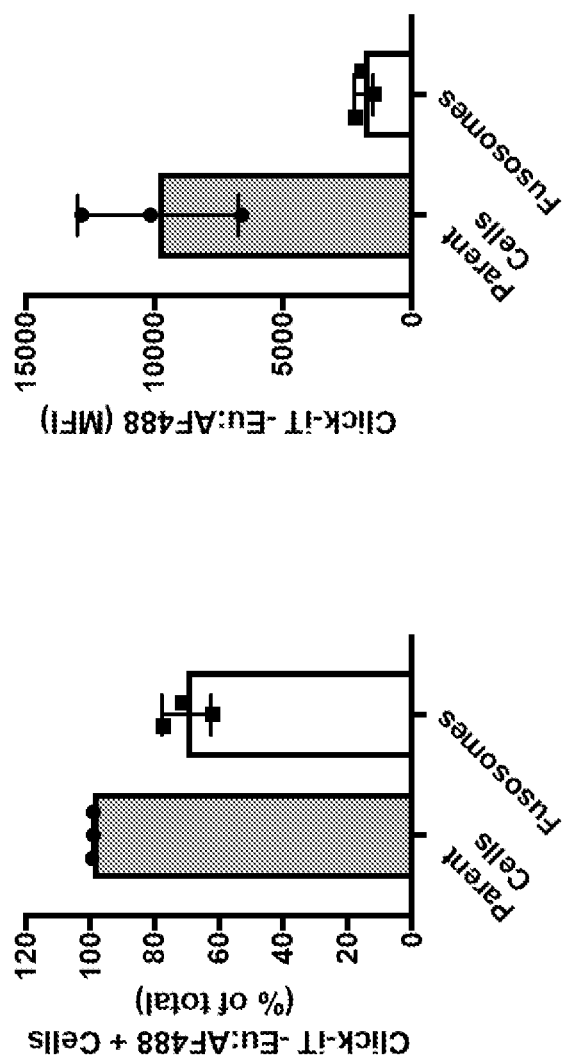
FIG. 14B is a series of graphs showing Eu:488 positive events (left panel) and median fluorescence intensity (MFI; right panel) of AF488 of parental cells and fusosomes.

Attune NxT software was used for acquisition and FlowJo used analysis. For data acquisition the FSC and SSC channels were set on linear axis to determine a population representative of the cells or fusosomes. This population was then gated and events only inside this gate were used to display events in the 530+/−30 nm emission channel on a logarithmic scale. A minimum of 10,000 events within the cells or fusosomes gate was collected for in each condition. For data analysis, the FSC and SSC channels were set on linear axis to determine a population representative of the cells or fusosomes. This population was then gated and events only inside this gate were used to display events in the 530+/−30 nm emission channel on a logarithmic scale. The negative control 530+/−30 nm emission was used to determine where to place the gate on the histogram such that it was less the gate include less than 1% positive. Using analysis criteria listed above parent cells demonstrated 99.17%±0.20 Eu:AF488 events, as surrogate measure of transcriptional activity by including Eu in newly transcribing mRNA transcripts, where Fusosomes demonstrated 70.17%±7.60 AF488 events (FIG. 14B). The median fluorescence intensity of AF488, and thus measure about of how much Eu incorporation, therefore how many newly synthesized mRNA transcripts, relative, was 9867±3121 events for parental cells and 1883±366.3 for fusosomes (FIG. 14B). The example demonstrates that fusosomes lack transcriptional activity relative to parental cells.

Example 116: Lack of DNA Replication or Replication Activity

This Example describes quantification of DNA replication activity in fusosomes compared to parent cells, e.g., source cells, used for fusosome generation. DNA replication activity can be low or absent in fusosomes compared to the parent cells, e.g., source cells.

Fusosomes can be used as a chassis for the delivery of therapeutic agents. Therapeutic agents, such as miRNA, mRNAs, proteins and/or organelles that can be delivered to cells or local tissue environments with high efficiency could be used to modulate pathways that are not normally active or active at pathological low or high levels in recipient tissue. The observation that fusosomes can be incapable of DNA replication, or that fusosomes can have DNA replication activity of less than their parent cell, can demonstrate that removal of nuclear material has sufficiently occurred.

Fusosomes were prepared as described herein. Control particles (non-fusogenic fusosomes) were produced from HEK-293T cells reverse transiently transfected with pcDNA3.1 empty vector. Translational activity of fusosomes was then compared to parent cells, e.g., source cells, used for fusosome generation by using the Click-iT EdU Imaging kit (ThermoFisher).

Briefly, approximately 3×10⁶ fusosomes corresponding to 60 µL of a standard VSV-G fusosome preparation and 1×10⁶ parent cells used to generate the fusosomes were plated in, in triplicate, 1 mL of complete media in a 6 well low-attachment multi-well plate in complete containing 1 mM fluorescent-taggable alkyne-nucleoside EdU for 4 hours at 37° C. and 5% $CO_2$. For the negative control, 3×10⁶ fusosomes were plated into a 6 well low-attachment multi-well plate in complete media but with no alkyne-nucleoside EdU. After the 4-hour incubation, the samples were processed following the manufacturer's instructions (ThermoFisher Scientific). Briefly, the cell and fusosome samples including the negative controls are washed thrice with 1×PBS buffer and resuspended in 1×PBS buffer and analyzed by flow cytometry (Attune, ThermoFisher) using a 638 nm laser for excitation, and 670+/−14 nm filter emission, as shown in the table below:

Flow Cytometer Settings

| Dye | Attune Laser/Filter | Laser Wavelength | Emission Filter (nm) |
| --- | --- | --- | --- |
| AF47 | RL1 | 638 | 670/14 |

Figure 14C:
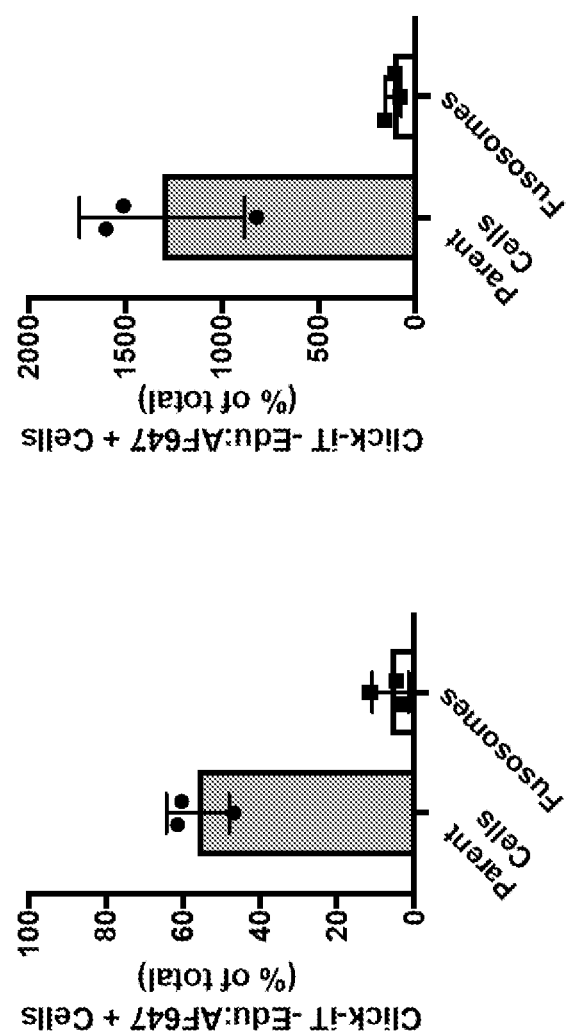
FIG. 14C is a series of graphs showing Edu:647 positive events and median fluorescence intensity of AF647 of parental cells and fusosomes.

Attune NxT software was used for acquisition and FlowJo used analysis. For data acquisition the FSC and SSC channels were set on linear axis to determine a population representative of the cells or fusosomes. This population was then gated and events only inside this gate were used to display events in the 670+/−14 nm emission channel on a logarithmic scale. A minimum of 10,000 events within the cells or fusosomes gate was collected for in each condition. For data analysis, the FSC and SSC channels were set on linear axis to determine a population representative of the cells or fusosomes. This population was then gated and events only inside this gate were used to display events in the 670+/−14 nm emission channel on a logarithmic scale. The negative control 670+/−14 nm emission was used to determine where to place the gate on the histogram such that it was less the gate include less than 1% positive. Using analysis criteria listed above parent cells demonstrated 56.17%±8.13 Edu:647 events, as surrogate measure of translational activity by including Edu in newly synthesized DNA, where Fusosomes demonstrated 6.23%±4.65 AF488 events (FIG. 14C). The median fluorescence intensity of AF647, a measure of Edu incorporation and thus newly synthesized DNA was 1311±426.2 for parental cells and 116.6±40.74 for fusosomes (FIG. 14C). The example demonstrates that fusosomes lack DNA replication activity relative to parental cells.

Example 117: Fusosomes with Lipid Bilayer Structure

This example describes a composition of fusosomes. In an embodiment, the fusosome composition comprises a lipid bilayer structure, with a lumen in the center. Without wishing to be bound by theory, the lipid bilayer structure of a fusosome promotes fusion with a target cell, and allows fusosomes to load different therapeutics.

Figure 15:
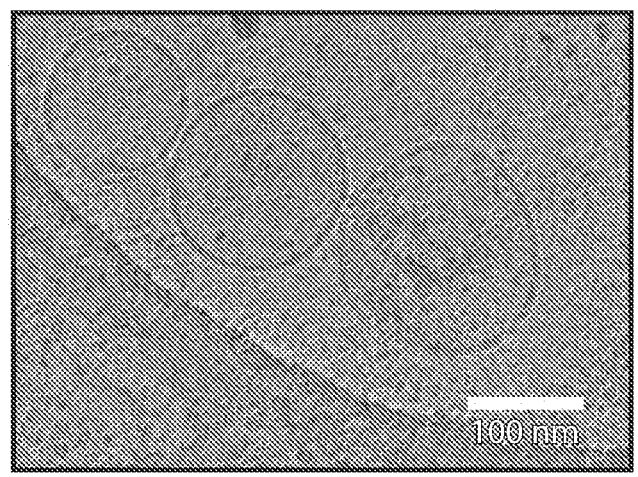
FIG. 15 is an electron microscopy image showing fusosomes with a lipid bilayer structure.

Fusosomes were prepared as described in previous Examples by transient transfection of 293 F cells with VSV-G, followed by filtration and ultracentrifugation of conditioned media 48 h after transfection. For each sample, small molecular weight contaminants were removed with Exosome Spin Columns (Invitrogen #4484449) according to the manufacturer's instructions. Large protein removal, desalting, and buffer exchanged were carried out using an Amicon Ultra 0.5 mL Centrifugal Filter Ultracel 100K 100,000 NMWL unit (Millipore #UFC510024). Fusosomes were reconstituted in PBS. Three holy carbon grids (Electron Microscopy Services #Q2100CR1.3) per sample were glow discharged for 25 seconds to render the surface hydrophilic. The sample was briefly vortexed, and 3 gL of the fusosomes were placed on top of each grid and incubated for 1-2 minutes. Fusosomes were plunge-frozen using a Gatan Cryoplunge3 semi-automatted plunge-freezing instrument according to manufacturer's instructions. The frozen hydrated grids were loaded into the cryo transfer of holder of an FEI Tecnai Arctica Cryo-TEM. Fusosomes were then scanned in low dose search mode and imaged at 200 kV at 23,500× and 39,000× magnifications (FIG. 15).

Example 118: Detecting Fusogen Expression

This example describes quantification of fusogen expression in fusosomes. Fusosomes were prepared as described herein by transient transfection of HEK293T with VSV-G, Cre recombinase, and miRFP670 in 10 cm dishes, followed by filtration and ultracentrifugation of the conditioned media 48 h after transfection to obtain fusosomes. The positive control was the unprocessed transiently transfected 293T cells. The negative control was untransfected 293T cells.

Figure 16:
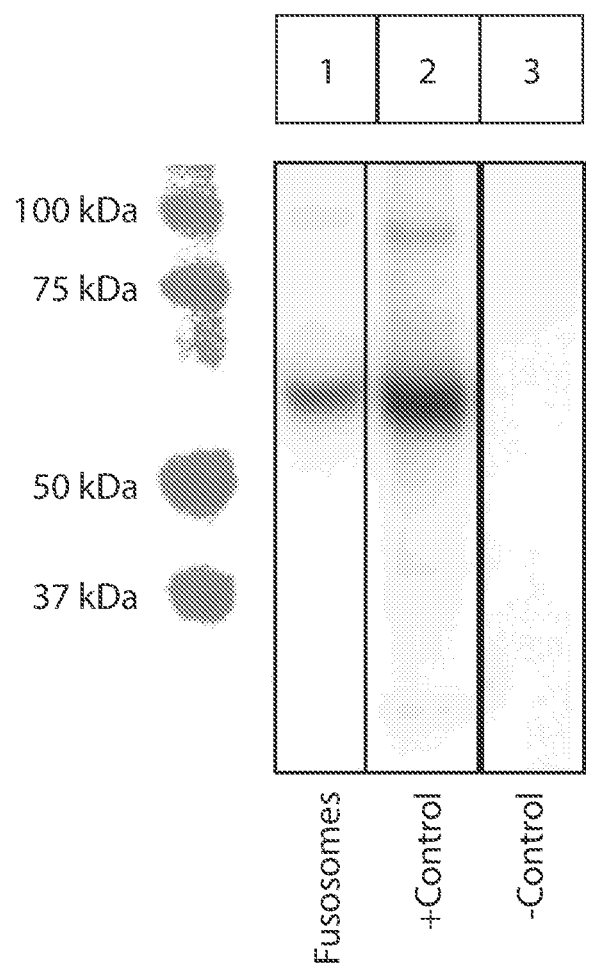
FIG. 16 is a diagram showing detection of VSV-G expression by Western blot. "+Control" represents 293T cells transfected with VSV-G. "—Control" represents untransfected 293T cells.

The fusosomes were lysed with RIPA buffer and centrifuged at 15,000×g for 10 minutes, after which the protein was recovered from the supernatant. The samples were run on a 4-12% Bis-Tris denaturing SDS-PAGE gel and then transferred to a PVDF membrane. Each membrane was blocked for 30 k minutes in 3% BSA+0.1% Triton X-100 in PBS. The membranes were then incubated with anti-VSVG tag (ab 1874, Abcam, Cambridge, Mass.) primary antibody in the blocking solution overnight at 4° C., then washed three times for 5 minutes each in 0.1% Triton X-100 in PBS. The membranes were then incubated with a HRP-conjugated secondary antibody (#7074P2, Cell Signaling Technologies, Danvers, Mass.) in the blocking solution for 4 hours at 4° C. HRP substrate was added and the chemiluminescent signal was recorded by an Alpha Innotech MultiImage3 (FIG. 16).

Example 119: Measuring the Average Size of Fusosomes

This Example describes measurement of the average size of fusosomes.

Fusosomes were prepared as described herein by transient transfection of HEK293T with VSV-G, enucleation and subsequent fractionation with Ficoll. The fusosomes were measured to determine the average size using commercially available systems for submicron (Nanosight NS300, Malvern Instruments) and supra-micron (Zeiss 780 Inverted Laser Confocal, Zeiss) measurements. Each system was used with software according to manufacturer's instructions. Fusosomes and parental cells were resuspended in PBS and stained with 1 µM of CalceinAM to a final concentration of approximately 1 mg protein/mL. Fusosomes and parental cells were then diluted 100-fold in PBS prior to measurement. For sub-micron measurements on the Nanosight NS300 the parameters shown in FIG. 17A were used. For supra-micron measurements on the 780 Inverted Confocal Microscope, the parameters shown in FIG. 17B were used.

Figure 17C:
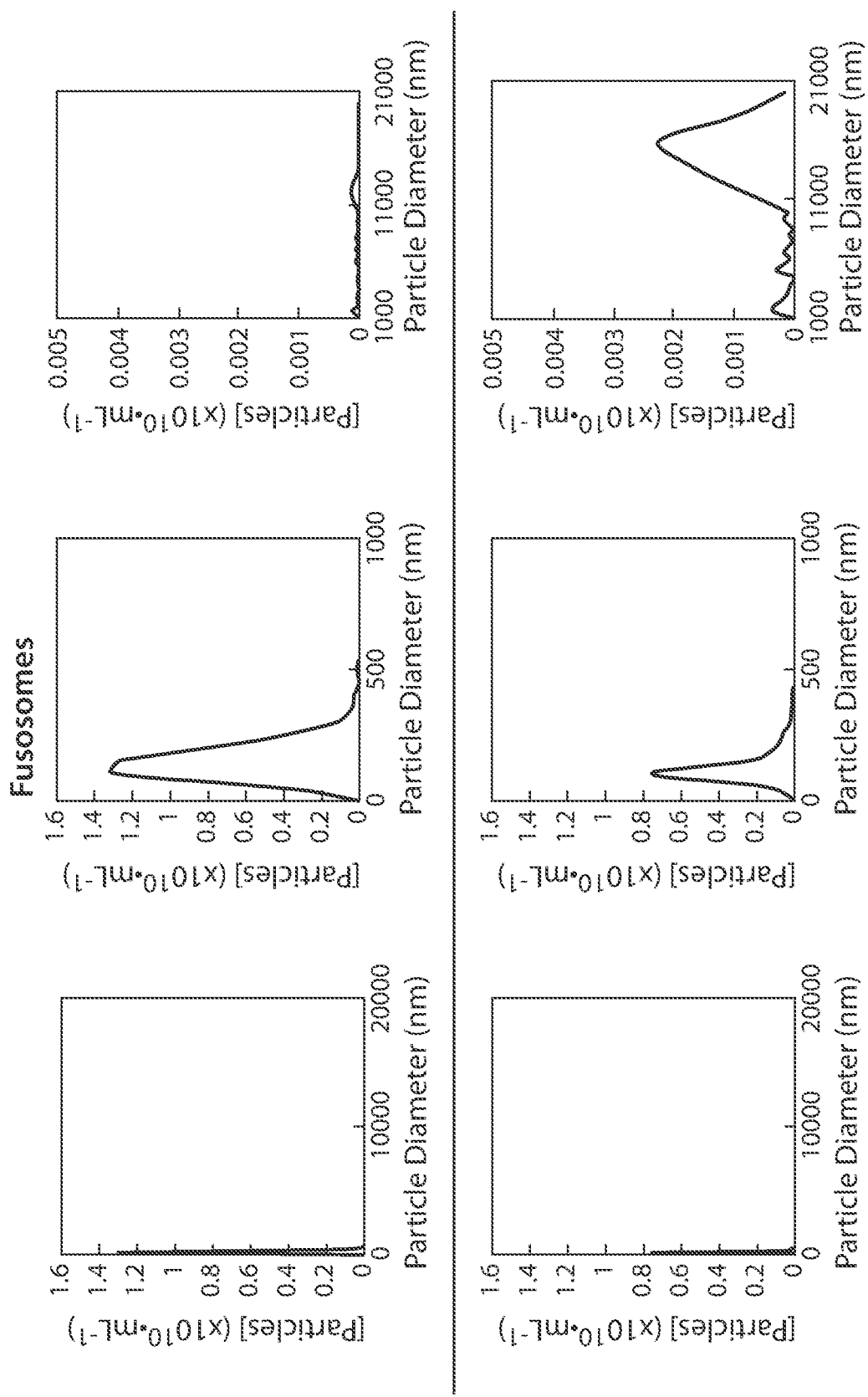
FIG. 17C is a series of graphs showing the size distribution of fusosomes and parental cells as measured by NTA and microscopy.

All fusosomes were analyzed within 8 hours of isolation. Measurements for particles <500 nm were taken from the NTA and added to measurements for particles >500 nm from the Zeiss microscope to obtain a full measurement from 50-20,000 nm. The size distribution of fusosomes and parental cells is shown in FIG. 17C. The distribution of all particles was averaged to obtain the average size of fusosomes, as shown in FIG. 17D. It is contemplated that the fusosomes can have a size less than parental cells. It is contemplated that the fusosomes can have a size within about 73% of the parental cells.

Example 120: Measuring the Average Size Distribution of Fusosomes

This Example describes measurement of the size distribution of fusosomes.

Fusosomes were prepared as described herein by transient transfection of HEK293T with VSV-G, enucleation and subsequent fractionation with Ficoll. The fusosomes were measured to determine the size distribution using the method of Example 30, as shown in FIG. 18. It is contemplated that the fusosomes can have less than about 50%, 40%, 30%, 20%, 10%, 5%, or less of the parental cell's variability in size distribution within 90% of the sample. It is contemplated that the fusosomes can have 58% less of the parental cell's variability in size distribution within 90% of the sample.

Example 121: Average Volume of Fusosomes

This example describes measurement of the average volume of fusosomes. Varying the size (e.g., volume) of fusosomes can make them versatile for distinct cargo loading, therapeutic design or application.

Fusosomes were prepared as described herein by transient transfection of HEK293T with VSV-G, enucleation and subsequent fractionation with Ficoll. The positive control was HEK293T cells.

Analysis with a combination of NTA and confocal microscopy as described in Example 30 was used to determine the size of the fusosomes. The diameter of the fusosomes were measured and the volume calculated, as shown in FIG. 19. It is contemplated that fusosomes can have an average size of greater than 50 nm in diameter. It is contemplated that fusosomes can have an average size of 129 nm in diameter.

Example 122: Measuring Organelle Content in Fusosomes

This Example describes detection of organelles in fusosomes.

Fusosomes were prepared as described herein by transient transfection of HEK293T cells with VSV-G, enucleation and subsequent fractionation with Ficoll. For detection of endoplasmic reticulum (ER), lysosomes, and mitochondria, fusosomes or HEK293T cells were stained with 1 µM ER stain (E34251, Thermo Fisher, Waltham, Mass.), 50 nM lysosome stain (L7528, Thermo Fisher Waltham, Mass.), or 100 nM mitochondria stain (M22426, Thermo Fisher Waltham, Mass.), respectively.

Stained fusosomes were run on a flow cytometer (Thermo Fisher, Waltham, Mass.) and fluorescence intensity was measured for each dye according to the table below. Validation for the presence of organelles was made by comparing fluorescence intensity of stained fusosomes to unstained fusosomes (negative control) and stained cells (positive control). Fusosome stains were performed using the microscopy settings shown in Table Y:

TABLE Y

| Stain | Attune Laser/Filter | Laser Wavelength | Emission Filter (nm) |
|---|---|---|---|
| ER-Tracker Green | BL1 | 488 | 530/30 |
| LysoTracker Red | YL1 | 561 | 585/16 |
| MitoTracker Deep Red FM | RL1 | 638 | 670/14 |

Figure 20C:
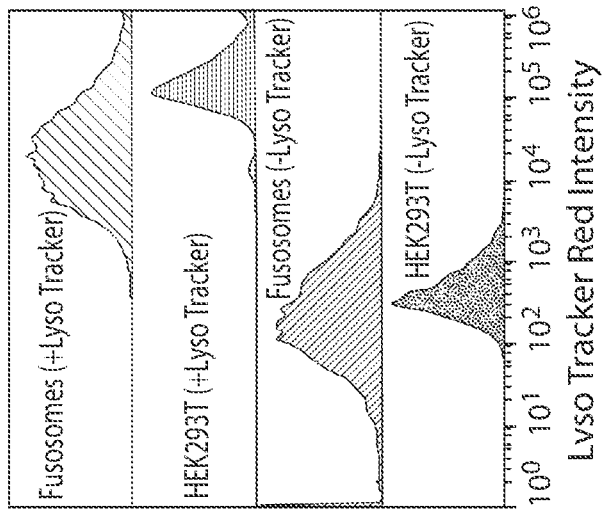
FIGS. 20A-20C are a series of graphs showing detection of organelles in fusosomes. (A) Endoplasmic reticulum; (B) Mitochondria; (C) Lysosomes.
Figure 20B:
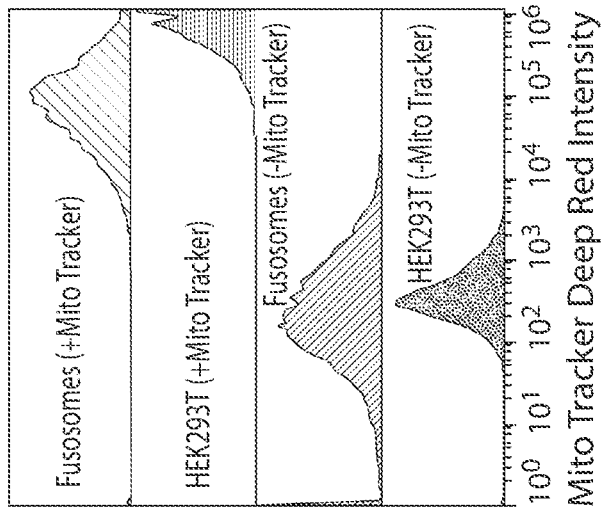
Figure 20A:
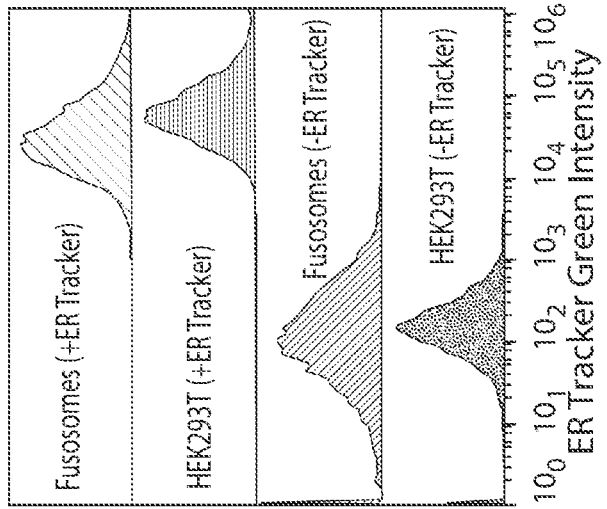

As shown in FIG. 20, fusosomes stained positive for endoplasmic reticulum (FIG. 20A), mitochondria (FIG. 20B), and lysosomes (FIG. 20C) at 4 hours post-enucleation.

Example 123: Comparison of Soluble to Insoluble Protein Mass

This Example describes quantification of the soluble:insoluble ratio of protein mass in fusosomes. The soluble:insoluble ratio of protein mass in fusosomes can, in some instances, be similar to that of nucleated cells.

Fusosomes were prepared as described herein by transient transfection of HEK293T with VSV-G, enucleation and subsequent fractionation with Ficoll. The fusosome preparation was tested to determine the soluble:insoluble protein ratio using a standard bicinchoninic acid assay (BCA) (Pierce™ BCA Protein Assay Kit, Thermo Fischer product #23225). Soluble protein samples were prepared by suspending the prepared fusosomes or parental cells at a concentration of $1\times10^7$ cells or ~1 mg/mL total fusosomes in PBS and centrifuging at 1,500×g to pellet the cells or 16,000×g to pellet the fusosomes. The supernatant was collected as the soluble protein fraction.

The fusosomes or cells were then resuspended in PBS. This suspension represents the insoluble protein fraction.

Figure 21:
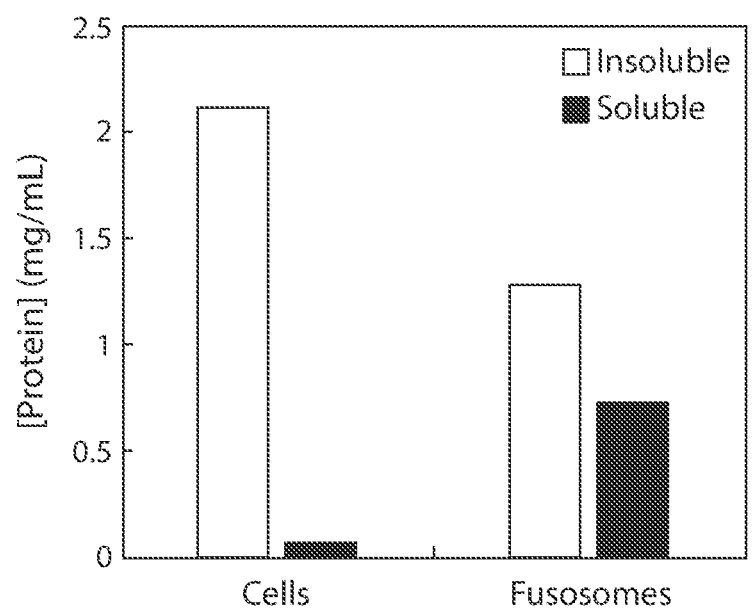
FIG. 21 is a series of diagrams showing the soluble: insoluble ratio observed for fusosomes or a cell preparation.

A standard curve was generated using the supplied BSA, from 0 to 15 μg of BSA per well (in duplicate). The fusosome or cell preparation was diluted such that the quantity measured is within the range of the standards. The fusosome preparation was analyzed in duplicate and the mean value was used. The soluble protein concentration was divided by the insoluble protein concentration to yield the soluble:insoluble protein ratio (FIG. 21).

Example 124: Measuring Fusion with a Target Cell

Fusosomes derived from HEK-293T cells expressing the engineered hemagglutinin glycoprotein of measles virus (MvH) and the fusion protein (F) on the cell surface and containing Cre recombinase protein were generated, as described herein. The MvH was engineered so that its natural receptor binding is ablated and target cell specificity is provided through a single-chain antibody (scFv) that recognizes the cell surface antigen, in this case the scFv is designed to target CD8, a co-receptor for the T cell receptor. A control fusosome was used which was derived from HEK-293T cells expressing the fusogen VSV-G on its surface and containing Cre recombinase protein. The target cell was a HEK-293T cell engineered to express a "Loxp-GFP-stop-Loxp-RFP" cassette under CMV promoter, as well as engineered to over-express the co-receptors CD8a and CD8b. The non-target cell was the same HEK-293T cell expressing "Loxp-GFP-stop-Loxp-RFP" cassette but without CD8a/b over-expression. The target or non-target recipient cells were plated 30,000 cells/well into a black, clear-bottom 96-well plate and cultured in DMEM media with 10% fetal bovine serum at 37° C. and 5% $CO_2$. Four to six hours after plating the recipient cells, the fusosomes expressing Cre recombinase protein and MvH+F were applied to the target or non-target recipient cells in DMEM media. Recipient cells were treated with 10 μg of fusosomes and incubated for 24 hours at 37° C. and 5% $CO_2$.

Cell plates were imaged using an automated microscope (www.biotek.com/products/imaging-microscopy-automated-cell-imagers/lionheart-fx-automated-live-cell-imager/). The total cell population in a given well was determined by staining the cells with Hoechst 33342 in DMEM media for 10 minutes. Hoechst 33342 stains cell nuclei by intercalating into DNA and therefore is used to identify individual cells. The Hoechst was imaged using the 405 nm LED and DAPI filter cube. GFP was imaged using the 465 nm LED and GFP filter cube, while RFP was imaged using 523 nm LED and RFP filter cube. Images of target and non-target cell wells were acquired by first establishing the LED intensity and integration times on a positive-control well; i.e., recipient cells treated with adenovirus coding for Cre recombinase instead of fusosomes.

Acquisition settings were set so that Hoescht, RFP, and GFP intensities are at the maximum pixel intensity values but not saturated. The wells of interest were then imaged using the established settings. Focus was set on each well by autofocusing on the Hoescht channel and then using the established focal plane for the GFP and RFP channels. Analysis of GFP and RFP-positive cells was performed with GenS software provided with automated fluorescent microscope (https://www.biotek.com/products/software-robotics-software/gen5-microplate-reader-and-imager-software/).

The images were pre-processed using a rolling ball background subtraction algorithm with a 60 μm width. Cells with GFP intensity significantly above background intensities were thresholded and areas too small or large to be GFP-positive cells were excluded. The same analysis steps were applied to the RFP channel. The number of RFP-positive cells (recipient cells receiving Cre) was then divided by the sum of the GFP-positive cells (recipient cells that did not show delivery) and RFP-positive cells to quantify the percent RFP conversion, which describes the amount of fusosome fusion within the target and non-target recipient cell population. For amounts of targeted fusion (fusosome fusion to targeted recipient cells), the percent RFP conversion value is normalized to the percentage of recipient cells that are target recipient cells (i.e., expressing CD8), which was assessed by staining with anti-CD8 antibody conjugated to phycoerythrin (PE) and analyzed by flow cytometry. Finally, the absolute amount of targeted fusion was determined by subtracting the amount of non-target cell fusion from the target cell fusion amount (any value <0 was considered to be 0).

Figure 22:
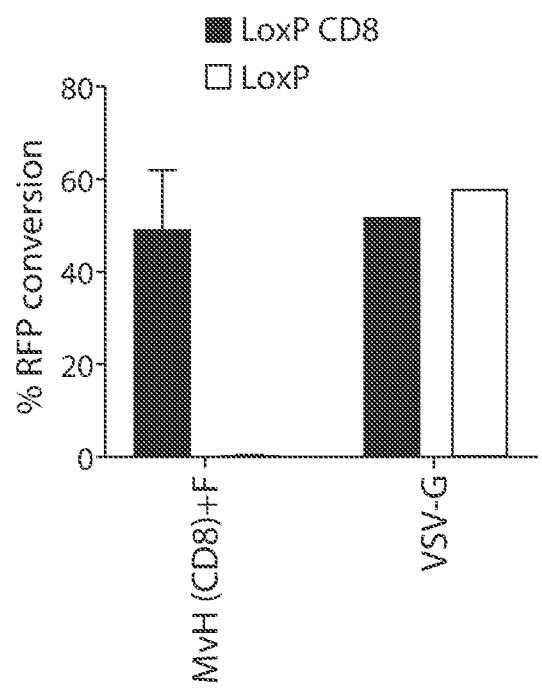
FIG. 22 is a series of diagrams showing MvH(CD8)+F fusosome fusion to target or non-target cells and absolute amount of targeted fusion.

With this assay, the fusosome derived from a HEK-293T cell expressing the engineered MvH(CD8)+F on its surface and containing Cre recombinase protein showed a percentage RFP conversion of 25.2+/−6.4% when the recipient cell was the target HEK-293T cell expressing the "Loxp-GFP-stop-Loxp-RFP" cassette, and 51.1% of these recipient cells were observed to be CD8-positive. From these results, the normalized percentage RFP conversion or amount of targeted fusion was determined to be 49.3+/−12.7% for targeted fusion. The same fusosome showed a percentage RFP conversion of 0.5+/−0.1% when the recipient was the non-target HEK-293T cell expressing "Loxp-GFP-stop-Loxp-RFP" but with no expression of CD8. Based on the above, the absolute amount of targeted fusion for the MvH(CD8)+F fusosome determined to be 48.8% and the absolute amount of targeted fusion for the control VSV-G fusosome was determined to be 0% (FIG. 22).

Example 125: In Vitro Fusion to Deliver a Membrane Protein

Fusosomes from HEK-293T cells expressing the placental cell-cell fusion protein syncytin-1 (Syn1) and the membrane protein, human OX40 ligand (hOx40L, ligand for CD134), on the cell surface were generated as described herein. Control particles (non-fusogenic fusosomes) from the same cells expressing hOx40L but not Syn1 were also generated to control for non-fusion-mediated delivery of hOx40L to recipient cells. The recipient cells were human prostate cancer cells (PC-3), which were plated at 120,000 cells/well in a 24-well tissue culture plate 4-6 hours before treating with fusosomes. Recipient cells were treated with 40 ug of Syn1 fusosomes or control particles at t=0 and incubated for 24 hours at 37° C. and 5% $CO_2$.

After incubating with fusosomes or particles for 24 hours, recipient cells were trypsinized to detach from the plate, pelleted by centrifugation at 500 g for 5 min and resuspended in 4% PFA in PBS for 15 minutes to fix the cells. After fixation cells were washed twice in PBS followed by incubation in 1% bovine serum albumen (in PBS) for 30 min at room temperature. Primary antibody directed against hOx40L and conjugated to Brilliant Violet 421 dye (BV421, BD Biosciences, Cat #744881) was then added to the cells at a concentration of 0.01 ug/µL and incubated at room temperature for 30 minutes. Cells were then washed three-times in PBS and finally resuspended in PBS with propidium iodide. Propidium iodide stains cell nuclei of fixed/permeabilized cells by intercalating into DNA and therefore is used to identify individual cells vs. small debris or fusosomes/particles (propidium iodide-negative).

Cells were then analyzed for BV421 and propidium iodide fluorescence using an Attune NxT Flow Cytometer (Thermo Fisher, Waltham, Mass.) to determine the fluorescence intensity of each fluorophore according to Table Z below.

TABLE Z

| Flow cytometer settings | | | |
|---|---|---|---|
| Stain | Attune Laser/Filter | Laser Wavelength | Emission Filter (nm) |
| BV421 | VL1 | 405 | 450/40 |
| Propidium iodide | YL1 | 561 | 585/16 |

Figure 23:
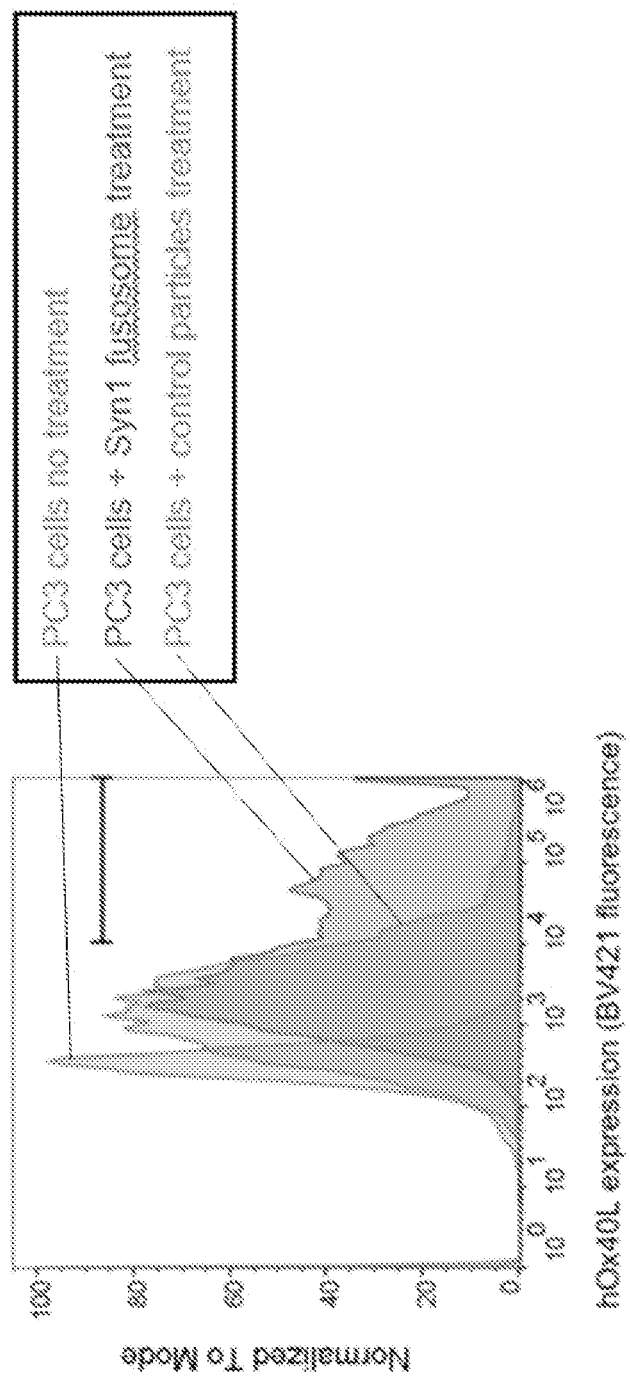
FIG. 23 is a diagram showing hOx40L expression in PC3 cells treated with fusosomes.

Negative controls are generated using the same staining procedure but with no primary antibody added. Attune NxT acquisition software is used for acquisition and FlowJo software is used for analysis. The light scatter channels are set on linear gains, and the fluorescence channels on a logarithmic scale, with a minimum of 10,000 cells analyzed in each condition. Cell events are first gated on forward and side scatter channels to remove small debris events, and then propidium iodide-positive cells are gated as the "all cells" gate (propidium iodide-positive gate is set so that cells without propidium iodide staining show <0.5% positive cells). The intensity of BV421 fluorescence is then examined based off the "all cells" gate and the BV421-positive cells gate is set so that PC-3 cells with no fusosome/particle treatment show <0.5% BV421-positive cells (see black line gate in FIG. 23). The percentage of BV421-positive cells value was then calculated for each group and used as the quantification of % cells with hOx40L delivery.

With this assay the fusosome derived from a HEK-293T cell expressing the Syn1 and hOx40L showed a percentage of cells with hOx40L delivery of 43.6% to PC-3 recipient cells. Control particles without Syn1 expression showed a percentage of cells with hOx40L delivery of 11.4%. The amount of hOx40L delivery observed with control particles represented the background level of hOx40L delivery resulting from non-fusosome-mediated delivery. Thus to calculate the percentage of cells with fusosome-mediated delivery of hOx40L the percentage of cells with hOx40L delivery under the control particle treatment condition was subtracted from the percentage of cells with hOx40L delivery under the fusosome treatment condition. The percentage of cells with fusosome-mediated delivery of hOx40L was 32.2% (FIG. 23), which demonstrated in vitro fusosome-mediated delivery of a membrane protein.

Example 126: Measuring Ability to Transport Glucose Across Cell Membrane

Fusosomes from HEK-293T cells expressing the envelope glycoprotein G from vesicular stomatitis virus (VSV-G) on the cell surface and expressing Cre recombinase protein were generated according by the standard procedure of ultracentrifugation through a Ficoll gradient to obtain small particle fusosomes as described herein. To measure the ability of the fusosomes to transport glucose across the cell membrane, the levels of a 2-NBDG (2-(N-(7-Nitrobenz-2-oxa-1,3-diazol-4-yl)Amino)-2-Deoxyglucose) fluorescent glucose analog, that can be used to monitor glucose uptake in live cells, was quantified to assess active transport across the lipid bilayer. A commercially-available kit from Biovision Inc. (Cat #K682) was used for the assay according to manufacturer's instructions.

Briefly, the fusosome sample was measured for total protein content by bicinchoninic acid assay (BCA, ThermoFisher, Cat #23225) according to manufacturer's instructions. Next 40 ug of fusosome total protein was pelleted by centrifugation at 3000 g for 5 minutes in a table-top centrifuge, followed by resuspension in 400 uL of DMEM supplemented with 0.5% fetal bovine serum. This was done in duplicate for each sample, and one of the duplicates was treated with 4 uL of phloretin (provided with the kit), a natural phenol that inhibits glucose uptake, as a control for glucose uptake inhibition. The samples were then incubated for 1 hour at room temperature. After the incubation, the fusosome sample was pelleted and resuspended in 400 uL of glucose uptake mix prepared previously (see Table A below for formulation). Samples pre-treated with phloretin were resuspended in glucose uptake mix with phloretin; samples not pre-treated were resuspended in glucose uptake mix with 20 uL of PBS instead of phloretin. Also a parallel set of fusosome samples were resuspended in DMEM media with 0.5% FBS only as a negative control for flow cytometry analysis.

TABLE A

| Glucose uptake mix formulation | |
|---|---|
| Reagent | Volume (uL) |
| DMEM media with 0.5% FBS | 1880 |
| 2-NBDG reagent | 20 |
| Glucose Uptake Enhancer | 100 |
| Optional: Phloretin | 20 |

The samples were then incubated at 37° C. with 5% $CO_2$ for 30 minutes. After the incubation cells were pelleted, washed once with 1 mL of 1× Analysis Buffer (provided with kit), pelleted again, and resuspended in 400 uL of 1× Analysis Buffer.

The samples were then measured for 2-NBDG uptake by flow cytometry analysis using an Invitrogen Attune NxT acoustic focusing cytometer. 2-NBDG was excited with a 488 nm laser and emission captured at 513±26 nm. Forward and side scatter gating was initially used to capture fusosome-sized events and discard small debris. Events positive for 2-NBDG were determined by gating at the minimum level for which the 2-NBDG negative control sample showed <0.5% of events positive for 2-NBDG staining. The gated cells positive for 2-NBDG fluorescence were then assessed for the mean fluorescence intensity (F.I.) of 2-NBDG in order to calculate a value for glucose uptake for the fusosomes with and without phloretin treatment.

Figure 24:
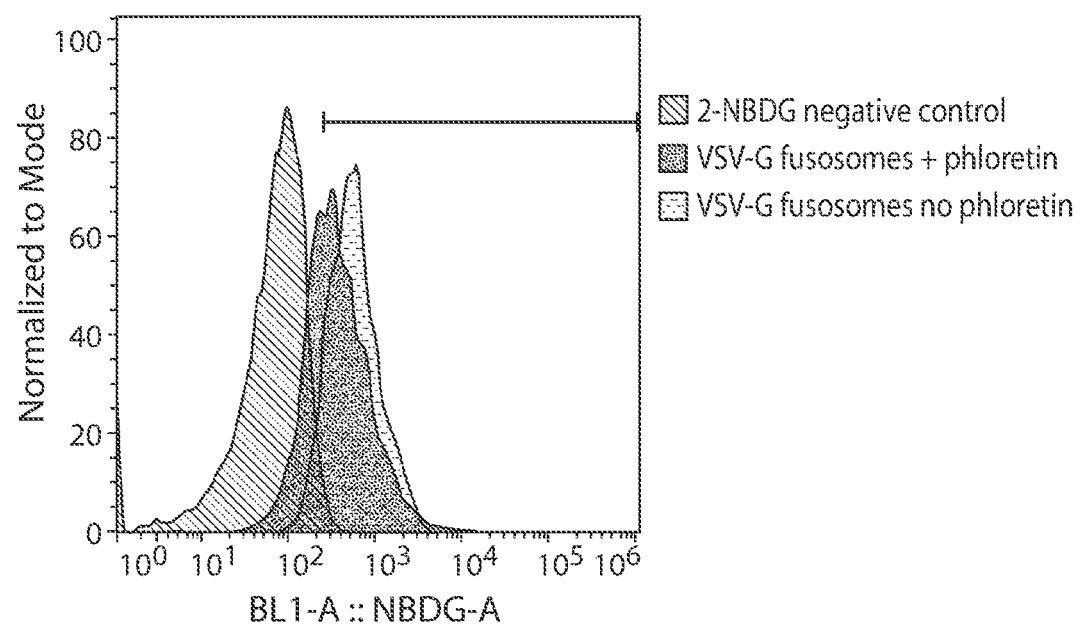
FIG. 24 is a diagram showing 2-NBDG mean fluorescence intensity in VSV-G fusosomes.

With this assay, the fusosome derived from a HEK-293T cell expressing the VSV-G and Cre showed a 2-NBDG mean F.I. of 631.0+/−1.4 without phloretin treatment and a mean F.I. of 565.5+/−4.9 with phloretin treatment (FIG. 24).

Example 127: Measuring Esterase Activity in the Cytosol

Fusosomes from C2C12 cells were generated according to the standard procedure of ultracentrifugation through a Ficoll gradient to obtain small particle fusosomes as described herein. To measure the esterase activity in the cytosol of the fusosomes, samples were stained with Calcein AM (BD Pharmigen, Cat #564061), a fluorescein derivative and nonfluorescent vital dye that passively crosses the cell membrane of viable cells and is converted by cytosolic esterases into green fluorescent calcein, which is retained by cells with intact membranes and inactive multidrug resistance protein.

Briefly, the fusosome sample was measured for total protein content by bicinchoninic acid assay (BCA, ThermoFisher, Cat #23225) according to manufacturer's instructions. Next 20 ug of fusosome total protein was pelleted by centrifugation at 3000 g for 5 minutes in a table-top centrifuge, followed by resuspension in 400 uL of DMEM supplemented with 0.5% fetal bovine serum. The membrane-permeable dye, calcein-AM was prepared as a stock solution of 10 mM in dimethylsulfoxide and as a working solution of 1 mM in PBS buffer, pH 7.4. VSV-G fusosomes were stained with 1 M solution of calcein-AM diluted in DMEM media. Samples were incubated at 37° C. in the dark for 30 minutes and then pelleted by centrifugation. After washing twice with PBS buffer, fusosomes were resuspended in PBS and analyzed by flow cytometry.

The samples were measured for calcein fluorescence retention using an Invitrogen Attune NxT acoustic focusing cytometer. Calcein AM was excited with a 488 nm laser and emission captured at 513±26 nm. Forward and side scatter gating was initially used to capture fusosome-sized events and discard small debris. Events positive for calcein were determined by gating at the minimum level for which the calcein negative control sample showed <0.5% of events positive for calcein staining. The gated cells positive for calcein fluorescence were then assessed for the mean fluorescence intensity (F.I.) of calcein in order to calculate a value for esterase activity in the cytosol of fusosomes.

Figure 25:
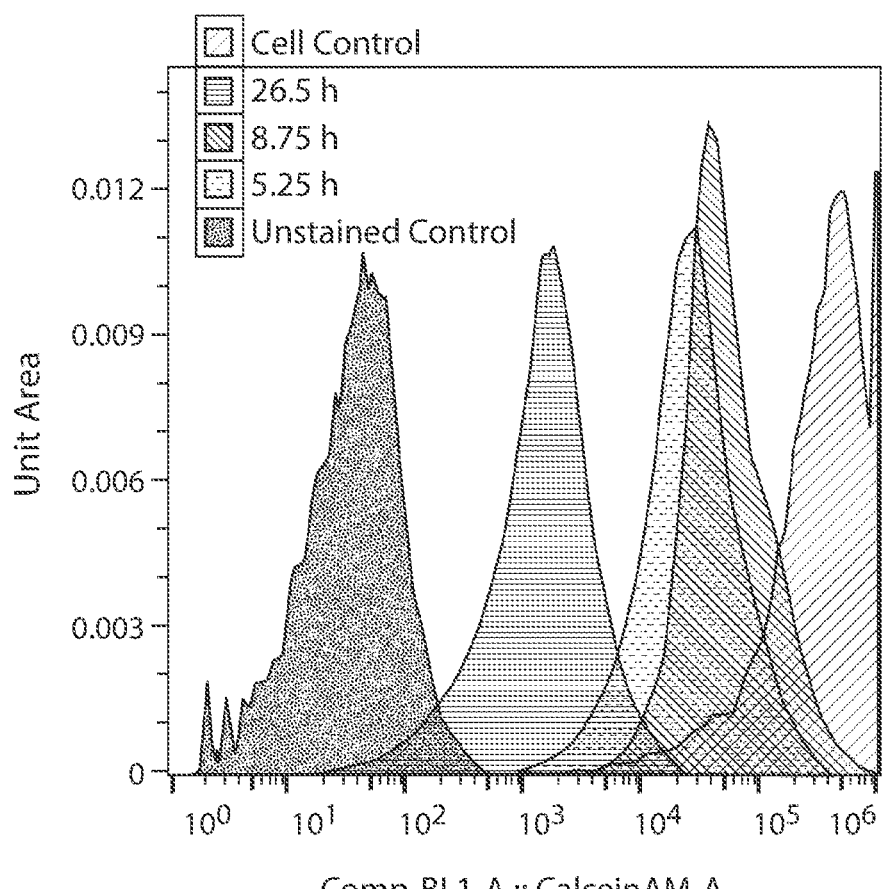
FIG. 25 is a diagram showing esterase activity in the cytosol of VSV-G fusosomes.

With this assay the fusosome derived from a C2C12 cell showed an esterase activity (mean calcein F.I.) of 631.0+/−1.4 (FIG. 25).

Example 128: Measuring Acetylcholinesterase Activity in Fusosomes

Fusosomes from HEK-293T cells expressing the placental cell-cell fusion protein syncytin-1 (Syn1) on the cell surface and expressing Cre recombinase protein were generated as described herein. Acetylcholinesterase activity was measured using the FluoroCet Quantitation Kit (System Biosciences, Cat #FCET96A-1) following the manufacturer's recommendations.

Briefly, fusosomes were pelleted via ultracentrifugation at 120,000 g for 90 minutes and resuspended carefully in phosphate-buffered saline (PBS). Next fusosomes were quantified for total protein content by bicinchoninic acid assay (BCA, ThermoFisher, Cat #23225) according to manufacturer's instructions. After BCA quantification of protein concentration, 1000 ng of total fusosome protein was diluted with PBS to a volume of 60 uL, followed by addition of 60 uL of Lysis Buffer to lyse the particles. After a 30 minute incubation on ice the samples were ready to run in the FluoroCet assay.

In duplicate wells of a 96-well plate, 50 uL of lysed fusosome sample was mixed with 50 uL of Working stock of Buffer A and 50 uL of Working stock of Buffer B. In parallel, a standard curve was prepared by pipetting 2 uL of the provided standard in 126 uL of 1× Reaction buffer. This standard solution was then serial diluted 5× to make a six-point standard curve consisting of 2.0E+08, 1.0E+08, 5.0E+07, 2.5E+07, 1.25E+07, and 6.25E+06 exosome equivalents of acetylcholinesterase activity. 50 uL of each standard was then mixed with 50 uL of Working stock of Buffer A and 50 uL of Working stock of Buffer B in duplicate wells of the 96-well plate. 50 uL of 1× Reaction buffer was used as a blank. The plate was mixed by tapping the sides followed by incubation in the dark for 20 minutes at room temperature. The plate was then measured immediately using a fluorescence plate reader set at Excitation: 530-570 nm and Emission: 590-600 nm. The plate was shaken for 30 sec before reading.

The relative fluorescence units (RFU) were then plotted against the known exosome equivalents of acetylcholinesterase activity after subtracting the RFU values from the blank wells. A linear regression line was then calculated and the equation used to determine the acetylcholinesterase activity (in exosome equivalents) for the fusosome samples from the measured RFU values. The measured acetylcholinesterase activity for Syn1 fusosomes are shown in Table B:

TABLE B

Acetylcholinesterase activity in fusosomes and control particles

| Sample | Acetylcholinesterase activity (exosome equivalents) |
|---|---|
| Syn1 fusosomes | 6.83E+05 +/− 2.21E+05 |

Example 129: Measuring Metabolic Activity Level

Fusosomes from HEK-293T cells expressing the envelope glycoprotein G from vesicular stomatitis virus (VSV-G) on the cell surface and expressing Cre recombinase protein were generated as described herein. To determine the metabolic activity level of the fusosome preparation, citrate synthase activity was assessed using a commercially available kit from Sigma (Cat #CS0720) which provides all of the necessary reagents. Citrate synthase is an enzyme within the tricarboxylic acid (TCA) cycle that catalyzes the reaction between oxaloacetate (OAA) and acetyl-CoA to generate citrate. Upon hydrolysis of acetyl-CoA, there is a release of CoA with a thiol group (CoA-SH). The thiol group reacts with a chemical reagent, 5,5-Dithiobis-(2-nitrobenzoic acid) (DTNB), to form 5-thio-2-nitrobenzoic acid (TNB), which has a yellow product that can be measured spectrophotometrically at 412 nm.

The assay was performed as per the manufacturer's recommendations. Briefly, fusosome sample was measured for total protein content by bicinchoninic acid assay (BCA, ThermoFisher, Cat #23225) according to manufacturer's instructions. Next 400 ug of fusosome total protein was pelleted by centrifugation at 3000 g for 5 minutes in a table-top centrifuge. The fusosomes were washed once by pelleting again and resuspending in ice-cold PBS. Fusosomes were pelleted again and supernatant was removed. The pellet was lysed in 100 uL of CellLytic M buffer with 1× protease inhibitors. After mixing by pipetting, the lysed sample was incubated for 15 minutes at room temperature to complete lysis. The sample was then centrifuged at 12,000 g for 10 minutes and the supernatant was transferred to a new microcentrifuge tube and stored at −80° C. until the subsequent assay was performed.

To initiate the citrate synthase activity assay, all assay solutions were warmed to room temperature prior to using. The lysed fusosome sample was mixed with assay solutions according to Table C below:

TABLE C

Reaction Scheme for Citrate Synthase Activity Measurement in 96 Well Plate

| Sample | Assay buffer | 30 mM Acetyl CoA solution | 10 mM DTNB solution | 10 mM OAA solution (added last) |
|---|---|---|---|---|
| 4 uL | 182 uL | 2 uL | 2 uL | 10 uL |

The volumes in Table C represent volumes for a single well of a 96-well plate. Samples were measured in duplicates. All components of the reaction were mixed and pipetted into a single well of a 96-well plate. The absorbance at 412 nm was then analyzed on a microplate reader for 1.5 minutes to measure the baseline reaction. Next, 10 uL of the 10 mM OAA solution was added to each well to initiate the reaction. The plate was shaken for 10 seconds in the microplate reader before reading the absorbance at 412 nm for 1.5 minutes with a measurement every 10 seconds.

To calculate the citrate synthase activity, the absorbance at 412 nm was plotted against time for each reaction. The change in absorbance per minute was calculated for the linear range of the plot for before (endogenous activity) and after (total activity) OAA addition. The net citrate synthase activity was then calculated by subtracting the endogenous activity from the total activity for the sample. This value was then used to calculate the citrate synthase activity based on the equation and constant values provided by the manufacturer. The measured citrate synthase activity for the VSV-G fusosomes was 1.57E-02+/−1.86E-03 umol/ug fusosome/min.

Example 130: Measuring Respiration Levels

Fusosomes from HEK-293T cells expressing the envelope glycoprotein G from vesicular stomatitis virus (VSV-G) on the cell surface were generated according by the standard procedure of ultracentrifugation through a Ficoll gradient to obtain small particle fusosomes as described herein. Respiration level in the fusosome preparation were determined by measuring mitochondrial oxygen consumption rates by a Seahorse extracellular flux analyzer (Agilent).

Briefly, the fusosome sample was measured for total protein content by bicinchoninic acid assay (BCA, ThermoFisher, Cat #23225) according to manufacturer's instructions. Next 20 μg of fusosome total protein was pelleted by centrifugation at 3000 g for 5 minutes in a table-top centrifuge, followed by resuspension (in quadruplicates) in 150 μL of XF Assay media (Agilent Cat #103575-100) supplemented with 25 mM glucose and 2 mM glutamine (pH 7.4). The resuspended samples were then added to one well of a 96-well Seahorse plate (Agilent).

Oxygen consumption assays were initiated by incubating the 96-well Seahorse plate with samples at 37° C. for 60 minutes to allow temperature and pH to reach equilibrium. The microplate was then assayed in the XF96 Extracellular Flux Analyzer (Agilent) to measure extracellular flux changes of oxygen and pH in the media immediately surrounding the fusosomes. After obtaining steady state oxygen consumption and extracellular acidification rates, oligomycin (5 μM), which inhibits ATP synthase, and proton ionophore FCCP (carbonyl cyanide 4-(trifluoromethoxy) phenylhydrazone; 2 μM), which uncouples mitochondria, were injected sequentially through reagent delivery chambers for each well in the microplate to obtain values for maximal oxygen consumption rates. Finally, 5 μM antimycin A (inhibitor of mitochondrial complex III) was injected to confirm that respiration changes were due mainly to mitochondrial respiration. The rates of antimycin A respiration were subtracted from the other three respiration rates in order to determine the basal, uncoupled (oligomycin-resistant), and maximal (FCCP-induced) mitochondrial respiration rates.

Using this assay it was determined that donor VSV-G fusosomes showed basal, uncoupled, and maximal oxygen consumption (respiration) rates according to Table D below.

TABLE D

Respiration rates of VSV-G fusosomes

| Respiration state | Mitochondrial oxygen consumption (respiration) rate (pmol/min/20 μg fusosome) AVG ± SEM |
|---|---|
| Basal | 11.3 ± 3.0 |
| Uncoupled | 10.1 ± 2.3 |
| Maximal | 20.0 ± 1.9 |

Example 131: Measuring Phosphatidylserine Levels of Fusosomes

Fusosomes from HEK-293T cells expressing the envelope glycoprotein G from vesicular stomatitis virus (VSV-G) on the cell surface and expressing Cre recombinase protein were generated according by the standard procedure of ultracentrifugation through a Ficoll gradient to obtain small particle fusosomes as described herein. To measure the phosphatidylserine levels of the fusosomes, annexin V staining was performed using a commercially available annexin V conjugated with Alexa Fluor 647 dye (Cat #A23204) according to the manufacturer's instructions. Annexin V is a cellular protein that can bind phosphatidylserine when it is exposed on the outer leaflet of the plasma membrane; thus, the readout of annexin V binding to a sample can provide an assessment of phosphatidylserine levels in the sample.

Briefly, the fusosome sample was measured for total protein content by bicinchoninic acid assay (BCA, ThermoFisher, Cat #23225) according to manufacturer's instructions. Next 40 μg of fusosome total protein was pelleted by centrifugation (in sample triplicates) at 3000 g for 5 minutes in a table-top centrifuge, followed by resuspension in 400 μL of DMEM supplemented with 2% fetal bovine serum. One sample was treated with 40 µM antimycin A. The samples were then incubated for 1 hour at 37 C. After the incubation samples were then pelleted by centrifugation again and resuspended in 100 µL annexin-binding buffer (ABB; 10 mM HEPES, 140 mM NaCl, 2.5 mM $CaCl_2$, pH 7.4). Next 5 µL of annexin V conjugated with Alexa Fluor 647 was added to each sample (except for the negative control with no annexin V staining). The samples were incubated for 15 minutes at room temperature followed by addition of 400 µL ABB.

The samples were then measured for annexin V staining by flow cytometry analysis using an Invitrogen Attune NxT acoustic focusing cytometer. Annexin V conjugated with Alexa Fluor 647 was excited with a 638 nm laser and emission captured at 670±14 nm. Forward and side scatter gating was initially used to capture fusosome-sized events and discard small debris. Events positive for Alexa Fluor 647 (annexin V) staining were determined by gating at the minimum level for which the unstained, annexin V-negative control sample showed <0.5% of events positive for Alexa Fluor 647 staining. The gated events positive for Alexa Fluor 647 staining were then assessed for the percentage of annexin V-positive events of the total parent population (fusosome-sized events in the forward/side scatter gate) and this value was used as the quantification of phosphatidyl-serine levels in the fusosome sample.

With this assay the fusosome derived from a HEK-293T cell expressing the VSV-G and Cre showed a % annexin V-positive fusosomes of 63.3±2.3% without antimycin A treatment and percentage of annexin V-positive fusosomes of 67.6±5.7% with antimycin A treatment.

Example 132: Measuring Average Mitochondrial Membrane Potential

Fusosomes from HEK-293T cells expressing the envelope glycoprotein G from vesicular stomatitis virus (VSV-G) on the cell surface and expressing Cre recombinase protein were generated according by the standard procedure of ultracentrifugation through a Ficoll gradient to obtain small particle fusosomes as described herein. To measure the average mitochondrial membrane potential levels of the fusosomes, a commercially available dye that is mitochondrial membrane potential sensitive, tetramethyl rhodamine, ethyl ester, perchlorate (TMRE; Abcam, Cat #T669) was used for assessing mitochondrial membrane potential. To normalize TMRE fluorescence intensity (FI) to the amount of mitochondria in the sample, MitoTracker Green FM dye (MTG; ThermoFisher, Cat #M7514) was used to co-stain samples in order to normalize TMRE FI to the MTG FI and thus to the amount of mitochondria in the sample. In addition, carbonyl cyanide-p-trifluoromethoxyphenylhydrazone (FCCP; Sigma Cat #C2920) was used to treat a parallel set of samples in order to fully depolarize the mitochondrial membrane potential and thus allow quantification of mitochondrial membrane potential in millivolts based on the decrease in TMRE FI.

Briefly, the fusosome sample was measured for total protein content by bicinchoninic acid assay (BCA, ThermoFisher, Cat #23225) according to manufacturer's instructions. Next 40 µg of fusosome total protein was pelleted by centrifugation (in sample quadruplicates for untreated and FCCP-treated duplicates) at 3000 g for 5 minutes in a table-top centrifuge, followed by resuspension in 100 µL of DMEM supplemented with 2% fetal bovine serum and containing TMRE and MTG dyes at a final concentration of 30 nM and 200 nM, respectively. A parallel set of fusosome samples was left unstained as a negative control. The samples were incubated at for 45 minutes at 37° C. After incubation, samples were pelleted by centrifugation and resuspended in 400 µL of phenol red-free DMEM media containing 30 nm TMRE. One set of duplicates was treated with 20 µM FCCP for 5 minutes before assessment by flow cytometry.

The samples were then measured for annexin V staining by flow cytometry analysis using an Invitrogen Attune NxT acoustic focusing cytometer. MTG was excited with a 488 nm laser and emission captured at 530±30 nm. TMRE was excited with a 561 nm laser and emission captured at 585±16 nm. Forward and side scatter gating was initially used to capture fusosome-sized events and discard small debris. Events positive for MTG and TMRE staining were determined by gating at the minimum level for which the unstained control sample showed <0.5% of events positive for MTG or TMRE staining. The gated events positive for MTG and TMRE staining were then assessed for the mean FI of MTG and TMRE.

Membrane potential values (in millivolts, mV) are calculated based on the intensity of TMRE after normalizing TMRE FI values to MTG FI values. This TMRE/MTG ratio value allows for normalization TMRE intensity to the amount of mitochondria in the sample. The TMRE/MTG ratio value for both the untreated and FCCP-treated samples are calculated and used to determine the membrane potential in millivolts using a modified Nernst equation (see below) that can determine mitochondrial membrane potential based on TMRE fluorescence (as TMRE accumulates in mitochondria in a Nernstian fashion). Fusosome membrane potential is calculated with the following formula: (mV)=−61.5*log (FI(untreated)/FI(FCCP-treated)). Using this equation, the calculated mitochondrial membrane potential of the VSV-G fusosome sample was −29.6±1.5 millivolts.

Example 133: Measuring Persistence Half-Life in a Subject

This example describes measurement of fusosome half-life. Fusosomes underwent acute transfection for 2 hours prior to preparation; they were derived using methods described herein and were loaded with firefly luciferase mRNA.

Following preparation, fusosomes were pelleted by centrifugation and fusosome particles were re-suspended in sterile phosphate buffered saline for injection. A buffered solution lacking fusosomes was used as a negative control.

The fusosomes were delivered into 9-week-old FVB (Jackson Laboratory, 001800) mice via intramuscular (IM) administration to the tibialis anterior. The solution was handled in a manner to ensure continued sterility of the contents. Anesthesia was performed in an induction chamber (~4% isoflurane, to effect) and maintained via nose cone (~2% isoflurane, to effect) with animals placed on a warmed (35° C.) surgical table. The skin over the mid belly of the tibialis anterior (TA) muscle was prepared by depilating the area (Nair Hair Remover cream for 45 seconds, followed by cleaning the area with 70% ethanol). Using a tuberculin syringe, 50 µL of fusosome solution 15 g protein/µL, mean (SEM)) was injected intramuscularly into the belly of the TA. Upon completion of injection, the syringe was removed and pressure was applied to the injection site. The contralateral leg was treated with PBS utilizing the same method as a control.

After delivery, mRNA luciferase is translated in the recipient cytoplasm into luciferase protein. Intraperitoneal (I.P.) administration of D-luciferin (Perkin Elmer, 150 mg/kg) enabled the detection of luciferase expression via in vivo bioluminescent imaging. The animal was placed into an in vivo bioluminescent imaging chamber (Perkin Elmer) which houses a cone anesthetizer (isoflurane) to prevent animal motion. Photon collection was carried out between 3-35 minutes post-injection to observe the maximum bioluminescent signal due to D-luciferin pharmacokinetic clearance. Maximum radiance was recorded in photons/sec/cm2/radians. Total flux, which integrates the radiance over the area, was quantified using a region of interest (ROI) tool within the Living Image Software (Perkin Elmer) and reported in photons/sec. The fusosome treated and PBS treated tibialis anterior muscle tissues were monitored specifically for radiance measurements compared to negative controls (negative control unthreaded (chest) and stage). Measurements were carried out at 1, 6, 12, 24, and 48 hours post-injection to observe firefly luciferase presence.

Figure 26A:
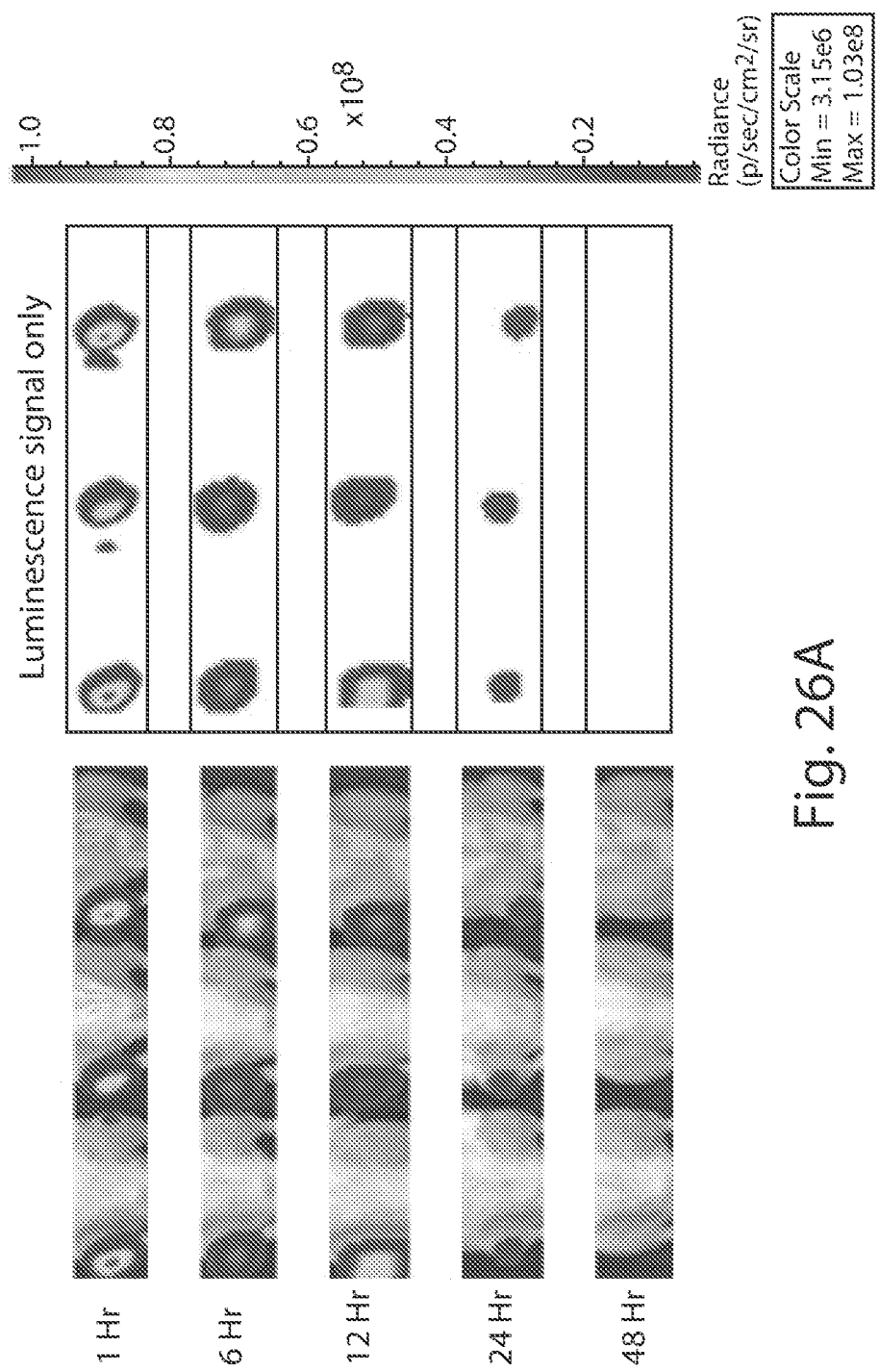
FIGS. 26A-26B are a series of diagrams showing persistence of firefly luciferase signal in the tissues of mice injected with fusosomes. (A) Ventral image and luminescent signal of fusosome (right leg) treated versus PBS (left leg) treated of FVB mice. Left side is an overlay of image and luminescent signal and the right side is luminescent signal only. (B) Total flux signal of fusosome treated TA (dark square), PBS treated TA (open circle), mouse background (dark hexagon), and stage background (open hexagon); y-scale is on log 10 scale. Fusosome treated leg had a significantly greater signal at 1 ($p<0.0001$), 6 ($p<0.01$), and 12 ($p<0.01$) hours post-treatment.
Figure 26B:
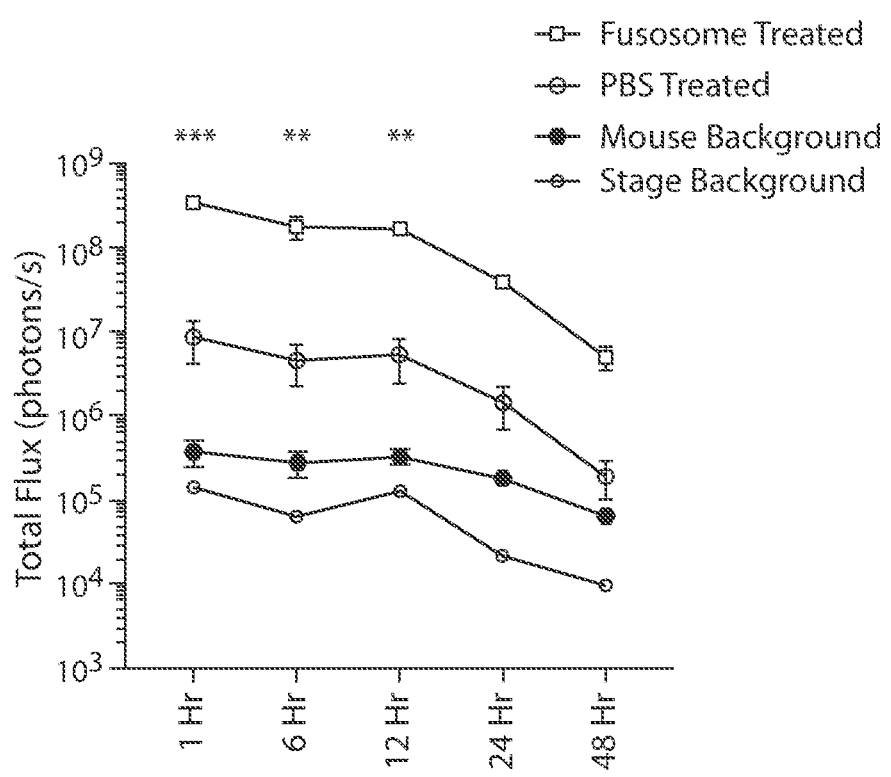

Evidence of firefly luciferase presence was detected by bioluminescent imaging in the recipient tissue of the animal, as shown in FIGS. 26A-26B.

Example 134: Measuring Targeting Potential in a Subject (BiVs-Cre Gesicles)

This example assesses the ability of a fusosome to target a specific body site. Fusosomes were derived using methods as described herein and were loaded with cre-recombinase protein.

Two doses of fusosomes (1× and 3×) were delivered into Loxp Luciferase (Jackson Laboratory, 005125) mice were injected intravenously (I.V.) via tail vein. Mice were placed underneath a heat lamp (utilizing a 250 W (infrared) heat lamp bulb) for ~5 minutes (or until mice begin to groom their whiskers excessively) to dilate the tail vein. Mice were placed on a restrainer and tail was wiped down with 70% ethanol to better visualize the vein.

Using a tuberculin syringe, 200 µL of fusosome 1× solution (8.5e8±1.4e8 particles/µL, mean (SEM)) or 3× solution (2.55e9±1.4e8 particles/µL, mean (SEM)) was injected IV. Upon completion of injection, the syringe was removed, and pressure was applied to the injection site.

After fusion, CRE protein translocated to the nucleus to carry out recombination, which resulted in the constitutive expression of luciferase. Three days post-treatment, the ventral region of subjects was prepared by depilating the area (Nair Hair Remover cream for 45 seconds, followed by cleaning the area with 70% ethanol). Subjects were then treated with D-luciferin (Perkin Elmer, 150 mg/kg) via intraperitoneal administration. This enabled the detection of luciferase expression via in vivo bioluminescent imaging. The animal was placed into an in vivo bioluminescent imaging chamber (Perkin Elmer) which houses a cone anesthetizer (isoflurane) to prevent animal motion. Photon collection was carried out between 3-15 minutes post-injection to observe the maximum bioluminescent signal due to D-luciferin pharmacokinetic clearance. Maximum radiance was recorded in photons/sec/cm2/radians. Total flux, which integrates the radiance over the area, was quantified using a region of interest (ROI) tool within the Living Image Software (Perkin Elmer) and reported in photons/sec.

Figure 27A:
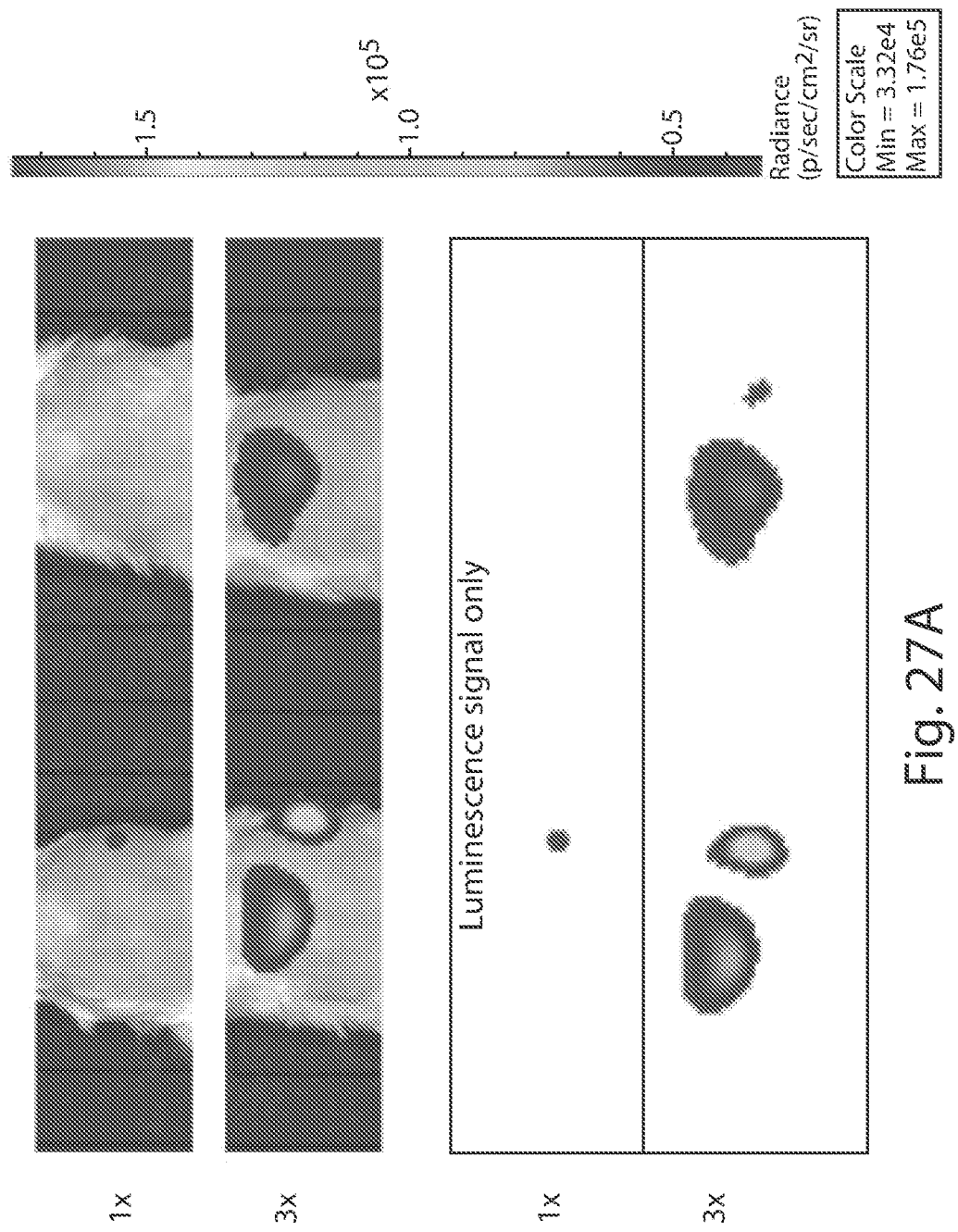
FIGS. 27A-27B are a series of diagrams showing Cre recombinase delivery by fusosomes as detected by bioluminescent imaging in mice. (A) Ventral image and luminescent signal overlay of exposed liver and spleen of IV fusosome treated mice (1× and 3× concentration). Lower portion is luminescent signal alone. (B) Total flux signal of fusosome targeted spleen and liver; y-scale is on log 10 scale. Mice treated with a concentration of 3× fusosome treatment had a significantly greater signal in the spleen ($p=0.0004$) than background 72 hours post-treatment.
Figure 27B:
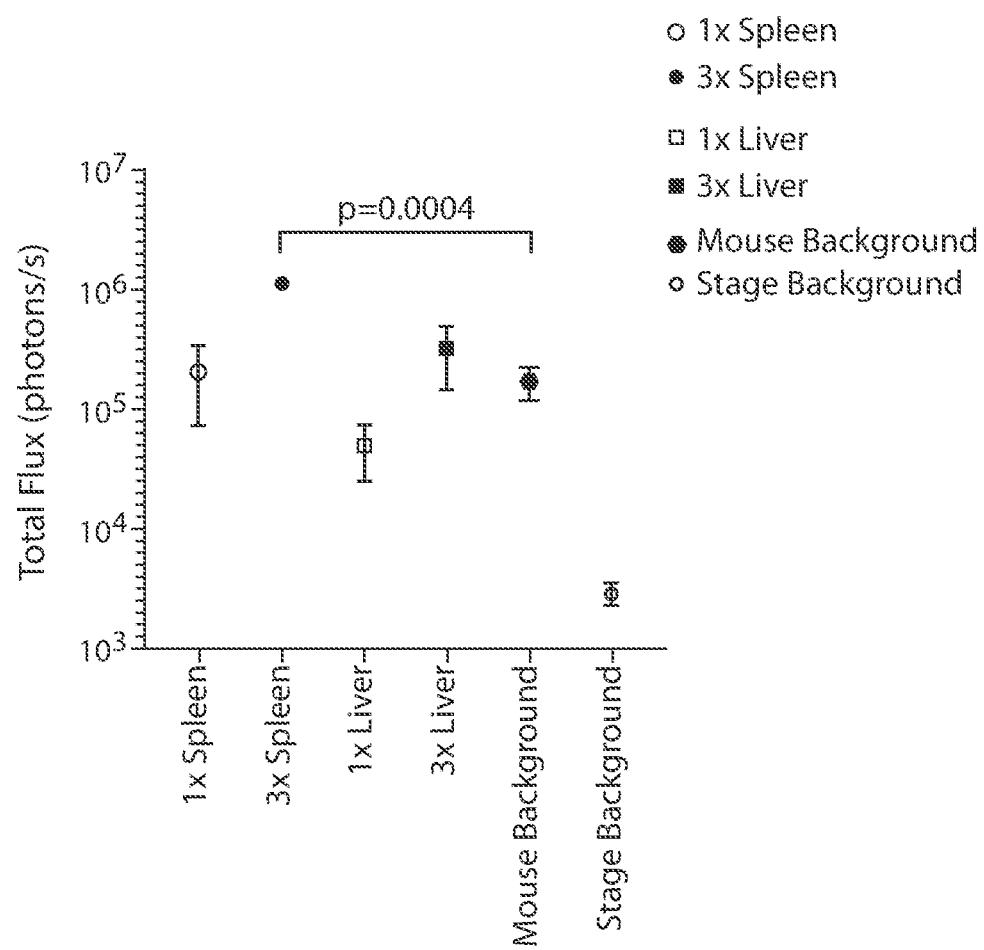

Evidence of protein (Cre recombinase) delivery by fusosomes was detected by bioluminescent imaging in the recipient tissue of the animal, as shown in FIGS. 27A-27B. Signal was seen primarily in the spleen and liver, with the 3× group showing the highest signal.

Figure 28A:
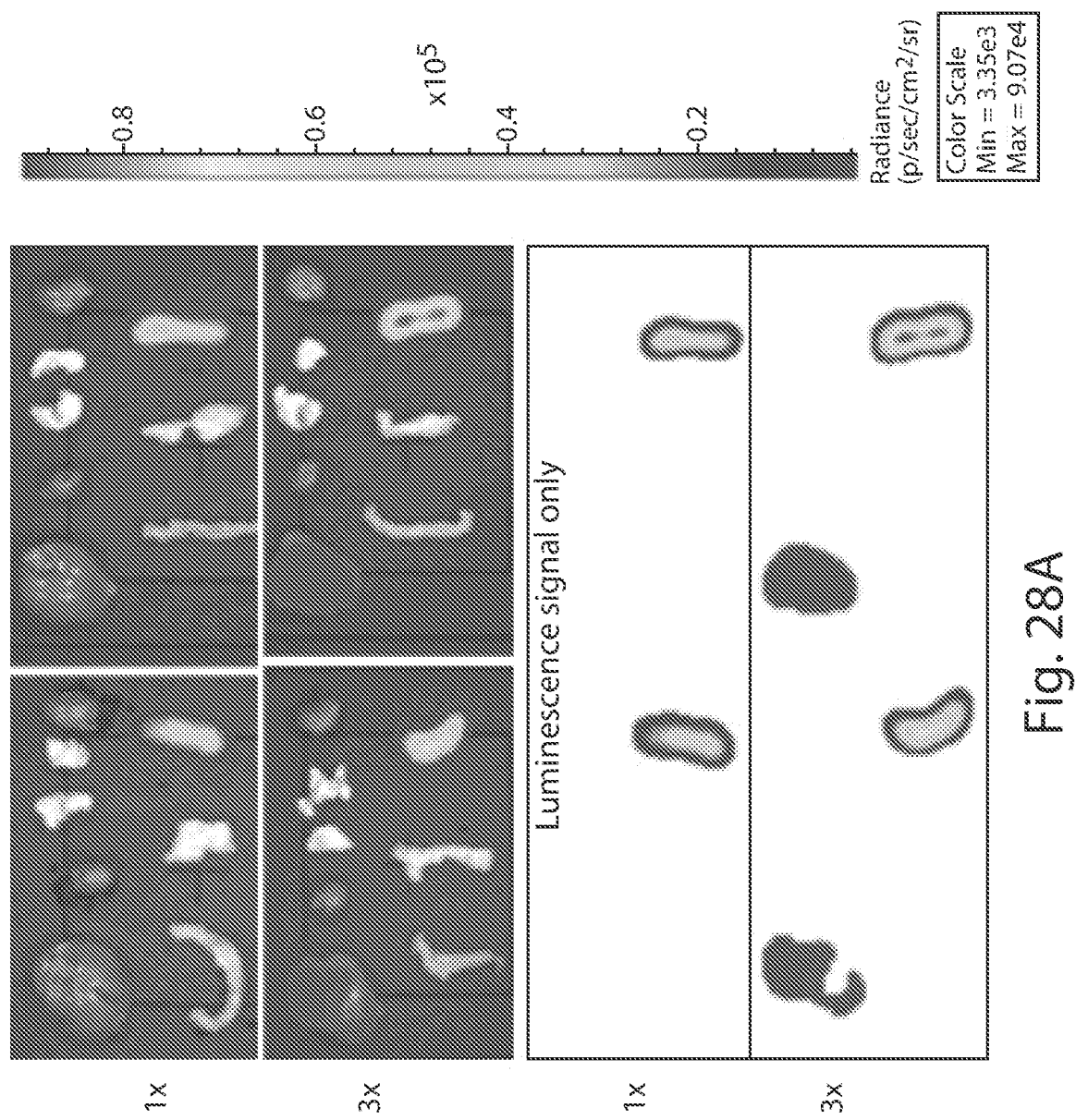
FIGS. 28A-28B are a series of diagrams showing Cre recombinase to murine liver and spleen by fusosomes as detected by bioluminescent imaging. (A) From left to right; dorsal image and luminescent signal overlay of excised liver, heart, lungs, kidney, small intestines, pancreas, and spleen collected and imaged within 5 minutes of euthanasia. Lower portion is luminescent signal alone. (B) Total flux signal of fusosome targeted spleen and liver and other tissues; y-scale is on log 10 scale. Mice treated with a concentration of 3× fusosome treatment had a significantly greater signal in the spleen ($p<0.0001$) as compared to the tissue with the lowest signal (heart).
Figure 28B:
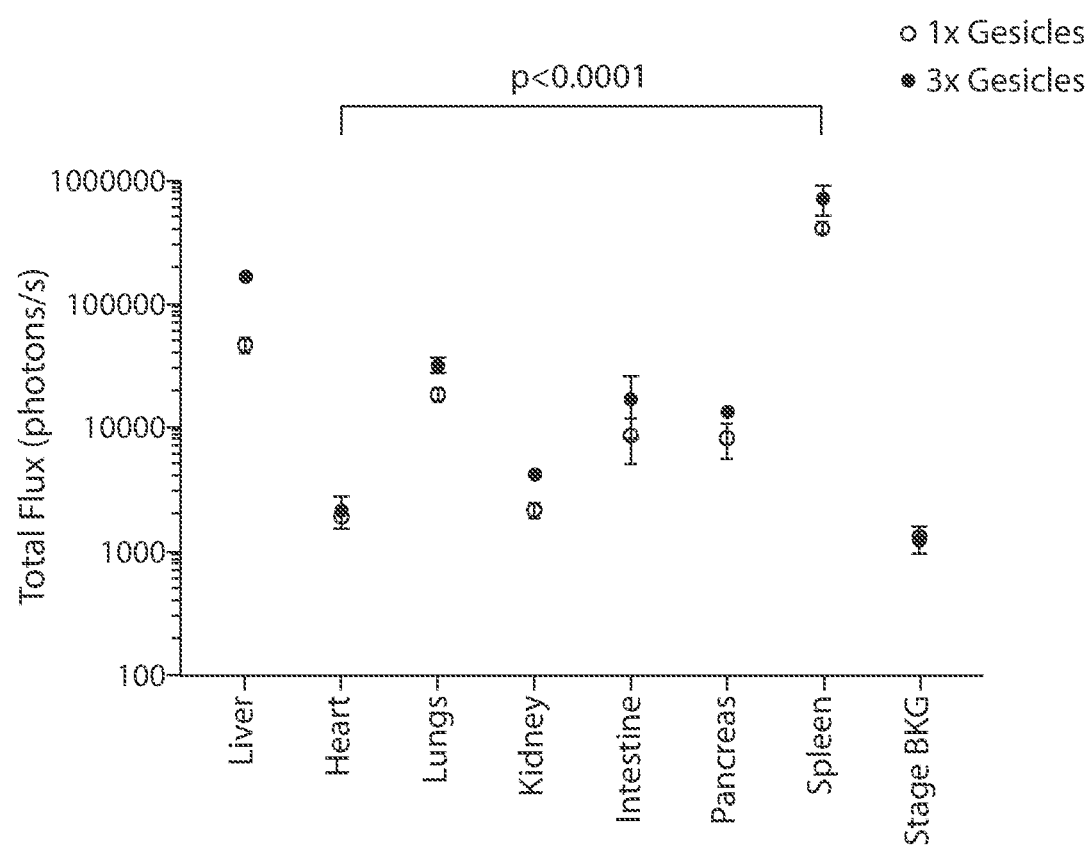

Following whole body imaging, mice were cervically dislocated and liver, heart, lungs, kidney, small intestines, pancreas, and spleen were collected and imaged within 5 minutes of euthanasia. Evidence of protein (Cre recombinase) delivery to the liver and spleen by fusosomes was detected by bioluminescent imaging in the extracted recipient tissue of the animals. This can be seen in FIGS. 28A-28B. Signal was highest in spleen and the lowest in heart, with the 3× group showing the highest significant signal (p=0.0004 as compared to heart).

Example 135: Delivery of Fusosomes Via a Pathway that is Independent of Lysosome Acidification Often, entry of complex biological cargo into target cells is accomplished by endocytosis. Endocytosis requires the cargo to enter an endosome, which matures into an acidified lysosome. Disadvantageously, cargo that enters a cell through endocytosis may become trapped in an endosome or lysosome and be unable to reach the cytoplasm. The cargo may also be damaged by acidic conditions in the lysosome. Some viruses are capable of non-endocytic entry into target cells; however this process is incompletely understood. This example demonstrates that a viral fusogen can be isolated from the rest of the virus and confer non-endocytic entry on a fusosome that lacks other viral proteins.

Fusosomes from HEK-293T cells expressing the Nipah virus receptor-binding G protein and fusion F protein (NivG+F) on the cell surface and expressing Cre recombinase protein were generated according by the standard procedure of ultracentrifugation through a Ficoll gradient to obtain small particle fusosomes, as described herein. To demonstrate delivery of the fusosome to a recipient cell via a non-endocytic pathway, the NivG+F fusosomes were used to treat recipient HEK-293T cells engineered to express a "Loxp-GFP-stop-Loxp-RFP" cassette under CMV promoter. NivF protein is a pH-independent envelope glycoprotein that has been shown to not require environmental acidification for activation and subsequent fusion activity (Tamin, 2002).

The recipient cells were plated 30,000 cells/well into a black, clear-bottom 96-well plate. Four to six hours after plating the recipient cells, the NivG+F fusosomes expressing Cre recombinase protein were applied to the target or non-target recipient cells in DMEM media. The fusosome sample was first measured for total protein content by bicinchoninic acid assay (BCA, ThermoFisher, Cat #23225) according to manufacturer's instructions. Recipient cells were treated with 10 µg of fusosomes and incubated for 24 hrs at 37° C. and 5% CO2. To demonstrate that Cre delivery via NivG+F fusosomes was through a non-endocytic pathway, a parallel wells of recipient cells receiving NivG+F fusosome treatment were co-treated with an inhibitor of endosome/lysosome acidification, bafilomycin A1 (Baf; 100 nM; Sigma, Cat #B1793).

Cell plates were imaged using an automated microscope (www.biotek.com/products/imaging-microscopy-automated-cell-imagers/lionheart-fx-automated-live-cell-imager/). The total cell population in a given well was determined by staining the cells with Hoechst 33342 in DMEM media for 10 minutes. Hoechst 33342 stains cell nuclei by intercalating into DNA and was therefore used to identify individual cells. Hoechst staining was imaged using the 405 nm LED and DAPI filter cube. GFP was imaged using the 465 nm LED and GFP filter cube, while RFP was imaged using the 523 nm LED and RFP filter cube. Images of target and non-target cell wells were acquired by first establishing the LED intensity and integration times on a positive control well containing recipient cells treated with adenovirus coding for Cre recombinase instead of fusosomes.

Acquisition settings were set so that Hoescht, RFP, and GFP intensities were at the maximum pixel intensity values but not saturated. The wells of interest were then imaged using the established settings. Focus was set on each well by autofocusing on the Hoescht channel and then using the established focal plane for the GFP and RFP channels. Analysis of GFP and RFP-positive cells was performed with Gen5 software provided with automated fluorescent microscope (https://www.biotek.com/products/software-robotics-software/gen5-microplate-reader-and-imager-software/).

The images were pre-processed using a rolling ball background subtraction algorithm with a 60 µm width. Cells with GFP intensity significantly above background intensities were thresholded and areas too small or large to be GFP-positive cells were excluded. The same analysis steps were applied to the RFP channel. The number of RFP-positive cells (recipient cells receiving Cre) was then divided by the sum of the GFP-positive cells (recipient cells that did not show delivery) and RFP-positive cells to quantify the percentage RFP conversion, which indicates the amount of fusosome fusion with the recipient cells.

With this assay, the fusosome derived from a HEK-293T cell expressing NivG+F on its surface and containing Cre recombinase protein showed significant delivery via a lysosome-independent pathway, which is consistent with entry via a non-endocytic pathway, as evidenced by a significant delivery of Cre cargo by NivG+F fusosomes even when recipient cells were co-treated with Baf to inhibit endocytosis-mediated uptake (FIG. 29). In this case, the inhibition of cargo delivery by Baf co-treatment was 23.4%.

Example 136: Delivery of Fusosomes Via a Pathway that Involves Lysosomal Acidification Fusosomes from HEK-293T cells expressing the envelope glycoprotein G from vesicular stomatitis virus (VSV-G) on the cell surface and expressing Cre recombinase protein were generated by the standard procedure of ultracentrifugation through a Ficoll gradient to obtain small particle fusosomes as described herein. To demonstrate delivery of the fusosome to a recipient cell via an endocytic pathway, the VSV-G fusosomes were used to treat recipient HEK-293T cells engineered to express a "Loxp-GFP-stop-Loxp-RFP" cassette under CMV promoter. VSV-G is a pH-dependent envelope glycoprotein that has been shown to be activated at low pH environments (pH-6) of late endosomes or lysosomes (Yao, 2003). The recipient cells were plated 30,000 cells/well into a black, clear-bottom 96-well plate. Four-six hours after plating the recipient cells, the VSV-G fusosomes expressing Cre recombinase protein were applied to the target or non-target recipient cells in DMEM media. The fusosome sample was first measured for total protein content by bicinchoninic acid assay (BCA, ThermoFisher, Cat #23225) according to manufacturer's instructions. Recipient cells were treated with 10 µg of fusosomes and incubated for 24 hrs at 37° C. and 5% CO2. To demonstrate that Cre delivery via VSV-G fusosomes was through an endocytic pathway, a parallel wells of recipient cells receiving VSV-G fusosome treatment were co-treated with an inhibitor of endosome/lysosome acidification, bafilomycin A1 (Baf; 100 nM; Sigma, Cat #B1793).

Cell plates were imaged using an automated microscope (www.biotek.com/products/imaging-microscopy-automated-cell-imagers/lionheart-fx-automated-live-cell-imager/). The total cell population in a given well was determined by staining the cells with Hoechst 33342 in DMEM media for 10 minutes. Hoechst 33342 stains cell nuclei by intercalating into DNA and therefore was used to identify individual cells. Hoechst staining was imaged using the 405 nm LED and DAPI filter cube. GFP was imaged using the 465 nm LED and GFP filter cube, while RFP was imaged using 523 nm LED and RFP filter cube. Images of cell wells were acquired by first establishing the LED intensity and integration times on a positive-control well containing recipient cells treated with adenovirus coding for Cre recombinase instead of fusosomes.

Acquisition settings were set so that Hoescht, RFP, and GFP intensities are at the maximum pixel intensity values but not saturated. The wells of interest were then imaged using the established settings. Focus was set on each well by autofocusing on the Hoescht channel and then using the established focal plane for the GFP and RFP channels. Analysis of GFP and RFP-positive cells was performed with Gen5 software provided with automated fluorescent microscope (see www.biotek.com/products/software-robotics-software/gen5-microplate-reader-and-imager-software/).

The images were pre-processed using a rolling ball background subtraction algorithm with a 60 m width. Cells with GFP intensity significantly above background intensities were thresholded and areas too small or large to be GFP-positive cells were excluded. The same analysis steps were applied to the RFP channel. The number of RFP-positive cells (recipient cells receiving Cre) was then divided by the sum of the GFP-positive cells (recipient cells that did not show delivery) and RFP-positive cells to quantify the percentage RFP conversion, which describes the amount of fusosome fusion with the recipient cells.

Figure 30:
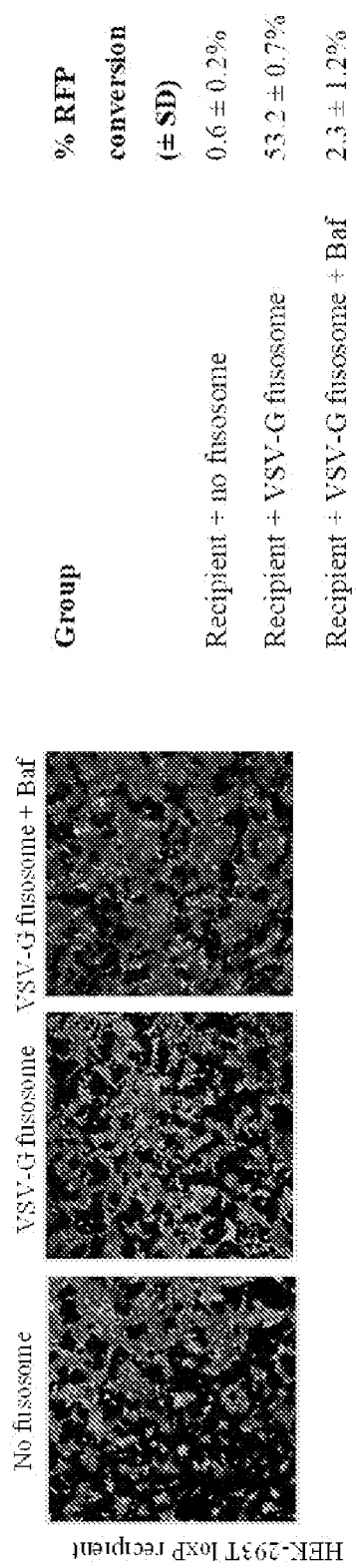
FIG. 30 is a series of images showing delivery of Cre cargo by VSV-G fusosomes via the endocytic pathway.

With this assay, the fusosome derived from a HEK-293T cell expressing VSV-G on its surface and containing Cre recombinase protein showed a significant delivery via an endocytic pathway as evidenced by a significant inhibition of Cre cargo delivery by VSV-G fusosomes when recipient cells were co-treated with Baf to inhibit endocytosis-mediated uptake (FIG. 30). In this case, the inhibition of cargo delivery by Baf co-treatment was 95.7%.

Example 137: Delivery of Organelles

Fusosomes were generated comprising a HeLa cell expressing the placental cell-cell fusion protein syncytin-1 (Syn1) on the cell surface and expressing mitochondrial-targeted DsRED fluorescent protein (mtDsRED). The recipient cell was a HeLa Rho0 cell, that had been produced to lack mitochondrial DNA (mtDNA) by long-term (>6 weeks) culture of HeLa cells in zalcitabine, a nucleoside analog reverse transcriptase inhibitor. The HeLa Rho0 cells are deficient in mtDNA (as assessed by qPCR) and show significantly deficient mitochondrial oxygen consumption (as measured by Seahorse extracellular flux assay). Recipient HeLa Rho0 cells were also engineered to expressing mitochondrial-targeted GFP (mtGFP) via adenoviral transduction for 2 days.

Recipient HeLa Rho0 cells were plated into 6-well dishes and one hour later Syn1 HeLa cell fusosomes were applied to the recipient cells. The cells were then incubated for 24 hours at 37° C. and 5% $CO_2$. Cells were then sorted for double-positive (fused) cells via fluorescence-assisted cell sorting using a BD FACS Aria SORP cell sorter. The population of cells double-positive for mtGFP and mtDsRED was assessed in order to sort the recipient HeLa Rho0 cells that had received mitochondrial donation (mtDsRED) from the Syn1 HeLa cell fusosomes. mtGFP was excited with a 488 nm laser and emission captured at 513±26 nm. mtDsRED was excited with a 543 nm laser and emission captured at 570±26 nm. Forward and side scatter gating was initially used to capture cell-sized events and discard small debris. Events double-positive for mtGFP and mtDsRED were determined by gating at the minimum level for which each appropriately negative control sample showed less than 1% of events positive for the specific fluorescent marker (i.e. unstained and single-mtGFP-positive samples show less than 1% events positive for mtDsRED). The double-positive events, as well as the single-positive mtGFP (recipient cells with no fusosome delivery) and single-positive mtDsRED (donor fusosomes that did not fuse to recipient cells) events, were then sorted into DMEM media with 10% FBS and antibiotics. The sorted cells were counted and seeded at 25,000 cells per well (in 6 replicates for each group) in a 96-well Seahorse plate (Agilent). The plate was incubated at 37° C. and 5% $CO_2$ for 24 hours.

Oxygen consumption assays were initiated by removing growth medium, replacing with low-buffered DMEM minimal medium containing 25 mM glucose and 2 mM glutamine (Agilent) and incubating at 37° C. for 60 minutes to allow temperature and pH to reach equilibrium. The microplate was then assayed in the XF96 Extracellular Flux Analyzer (Agilent) to measure extracellular flux changes of oxygen and pH in the media immediately surrounding adherent cells. After obtaining steady state oxygen consumption and extracellular acidification rates, oligomycin (5M), which inhibits ATP synthase, and proton ionophore FCCP (carbonyl cyanide 4-(trifluoromethoxy) phenylhydrazone; 2 µM), which uncouples mitochondria, were injected sequentially through reagent delivery chambers for each cell well in the microplate to obtain values for maximal oxygen consumption rates. Finally, 5 M antimycin A (inhibitor of mitochondrial complex III) was injected in order to confirm that respiration changes were due mainly to mitochondrial respiration. The rates of antimycin A respiration were subtracted from the other three respiration rates in order to determine the basal, uncoupled (oligomycin-resistant), and maximal (FCCP-induced) mitochondrial respiration rates.

Figure 31:
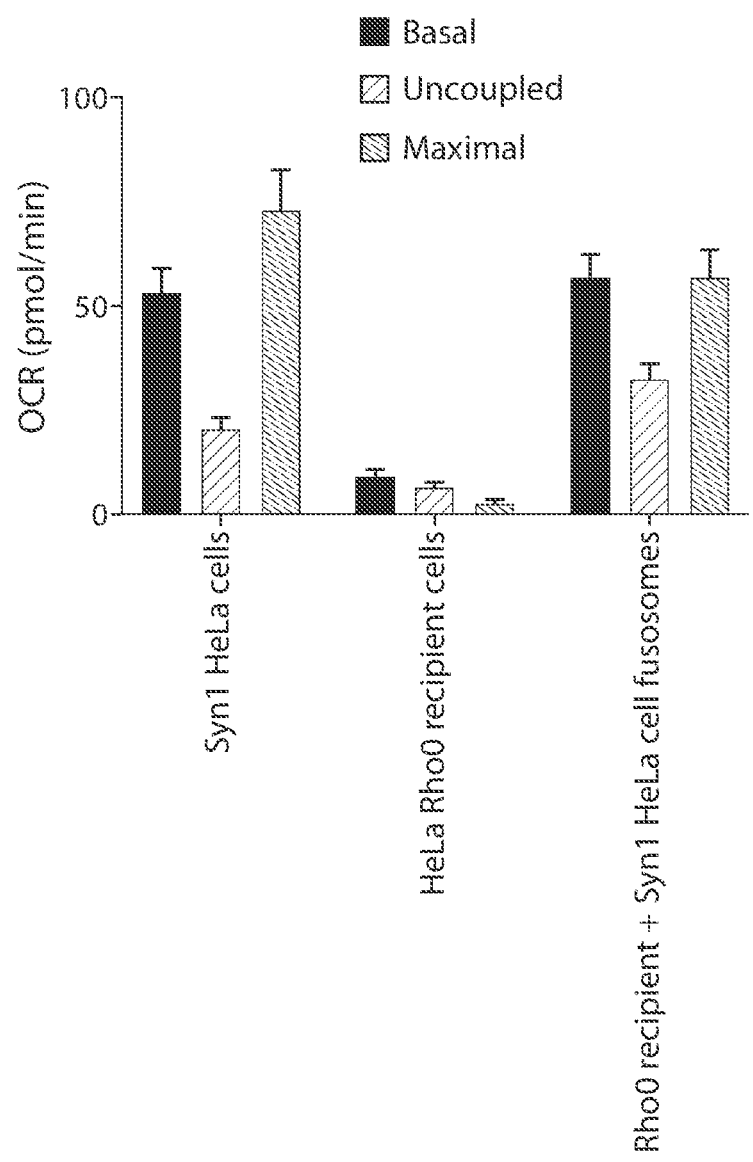
FIG. 31 is a graph showing delivery of functional mitochondria using Syn1 HeLa cell fusosomes to recipient HeLa Rho0 cells.

Using this assay it was determined that donor Syn1 HeLa cells showed active basal and maximal oxygen consumption rates, while recipient cells with no fusosome delivery showed low rates of all three states of mitochondrial oxygen consumption. Delivery of mitochondria with Syn1 HeLa cell fusosomes to recipient HeLa Rho0 cells showed a return to mitochondrial oxygen consumption rates near donor Syn1 HeLa cell rates (FIG. 31).

Example 138: In Vitro Delivery of DNA

Fusosomes were generated by the standard procedure of harvesting and preparing fusosomes produced from HEK-293T cells expressing the envelope glycoprotein G from vesicular stomatitis virus (VSV-G) on the cell surface as described herein. Control particles (non-fusogenic fusosomes) were produced from HEK-293T cells reverse transiently transfected with pcDNA3.1 empty vector. A payload was then loaded into the VSV-G fusosomes by sonication, as outlined in Lamichhane, T N, et al., Oncogene Knockdown via Active Loading of Small RNAs into Extracellular Vesicles by Sonication. *Cell Mol Bioeng*, (2016). In this experiment, the nucleic acid payload was plasmid DNA encoding the bacteriophage P1 Cre Recombinase with a SV40 Nuclear localization sequence (ThermoFisher). The DNA loaded fusosomes were then used to treat and show payload delivery to recipient HEK-293T cells engineered to express a "LoxP-GFP-stop-LoxP-RFP" cassette under control of the CMV promoter.

Briefly, approximately $40^6$ fusosomes or control particles (non-fusogenic fusosomes) corresponding to 80 µg of a standard VSV-G fusosome preparation were mixed with 140 µg DNA and incubated at room temperature for 30 minutes. The fusosome (or control particle)/nucleic acid mixture was then sonicated for 30 seconds at room temperature using a water bath sonicator (Branson model #1510R-DTH) operated at 40 kHz. The mixture was then placed on ice for one minute followed by a second round of sonication at 40 kHz for 30 seconds. The mixture was then centrifuged at 16,000 g for 5 minutes at 4° C. to pellet the fusosomes containing nucleic acid. The supernatant containing unincorporated nucleic acid was removed and the pellet was resuspended in 30 µL phosphate-buffered saline. After DNA loading, the loaded fusosomes/control particles were kept on ice before use.

The recipient HEK-293T cells engineered to express a "LoxP-GFP-stop-LoxP-RFP" cassette were plated 30,000 cells/well into a black, clear-bottom 96-well plate in complete media. Twenty four hours after plating the recipient cells, the DNA loaded fusosomes were applied to LoxP-GFP-stop-LoxP-RFP HEK-293T cells. Recipient cells were treated with 8 µL of DNA loaded fusosomes or 8 µL of DNA loaded control particles (non-fusogenic fusosomes) and incubated for 24 hrs at 37° C. and 5% CO2. Twenty-four hours later cell plates, were incubated at 37° C. and 5% $CO_2$ for 30 minutes with 1 µg/mL Hoechst 33342 diluted in complete media before being imaged using an automated microscope (www.biotek.com/products/imaging-microscopy-automated-cell-imagers/lionheart-fx-automated-live-cell-imager/). The Hoechst fluorescence of the recipient cell was imaged using the 405 nm LED and BFP filter cube The GFP fluorescence of the recipient cell was imaged using the 488 nm LED and GFP filter cube. RFP fluorescence of the recipient cell was imaged using the 523 nm LED and RFP filter cube. Images of cells in the well were acquired by first establishing the LED intensity and integration times on a positive-control well containing recipient cells treated with 1.25 µL Cre recombinase gesicles (Takara, Cat #631449).

Acquisition settings were set so that RFP, GFP and RFP intensities are at the maximum pixel intensity values but not saturated. The wells of interest were then imaged using the established settings. Focus was set on each well by autofocusing on the BFP channel and then using the established focal plane for the GFP and RFP channels. Analysis of RFP-positive cells was performed with Gen5 software provided with automated fluorescent microscope (https://www.biotek.com/products/software-robotics-software/gen5-microplate-reader-and-imager-software/).

The images were pre-processed using a rolling ball background subtraction algorithm with a 60 µm width. Cells with GFP intensity significantly above background intensities were thresholded and areas too small or large to be GFP-positive cells were excluded. The same analysis steps were applied to the RFP channel. The number of RFP-positive cells (recipient cells receiving Cre DNA) was then divided by the sum of the GFP positive cells (total recipient cells) to quantify the percentage of cells that received Cre DNA delivery, which describes the amount of recipient cells receiving Cre DNA payload that was loaded into fusosomes via sonication.

Figure 32:
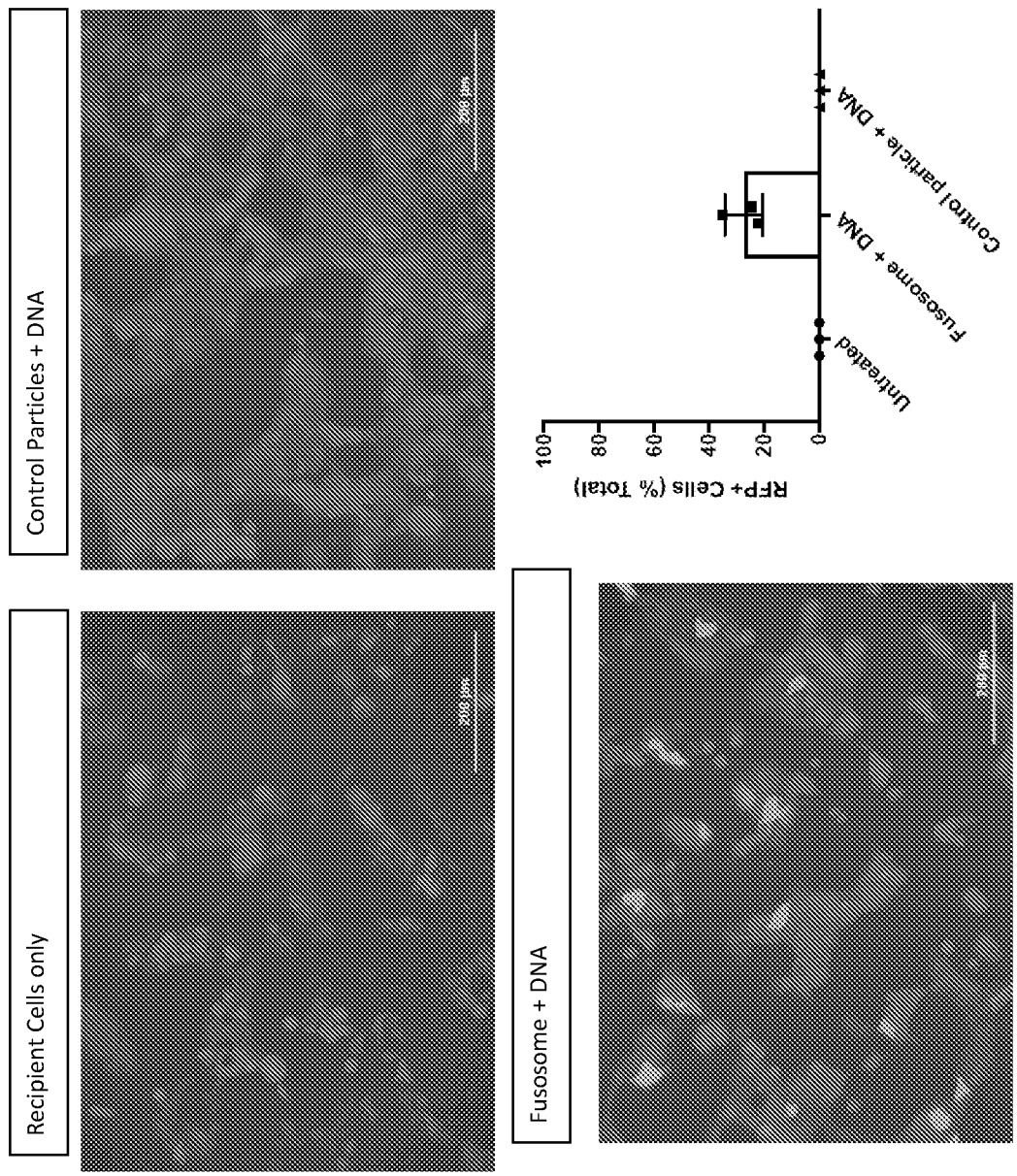
FIG. 32 is a series of images showing in vitro delivery of DNA to recipient cells via fusosomes.
Figure 33:
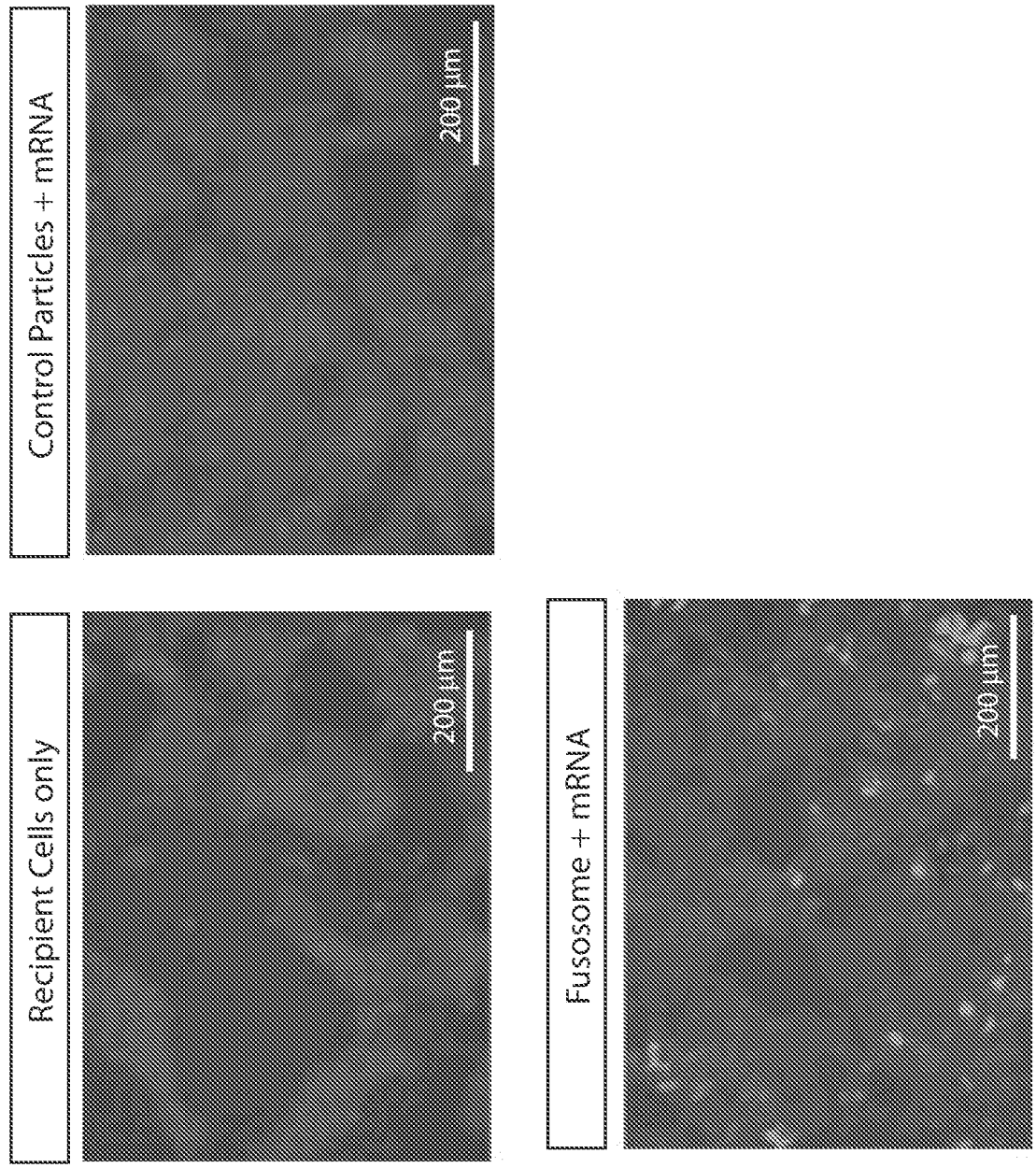
FIG. 33 is a series of images showing in vitro delivery of mRNA to recipient cells via fusosomes.
Figure 34:
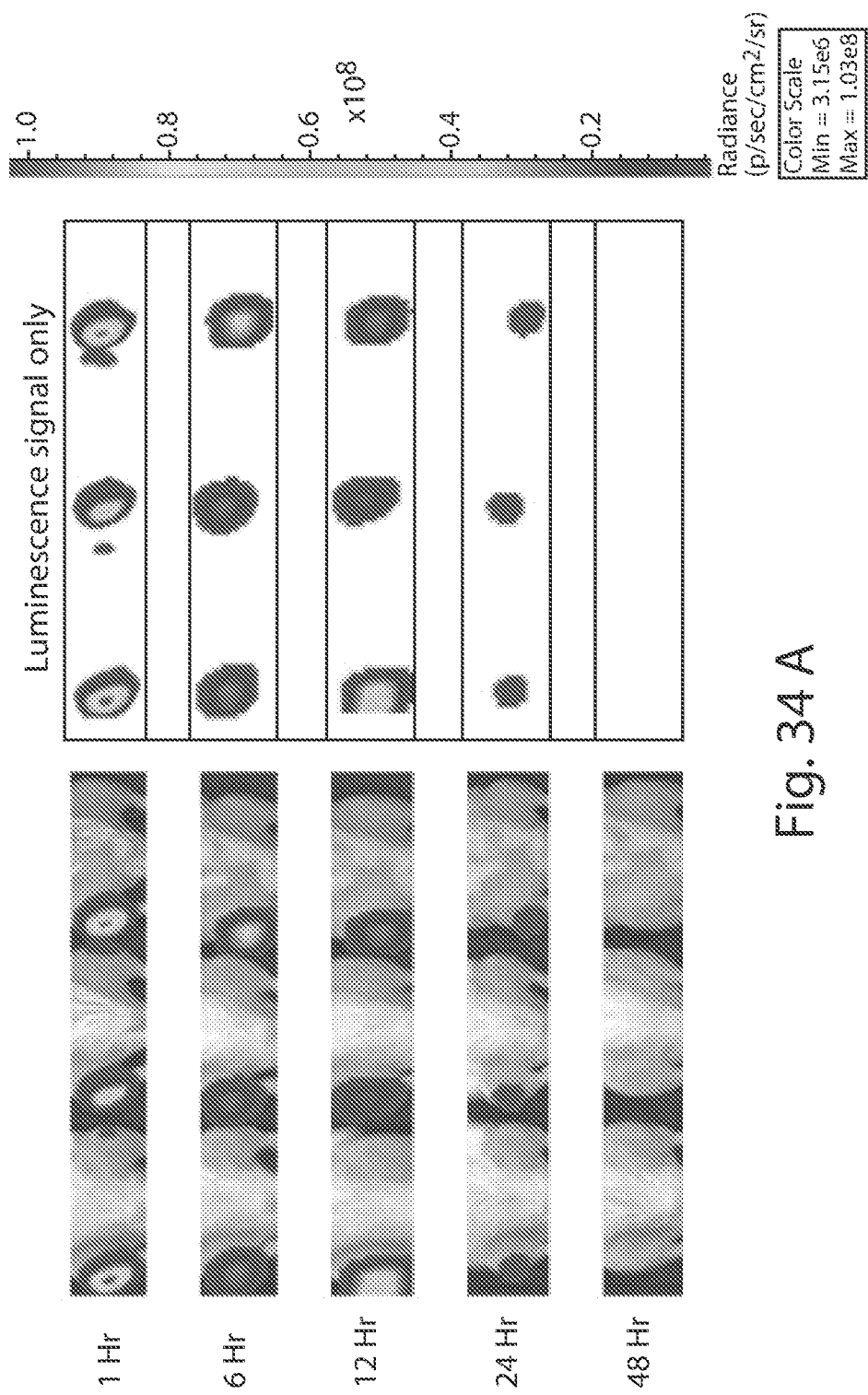
FIGS. 34A-34B are a series of diagrams showing in vivo delivery of mRNA encoding firefly luciferase into the tissues of mice using fusosomes. (A) Ventral image and luminescent signal of fusosome (right leg) treated versus PBS (left leg) treated of FVB mice. Left side is an overlay of image and luminescent signal and the right side is luminescent signal only. (B) Total flux signal of fusosome treated TA (dark square), PBS treated TA (open circle), mouse background (dark hexagon), and stage background (open hexagon); y-scale is on log 10 scale. Fusosome treated leg had a significantly greater signal at 1 ($p<0.0001$), 6 ($p<0.01$), and 12 ($p<0.01$) hours post-treatment.
Figure 34B:
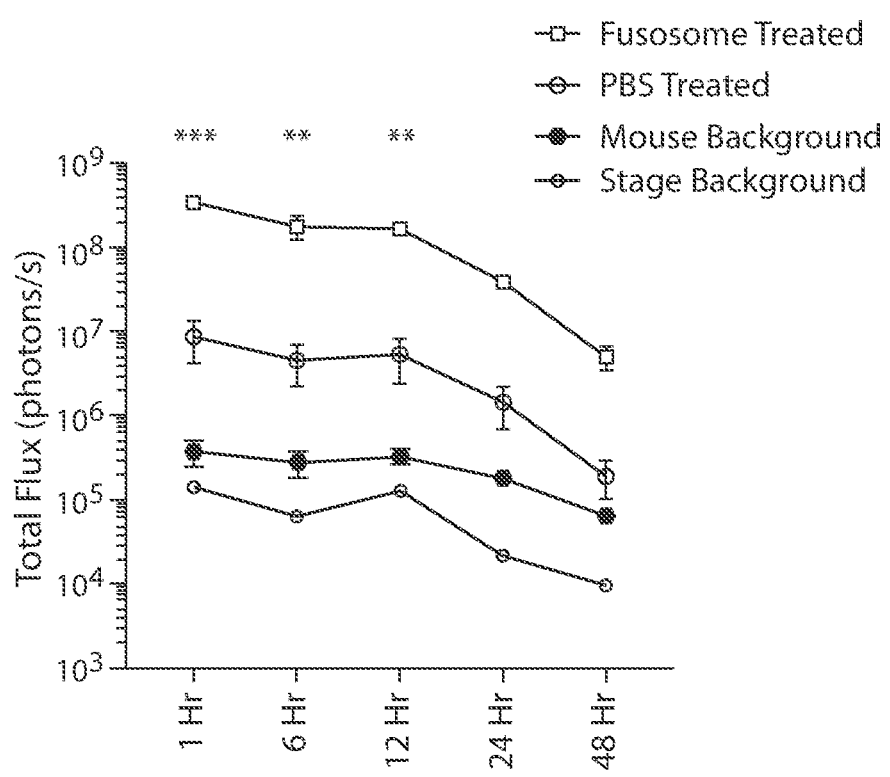

With this assay the Cre DNA loaded fusosome showed an observable level of Cre DNA delivery corresponding to 10.7±3.3% RFP-positive cells of total GFP-positive recipient cells (FIG. 32). Untreated recipient cells or cells treated with fusosome alone, or DNA loaded control particles did not show any appreciable RFP-positive cells.

Example 139: In Vitro Delivery of mRNA

Fusosomes were generated by the standard procedure of harvesting and preparing fusosomes produced from HEK-293T cells expressing the envelope glycoprotein G from vesicular stomatitis virus (VSV-G) on the cell surface as described herein. Control particles (non-fusogenic fusosomes) were produced from HEK-293T cells reverse transiently transfected with pcDNA3.1 empty vector. A payload was then loaded into the VSV-G fusosomes by sonication, as outlined in Lamichhane, T N, et al., Oncogene Knockdown via Active Loading of Small RNAs into Extracellular Vesicles by Sonication. *Cell Mol Bioeng*, (2016). In this experiment, the nucleic acid payload was an in vitro transcribed messenger RNA encoding the bacteriophage P1 Cre Recombinase with a SV40 Nuclear localization sequence (TriLink, Cat #L-7211). The mRNA loaded fusosomes were then used to treat and show payload delivery to recipient HEK-293T cells engineered to express a "LoxP-GFP-stop-LoxP-RFP" cassette under control of the CMV promoter.

Briefly, approximately $10^6$ fusosomes or control particles (non-fusogenic fusosomes) corresponding to 20 μL of a standard VSV-G fusosome preparation were mixed with 10 μg mRNA and incubated at room temperature for 30 minutes. The fusosome (or control particle)/nucleic acid mixture was then sonicated for 30 seconds at room temperature using a water bath sonicator (Brason model #1510R-DTH) operated at 40 kHz. The mixture was then placed on ice for one minute followed by a second round of sonication at 40 kHz for 30 seconds. The mixture was then centrifuged at 16,000 g for 5 minutes at 4° C. to pellet the fusosomes containing nucleic acid. The supernatant containing unincorporated nucleic acid was removed and the pellet was resuspended in 30 L phosphate-buffered saline. After mRNA loading, the loaded fusosomes/control particles were kept on ice before use.

The recipient HEK-293T cells engineered to express a "LoxP-GFP-stop-LoxP-RFP" cassette were plated 30,000 cells/well into a black, clear-bottom 96-well plate in complete media. Twenty-four hours after plating the recipient cells, the mRNA loaded fusosomes were applied to LoxP-GFP-stop-LoxP-RFP HEK-293T cells. Recipient cells were treated with 8 L of mRNA loaded fusosomes or 8 μL of mRNA loaded control particles (non-fusogenic fusosomes) and incubated for 24 hrs at 37° C. and 5% CO2. Twenty-four hours later cell plates, were incubated at 37° C. and 5% $CO_2$ for 30 min with 1 μg/mL Hoechst 33342 diluted in complete media before being imaged using an automated microscope (www.biotek. com/products/imaging-microscopy-automated-cell-imagers/lionheart-fx-automated-live-cell-imager/). The Hoechst fluorescence of the recipient cell was imaged using the 405 nm LED and BFP filter cube The GFP fluorescence of the recipient cell was imaged using the 488 nm LED and GFP filter cube. RFP fluorescence of the recipient cell was imaged using the 523 nm LED and RFP filter cube. Images of cells in the well were acquired by first establishing the LED intensity and integration times on a positive-control well containing recipient cells treated with Cre recombinase gesicles (Takara, Cat #631449).

Acquisition settings were set so that RFP, GFP and RFP intensities are at the maximum pixel intensity values but not saturated. The wells of interest were then imaged using the established settings. Focus was set on each well by autofocusing on the BFP channel and then using the established focal plane for the GFP and RFP channels. Analysis of RFP-positive cells was performed with GenS software provided with automated fluorescent microscope (https://www.biotek.com/products/software-robotics-software/gen5-microplate-reader-and-imager-software/).

The images were pre-processed using a rolling ball background subtraction algorithm with a 60 μm width. Cells with GFP intensity significantly above background intensities were thresholded and areas too small or large to be GFP-positive cells were excluded. The same analysis steps were applied to the RFP channel. The number of RFP-positive cells (recipient cells receiving Cre mRNA) was then divided by the sum of the GFP positive cells (total recipient cells) to quantify the percentage of cells that received Cre mRNA delivery, which describes the amount of recipient cells receiving Cre mRNA payload that was loaded into fusosomes via sonication.

With this assay the Cre mRNA loaded fusosome showed an observable level of Cre mRNA delivery corresponding to 52.8±7.8% RFP-positive cells of total GFP-positive recipient cells (FIG. 96). Recipient cells treated with miRFP670 DNA alone, fusosome alone, or sonicated fusosome alone did not show any appreciable miRFP670-positive cells.

Example 140: In Vivo Delivery of mRNA

This example describes the delivery of messenger RNA (mRNA) to cells in vivo via fusosomes. Delivery of mRNA to cells in vivo resulted in the expression of proteins within the recipient cell. This method of delivery was used to introduce a protein not present, which would permit the cleavage of loxp sites and subsequent expression of a non-endogenous molecule. Fusosomes underwent acute transfection for 2 hours prior to preparation; they were derived using methods as described herein and were loaded with firefly luciferase mRNA.

Following preparation, fusosomes were pelleted by centrifugation and fusosome particles were re-suspended in sterile phosphate buffered saline for injection. A buffered solution lacking fusosomes was used as a negative control.

The fusosomes were delivered into 9-week-old FVB (Jackson Laboratory, 001800) mice via intramuscular (IM) administration to the tibalis anterior. The solution was handled in a manner to ensure continued sterility of the contents. Anesthesia was performed in an induction chamber (~4% isoflurane, to effect) and maintained via nose cone (~2% isoflurane, to effect) with animals placed on a warmed (35° C.) surgical table. The skin over the mid belly of the tibialis anterior (TA) muscle was prepared by depilating the area (Nair Hair Remover cream for 45 seconds, followed by cleaning the area with 70% ethanol). Using a tuberculin syringe, 50 μL of fusosome solution 15 g protein/μL, mean (SEM)) was injected intramuscularly into the belly of the TA. Upon completion of injection, the syringe was removed and pressure was applied to the injection site. The contralateral leg was treated with PBS utilizing the same method as a control.

After delivery, mRNA luciferase is translated in the recipient cytoplasm into luciferase protein. Intraperitoneal (I.P.) administration of D-luciferin (Perkin Elmer, 150 mg/kg) enabled the detection of luciferase expression via in vivo bioluminescent imaging. The animal was placed into an in vivo bioluminescent imaging chamber (Perkin Elmer) which houses a cone anesthetizer (isoflurane) to prevent animal motion. Photon collection was carried out between 3-35 minutes post-injection to observe the maximum bioluminescent signal due to D-luciferin pharmacokinetic clearance. Maximum radiance is recorded in photons/sec/cm2/radians. Total flux, which integrates the radiance over the area, is quantified using a region of interest (ROI) tool within the Living Image Software (Perkin Elmer) and reported in photons/sec. The fusosome treated and PBS treated tibialis anterior muscle tissues were monitored specifically for radiance measurements compared to negative controls (negative control unthreaded (chest) and stage). Measurements were carried out at 1, 6, 12, 24, and 48 hours post-injection to observe firefly luciferase presence.

Evidence of firefly luciferase presence was detected by bioluminescent imaging in the recipient tissue of the animal, as shown in FIGS. 15A-15B. (A) Ventral image and luminescent signal of fusosome (right leg) treated versus PBS (left leg) treated of FVB mice. Left side is an overlay of image and luminescent signal and the right side is luminescent signal only. (B) Total flux signal of fusosome treated TA (dark square), PBS treated TA (open circle), mouse background (dark hexagon), and stage background (open hexagon); y-scale is on log 10 scale. Fusosome treated leg had a significantly greater signal at 1 ($p<0.0001$), 6 ($p<^{0.01}$), and 12 ($p<0.01$) hours post-treatment.

Example 141: In Vitro Delivery of Protein

Fusosomes were generated by the standard procedure of harvesting and preparing fusosomes produced from HEK-293T cells expressing the envelope glycoprotein G from vesicular stomatitis virus (VSV-G) on the cell surface as described herein. Control particles (non-fusogenic fusosomes) were produced from HEK-293T cells reverse transiently transfected with pcDNA3.1 empty vector. A payload was then loaded into the VSV-G fusosomes by sonication, as outlined in Lamichhane, T N, et al., Oncogene Knockdown via Active Loading of Small RNAs into Extracellular Vesicles by Sonication. *Cell Mol Bioeng*, (2016). In this experiment, the payload was a bacteriophage P1 Cre recombinase with a SV40 Nuclear localization sequence recombinant protein (NEB, Cat #M0298M). The protein loaded fusosomes were then used to treat and show payload delivery to recipient HEK-293T cells engineered to express a "LoxP-GFP-stop-LoxP-RFP" cassette under control of the CMV promoter.

Briefly, approximately $10^6$ fusosomes or control particles (non-fusogenic fusosomes) corresponding to 20 µL of a standard VSV-G fusosome preparation were mixed with 5 µL protein (NEB #M0298M) and incubated at room temperature for 30 minutes. The fusosome (or control particle)/protein mixture was then sonicated for 30 seconds at room temperature using a water bath sonicator (Brason model #1510R-DTH) operated at 40 kHz. The mixture was then placed on ice for one minute followed by a second round of sonication at 40 kHz for 30 seconds. The mixture was then centrifuged at 16,000 g for 5 minutes at 4° C. to pellet the fusosomes containing nucleic acid. The supernatant containing unincorporated protein was removed and the pellet was resuspended in 30 µL phosphate-buffered saline. After protein loading, the loaded fusosomes/control particles were kept on ice before use.

The recipient HEK-293T cells engineered to express a "LoxP-GFP-stop-LoxP-RFP" cassette were plated 30,000 cells/well into a black, clear-bottom 96-well plate in complete media. Twenty-four hours after plating the recipient cells, the protein loaded fusosomes were applied to LoxP-GFP-stop-LoxP-RFP HEK-293T cells. Recipient cells were treated with 8 L of protein loaded fusosomes or 8 µL of protein loaded control particles (non-fusogenic fusosomes) and incubated for 24 hrs at 37° C. and 5% $CO_2$. Twenty-four hours later cell plates were incubated at 37° C. and 5% $CO_2$ for 30 min with 1 µg/mL Hoechst 33342 diluted in complete media before being imaged using an automated microscope (www.biotek.com/products/imaging-microscopy-automated-cell-imagers/lionheart-fx-automated-live-cell-imager/). The Hoechst fluorescence of the recipient cell was imaged using the 405 nm LED and BFP filter cube The GFP fluorescence of the recipient cell was imaged using the 488 nm LED and GFP filter cube. RFP fluorescence of the recipient cell was imaged using the 523 nm LED and RFP filter cube. Images of cells in the well were acquired by first establishing the LED intensity and integration times on a positive-control well containing recipient cells treated with Cre recombinase gesicles (Takara, Cat #631449).

Acquisition settings were set so that RFP, GFP and RFP intensities are at the maximum pixel intensity values but not saturated. The wells of interest were then imaged using the established settings. Focus was set on each well by autofocusing on the BFP channel and then using the established focal plane for the GFP and RFP channels. Analysis of RFP-positive cells was performed with Gen5 software provided with automated fluorescent microscope (see www.biotek.com/products/software-robotics-software/gen5-microplate-reader-and-imager-software/).

The images were pre-processed using a rolling ball background subtraction algorithm with a 60 µm width. Cells with GFP intensity significantly above background intensities were thresholded and areas too small or large to be GFP-positive cells were excluded. The same analysis steps were applied to the RFP channel. The number of RFP-positive cells (recipient cells receiving Cre protein) was then divided by the sum of the GFP positive cells (total recipient cells) to quantify the % of cells that received Cre protein delivery, which describes the amount of recipient cells receiving Cre protein payload that was loaded into fusosomes via sonication.

Figure 35:
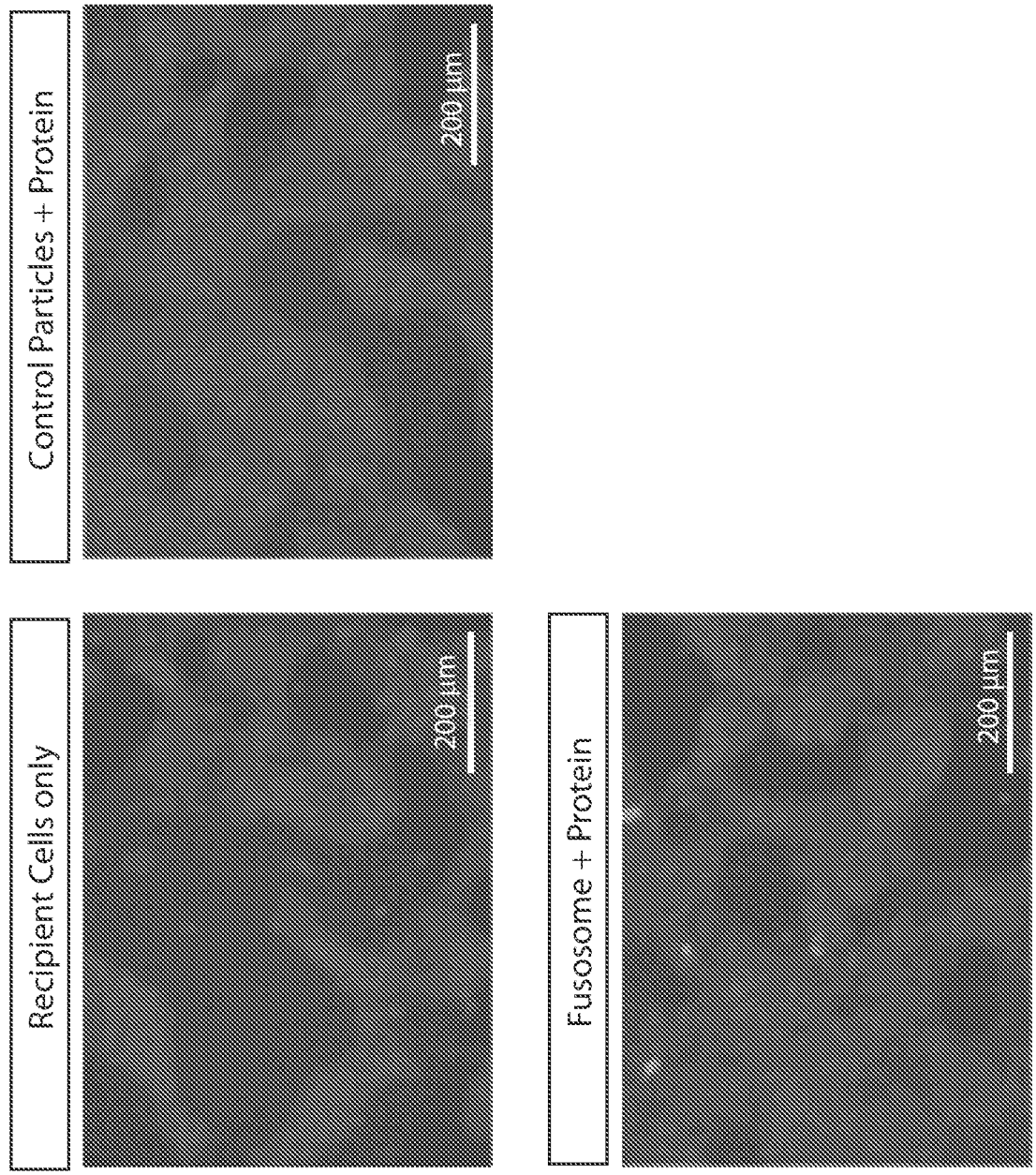
FIG. 35 is a series of images showing in vitro delivery of protein to recipient cells via fusosomes.

With this assay the Cre protein loaded fusosomes showed a statistically significant level of Cre protein delivery corresponding to 27.4±6.8% RFP-positive cells of total GFP-positive recipient cells (FIG. 35). Untreated recipient cells or cells treated with fusosome alone, or protein loaded control particles, did not show any appreciable RFP-positive cells.

Example 142: In Vivo Delivery of Protein (BiVs-Cre Gesicles)

This example describes the delivery of therapeutic agents to the muscle by fusosomes. Fusosomes were derived using methods described herein and were loaded with CRE-recombinase protein.

The fusosomes were delivered into Loxp Luciferase (Jackson Laboratory, 005125) mice via intramuscular (IM) administration to the tibalis anterior. The solution was handled in a manner to ensure continued sterility of the contents. Anesthesia was induced in an induction chamber (~4% isoflurane, to effect) and maintained via nose cone (~2% isoflurane, to effect) with animals placed on a warmed (35° C.) surgical table. The skin over the mid belly of the tibialis anterior (TA) muscle was prepared by depilating the area (Nair Hair Remover cream for 45 seconds, followed by cleaning the area with 70% ethanol). Using a tuberculin syringe, 50 µL of fusosome solution (8.5e8±1.4e8 particles/µL, mean (SEM)) was injected intramuscularly into the belly of the TA. Upon completion of injection, the syringe was removed, and pressure was applied to the injection site. The contralateral leg was not treated.

After fusion, CRE protein translocated to the nucleus to carry out recombination, which resulted in the constitutive expression of luciferase. Intraperitoneal administration of D-luciferin (Perkin Elmer, 150 mg/kg) enabled the detection of luciferase expression via in vivo bioluminescent imaging. The animal was placed into an in vivo bioluminescent imaging chamber (Perkin Elmer) which houses a cone anesthetizer (isoflurane) to prevent animal motion. Photon collection was carried out between 3-35 minutes post-injection to observe the maximum bioluminescent signal due to D-luciferin pharmacokinetic clearance. Maximum radiance is recorded in photons/sec/cm$^2$/radians. Total flux, which integrates the radiance over the area, is quantified using a region of interest (ROI) tool within the Living Image Software (Perkin Elmer) and reported in photons/sec. The fusosomes treated tibialis anterior muscle tissue was monitored specifically for radiance measurements compared to negative controls (negative control unthreaded (chest), contralateral hindlimb, and stage). Measurements were carried out on day 14 post-injection to observe firefly luciferase presence.

Figure 36A:
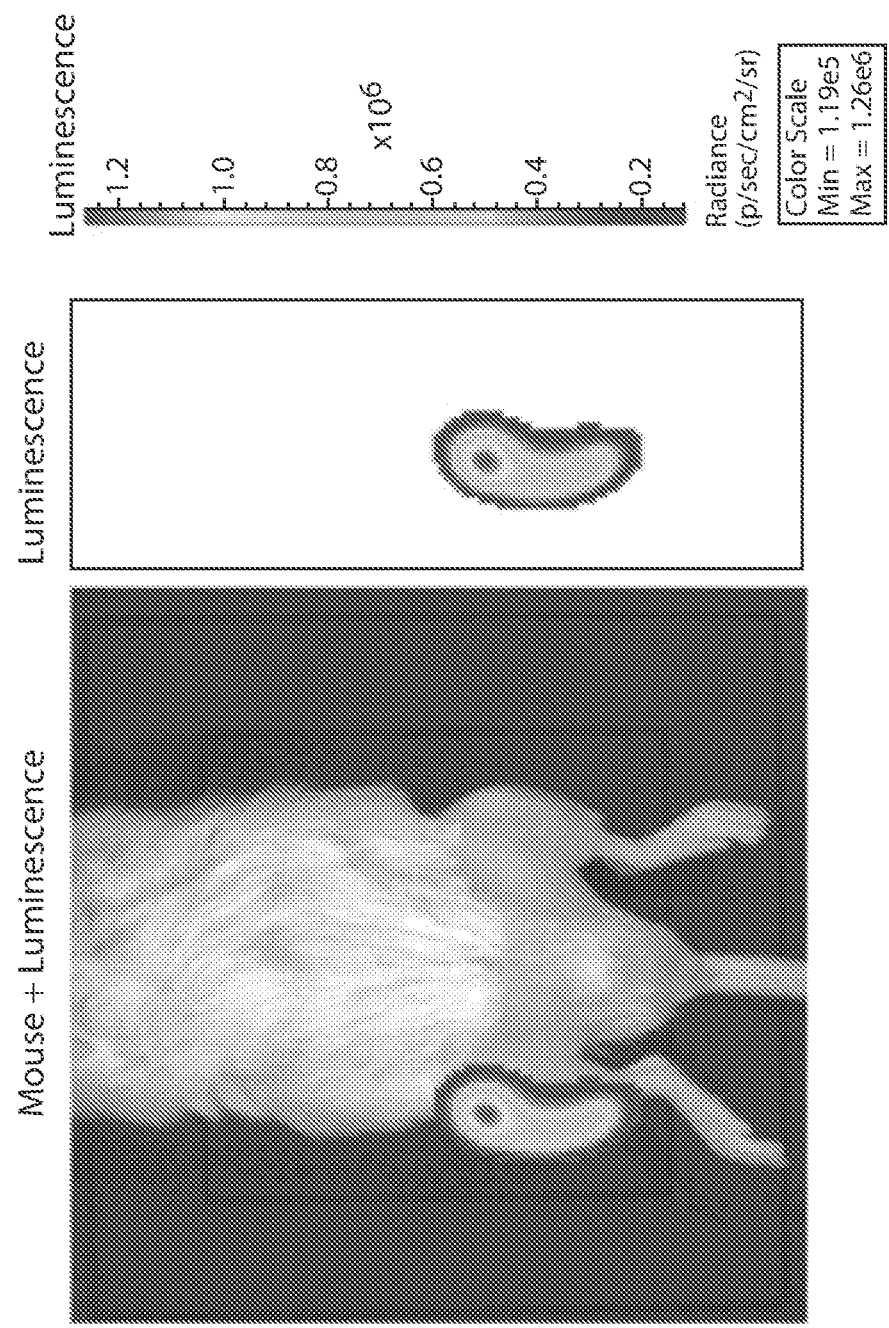
FIGS. 36A-36B is a series of diagrams showing in vivo delivery of Cre recombinase protein into the tissues of mice using fusosomes. (A) From left to right; Luminescent signal of ventrally exposed treated TA and image of mouse, and luminescent signal alone. (B) Total Flux of treated versus untreated leg, background (mouse chest), and stage background; y-scale is on log 10 scale.
Figure 36B:
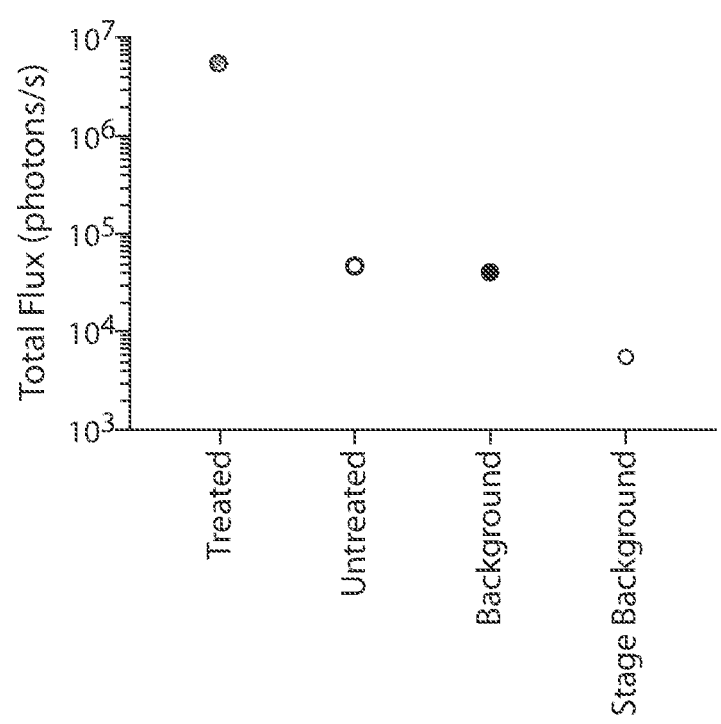

Evidence of protein (Cre recombinase) delivery by fusosomes was detected by bioluminescent imaging in the recipient tissue of the animal, as shown in FIGS. 36A-36B.

Example 143: Sonication-Mediated Loading of Nucleic Acid in Fusosomes

Fusosomes were generated by the standard procedure of harvesting and preparing fusosomes produced from HEK-293T cells expressing the envelope glycoprotein G from vesicular stomatitis virus (VSV-G) on the cell surface and expressing Cre recombinase protein as described herein. A nucleic acid payload was then loaded into the VSV-G fusosomes by sonication, as outlined in Lamichhane, T N, et al., Oncogene Knockdown via Active Loading of Small RNAs into Extracellular Vesicles by Sonication. *Cell Mol Bioeng*, (2016). In this experiment the nucleic acid payload was a DNA plasmid encoding the fluorescent protein miRFP670. The nucleic acid-loaded fusosomes were then used to treat and show payload delivery to recipient HEK-293T cells engineered to express a "Loxp-BFP-stop-Loxp-Clover" cassette under CMV promoter.

Briefly, approximately $10^6$ fusosomes corresponding to 50 L of a standard VSV-G fusosome preparation were mixed with 10 µg nucleic acid and incubated at room temperature for 30 minutes. The fusosome/nucleic acid mixture was then sonicated for 30 seconds at room temperature using a water bath sonicator (Brason model #1510R-DTH) operated at 40 kHz. The mixture was then placed on ice for one minute followed by a second round of sonication at 40 kHz for 30 seconds. The mixture was then centrifuged at 16,000 g for 5 minutes at 4° C. to pellet the fusosomes containing nucleic acid. The supernatant containing unincorporated nucleic acid was removed and the pellet was resuspended in phosphate-buffered saline. After DNA loading, the loaded fusosomes were kept on ice before use.

The recipient HEK-293T cells engineered to express a "Loxp-BFP-stop-Loxp-Clover" cassette were plated 30,000 cells/well into a black, clear-bottom 96-well plate. Four-six hours after plating the recipient cells, the DNA loaded fusosomes were applied to the target or non-target recipient cells in DMEM media. Recipient cells were treated with 4 µL of DNA loaded fusosomes and incubated for 48 hours at 37° C. and 5% $CO_2$. Cell plates were imaged using an automated microscope (www.biotek. com/products/imaging-microscopy-automated-cell-imagers/lionheart-fx-automated-live-cell-imager/). The BFP fluorescence of the recipient cell was imaged using the 405 nm LED and BFP filter cube. Clover fluorescence of the recipient cell was imaged using the 465 nm LED and GFP filter cube, while miRFP670 was imaged using 623 nm LED and Cy5 filter cube. Images of cell wells were acquired by first establishing the LED intensity and integration times on a positive-control well; i.e., recipient cells treated with adenovirus coding for Cre recombinase instead of fusosomes.

Acquisition settings were set so that BFP, Clover, and miRFP670 intensities are at the maximum pixel intensity values but not saturated. The wells of interest were then imaged using the established settings. Focus was set on each well by autofocusing on the BFP channel and then using the established focal plane for the Clover and miRFP670 channels. Analysis of miRFP670-positive cells was performed with Gen5 software provided with automated fluorescent microscope (see www.biotek. com/products/software-robotics-software/gen5-microplate-reader-and-imager-software/).

The images were pre-processed using a rolling ball background subtraction algorithm with a 60 µm width. Cells with BFP intensity significantly above background intensities were thresholded and areas too small or large to be BFP-positive cells were excluded. The same analysis steps were applied to the Clover and miRFP670 channels. The number of miRFP670-positive cells (recipient cells receiving miRFP670 DNA plasmid) was then divided by the sum of the BFP-positive cells (total recipient cells) to quantify the percentage miRFP670 DNA delivery, which describes the amount of recipient cells receiving miRFP670 payload that was loaded into fusosomes via sonication.

Figure 37:
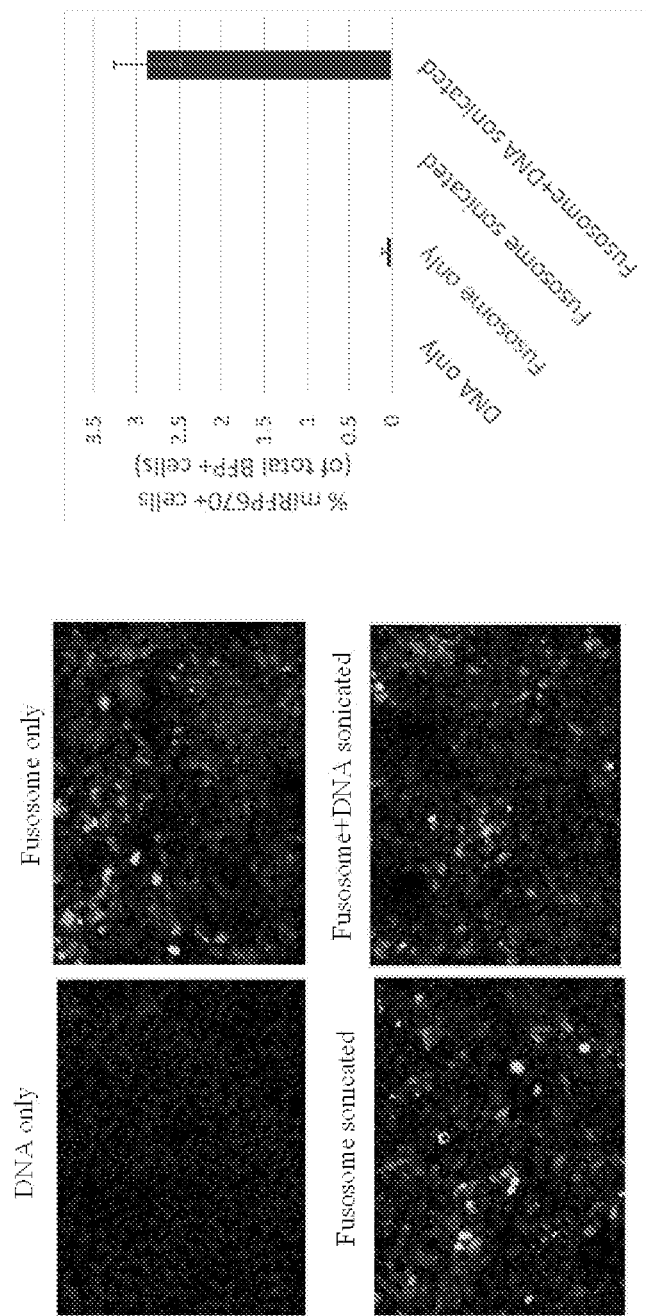
FIG. 37 is a series of diagrams showing delivery of miRFP670 DNA to recipient cells via fusosomes loaded by sonication.

With this assay the miRFP670 DNA loaded fusosome showed an observable level of miRFP670 delivery corresponding to 2.9±0.4% miRFP670-positive cells of total BFP-positive recipient cells (FIG. 37). Recipient cells treated with miRFP670 DNA alone, fusosome alone, or sonicated fusosome alone did not show any appreciable miRFP670-positive cells (defined as <0.5%).

Example 144: Sonication-Mediated Loading of Protein in Fusosomes

Fusosomes were generated by the standard procedure of harvesting and preparing fusosomes produced from HEK-293T cells expressing the envelope glycoprotein G from vesicular stomatitis virus (VSV-G) on the cell surface and expressing Cre recombinase protein as described herein. A protein payload was then loaded into the VSV-G fusosomes by sonication, as outlined in Lamichhane, T N, et al., Oncogene Knockdown via Active Loading of Small RNAs into Extracellular Vesicles by Sonication. *Cell Mol Bioeng*, (2016). In this experiment the protein payload was a bovine serum albumin protein conjugated to the fluorescent dye Alexa Fluor 647 (BSA-AF647; ThermoFisher Cat #A34785). The protein-loaded fusosomes were then used to treat and show payload delivery to recipient HEK-293T cells engineered to express a "Loxp-BFP-stop-Loxp-Clover" cassette under CMV promoter.

Briefly, approximately $10^6$ fusosomes corresponding to 50 µL of a standard VSV-G fusosome preparation were mixed with 10 µg BSA-AF647 and incubated at room temperature for 30 minutes. The fusosome/protein mixture was then sonicated for 30 seconds at room temperature using a water bath sonicator (Brason model #1510R-DTH) operated at 40 kHz. The mixture was then placed on ice for one minute followed by a second round of sonication at 40 kHz for 30 seconds. The mixture was then centrifuged at 16,000 g for 5 minutes at 4° C. to pellet the fusosomes containing BSA-AF647. The supernatant containing unincorporated protein was removed and the pellet was resuspended in phosphate-buffered saline. After protein loading, the loaded fusosomes were kept on ice before use.

The recipient HEK-293T cells engineered to express a "Loxp-BFP-stop-Loxp-Clover" cassette were plated 30,000 cells/well into a black, clear-bottom 96-well plate. Four-six hours after plating the recipient cells, the BSA-AF647 loaded fusosomes were applied to the target or non-target recipient cells in DMEM media. Recipient cells were treated with 4 µL of BSA-AF647 loaded fusosomes and incubated for 72 hrs at 37° C. and 5% $CO_2$. Cell plates were imaged using an automated microscope (www.biotek.com/products/imaging-microscopy-automated-cell-imagers/lion-heart-fx-automated-live-cell-imager/). The BFP fluorescence of the recipient cell was imaged using the 405 nm LED and BFP filter cube. Clover fluorescence of the recipient cell was imaged using the 465 nm LED and GFP filter cube, while BSA-AF647 was imaged using 623 nm LED and Cy5 filter cube. Images of cell wells were acquired by first establishing the LED intensity and integration times on a positive-control well; i.e., recipient cells treated with adenovirus coding for Cre recombinase instead of fusosomes.

Acquisition settings were set so that BFP, Clover, and BSA-AF647 intensities are at the maximum pixel intensity values but not saturated. The wells of interest were then imaged using the established settings. Focus was set on each well by autofocusing on the BFP channel and then using the established focal plane for the Clover and BSA-AF647 channels. Analysis of BSA-AF647-positive cells was performed with Gen5 software provided with automated fluorescent microscope (see www.biotek.com/products/software-robotics-software/gen5-microplate-reader-and-imager-software/).

The images were pre-processed using a rolling ball background subtraction algorithm with a 60 um width. Cells with BFP intensity significantly above background intensities were thresholded and areas too small or large to be BFP-positive cells were excluded. The same analysis steps were applied to the Clover and BSA-AF647 channels. The number of BSA-AF647-positive cells (recipient cells receiving BSA-AF647 protein) was then divided by the sum of the BFP-positive cells (total recipient cells) to quantify the percentage of BSA-AF647 delivery, which describes the amount of recipient cells receiving BSA-AF647 protein payload that was loaded into fusosomes via sonication.

Figure 38:
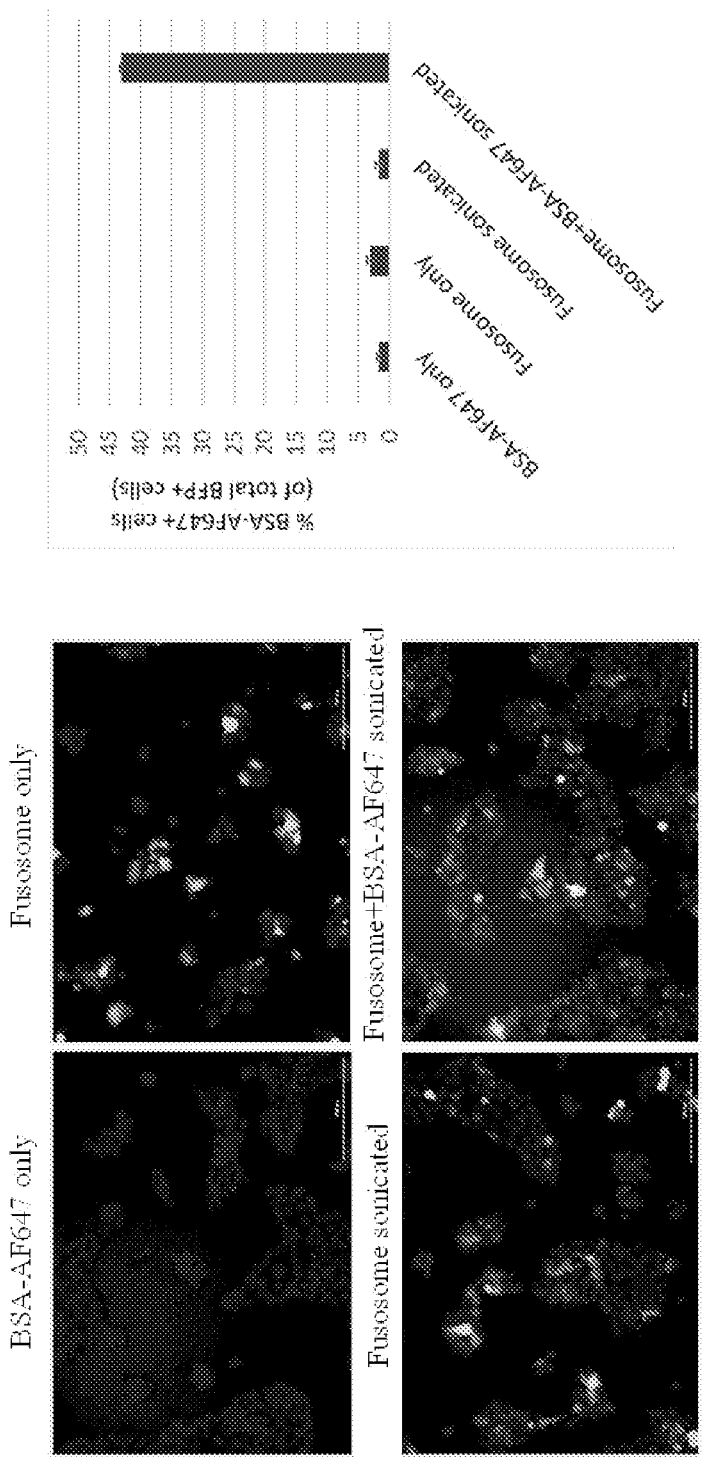
FIG. 38 is a series of diagrams showing delivery of BSA-AF647 protein to recipient cells via fusosomes loaded by sonication.

With this assay the BSA-AF647 loaded fusosome showed an observable level of BSA-AF647 delivery corresponding to 43.2±0.2% BSA-AF647-positive cells of total BFP-positive recipient cells (FIG. 38). Recipient cells treated with BSA-AF647 protein alone, fusosome alone, or sonicated fusosome alone did not show any appreciable BSA-AF647-positive cells (defined as less than 5%).

Example 145: Generating and Isolating Fusosome Ghosts

This example describes the generation and isolation of fusosome ghosts via hypotonic treatment and centrifugation. This is one of the methods by which fusosomes may be produced.

Fusosomes ghosts were generated from HEK-293T cells expressing the envelope glycoprotein G from vesicular stomatitis virus (VSV-G), as described herein. The fusosome ghosts were generated and the analyzed by fluorescent Nanoparticle Tracking Analysis (fNTA).

Fusosomes were prepared as follows. $9.2 \times 10^6$ HEK-293T were reverse transfected using a polymeric transfection reagent with 10 µg of the pcDNA3.1 expression plasmid containing the open reading frame for VSVg and 15 µg of the pcDNA3.1 empty expression plasmid in 7.5 mL of complete media (DMEM+10% FBS+1× Pen/Strep) in a 100-mm collagen coated dish. To produce fusosome ghosts, 24 hours after transfection the cells were washed with phosphate-buffered saline (PBS), dissociated with TryPLE, centrifuged 500×g, 5 mins and re-suspended in media. $1 \times 10^7$ cells were re-suspended in 7 mL of PBS and pelleted via centrifugation at 500×g for 5 min. The cells were re-suspended in cold TM buffer (10 mM Tris, 1.6 mM $MgCl_2$, pH 7.4) and sonicated for 5 sec at 27% amplitude (ColeParmer Cat #CPX130). Immediately after sonication, TM buffer containing sucrose (60% w/v) was added to the solution at a final concentration of 0.25M sucrose. The solution was then centrifuged at 6,000×g, 4° C. for 15 min. The supernatant was discarded and the pellet was washed twice in 0.25M sucrose TM buffer, pH 7.4. The pellet was then re-suspended in 0.25M sucrose TM buffer, pH 7.4 and the re-suspended pellet was then sonicated for 5 seconds at 27% amplitude (ColeParmer Cat #CPX130). The solution was then centrifuged at 6,000×g, 4° C. for 15 min. The supernatant was discarded and the pellet was washed twice in 0.25M sucrose TM buffer, pH 7.4. The pellet was then re-suspended in 0.25M sucrose TM buffer, pH 7.4 and the re-suspended pellet was then sonicated for 2 min at 27% amplitude (ColeParmer Cat #CPX130). The solution was then centrifuged at 800×g, 4° C. for 15 min and then filtered through a 0.45 m syringe filter.

Figure 39:
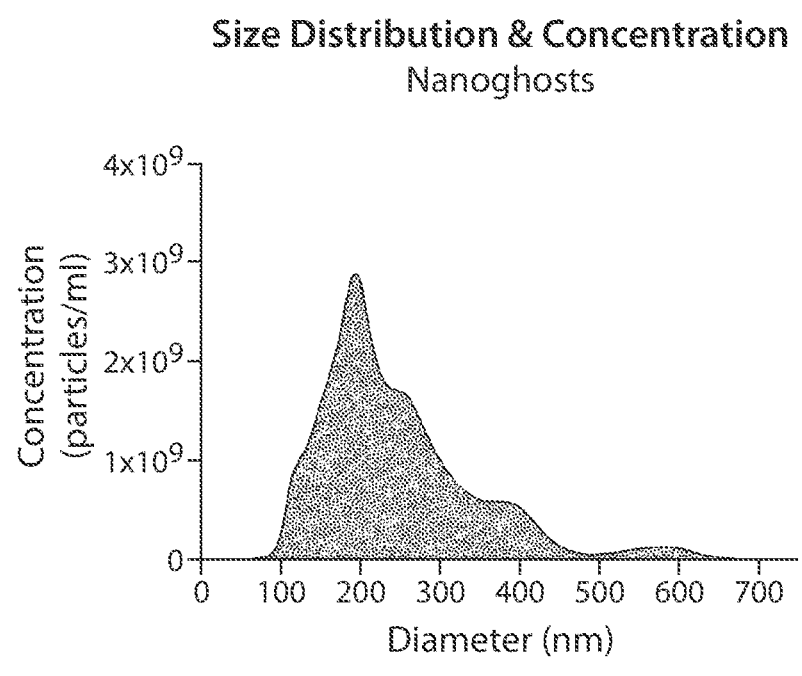
FIG. 39 is a histogram showing the size distribution and concentration of fusosome ghosts.

Finally, to concentrate the fusosome ghosts, the solution was then ultra-centrifuged at 150,000×g, 4° C. for 45 min and the pellet containing the fusosome ghosts was resuspended in PBS. To analyze fusosome ghost composition via fNTA, fusosome ghosts were incubated with 1:1 with CellMask Orange (ThermoFisher) and then diluted 1:1000 before loading into the tracking machine and analyzed per manufacturer instructions. The size distribution of the fusosome ghosts is shown in FIG. 39. Fusosomes were successfully generated by the preparation of ghosts from HEK-293T cells expressing VSV-G.

Example 146: Lack of Translational Activity in Fusosomes

Fusosomes were generated by the standard procedure of harvesting and preparing fusosomes produced from HEK-293T cells expressing the envelope glycoprotein G from vesicular stomatitis virus (VSV-G) on the cell surface, as described herein. Control particles (non-fusogenic fusosomes) were produced from HEK-293T cells reverse transiently transfected with pcDNA3.1 empty vector. Translational activity of fusosomes was then compared to parent cells, e.g., source cells, used for fusosome generation by using the Click-iT EdU Imaging kit (ThermoFisher).

Briefly, approximately $3 \times 10^6$ fusosomes corresponding to 60 µL of a standard VSV-G fusosome preparation and $1 \times 10^6$ parent cells used to generate the fusosomes were plated in, in triplicate, 1 mL of complete media in a 6 well low-attachment multi-well plate in complete containing 1 mM fluorescent-taggable alkyne-nucleoside EdU for 4 hr at 37°

C. and 5% $CO_2$. For the negative control, $3 \times 10^6$ fusosomes were plated into a 6 well low-attachment multi-well plate in complete media but with no alkyne-nucleoside EdU. After the 4-hour incubation, the samples were processed following the manufacturer's instructions (ThermoFisher Scientific). Briefly, the cell and fusosome samples including the negative controls were washed thrice with 1×PBS buffer and resuspended in 1×PBS buffer and analyzed by flow cytometry (Attune, ThermoFisher) using a 638 nm laser for excitation, and 670+/−14 nm filter emission (Table M). Attune NxT software was used for acquisition and FlowJo used analysis. For data acquisition the FSC and SSC channels were set on linear axis to determine a population representative of the cells or fusosomes. This population was then gated and events only inside this gate were used to display events in the 670+/−14 nm emission channel on a logarithmic scale. A minimum of 10,000 events within the cells or fusosomes gate was collected for in each condition.

Figure 40:
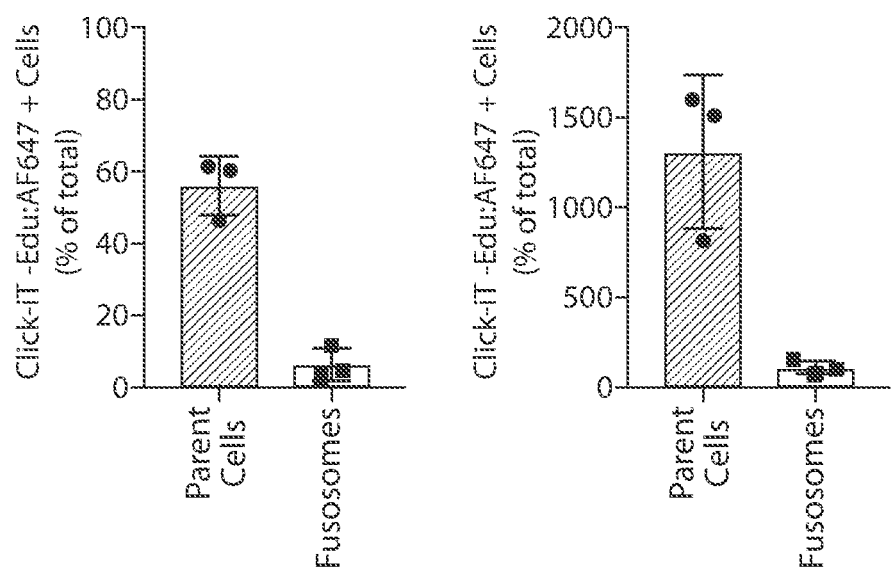
FIG. 40 is a series of graphs showing Edu:647 positive events and median fluorescence intensity of AF647 of parental cells and fusosomes.

For data analysis, the FSC and SSC channels were set on linear axis to determine a population representative of the cells or fusosomes. This population was then gated and events only inside this gate were used to display events in the 670+/−14 nm emission channel on a logarithmic scale. The negative control 670+/−14 nm emission was used to determine where to place the gate on the histogram such that the gate included less than 1% positive. Using analysis criteria listed above, parent cells demonstrated 56.17%±8.13 Edu:647 events, as a surrogate measure of translational activity by including Edu in newly synthesized DNA, whereas fusosomes demonstrated 6.23%±4.65 AF488 events (FIG. 40, left panel). The median fluorescence intensity of AF647, a measure of Edu incorporation, and therefore a relative measure of newly synthesized DNA, was 1311±426.2 events for parental cells and 116.6±40.74 for fusosomes (FIG. 40, right panel). This demonstrates that fusosomes lack translational activity relative to parental cells.

TABLE M

Flow cytometer settings

| Dye | Attune Laser/Filter | Laser Wavelength | Emission Filter (nm) |
|---|---|---|---|
| AF47 | RL1 | 638 | 670/14 |

Example 147: Measuring Ability to Polymerize Actin for Mobility

Fusosomes were generated by the standard procedure of harvesting and preparing fusosomes produced from HEK-293T cells expressing the envelope glycoprotein G from vesicular stomatitis virus (VSV-G) on the cell surface, as described herein. Control particles (non-fusogenic fusosomes) were produced from HEK-293T cells reverse transiently transfected with pcDNA3.1 empty vector. Fusosomes and parental cells were then assayed for their ability to polymerize actin (over time) using a rhodamine phalloidin-flow cytometry assay and Tubulin ELISA. Briefly, approximately $1 \times 10^6$ fusosomes corresponding to 60 µL of a standard VSV-G fusosome preparation and $1 \times 10^5$ parent cells used to generate the fusosomes were plated in 1 mL of complete media in a 96 well low-attachment multi-well plate in complete and incubated at 37° C. and 5% $CO_2$. Samples were taken periodically, at 3 hr, 5 hr and 24 hr post plating. Samples were centrifuged at 21,000×g for 10 mins, resuspended in 200 µL 4% (v/v) PFA in phosphate buffered saline for 10 mins, washed with 1 mL of phosphate buffered saline, centrifuged at 21,000×g for 10 mins, washed again and stored at 4° C. until further use.

For rhoamine-phalloidin staining, samples were centrifuged at 21,000×g for 10 mins, and incubated in 100 µL of 0.1% (v/v) Triton X-100 in phosphate buffered saline for 20 mins. Following the 20-min incubation, an additional 100 µL of 0.1% (v/v) Triton X-100 in phosphate buffered saline containing 165 µM rhodamine-phalloidin was added to the sample and pipette mixed, negative control received and additional 100 µL of 100 µL of 0.1% (v/v) Triton X-100 in phosphate buffered saline only. Samples were incubated for 45 mins before being washed with 1 mL of phosphate buffered saline, centrifuged at 21,000×g for 10 mins, washed again and re-suspended in 300 µL of phosphate buffered saline and analyzed by flow cytometry (Attune, ThermoFisher) using a 561 nm laser for excitation, and 585+/−16 nm filter emission, as shown in the table below:

Flow Cytometer Settings

| Dye | Attune Laser/Filter | Laser Wavelength | Emission Filter (nm) |
|---|---|---|---|
| AF47 | YL1 | 585 | 585/16 |

Figure 14D:
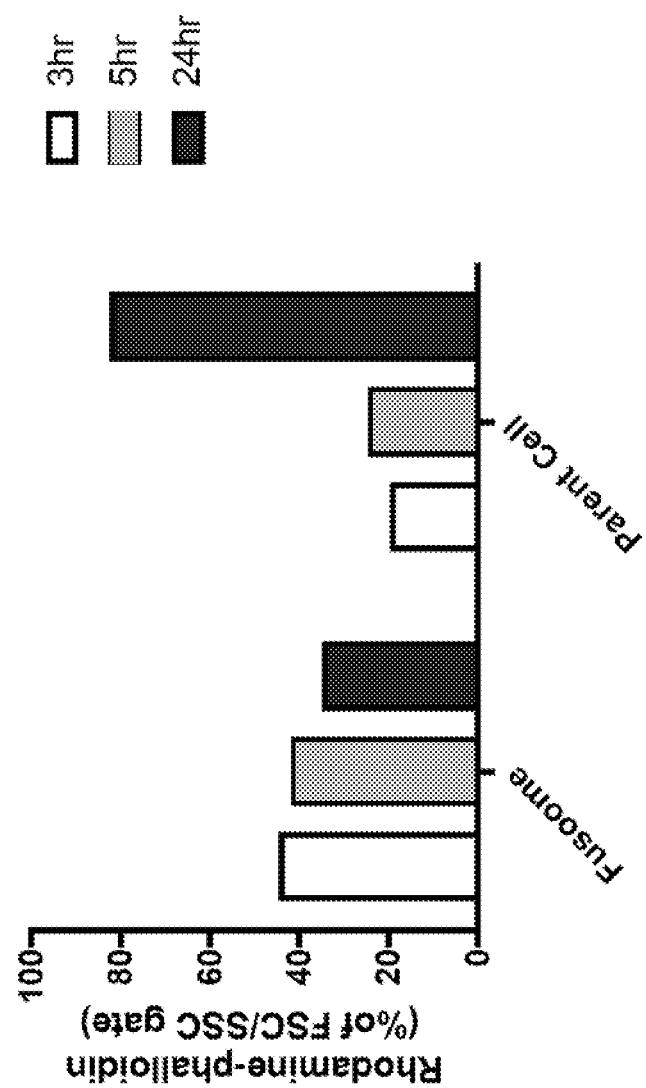
FIG. 14D is a graph showing the capacity for fusosomes and parent cells to polymerase actin over a period of 3, 5, and 24 hours.

Attune NxT software was used for acquisition and FlowJo used analysis. For data acquisition the FSC and SSC channels were set on linear axis to determine a population representative of the cells or fusosomes. This population was then gated and events only inside this gate were used to display events in the 585+/−16 nm emission channel on a logarithmic scale. A minimum of 10,000 events within the cells or fusosomes gate was collected for in each condition. For data analysis, the FSC and SSC channels were set on linear axis to determine a population representative of the cells or fusosomes. This population was then gated and events only inside this gate were used to display events in the 585+/−16 nm emission channel on a logarithmic scale. The negative control 585+/−16 nm emission was used to determine where to place the gate on the histogram such that it was less the gate include less than 1% positive. Using analysis criteria listed above parent cells demonstrated 19.9%, 24.8% and 82.5% rhodamine-phalloidin positive events, at the 3 hr, 5 hr and 24 hr time-points, respectively. The fusosomes were 44.6%, 41.9% and 34.9% rhodamine-phalloidin at the 3 hr, 5 hr and 24 hr time-points, respectively (FIG. 14D). This example demonstrates that fusosomes do not increase in amount of actin over time, whereas the parent cells do.

Example 148: Immunogenicity of Recipient Cell Compositions

1. IgG and IgM Response

This Example describes quantification of antibody titers against recipient cells (cells that have fused with fusosomes) using flow cytometry. A measure of the immunogenicity of recipient cells is the antibody response. Antibodies that recognize recipient cells can bind in a manner that can limit cell activity or longevity. In an embodiment, recipient cells will not be targeted by an antibody response, or an antibody response will be below a reference level.

In this Example, anti-recipient cell antibody titers in a subject (e.g., human, rat, or monkey) are tested. In addition, the protocol may be adapted to any cell type for which suitable surface markers exist. In this example, the target recipient cell is a CD3+ cell.

Mice are treated with fusosomes produced via any of the methods described in this application or with PBS (negative control) daily for 5 days. 28 days following the final treatment, peripheral blood is collected from mice that received fusosomes and mice that received PBS treatment. Blood is collected into 1 ml PBS containing 5 µM EDTA and mixed immediately to prevent clotting. The tubes are kept on ice and red blood cells are removed using a buffered ammonium chloride (ACK) solution. Cells are stained with a murine CD3-FITC antibody (Thermo Fisher Catalog #: 11-0032-82), at 4° C. for 30 minutes in the dark, after being blocked with bovine serum albumin for 10 minutes. After being washed two times with PBS, cells are analyzed on a LSR II (BD Biosciences, San Jose, Calif.) with 488 nm laser excitation and emission collected at 530+/−30 nm running the FACSDiva™ software (BD Biosciences, San Jose, Calif.). CD3+ cells are sorted.

The sorted CD3+ cells are then stained with IgM antibodies by incubation of the reaction mixture with PE-conjugated goat antibodies specific for the Fc portion of mouse IgM (BD Bioscience) at 4° C. for 45 min. Notably, anti-mouse IgG1 or IgG2 secondary antibodies may also be used. Cells from all groups are washed twice with PBS containing 2% FCS and then analyzed on a FACS system (BD Biosciences). Fluorescence data are collected by use of logarithmic amplification and expressed as mean fluorescent intensity. The mean fluorescence intensity is calculated for the sorted CD3 cells from mice treated with fusosomes and the mice treated with PBS.

A low mean fluorescence intensity is indicative of a low humoral response against the recipient cells. Mice treated with PBS are expected to have low mean fluorescence intensity. In an embodiment, the mean fluorescence intensity will be similar for recipient cells from mice treated with fusosomes and mice treated with PBS.

2. Macrophage Phagocytosis

This Example describes quantification of macrophage response against recipient cells with a phagocytosis assay.

A measure of the immunogenicity of recipient cells is the macrophage response. Macrophages engage in phagocytosis, engulfing cells and enabling the sequestration and destruction of foreign invaders, like bacteria or dead cells. In some embodiments, phagocytosis of recipient cells by macrophages would reduce their activity.

In an embodiment, recipient cells are not targeted by macrophages. In this Example, the macrophage response against recipient cells in a subject is tested. In addition, the protocol may be adapted to any cell type for which suitable surface markers exist. In this example, the target recipient cell is a CD3+ cell.

Mice are treated with fusosomes produced via any of the methods described in this application or with PBS (negative control) daily for 5 days. 28 days following the final treatment, peripheral blood is collected from mice that received fusosomes and mice that received PBS treatment. Blood is collected into 1 ml PBS containing 5 µM EDTA and mixed immediately to prevent clotting. The tubes are kept on ice and red blood cells are removed using a buffered ammonium chloride (ACK) solution.

Cells are stained with a murine CD3-FITC antibody (Thermo Fisher Catalog #: 11-0032-82), at 4° C. for 30 minutes in the dark, after being blocked with bovine serum albumin for 10 minutes. After being washed two times with PBS, cells are analyzed on a LSR II (BD Biosciences, San Jose, Calif.) with 488 nm laser excitation and emission collected at 530+/−30 nm running the FACSDiva™ software (BD Biosciences, San Jose, Calif.). CD3+ cells are then sorted.

A phagocytosis assay is run to assess macrophage mediated immune clearance according to the following protocol. Macrophages are plated immediately after harvest in confocal glass bottom dishes. Macrophages are incubated in DMEM+10% FBS+1% P/S for 1 h to attach. An appropriate number of sorted and FITC-stained CD3+ cells derived from mice that received fusosomes and PBS are added to the macrophages as indicated in the protocol, and are incubated for 2 h, e.g., as described in tools.thermofisher.com/content/sfs/manuals/mp06694.pdf.

After 2 h, the dish is gently washed and intracellular fluorescence is examined. To identify macrophages, cells are first incubated with Fc-receptor blocking antibody (eBioscence cat. no. 14-0161-86, clone 93) for 15 min on ice to block the binding of labeled mAbs to Fc receptors, which are abundantly expressed on macrophages. Following this step anti-F4/80-PE (ThermoFisher cat. No. 12-4801-82, clone BM8) and anti-CD1 b-PerCP-Cy5.5 (BD Biosciences cat. No. 550993, clone M1/70) conjugated antibodies are added to stain macrophage surface antigens. Cells are incubated for 30 min in the dark at 4 C followed by centrifugation and washing in PBS. The cells are then resuspended in PBS. Flow cytometry of samples is then performed and macrophages are identified via positive fluorescence signal for F4/80-PE and CD11b-PerCP-Cy5.5 using 533 nm and 647 nm laser excitation, respectively. After gating for macrophages, intracellular fluorescence emitted by engulfed recipient cells is assessed by 488 nm laser excitation. The number of phagocytotic positive macrophage is quantified using imaging software. The data is expressed as the phagocytic index=(total number of engulfed cells/total number of counted macrophages)×(number of macrophages containing engulfed cells/total number of counted macrophages)×100.

A low phagocytic index is indicative of low phagocytosis and targeting by macrophages. Mice treated with PBS are expected to have a low phagocytic index. In an embodiment, the phagocytic index will be similar for recipient cells derived from mice treated with fusosomes and mice treated with PBS.

3. Cytotoxicity Measured by PBMC Lysis

This Example describes quantification of a PBMC response against recipient cells with a cell lysis assay.

A measure of the immunogenicity of recipient cells is the PBMC response. In an embodiment, cytotoxicity mediated cell lysis of recipient cells by PBMCs is a measure of immunogenicity, as lysis will reduce, e.g., inhibit or stop, the activity of a fusosome.

In an embodiment, recipient cells do not elicit a PBMC response. In this Example, the PBMC response against recipient cells in a subject is tested.

In addition, the protocol may be adapted to any cell type for which suitable surface markers exist. In this example, the target recipient cell is a CD3+ cell.

Mice are treated with fusosomes produced via any of the methods described in this application or with PBS (negative control) daily for 5 days. 28 days following the final treatment, peripheral blood is collected from mice that received fusosomes and mice that received PBS treatment. Blood is collected into 1 ml PBS containing 5 µM EDTA and mixed immediately to prevent clotting. The tubes are kept on ice and red blood cells are removed using a buffered ammonium chloride (ACK) solution. Cells are stained with a murine CD3:APC-Cy7 antibody (Biolgend Catalog #:

100330) or an isotype control APC-Cy7 (IC:APC-Cy7) antibody (Biolgend Catalog #: 400230) at 4° C. for 30 minutes in the dark, after being Fc blocked (Biolgend Catalog #: 101319) in cell staining buffer (Biolgend Catalog #: 420201) for 10 minutes. After being washed two times with PBS, cells are analyzed on a FACS Aria (BD Biosciences, San Jose, Calif.) with 640 nm laser excitation and emission collected at 780−/+60 nm running the FACSDiva™ software (BD Biosciences, San Jose, Calif.) to set negative gates using the isotype control APC-Cy7 antibody labelled cells and then APC-Cy7 positive cells are sorted and collected. Sorted CD3+ cells are then labelled with either CellMask™ Green Plasma membrane Stain (CMG, ThermoFisher Catalog #: C37608) or DMSO as the negative control.

7 days prior to the isolation of CD3+ cells from the mice treated with fusomes or PBS, PBMCs are isolated from mice treated with fusomes or PBS according to the methods in Crop et al. Cell transplantation (20):1547-1559; 2011 and simulated in the presence of IL-2 recombinant mouse protein (R&D Systems Catalog #: 402-ML-020) and CD3/CD28 beads (ThermoFisher Catalog #: 11456D) in a round bottom 96 well plate for 7 days at 37 C. At day 7, the stimulated PBMCs are co-incubated with CD3+/CMG+ or CD3+/DMSO control cells for 1, 2, 3, 4, 5, 6, 8, 10, 15, 20, 24, 48 hours at a plating ratio of PBMC:CD3+/CMG+ or PBMC: CD3+/DMSO control cells ranging from 1000:1-1:1 and 1:1.25-1:1000. A negative control a set of wells would receive CD3+/CMG+ and CD3+/DMSO control cells only, no PBMCs. After incubation, the plates are centrifuged and processed so that they are labelled with either murine CD3:APC-Cy7 antibody or an IC:APC-Cy7 antibody as per above. After being washed two times with PBS, cells are re-suspended in PBS and analyzed on a FACS Aria (APC-Cy7: 640 nm laser excitation/emission collected at 780−/+60 nm and CMG 561 nm laser excitation/emission collected at 585−/+16 nm) running the FACSDiva™ software (BD Biosciences, San Jose, Calif.). The FSC/SSC event data would then be used initially to set the gate for events labelled "cells". This "cells" gate would be then used to display events to set the PMT voltage for the 640 nm and 561 nm laser analyzing samples labelled with IC:APC-Cy7/DMSO only. This sample would also be used to set the gates for negative cells for both APC-Cy7 and CMG. The CD3+/CMG+ cells that did not receive any PBMCs would then used to set the positive gates for CD3+ and CMG+ cells.

The data is analyzed by looking at the percentage of CD3+/CMG+ cells in the population of total cells. When comparing treatment groups, a relatively lower percentage of CD3+/CMG+ cells at any given assay ratio of PBMC:CD3+/CMG+ cells is indicative of recipient cell lysis. In an embodiment, the percent of CD3+/CMG+ will be similar for recipient cells derived from mice treated with fusosomes and mice treated with PBS.

4. NK Cell Targeting

This Example describes quantification of a natural killer cell response against recipient cells with a cell lysis assay.

A measure of the immunogenicity of recipient cells is the natural killer cell response. In an embodiment, cytotoxicity mediated cell lysis of recipient cells by natural killer cells is a measure of immunogenicity, as lysis will reduce, e.g., inhibit or stop, the activity of a fusosome.

In an embodiment, recipient cells do not elicit a natural killer cell response. In this Example, the natural killer response against recipient cells in a subject is tested. In addition, the protocol may be adapted to any cell type for which suitable surface markers exist. In this example, the target recipient cell is a CD3+ cell.

Mice are treated with fusosomes produced via any of the methods described in this application or with PBS (negative control) daily for 5 days. 28 days following the final treatment, peripheral blood is collected from mice that received fusosomes and mice that received PBS treatment. Blood is collected into 1 ml PBS containing 5 μM EDTA and mixed immediately to prevent clotting. The tubes are kept on ice and red blood cells are removed using a buffered ammonium chloride (ACK) solution. Cells are stained with a murine CD3:APC-Cy7 antibody (Biolgend Catalog #: 100330) or an isotype control APC-Cy7 antibody (Biolgend Catalog #: 400230) at 4° C. for 30 minutes in the dark, after being Fc blocked (Biolgend Catalog #: 101319) in cell staining buffer (Biolgend Catalog #: 420201) for 10 minutes. After being washed two times with PBS, cells are analyzed on a FACS Aria (BD Biosciences, San Jose, Calif.) with 640 nm laser excitation and emission collected at 780−/+60 nm running the FACSDiva™ software (BD Biosciences, San Jose, Calif.) to set negative gates using the isotype control APC-Cy7 antibody labeled cells and then APC-Cy7 positive cells are sorted and collected. Sorted CD3+ cells are then labelled with CellMask™ Green Plasma membrane Stain (CMG, ThermoFisher Catalog #: C37608).

7 days prior to the isolation of CD3+ cells from the mice treated with fusomes or PBS, NK cells are isolated from mice treated with fusomes or PBS according to the methods in Crop et al. Cell transplantation (20):1547-1559; 2011 and simulated in the presence of IL-2 recombinant mouse protein (R&D Systems Catalog #: 402-ML-020) and CD3/CD28 beads (ThermoFisher Catalog #: 11456D) in a round bottom 96 well plate for 7 days at 37 C. At day 7, the stimulated NK cells are co-incubated with CD3+/CMG+ or CD3+/DMSO control cells for 1, 2, 3, 4, 5, 6, 8, 10, 15, 20, 24, 48 hours at a plating ratio of NK cells:CD3+/CMG+ or NK cells:CD3+/DMSO control cells ranging from 1000:1-1:1 and 1:1.25-1:1000. A negative control a set of wells would receive CD3+/CMG+ and CD3+/DMSO control cells only, no NK cells. After incubation, the plates are centrifuged and processed so that they are labelled with either murine CD3:APC-Cy7 antibody or an IC:APC-Cy7 antibody as per above. After being washed two times with PBS, cells are re-suspended in PBS and analyzed on a FACS Aria (APC-Cy7: 640 nm laser excitation/emission collected at 780−/+60 nm and CMG 561 nm laser excitation/emission collected at 585−/+16 nm) running the FACSDiva™ software (BD Biosciences, San Jose, Calif.). The FSC/SSC event data would then be used initially to set the gate for events labelled "cells". This "cells" gate would be then used to display events to set the PMT voltage for the 640 nm and 561 nm laser analyzing samples labelled with IC:APC-Cy7/DMSO only. This sample would also be used to set the gates for negative cells for both APC-Cy7 and CMG. The CD3+/CMG+ cells that did not receive any NK cells would then used to set the positive gates for CD3+ and CMG+ cells.

The data is analyzed by looking at the percentage of CD3+/CMG+ cells in the population of total cells. When comparing treatment groups, a relatively lower percentage of CD3+/CMG+ cells at any given assay ratio of NK cells:CD3+/CMG+ cells is indicative of recipient cell lysis. In an embodiment, the percent of CD3+/CMG+ will be similar for recipient cells derived from mice treated with fusosomes and mice treated with PBS.

5. CD8 T Cell Lysis

This Example describes quantification of a CD8+ T cell response against recipient cells (cells that have fused with fusosomes) with a cell lysis assay.

A measure of the immunogenicity of recipient cells is the CD8+ T cell response. In an embodiment, cytotoxicity mediated cell lysis of recipient cells by CD8+ T cells is a measure of immunogenicity, as lysis will reduce, e.g., inhibit or stop, the activity of a fusosome.

In an embodiment, recipient cells do not elicit a CD8+ T cell response. In this Example, the CD8+ T cell response against recipient cells in a subject is tested. In addition, the protocol may be adapted to any cell type for which suitable surface markers exist. In this example, the target recipient cell is a CD3+ cell.

Mice are treated with fusosomes produced via any of the methods described in this application or with PBS (negative control) daily for 5 days. 28 days following the final treatment, peripheral blood is collected from mice that received fusosomes and mice that received PBS treatment. Blood is collected into 1 ml PBS containing 5 µM EDTA and mixed immediately to prevent clotting. The tubes are kept on ice and red blood cells are removed using a buffered ammonium chloride (ACK) solution. Cells are stained with a murine CD3:APC-Cy7 antibody (Biolgend Catalog #: 100330) or an isotype control APC-Cy7 antibody (Biolgend Catalog #: 400230) at 4° C. for 30 minutes in the dark, after being Fc blocked (Biolgend Catalog #: 101319) in cell staining buffer (Biolgend Catalog #: 420201) for 10 minutes. After being washed two times with PBS, cells are analyzed on a FACS Aria (BD Biosciences, San Jose, Calif.) with 640 nm laser excitation and emission collected at 780−/+60 nm running the FACSDiva™ software (BD Biosciences, San Jose, Calif.) to set negative gates using the isotype control APC-Cy7 antibody labeled cells and then APC-Cy7 positive cells are sorted and collected. Sorted CD3+ cells are then labelled with CellMask™ Green Plasma membrane Stain (CMG, ThermoFisher Catalog #: C37608).

7 days prior to the isolation of CD3+ cells from the mice treated with fusomes or PBS, CD8+ cells are isolated from mice treated with fusosomes or PBS according to the methods in Crop et al. Cell transplantation (20):1547-1559; 2011 and simulated in the presence of IL-2 recombinant mouse protein (R&D Systems Catalog #: 402-ML-020) and CD3/CD28 beads (ThermoFisher Catalog #: 11456D) in a round bottom 96 well plate for 7 days at 37 C. At day 7, the stimulated CD8+ cells are co-incubated with CD3+/CMG+ or CD3+/DMSO control cells for 1, 2, 3, 4, 5, 6, 8, 10, 15, 20, 24, 48 hours at a plating ratio of CD8+ cells:CD3+/CMG+ or CD8+ cells:CD3+/DMSO control cells ranging from 1000:1-1:1 and 1:1.25-1:1000. A negative control a set of wells would receive CD3+/CMG+ and CD3+/DMSO control cells only, no CD8+ cells. After incubation, the plates are centrifuged and processed so that they are labelled with either murine CD3:APC-Cy7 antibody or an IC:APC-Cy7 antibody as per above. After being washed two times with PBS, cells are re-suspended in PBS and analyzed on a FACS Aria (APC-Cy7: 640 nm laser excitation/emission collected at 780−/+60 nm and CMG 561 nm laser excitation/emission collected at 585−/+16 nm) running the FACS-Diva™ software (BD Biosciences, San Jose, Calif.). The FSC/SSC event data would then be used initially to set the gate for events labelled "cells". This "cells" gate would be then used to display events to set the PMT voltage for the 640 nm and 561 nm laser analyzing samples labelled with IC:APC-Cy7/DMSO only. This sample would also be used to set the gates for negative cells for both APC-Cy7 and CMG. The CD3+/CMG+ cells that did not receive any CD8+ cells would then used to set the positive gates for CD3+ and CMG+ cells.

The data is analyzed by looking at the percentage of CD3+/CMG+ cells in the population of total cells. When comparing treatment groups, a relatively lower percentage of CD3+/CMG+ cells at any given assay ratio of CD8+ cells:CD3+/CMG+ cells is indicative of recipient cell lysis. In an embodiment, the percent of CD3+/CMG+ will be similar for recipient cells derived from mice treated with fusosomes and mice treated with PBS.

Example 149: Measuring GAPDH in Fusosomes

This example describes quantification of the level of glyceraldehyde 3-phosphate dehydrogenase (GAPDH) in the fusosomes, and the relative level of GAPDH in the fusosomes compared to the parental cells. Fusosomes were prepared as described in Examples 114 and 154.

GAPDH was measured in the parental cells and the fusosomes using a standard commercially available ELISA for GAPDH (ab176642, Abcam) per the manufacturer's directions. Total protein levels were similarly measured via bicinchoninic acid assay. Measured GAPDH and protein levels are shown in the table below:

|  | [Protein] (mg/mL) | [GAPDH] (ng/mL) | GAPDH:Protein (µg/g) |
| --- | --- | --- | --- |
| Fusosomes | 0.82 | 37.2 | 45.3 |
| Cells | 0.45 | 50.4 | 112.0 |

Figure 41:
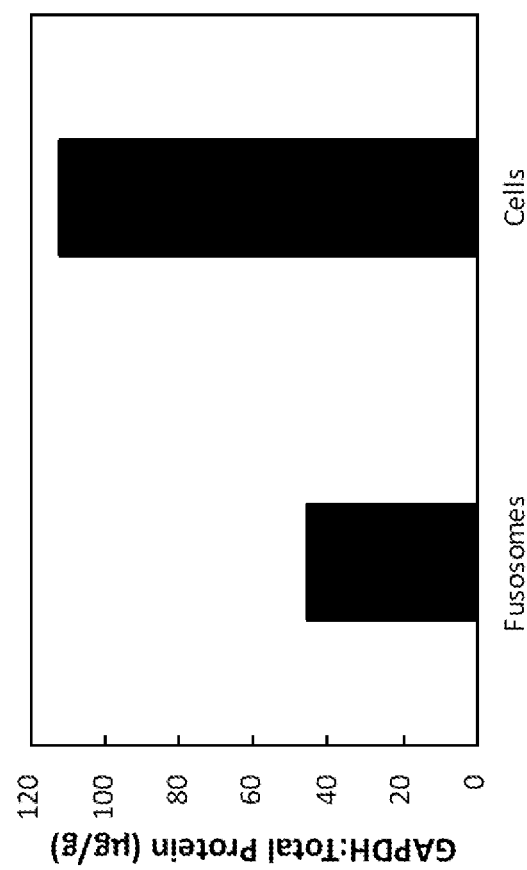
FIG. 41 is a graph showing GAPDH: Total protein ratios measured by bicinchoninic acid assay in fusosomes and parental cells.

GAPDH: Total protein ratios are also shown in FIG. 41.

Example 150: Ratio of Lipids to Proteins in Fusosomes

This Example describes quantification of the ratio of lipid mass to protein mass in fusosomes. It is contemplated that fusosomes can have a ratio of lipid mass to protein mass that is similar to that of nucleated cells. Fusosomes and parental cells were prepared as described herein in Examples 114 and 154.

Figure 42:
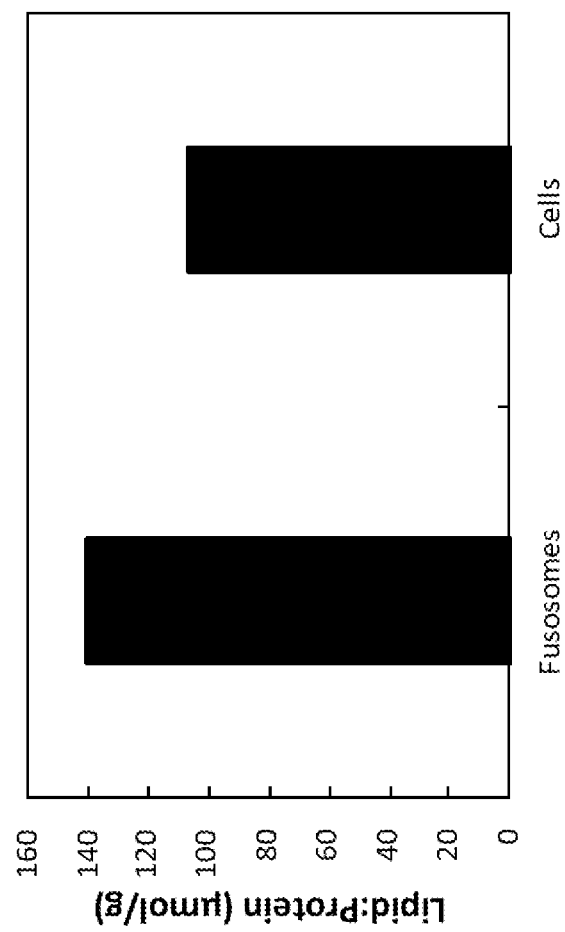
FIG. 42 is a graph showing lipid: protein ratios measured by bicinchoninic acid assay in fusosomes and parental cells.

The lipid content was calculated using choline-containing phospholipids as a subset of total lipids using a commercially available phospholipid assay kit (MAK122 Sigma St. Louis, Mo.) according to manufacturer's instructions. Total protein content of the fusosomes was measured via bicinchoninic acid assay as described herein. Measured phospholipid levels, protein levels, and the ratio of phospholipids to protein are shown in FIG. 42 and the table below:

|  | Phospholipids (µM) | Protein (g/L) | Phospholipids:Protein (µmol/g) |
| --- | --- | --- | --- |
| Fusosomes | 115.6 | 0.82 | 141.0 |
| Cells | 47.9 | 0.45 | 106.4 |

Example 151: Ratio of Proteins to DNA in Fusosomes

This Example describes quantification of the ratio of protein mass to DNA mass in fusosomes. It is contemplated that fusosomes can have a ratio of protein mass to DNA mass that is much greater than that of cells. Fusosomes were prepared as described in Examples 114 and 154.

Figure 43:
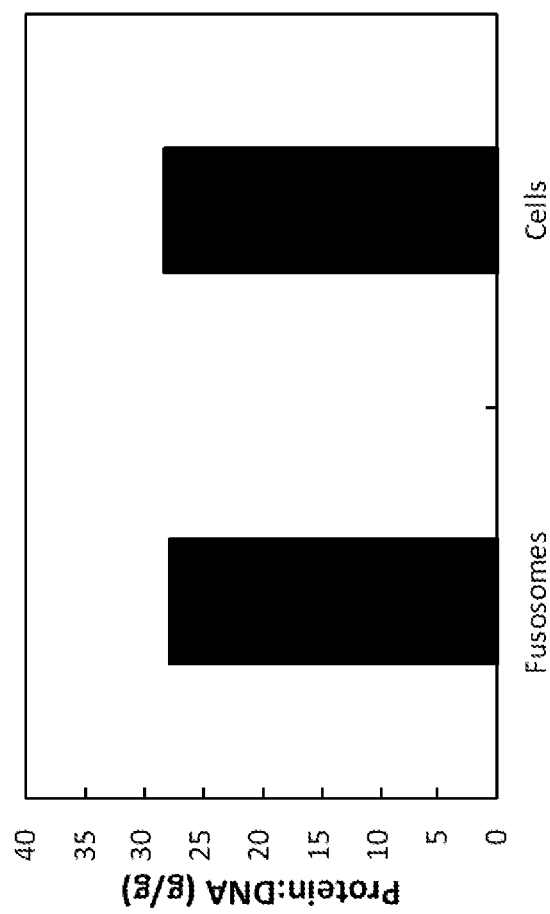
FIG. 43 is a graph showing protein: DNA ratios measured by bicinchoninic acid assay in fusosomes and parental cells.

Total protein content of the fusosomes and cells was measured via bicinchoninic acid as described herein. The DNA mass of fusosomes and cells were measured by absorption at 280 nm after extraction of total DNA using a commercially available isolation kit (#69504 Qiagen Hilden, Germany) according to the manufacturer's instructions. The ratio of proteins to total nucleic acids was determined by dividing the total protein content by the total DNA content to yield a ratio within a given range for a typical fusosome preparation. Measured protein levels, DNA levels, and the ratio of protein to DNA are shown in FIG. 43 and the table below:

|  | [Protein] (mg/mL) | [DNA] (ng/µL) | Protein:DNA (g/g) |
| --- | --- | --- | --- |
| Fusosomes | 0.82 | 29.5 | 27.8 |
| Cells | 0.45 | 15.9 | 28.3 |

Example 152: Ratio of Lipids to DNA in Fusosomes

This Example describes quantification of the ratio of lipids to DNA in fusosomes compared to parental cells. In an embodiment, fusosomes will have a greater ratio of lipids to DNA compared to parental cells. Fusosomes were prepared as described previously in Examples 114 and 154.

Figure 44:
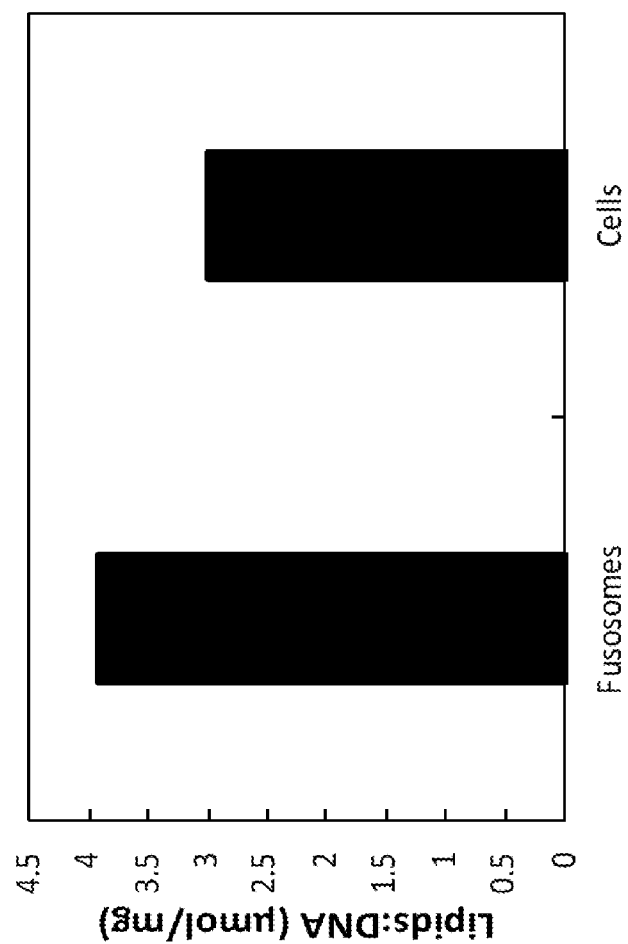
FIG. 44 is a graph showing lipids: DNA ratios measured by bicinchoninic acid assay in fusosomes and parental cells.

This ratio is defined as the lipid content outlined in Example 49, and nucleic acid content is determined as described in Example 50. Measured lipid levels, DNA levels, and the ratio of lipid to DNA are shown in FIG. 44 and the table below:

|  | [Lipids] (µM) | [DNA] (ng/µL) | Lipids:DNA (µmol/mg) |
| --- | --- | --- | --- |
| Fusosomes | 115.6 | 29.5 | 3.92 |
| Cells | 47.9 | 15.9 | 3.01 |

Example 153: Delivery of Fusosomes Via a Dynamin-Mediated Pathway

This example describes fusosome-based delivery of Cre to recipient cells via a dynamin-mediated pathway. Briefly, fusosomes encapsulating Cre were generated by the standard procedure of harvesting and preparing fusosomes produced from HEK-293T cells expressing the envelope glycoprotein G from vesicular stomatitis virus (VSV-G) on the cell surface, as described herein. The dependence of Cre delivery on a dynamin-mediated pathway was then determined as follows.

Recipient HEK-293T cells engineered to express a "LoxP-GFP-stop-LoxP-RFP" cassette were plated 30,000 cells/well into a black, clear-bottom 96-well plate in complete media. Twenty-four hours after plating the recipient cells, the fusosomes encapsulating Cre were applied to the recipient LoxP-GFP-stop-LoxP-RFP HEK-293T cells.

To quantify the extent to which Cre delivery depends upon a dynamin-mediated pathway, at the time of fusosome application, one group of recipient cells was treated with the dynamin inhibitor Dynasore at 120 M, a concentration sufficient to partially inhibit endocytosis via dynamin. Fusosomes were incubated with the recipient cells for 24 hr at 37° C. and 5% CO2. Twenty-four hours later, 1 µg/mL Hoechst 33342 was diluted in complete media and incubated with the cells for 30 min at 37° C. and 5% CO2. Following addition of Hoescht, the cells were imaged using an automated microscope (www.biotek.com/products/imaging-microscopy-automated-cell-imagers/lionheart-fx-automated-live-cell-imager/). The Hoechst fluorescence of the recipient cells was imaged using the 405 nm LED and BFP filter cube. The GFP fluorescence of the recipient cells was imaged using the 488 nm LED and GFP filter cube. The RFP fluorescence of the recipient cells was imaged using the 523 nm LED and RFP filter cube. Images of cells in the well were acquired by first establishing the LED intensity and integration times on a positive-control well; i.e., recipient cells treated with 1.25 µL Gesicles recombinase gesicles (Takara, Cat #631449).

Acquisition settings were set so that BFP, GFP and RFP intensities were at the maximum pixel intensity values but not saturated. The wells of interest were then imaged using the established settings. Focus was set on each well by autofocusing on the BFP channel and then using the established focal plane for the GFP and RFP channels. Analysis of RFP-positive cells was performed with Gen5 software provided with automated fluorescent microscope (see www.biotek.com/products/software-robotics-software/gen5-microplate-reader-and-imager-software/).

The images were pre-processed using a rolling ball background subtraction algorithm with a 60 m width. Cells with GFP intensity significantly above background intensities were thresholded and areas too small or large to be GFP-positive cells were excluded. The same analysis steps were applied to the RFP channel. The number of RFP-positive cells (recipient cells receiving Cre recombinase) was then divided by the sum of the GFP positive cells (total recipient cells) to quantify the percentage of RFP-positive cells, as a metric for Cre delivery.

Figure 45:
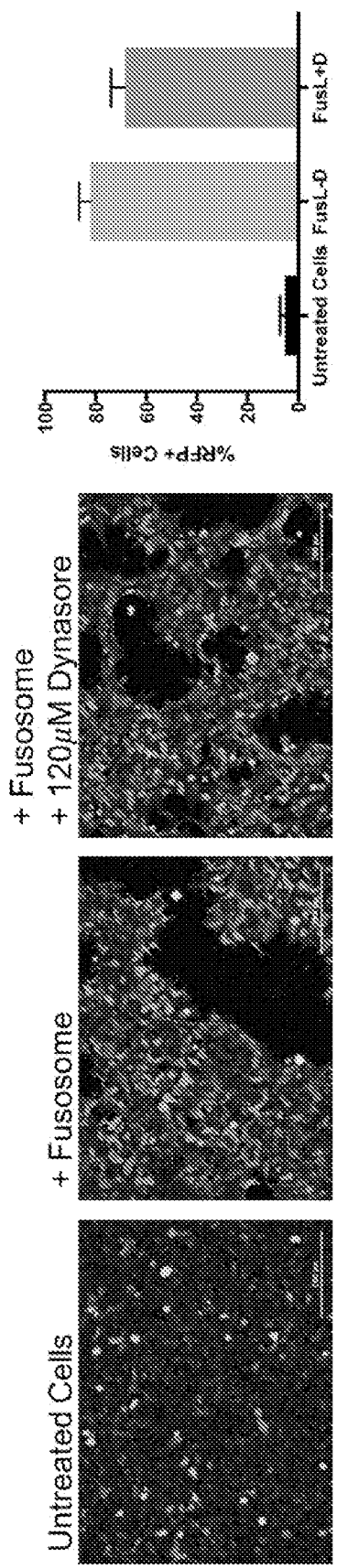
FIG. 45 is a series of images showing delivery of Cre into cells by VSV-G fusosomes in the presence or absence of the dynamin inhibitor Dynasore.

In the absence of Dynasore, the Cre-loaded fusosomes showed an observable level of Cre delivery corresponding to 82.1±4.5% RFP-positive cells of total GFP-positive recipient cells (FIG. 45). As noted above, the Dynasore concentration used was sufficient to partially inhibit endocytosis. Consistent with this, the VSV-G fusosomes used in this example, which are known to operate through an endocytic pathway, were partially inhibited in the presence of 120 M Dynasore, with a level of Cre delivery corresponding to 68.5±5.5% RFP-positive cells (FIG. 45). Untreated recipient cells did not show any appreciable RFP-positive cells. Taken together, these data illustrate the dynamin-dependence of fusosome-based Cre delivery.

Example 154: Measuring Lipid Composition in Fusosomes

This Example describes quantification of the lipid composition of fusosomes. It is contemplated that the lipid composition of fusosomes can be similar to the cells from which they are derived. Lipid composition affects important biophysical parameters of fusosomes and cells, such as size, electrostatic interactions, and colloidal behavior.

The lipid measurements were based on mass spectrometry. Fusosomes were prepared as described herein by transient transfection of VSV-G and GFP in 10 cm dishes, followed by filtration and ultracentrifugation of the conditioned media 48 h after transfection to obtain fusosomes. Transfected cells were harvested in parallel to the conditioned media and submitted for analysis. Exosomes were also harvested from cells that were not transfected with VSV-G or GFP.

Mass spectrometry-based lipid analysis was performed by Lipotype GmbH (Dresden, Germany) as described (Sampaio et al. 2011). Lipids were extracted using a two-step chloroform/methanol procedure (Ejsing et al. 2009). Samples were spiked with internal lipid standard mixture containing: cardiolipin 16:1/15:0/15:0/15:0 (CL), ceramide 18:1; 2/17:0 (Cer), diacylglycerol 17:0/17:0 (DAG), hexosylceramide 18:1; 2/12:0 (HexCer), lyso-phosphatidate 17:0 (LPA), lyso-phosphatidylcholine 12:0 (LPC), lyso-phosphatidylethanolamine 17:1 (LPE), lyso-phosphatidylglycerol 17:1 (LPG), lyso-phosphatidylinositol 17:1 (LPI), lyso-phosphatidylserine 17:1 (LPS), phosphatidate 17:0/17:0 (PA), phosphatidylcholine 17:0/17:0 (PC), phosphatidylethanolamine 17:0/17:0 (PE), phosphatidylglycerol 17:0/17:0 (PG), phosphatidylinositol 16:0/16:0 (PI), phosphatidylserine 17:0/17:0 (PS), cholesterol ester 20:0 (CE), sphingomyelin 18:1; 2/12:0; 0 (SM), triacylglycerol 17:0/17:0/17:0 (TAG) and cholesterol D6 (Chol).

After extraction, the organic phase was transferred to an infusion plate and dried in a speed vacuum concentrator. 1st step dry extract was re-suspended in 7.5 mM ammonium acetate in chloroform/methanol/propanol (1:2:4, V:V:V) and 2nd step dry extract in 33% ethanol solution of methylamine in chloroform/methanol (0.003:5:1; V:V:V). All liquid handling steps were performed using Hamilton Robotics STARlet robotic platform with the Anti Droplet Control feature for organic solvents pipetting.

Samples were analyzed by direct infusion on a QExactive mass spectrometer (Thermo Scientific) equipped with a TriVersa NanoMate ion source (Advion Biosciences). Samples were analyzed in both positive and negative ion modes with a resolution of Rm/z=200=280000 for MS and Rm/z=200=17500 for MSMS experiments, in a single acquisition. MSMS was triggered by an inclusion list encompassing corresponding MS mass ranges scanned in 1 Da increments (Surma et al. 2015). Both MS and MSMS data were combined to monitor CE, DAG and TAG ions as ammonium adducts; PC, PC O-, as acetate adducts; and CL, PA, PE, PE O-, PG, PI and PS as deprotonated anions. MS only was used to monitor LPA, LPE, LPE O-, LPI and LPS as deprotonated anions; Cer, HexCer, SM, LPC and LPC O- as acetate adducts and cholesterol as ammonium adduct of an acetylated derivative (Liebisch et al. 2006).

Data were analyzed with in-house developed lipid identification software based on LipidXplorer (Herzog et al. 2011; Herzog et al. 2012). Data post-processing and normalization were performed using an in-house developed data management system. Only lipid identifications with a signal-to-noise ratio >5, and a signal intensity 5-fold higher than in corresponding blank samples were considered for further data analysis.

Fusosome lipid composition was compared to lipid compositions of parental cells, with undetected lipid species assigned a value of zero. The lipid species identified in fusosomes and parental cells are shown in the table below:

| | Total Lipid Species Identified | Shared Lipid Species (identified in both parental cells and fusomes) | Shared Lipid Species with 25% of parental expression in fusosomes | Fraction of Shared Lipid Species to Total Lipids |
|---|---|---|---|---|
| Fusosomes | 679 | 569 | 548 | 0.700 |
| Parental Cells | 783 | | | |

It is contemplated that fusosomes and parental cells can have a similar lipid composition if 270% of the lipid species identified in any replicate sample of the parental cells are present in any replicate sample of the fusosomes, and of those identified lipids, the average level in the fusosome can be >25% of the corresponding average lipid species level in the parental cell.

Example 155: Measuring Proteomic Composition in Fusosomes

This Example describes quantification of the protein composition of fusosomes. It is contemplated that the protein composition of fusosomes can be similar to the parental cells from which they are derived.

Fusosomes and parental cells were prepared as described herein by the method of Examples 114 and 154.

Each sample was resuspended in lysis buffer (6 M urea, 2 M thiourea, 4% CHAPS, 50 mM Tris pH 8.0), sonicated on an ice bath and ran through a small gauge syringe. Proteins were reduced with 10 mM DTT for 15 minutes at 65° C. and alkylated with 15 mM iodoacetamide (IAA) for 30 minutes in the dark at room temperature. Excess IAA was quenched with an additional 10 mM DTT. Proteins were then precipitated with the addition of 8 volumes of ice cold acetone+1 volume of ice cold methanol and placed at −80° C. overnight. The precipitated proteins were pelleted by centrifugation. Remaining lysis buffer was washed with 200 μl of ice cold methanol 3 times. Proteins were resuspended in 0.75 M urea+50 mM Tris pH 8.0+1 μg Trypsin/LysC and pre-digested for 4 hours at 37° C. with agitation. An additional 1 μg of trypsin/LysC was added to the proteins and the digestion was continued overnight. Peptides were purified by reversed phase SPE and analyzed by LC-MS.

A replicate sample for each condition was lysed and combined in one tube. This pool was then either subjected to the same preparation protocol as the samples and analyzed by LC-MS in information dependent acquisition or separated on a gel as described below.

A total of 100 μg of pooled proteins was placed in 2× Laemmli loading buffer and separated on a 12.5% SDS PAGE. Proteins were briefly stained with Coomassie blue and the protein lanes were separated into 12 fractions. Each fraction was then dehydrated with 50% acetonitrile and rehydrated with 10 mM DTT for the reduction. Gel pieces were placed at 65° C. for 15 minutes and alkylated for 30 minutes at room temperature with 15 mM IAA in the dark. Gels were further dehydrated with 50% acetonitrile and rehydrated in 50 mM Tris pH 8 with 1 μg of trypsin/LysC overnight at 37° C. Peptides were extracted from the gel by dehydration and sonication. Peptides were purified by reversed phase SPE and analyzed by LC-MS/MS (1×IDA per fraction).

Acquisition was performed with an ABSciex TripleTOF 5600 (ABSciex, Foster City, Calif., USA) equipped with an electrospray interface with a 25 μm iD capillary and coupled to an Eksigent gUHPLC (Eksigent, Redwood City, Calif., USA). Analyst TF 1.7 software was used to control the instrument and for data processing and acquisition. Acquisition was performed in Information Dependent Acquisition (IDA) mode for the 12 fractions from the gel or the unfractionated pool. The samples were analyzed in SWATH acquisition mode. For the IDA mode, the source voltage was set to 5.2 kV and maintained at 225° C., curtain gas was set at 27 psi, gas one at 12 psi and gas two at 10 psi. For the SWATH mode, the source voltage was set to 5.5 kV and maintained at 225° C., curtain gas was set at 25 psi, gas one at 16 psi and gas two at 15 psi. Separation was performed on a reversed phase HALO C18-ES column 0.3 mm i.d., 2.7 μm particles, 150 mm long (Advance Materials Technology, Wilmington, Del.) which was maintained at 60° C. Samples were injected by loop overfilling into a 5 gL loop. For the 60 minutes LC gradient, the mobile phase consisted of the following solvent A (0.2% v/v formic acid and 3% DMSO v/v in water) and solvent B (0.2% v/v formic acid and 3% DMSO in EtOH) at a flow rate of 3 μL/min.

To generate the ion library for the analysis of the samples, the ProteinPilot software was run on the wiff files that were generated by the IDA runs. This database was used in the Peakview software (ABSciex) to quantify the proteins in each of the samples, using 3 transition/peptide and 15 peptide/protein. To maximize the number of quantified proteins, the samples were quantified on a publicly available human SWATH database (Atlas) with the same parameters. A peptide was considered as adequately measured if the score computed by Peakview was superior to 1.5 and had an FDR<1%. The quantification from each of the database was combined into one final quantification using the protein name from both databases. A correction factor was computed for every sample by taking into account the total signal of every protein in that sample when compared to the average of the total signal for every sample.

The fusosome proteomic composition was compared to the parental cell proteomic composition. A similar proteomic composition between fusosomes and parental cells was observed when >33% of the identified proteins were present in the fusosome, and of those identified proteins, the level was >25% of the corresponding protein level in the parental cell, as shown in the table below.

|  | Total Proteins Identified | Shared proteins (identified in both parental cells and fusomes) | Shared proteins with 25% of parental expression in fusosomes | Fraction of shared proteins to total proteins |
|---|---|---|---|---|
| Fusosomes | 1926 | 1487 | 957 | 0.333 |
| Cells | 2870 | | | |

Example 156: Quantifying an Endogenous or Synthetic Protein Level Per Fusosome

This example describes quantification of an endogenous or synthetic protein cargo in fusosomes. Fusosomes can, in some instances, comprise an endogenous or synthetic protein cargo. The fusosome or parental cell described in this Example was engineered to alter the expression of an endogenous protein or express a synthetic cargo that mediates a therapeutic or novel cellular function.

Fusosomes and parental cells expressing GFP were prepared as described herein by the method of Examples 114 and 154. Quantification of GFP in fusosomes was accomplished using a commercially available ELISA kit (ab171581 Abcam Cambridge, United Kingdom) according to the manufacturer's instructions. Fusosome quantification was performed by Nanoparticle Tracking Analysis using a NanoSight NS300 (Malvern Instruments, Malvern, Worcestershire, United Kingdom). Results are shown in the table below.

|  | Concentration (#/mL) |
|---|---|
| GFP Protein | $4.41 \times 10^{13}$ |
| Fusosomes | $2.66 \times 10^{11}$ |
| GFP:Fusosome | 165.8 |

It is contemplated that the fusosomes can have at least 1, 2, 3, 4, 5, 10, 20, 50, 100, or more protein agent molecules per fusosome. In an embodiment, the fusosomes will have 166 protein agent molecules per fusosome.

Example 157: Measuring Markers of Exosomal Proteins in Fusosomes

This assay describes quantification of the proportion of proteins that are known to be specific markers of exosomes.

Fusosomes were prepared as described herein by the method of Examples 114 and 154. Exosomes were prepared as described herein for fusosomes by the method of Examples 114 and 154 with the exception that the parental cells were not transfected with VSV-G or GFP. Protein quantification by mass spectrometry for fusosomes and exosomes was performed as described herein in Example 42.

Figure 46:
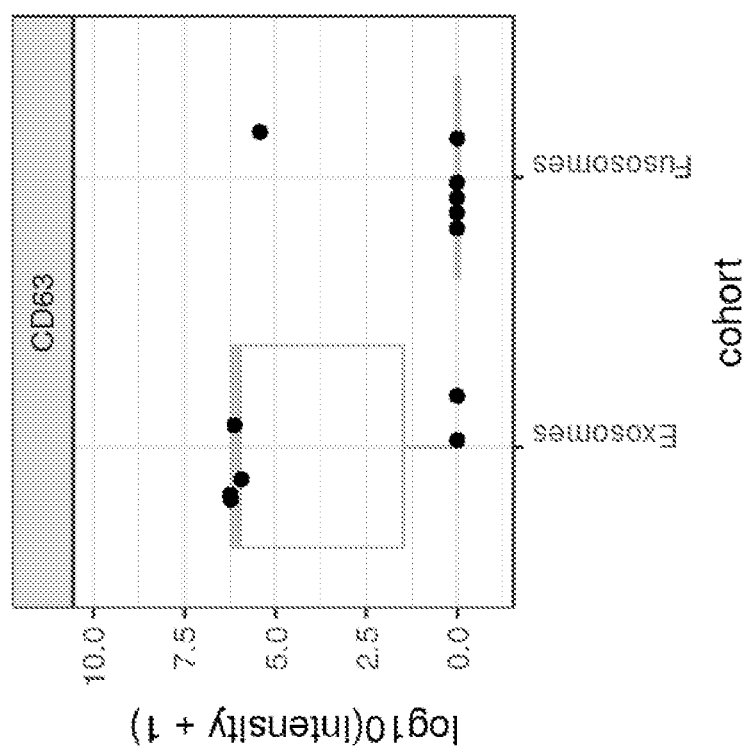
FIG. 46 is a graph showing protein levels of the exosome marker CD63 in exosomes and fusosomes.

The resulting protein quantification data was analyzed to determine protein levels and proportions of the known exosomal marker CD63. Average log intensities per group were calculated by adding 1 to intensity values from mass spectrometry, transforming by log 10, and computing the mean across replicates. The results are shown in FIG. 46.

Example 158: Measuring Calnexin in Fusosomes

This assay describes quantification of the level of calnexin (CNX) in the fusosomes, and the relative level of CNX in the fusosomes compared to the parental cells.

Figure 47:
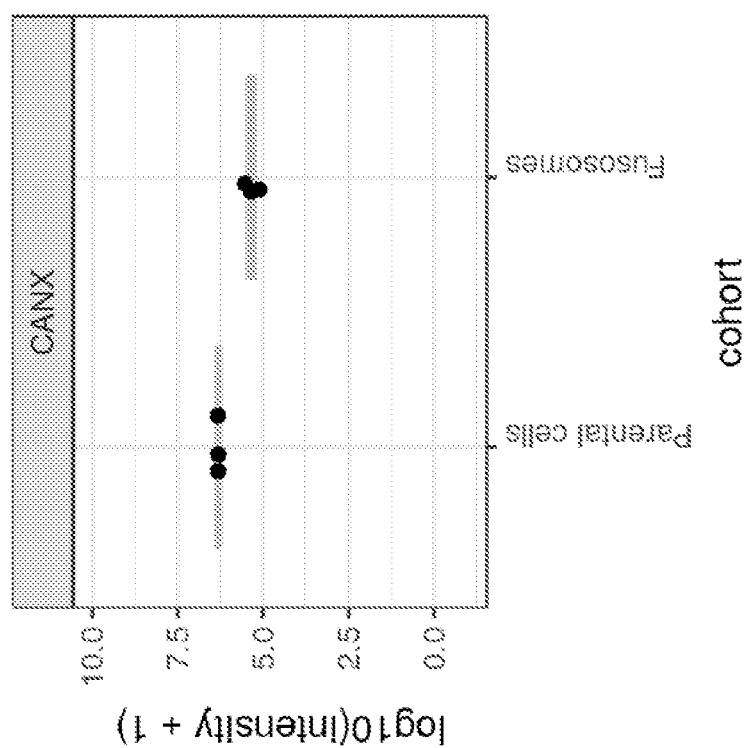
FIG. 47 is a graph showing the intensity of calnexin signal detected in fusosomes and parental cells.

Fusosomes and parental cells were prepared as described herein in Examples 114 and 154. Calnexin and total protein was measured using mass spectrometry conducted according to the method of Example 42. The calnexin signal intensity determined for parental cells and fusosomes is shown in FIG. 47.

In embodiments, using this assay, the average fractional content (calculated as described herein in Example 42) of CNX in the fusosomes will be $<2.43 \times 10^{-4}$.

In an embodiment, the decrease in calnexin per total protein in ng/μg from the parent cell to the preparation will be more than 88%.

Example 159: Ratio of Lipids to DNA in Fusosomes

This Example describes quantification of the ratio of lipids to DNA in fusosomes compared to parental cells. In an embodiment, fusosomes will have a greater ratio of lipids to DNA compared to parental cells. Fusosomes were prepared as described previously in Examples 114 and 154.

Figure 48:
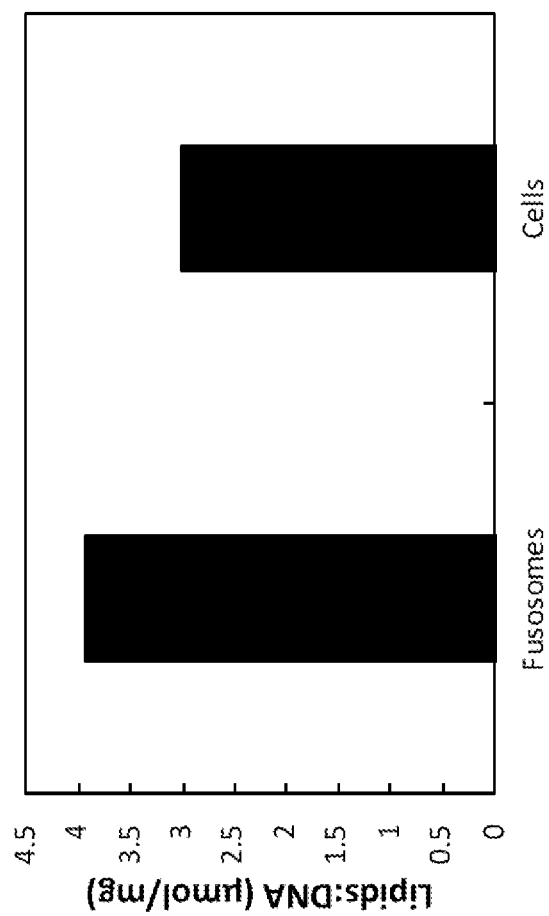
FIG. 48 is a graph showing lipid:DNA ratios determined for fusosomes and parental cells.

This ratio is defined as the lipid content outlined in Example 49, and nucleic acid content is determined as described in Example 50. As shown in FIG. 48 and in the table below, fusosomes were found to exhibit a greater lipid:DNA ratio than parental cells.

|  | [Lipids] (μM) | [DNA] (ng/μL) | Lipids:DNA (μmol/mg) |
|---|---|---|---|
| Fusosomes | 115.6 | 29.5 | 3.92 |
| Cells | 47.9 | 15.9 | 3.01 |

Example 160: Analyzing Surface Markers on Fusosomes

This assay describes identification of surface markers on the fusosomes.

Fusosomes were prepared as described herein in Examples 114 and 154. Phosphatidylserine was measured by mass spectrometry as described herein in Examples 114 and 154. The quantity of phosphatidylserine relative to total lipids in fusosomes was determined to be 121% greater than the quantity of phosphatidylserine relative to total lipid in parental cells, as shown in the table below.

|  | Phosphatidylserine (molar %) | Phosphatidylserine Percent change |
|---|---|---|
| Fusosomes | 14.6 | 121% |
| Parental Cells | 6.6 |  |

Example 161: Analysis of Viral Capsid Proteins in Fusosomes

In this example, the makeup of the sample preparation was analyzed and the proportion of proteins that are derived from viral capsid sources was assessed.

Fusosomes were prepared as described herein by the method of Examples 114 and 154. Protein quantification by mass spectrometry for fusosomes was performed as described herein in Example 42. The fractional content of the viral capsid proteins was calculated as described herein in Example 42, averaged over fusosome samples, and expressed as a percent.

Using this approach, the sample was found to contain 0.05% viral capsid protein, as shown in the table below. The only viral capsid protein detected was Complex of Rabbit Endogenous Lentivirus (RELIK) Capsid with Cyclophilin A (PDB 2XGY|B).

|  | Raw MS Intensity | Viral:Total Protein (%) |
|---|---|---|
| Viral Capsid Proteins | $5.10 \times 10^5$ | 0.05 |
| Total Proteins | $9.46 \times 10^8$ |  |

Example 162: Quantification of Fusogen Protein Ratios in Fusosomes

This example describes quantification of the ratio of fusogen protein to total protein or other proteins of interest in fusosomes. Other proteins of interest may include, but are not limited to, EGFP, CD63, ARRDC1, GAPDH, Calnexin (CNX), and TSG101. Fusosomes were prepared as described herein by the method of Examples 114 and 154. Protein quantification by mass spectrometry for fusosomes was performed as described herein in Example 42. The quantification of all proteins was calculated as described herein in Example 42, averaged over fusosome samples, and expressed as a fraction.

As shown in the table below, the fusogen was found to have a ratio to EGFP of 156.9, a ratio to CD63 of 2912.0, a ratio to ARRDC1 of 664.9, a ratio to GAPDH of 69.0, a ratio to CNX of 558.4, and a ratio to TSG101 of 3064.1.

| Proteins | Raw MS Intensity | Fusogen:Protein(s) Ratio |
|---|---|---|
| VSV-G | $1.29 \times 10^8$ | N/A |
| Total Proteins | $9.46 \times 10^8$ | 0.136 |
| EGFP | $8.22 \times 10^5$ | 156.9 |
| CD63 | $4.43 \times 10^4$ | 2912.0 |
| ARRDC1 | $1.94 \times 10^5$ | 664.9 |
| GAPDH | $1.87 \times 10^6$ | 69.0 |
| CNX | $2.31 \times 10^5$ | 558.4 |
| TSG101 | $4.21 \times 10^4$ | 3064.1 |

Example 163: Quantification of Endogenous and Synthetic Protein Ratios in Fusosomes This example describes the quantification of an endogenous or synthetic protein cargo relative to total protein or other proteins of interest in fusosomes. Other proteins of interest may include, but are not limited to, VSV-G, CD63, ARRDC1, GAPDH, Calnexin (CNX), or TSG101. Fusosomes were prepared as described herein by the method of Examples 114 and 154. Protein quantification by mass spectrometry for fusosomes was performed as described herein in Example 42. The quantification of all proteins was calculated as described herein in Example 42, averaged over fusosome samples, and expressed as a fraction.

As shown in the table below, the synthetic protein cargo was found to have a ratio to VSV-G of $6.37 \times 10^{-3}$, a ratio to CD63 of 18.6, a ratio to ARRDC1 of 4.24, a ratio to GAPDH of 0.44, a ratio to CNX of 3.56, and a ratio to TSG101 of 19.52.

| Proteins | Raw MS Intensity | Protein Cargo:Protein(s) Ratio |
|---|---|---|
| EGFP | $8.22 \times 10^5$ | N/A |
| Total Proteins | $9.46 \times 10^8$ | $8.69 \times 10^{-4}$ |
| VSV-G | $1.29 \times 10^8$ | $6.37 \times 10^{-3}$ |
| CD63 | $4.43 \times 10^4$ | 18.6 |
| ARRDC1 | $1.94 \times 10^5$ | 4.24 |
| GAPDH | $1.87 \times 10^6$ | 0.44 |
| CNX | $2.31 \times 10^5$ | 3.56 |
| TSG101 | $4.21 \times 10^4$ | 19.52 |

Example 164: Enriched Lipid Composition in Fusosomes

This Example describes quantification of the lipid composition of fusosomes, parental cells, and exosomes. It is contemplated that the lipid composition of fusosomes can be enriched and/or depleted for specific lipids relative to the cells from which they are derived. Lipid composition affects important biophysical parameters of fusosomes and cells, such as size, electrostatic interactions, and colloidal behavior.

The lipid composition was measured as described in Examples 114 and 154. Fusosomes were prepared as described herein by transient transfection of VSV-G and GFP in 10 cm dishes, followed by filtration and ultracentrifugation of the conditioned media 48 hours after transfection to obtain fusosomes. Transfected cells were harvested in parallel to the conditioned media and submitted for analysis. Exosomes were prepared as described herein for fusosomes with the exception that the parental cells were not transfected with VSV-G or GFP.

Figure 49A:
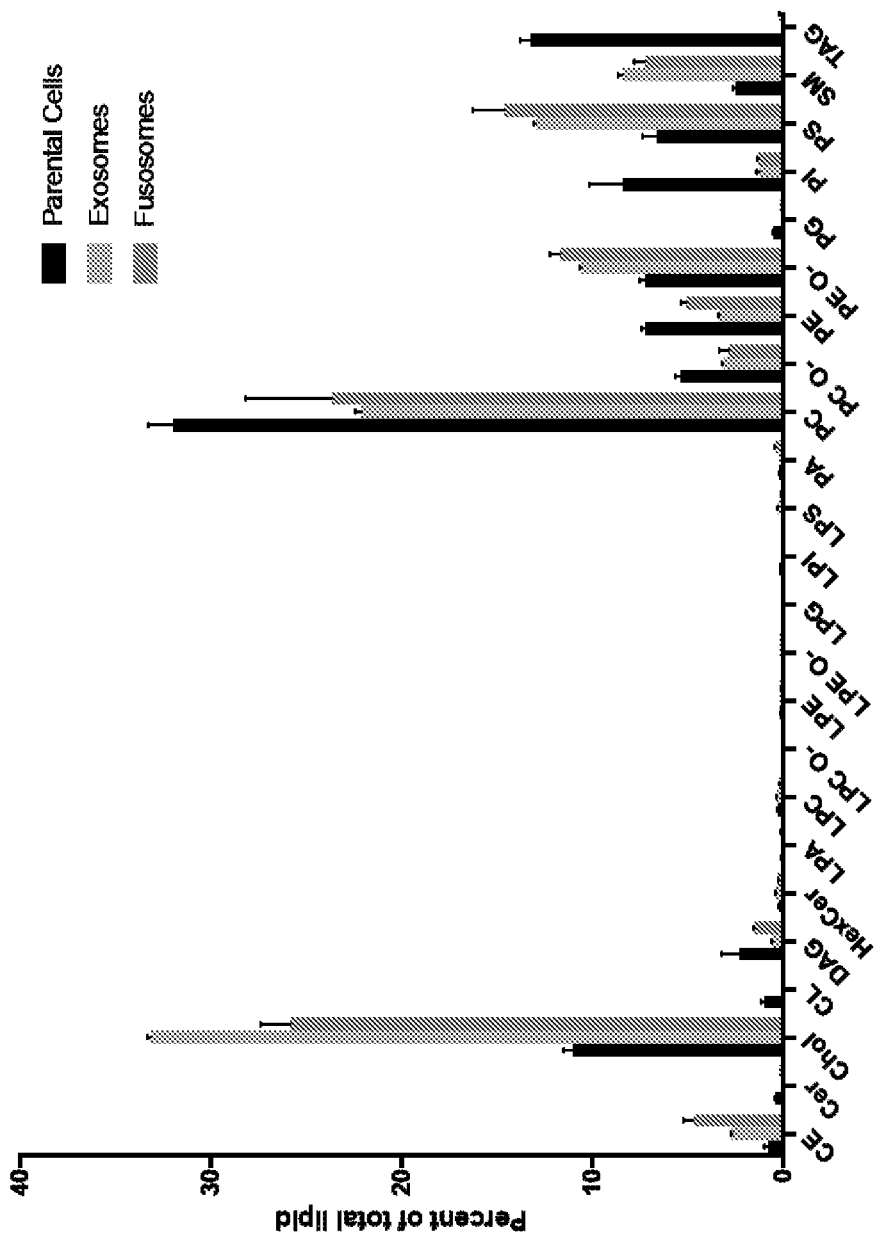
FIGS. 49A-49B are a series of graphs showing the proportion of lipid species as a percentage of total lipids in parental cells, exosomes, and fusosomes.
Figure 49B:
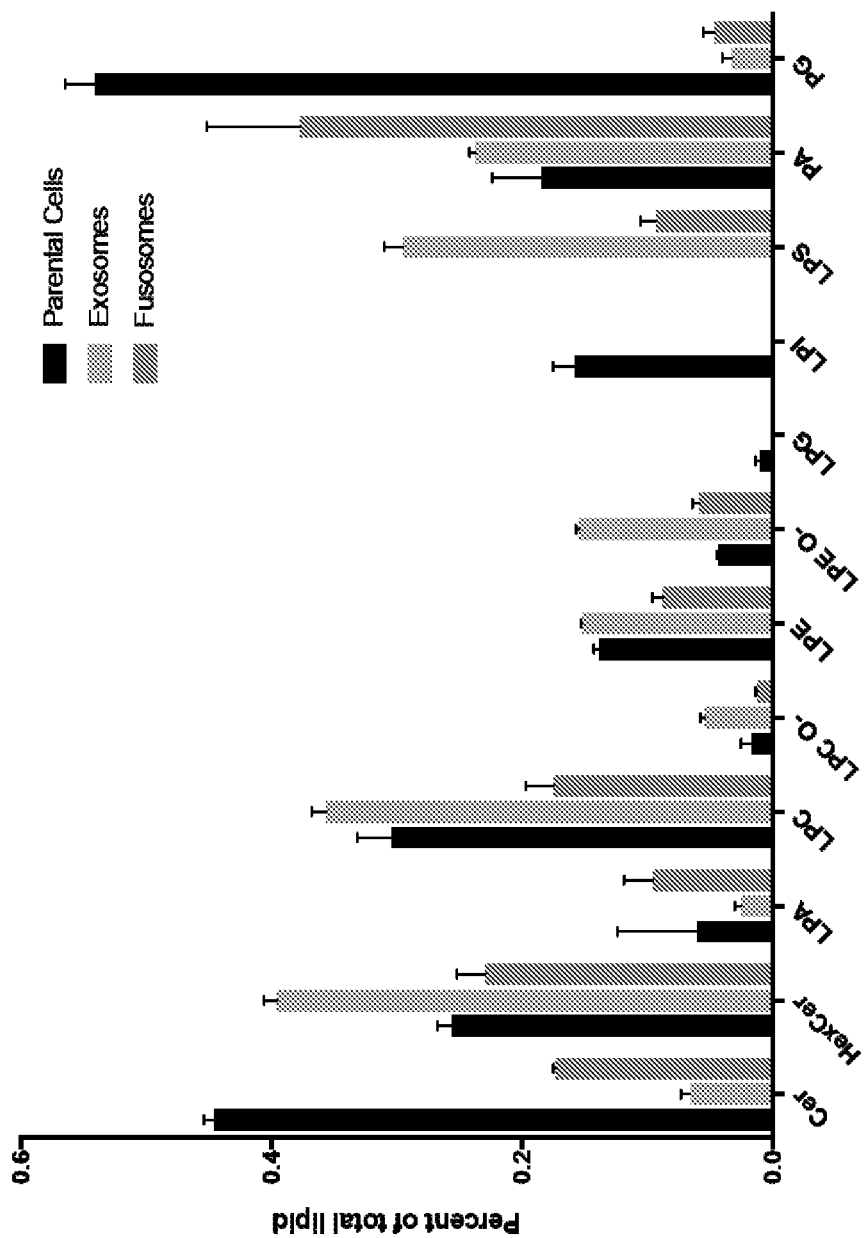

The lipid composition for fusosomes, exosomes, and parental cells is shown in FIGS. 49A-49B. Compared to parental cells, fusosomes were enriched for cholesteryl ester, free cholesterol, ether-linked lyso-phosphatidylethanolamine, lyso-phosphatidylserine, phosphatidate, ether-linked phosphatidylethanolamine, phosphatidylserine, and sphingomyelin. Compared to parental cells, fusosomes are depleted for ceramide, cardiolipin, lyso-phosphatidylcholine, lyso-phosphatidylethanolamine, lyso-phosphatidylglycerol, lyso-phosphatidylinositol, ether-linked phosphatidylcholine, phosphatidylethanolamine, phosphatidylglycerol, phosphatidylinositol, and triacylglycerol. Compared to exosomes, fusosomes were enriched for cholesteryl ester, ceramide, diacylglycerol, lyso-phosphatidate, and phosphatidylethanolamine, triacylglycerol. Compared to exosomes, fusosomes are depleted for free cholesterol, hexosyl ceramide, lyso-phosphatidylcholine, ether-linked lyso-phosphatidylcholine, lyso-phosphatidylethanolamine, ether-linked lyso-phosphatidylethanolamine, and lyso-phosphatidylserine, Example 165: Measuring Compartment-Specific Proteomic Content of Fusosomes This Example describes quantification of the proportion of proteins that are known to be derived from specific cellular compartments in fusosomes, fusosome parental cells, and exosomes.

Fusosomes and parental cells were prepared as described herein by the method of Examples 114 and 154. Exosomes were prepared as described herein for fusosomes by the method of Examples 114 and 154 with the exception that the parental cells were not transfected with VSV-G or GFP. Protein quantification by mass spectrometry for fusosomes and exosomes was performed as described herein in Example 42. The resulting protein quantification data was analyzed to determine protein levels and proportions of known exosomal, endoplasmic reticulum, ribosome, nuclear, and mitochondrial proteins as annotated by Gene Ontology Cellular Compartment annotation terms (exosome: GO:0070062, endoplasmic reticulum: GO:0005783, ribosome: GO:0005840, GO:0022625, GO:0022626, GO:0022627, GO:0044391, GO:0042788, GO:0000313) with evidence code IDA (inferred by direct assay). The fraction of compartment-specific proteins relative to total protein in each sample was determined for fusosome samples, exosome samples, and parental cells.

Figure 50:
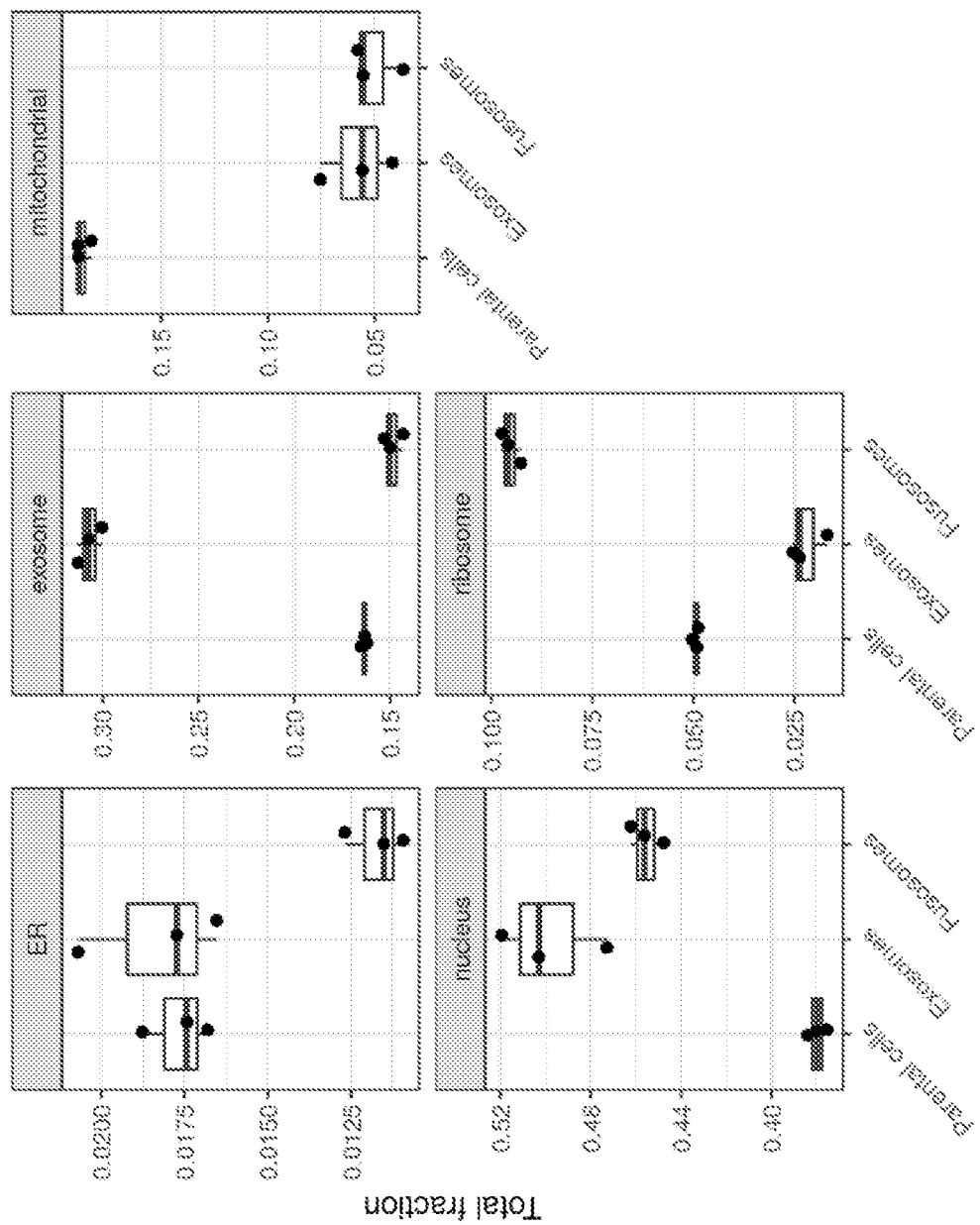
FIG. 50 is a series of graphs showing the protein content of parental cells, exosomes, and fusosomes with respect to proteins associated with specific compartments, as indicated.

As shown in FIG. 50, fusosomes were found to be depleted with endoplasmic reticulum protein compared to parental cells and exosomes. Fusosomes were also found to be depleted for exosomal protein compared to exosomes. Fusosomes were depleted for mitochondrial protein compared to parental cells. Fusosomes were enriched for nuclear protein compared to parental cells. Fusosomes were enriched for ribosomal proteins compared to parental cells and exosomes.

Example 166: Measuring TSG101 and ARRDC1 Content in Fusosomes

This Example describes quantification of the proportion of proteins that are known to be important in fusosome release from cells.

Fusosomes and parental cells were prepared as described herein by the method of Examples 114 and 154. Exosomes were prepared as described herein for fusosomes by the method of Examples 114 and 154 with the exception that the parental cells were not transfected with VSV-G or GFP. Protein quantification by mass spectrometry for fusosomes and exosomes was performed as described herein in Example 42. The resulting protein quantification data was analyzed to determine protein levels and proportions of the protein TSG101 and ARRDC1. Average log intensities per group were calculated by adding 1 to intensity values from mass spectrometry, transforming by log 10, and computing the mean across replicates. The percentage of total protein content of TSG101 or ARRDC1 in fusosomes relative to exosomes or parental cells was determined as the average log intensity of TSG101 or ARRDC1 for each sample, divided by the sum of intensities of all proteins in the same sample, averaged over replicates and expressed as a percent.

Figure 51:
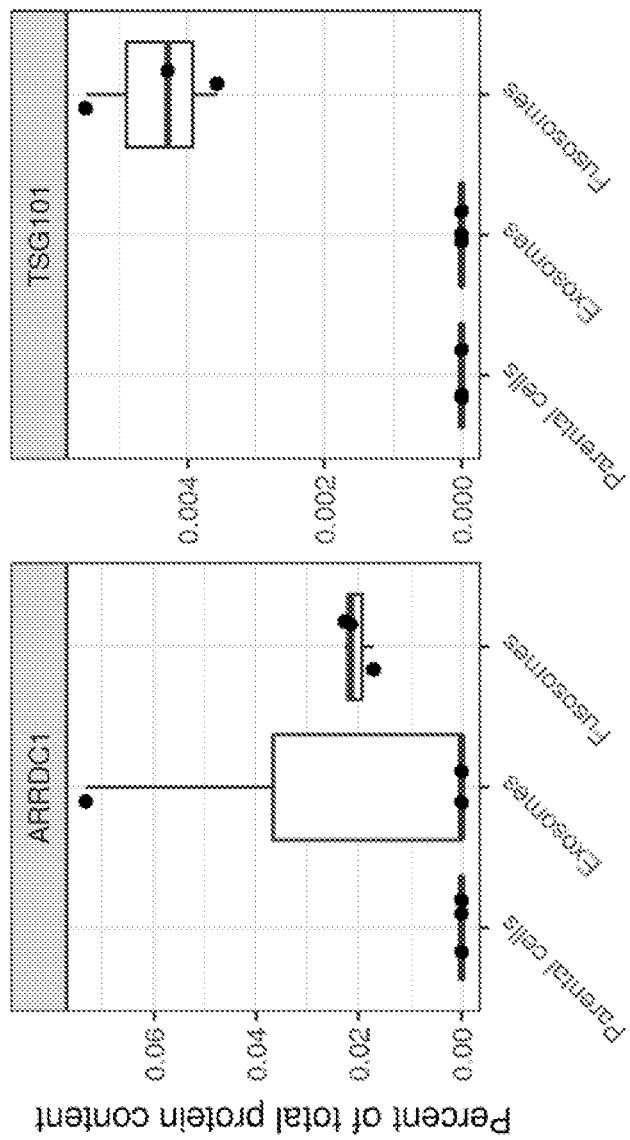
FIG. 51 is a series of graphs showing the level of ARRDC1 (left panel) or TSG101 (right panel) as a percentage of total protein content in parental cells, exosomes, and fusosomes.

As shown in FIG. 51, ARRDC1 was found to be present at greater levels as a percentage of total protein content in fusosomes than in parental cells or exosomes. The level of ARRDC1 as a percentage of total protein content was at least 0.02% in fusosomes. TSG101 was found to be present at greater levels as a percentage of total protein content in fusosomes than in parental cells or exosomes. The level of TSG101 as a percentage of total protein content was at least 0.004% in fusosomes.

Example 167: Measuring Pre-Existing Serum Inactivation of Fusosomes

This Example describes quantification of pre-existing serum inactivation of fusosomes using an in vitro delivery assay.

A measure of immunogenicity for fusosomes is serum inactivation. Serum inactivation of fusosomes may be due to antibody-mediated neutralization or complement mediated degradation. In an embodiment, some recipients of a fusosome described herein will have factors in their serum which bind to and inactivate fusosomes.

In this Example, a fusosome naïve mouse is assessed for the presence of factors that inactivate fusosomes in serum. Notably, the methods described herein may be equally applicable to humans, rats, monkeys with optimization to the protocol. The negative control is heat inactivated mouse serum, and the positive control is serum derived from a mouse that has received multiple injections of fusosomes generated from a xenogeneic source cell. Sera are collected from mice by collecting fresh whole blood and allowing it to clot completely for several hours. Clots are pelleted by centrifugation and the serum supernatants are removed. Negative control samples are heated at 56 degrees Celsius for 1 hour. Serum may be frozen in aliquots.

The fusosomes are tested for the dose at which 50% of cells in a recipient population receive the payload in the fusosomes. The fusosomes may be produced via any of the other examples described herein and may contain any of the payloads described herein. Many methods for assaying fusosome delivery of a payload to recipient cells are also described herein. In this particular example, the payload is Cre protein and the recipient cells are RPMI8226 cell which stably-expresses "LoxP-GFP-stop-LoxP-RFP" cassette under a CMV promoter, which upon recombination by Cre switches from GFP to RFP expression, indicating fusion and Cre, as a marker, of delivery. The identified dose at which 50% of the recipient cells are RFP positive is used for further experiments. In other embodiments, the identified dose at which 50% of the recipient cells receive the payload is used for further experiments. In preferred embodiments, the identified dose at which 50% of recipient cells receive the payload is similar across fusosomes.

To assess serum inactivation of fusosomes, fusosomes are diluted 1:5 into normal or heat-inactivated serum (or medium containing 10% heat-inactivated FBS as the no-serum control) and the mixture is incubated at 37 C for 1 h. Following the incubation, medium is added to the reaction for an additional 1:5 dilution and then serially diluted twice at a 1:10 ratio. Following this step, the fusosomes should be present at the previously identified dose at which 50% of the recipient cells have received the payload (e.g. are RFP positive).

Fusosomes that have been exposed to serum are then incubated with recipient cells. The percent of cells which receive the payload, and thus are RFP positive, is calculated. In some embodiments, the percent of cells which receive the payload is not different between fusosome samples that have been incubated with serum and heat-inactivated serum from fusosome naïve mice, indicating that there is not serum inactivation of fusosomes. In some embodiments, the percent of cells which receive the payload is not different between fusosome samples that have been incubated with serum from fusosome naïve mice and no-serum control incubations, indicating that there is not serum inactivation of fusosomes. In some embodiments, the percent of cells which receive the payload is less in fusosome samples that have been incubated with positive control serum than in fusosome samples that have been incubated with serum from fusosome naïve mice, indicating that there is not serum inactivation of fusosomes.

Example 168: Measuring Serum Inactivation of Fusosomes after Multiple Administrations This Example describes quantification of serum inactivation of fusosomes using an in vitro delivery assay following multiple administrations of the fusosome. It is contemplated that a modified fusosome, e.g., modified by a method described herein, can have a reduced (e.g., reduced compared to administration of an unmodified fusosome) serum inactivation following multiple (e.g., more than one, e.g., 2 or more), administrations of the modified fusosome. In some instances, a fusosome described herein will not be inactivated by serum following multiple administrations.

A measure of immunogenicity for fusosomes is serum inactivation. In an embodiment, repeated injections of a fusosome can lead to the development of anti-fusosome antibodies, e.g., antibodies that recognize fusosomes. In an embodiment, antibodies that recognize fusosomes can bind in a manner that can limit fusosome activity or longevity and mediate complement degradation.

In this Example, serum inactivation is examined after one or more administrations of fusosomes. Fusosomes are produced by any one of the previous Examples. In this example, fusosomes are generated from: HEK293 cells modified with a lentiviral-mediated expression of HLA-G (hereafter HEK293-HLA-G), and HEK293 modified with a lentiviral-mediated expression of an empty vector (hereafter HEK293). In some embodiments, fusosomes are derived from cells that are expressing other immunoregulatory proteins.

Serum is drawn from the different cohorts: mice injected systemically and/or locally with 1, 2, 3, 5, 10 injections of vehicle (Fusosome naïve group), HEK293-HLA-G fusosomes, or HEK293 fusosomes. Sera are collected from mice by collecting fresh whole blood and allowing it to clot completely for several hours. Clots are pelleted by centrifugation and the serum supernatants are removed. A negative control is heat inactivated mouse serum. Negative control samples are heated at 56 degrees Celsius for 1 hour. Serum may be frozen in aliquots.

The fusosomes are tested for the dose at which 50% of cells in a recipient population receive the payload in the fusosomes. The fusosomes may be produced via any of the other examples described herein and may contain any of the payloads described herein. Many methods for assaying fusosome delivery of a payload to recipient cells are also described herein. In this particular example, the payload is Cre protein and the recipient cells are RPMI8226 cell which stably-expresses "LoxP-GFP-stop-LoxP-RFP" cassette under a CMV promoter, which upon recombination by Cre switches from GFP to RFP expression, indicating fusion and Cre, as a marker, of delivery. The identified dose at which 50% of the recipient cells are RFP positive is used for further experiments. In other embodiments, the identified dose at which 50% of the recipient cells receive the payload is used for further experiments.

To assess serum inactivation of fusosomes, fusosomes are diluted 1:5 into normal or heat-inactivated serum (or medium containing 10% heat-inactivated FBS as the no-serum control) and the mixture is incubated at 37 C for 1 h. Following the incubation, medium is added to the reaction for an additional 1:5 dilution and then serially diluted twice at a 1:10 ratio. Following this step, the fusosomes should be present at the previously identified dose at which 50% of the recipient cells have received the payload (e.g. are RFP positive). It is contemplated that the identified dose at which 50% of recipient cells receive the payload may be similar across fusosomes.

Fusosomes that have been exposed to serum are then incubated with recipient cells. The percent of cells which receive the payload, and thus are RFP positive, is calculated. The percent of cells which receive the payload may not be different between fusosome samples that have been incubated with serum and heat-inactivated serum from mice treated with HEK293-HLA-G fusosomes, indicating that there is not serum inactivation of fusosomes or an adaptive immune response. The percent of cells that receive the payload may not be different between fusosome samples that have been incubated from mice treated 1, 2, 3, 5 or 10 times with HEK293-HLA-G fusosomes, which would indicate that there was not serum inactivation of fusosomes or an adaptive immune response. In some instances, the percent of cells which receive the payload is not different between fusosome samples that have been incubated with serum from mice treated with vehicle and from mice treated with HEK293-HLA-G fusosomes, indicating that there is not serum inactivation of fusosomes or an adaptive immune response. In some instances, the percent of cells which receive the payload is less for fusosomes derived with HEK293 than for HEK293-HLA-G fusosomes, indicating that there is not serum inactivation of HEK293-HLA-G fusosomes or an adaptive immune response.

Example 169: Measuring Complement Targeting of Fusosomes

This Example describes quantification of complement activity against fusosomes using an in vitro assay. It is contemplated that a modified fusosome described herein can induce reduced complement activity compared to a corresponding unmodified fusosome.

In this Example, serum from a mouse is assessed for complement activity against a fusosome. The example measures the level of complement C3a, which is a central node in all complement pathways. Notably, the methods described herein may be equally applicable to humans, rats, monkeys with optimization to the protocol.

In this Example, fusosomes are produced by any one of the previous Examples. Fusosomes are generated from HEK293 cells modified with a lentiviral-mediated expression of a complement regulatory protein DAF (HEK293-DAF fusosomes) or HEK 293 cells not expressing a complementary regulatory protein (HEK293 fusosomes). Other complement regulatory proteins may also be used, such as proteins that bind decay-accelerating factor (DAF, CD55), e.g. factor H (FH)-like protein-1 (FHL-1), e.g. C4b-binding protein (C4BP), e.g. complement receptor 1 (CD35), e.g. Membrane cofactor protein (MCP, CD46), eg. Profectin (CD59), e.g. proteins that inhibit the classical and alternative complement pathway CD/C5 convertase enzymes, e.g. proteins that regulate MAC assembly Serum is recovered from naïve mice, mice that are administered HEK293-DAF fusosomes, or mice that are administered HEK293 fusosomes. Sera are collected from mice by collecting fresh whole blood and allowing it to clot completely for several hours. Clots are pelleted by centrifugation and the serum supernatants are removed. A negative control is heat inactivated mouse serum. Negative control samples are heated at 56 degrees Celsius for 1 hour. Serum may be frozen in aliquots.

The different fusosomes are tested for the dose at which 50% of cells in a recipient population receive the payload in the fusosomes. The fusosomes may be produced via any of the other examples described herein and may contain any of the payloads described herein. Many methods for assaying fusosome delivery of a payload to recipient cells are also described herein. In this particular example, the payload is Cre protein and the recipient cells are RPMI8226 cell which stably-expresses "LoxP-GFP-stop-LoxP-RFP" cassette under a CMV promoter, which upon recombination by Cre switches from GFP to RFP expression, indicating fusion and Cre, as a marker, of delivery. The identified dose at which 50% of the recipient cells are RFP positive is used for further experiments. In other embodiments, the identified dose at which 50% of the recipient cells receive the payload is used for further experiments. In preferred embodiments, the identified dose at which 50% of recipient cells receive the payload is similar across fusosomes.

Two-fold dilutions of the fusosomes starting at the dose of fusosomes at which 50% of the recipient cells receive the payload in phosphate-buffered saline (PBS, pH 7.4) are mixed with a 1:10 dilution of the sera from mice treated with the same fusosomes or naïve mice (assay volume, 20 µl) and incubated for 1 h at 37° C. The samples are further diluted 1:500 and used in an enzyme-linked immunosorbant assay (ELISA) specific for C3a. The ELISA is mouse complement C3a ELISA Kit product LS-F4210 sold by LifeSpan Bio-Sciences Inc, which measures the concentration of C3a in a sample. The dose of fusosomes at which 200 µg/ml of C3a is present is compared across sera isolated from mice.

In some instances, the dose of fusosomes at which 200 µg/ml of C3a is present is greater for HEK293-DAF fusosomes incubated with HEK-293 DAF mouse sera than for HEK293 fusosomes incubated with HEK293 mouse sera, indicating that complement activity targeting fusosomes is greater in mice treated with HEK293 fusosomes than HEK293-DAF fusosomes. In some instances, the dose of fusosomes at which 200 µg/ml of C3a is present is greater for HEK293-DAF fusosomes incubated with naive mouse sera than for HEK293 fusosomes incubated with naive mouse sera, indicating that complement activity targeting fusosomes is greater in mice treated with HEK293 fusosomes than HEK293-DAF fusosomes.

Example 170: Incorporation of ARRDC1 into a Fusosome Production Protocol

This example describes the use of the arrestin domain-containing protein 1 (ARRDC1) into the fusosome production protocol, and describes the effects of AARDC 1 on fusosome number and delivery of Cre by the resultant fusosomes. Fusosomes encapsulating Cre were generated by the standard procedure of harvesting and preparing fusosomes produced from HEK-293T cells expressing the Nipah virus attachment (NiV-G) and fusion (NiV-F) envelope glycoproteins on the cell surface, the bacteriophage P1 recombinase Cre and the ARRDC1 protein. Control fusosomes were produced from HEK-293T cells expressing Cre and the NiV-G and NiV-F glycoproteins only. The effects of ARRDC1 on the ability of fusosomes to deliver Cre and fusosome number were then determined as follows.

Recipient HEK-293T cells engineered to express a "LoxP-GFP-stop-LoxP-RFP" cassette were plated 30,000 cells/well into a black, clear-bottom 96-well plate in complete media. Twenty-four hours after plating the recipient cells, a range of fusosome amounts encapsulating Cre were applied to the recipient LoxP-GFP-stop-LoxP-RFP HEK-293T cells.

To quantify the extent to which Cre delivery was enhanced by ARRDC1 incorporation into the production protocol, one group of recipient cells was treated with fusosomes produced from cells transfected with ARRDC1 (NiV-G+NiV-F+NLS-Cre+ARRDC1), and one group of cells was treated with control fusosomes (NiV-G+NiV-F+NLS-Cre). Fusosomes were incubated with the recipient cells for 24 hours at 37° C. and 5% $CO_2$. As a control, an additional group of recipient cells were also treated with 1.25 µL cer recombinase Gesicles (Takara, Cat #631449). Twenty-four hours later, 1 µg/mL Hoechst 33342 was diluted in complete media and incubated with the cells for 30 minutes at 37° C. and 5% $CO_2$.

Figures 52A, 52B:
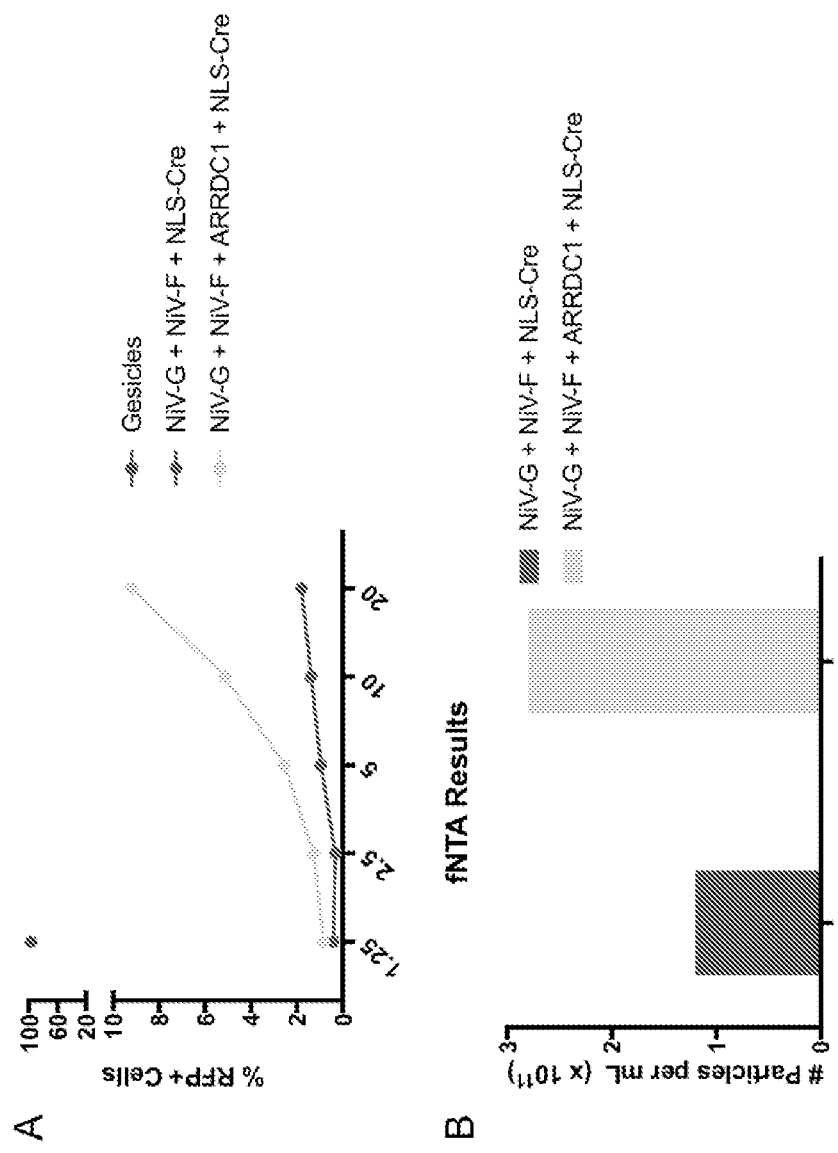
FIGS. 52A-52B are a series of graphs showing the effect of incorporating arrestin domain-containing protein 1 (ARRDC1) into the production of fusosomes encapsulating Cre. (A) The percentage of RFP-positive cells detected after incubation with fusosomes produced in the presence or absence of ARRDC1. (B) The number of particles per mL detected using Nanoparticle Tracking Analysis (fNTA) for fusosomes produced in the presence or absence of ARRDC1.

Following addition of Hoescht, the cells were analyzed via flow cytometry. Briefly, the recipient cell samples were dissociated, collected and washed thrice with 1×PBS buffer and resuspended in 1×PBS buffer and analyzed by flow cytometry (Attune, ThermoFisher) using 405 nm, 488 nm, and 561 nm lasers for excitation, and the 440/50BP (Hoescht), 530/30BP (GFP) and 585/16BP (RFP) emission filter sets for acquisition, receptively. Attune NxT software was used for acquisition and FlowJo software was used for analysis. For data acquisition and analysis, the FSC and SSC channels were set on a linear axis to determine a population representative of the recipient cells. This population was then gated and a minimum of 10,000 events within the cells gate was collected for each condition. A population representative of the recipient cells, in the Hoescht (440/50BP) emission channel was then gated, and this gate was used to display the GFP (530/30BP) events. A population representative of the GFP+recipient cells was then gated, and this gate was used to display the RFP (585/16BP) events. RFP-positive cells (recipient cells receiving Cre) was then quantified as a metric for Cre delivery by first setting a negative gate based on the untreated cells and a positive gate based on the RFP-positive cells from treated with Cre recombinase Gesicles. At the highest dose, Cre-loaded fusosomes produced from cells transfected with ARRDC1 showed an observable level of Cre delivery corresponding to 9.2% RFP-positive cells of total GFP-positive recipient cells (FIG. 52A). However, in the absence of ARRDC1, delivery of Cre was substantially reduced, with a level of delivery corresponding to 1.8% RFP-positive cells (FIG. 52A). Untreated recipient cells did not show any appreciable RFP-positive cells. Taken together, these data illustrate the ability of ARRDC1 to enhance fusosome-based Cre delivery.

Using fluorescent Nanoparticle Tracking Analysis (fNTA), fusosomes produced from cells transfected with ARRDC1 exhibited a concentration of $2.8 \times 10^{11}$ particles/mL, whereas fusosomes produced in the absence of ARRDC1, exhibited a concentration of $1.2 \times 10^{11}$ particles/mL (FIG. 52B), demonstrating that the presence of ARRDC1 in producer cells leads to the production of more CellMask Orange+(fNTA) particles.

---

What is claimed is:

1. A fusosome composition comprising a plurality of fusosomes derived from a source cell, wherein the fusosomes of the plurality comprise:

(a) a lipid bilayer, (b) a lumen comprising cytosol from the source cell, wherein the lumen is surrounded by the lipid bilayer, (c) an exogenous or overexpressed fusogen disposed in the lipid bilayer, wherein the fusogen comprises a protein selected from the group consisting of Nipah virus F and G proteins, measles virus F and H proteins, tupaia paramyxovirus F and H proteins, paramyxovirus F and G proteins or F and H proteins or F and HN proteins, Hendra virus F and G proteins, Henipavirus F and G proteins, Morbilivirus F and H proteins, respirovirus F and HN protein, a Sendai virus F and HN protein, rubulavirus F and HN proteins, or avulavirus F and HN proteins, a derivative thereof, and any combination thereof, and (d) a cargo; and wherein:

the fusosomes do not comprise a nucleus;

the amount of viral capsid protein in the fusosome composition is less than 1% of total protein in the fusosome composition; and the plurality of fusosomes, when contacted with a target cell population in the presence of an inhibitor of endocytosis, and when contacted with a reference target cell population not treated with the inhibitor of endocytosis, delivers at least 30% more of the cargo to the target cell population compared to the reference target cell population.

2. The fusosome composition of claim 1, which delivers the cargo to at least 40%, 50%, 60%, 70%, or 80% of the cells in the target cell population or delivers at least 40%, 50%, 60%, 70%, or 80% more of the cargo to the target cell population compared to the reference target cell population.

3. The fusosome composition of claim 1, wherein less than 10% of the cargo enters the cells of the target cell population by endocytosis.

4. The fusosome composition of claim 1, wherein the inhibitor of endocytosis is an inhibitor of lysosomal acidification.

5. The fusosome composition of claim 1, wherein the cargo enters the cells of the target cell population through a dynamin-independent pathway, a lysosomal acidification-independent pathway, a macropinocytosis-independent pathway, or an actin-independent pathway.

6. The fusosome composition of claim 1, wherein the fusosomes of the plurality comprise a targeting moiety.

7. The fusosome composition of claim 6, wherein the targeting moiety is comprised by the fusogen or is comprised by a separate molecule.

8. The fusosome composition of claim 1, wherein, when the plurality of fusosomes are contacted with a cell population comprising cells of the target cell population and cells of a non-target cell population, the cargo is delivered to at least 10-fold more target population cells than non-target population cells, or at least 10-fold more of the cargo is delivered to cells of the target cell population compared to cells of the reference target cell population.

9. The fusosome composition of claim 1, wherein the fusosomes of the plurality fuse at a higher rate with a target cell than with a non-target cell by at least 50%.

10. A fusosome composition comprising a plurality of fusosomes derived from a source cell, wherein the fusosomes of the plurality comprise:
  (a) a lipid bilayer,
  (b) a lumen comprising cytosol from the source cell, wherein the lumen is surrounded by the lipid bilayer,
  (c) an exogenous or overexpressed re-targeted fusogen disposed in the lipid bilayer, wherein the fusogen comprises a protein selected from the group consisting of Nipah virus F and G proteins, measles virus F and H proteins, tupaia paramyxovirus F and H proteins, paramyxovirus F and G proteins or F and H proteins or F and HN proteins, Hendra virus F and G proteins, Henipavirus F and G proteins, Morbilivirus F and H proteins, respirovirus F and HN protein, a Sendai virus F and HN protein, rubulavirus F and HN proteins, or avulavirus F and HN proteins, a derivative thereof, and any combination thereof, and
  (d) a cargo; and wherein:
  the fusosomes do not comprise a nucleus;
  the amount of viral capsid protein in the fusosome composition is less than 1% of total protein in the fusosome composition;
  when contacted with a target cell population, the fusosome composition delivers cargo to a target cell location other than an endosome or lysosome; and
    (i) when the plurality of fusosomes is contacted with a cell population comprising target cells and non-target cells, the cargo is delivered to at least 10-fold more target cells than non-target cells, or
    (ii) the fusosomes of the plurality fuse at a higher rate with a target cell than with a non-target cell, by at least at least 50%.

11. The fusosome composition of claim 10, wherein the fusosomes of the plurality comprise a targeting moiety.

12. The fusosome composition of claim 11, wherein the targeting moiety is specific for a cell surface marker on the target cell.

13. The fusosome composition of claim 6, wherein the targeting moiety is specific for a cell surface marker on the target cell.

14. The fusosome composition of claim 13, wherein the cell surface marker is a cell surface marker of a skin cell, a cardiomyocyte, a hepatocyte, an intestinal cell, a pancreatic cell, a brain cell, a prostate cell, a lung cell, a colon cell, or a bone marrow cell.

15. The fusosome composition of claim 10 wherein the plurality of fusosomes, when contacted with a target cell population in the presence of an inhibitor of endocytosis, delivers the cargo to at least 30% of the cells in the target cell population.

16. The fusosome composition of claim 1, which, when contacted with a target cell population, delivers cargo to a target cell location other than an endosome or a lysosome.

17. The fusosome composition of claim 16, wherein less than 50%, 40%, 30%, 20%, or 10% of the cargo is delivered to an endosome or a lysosome.

18. The fusosome composition of claim 1, wherein the fusosomes of the plurality comprise exosomes, microvesicles, or a combination thereof.

19. The fusosome composition of claim 1, wherein the fusosomes of the plurality have an average size of at least 50 nm, 100 nm, 200 nm, 500 nm, 1000 nm, 1200 nm, 1400 nm, or 1500 nm in diameter.

20. The fusosome composition of claim 1, wherein the fusosomes of the plurality have an average size of less than 100 nm, 80 nm, 60 nm, 40 nm, or 30 nm in diameter.

21. The fusosome composition of claim 1, wherein the source cell is selected from the group consisting of a neutrophil, a HEK293 cell, a granulocyte, a mesenchymal stem cell, a bone marrow stem cell, an induced pluripotent stem cell, an embryonic stem cell, a myeloblast, a myoblast, a hepatocyte, and a neuron.

22. The fusosome composition of claim 1, wherein the fusosomes of the plurality comprise a cell with partial or complete nuclear inactivation.

23. The fusosome composition of claim 1, wherein the fusosomes of the plurality comprise an enucleated cell.

24. The fusosome composition of claim 1, wherein the fusogen is present at a copy number of at least 10 copies per fusosome.

25. The fusosome composition of claim 1, wherein the cargo comprises an exogenous protein or an exogenous nucleic acid.

26. The fusosome composition of claim 1, wherein the cargo comprises or encodes a cytosolic protein or a membrane protein.

27. The fusosome composition of claim 1, wherein the cargo comprises a therapeutic agent.

28. The fusosome composition of claim 1, wherein the cargo is present at a copy number of at least 1, 2, 5, 10, 20, 50, 100, 200, 300, 400, 500, 600, 700, 800, or 900 copies per fusosome.

29. The fusosome composition of claim 1, wherein the ratio of the copy number of the fusogen to the copy number of the cargo is between 1000:1 and 1:1, between 500:1 and 1:1, between 250:1 and 1:1, between 150:1 and 1:1, between 100:1 and 1:1, between 75:1 and 1:1, between 50:1 and 1:1, between 25:1 and 1:1, between 20:1 and 1:1, between 15:1 and 1:1, between 10:1 and 1:1, between 5:1 and 1:1, between 2:1 and 1:1, or between 1:1 and 1:2.

30. The fusosome composition of claim 1, wherein:
  a) the ratio of fusogen to CD63 is about 100-10,000, 500-5,000, 1,000-5,000, 2,000-4,000, 2,500-3,500, 2,900-2,930, 2,910-2,915, or 2,912; and/or
  b) the ratio of protein cargo to CD63 is about 5-35, 10-30, 15-25, 16-19, 18-19, or 18.6; and/or
  c) less than 15%, 20%, or 25% of the protein in the fusosomes is exosomal protein.

31. The fusosome composition of claim 1, wherein:
a) the fusogen comprises about 1-30%, 5-20%, 10-15%, 12-15%, 13-14%, or 13.6% of the total protein in the fusosomes;
b) the fusogen to GAPDH ratio is about 20-120, 40-100, 50-90, 60-80, 65-75, 68-70, or 69;
c) the fusogen to CNX ratio is about 200-900, 300-800, 400-700, 500-600, 520-590, 530-580, 540-570, 550-560, or 558.4;
d) at least 1%, 2%, 3%, 4%, 5%, 6%, 7% 8%, 9% or 10% of the protein in the fusosomes is ribosomal protein, or about 1-20%, 3-15%, 5-12.5%, 7.5-11%, 8.5-10.5%, or 9-10% of the protein in the fusosomes is ribosomal protein.

32. A pharmaceutical composition comprising the fusosome composition of claim 1 and pharmaceutically acceptable carrier.

33. The pharmaceutical composition of claim 32, wherein the cargo comprises a therapeutic agent.

34. A method of delivering a cargo to a subject, comprising administering to the subject the pharmaceutical composition of claim 32, wherein the fusosome composition is administered in an amount and/or at a time such that the cargo is delivered.

35. A method of manufacturing a fusosome composition, comprising:
a) providing the fusosome composition of claim 1; and
b) formulating the fusosome composition as a pharmaceutical composition suitable for administration to a subject.

36. A method for release testing a fusosome composition, comprising:
a) providing the fusosome composition of claim 1; and
b) assaying one or more fusosomes of the plurality to determine the presence or level of one or more of the following factors: (i) an immunogenic molecule; (ii) a pathogen; or (iii) a contaminant; and
c) approving the plurality of fusosomes or the fusosome composition for release if the level of the one or more factors is below a reference value.

37. A fusosome composition comprising a plurality of fusosomes derived from a source cell, wherein the fusosomes of the plurality comprise:
(a) a lipid bilayer,
(b) a lumen comprising cytosol from the source cell, wherein the lumen is surrounded by the lipid bilayer,
(c) an exogenous or overexpressed fusogen, wherein the fusogen is disposed in the lipid bilayer and wherein the fusogen comprises a protein selected from the group consisting of Nipah virus F and G proteins, measles virus F and H proteins, tupaia paramyxovirus F and H proteins, paramyxovirus F and G proteins or F and H proteins or F and HN proteins, Hendra virus F and G proteins, Henipavirus F and G proteins, Morbilivirus F and H proteins, respirovirus F and HN protein, a Sendai virus F and HN protein, rubulavirus F and HN proteins, or avulavirus F and HN proteins, a derivative thereof, and any combination thereof, and
(d) a cargo; wherein:
the fusosomes do not comprise a nucleus;
when contacted with a target cell population, the fusosome composition delivers cargo to a target cell location other than an endosome or lysosome; and
wherein:
i) the fusogen is present at a copy number of at least 1,000 copies;
ii) the fusosomes comprise a therapeutic agent at a copy number of at least 1,000 copies;
iii) the fusosomes comprise a lipid, wherein one or more of CL, Cer, DAG, HexCer, LPA, LPC, LPE, LPG, LPI, LPS, PA, PC, PE, PG, Pl, PS, CE, SM and TAG is within 75% of the corresponding lipid level in the source cell;
iv) the fusosomes comprise a proteomic composition in which greater than 33% of the proteins of the source cell are present in the fusosome at an expression level that is at least 25% of the expression level in the source cell;
v) the fusosomes are capable of signal transduction;
vi) the fusosomes target a tissue; and/or
vii) the source cell is selected from the group consisting of a neutrophil, a granulocyte, a mesenchymal stem cell, a bone marrow stem cell, an induced pluripotent stem cell, an embryonic stem cell, a myeloblast, a myoblast, a hepatocyte, and a neuron.

38. The fusosome composition of claim 37, which comprises a viral capsid protein or a DNA integration polypeptide.

39. The fusosome composition of claim 37, wherein the cargo comprises a viral genome.

40. The fusosome composition of claim 1, which does not comprise a viral capsid protein.

* * * * *